US010239949B2

(12) United States Patent
Bienvenue et al.

(10) Patent No.: US 10,239,949 B2
(45) Date of Patent: Mar. 26, 2019

(54) ONCOFETAL ANTIGEN BINDING PROTEINS AND RELATED COMPOSITIONS AND METHODS

(71) Applicants: Aptevo Research and Development LLC, Seattle, WA (US); Alligator Bioscience AB, Lund (SE)

(72) Inventors: David Bienvenue, Seattle, WA (US); Gabriela Hernandez-Hoyos, Seattle, WA (US); Lynda Misher, Seattle, WA (US); Danielle Mitchell, Seattle, WA (US); Peter Ellmark, Lund (SE); Anna Sall, Lund (SE); Christina Furebring, Lund (SE); Laura von Schantz, Lund (SE); Sara Fritzell, Lund (SE); Laura Varas, Lund (SE)

(73) Assignees: Aptevo Research and Development, LLC, Seattle, WA (US); Alligator Bioscience AB, Lund (SE)

( * ) Notice: Subject to any disclaimer, the term of this patent is extended or adjusted under 35 U.S.C. 154(b) by 0 days.

(21) Appl. No.: 16/041,309

(22) Filed: Jul. 20, 2018

(65) Prior Publication Data

US 2019/0016816 A1 Jan. 17, 2019

Related U.S. Application Data

(60) Provisional application No. 62/648,072, filed on Mar. 26, 2018, provisional application No. 62/575,820, filed on Oct. 23, 2017, provisional application No. 62/535,107, filed on Jul. 20, 2017.

(51) Int. Cl.

| | |
|---|---|
| ***C07K 16/30*** | (2006.01) |
| ***A61K 39/395*** | (2006.01) |
| ***A61P 35/00*** | (2006.01) |
| ***C07K 16/28*** | (2006.01) |
| *A61K 39/00* | (2006.01) |

(52) U.S. Cl.

CPC .............. *C07K 16/30* (2013.01); *A61P 35/00* (2018.01); *C07K 16/2878* (2013.01); *A61K 39/395* (2013.01); *A61K 2039/505* (2013.01); *A61K 2039/5152* (2013.01); *C07K 2317/31* (2013.01); *C07K 2317/52* (2013.01); *C07K 2317/53* (2013.01); *C07K 2317/56* (2013.01); *C07K 2317/565* (2013.01); *C07K 2317/622* (2013.01); *C07K 2317/72* (2013.01); *C07K 2317/75* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 7,166,707 | B2 | 1/2007 | Feige |
| 8,409,577 | B2 | 4/2013 | Thompson et al. |
| 8,821,867 | B2 | 9/2014 | Ahrens et al. |
| 2006/0051844 | A1 | 3/2006 | Heavner et al. |
| 2007/0161080 | A1 | 7/2007 | Kingsman et al. |
| 2013/0095097 | A1 | 4/2013 | Blankenship et al. |
| 2013/0129723 | A1 | 5/2013 | Blankenship et al. |

FOREIGN PATENT DOCUMENTS

| | | | |
|---|---|---|---|
| WO | WO 2007/146968 | A2 | 12/2007 |
| WO | WO 2010/003108 | A2 | 1/2010 |
| WO | WO 2010/040105 | A2 | 4/2010 |
| WO | WO 2013/041687 | A1 | 3/2013 |
| WO | WO 2016/094873 | A2 | 6/2016 |
| WO | WO 2016/185016 | A1 | 11/2016 |
| WO | WO 2017/053469 | A2 | 3/2017 |
| WO | WO 2017/182672 | A1 | 10/2017 |

OTHER PUBLICATIONS

Akhmetzyanova et al., "CD137 Agonist Therapy Can Reprogram Regulatory T Cells into Cytotoxic CD4+ T Cells with Antitumor Activity" J Immunol 2016; 196:484-492.

Ascierto et al., "Clinical Experiences With Anti-CD137 and Anti-PD1 Therapeutic Antibodies" Semin Oncol. Oct. 2010;37(5):508-516.

Bienvenue, "Screening, Optimization and Characterization of a Novel 4-1BB × 5T4 ADAPTIR Bispecific Antibody," PEGS, Apr. 30-May 4, 2018, 13 pages.

Blahnik-Fagan, "Activation of the CD137 Pathway in T cells by a CD137 × 5T4 bispecific ADAPTIR™ Molecule Requires Co-engagement of CD137 and 5T4," AAI, May 4-8, 2018, 14 pages.

(Continued)

*Primary Examiner* — Hong Sang

(74) *Attorney, Agent, or Firm* — Cooley LLP

(57) ABSTRACT

The present disclosure relates to protein molecules that specifically bind to 5T4 and/or 4-1BB. The molecules may have at least one humanized 5T4-binding or 4-1BB-binding domain. Such molecules are useful for the treatment of cancer. The protein molecule binding to 5T4 or 4-1BB may have a second binding domain that binds to another target. The molecules may bind both 5T4-expressing cells and a cell-surface molecule expressed by an effector cell to enhance effector cell activation, proliferation, survival and/or effector-cell mediated cytotoxicity. The disclosure also provides pharmaceutical compositions comprising the 5T4-binding or 4-1BB-binding polypeptide or protein molecules, nucleic acid molecules encoding these polypeptides and methods of making and using these molecules.

20 Claims, 39 Drawing Sheets

Specification includes a Sequence Listing.

(56) References Cited

OTHER PUBLICATIONS

Blahnik-Fagan et al., "Activation of the CD137 Pathway in T cells by a CD137 × 5T4 bispecific ADAPTIR™ Molecule Requires Co-engagement of CD137 and 5T4," AAI, May 4-8, 2018, 1 page.
Brochet et al., "IMGTN-QUEST: the highly customized and integrated system for IG and TR standardized V-J and V-D-J sequence analysis," Nucleic Acids Res, Jul. 1, 2008; 36(Web Server issue):W503-508.
Castro et al., "5T4 oncofoetal antigen is expressed in high risk of relapse childhood pre-B acute lymphoblastic leukemia and is associated with a more invasive and chemotactic phenotype" Leukemia, Jul. 2012; 26(7): 1487-1498.
Claus et al., "A novel tumor-targeted 4-1BB agonist and its combination with T-cell bispecific antibodies: an off-the-shelf cancer immunotherapy alternative to CAR T-cells," Abstract 3634, Proceedings: AACR Annual Meeting 2017; Apr. 1-5, 2017; Washington, DC, 1 page.
Co et al., "Chimeric and humanized antibodies with specificity for the CD33 antigen," J Immunol, Feb. 15, 1992;148(4):1149-1154.
Co et al., "Humanized antibodies for antiviral therapy," Proc Natl Acad Sci USA, Apr. 1, 1991;88(7):2869-2873.
Dahlén et al., "Bispecific antibodies in cancer immunotherapy," Therapeutic Advances in Vaccines and Immunotherapy, 2018, vol. 6(1) 3-17.
Damelin et al., "Delineation of a Cellular Hierarchy in Lung Cancer Reveals an Oncofetal Antigen Expressed on Tumor-Initiating Cells," Cancer Res; 71(12); 4236-4246, 2011.
Dubrot et al., Treatment with anti-CD137 mAbs causes intense accumulations of liver T cells without selective antitumor immunotherapeutic effects in this organ, Cancer Immunol Immunother (2010) 59:1223-1233.
Elkord et al., "5T4 as a target for immunotherapy in renal cell carcinoma," Expert Rev. Anticancer Ther., 9(12), 1705-1709 (2009).
Elkord et al., "Immune evasion mechanisms in colorectal cancer liver metastasis patients vaccinated with TroVax (MVA-5T4)," Cancer Immunol Immunother (2009) 58:1657-1667.
Fiedler et al., "Tumor-restricted immune-modulation by multispecific molecules from the DARPin® toolbox," AACR 2018, Poster 4552, Chicago IL, Apr. 17, 2018, 1 page.
Forsberg et al., "Therapy of human non-small-cell lung carcinoma using antibody targeting of a modified superantigen," British Journal of Cancer (2001) 85(1), 129-136.
Fritzell et al., "Tumor Antigen-dependent T Cell Activation and Tumor Localization Induced by a Novel 4-1BB X 5T4 Adaptir™ Bispecific Antibody," Annual Meeting of the Association for Cancer Immunotherapy (CIMT) 2018, 1 page.
Garber, "Beyond Ipilimumab: New Approaches Target the Immunological Synapse," JNCI | News, vol. 103, Issue 14, Jul. 20, 2011, pp. 1079-108.
Gauttier et al., "Agonistic anti-CD137 antibody treatment leads to antitumor response in mice with liver cancer," Int. J. Cancer, 135, 2857-2867 (2014).
Giddabasappa et al., "Biodistribution and Targeting of Anti-5T4 Antibody-Drug Conjugate Using Fluorescence Molecular Tomography," Mol Cancer Ther; 15(10) Oct. 2016, 2530-2540.
Gunde et al., "A novel multi-specific antibody targeting PD-L1-overexpressing cancers that stimulates antigen-committed CD8+ T cells through concomitant engagement of a T cell costimulatory receptor," AACR Annual Meeting 2018, Chicago IL USA—Poster #3818, 1 page.
Harper et al., "Preclinical Evaluation of MEDI0641, a Pyrrolobenzodiazepine-Conjugated Antibody-Drug Conjugate Targeting 5T4," Mol Cancer Ther; 16(8) Aug. 2017, 1576-1587.
Hedlund et al, "A fusion protein between a 5T4 binding antibody fragment and an engineered superantigen (ANYARA) is a targeted immunotherapy effective alone and in combination with other cancer therapies," IBC, 2018.
Hinner et al., "Costimulatory T cell engagement via a novel bispecific anti-CD137 /anti-HER2 protein," Journal of Immunotherapy of Cancer, 2015, 3(Suppl 2):P187.
Hinner et al., "Costimulatory T-cell engagement by PRS-343, a 4-1BB (CD137)/HER2 bispecific, leads to tumor growth inhibition and TIL expansion in humanized mouse model," Abstract B016; Second CRI-CIMT-EATI-AACR International Cancer Immunotherapy Conference: Translating Science into Survival; Sep. 25-28, 2016; New York, NY, Sep. 25-28, 2016, 1 page.
Hinner et al., "Costimulatory T-cell engagement by the CD137/HER2 bispecific PRS-343 leads to strong anti-tumor effect in humanized mouse model," AACR, Apr. 16-20, 2016, 1 page.
Hinner et al., "Preclinical toxicology and pharmacology for the 4-1BB/HER2 bispecific PRS-343: A first-in-class costimulatory T cell engager," AACR Annual Meeting 2017 Abstract 3673, 1 page.
Hinner et al., "Target specific co-stimulatory T cell engagement by CD137/HER2 bispecific PRS-343," ITOC3 2016, Munich Mar. 21-23, 2016, 1 page.
Huang et al., "A 5T4 × CD3 Bispecific DART® Molecule with Extended Half-life for T-cell Immunotherapy of Cancers," Poster 4608 Presented at the American Association for Cancer Research Annual Meeting 2017, Apr. 1-5, 2017, Washington, DC, 1 page.
Houot et al, "Boosting antibody-dependant cellular cytotoxicity against tumor cells with a CD137 stimulatory antibody," Oncolmmunology 1:6, 957-958; Sep. 2012.
International Search Report and Written Opinion for International Application No. PCT/EP2018/069850, dated Oct. 10, 2018, 17 pages.
Kaufman et al., "Phase II trial of Modified Vaccinia Ankara (MVA) virus expressing 5T4 and high dose Interleukin-2 (IL-2) in patients with metastatic renal cell carcinoma," Journal of Translational Medicine 2009, 7:2, 11 pages.
Kim et al., "Divergent Effects of 4-1BB Antibodies on Antitumor Immunity and on Tumor-reactive T-Cell Generation," Cancer Research, 61, 2031-2037, Mar. 1, 2001.
Kohrt et al, "Stimulation of natural killer cells with a CD137-specific antibody enhances trastuzumab efficacy in xenotransplant models of breast cancer," J Clin Invest. 2012;122(3):1066-1075.
Kohrt et al., "Targeting CD137 enhances the efficacy of cetuximab," J Clin Invest. 2014;124(6):2668-2682.
Leal et al., "Preclinical Development of an anti-5T4 Antibody-Drug Conjugate: Pharmacokinetics in Mice, Rats, and NHP and Tumor/Tissue Distribution in Mice," Bioconjugate Chem. 2015, 26, 2223-2232.
Lee et al., "Molecular cloning of agonistic and antagonistic monoclonal antibodies against human 4-1BB" European Journal of Immunogenetics, Oct. 2002;29(5):449-52.
Li and Liu, "Immunotherapy of melanoma with the immune costimulatory monoclonal antibodies targeting CD137," Clinical Pharmacology: Advances and Applications, 2013:5 (Suppl 1) 47-53.
Link et al., "Preclinical pharmacology of MP0310: a 4-1BB/FAP bispecific DARPin® drug candidate promoting tumor-restricted T cell co-stimulation," AACR, Apr. 14-18, 2018, Poster 3752, 1 page.
Liu et al., "Tumor Antigen Expression-dependent Activation of the CD137 Costimulatory Pathway by Bispecific DART® Proteins," Poster 3642 Presented at the American Association for Cancer Research Annual Meeting 2017, Apr. 1-5, 2017, Washington, DC, 1 page.
Marvin and Zhu, "Recombinant approaches to IgG-like bispecific antibodies," Acta Pharmacologica Sinica, Jun. 2005;26(6):649-658.
McMillin et al., "Complete Regression of Large Solid Tumors Using Engineered Drug-Resistant Hematopoietic Cells and Anti-CD137 Immunotherapy" Human Gene Therapy vol. 17, No. 8, (Aug. 2006).
Melero et al., "Monoclonal antibodies against the 4-1BB T-cell activation molecule eradicate established tumors," Nature Medicine, vol. 3, No. 6, Jun. 1997, pp. 682-685.
Miller et al., "4-1BB-Specific Monoclonal Antibody Promotes the Generation of Tumor-Specific Immune Responses by Direct Activation of CD8 T Cells in a CD40-Dependent Manner," The Journal of Immunology, 2002, 169:1792-1800.
Molecular Partners AG, "Making the DARPin® Difference Reality for Patients," Corporate Presentation of Molecular Partners AG, Switzerland (SIX: MOLN), Apr. 21, 2018, 51 pages.

(56) References Cited

OTHER PUBLICATIONS

Niu et al., "Cytokine-Mediated Disruption of Lymphocyte Trafficking, Hemopoiesis, and Induction of Lymphopenia, Anemia, and Thrombocytopenia in Anti-CD137-Treated Mice," J Immunol, 2007, 178:4194-4213.

Owens et al, "Preclinical Assessment of CAR T-Cell Therapy Targeting the Tumor Antigen 5T4 in Ovarian Cancer," J Immunother 2018; 41:130-140.

Pulle et al., "IL-15-Dependent Induction of 4-1BB Promotes Antigen-Independent CD8 Memory T Cell Survival," J Immunol 2006; 176:2739-2748.

Rabu et al., "Production of Recombinant Human Trimeric CD137L (4-1BBL), Cross-linking is Essential to its T Cell Co-Stimulation Activity," The Journal of Biological Chemistry vol. 280, No. 50, pp. 41472-41481, Dec. 16, 2005.

Reichen et al., "FAP-mediated tumor accumulation of a T cell agonistic 4-1BB/FAP DARPin® drug candidate analyzed by SPECT/CT and quantitative biodistribution," AACR, Apr. 14-18, 2018, Poster 3029, 1 page.

Sallin et al., "The anti-lymphoma activities of anti-CD137 monoclonal antibodies are enhanced in FcγRIII-/-mice" Cancer Immunol Immunother (2014) 63:947-958.

Sapra et al., "Long-term Tumor Regression Induced by an Antibody-Drug Conjugate That Targets 5T4, an Oncofetal Antigen Expressed on Tumor-Initiating Cells," Mol Cancer Ther 2013;12:38-47.

Shapiro et al., "First-in-human trial of an anti-5T4 antibody-monomethylauristatin conjugate, PF-06263507, in patients with advanced solid tumors," Invest New Drugs, Jun. 2017;35(3):315-323.

Shor et al., "Enhanced Antitumor Activity of an Anti-5T4 Antibody-Drug Conjugate in Combination with PI3K/mTOR inhibitors or Taxanes," Clinical Cancer Research; 22(2) Jan. 15, 2016, 383-394.

Shuford et al., "4-1BB Costimulatory Signals Preferentially Induce CD8 1 T Cell Proliferation and Lead to the Amplification In Vivo of Cytotoxic T Cell Responses" J. Exp. Med., vol. 186, No. 1, Jul. 7, 1997, pp. 47-55.

So et al., "Immune regulation and control of regulatory T cells by OX40 and 4-1BB," Cytokine & Growth Factor Reviews 19 (2008) 253-262.

Southgate et al., "CXCR4 mediated chemotaxis is regulated by 5T4 oncofetal glycoprotein in mouse embryonic cells", PLoS One. Apr. 1, 2010;5(4):e9982.

Southall et al., "Immunohistological distribution of 5T4 antigen in normal and malignant tissues," Br. J. Cancer (1990), 61, 89-95.

Stern et al., "5T4 oncofoetal antigen: an attractive target for immune intervention in cancer," Cancer Immunol Immunother (2017) 66:415-426.

Sun et al., "Co-stimulation agonists as a new immunotherapy for autoimmune diseases," Trends in Molecular Medicine, vol. 9 ,No. 11, Nov. 2003, pp. 483-489.

Tang et al., "Selection of linkers for a catalytic single-chain antibody using phage display technology," J Biol Chem., Jun. 28, 1996;271(26):15682-15686.

Taraban et al., "Expression and costimulatory effects of the TNF receptor superfamily members CD134 (OX40) and CD137 (4-1BB), and their role in the generation of anti-tumor immune responses," Eur. J. Immunol. 2002., 32: 3617-3627.

Uno et al., "Eradication of established tumors in mice by a combination antibody-based therapy," Nature Medicine, vol. 12, No. 6, Jun. 2006, pp. 693-698.

Vinay and Kwon, "Immunotherapy of Cancer with 4-1BB," Mol Cancer Ther 2012;11:1062-1070.

Verhoeyen, et al., "Reshaping Human Antibodies: Grafting an Antilysozyme Activity," Science, Mar. 25, 1988;239(4847):1534-1536.

von Schantz et al., "Screening, Optimization and Characterization of a Novel 4-1BB x 5T4 ADAPTIR™ Bispecific Antibody", Proceedings of the National Academy of Sciences of the United States of America, PEGS Meeting Apr. 30-May, 2018, 1 page.

Ward et al., "The effector functions of immunoglobulins: implications for therapy," Ther Immunol., Apr. 1995;2(2):77-94.

Wilcox et al., "Provision of antigen and CD137 signaling breaks immunological ignorance, promoting regression of poorly immunogenic tumors," J. Clin. Invest. 109:651-659 (2002).

Wyzgol et al., "Trimer Stabilization, Oligomerization, and Antibody-Mediated Cell Surface Immobilization Improve the Activity of Soluble Trimers of CD27L, CD4OL, 41BBL, and Glucocorticoid-Induced TNF Receptor Ligand," The Journal of Immunology, 2009, 183: 1851-1861.

Zhang et al., "Immune suppression or enhancement by CD137 T cell costimulation during acute viral infectionis time dependent," J Clin Invest., 2007;117(10):3029-3041.

| Construct | $EC_{50}$ value (pM) |
|---|---|
| ALG.APV-004 | 41 |
| ALG.APV-006 | 119 |
| ALG.APV-099 | 63 |
| ALG.APV-127 | 20 |
| ALG.APV-148 | 49 |
| ALG.APV-150 | 29 |

| Construct | $EC_{50}$ value (nM) |
|---|---|
| ALG.APV-006 | 1.2 |
| ALG.APV-178 | 1.0 |
| ALG.APV-179 | 0.9 |
| ALG.APV-187 | 0.9 |
| ALG.APV-191 | 1.1 |
| ALG.APV-196 | 0.9 |
| ALG.APV-198 | 1.0 |

| Construct | $EC_{50}$ value (nM) |
|---|---|
| ALG.APV-006 | 1.8 |
| ALG.APV-178 | 1.7 |
| ALG.APV-179 | 1.7 |
| ALG.APV-187 | 1.7 |
| ALG.APV-191 | 1.7 |
| ALG.APV-196 | 1.8 |
| ALG.APV-198 | 1.8 |

| Construct | $EC_{50}$ value (nM) | Maximum MFI |
|---|---|---|
| ALG.APV-006 | 8.6 | 14842 |
| ALG.APV-178 | 8.8 | 14074 |
| ALG.APV-179 | 10.1 | 14222 |
| ALG.APV-187 | 5.6 | 13488 |
| ALG.APV-191 | 10.9 | 14124 |
| ALG.APV-196 | 3.4 | 13475 |
| ALG.APV-198 | 3.1 | 13212 |

| Construct | $EC_{50}$ value (nM) | Maximum MFI |
|---|---|---|
| ALG.APV-006 | 7.0 | 1658 |
| ALG.APV-178 | 7.8 | 1652 |
| ALG.APV-179 | 15.8 | 1777 |
| ALG.APV-187 | 9.2 | 1795 |
| ALG.APV-196 | 1.7 | 1126 |
| ALG.APV-198 | 1.8 | 1066 |

| Construct | $EC_{50}$ value (nM) | Maximum MFI |
|---|---|---|
| ALG.APV-006 | 22 | 24810 |
| ALG.APV-178 | 32 | 26076 |
| ALG.APV-179 | 51 | 31075 |
| ALG.APV-187 | 21 | 25385 |
| ALG.APV-191 | 22 | 25087 |
| ALG.APV-196 | 7 | 21120 |
| ALG.APV-198 | 7 | 20561 |

| Construct | $EC_{50}$ value (pM) |
|---|---|
| ALG.APV-004 | 171 |
| ALG.APV-006 | 189 |
| ALG.APV-178 | 32 |
| ALG.APV-179 | 40 |
| ALG.APV-187 | 33 |
| ALG.APV-191 | 92 |
| ALG.APV-196 | 76 |
| ALG.APV-198 | 42 |

| Construct | EC50 value (nM) | Maximum MFI |
|---|---|---|
| ALG.APV-004 | 0.39 | 7785 |
| ALG.APV-178 | 0.36 | 6722 |
| ALG.APV-179 | 0.39 | 8207 |
| ALG.APV-187 | 0.41 | 8718 |
| ALG.APV-208 | 0.60 | 8667 |
| ALG.APV-209 | 0.56 | 8630 |
| ALG.APV-210 | 0.56 | 8972 |

Binding of anti-CD137 x anti-5T4 bispecific construct to CHO-K1 / human CD137 cells Binding of anti-CD137 x anti-5T4 bispecific constructs on CT26 human 5T4 cells

| Construct | EC50 value (nM) | Maximum MFI |
|---|---|---|
| ALG.APV-004 | 1.5 | 1252 |
| ALG.APV-178 | 1.8 | 1478 |
| ALG.APV-179 | 2.5 | 1745 |
| ALG.APV-187 | 2.2 | 1732 |
| ALG.APV-208 | 2.1 | 1459 |
| ALG.APV-209 | 2.9 | 1711 |
| ALG.APV-210 | 2.7 | 1733 |

| Construct | EC50 value (nM) | Maximum MFI |
|---|---|---|
| ALG.APV-004 | 6.5 | 26580 |
| ALG.APV-178 | 9.5 | 26675 |
| ALG.APV-179 | 10.1 | 26834 |
| ALG.APV-187 | 8.5 | 25958 |
| ALG.APV-208 | 7.4 | 24943 |
| ALG.APV-209 | 8.9 | 25431 |
| ALG.APV-210 | 7.2 | 23799 |

Activity of anti-Cd137 x anti-5T4 bispecific constructs in CD137 reporter assay with HCC1143 target cells Activity of anti-CD137 x anti-5T4 bispecific constructs in CC137 reporter assay with MOLM13 control target cells

| Construct | EC50 value (nM) |
|---|---|
| ALG.APV-004 | 0.20 |
| ALG.APV-178 | 0.03 |
| ALG.APV-208 | 0.02 |
| ALG.APV-179 | 0.03 |
| ALG.APV-209 | 0.02 |
| ALG.APV-187 | 0.03 |
| ALG.APV-210 | 0.03 |

SEQUENCE LISTING

```
<160> NUMBER OF SEQ ID NOS: 181

<210> SEQ ID NO 1
<211> LENGTH: 24
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 1

ggattcacct tttctcacgg ttct                                              24


<210> SEQ ID NO 2
<211> LENGTH: 8
<212> TYPE: PRT
<213> ORGANISM: Artificial Sequence
<220> FEATURE:
<223> OTHER INFORMATION: Made in Lab - antibody fragments

<400> SEQUENCE: 2

Gly Phe Thr Phe Ser His Gly Ser
1               5


<210> SEQ ID NO 3
<211> LENGTH: 24
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 3

atttcttctg gttctggttc taca                                              24


<210> SEQ ID NO 4
<211> LENGTH: 8
<212> TYPE: PRT
<213> ORGANISM: Artificial Sequence
<220> FEATURE:
<223> OTHER INFORMATION: Made in Lab - antibody fragments

<400> SEQUENCE: 4

Ile Ser Ser Gly Ser Gly Ser Thr
1               5
```

-continued

<210> SEQ ID NO 5
<211> LENGTH: 42
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 5
gcgcgctctt cttactacgg ttcttactac tctattgact at 42

<210> SEQ ID NO 6
<211> LENGTH: 14
<212> TYPE: PRT
<213> ORGANISM: Artificial Sequence
<220> FEATURE:
<223> OTHER INFORMATION: Made in Lab - antibody fragments

<400> SEQUENCE: 6

Ala Arg Ser Ser Tyr Tyr Gly Ser Tyr Tyr Ser Ile Asp Tyr
1 5 10

<210> SEQ ID NO 7
<211> LENGTH: 18
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 7
cagagcatta gcagctat 18

<210> SEQ ID NO 8
<211> LENGTH: 6
<212> TYPE: PRT
<213> ORGANISM: Artificial Sequence
<220> FEATURE:
<223> OTHER INFORMATION: Made in Lab - antibody fragments

<400> SEQUENCE: 8

Gln Ser Ile Ser Ser Tyr
1 5

<210> SEQ ID NO 9
<211> LENGTH: 9
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 9 gctgcatcc 9

<210> SEQ ID NO 10
<211> LENGTH: 3
<212> TYPE: PRT
<213> ORGANISM: Artificial Sequence
<220> FEATURE:
<223> OTHER INFORMATION: Made in Lab - antibody fragments

<400> SEQUENCE: 10

Ala Ala Ser
1

<210> SEQ ID NO 11
<211> LENGTH: 27
<212> TYPE: DNA
<213> ORGANISM: ARTIFICIAL SEQUENCE

```
<220> FEATURE:
<223> OTHER INFORMATION: Made in Lab - antibody fragments

<400> SEQUENCE: 11

caacagtact acgacaacct gcccact                                    27


<210> SEQ ID NO 12
<211> LENGTH: 9
<212> TYPE: PRT
<213> ORGANISM: Artificial Sequence
<220> FEATURE:
<223> OTHER INFORMATION: Made in Lab - antibody fragments

<400> SEQUENCE: 12

Gln Gln Tyr Tyr Asp Asn Leu Pro Thr
1               5


<210> SEQ ID NO 13
<211> LENGTH: 363
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 13

gaggtgcagc tgttggagag cgggggaggc ttggtacagc ctggggggtc cctgcgcctc     60

tcctgtgcag ccagcggatt caccttttct cacggttcta tgtactgggt ccgccaggct    120

ccagggaagg ggctggagtg ggtctcatct atttcttctg gttctggttc tacatactat    180

gcagactccg tgaagggccg gttcaccatc tcccatgaca attccaagaa cacgctgtat    240

ctgcaaatga acagcctgcg tgccgaggac acggctgtat attattgtgc gcgctcttct    300

tactacggtt cttactactc tattgactat tggggccagg gaaccctggt caccgtctcc    360

tca                                                                  363


<210> SEQ ID NO 14
<211> LENGTH: 121
<212> TYPE: PRT
<213> ORGANISM: Artificial Sequence
<220> FEATURE:
<223> OTHER INFORMATION: Made in Lab - antibody fragments

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser His Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120
```

<210> SEQ ID NO 15
<211> LENGTH: 321
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 15
gacatccaga tgacccagtc tccatcctcc ctgagcgcat ctgtaggaga ccgcgtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
cgtttcagtg gcagtggaag cgggacagat ttcactctca ccatcagcag tctacaacct 240
gaagattttg caacttatta ctgtcaacag tactacgaca acctgcccac ttttggccag 300
gggaccaagc tggagatcaa a 321

<210> SEQ ID NO 16
<211> LENGTH: 107
<212> TYPE: PRT
<213> ORGANISM: Artificial Sequence
<220> FEATURE:
<223> OTHER INFORMATION: Made in Lab - antibody fragments

<400> SEQUENCE: 16

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Asp Asn Leu Pro
85 90 95

Thr Phe Gly Gln Gly Thr Lys Leu Glu Ile Lys
100 105

<210> SEQ ID NO 17
<211> LENGTH: 24
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 17
ggattcacct ttgattacgg ttct 24

<210> SEQ ID NO 18
<211> LENGTH: 8
<212> TYPE: PRT
<213> ORGANISM: Artificial Sequence
<220> FEATURE:
<223> OTHER INFORMATION: Made in Lab - antibody fragments

<400> SEQUENCE: 18

Gly Phe Thr Phe Asp Tyr Gly Ser
1 5

<210> SEQ ID NO 19

<211> LENGTH: 363
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 19

```
gaggtgcagc tgttggagag cgggggaggc ttggtacagc ctgggggtc cctgcgcctc      60

tcctgtgcag ccagcggatt cacctttgat tacggttcta tgtactgggt ccgccaggct    120

ccagggaagg ggctggagtg ggtctcatct atttcttctg gttctggttc tacatactat    180

gcagactccg tgaagggccg gttcaccatc tcccacgaca attccaagaa cacgctgtat    240

ctgcaaatga acagcctgcg tgccgaggac acggctgtat attattgtgc gcgctcttct    300

tactacggtt cttactactc tattgactat tggggccagg gaaccctggt caccgtctcc    360

tca                                                                  363
```

<210> SEQ ID NO 20
<211> LENGTH: 121
<212> TYPE: PRT
<213> ORGANISM: Artificial Sequence
<220> FEATURE:
<223> OTHER INFORMATION: Made in Lab - antibody fragments

<400> SEQUENCE: 20

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser His Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120
```

<210> SEQ ID NO 21
<211> LENGTH: 321
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 21

```
gacatccaga tgacccagtc tccatcctcc ctgagcgcat ctgtaggaga ccgcgtcacc      60

atcacttgcc gggcaagtca gagcattagc agctatttaa attggtatca gcagaaacca    120

gggaaagccc ctaagctcct gatctatgct gcatccagtt tgcacagtgg ggtcccatca    180

cgtttcagtg gcagtggaag cgggacagat ttcactctca ccatcagcag tctgcaacct    240

gaagattttg caacttatta ctgtcaacag tactacgaca acctgcccac ttttggccag    300

gggaccaagc tggagatcaa a                                              321
```

```
<210> SEQ ID NO 22
<211> LENGTH: 107
<212> TYPE: PRT
<213> ORGANISM: Artificial Sequence
<220> FEATURE:
<223> OTHER INFORMATION: Made in Lab - antibody fragments

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105


<210> SEQ ID NO 23
<211> LENGTH: 24
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 23

ggattcacct tttcttacgg ttct                                            24


<210> SEQ ID NO 24
<211> LENGTH: 8
<212> TYPE: PRT
<213> ORGANISM: Artificial Sequence
<220> FEATURE:
<223> OTHER INFORMATION: Made in Lab - antibody fragments

<400> SEQUENCE: 24

Gly Phe Thr Phe Ser Tyr Gly Ser
1               5


<210> SEQ ID NO 25
<211> LENGTH: 363
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 25

gaggtgcagc tgttggagag cgggggaggc ttggtacagc ctggggggtc cctgcgcctc      60

tcctgtgcag ccagcggatt caccttttct tacggttcta tgtactgggt ccgccaggct     120

ccagggaagg ggctggagtg ggtctcatct atttcttctg gttctggttc tacatactat     180

gcagactccg tgaagggccg gttcaccatc tcccatgaca attccaagaa cacgctgtat     240

ctgcaaatga acagcctgcg tgccgaggac acggctgtat attattgtgc gcgctcttct     300

tactacggtt cttactactc tattgactat tggggccagg gaaccctggt caccgtctcc     360

tca                                                                   363
```

<210> SEQ ID NO 26
<211> LENGTH: 121
<212> TYPE: PRT
<213> ORGANISM: Artificial Sequence
<220> FEATURE:
<223> OTHER INFORMATION: Made in Lab - antibody fragments

<400> SEQUENCE: 26

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser His Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120
```

<210> SEQ ID NO 27
<211> LENGTH: 363
<212> TYPE: DNA
<213> ORGANISM: ARTIFICIAL SEQUENCE
<220> FEATURE:
<223> OTHER INFORMATION: Made in Lab - antibody fragments

<400> SEQUENCE: 27

```
gaggtgcagc tgttggagag cggggggaggc ttggtacagc ctgggggggtc cctgcgcctc     60

tcctgtgcag ccagcggatt caccttttct tacggttcta tgtactgggt ccgccaggct    120

ccagggaagg ggctggagtg ggtctcatct atttcttctg gttctggttc tacatactat    180

gcagactccg tgaagggccg gttcaccatc tcccgtgaca attccaagaa cacgctgtat    240

ctgcaaatga acagcctgcg tgccgaggac acggctgtat attattgtgc gcgctcttct    300

tactacggtt cttactactc tattgactat tggggccagg gaaccctggt caccgtctcc    360

tca                                                                  363
```

<210> SEQ ID NO 28
<211> LENGTH: 121
<212> TYPE: PRT
<213> ORGANISM: Artificial Sequence
<220> FEATURE:
<223> OTHER INFORMATION: Made in Lab - antibody fragments

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60
```

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Ser Tyr Tyr Gly Ser Tyr Tyr Ser Ile Asp Tyr Trp Gly
100 105 110

Gln Gly Thr Leu Val Thr Val Ser Ser
115 120

<210> SEQ ID NO 29
<211> LENGTH: 24
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 29
ggcttcacat tcagcagcta tgct 24

<210> SEQ ID NO 30
<211> LENGTH: 8
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 30

Gly Phe Thr Phe Ser Ser Tyr Ala
1 5

<210> SEQ ID NO 31
<211> LENGTH: 24
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 31
atctccggca gcggcggaag cacc 24

<210> SEQ ID NO 32
<211> LENGTH: 8
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 32

Ile Ser Gly Ser Gly Gly Ser Thr
1 5

<210> SEQ ID NO 33
<211> LENGTH: 42
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 33
gccaggtact atggcggcta ctactccgcc tggatggact ac 42

<210> SEQ ID NO 34
<211> LENGTH: 14
<212> TYPE: PRT

<213> ORGANISM: ARTIFICIAL SEQUENCE
<220> FEATURE:
<223> OTHER INFORMATION: Made in Lab - antibody fragment

<400> SEQUENCE: 34

Ala Arg Tyr Tyr Gly Gly Tyr Tyr Ser Ala Trp Met Asp Tyr
1 5 10

<210> SEQ ID NO 35
<211> LENGTH: 27
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 35
cagcagacct atggctacct gcacacc 27

<210> SEQ ID NO 36
<211> LENGTH: 9
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 36

Gln Gln Thr Tyr Gly Tyr Leu His Thr
1 5

<210> SEQ ID NO 37
<211> LENGTH: 363
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 37
gaagtgcagc tgctggagtc cggaggagga ctggtgcagc ctggcggaag cctgaggctg 60
agctgcgctg cctccggctt cacattcagc agctatgcta tgagctgggt gaggcaagcc 120
cctggaaagg gcctggagtg ggtgtccgct atctccggca gcggcggaag cacctactac 180
gctgactccg tcaagggcag gttcaccatc agccgggaca acagcaagaa caccctgtac 240
ctgcagatga atagcctcag ggctgaagac accgctgtgt actactgcgc caggtactat 300
ggcggctact actccgcctg gatggactac tggggacagg gcacactggt gaccgtgtcc 360
agc 363

<210> SEQ ID NO 38
<211> LENGTH: 121
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 38

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120


<210> SEQ ID NO 39
<211> LENGTH: 321
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 39

gatattcaga tgacacagtc ccctagctcc ctgtccgcca gcgtgggaga tcgggtgacc      60

atcacctgca gggccagcca gtccatctcc agctatttaa actggtacca gcagaagcct     120

ggaaaggctc ccaagctgct gatctacgcc gcttccagcc tccagagcgg cgtgcctagc     180

aggttctccg gctccggaag cggaacagac ttcaccctga ccatcagctc cctgcagccc     240

gaggactccg ctacctacta ctgccagcag acctatggct acctgcacac cttcggccag     300

ggcacaaagc tggagatcaa g                                               321


<210> SEQ ID NO 40
<211> LENGTH: 107
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105


<210> SEQ ID NO 41
<211> LENGTH: 18
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 41

cagtccatct ccagcttc                                                    18
```

<210> SEQ ID NO 42
<211> LENGTH: 6
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 42

Gln Ser Ile Ser Ser Phe
1 5

<210> SEQ ID NO 43
<211> LENGTH: 321
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 43
gatattcaga tgacacagtc ccctagctcc ctgtccgcca gcgtgggaga tcgggtgacc 60
atcacctgca gggccagcca gtccatctcc agcttcttaa actggtacca gcagaagcct 120
ggaaaggctc ccaagctgct gatctacgcc gcttccagcc tccagagcgg cgtgcctagc 180
aggttctccg gctccggaag cggaacagac ttcaccctga ccatcagctc cctgcagccc 240
gaggactccg ctacctacta ctgccagcag acctatggct acctgcacac cttcggccag 300
ggcacaaagc tggagatcaa g 321

<210> SEQ ID NO 44
<211> LENGTH: 107
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 44

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Phe
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ser Ala Thr Tyr Tyr Cys Gln Gln Thr Tyr Gly Tyr Leu His
85 90 95

Thr Phe Gly Gln Gly Thr Lys Leu Glu Ile Lys
100 105

<210> SEQ ID NO 45
<211> LENGTH: 363
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 45
gaagtgcagc tgctggagtc cggaggagga ctggtgcagc ctggcggaag cctgaggctg 60
agctgcgctg cctccggctt cacattcagc agctatgcta tgagctgggt gaggcaagcc 120

-continued

```
cctggaaagt gcctggagtg ggtgtccgct atctccggca gcggcggaag cacctactac    180

gctgactccg tcaagggcag gttcaccatc agccgggaca acagcaagaa caccctgtac    240

ctgcagatga atagcctcag ggctgaagac accgctgtgt actactgcgc caggtactat    300

ggcggctact actccgcctg gatggactac tggggacagg gcacactggt gaccgtgtcc    360

agc                                                                  363
```

<210> SEQ ID NO 46
<211> LENGTH: 121
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 46

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120
```

<210> SEQ ID NO 47
<211> LENGTH: 321
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 47

```
gatattcaga tgacacagtc ccctagctcc ctgtccgcca gcgtgggaga tcgggtgacc     60

atcacctgca gggccagcca gtccatctcc agcttcttaa actggtacca gcagaagcct    120

ggaaaggctc ccaagctgct gatctacgcc gcttccagcc tccagagcgg cgtgcctagc    180

aggttctccg gctccggaag cggaacagac ttcaccctga ccatcagctc cctgcagccc    240

gaggactccg ctacctacta ctgccagcag acctatggct acctgcacac cttcggctgc    300

ggcacaaagc tggagatcaa g                                              321
```

<210> SEQ ID NO 48
<211> LENGTH: 107
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 48

```
Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Thr Tyr Gly Tyr Leu His
                85                  90                  95

Thr Phe Gly Cys Gly Thr Lys Leu Glu Ile Lys
            100                 105


<210> SEQ ID NO 49
<211> LENGTH: 321
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 49

gatattcaga tgacacagtc ccctagctcc ctgtccgcca gcgtgggaga tcgggtgacc      60

atcacctgca gggccagcca gtccatctcc agcttcttaa actggtacca gcagaagcct     120

ggaaaggctc ccaagctgct gatctacgcc gcttccagcc tccagagcgg cgtgcctagc     180

aggttctccg gctccggaag cggaacagac ttcaccctga ccatcagctc cctgcagccc     240

gaggacttcg ctacctacta ctgccagcag acctatggct acctgcacac cttcggctgc     300

ggcacaaagc tggagatcaa g                                               321


<210> SEQ ID NO 50
<211> LENGTH: 107
<212> TYPE: PRT
<213> ORGANISM: Artificial Sequence
<220> FEATURE:
<223> OTHER INFORMATION: Made in Lab - antibody fragment

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Cys Gly Thr Lys Leu Glu Ile Lys
            100                 105


<210> SEQ ID NO 51
<211> LENGTH: 24
<212> TYPE: DNA
<213> ORGANISM: ARTIFICIAL SEQUENCE
<220> FEATURE:
<223> OTHER INFORMATION: Made in Lab - antibody fragment
```

<400> SEQUENCE: 51
ggcttcgact tcgagagcta tgct 24

<210> SEQ ID NO 52
<211> LENGTH: 8
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 52

Gly Phe Asp Phe Glu Ser Tyr Ala
1 5

<210> SEQ ID NO 53
<211> LENGTH: 18
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 53
cagtccatca ggagcgcc 18

<210> SEQ ID NO 54
<211> LENGTH: 6
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 54

Gln Ser Ile Arg Ser Ala
1 5

<210> SEQ ID NO 55
<211> LENGTH: 363
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 55
gaagtgcagc tgctggagtc cggaggagga ctggtgcagc ctggcggaag cctgaggctg 60
agctgcgctg cctccggctt cgacttcgag agctatgcta tgagctgggt gaggcaagcc 120
cctggaaagt gcctggagtg ggtgtccgct atctccggca gcggcggaag cacctactac 180
gctgactccg tcaagggcag gttcaccatc agccgggaca acagcaagaa caccctgtac 240
ctgcagatga atagcctcag ggctgaagac accgctgtgt actactgcgc caggtactat 300
ggcggctact actccgcctg gatggactac tggggacagg gcacactggt gaccgtgtcc 360
agc 363

<210> SEQ ID NO 56
<211> LENGTH: 121
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 56

Glu Val Gln Leu Leu Glu Ser Gly Gly Gly Leu Val Gln Pro Gly Gly
1 5 10 15

```
Ser Leu Arg Leu Ser Cys Ala Ala Ser Gly Phe Asp Phe Glu Ser Tyr
            20                  25                  30

Ala Met Ser Trp Val Arg Gln Ala Pro Gly Lys Cys Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120
```

<210> SEQ ID NO 57
<211> LENGTH: 321
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 57

```
gatattcaga tgacacagtc ccctagctcc ctgtccgcca gcgtgggaga tcgggtgacc      60

atcacctgca gggccagcca gtccatcagg agcgccctga actggtacca gcagaagcct     120

ggaaaggctc ccaagctgct gatctacgcc gcttccagcc tccagagcgg cgtgcctagc     180

aggttctccg gctccggaag cggaacagac ttcaccctga ccatcagctc cctgcagccc     240

gaggacttcg ctacctacta ctgccagcag acctatggct acctgcacac cttcggctgc     300

ggcacaaagc tggagatcaa g                                               321
```

<210> SEQ ID NO 58
<211> LENGTH: 107
<212> TYPE: PRT
<213> ORGANISM: ARTIFICIAL SEQUENCE
<220> FEATURE:
<223> OTHER INFORMATION: Made in Lab - antibody fragment

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Ala
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Cys Gly Thr Lys Leu Glu Ile Lys
            100                 105
```

<210> SEQ ID NO 59
<211> LENGTH: 24
<212> TYPE: DNA
<213> ORGANISM: ARTIFICIAL SEQUENCE

<220> FEATURE:
<223> OTHER INFORMATION: Made in Lab - antibody fragment

<400> SEQUENCE: 59
ggcttcgact tcgacagcta tgct 24

<210> SEQ ID NO 60
<211> LENGTH: 8
<212> TYPE: PRT
<213> ORGANISM: Artificial Sequence
<220> FEATURE:
<223> OTHER INFORMATION: Made in Lab - antibody fragment

<400> SEQUENCE: 60

Gly Phe Asp Phe Asp Ser Tyr Ala
1 5

<210> SEQ ID NO 61
<211> LENGTH: 24
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 61
atctccggca ggggcggaag cacc 24

<210> SEQ ID NO 62
<211> LENGTH: 8
<212> TYPE: PRT
<213> ORGANISM: Artificial Sequence
<220> FEATURE:
<223> OTHER INFORMATION: Made in Lab - antibody fragment

<400> SEQUENCE: 62

Ile Ser Gly Arg Gly Gly Ser Thr
1 5

<210> SEQ ID NO 63
<211> LENGTH: 363
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 63
gaagtgcagc tgctggagtc cggaggagga ctggtgcagc ctggcggaag cctgaggctg 60
agctgcgctg cctccggctt cgacttcgac agctatgcta tgagctgggt gaggcaagcc 120
cctggaaagt gcctggagtg ggtgtccgct atctccggca ggggcggaag cacctactac 180
gctgactccg tcaagggcag gttcaccatc agccgggaca acagcaagaa caccctgtac 240
ctgcagatga atagcctcag ggctgaagac accgctgtgt actactgcgc caggtactat 300
ggcggctact actccgcctg gatggactac tggggacagg gcacactggt gaccgtgtcc 360
agc 363

<210> SEQ ID NO 64
<211> LENGTH: 121
<212> TYPE: PRT
<213> ORGANISM: Artificial Sequence
<220> FEATURE:
<223> OTHER INFORMATION: Made in Lab - antibody fragment

<400> SEQUENCE: 64

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Ala Met Ser Trp Val Arg Gln Ala Pro Gly Lys Cys Leu Glu Trp Val
        35                  40                  45

Ser Ala Ile Ser Gly Arg Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120
```

<210> SEQ ID NO 65
<211> LENGTH: 321
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 65

```
gacatccaga tgacccagtc tccatcctcc ctgagcgcat ctgtaggaga ccgcgtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

cgtttcagtg gcagtggaag cgggacagat ttcactctca ccatcagcag tctgcaacct    240

gaagattttg caacttatta ctgtcaacag acttacggtt acctgcacac ttttggctgt    300

gggaccaggc tggagatcaa a                                              321
```

<210> SEQ ID NO 66
<211> LENGTH: 107
<212> TYPE: PRT
<213> ORGANISM: Artificial Sequence
<220> FEATURE:
<223> OTHER INFORMATION: Made in Lab - antibody fragment

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Cys Gly Thr Arg Leu Glu Ile Lys
            100                 105
```

<210> SEQ ID NO 67

<211> LENGTH: 321
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 67

```
gacatccaga tgacccagtc tccatcctcc ctgagcgcat ctgtaggaga ccgcgtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

cgtttcagtg gcagtggaag cgggacagat ttcactctca ccatcagcag tctgcaacct    240

gaagattttg caacttatta ctgtcaacag acttacggtt acctgcacac ttttggccag    300

gggaccaagc tggagatcaa a                                              321
```

<210> SEQ ID NO 68
<211> LENGTH: 107
<212> TYPE: PRT
<213> ORGANISM: Artificial Sequence
<220> FEATURE:
<223> OTHER INFORMATION: Made in Lab - antibody fragment

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105
```

<210> SEQ ID NO 69
<211> LENGTH: 321
<212> TYPE: DNA
<213> ORGANISM: ARTIFICIAL SEQUENCE
<220> FEATURE:
<223> OTHER INFORMATION: Made in Lab - antibody fragment

<400> SEQUENCE: 69

```
gacatccaga tgacccagtc tccatcctcc ctgagcgcat ctgtaggaga ccgcgtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

cgtttcagtg gcagtggaag cgggacagat ttcactctca ccatcagcag tctgcaacct    240

gaagattttg caacttatta ctgtcaacag acttacggtt acctgcacac ttttggctgc    300

gggaccaagc tggagatcaa a                                              321
```

<210> SEQ ID NO 70
<211> LENGTH: 107
<212> TYPE: PRT
<213> ORGANISM: Artificial Sequence
<220> FEATURE:

<223> OTHER INFORMATION: Made in Lab - antibody fragment

<400> SEQUENCE: 70

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Tyr Gly Tyr Leu His
85 90 95

Thr Phe Gly Cys Gly Thr Lys Leu Glu Ile Lys
100 105

<210> SEQ ID NO 71
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 71

Glu Pro Lys Ser Ser Asp Lys Thr His Thr Ser Pro Pro Ser Ser
1 5 10 15

<210> SEQ ID NO 72
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 72

Glu Pro Lys Ser Cys Asp Lys Thr His Thr Ser Pro Pro Cys Ser
1 5 10 15

<210> SEQ ID NO 73
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 73

Glu Pro Lys Ser Ser Asp Lys Thr His Thr Ser Pro Pro Cys Ser
1 5 10 15

<210> SEQ ID NO 74
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 74

Glu Pro Lys Ser Ser Asp Lys Thr His Thr Cys Pro Pro Cys Ser
1 5 10 15

<210> SEQ ID NO 75

<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 75

Glu Pro Lys Ser Cys Asp Lys Thr His Thr Ser Pro Pro Ser Ser
1 5 10 15

<210> SEQ ID NO 76
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 76

Glu Pro Lys Ser Ser Asp Lys Thr His Thr Cys Pro Pro Ser Ser
1 5 10 15

<210> SEQ ID NO 77
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 77

Glu Pro Lys Ser Cys Asp Lys Thr His Thr Ser Pro Pro Cys Ser
1 5 10 15

<210> SEQ ID NO 78
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 78

Glu Pro Lys Ser Cys Asp Lys Thr His Thr Ser Pro Pro Cys Pro
1 5 10 15

<210> SEQ ID NO 79
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 79

Glu Pro Lys Ser Ser Asp Lys Thr His Thr Ser Pro Pro Ser Pro
1 5 10 15

<210> SEQ ID NO 80
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 80

Glu Pro Lys Ser Cys Asp Lys Thr His Thr Ser Pro Pro Cys Pro
1 5 10 15

<210> SEQ ID NO 81
<211> LENGTH: 15

<212> TYPE: PRT
<213> ORGANISM: Artificial Sequence
<220> FEATURE:
<223> OTHER INFORMATION: Made in Lab - Hinge/Linker sequence

<400> SEQUENCE: 81

Glu Pro Lys Ser Ser Asp Lys Thr His Thr Ser Pro Pro Cys Pro
1 5 10 15

<210> SEQ ID NO 82
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 82

Glu Pro Lys Ser Ser Asp Lys Thr His Thr Cys Pro Pro Cys Pro
1 5 10 15

<210> SEQ ID NO 83
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 83

Glu Pro Lys Ser Cys Asp Lys Thr His Thr Ser Pro Pro Ser Pro
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 84

Glu Pro Lys Ser Ser Asp Lys Thr His Thr Cys Pro Pro Ser Pro
1 5 10 15

<210> SEQ ID NO 85
<211> LENGTH: 6
<212> TYPE: PRT
<213> ORGANISM: Artificial Sequence
<220> FEATURE:
<223> OTHER INFORMATION: Made in Lab - Hinge/Linker sequence

<400> SEQUENCE: 85

Ser Cys Pro Pro Cys Pro
1 5

<210> SEQ ID NO 86
<211> LENGTH: 20
<212> TYPE: PRT
<213> ORGANISM: Artificial Sequence
<220> FEATURE:
<223> OTHER INFORMATION: Made in Lab - Hinge/Linker sequence

<400> SEQUENCE: 86

Asn Tyr Gly Gly Gly Gly Ser Gly Gly Gly Gly Ser Gly Gly Gly Gly
1 5 10 15

Ser Gly Asn Ser
20

<210> SEQ ID NO 87
<211> LENGTH: 38
<212> TYPE: PRT
<213> ORGANISM: Artificial Sequence
<220> FEATURE:
<223> OTHER INFORMATION: Made in Lab - Hinge/Linker sequence

<400> SEQUENCE: 87

Asn Tyr Gly Gly Gly Gly Ser Gly Gly Gly Gly Ser Gly Gly Gly Gly
1               5                   10                  15

Ser Gly Asn Tyr Gly Gly Gly Gly Ser Gly Gly Gly Gly Ser Gly Gly
            20                  25                  30

Gly Gly Ser Gly Asn Ser
        35

<210> SEQ ID NO 88
<211> LENGTH: 2
<212> TYPE: PRT
<213> ORGANISM: Artificial Sequence
<220> FEATURE:
<223> OTHER INFORMATION: Made in Lab - Hinge/Linker sequence

<400> SEQUENCE: 88

Asn Ser
1

<210> SEQ ID NO 89
<211> LENGTH: 8
<212> TYPE: PRT
<213> ORGANISM: Artificial Sequence
<220> FEATURE:
<223> OTHER INFORMATION: Made in Lab - Hinge/Linker sequence

<400> SEQUENCE: 89

Gly Gly Gly Gly Ser Gly Asn Ser
1               5

<210> SEQ ID NO 90
<211> LENGTH: 10
<212> TYPE: PRT
<213> ORGANISM: Artificial Sequence
<220> FEATURE:
<223> OTHER INFORMATION: Made in Lab - Hinge/Linker sequence

<400> SEQUENCE: 90

Asn Tyr Gly Gly Gly Gly Ser Gly Asn Ser
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Made in Lab - Hinge/Linker sequence

<400> SEQUENCE: 91

Gly Gly Gly Gly Ser Gly Gly Gly Gly Ser Gly Asn Ser
1               5                   10

<210> SEQ ID NO 92
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 92

Asn Tyr Gly Gly Gly Gly Ser Gly Gly Gly Gly Ser Gly Asn Ser
1 5 10 15

<210> SEQ ID NO 93
<211> LENGTH: 18
<212> TYPE: PRT
<213> ORGANISM: Artificial Sequence
<220> FEATURE:
<223> OTHER INFORMATION: Made in Lab - Hinge/Linker sequence

<400> SEQUENCE: 93

Gly Gly Gly Gly Ser Gly Gly Gly Gly Ser Gly Gly Gly Gly Ser Gly
1 5 10 15

Asn Ser

<210> SEQ ID NO 94
<211> LENGTH: 8
<212> TYPE: PRT
<213> ORGANISM: Artificial Sequence
<220> FEATURE:
<223> OTHER INFORMATION: Made in Lab - Hinge/Linker sequence

<400> SEQUENCE: 94

Gly Cys Pro Pro Cys Pro Asn Ser
1 5

<210> SEQ ID NO 95
<211> LENGTH: 5
<212> TYPE: PRT
<213> ORGANISM: Artificial Sequence
<220> FEATURE:
<223> OTHER INFORMATION: Made in Lab - Hinge/Linker sequence

<400> SEQUENCE: 95

Gly Gly Gly Gly Ser
1 5

<210> SEQ ID NO 96
<211> LENGTH: 15
<212> TYPE: PRT
<213> ORGANISM: Artificial Sequence
<220> FEATURE:
<223> OTHER INFORMATION: Made in Lab - Hinge/Linker sequence

<400> SEQUENCE: 96

Gly Gly Gly Gly Ser Gly Gly Gly Gly Ser Gly Gly Gly Gly Ser
1 5 10 15

<210> SEQ ID NO 97
<211> LENGTH: 16
<212> TYPE: PRT
<213> ORGANISM: Artificial Sequence
<220> FEATURE:
<223> OTHER INFORMATION: Made in Lab - Hinge/Linker sequence

<400> SEQUENCE: 97

Ser Gly Gly Gly Gly Ser Gly Gly Gly Gly Ser Gly Gly Gly Gly Ser
1 5 10 15

<210> SEQ ID NO 98
<211> LENGTH: 20
<212> TYPE: PRT
<213> ORGANISM: Artificial Sequence
<220> FEATURE:
<223> OTHER INFORMATION: Made in Lab - Hinge/Linker sequence

<400> SEQUENCE: 98

Gly Gly Gly Gly Ser Gly Gly Gly Gly Ser Gly Gly Gly Gly Ser Gly
1 5 10 15

Gly Gly Gly Ser
20

<210> SEQ ID NO 99
<211> LENGTH: 21
<212> TYPE: PRT
<213> ORGANISM: Artificial Sequence
<220> FEATURE:
<223> OTHER INFORMATION: Made in Lab - Hinge/Linker sequence

<400> SEQUENCE: 99

Gln Arg His Asn Asn Ser Ser Leu Asn Thr Gly Thr Gln Met Ala Gly
1 5 10 15

His Ser Pro Asn Ser
20

<210> SEQ ID NO 100
<211> LENGTH: 16
<212> TYPE: PRT
<213> ORGANISM: Artificial Sequence
<220> FEATURE:
<223> OTHER INFORMATION: Made in Lab - Hinge/Linker sequence

<400> SEQUENCE: 100

Ser Ser Leu Asn Thr Gly Thr Gln Met Ala Gly His Ser Pro Asn Ser
1 5 10 15

<210> SEQ ID NO 101
<211> LENGTH: 18
<212> TYPE: PRT
<213> ORGANISM: Artificial Sequence
<220> FEATURE:
<223> OTHER INFORMATION: Made in Lab - Hinge/Linker sequence

<400> SEQUENCE: 101

Gln Arg His Asn Asn Ser Ser Leu Asn Thr Gly Thr Gln Met Ala Gly
1 5 10 15

His Ser

<210> SEQ ID NO 102
<211> LENGTH: 14
<212> TYPE: PRT
<213> ORGANISM: Artificial Sequence
<220> FEATURE:
<223> OTHER INFORMATION: Made in Lab - Hinge/Linker sequence

<400> SEQUENCE: 102

Glu Val Gln Ile Pro Leu Thr Glu Ser Tyr Ser Pro Asn Ser
1 5 10

<210> SEQ ID NO 103
<211> LENGTH: 20
<212> TYPE: PRT
<213> ORGANISM: Artificial Sequence
<220> FEATURE:
<223> OTHER INFORMATION: Made in Lab - Hinge/Linker sequence

<400> SEQUENCE: 103

Asn Ser Leu Ala Asn Gln Glu Val Gln Ile Pro Leu Thr Glu Ser Tyr
1 5 10 15

Ser Pro Asn Ser

20

<210> SEQ ID NO 104
<211> LENGTH: 19
<212> TYPE: PRT
<213> ORGANISM: Artificial Sequence
<220> FEATURE:
<223> OTHER INFORMATION: Made in Lab - Hinge/Linker sequence

<400> SEQUENCE: 104

Ser Gly Gly Gly Gly Ser Gly Gly Gly Gly Ser Gly Gly Gly Gly Ser
1 5 10 15

Pro Asn Ser

<210> SEQ ID NO 105
<211> LENGTH: 19
<212> TYPE: PRT
<213> ORGANISM: Artificial Sequence
<220> FEATURE:
<223> OTHER INFORMATION: Made in Lab - Hinge/Linker sequence

<400> SEQUENCE: 105

Ser Gly Gly Gly Gly Ser Gly Gly Gly Gly Ser Gly Gly Gly Gly Ser
1 5 10 15

Pro Gly Ser

<210> SEQ ID NO 106
<211> LENGTH: 19
<212> TYPE: PRT
<213> ORGANISM: Artificial Sequence
<220> FEATURE:
<223> OTHER INFORMATION: Made in Lab - Hinge/Linker sequence

<400> SEQUENCE: 106

Ser Gly Gly Gly Gly Ser Gly Gly Gly Gly Ser Gly Gly Gly Gly Ser
1 5 10 15

Pro Ala Ser

<210> SEQ ID NO 107
<211> LENGTH: 18
<212> TYPE: PRT
<213> ORGANISM: Artificial Sequence
<220> FEATURE:
<223> OTHER INFORMATION: Made in Lab - Hinge/Linker sequence

<400> SEQUENCE: 107

Ser Gly Gly Gly Gly Ser Gly Gly Gly Gly Ser Gly Gly Gly Gly Ser
1 5 10 15

Pro Ser

<210> SEQ ID NO 108
<211> LENGTH: 19
<212> TYPE: PRT
<213> ORGANISM: Artificial Sequence
<220> FEATURE:
<223> OTHER INFORMATION: Made in Lab - Hinge/Linker sequence

<400> SEQUENCE: 108

Ser Gly Gly Gly Gly Ser Gly Gly Gly Gly Ser Gly Gly Gly Gly Ser
1 5 10 15

Pro Ser Ser

<210> SEQ ID NO 109

<211> LENGTH: 744
<212> TYPE: DNA
<213> ORGANISM: Artificial Sequence
<220> FEATURE:
<223> OTHER INFORMATION: Made in Lab - Synthesized scFv sequence

<400> SEQUENCE: 109

```
gaggtgcagc tgttggagag cgggggaggc ttggtacagc ctggggggtc cctgcgcctc     60

tcctgtgcag ccagcggatt caccttttct cacggttcta tgtactgggt ccgccaggct    120

ccagggaagg ggctggagtg ggtctcatct atttcttctg gttctggttc tacatactat    180

gcagactccg tgaagggccg gttcaccatc tcccatgaca attccaagaa cacgctgtat    240

ctgcaaatga acagcctgcg tgccgaggac acggctgtat attattgtgc gcgctcttct    300

tactacggtt cttactactc tattgactat tggggccagg gaaccctggt caccgtctcc    360

tcaggtggag gtggctccgg gggtggaggt tccggaggag gcggatcagg tggaggcgga    420

agcgacatcc agatgaccca gtctccatcc tccctgagcg catctgtagg agaccgcgtc    480

accatcactt gccgggcaag tcagagcatt agcagctatt taaattggta tcagcagaaa    540

ccagggaaag cccctaagct cctgatctat gctgcatcca gtttgcaaag tggggtccca    600

tcacgtttca gtggcagtgg aagcgggaca gatttcactc tcaccatcag cagtctacaa    660

cctgaagatt ttgcaactta ttactgtcaa cagtactacg acaacctgcc cacttttggc    720

caggggacca agctggagat caaa                                           744
```

<210> SEQ ID NO 110
<211> LENGTH: 248
<212> TYPE: PRT
<213> ORGANISM: Artificial Sequence
<220> FEATURE:
<223> OTHER INFORMATION: Made in Lab - Synthesized scFv sequence

<400> SEQUENCE: 110

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser His Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190
```

```
Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Tyr Tyr Asp Asn Leu Pro Thr Phe Gly
225                 230                 235                 240

Gln Gly Thr Lys Leu Glu Ile Lys
                245


<210> SEQ ID NO 111
<211> LENGTH: 744
<212> TYPE: DNA
<213> ORGANISM: Artificial Sequence
<220> FEATURE:
<223> OTHER INFORMATION: Made in Lab - Synthesized scFv sequence

<400> SEQUENCE: 111

gaggtgcagc tgttggagag cgggggaggc ttggtacagc ctggggggtc cctgcgcctc      60

tcctgtgcag ccagcggatt cacctttgat tacggttcta tgtactgggt ccgccaggct     120

ccagggaagg ggctggagtg ggtctcatct atttcttctg gttctggttc tacatactat     180

gcagactccg tgaagggccg gttcaccatc tcccacgaca attccaagaa cacgctgtat     240

ctgcaaatga acagcctgcg tgccgaggac acggctgtat attattgtgc gcgctcttct     300

tactacggtt cttactactc tattgactat tggggccagg gaaccctggt caccgtctcc     360

tcaggtggag gtggctccgg gggtggaggt tccggaggag gcggatcagg tggaggcgga     420

agcgacatcc agatgaccca gtctccatcc tccctgagcg catctgtagg agaccgcgtc     480

accatcactt gccgggcaag tcagagcatt agcagctatt taaattggta tcagcagaaa     540

ccagggaaag cccctaagct cctgatctat gctgcatcca gtttgcacag tggggtccca     600

tcacgtttca gtggcagtgg aagcgggaca gatttcactc tcaccatcag cagtctgcaa     660

cctgaagatt ttgcaactta ttactgtcaa cagtactacg acaacctgcc cacttttggc     720

caggggacca agctggagat caaa                                            744


<210> SEQ ID NO 112
<211> LENGTH: 248
<212> TYPE: PRT
<213> ORGANISM: Artificial Sequence
<220> FEATURE:
<223> OTHER INFORMATION: Made in Lab - Synthesized scFv sequence

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser His Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110
```

Gln Gly Thr Leu Val Thr Val Ser Ser Gly Gly Gly Gly Ser Gly Gly
115 120 125

Gly Gly Ser Gly Gly Gly Gly Ser Gly Gly Gly Gly Ser Asp Ile Gln
130 135 140

Met Thr Gln Ser Pro Ser Ser Leu Ser Ala Ser Val Gly Asp Arg Val
145 150 155 160

Thr Ile Thr Cys Arg Ala Ser Gln Ser Ile Ser Ser Tyr Leu Asn Trp
165 170 175

Tyr Gln Gln Lys Pro Gly Lys Ala Pro Lys Leu Leu Ile Tyr Ala Ala
180 185 190

Ser Ser Leu His Ser Gly Val Pro Ser Arg Phe Ser Gly Ser Gly Ser
195 200 205

Gly Thr Asp Phe Thr Leu Thr Ile Ser Ser Leu Gln Pro Glu Asp Phe
210 215 220

Ala Thr Tyr Tyr Cys Gln Gln Tyr Tyr Asp Asn Leu Pro Thr Phe Gly
225 230 235 240

Gln Gly Thr Lys Leu Glu Ile Lys
245

<210> SEQ ID NO 113
<211> LENGTH: 744
<212> TYPE: DNA
<213> ORGANISM: Artificial Sequence
<220> FEATURE:
<223> OTHER INFORMATION: Made in Lab - Synthesized scFv sequence

<400> SEQUENCE: 113
gaggtgcagc tgttggagag cgggggaggc ttggtacagc ctgggggtc cctgcgcctc 60 tcctgtgcag ccagcggatt caccttttct tacggttcta tgtactgggt ccgccaggct 120
ccagggaagg ggctggagtg ggtctcatct atttcttctg gttctggttc tacatactat 180
gcagactccg tgaagggccg gttcaccatc tcccatgaca attccaagaa cacgctgtat 240
ctgcaaatga acagcctgcg tgccgaggac acggctgtat attattgtgc gcgctcttct 300
tactacggtt cttactactc tattgactat tggggccagg gaaccctggt caccgtctcc 360
tcaggtggag gtggctccgg gggtggaggt tccggaggag gcggatcagg tggaggcgga 420
agcgacatcc agatgaccca gtctccatcc tccctgagcg catctgtagg agaccgcgtc 480
accatcactt gccgggcaag tcagagcatt agcagctatt taaattggta tcagcagaaa 540
ccagggaaag cccctaagct cctgatctat gctgcatcca gtttgcaaag tggggtccca 600
tcacgtttca gtggcagtgg aagcgggaca gatttcactc tcaccatcag cagtctacaa 660
cctgaagatt ttgcaactta ttactgtcaa cagtactacg acaacctgcc cacttttggc 720
caggggacca agctggagat caaa 744

<210> SEQ ID NO 114
<211> LENGTH: 248
<212> TYPE: PRT
<213> ORGANISM: Artificial Sequence
<220> FEATURE:
<223> OTHER INFORMATION: Made in Lab - Synthesized scFv sequence

<400> SEQUENCE: 114

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Tyr Gly
20 25 30

```
Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser His Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Tyr Tyr Asp Asn Leu Pro Thr Phe Gly
225                 230                 235                 240

Gln Gly Thr Lys Leu Glu Ile Lys
                245
```

<210> SEQ ID NO 115
<211> LENGTH: 744
<212> TYPE: DNA
<213> ORGANISM: Artificial Sequence
<220> FEATURE:
<223> OTHER INFORMATION: Made in Lab - Synthesized scFv sequence

<400> SEQUENCE: 115

```
gaggtgcagc tgttggagag cgggggaggc ttggtacagc ctgggggtc cctgcgcctc      60

tcctgtgcag ccagcggatt caccttttct tacggttcta tgtactgggt ccgccaggct    120

ccagggaagg ggctggagtg ggtctcatct atttcttctg gttctggttc tacatactat    180

gcagactccg tgaagggccg gttcaccatc tcccgtgaca attccaagaa cacgctgtat    240

ctgcaaatga acagcctgcg tgccgaggac acggctgtat attattgtgc gcgctcttct    300

tactacggtt cttactactc tattgactat tggggccagg gaaccctggt caccgtctcc    360

tcaggcggcg gcggcagcgg cggcggcggc agcggcggcg gaggctccgg cggcggcggc    420

agcgacatcc agatgaccca gtctccatcc tccctgagcg catctgtagg agaccgcgtc    480

accatcactt gccgggcaag tcagagcatt agcagctatt taaattggta tcagcagaaa    540

ccagggaaag cccctaagct cctgatctat gctgcatcca gtttgcaaag tggggtccca    600

tcacgtttca gtggcagtgg aagcgggaca gatttcactc tcaccatcag cagtctgcaa    660

cctgaagatt ttgcaactta ttactgtcaa cagtactacg acaacctgcc cacttttggc    720

caggggacca agctggagat caaa                                           744
```

<210> SEQ ID NO 116
<211> LENGTH: 248
<212> TYPE: PRT
<213> ORGANISM: Artificial Sequence
<220> FEATURE:
<223> OTHER INFORMATION: Made in Lab - Synthesized scFv sequence

<400> SEQUENCE: 116

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Tyr Tyr Asp Asn Leu Pro Thr Phe Gly
225                 230                 235                 240

Gln Gly Thr Lys Leu Glu Ile Lys
                245
```

<210> SEQ ID NO 117
<211> LENGTH: 744
<212> TYPE: DNA
<213> ORGANISM: ARTIFICIAL SEQUENCE
<220> FEATURE:
<223> OTHER INFORMATION: Made in Lab - Synthesized scFv sequence

<400> SEQUENCE: 117

```
gaagtgcagc tgctggagtc cggaggagga ctggtgcagc ctggcggaag cctgaggctg      60

agctgcgctg cctccggctt cacattcagc agctatgcta tgagctgggt gaggcaagcc     120

cctggaaagg gcctggagtg ggtgtccgct atctccggca gcggcggaag cacctactac     180

gctgactccg tcaagggcag gttcaccatc agccgggaca acagcaagaa caccctgtac     240

ctgcagatga atagcctcag ggctgaagac accgctgtgt actactgcgc caggtactat     300

ggcggctact actccgcctg gatggactac tggggacagg gcacactggt gaccgtgtcc     360
```

```
agcggcggag gcggctccgg aggcggtggc tccggaggag gcggaagcgg aggaggaggc    420

tccgatattc agatgacaca gtcccctagc tccctgtccg ccagcgtggg agatcgggtg    480

accatcacct gcagggccag ccagtccatc tccagctatt taaactggta ccagcagaag    540

cctggaaagg ctcccaagct gctgatctac gccgcttcca gcctccagag cggcgtgcct    600

agcaggttct ccggctccgg aagcggaaca gacttcaccc tgaccatcag ctccctgcag    660

cccgaggact ccgctaccta ctactgccag cagacctatg gctacctgca caccttcggc    720

cagggcacaa agctggagat caag                                           744
```

<210> SEQ ID NO 118
<211> LENGTH: 248
<212> TYPE: PRT
<213> ORGANISM: ARTIFICIAL SEQUENCE
<220> FEATURE:
<223> OTHER INFORMATION: Made in Lab - Synthesized scFv sequence

<400> SEQUENCE: 118

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Ser
    210                 215                 220

Ala Thr Tyr Tyr Cys Gln Gln Thr Tyr Gly Tyr Leu His Thr Phe Gly
225                 230                 235                 240

Gln Gly Thr Lys Leu Glu Ile Lys
                245
```

<210> SEQ ID NO 119
<211> LENGTH: 744
<212> TYPE: DNA
<213> ORGANISM: ARTIFICIAL SEQUENCE
<220> FEATURE:

<223> OTHER INFORMATION: Made in Lab - Synthesized scFv sequence

<400> SEQUENCE: 119

```
gaagtgcagc tgctggagtc cggaggagga ctggtgcagc ctggcggaag cctgaggctg      60
agctgcgctg cctccggctt cacattcagc agctatgcta tgagctgggt gaggcaagcc     120
cctggaaagg gcctggagtg ggtgtccgct atctccggca gcggcggaag cacctactac     180
gctgactccg tcaagggcag gttcaccatc agccgggaca acagcaagaa caccctgtac     240
ctgcagatga atagcctcag ggctgaagac accgctgtgt actactgcgc caggtactat     300
ggcggctact actccgcctg gatggactac tggggacagg gcacactggt gaccgtgtcc     360
agcggcggag gcggctccgg aggcggtggc tccggaggag gcggaagcgg aggaggaggc     420
tccgatattc agatgacaca gtcccctagc tccctgtccg ccagcgtggg agatcgggtg     480
accatcacct gcagggccag ccagtccatc tccagcttct taaactggta ccagcagaag     540
cctggaaagg ctcccaagct gctgatctac gccgcttcca gcctccagag cggcgtgcct     600
agcaggttct ccggctccgg aagcggaaca gacttcaccc tgaccatcag ctccctgcag     660
cccgaggact ccgctaccta ctactgccag cagacctatg gctacctgca caccttcggc     720
cagggcacaa agctggagat caag                                            744
```

<210> SEQ ID NO 120
<211> LENGTH: 248
<212> TYPE: PRT
<213> ORGANISM: ARTIFICIAL SEQUENCE
<220> FEATURE:
<223> OTHER INFORMATION: Made in Lab - Synthesized scFv sequence

<400> SEQUENCE: 120

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Phe Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205
```

```
Gly Thr Asp Phe Thr Leu Thr Ile Ser Ser Leu Gln Pro Glu Asp Ser
    210                 215                 220

Ala Thr Tyr Tyr Cys Gln Gln Thr Tyr Gly Tyr Leu His Thr Phe Gly
225                 230                 235                 240

Gln Gly Thr Lys Leu Glu Ile Lys
                245


<210> SEQ ID NO 121
<211> LENGTH: 744
<212> TYPE: DNA
<213> ORGANISM: ARTIFICIAL SEQUENCE
<220> FEATURE:
<223> OTHER INFORMATION: Made in Lab - Synthesized scFv sequence

<400> SEQUENCE: 121

gaagtgcagc tgctggagtc cggaggagga ctggtgcagc ctggcggaag cctgaggctg      60

agctgcgctg cctccggctt cacattcagc agctatgcta tgagctgggt gaggcaagcc     120

cctggaaagt gcctggagtg ggtgtccgct atctccggca gcggcggaag cacctactac     180

gctgactccg tcaagggcag gttcaccatc agccgggaca acagcaagaa caccctgtac     240

ctgcagatga atagcctcag ggctgaagac accgctgtgt actactgcgc caggtactat     300

ggcggctact actccgcctg gatggactac tggggacagg gcacactggt gaccgtgtcc     360

agcggcggag gcggctccgg aggcggtggc tccggaggag gcggaagcgg aggaggaggc     420

tccgatattc agatgacaca gtcccctagc tccctgtccg ccagcgtggg agatcgggtg     480

accatcacct gcagggccag ccagtccatc tccagcttct taaactggta ccagcagaag     540

cctggaaagg ctcccaagct gctgatctac gccgcttcca gcctccagag cggcgtgcct     600

agcaggttct ccggctccgg aagcggaaca gacttcaccc tgaccatcag ctccctgcag     660

cccgaggact ccgctaccta ctactgccag cagacctatg gctacctgca caccttcggc     720

tgcggcacaa agctggagat caag                                            744


<210> SEQ ID NO 122
<211> LENGTH: 248
<212> TYPE: PRT
<213> ORGANISM: ARTIFICIAL SEQUENCE
<220> FEATURE:
<223> OTHER INFORMATION: Made in Lab - Synthesized scFv sequence

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser Gly Gly Gly Gly Ser Gly Gly
        115                 120                 125
```

```
Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Phe Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Ser
    210                 215                 220

Ala Thr Tyr Tyr Cys Gln Gln Thr Tyr Gly Tyr Leu His Thr Phe Gly
225                 230                 235                 240

Cys Gly Thr Lys Leu Glu Ile Lys
                245


<210> SEQ ID NO 123
<211> LENGTH: 744
<212> TYPE: DNA
<213> ORGANISM: ARTIFICIAL SEQUENCE
<220> FEATURE:
<223> OTHER INFORMATION: Made in Lab - Synthesized scFv sequence

<400> SEQUENCE: 123

gaagtgcagc tgctggagtc cggaggagga ctggtgcagc ctggcggaag cctgaggctg     60

agctgcgctg cctccggctt cacattcagc agctatgcta tgagctgggt gaggcaagcc    120

cctggaaagt gcctggagtg ggtgtccgct atctccggca gcggcggaag cacctactac    180

gctgactccg tcaagggcag gttcaccatc agccgggaca acagcaagaa caccctgtac    240

ctgcagatga atagcctcag ggctgaagac accgctgtgt actactgcgc caggtactat    300

ggcggctact actccgcctg gatggactac tggggacagg gcacactggt gaccgtgtcc    360

agcggcggag gcggctccgg aggcggtggc tccggaggag gcggaagcgg aggaggaggc    420

tccgatattc agatgacaca gtcccctagc tccctgtccg ccagcgtggg agatcgggtg    480

accatcacct gcagggccag ccagtccatc tccagcttct taaactggta ccagcagaag    540

cctggaaagg ctcccaagct gctgatctac gccgcttcca gcctccagag cggcgtgcct    600

agcaggttct ccggctccgg aagcggaaca gacttcaccc tgaccatcag ctccctgcag    660

cccgaggact tcgctaccta ctactgccag cagacctatg gctacctgca caccttcggc    720

tgcggcacaa agctggagat caag                                           744


<210> SEQ ID NO 124
<211> LENGTH: 248
<212> TYPE: PRT
<213> ORGANISM: ARTIFICIAL SEQUENCE
<220> FEATURE:
<223> OTHER INFORMATION: Made in Lab - Synthesized scFv sequence

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Phe Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Thr Tyr Gly Tyr Leu His Thr Phe Gly
225                 230                 235                 240

Cys Gly Thr Lys Leu Glu Ile Lys
                245
```

<210> SEQ ID NO 125
<211> LENGTH: 744
<212> TYPE: DNA
<213> ORGANISM: ARTIFICIAL SEQUENCE
<220> FEATURE:
<223> OTHER INFORMATION: Made in Lab - Synthesized scFv sequence

<400> SEQUENCE: 125

```
gaagtgcagc tgctggagtc cggaggagga ctggtgcagc ctggcggaag cctgaggctg      60

agctgcgctg cctccggctt cgacttcgag agctatgcta tgagctgggt gaggcaagcc     120

cctggaaagt gcctggagtg ggtgtccgct atctccggca gcggcggaag cacctactac     180

gctgactccg tcaagggcag gttcaccatc agccgggaca acagcaagaa caccctgtac     240

ctgcagatga atagcctcag ggctgaagac accgctgtgt actactgcgc caggtactat     300

ggcggctact actccgcctg gatggactac tggggacagg gcacactggt gaccgtgtcc     360

agcggcggag gcggctccgg aggcggtggc tccggaggag gcggaagcgg aggaggaggc     420

tccgatattc agatgacaca gtcccctagc tccctgtccg ccagcgtggg agatcgggtg     480

accatcacct gcagggccag ccagtccatc aggagcgccc tgaactggta ccagcagaag     540

cctggaaagg ctcccaagct gctgatctac gccgcttcca gcctccagag cggcgtgcct     600

agcaggttct ccggctccgg aagcggaaca gacttcaccc tgaccatcag ctccctgcag     660

cccgaggact tcgctaccta ctactgccag cagacctatg gctacctgca caccttcggc     720

tgcggcacaa agctggagat caag                                           744
```

<210> SEQ ID NO 126
<211> LENGTH: 248
<212> TYPE: PRT

<213> ORGANISM: ARTIFICIAL SEQUENCE
<220> FEATURE:
<223> OTHER INFORMATION: Made in Lab - Synthesized scFv sequence

<400> SEQUENCE: 126

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Glu Ser Tyr
            20                  25                  30

Ala Met Ser Trp Val Arg Gln Ala Pro Gly Lys Cys Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Arg Ser Ala Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Thr Tyr Gly Tyr Leu His Thr Phe Gly
225                 230                 235                 240

Cys Gly Thr Lys Leu Glu Ile Lys
                245
```

<210> SEQ ID NO 127
<211> LENGTH: 744
<212> TYPE: DNA
<213> ORGANISM: ARTIFICIAL SEQUENCE
<220> FEATURE:
<223> OTHER INFORMATION: Made in Lab - Synthesized scFv sequence

<400> SEQUENCE: 127

```
gaagtgcagc tgctggagtc cggaggagga ctggtgcagc ctggcggaag cctgaggctg      60

agctgcgctg cctccggctt cgacttcgac agctatgcta tgagctgggt gaggcaagcc     120

cctggaaagt gcctggagtg ggtgtccgct atctccggca ggggcggaag cacctactac     180

gctgactccg tcaagggcag gttcaccatc agccgggaca acagcaagaa caccctgtac     240

ctgcagatga atagcctcag ggctgaagac accgctgtgt actactgcgc caggtactat     300

ggcggctact actccgcctg gatggactac tggggacagg gcacactggt gaccgtgtcc     360

agcggcggag gcggctccgg aggcggtggc tccggaggag gcggaagcgg aggaggaggc     420

tccgatattc agatgacaca gtcccctagc tccctgtccg ccagcgtggg agatcgggtg     480
```

```
accatcacct gcagggccag ccagtccatc aggagcgccc tgaactggta ccagcagaag    540

cctggaaagg ctcccaagct gctgatctac gccgcttcca gcctccagag cggcgtgcct    600

agcaggttct ccggctccgg aagcggaaca gacttcaccc tgaccatcag ctccctgcag    660

cccgaggact tcgctaccta ctactgccag cagacctatg gctacctgca caccttcggc    720

tgcggcacaa agctggagat caag                                           744
```

<210> SEQ ID NO 128
<211> LENGTH: 248
<212> TYPE: PRT
<213> ORGANISM: ARTIFICIAL SEQUENCE
<220> FEATURE:
<223> OTHER INFORMATION: Made in Lab - Synthesized scFv sequence

<400> SEQUENCE: 128

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Ala Met Ser Trp Val Arg Gln Ala Pro Gly Lys Cys Leu Glu Trp Val
        35                  40                  45

Ser Ala Ile Ser Gly Arg Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Arg Ser Ala Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Thr Tyr Gly Tyr Leu His Thr Phe Gly
225                 230                 235                 240

Cys Gly Thr Lys Leu Glu Ile Lys
                245
```

<210> SEQ ID NO 129
<211> LENGTH: 744
<212> TYPE: DNA
<213> ORGANISM: ARTIFICIAL SEQUENCE
<220> FEATURE:
<223> OTHER INFORMATION: Made in Lab - Synthesized scFv sequence

<400> SEQUENCE: 129

-continued

```
gaggtgcagc tgttggagag cgggggaggc ttggtacagc ctgggggtc cctgcgcctc      60

tcctgtgcag ccagcggatt cacctttagc agctatgcca tgagctgggt ccgccaggct    120

ccagggaagg ggctggagtg ggtctcagct attagtggta gtggtggtag cacatactat    180

gcagactccg tgaagggccg gttcaccatc tcccgtgaca attccaagaa cacgctgtat    240

ctgcaaatga acagcctgcg tgccgaggac acggctgtat attattgtgc gcgctactac    300

ggtggttact actctgcttg gatggactat tggggccagg gaaccctggt caccgtctcc    360

tcaggcggtg gaggcagcgg tgggggtggg tctggaggcg gtggcagtgg cggcggaggc    420

tctgacatcc agatgaccca gtctccatcc tccctgagcg catctgtagg agaccgcgtc    480

accatcactt gccgggcaag tcagagcatt agcagctatt taaattggta tcagcagaaa    540

ccagggaaag cccctaagct cctgatctat gctgcatcca gtttgcaaag tggggtccca    600

tcacgtttca gtggcagtgg aagcgggaca gatttcactc tcaccatcag cagtctgcaa    660

cctgaagatt ttgcaactta ttactgtcaa cagacttacg gttacctgca cacttttggc    720

caggggacca agctggagat caaa                                            744
```

<210> SEQ ID NO 130
<211> LENGTH: 248
<212> TYPE: PRT
<213> ORGANISM: ARTIFICIAL SEQUENCE
<220> FEATURE:
<223> OTHER INFORMATION: Made in Lab - Synthesized scFv sequence

<400> SEQUENCE: 130

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Thr Tyr Gly Tyr Leu His Thr Phe Gly
```

-continued

```
225                 230                 235                 240

Gln Gly Thr Lys Leu Glu Ile Lys
                245


<210> SEQ ID NO 131
<211> LENGTH: 744
<212> TYPE: DNA
<213> ORGANISM: ARTIFICIAL SEQUENCE
<220> FEATURE:
<223> OTHER INFORMATION: Made in Lab - Synthesized scFv sequence

<400> SEQUENCE: 131

gaggtgcagc tgttggagag cgggggaggc ttggtacagc ctggggggtc cctgcgcctc      60

tcctgtgcag ccagcggatt cacctttagc agctatgcca tgagctgggt ccgccaggct     120

ccagggaagt gcctggagtg ggtctcagct attagtggta gtggtggtag cacatactat     180

gcagactccg tgaagggccg gttcaccatc tcccgtgaca attccaagaa cacgctgtat     240

ctgcaaatga acagcctgcg tgccgaggac acggctgtat attattgtgc gcgctactac     300

ggtggttact actctgcttg gatggactat tggggccagg gaaccctggt caccgtctcc     360

tcaggcggtg gaggcagcgg tgggggtggg tctggaggcg gtggcagtgg cggcggaggc     420

tctgacatcc agatgaccca gtctccatcc tccctgagcg catctgtagg agaccgcgtc     480

accatcactt gccgggcaag tcagagcatt agcagctatt taaattggta tcagcagaaa     540

ccagggaaag cccctaagct cctgatctat gctgcatcca gtttgcaaag tggggtccca     600

tcacgtttca gtggcagtgg aagcgggaca gatttcactc tcaccatcag cagtctgcaa     660

cctgaagatt ttgcaactta ttactgtcaa cagacttacg gttacctgca cacttttggc     720

tgcgggacca agctggagat caaa                                            744


<210> SEQ ID NO 132
<211> LENGTH: 248
<212> TYPE: PRT
<213> ORGANISM: ARTIFICIAL SEQUENCE
<220> FEATURE:
<223> OTHER INFORMATION: Made in Lab - Synthesized scFv sequence

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
```

```
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Thr Tyr Gly Tyr Leu His Thr Phe Gly
225                 230                 235                 240

Cys Gly Thr Lys Leu Glu Ile Lys
                245


<210> SEQ ID NO 133
<211> LENGTH: 744
<212> TYPE: DNA
<213> ORGANISM: ARTIFICIAL SEQUENCE
<220> FEATURE:
<223> OTHER INFORMATION: Made in Lab - Synthesized scFv sequence

<400> SEQUENCE: 133

gacatccaga tgacccagtc tccatcctcc ctgagcgcat ctgtaggaga ccgcgtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

cgtttcagtg gcagtggaag cgggacagat ttcactctca ccatcagcag tctgcaacct    240

gaagattttg caacttatta ctgtcaacag acttacggtt acctgcacac ttttggctgc    300

gggaccaagc tggagatcaa aggcggtgga ggcagcggtg gggtgggtc tggaggcggt    360

ggcagtggcg gcggaggctc tgaggtgcag ctgttggaga gcgggggagg cttggtacag    420

cctggggggt ccctgcgcct ctcctgtgca gccagcggat tcacctttag cagctatgcc    480

atgagctggg tccgccaggc tccagggaag tgcctggagt gggtctcagc tattagtggt    540

agtggtggta gcacatacta tgcagactcc gtgaagggcc ggttcaccat ctcccgtgac    600

aattccaaga acacgctgta tctgcaaatg aacagcctgc gtgccgagga cacggctgta    660

tattattgtg cgcgctacta cggtggttac tactctgctt ggatggacta ttggggccag    720

ggaaccctgg tcaccgtctc ctca                                           744


<210> SEQ ID NO 134
<211> LENGTH: 248
<212> TYPE: PRT
<213> ORGANISM: ARTIFICIAL SEQUENCE
<220> FEATURE:
<223> OTHER INFORMATION: Made in Lab - Synthesized scFv sequence

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Thr Tyr Gly Tyr Leu His
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Leu Glu Ser Gly Gly Gly Leu Val Gln Pro Gly Gly Ser
    130                 135                 140

Leu Arg Leu Ser Cys Ala Ala Ser Gly Phe Thr Phe Ser Ser Tyr Ala
145                 150                 155                 160

Met Ser Trp Val Arg Gln Ala Pro Gly Lys Cys Leu Glu Trp Val Ser
                165                 170                 175

Ala Ile Ser Gly Ser Gly Gly Ser Thr Tyr Tyr Ala Asp Ser Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Arg Tyr Tyr Gly Gly Tyr Tyr Ser Ala Trp Met Asp Tyr Trp Gly Gln
225                 230                 235                 240

Gly Thr Leu Val Thr Val Ser Ser
                245
```

```
<210> SEQ ID NO 135
<211> LENGTH: 2304
<212> TYPE: DNA
<213> ORGANISM: Artificial Sequence
<220> FEATURE:
<223> OTHER INFORMATION: Made in Lab - anti-5T4 x anti-4-1BB
      polynucleotide construct

<400> SEQUENCE: 135

atggaagcac cagcgcagct tctcttcctc ctgctactct ggctcccaga taccaccggt     60

gaggtgcagc tgttggagag cgggggaggc ttggtacagc ctgggggtc cctgcgcctc    120

tcctgtgcag ccagcggatt cacctttct cacggttcta tgtactgggt ccgccaggct    180

ccagggaagg ggctggagtg ggtctcatct atttcttctg gttctggttc tacatactat    240

gcagactccg tgaagggccg gttcaccatc tcccatgaca attccaagaa cacgctgtat    300

ctgcaaatga acagcctgcg tgccgaggac acggctgtat attattgtgc gcgctcttct    360

tactacggtt cttactactc tattgactat tggggccagg gaaccctggt caccgtctcc    420

tcaggtggag gtggctccgg gggtggaggt tccggaggag gcggatcagg tggaggcgga    480

agcgacatcc agatgaccca gtctccatcc tccctgagcg catctgtagg agaccgcgtc    540

accatcactt gccgggcaag tcagagcatt agcagctatt taaattggta tcagcagaaa    600

ccagggaaag cccctaagct cctgatctat gctgcatcca gtttgcaaag tggggtccca    660

tcacgtttca gtggcagtgg aagcgggaca gatttcactc tcaccatcag cagtctacaa    720

cctgaagatt ttgcaactta ttactgtcaa cagtactacg acaacctgcc cacttttggc    780

caggggacca agctggagat caaatcgagt gagcccaaat cttctgacaa aactcacaca    840

tgcccaccgt gcccagcacc tgaagccgcg ggtgcaccgt cagtcttcct cttcccccca    900

aaacccaagg acaccctcat gatctcccgg acccctgagg tcacatgcgt ggtggtggac    960

gtgagccacg aagaccctga ggtcaagttc aactggtacg tggacggcgt ggaggtgcat   1020
```

```
aatgccaaga caaagccgcg ggaggagcag tacaacagca cgtaccgtgt ggtcagcgtc   1080

ctcaccgtcc tgcaccagga ctggctgaat ggcaaggaat acaagtgcgc ggtctccaac   1140

aaagccctcc cagcccccat cgagaaaacc atctccaaag ccaaagggca gccccgagaa   1200

ccacaggtgt acaccctgcc cccatcccgg gatgagctga ccaagaacca ggtcagcctg   1260

acctgcctgg tcaaaggctt ctatccaagc gacatcgccg tggagtggga gagcaatggg   1320

cagccggaga acaactacaa gaccacgcct cccgtgctgg actccgacgg ctccttcttc   1380

ctctacagca agctcaccgt ggacaagagc aggtggcagc aggggaacgt cttctcatgc   1440

tccgtgatgc atgaggctct gcacaaccac tacacgcaga agagcctctc cctgtctccg   1500

ggttccggag gtggcggttc gggaggtggc gggtcaggag gtgggggatc cccttcagaa   1560

gtgcagctgc tggagtccgg aggaggactg gtgcagcctg gcggaagcct gaggctgagc   1620

tgcgctgcct ccggcttcac attcagcagc tatgctatga gctgggtgag gcaagcccct   1680

ggaaagggcc tggagtgggt gtccgctatc tccggcagcg gcggaagcac ctactacgct   1740

gactccgtca agggcaggtt caccatcagc cgggacaaca gcaagaacac cctgtacctg   1800

cagatgaata gcctcagggc tgaagacacc gctgtgtact actgcgccag gtactatggc   1860

ggctactact ccgcctggat ggactactgg ggacagggca cactggtgac cgtgtccagc   1920

ggcggaggcg gctccggagg cggtggctcc ggaggaggcg gaagcggagg aggaggctcc   1980

gatattcaga tgacacagtc ccctagctcc ctgtccgcca gcgtgggaga tcgggtgacc   2040

atcacctgca gggccagcca gtccatctcc agctatttaa actggtacca gcagaagcct   2100

ggaaaggctc ccaagctgct gatctacgcc gcttccagcc tccagagcgg cgtgcctagc   2160

aggttctccg gctccggaag cggaacagac ttcaccctga ccatcagctc cctgcagccc   2220

gaggactccg ctacctacta ctgccagcag acctatggct acctgcacac cttcggccag   2280

ggcacaaagc tggagatcaa gcgc                                          2304
```

```
<210> SEQ ID NO 136
<211> LENGTH: 768
<212> TYPE: PRT
<213> ORGANISM: Artificial Sequence
<220> FEATURE:
<223> OTHER INFORMATION: Made in Lab - anti-5T4 x anti-4-1BB polypeptide
      construct

<400> SEQUENCE: 136

Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser His Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser His Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125
```

-continued

```
Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Ser Ser Glu Pro
            260                 265                 270

Lys Ser Ser Asp Lys Thr His Thr Cys Pro Pro Cys Pro Ala Pro Glu
        275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Ala Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Ser Gly Gly Gly Gly Ser Gly Gly Gly Gly Ser
            500                 505                 510

Gly Gly Gly Gly Ser Pro Ser Glu Val Gln Leu Leu Glu Ser Gly Gly
        515                 520                 525

Gly Leu Val Gln Pro Gly Gly Ser Leu Arg Leu Ser Cys Ala Ala Ser
    530                 535                 540
```

-continued

```
Gly Phe Thr Phe Ser Ser Tyr Ala Met Ser Trp Val Arg Gln Ala Pro
545                 550                 555                 560

Gly Lys Gly Leu Glu Trp Val Ser Ala Ile Ser Gly Ser Gly Gly Ser
                565                 570                 575

Thr Tyr Tyr Ala Asp Ser Val Lys Gly Arg Phe Thr Ile Ser Arg Asp
            580                 585                 590

Asn Ser Lys Asn Thr Leu Tyr Leu Gln Met Asn Ser Leu Arg Ala Glu
        595                 600                 605

Asp Thr Ala Val Tyr Tyr Cys Ala Arg Tyr Tyr Gly Gly Tyr Tyr Ser
    610                 615                 620

Ala Trp Met Asp Tyr Trp Gly Gln Gly Thr Leu Val Thr Val Ser Ser
625                 630                 635                 640

Gly Gly Gly Gly Ser Gly Gly Gly Gly Ser Gly Gly Gly Gly Ser Gly
                645                 650                 655

Gly Gly Gly Ser Asp Ile Gln Met Thr Gln Ser Pro Ser Ser Leu Ser
            660                 665                 670

Ala Ser Val Gly Asp Arg Val Thr Ile Thr Cys Arg Ala Ser Gln Ser
        675                 680                 685

Ile Ser Ser Tyr Leu Asn Trp Tyr Gln Gln Lys Pro Gly Lys Ala Pro
    690                 695                 700

Lys Leu Leu Ile Tyr Ala Ala Ser Ser Leu Gln Ser Gly Val Pro Ser
705                 710                 715                 720

Arg Phe Ser Gly Ser Gly Ser Gly Thr Asp Phe Thr Leu Thr Ile Ser
                725                 730                 735

Ser Leu Gln Pro Glu Asp Ser Ala Thr Tyr Tyr Cys Gln Gln Thr Tyr
            740                 745                 750

Gly Tyr Leu His Thr Phe Gly Gln Gly Thr Lys Leu Glu Ile Lys Arg
        755                 760                 765
```

<210> SEQ ID NO 137
<211> LENGTH: 2304
<212> TYPE: DNA
<213> ORGANISM: Artificial Sequence
<220> FEATURE:
<223> OTHER INFORMATION: Made in Lab - anti-5T4 x anti-4-1BB
polynucleotide construct

<400> SEQUENCE: 137

```
atggaagcac cagcgcagct tctcttcctc ctgctactct ggctcccaga taccaccggt     60

gaggtgcagc tgttggagag cgggggaggc ttggtacagc ctggggggtc cctgcgcctc    120

tcctgtgcag ccagcggatt caccttttct cacggttcta tgtactgggt ccgccaggct    180

ccagggaagg ggctggagtg ggtctcatct atttcttctg gttctggttc tacatactat    240

gcagactccg tgaagggccg gttcaccatc tcccatgaca attccaagaa cacgctgtat    300

ctgcaaatga acagcctgcg tgccgaggac acggctgtat attattgtgc gcgctcttct    360

tactacggtt cttactactc tattgactat tggggccagg gaaccctggt caccgtctcc    420

tcaggtggag gtggctccgg gggtggaggt tccggaggag gcggatcagg tggaggcgga    480

agcgacatcc agatgaccca gtctccatcc tccctgagcg catctgtagg agaccgcgtc    540

accatcactt gccgggcaag tcagagcatt agcagctatt taaattggta tcagcagaaa    600

ccagggaaag cccctaagct cctgatctat gctgcatcca gtttgcaaag tggggtccca    660

tcacgtttca gtggcagtgg aagcgggaca gatttcactc tcaccatcag cagtctacaa    720

cctgaagatt ttgcaactta ttactgtcaa cagtactacg acaacctgcc cacttttggc    780
```

-continued

```
caggggacca agctggagat caaatcgagt gagcccaaat cttctgacaa aactcacaca    840

tgcccaccgt gcccagcacc tgaagccgcg ggtgcaccgt cagtcttcct cttcccccca    900

aaacccaagg acaccctcat gatctcccgg acccctgagg tcacatgcgt ggtggtggac    960

gtgagccacg aagaccctga ggtcaagttc aactggtacg tggacggcgt ggaggtgcat   1020

aatgccaaga caaagccgcg ggaggagcag tacaacagca cgtaccgtgt ggtcagcgtc   1080

ctcaccgtcc tgcaccagga ctggctgaat ggcaaggaat acaagtgcgc ggtctccaac   1140

aaagccctcc cagcccccat cgagaaaacc atctccaaag ccaaagggca gccccgagaa   1200

ccacaggtgt acaccctgcc cccatcccgg gatgagctga ccaagaacca ggtcagcctg   1260

acctgcctgg tcaaaggctt ctatccaagc gacatcgccg tggagtggga gagcaatggg   1320

cagccggaga acaactacaa gaccacgcct cccgtgctgg actccgacgg ctccttcttc   1380

ctctacagca agctcaccgt ggacaagagc aggtggcagc aggggaacgt cttctcatgc   1440

tccgtgatgc atgaggctct gcacaaccac tacacgcaga agagcctctc cctgtctccg   1500

ggttccggag gtggcggttc gggaggtggc gggtcaggag gtgggggatc cccttcagaa   1560

gtgcagctgc tggagtccgg aggaggactg gtgcagcctg gcggaagcct gaggctgagc   1620

tgcgctgcct ccggcttcac attcagcagc tatgctatga gctgggtgag gcaagcccct   1680

ggaaagggcc tggagtgggt gtccgctatc tccggcagcg gcggaagcac ctactacgct   1740

gactccgtca agggcaggtt caccatcagc cgggacaaca gcaagaacac cctgtacctg   1800

cagatgaata gcctcagggc tgaagacacc gctgtgtact actgcgccag gtactatggc   1860

ggctactact ccgcctggat ggactactgg ggacagggca cactggtgac cgtgtccagc   1920

ggcggaggcg gctccggagg cggtggctcc ggaggaggcg gaagcggagg aggaggctcc   1980

gatattcaga tgacacagtc ccctagctcc ctgtccgcca gcgtgggaga tcgggtgacc   2040

atcacctgca gggccagcca gtccatctcc agcttcttaa actggtacca gcagaagcct   2100

ggaaaggctc ccaagctgct gatctacgcc gcttccagcc tccagagcgg cgtgcctagc   2160

aggttctccg gctccggaag cggaacagac ttcaccctga ccatcagctc cctgcagccc   2220

gaggactccg ctacctacta ctgccagcag acctatggct acctgcacac cttcggccag   2280

ggcacaaagc tggagatcaa gcgc                                          2304
```

<210> SEQ ID NO 138
<211> LENGTH: 768
<212> TYPE: PRT
<213> ORGANISM: Artificial Sequence
<220> FEATURE:
<223> OTHER INFORMATION: Made in Lab - anti-5T4 x anti-4-1BB polypeptide construct

<400> SEQUENCE: 138

```
Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser His Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser His Asp Asn Ser Lys
```

-continued

```
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Ser Ser Glu Pro
            260                 265                 270

Lys Ser Ser Asp Lys Thr His Thr Cys Pro Pro Cys Pro Ala Pro Glu
        275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Ala Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Ser Gly Gly Gly Gly Ser Gly Gly Gly Gly Ser
            500                 505                 510
```

```
Gly Gly Gly Gly Ser Pro Ser Glu Val Gln Leu Leu Glu Ser Gly Gly
        515                 520                 525

Gly Leu Val Gln Pro Gly Gly Ser Leu Arg Leu Ser Cys Ala Ala Ser
    530                 535                 540

Gly Phe Thr Phe Ser Ser Tyr Ala Met Ser Trp Val Arg Gln Ala Pro
545                 550                 555                 560

Gly Lys Gly Leu Glu Trp Val Ser Ala Ile Ser Gly Ser Gly Gly Ser
            565                 570                 575

Thr Tyr Tyr Ala Asp Ser Val Lys Gly Arg Phe Thr Ile Ser Arg Asp
            580                 585                 590

Asn Ser Lys Asn Thr Leu Tyr Leu Gln Met Asn Ser Leu Arg Ala Glu
        595                 600                 605

Asp Thr Ala Val Tyr Tyr Cys Ala Arg Tyr Tyr Gly Gly Tyr Tyr Ser
    610                 615                 620

Ala Trp Met Asp Tyr Trp Gly Gln Gly Thr Leu Val Thr Val Ser Ser
625                 630                 635                 640

Gly Gly Gly Gly Ser Gly Gly Gly Gly Ser Gly Gly Gly Gly Ser Gly
            645                 650                 655

Gly Gly Gly Ser Asp Ile Gln Met Thr Gln Ser Pro Ser Ser Leu Ser
            660                 665                 670

Ala Ser Val Gly Asp Arg Val Thr Ile Thr Cys Arg Ala Ser Gln Ser
        675                 680                 685

Ile Ser Ser Phe Leu Asn Trp Tyr Gln Gln Lys Pro Gly Lys Ala Pro
    690                 695                 700

Lys Leu Leu Ile Tyr Ala Ala Ser Ser Leu Gln Ser Gly Val Pro Ser
705                 710                 715                 720

Arg Phe Ser Gly Ser Gly Ser Gly Thr Asp Phe Thr Leu Thr Ile Ser
            725                 730                 735

Ser Leu Gln Pro Glu Asp Ser Ala Thr Tyr Tyr Cys Gln Gln Thr Tyr
            740                 745                 750

Gly Tyr Leu His Thr Phe Gly Gln Gly Thr Lys Leu Glu Ile Lys Arg
        755                 760                 765
```

<210> SEQ ID NO 139
<211> LENGTH: 2304
<212> TYPE: DNA
<213> ORGANISM: Artificial Sequence
<220> FEATURE:
<223> OTHER INFORMATION: Made in Lab - anti-5T4 x anti-4-1BB polynucleotide construct

<400> SEQUENCE: 139

```
atggaagcac cagcgcagct tctcttcctc ctgctactct ggctcccaga taccaccggt      60

gaggtgcagc tgttggagag cgggggaggc ttggtacagc ctggggggtc cctgcgcctc     120

tcctgtgcag ccagcggatt caccttttct cacggttcta tgtactgggt ccgccaggct     180

ccagggaagg ggctggagtg ggtctcatct atttcttctg gttctggttc tacatactat     240

gcagactccg tgaagggccg gttcaccatc tcccatgaca attccaagaa cacgctgtat     300

ctgcaaatga acagcctgcg tgccgaggac acggctgtat attattgtgc gcgctcttct     360

tactacggtt cttactactc tattgactat tggggccagg gaaccctggt caccgtctcc     420

tcaggtggag gtggctccgg gggtggaggt tccggaggag gcggatcagg tggaggcgga     480

agcgacatcc agatgaccca gtctccatcc tccctgagcg catctgtagg agaccgcgtc     540

accatcactt gccgggcaag tcagagcatt agcagctatt taaattggta tcagcagaaa     600
```

```
ccagggaaag cccctaagct cctgatctat gctgcatcca gtttgcaaag tggggtccca    660

tcacgtttca gtggcagtgg aagcgggaca gatttcactc tcaccatcag cagtctacaa    720

cctgaagatt ttgcaactta ttactgtcaa cagtactacg acaacctgcc cacttttggc    780

caggggacca agctggagat caaatcgagt gagcccaaat cttctgacaa aactcacaca    840

tgcccaccgt gcccagcacc tgaagccgcg ggtgcaccgt cagtcttcct cttcccccca    900

aaacccaagg acaccctcat gatctcccgg acccctgagg tcacatgcgt ggtggtggac    960

gtgagccacg aagaccctga ggtcaagttc aactggtacg tggacggcgt ggaggtgcat   1020

aatgccaaga caaagccgcg ggaggagcag tacaacagca cgtaccgtgt ggtcagcgtc   1080

ctcaccgtcc tgcaccagga ctggctgaat ggcaaggaat acaagtgcgc ggtctccaac   1140

aaagccctcc cagcccccat cgagaaaacc atctccaaag ccaaagggca gccccgagaa   1200

ccacaggtgt acaccctgcc cccatcccgg gatgagctga ccaagaacca ggtcagcctg   1260

acctgcctgg tcaaaggctt ctatccaagc gacatcgccg tggagtggga gagcaatggg   1320

cagccggaga acaactacaa gaccacgcct cccgtgctgg actccgacgg ctccttcttc   1380

ctctacagca agctcaccgt ggacaagagc aggtggcagc aggggaacgt cttctcatgc   1440

tccgtgatgc atgaggctct gcacaaccac tacacgcaga agagcctctc cctgtctccg   1500

ggttccggag gtggcggttc gggaggtggc gggtcaggag gtgggggatc cccttcagaa   1560

gtgcagctgc tggagtccgg aggaggactg gtgcagcctg gcggaagcct gaggctgagc   1620

tgcgctgcct ccggcttcac attcagcagc tatgctatga gctgggtgag gcaagcccct   1680

ggaaagtgcc tggagtgggt gtccgctatc tccggcagcg gcggaagcac ctactacgct   1740

gactccgtca agggcaggtt caccatcagc cgggacaaca gcaagaacac cctgtacctg   1800

cagatgaata gcctcagggc tgaagacacc gctgtgtact actgcgccag gtactatggc   1860

ggctactact ccgcctggat ggactactgg ggacagggca cactggtgac cgtgtccagc   1920

ggcggaggcg gctccggagg cggtggctcc ggaggaggcg gaagcggagg aggaggctcc   1980

gatattcaga tgacacagtc ccctagctcc ctgtccgcca gcgtgggaga tcgggtgacc   2040

atcacctgca gggccagcca gtccatctcc agcttcttaa actggtacca gcagaagcct   2100

ggaaaggctc ccaagctgct gatctacgcc gcttccagcc tccagagcgg cgtgcctagc   2160

aggttctccg gctccggaag cggaacagac ttcaccctga ccatcagctc cctgcagccc   2220

gaggactccg ctacctacta ctgccagcag acctatggct acctgcacac cttcggctgc   2280

ggcacaaagc tggagatcaa gcgc                                          2304
```

<210> SEQ ID NO 140
<211> LENGTH: 768
<212> TYPE: PRT
<213> ORGANISM: Artificial Sequence
<220> FEATURE:
<223> OTHER INFORMATION: Made in Lab - anti-5T4 x anti-4-1BB polypeptide construct

<400> SEQUENCE: 140

```
Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45
```

```
Phe Ser His Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser His Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Ser Ser Glu Pro
            260                 265                 270

Lys Ser Ser Asp Lys Thr His Thr Cys Pro Pro Cys Pro Ala Pro Glu
        275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Ala Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
```

-continued

```
465                 470                 475                 480

Ser Val Met His Glu Ala Leu His Asn His Tyr Thr Gln Lys Ser Leu
                485                 490                 495

Ser Leu Ser Pro Gly Ser Gly Gly Gly Gly Ser Gly Gly Gly Gly Ser
            500                 505                 510

Gly Gly Gly Gly Ser Pro Ser Glu Val Gln Leu Leu Glu Ser Gly Gly
        515                 520                 525

Gly Leu Val Gln Pro Gly Gly Ser Leu Arg Leu Ser Cys Ala Ala Ser
    530                 535                 540

Gly Phe Thr Phe Ser Ser Tyr Ala Met Ser Trp Val Arg Gln Ala Pro
545                 550                 555                 560

Gly Lys Cys Leu Glu Trp Val Ser Ala Ile Ser Gly Ser Gly Gly Ser
                565                 570                 575

Thr Tyr Tyr Ala Asp Ser Val Lys Gly Arg Phe Thr Ile Ser Arg Asp
            580                 585                 590

Asn Ser Lys Asn Thr Leu Tyr Leu Gln Met Asn Ser Leu Arg Ala Glu
        595                 600                 605

Asp Thr Ala Val Tyr Tyr Cys Ala Arg Tyr Tyr Gly Gly Tyr Tyr Ser
    610                 615                 620

Ala Trp Met Asp Tyr Trp Gly Gln Gly Thr Leu Val Thr Val Ser Ser
625                 630                 635                 640

Gly Gly Gly Gly Ser Gly Gly Gly Gly Ser Gly Gly Gly Gly Ser Gly
                645                 650                 655

Gly Gly Gly Ser Asp Ile Gln Met Thr Gln Ser Pro Ser Ser Leu Ser
            660                 665                 670

Ala Ser Val Gly Asp Arg Val Thr Ile Thr Cys Arg Ala Ser Gln Ser
        675                 680                 685

Ile Ser Ser Phe Leu Asn Trp Tyr Gln Gln Lys Pro Gly Lys Ala Pro
    690                 695                 700

Lys Leu Leu Ile Tyr Ala Ala Ser Ser Leu Gln Ser Gly Val Pro Ser
705                 710                 715                 720

Arg Phe Ser Gly Ser Gly Ser Gly Thr Asp Phe Thr Leu Thr Ile Ser
                725                 730                 735

Ser Leu Gln Pro Glu Asp Ser Ala Thr Tyr Tyr Cys Gln Gln Thr Tyr
            740                 745                 750

Gly Tyr Leu His Thr Phe Gly Cys Gly Thr Lys Leu Glu Ile Lys Arg
        755                 760                 765
```

<210> SEQ ID NO 141
<211> LENGTH: 2304
<212> TYPE: DNA
<213> ORGANISM: Artificial Sequence
<220> FEATURE:
<223> OTHER INFORMATION: Made in Lab - anti-5T4 x anti-4-1BB polynucleotide construct

<400> SEQUENCE: 141

```
atggaagcac cagcgcagct tctcttcctc ctgctactct ggctcccaga taccaccggt     60

gaggtgcagc tgttggagag cgggggaggc ttggtacagc ctgggggtc cctgcgcctc    120

tcctgtgcag ccagcggatt cacctttgat tacggttcta tgtactgggt ccgccaggct    180

ccagggaagg ggctggagtg ggtctcatct atttcttctg gttctggttc tacatactat    240

gcagactccg tgaagggccg gttcaccatc tcccacgaca attccaagaa cacgctgtat    300

ctgcaaatga acagcctgcg tgccgaggac acggctgtat attattgtgc gcgctcttct    360
```

```
tactacggtt cttactactc tattgactat tggggccagg gaaccctggt caccgtctcc    420

tcaggtggag gtggctccgg gggtggaggt tccggaggag gcggatcagg tggaggcgga    480

agcgacatcc agatgaccca gtctccatcc tccctgagcg catctgtagg agaccgcgtc    540

accatcactt gccgggcaag tcagagcatt agcagctatt taaattggta tcagcagaaa    600

ccagggaaag cccctaagct cctgatctat gctgcatcca gtttgcacag tggggtccca    660

tcacgtttca gtggcagtgg aagcgggaca gatttcactc tcaccatcag cagtctgcaa    720

cctgaagatt ttgcaactta ttactgtcaa cagtactacg acaacctgcc cacttttggc    780

caggggacca agctggagat caaatcctcg gagcccaaat cttctgacaa aactcacaca    840

tgcccaccgt gcccagcacc tgaagccgcg ggtgcaccgt cagtcttcct cttcccccca    900

aaacccaagg acaccctcat gatctcccgg acccctgagg tcacatgcgt ggtggtggac    960

gtgagccacg aagaccctga ggtcaagttc aactggtacg tggacggcgt ggaggtgcat   1020

aatgccaaga caaagccgcg ggaggagcag tacaacagca cgtaccgtgt ggtcagcgtc   1080

ctcaccgtcc tgcaccagga ctggctgaat ggcaaggaat acaagtgcgc ggtctccaac   1140

aaagccctcc cagcccccat cgagaaaacc atctccaaag ccaaagggca gccccgagaa   1200

ccacaggtgt acaccctgcc cccatcccgg gatgagctga ccaagaacca ggtcagcctg   1260

acctgcctgg tcaaaggctt ctatccaagc gacatcgccg tggagtggga gagcaatggg   1320

cagccggaga acaactacaa gaccacgcct cccgtgctgg actccgacgg ctccttcttc   1380

ctctacagca agctcaccgt ggacaagagc aggtggcagc aggggaacgt cttctcatgc   1440

tccgtgatgc atgaggctct gcacaaccac tacacgcaga agagcctctc cctgtctccg   1500

ggttccggag gtggcggttc gggaggtggc gggtcaggag gtgggggatc cccttcagaa   1560

gtgcagctgc tggagtccgg aggaggactg gtgcagcctg gcggaagcct gaggctgagc   1620

tgcgctgcct ccggcttcac attcagcagc tatgctatga gctgggtgag gcaagcccct   1680

ggaaagtgcc tggagtgggt gtccgctatc tccggcagcg gcggaagcac ctactacgct   1740

gactccgtca agggcaggtt caccatcagc cgggacaaca gcaagaacac cctgtacctg   1800

cagatgaata gcctcagggc tgaagacacc gctgtgtact actgcgccag gtactatggc   1860

ggctactact ccgcctggat ggactactgg ggacagggca cactggtgac cgtgtccagc   1920

ggcggaggcg gctccggagg cggtggctcc ggaggaggcg gaagcggagg aggaggctcc   1980

gatattcaga tgacacagtc ccctagctcc ctgtccgcca gcgtgggaga tcgggtgacc   2040

atcacctgca gggccagcca gtccatctcc agcttcttaa actggtacca gcagaagcct   2100

ggaaaggctc ccaagctgct gatctacgcc gcttccagcc tccagagcgg cgtgcctagc   2160

aggttctccg gctccggaag cggaacagac ttcaccctga ccatcagctc cctgcagccc   2220

gaggacttcg ctacctacta ctgccagcag acctatggct acctgcacac cttcggctgc   2280

ggcacaaagc tggagatcaa gagc                                          2304
```

<210> SEQ ID NO 142
<211> LENGTH: 768
<212> TYPE: PRT
<213> ORGANISM: Artificial Sequence
<220> FEATURE:
<223> OTHER INFORMATION: Made in Lab - anti-5T4 x anti-4-1BB polypeptide construct

<400> SEQUENCE: 142

```
Met Glu Ala Pro Ala Gln Leu Leu Phe Leu Leu Leu Leu Trp Leu Pro
1               5                   10                  15
```

```
Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Asp Tyr Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser His Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu His Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Ser Ser Glu Pro
            260                 265                 270

Lys Ser Ser Asp Lys Thr His Thr Cys Pro Pro Cys Pro Ala Pro Glu
        275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Ala Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430
```

```
Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Ser Gly Gly Gly Gly Ser Gly Gly Gly Gly Ser
            500                 505                 510

Gly Gly Gly Gly Ser Pro Ser Glu Val Gln Leu Leu Glu Ser Gly Gly
        515                 520                 525

Gly Leu Val Gln Pro Gly Gly Ser Leu Arg Leu Ser Cys Ala Ala Ser
    530                 535                 540

Gly Phe Thr Phe Ser Ser Tyr Ala Met Ser Trp Val Arg Gln Ala Pro
545                 550                 555                 560

Gly Lys Cys Leu Glu Trp Val Ser Ala Ile Ser Gly Ser Gly Gly Ser
                565                 570                 575

Thr Tyr Tyr Ala Asp Ser Val Lys Gly Arg Phe Thr Ile Ser Arg Asp
            580                 585                 590

Asn Ser Lys Asn Thr Leu Tyr Leu Gln Met Asn Ser Leu Arg Ala Glu
        595                 600                 605

Asp Thr Ala Val Tyr Tyr Cys Ala Arg Tyr Tyr Gly Gly Tyr Tyr Ser
    610                 615                 620

Ala Trp Met Asp Tyr Trp Gly Gln Gly Thr Leu Val Thr Val Ser Ser
625                 630                 635                 640

Gly Gly Gly Gly Ser Gly Gly Gly Gly Ser Gly Gly Gly Gly Ser Gly
                645                 650                 655

Gly Gly Gly Ser Asp Ile Gln Met Thr Gln Ser Pro Ser Ser Leu Ser
            660                 665                 670

Ala Ser Val Gly Asp Arg Val Thr Ile Thr Cys Arg Ala Ser Gln Ser
        675                 680                 685

Ile Ser Ser Phe Leu Asn Trp Tyr Gln Gln Lys Pro Gly Lys Ala Pro
    690                 695                 700

Lys Leu Leu Ile Tyr Ala Ala Ser Ser Leu Gln Ser Gly Val Pro Ser
705                 710                 715                 720

Arg Phe Ser Gly Ser Gly Ser Gly Thr Asp Phe Thr Leu Thr Ile Ser
                725                 730                 735

Ser Leu Gln Pro Glu Asp Phe Ala Thr Tyr Tyr Cys Gln Gln Thr Tyr
            740                 745                 750

Gly Tyr Leu His Thr Phe Gly Cys Gly Thr Lys Leu Glu Ile Lys Ser
        755                 760                 765
```

<210> SEQ ID NO 143
<211> LENGTH: 2304
<212> TYPE: DNA
<213> ORGANISM: Artificial Sequence
<220> FEATURE:
<223> OTHER INFORMATION: Made in Lab - anti-5T4 x anti-4-1BB polynucleotide construct

<400> SEQUENCE: 143

```
atggaagcac cagcgcagct tctcttcctc ctgctactct ggctcccaga taccaccggt     60

gaggtgcagc tgttggagag cgggggaggc ttggtacagc ctgggggtc cctgcgcctc    120

tcctgtgcag ccagcggatt caccttttct tacggttcta tgtactgggt ccgccaggct    180
```

```
ccagggaagg ggctggagtg ggtctcatct atttcttctg gttctggttc tacatactat    240
gcagactccg tgaagggccg gttcaccatc tcccatgaca attccaagaa cacgctgtat    300
ctgcaaatga acagcctgcg tgccgaggac acggctgtat attattgtgc gcgctcttct    360
tactacggtt cttactactc tattgactat tggggccagg gaaccctggt caccgtctcc    420
tcaggtggag gtggctccgg gggtggaggt tccggaggag gcggatcagg tggaggcgga    480
agcgacatcc agatgaccca gtctccatcc tccctgagcg catctgtagg agaccgcgtc    540
accatcactt gccgggcaag tcagagcatt agcagctatt taaattggta tcagcagaaa    600
ccagggaaag cccctaagct cctgatctat gctgcatcca gtttgcaaag tggggtccca    660
tcacgtttca gtggcagtgg aagcgggaca gatttcactc tcaccatcag cagtctacaa    720
cctgaagatt ttgcaactta ttactgtcaa cagtactacg acaacctgcc cacttttggc    780
caggggacca agctggagat caaatcctcg gagcccaaat cttctgacaa aactcacaca    840
tgcccaccgt gcccagcacc tgaagccgcg ggtgcaccgt cagtcttcct cttcccccca    900
aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggaat acaagtgcgc ggtctccaac   1140
aaagccctcc cagcccccat cgagaaaacc atctccaaag ccaaagggca gccccgagaa   1200
ccacaggtgt acaccctgcc cccatcccgg gatgagctga ccaagaacca ggtcagcctg   1260
acctgcctgg tcaaaggctt ctatccaagc gacatcgccg tggagtggga gagcaatggg   1320
cagccggaga acaactacaa gaccacgcct cccgtgctgg actccgacgg ctccttcttc   1380
ctctacagca agctcaccgt ggacaagagc aggtggcagc aggggaacgt cttctcatgc   1440
tccgtgatgc atgaggctct gcacaaccac tacacgcaga agagcctctc cctgtctccg   1500
ggttccggag gtggcggttc gggaggtggc gggtcaggag gtgggggatc cccttcagaa   1560
gtgcagctgc tggagtccgg aggaggactg gtgcagcctg gcggaagcct gaggctgagc   1620
tgcgctgcct ccggcttcga cttcgagagc tatgctatga gctgggtgag gcaagcccct   1680
ggaaagtgcc tggagtgggt gtccgctatc tccggcagcg gcggaagcac ctactacgct   1740
gactccgtca agggcaggtt caccatcagc cgggacaaca gcaagaacac cctgtacctg   1800
cagatgaata gcctcagggc tgaagacacc gctgtgtact actgcgccag gtactatggc   1860
ggctactact ccgcctggat ggactactgg ggacagggca cactggtgac cgtgtccagc   1920
ggcggaggcg gctccggagg cggtggctcc ggaggaggcg gaagcggagg aggaggctcc   1980
gatattcaga tgacacagtc ccctagctcc ctgtccgcca gcgtgggaga tcgggtgacc   2040
atcacctgca gggccagcca gtccatcagg agcgccctga actggtacca gcagaagcct   2100
ggaaaggctc ccaagctgct gatctacgcc gcttccagcc tccagagcgg cgtgcctagc   2160
aggttctccg gctccggaag cggaacagac ttcaccctga ccatcagctc cctgcagccc   2220
gaggacttcg ctacctacta ctgccagcag acctatggct acctgcacac cttcggctgc   2280
ggcacaaagc tggagatcaa gcgc                                          2304
```

<210> SEQ ID NO 144
<211> LENGTH: 768
<212> TYPE: PRT
<213> ORGANISM: Artificial Sequence
<220> FEATURE:

<223> OTHER INFORMATION: Made in Lab - anti-5T4 x anti-4-1BB polypeptide construct

<400> SEQUENCE: 144

Met Glu Ala Pro Ala Gln Leu Leu Phe Leu Leu Leu Leu Trp Leu Pro
1 5 10 15

Asp Thr Thr Gly Glu Val Gln Leu Leu Glu Ser Gly Gly Gly Leu Val
20 25 30

Gln Pro Gly Gly Ser Leu Arg Leu Ser Cys Ala Ala Ser Gly Phe Thr
35 40 45

Phe Ser Tyr Gly Ser Met Tyr Trp Val Arg Gln Ala Pro Gly Lys Gly
50 55 60

Leu Glu Trp Val Ser Ser Ile Ser Ser Gly Ser Gly Ser Thr Tyr Tyr
65 70 75 80

Ala Asp Ser Val Lys Gly Arg Phe Thr Ile Ser His Asp Asn Ser Lys
85 90 95

Asn Thr Leu Tyr Leu Gln Met Asn Ser Leu Arg Ala Glu Asp Thr Ala
100 105 110

Val Tyr Tyr Cys Ala Arg Ser Ser Tyr Tyr Gly Ser Tyr Tyr Ser Ile
115 120 125

Asp Tyr Trp Gly Gln Gly Thr Leu Val Thr Val Ser Ser Gly Gly Gly
130 135 140

Gly Ser Gly Gly Gly Gly Ser Gly Gly Gly Gly Ser Gly Gly Gly Gly
145 150 155 160

Ser Asp Ile Gln Met Thr Gln Ser Pro Ser Ser Leu Ser Ala Ser Val
165 170 175

Gly Asp Arg Val Thr Ile Thr Cys Arg Ala Ser Gln Ser Ile Ser Ser
180 185 190

Tyr Leu Asn Trp Tyr Gln Gln Lys Pro Gly Lys Ala Pro Lys Leu Leu
195 200 205

Ile Tyr Ala Ala Ser Ser Leu Gln Ser Gly Val Pro Ser Arg Phe Ser
210 215 220

Gly Ser Gly Ser Gly Thr Asp Phe Thr Leu Thr Ile Ser Ser Leu Gln
225 230 235 240

Pro Glu Asp Phe Ala Thr Tyr Tyr Cys Gln Gln Tyr Tyr Asp Asn Leu
245 250 255

Pro Thr Phe Gly Gln Gly Thr Lys Leu Glu Ile Lys Ser Ser Glu Pro
260 265 270

Lys Ser Ser Asp Lys Thr His Thr Cys Pro Pro Cys Pro Ala Pro Glu
275 280 285

Ala Ala Gly Ala Pro Ser Val Phe Leu Phe Pro Pro Lys Pro Lys Asp
290 295 300

Thr Leu Met Ile Ser Arg Thr Pro Glu Val Thr Cys Val Val Val Asp
305 310 315 320

Val Ser His Glu Asp Pro Glu Val Lys Phe Asn Trp Tyr Val Asp Gly
325 330 335

Val Glu Val His Asn Ala Lys Thr Lys Pro Arg Glu Glu Gln Tyr Asn
340 345 350

Ser Thr Tyr Arg Val Val Ser Val Leu Thr Val Leu His Gln Asp Trp
355 360 365

Leu Asn Gly Lys Glu Tyr Lys Cys Ala Val Ser Asn Lys Ala Leu Pro
370 375 380

Ala Pro Ile Glu Lys Thr Ile Ser Lys Ala Lys Gly Gln Pro Arg Glu
385 390 395 400

Pro Gln Val Tyr Thr Leu Pro Pro Ser Arg Asp Glu Leu Thr Lys Asn
405 410 415

Gln Val Ser Leu Thr Cys Leu Val Lys Gly Phe Tyr Pro Ser Asp Ile
420 425 430

Ala Val Glu Trp Glu Ser Asn Gly Gln Pro Glu Asn Asn Tyr Lys Thr
435 440 445

Thr Pro Pro Val Leu Asp Ser Asp Gly Ser Phe Phe Leu Tyr Ser Lys
450 455 460

Leu Thr Val Asp Lys Ser Arg Trp Gln Gln Gly Asn Val Phe Ser Cys
465 470 475 480

Ser Val Met His Glu Ala Leu His Asn His Tyr Thr Gln Lys Ser Leu
485 490 495

Ser Leu Ser Pro Gly Ser Gly Gly Gly Gly Ser Gly Gly Gly Gly Ser
500 505 510

Gly Gly Gly Gly Ser Pro Ser Glu Val Gln Leu Leu Glu Ser Gly Gly
515 520 525

Gly Leu Val Gln Pro Gly Gly Ser Leu Arg Leu Ser Cys Ala Ala Ser
530 535 540

Gly Phe Asp Phe Glu Ser Tyr Ala Met Ser Trp Val Arg Gln Ala Pro
545 550 555 560

Gly Lys Cys Leu Glu Trp Val Ser Ala Ile Ser Gly Ser Gly Gly Ser
565 570 575

Thr Tyr Tyr Ala Asp Ser Val Lys Gly Arg Phe Thr Ile Ser Arg Asp
580 585 590

Asn Ser Lys Asn Thr Leu Tyr Leu Gln Met Asn Ser Leu Arg Ala Glu
595 600 605

Asp Thr Ala Val Tyr Tyr Cys Ala Arg Tyr Tyr Gly Gly Tyr Tyr Ser
610 615 620

Ala Trp Met Asp Tyr Trp Gly Gln Gly Thr Leu Val Thr Val Ser Ser
625 630 635 640

Gly Gly Gly Gly Ser Gly Gly Gly Gly Ser Gly Gly Gly Gly Ser Gly
645 650 655

Gly Gly Gly Ser Asp Ile Gln Met Thr Gln Ser Pro Ser Ser Leu Ser
660 665 670

Ala Ser Val Gly Asp Arg Val Thr Ile Thr Cys Arg Ala Ser Gln Ser
675 680 685

Ile Arg Ser Ala Leu Asn Trp Tyr Gln Gln Lys Pro Gly Lys Ala Pro
690 695 700

Lys Leu Leu Ile Tyr Ala Ala Ser Ser Leu Gln Ser Gly Val Pro Ser
705 710 715 720

Arg Phe Ser Gly Ser Gly Ser Gly Thr Asp Phe Thr Leu Thr Ile Ser
725 730 735

Ser Leu Gln Pro Glu Asp Phe Ala Thr Tyr Tyr Cys Gln Gln Thr Tyr
740 745 750

Gly Tyr Leu His Thr Phe Gly Cys Gly Thr Lys Leu Glu Ile Lys Arg
755 760 765

<210> SEQ ID NO 145
<211> LENGTH: 2304
<212> TYPE: DNA
<213> ORGANISM: Artificial Sequence
<220> FEATURE:
<223> OTHER INFORMATION: Made in Lab - anti-5T4 x anti-4-1BB
polynucleotide construct

<400> SEQUENCE: 145

```
atggaagcac cagcgcagct tctcttcctc ctgctactct ggctcccaga taccaccggt      60
gaggtgcagc tgttggagag cgggggaggc ttggtacagc ctggggggtc cctgcgcctc     120
tcctgtgcag ccagcggatt caccttttct cacggttcta tgtactgggt ccgccaggct     180
ccagggaagg ggctggagtg ggtctcatct atttcttctg gttctggttc tacatactat     240
gcagactccg tgaagggccg gttcaccatc tcccatgaca attccaagaa cacgctgtat     300
ctgcaaatga acagcctgcg tgccgaggac acggctgtat attattgtgc gcgctcttct     360
tactacggtt cttactactc tattgactat tggggccagg gaaccctggt caccgtctcc     420
tcaggtggag gtggctccgg gggtggaggt tccggaggag gcggatcagg tggaggcgga     480
agcgacatcc agatgaccca gtctccatcc tccctgagcg catctgtagg agaccgcgtc     540
accatcactt gccgggcaag tcagagcatt agcagctatt taaattggta tcagcagaaa     600
ccagggaaag cccctaagct cctgatctat gctgcatcca gtttgcaaag tggggtccca     660
tcacgtttca gtggcagtgg aagcgggaca gatttcactc tcaccatcag cagtctacaa     720
cctgaagatt ttgcaactta ttactgtcaa cagtactacg acaacctgcc cacttttggc     780
caggggacca agctggagat caaatcgagt gagcccaaat cttctgacaa aactcacaca     840
tgcccaccgt gcccagcacc tgaagccgcg ggtgcaccgt cagtcttcct cttcccccca     900
aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagcccccat cgagaaaacc atctccaaag ccaaagggca gccccgagaa    1200
ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga acaactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggttccggag gtggcggttc gggaggtggc gggtcaggag gtgggggatc cccttcagaa    1560
gtgcagctgc tggagtccgg aggaggactg gtgcagcctg gcggaagcct gaggctgagc    1620
tgcgctgcct ccggcttcga cttcgagagc tatgctatga gctgggtgag gcaagcccct    1680
ggaaagtgcc tggagtgggt gtccgctatc tccggcagcg gcggaagcac ctactacgct    1740
gactccgtca agggcaggtt caccatcagc cgggacaaca gcaagaacac cctgtacctg    1800
cagatgaata gcctcagggc tgaagacacc gctgtgtact actgcgccag gtactatggc    1860
ggctactact ccgcctggat ggactactgg ggacagggca cactggtgac cgtgtccagc    1920
ggcggaggcg gctccggagg cggtggctcc ggaggaggcg gaagcggagg aggaggctcc    1980
gatattcaga tgacacagtc ccctagctcc ctgtccgcca gcgtgggaga tcgggtgacc    2040
atcacctgca gggccagcca gtccatcagg agcgccctga actggtacca gcagaagcct    2100
ggaaaggctc ccaagctgct gatctacgcc gcttccagcc tccagagcgg cgtgcctagc    2160
aggttctccg gctccggaag cggaacagac ttcaccctga ccatcagctc cctgcagccc    2220
gaggacttcg ctacctacta ctgccagcag acctatggct acctgcacac cttcggctgc    2280
ggcacaaagc tggagatcaa gcgc                                           2304
```

<210> SEQ ID NO 146
<211> LENGTH: 768
<212> TYPE: PRT
<213> ORGANISM: Artificial Sequence
<220> FEATURE:
<223> OTHER INFORMATION: Made in Lab - anti-5T4 x anti-4-1BB polypeptide construct

<400> SEQUENCE: 146

```
Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser His Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser His Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Ser Ser Glu Pro
            260                 265                 270

Lys Ser Ser Asp Lys Thr His Thr Cys Pro Pro Cys Pro Ala Pro Glu
        275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
```

```
        355                 360                 365

Leu Asn Gly Lys Glu Tyr Lys Cys Ala Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Ser Gly Gly Gly Gly Ser Gly Gly Gly Gly Ser
            500                 505                 510

Gly Gly Gly Gly Ser Pro Ser Glu Val Gln Leu Leu Glu Ser Gly Gly
        515                 520                 525

Gly Leu Val Gln Pro Gly Gly Ser Leu Arg Leu Ser Cys Ala Ala Ser
    530                 535                 540

Gly Phe Asp Phe Glu Ser Tyr Ala Met Ser Trp Val Arg Gln Ala Pro
545                 550                 555                 560

Gly Lys Cys Leu Glu Trp Val Ser Ala Ile Ser Gly Ser Gly Gly Ser
                565                 570                 575

Thr Tyr Tyr Ala Asp Ser Val Lys Gly Arg Phe Thr Ile Ser Arg Asp
            580                 585                 590

Asn Ser Lys Asn Thr Leu Tyr Leu Gln Met Asn Ser Leu Arg Ala Glu
        595                 600                 605

Asp Thr Ala Val Tyr Tyr Cys Ala Arg Tyr Tyr Gly Gly Tyr Tyr Ser
    610                 615                 620

Ala Trp Met Asp Tyr Trp Gly Gln Gly Thr Leu Val Thr Val Ser Ser
625                 630                 635                 640

Gly Gly Gly Gly Ser Gly Gly Gly Gly Ser Gly Gly Gly Gly Ser Gly
                645                 650                 655

Gly Gly Gly Ser Asp Ile Gln Met Thr Gln Ser Pro Ser Ser Leu Ser
            660                 665                 670

Ala Ser Val Gly Asp Arg Val Thr Ile Thr Cys Arg Ala Ser Gln Ser
        675                 680                 685

Ile Arg Ser Ala Leu Asn Trp Tyr Gln Gln Lys Pro Gly Lys Ala Pro
    690                 695                 700

Lys Leu Leu Ile Tyr Ala Ala Ser Ser Leu Gln Ser Gly Val Pro Ser
705                 710                 715                 720

Arg Phe Ser Gly Ser Gly Ser Gly Thr Asp Phe Thr Leu Thr Ile Ser
                725                 730                 735

Ser Leu Gln Pro Glu Asp Phe Ala Thr Tyr Tyr Cys Gln Gln Thr Tyr
            740                 745                 750

Gly Tyr Leu His Thr Phe Gly Cys Gly Thr Lys Leu Glu Ile Lys Arg
        755                 760                 765
```

<210> SEQ ID NO 147

<211> LENGTH: 2304
<212> TYPE: DNA
<213> ORGANISM: Artificial Sequence
<220> FEATURE:
<223> OTHER INFORMATION: Made in Lab - anti-5T4 x anti-4-1BB
polynucleotide construct

<400> SEQUENCE: 147
atggaagcac cagcgcagct tctcttcctc ctgctactct ggctcccaga taccaccggt 60
gaggtgcagc tgttggagag cgggggaggc ttggtacagc ctggggggtc cctgcgcctc 120
tcctgtgcag ccagcggatt caccttttct cacggttcta tgtactgggt ccgccaggct 180
ccagggaagg ggctggagtg ggtctcatct atttcttctg gttctggttc tacatactat 240
gcagactccg tgaagggccg gttcaccatc tcccatgaca attccaagaa cacgctgtat 300
ctgcaaatga acagcctgcg tgccgaggac acggctgtat attattgtgc gcgctcttct 360
tactacggtt cttactactc tattgactat tggggccagg gaaccctggt caccgtctcc 420
tcaggtggag gtggctccgg gggtggaggt tccggaggag gcggatcagg tggaggcgga 480
agcgacatcc agatgaccca gtctccatcc tccctgagcg catctgtagg agaccgcgtc 540
accatcactt gccgggcaag tcagagcatt agcagctatt taaattggta tcagcagaaa 600
ccagggaaag cccctaagct cctgatctat gctgcatcca gtttgcaaag tggggtccca 660
tcacgtttca gtggcagtgg aagcgggaca gatttcactc tcaccatcag cagtctacaa 720
cctgaagatt ttgcaactta ttactgtcaa cagtactacg acaacctgcc cacttttggc 780
caggggacca agctggagat caaatcgagt gagcccaaat cttctgacaa aactcacaca 840
tgcccaccgt gcccagcacc tgaagccgcg ggtgcaccgt cagtcttcct cttcccccca 900
aaacccaagg acaccctcat gatctcccgg acccctgagg tcacatgcgt ggtggtggac 960
gtgagccacg aagaccctga ggtcaagttc aactggtacg tggacggcgt ggaggtgcat 1020
aatgccaaga caaagccgcg ggaggagcag tacaacagca cgtaccgtgt ggtcagcgtc 1080
ctcaccgtcc tgcaccagga ctggctgaat ggcaaggaat acaagtgcgc ggtctccaac 1140
aaagccctcc cagcccccat cgagaaaacc atctccaaag ccaaagggca gccccgagaa 1200
ccacaggtgt acaccctgcc cccatcccgg gatgagctga ccaagaacca ggtcagcctg 1260
acctgcctgg tcaaaggctt ctatccaagc gacatcgccg tggagtggga gagcaatggg 1320
cagccggaga acaactacaa gaccacgcct cccgtgctgg actccgacgg ctccttcttc 1380
ctctacagca agctcaccgt ggacaagagc aggtggcagc aggggaacgt cttctcatgc 1440
tccgtgatgc atgaggctct gcacaaccac tacacgcaga agagcctctc cctgtctccg 1500
ggttccggag gtggcggttc gggaggtggc gggtcaggag gtgggggatc cccttcagaa 1560
gtgcagctgc tggagtccgg aggaggactg gtgcagcctg gcggaagcct gaggctgagc 1620
tgcgctgcct ccggcttcga cttcgacagc tatgctatga gctgggtgag gcaagcccct 1680
ggaaagtgcc tggagtgggt gtccgctatc tccggcaggg gcggaagcac ctactacgct 1740
gactccgtca agggcaggtt caccatcagc cgggacaaca gcaagaacac cctgtacctg 1800
cagatgaata gcctcagggc tgaagacacc gctgtgtact actgcgccag gtactatggc 1860
ggctactact ccgcctggat ggactactgg ggacagggca cactggtgac cgtgtccagc 1920
ggcggaggcg gctccggagg cggtggctcc ggaggaggcg gaagcggagg aggaggctcc 1980
gatattcaga tgacacagtc ccctagctcc ctgtccgcca gcgtgggaga tcgggtgacc 2040
atcacctgca gggccagcca gtccatcagg agcgccctga actggtacca gcagaagcct 2100

-continued ggaaaggctc ccaagctgct gatctacgcc gcttccagcc tccagagcgg cgtgcctagc 2160
aggttctccg gctccggaag cggaacagac ttcaccctga ccatcagctc cctgcagccc 2220
gaggacttcg ctacctacta ctgccagcag acctatggct acctgcacac cttcggctgc 2280
ggcacaaagc tggagatcaa gcgc 2304

<210> SEQ ID NO 148
<211> LENGTH: 768
<212> TYPE: PRT
<213> ORGANISM: Artificial Sequence
<220> FEATURE:
<223> OTHER INFORMATION: Made in Lab - anti-5T4 x anti-4-1BB polypeptide construct

<400> SEQUENCE: 148

Met Glu Ala Pro Ala Gln Leu Leu Phe Leu Leu Leu Leu Trp Leu Pro
1 5 10 15

Asp Thr Thr Gly Glu Val Gln Leu Leu Glu Ser Gly Gly Gly Leu Val
20 25 30

Gln Pro Gly Gly Ser Leu Arg Leu Ser Cys Ala Ala Ser Gly Phe Thr
35 40 45

Phe Ser His Gly Ser Met Tyr Trp Val Arg Gln Ala Pro Gly Lys Gly
50 55 60

Leu Glu Trp Val Ser Ser Ile Ser Ser Gly Ser Gly Ser Thr Tyr Tyr
65 70 75 80

Ala Asp Ser Val Lys Gly Arg Phe Thr Ile Ser His Asp Asn Ser Lys
85 90 95

Asn Thr Leu Tyr Leu Gln Met Asn Ser Leu Arg Ala Glu Asp Thr Ala
100 105 110

Val Tyr Tyr Cys Ala Arg Ser Ser Tyr Tyr Gly Ser Tyr Tyr Ser Ile
115 120 125

Asp Tyr Trp Gly Gln Gly Thr Leu Val Thr Val Ser Ser Gly Gly Gly
130 135 140

Gly Ser Gly Gly Gly Gly Ser Gly Gly Gly Gly Ser Gly Gly Gly Gly
145 150 155 160

Ser Asp Ile Gln Met Thr Gln Ser Pro Ser Ser Leu Ser Ala Ser Val
165 170 175

Gly Asp Arg Val Thr Ile Thr Cys Arg Ala Ser Gln Ser Ile Ser Ser
180 185 190

Tyr Leu Asn Trp Tyr Gln Gln Lys Pro Gly Lys Ala Pro Lys Leu Leu
195 200 205

Ile Tyr Ala Ala Ser Ser Leu Gln Ser Gly Val Pro Ser Arg Phe Ser
210 215 220

Gly Ser Gly Ser Gly Thr Asp Phe Thr Leu Thr Ile Ser Ser Leu Gln
225 230 235 240

Pro Glu Asp Phe Ala Thr Tyr Tyr Cys Gln Gln Tyr Tyr Asp Asn Leu
245 250 255

Pro Thr Phe Gly Gln Gly Thr Lys Leu Glu Ile Lys Ser Ser Glu Pro
260 265 270

Lys Ser Ser Asp Lys Thr His Thr Cys Pro Pro Cys Pro Ala Pro Glu
275 280 285

Ala Ala Gly Ala Pro Ser Val Phe Leu Phe Pro Pro Lys Pro Lys Asp
290 295 300

Thr Leu Met Ile Ser Arg Thr Pro Glu Val Thr Cys Val Val Val Asp
305 310 315 320

```
Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Ala Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Ser Gly Gly Gly Gly Ser Gly Gly Gly Gly Ser
            500                 505                 510

Gly Gly Gly Gly Ser Pro Ser Glu Val Gln Leu Leu Glu Ser Gly Gly
        515                 520                 525

Gly Leu Val Gln Pro Gly Gly Ser Leu Arg Leu Ser Cys Ala Ala Ser
    530                 535                 540

Gly Phe Asp Phe Asp Ser Tyr Ala Met Ser Trp Val Arg Gln Ala Pro
545                 550                 555                 560

Gly Lys Cys Leu Glu Trp Val Ser Ala Ile Ser Gly Arg Gly Gly Ser
                565                 570                 575

Thr Tyr Tyr Ala Asp Ser Val Lys Gly Arg Phe Thr Ile Ser Arg Asp
            580                 585                 590

Asn Ser Lys Asn Thr Leu Tyr Leu Gln Met Asn Ser Leu Arg Ala Glu
        595                 600                 605

Asp Thr Ala Val Tyr Tyr Cys Ala Arg Tyr Tyr Gly Gly Tyr Tyr Ser
    610                 615                 620

Ala Trp Met Asp Tyr Trp Gly Gln Gly Thr Leu Val Thr Val Ser Ser
625                 630                 635                 640

Gly Gly Gly Gly Ser Gly Gly Gly Gly Ser Gly Gly Gly Gly Ser Gly
                645                 650                 655

Gly Gly Gly Ser Asp Ile Gln Met Thr Gln Ser Pro Ser Ser Leu Ser
            660                 665                 670

Ala Ser Val Gly Asp Arg Val Thr Ile Thr Cys Arg Ala Ser Gln Ser
        675                 680                 685

Ile Arg Ser Ala Leu Asn Trp Tyr Gln Gln Lys Pro Gly Lys Ala Pro
    690                 695                 700

Lys Leu Leu Ile Tyr Ala Ala Ser Ser Leu Gln Ser Gly Val Pro Ser
705                 710                 715                 720

Arg Phe Ser Gly Ser Gly Ser Gly Thr Asp Phe Thr Leu Thr Ile Ser
                725                 730                 735

Ser Leu Gln Pro Glu Asp Phe Ala Thr Tyr Tyr Cys Gln Gln Thr Tyr
```

740 745 750

Gly Tyr Leu His Thr Phe Gly Cys Gly Thr Lys Leu Glu Ile Lys Arg
755 760 765

<210> SEQ ID NO 149
<211> LENGTH: 2307
<212> TYPE: DNA
<213> ORGANISM: Artificial Sequence
<220> FEATURE:
<223> OTHER INFORMATION: Made in Lab - anti-5T4 x anti-4-1BB polynucleotide construct

<400> SEQUENCE: 149
atggaagcac cagcgcagct tctcttcctc ctgctactct ggctcccaga taccaccggt 60
gaggtgcagc tgttggagag cgggggaggc ttggtacagc ctggggggtc cctgcgcctc 120
tcctgtgcag ccagcggatt caccttttct tacggttcta tgtactgggt ccgccaggct 180
ccagggaagg ggctggagtg ggtctcatct atttcttctg gttctggttc tacatactat 240
gcagactccg tgaagggccg gttcaccatc tcccgtgaca attccaagaa cacgctgtat 300
ctgcaaatga acagcctgcg tgccgaggac acggctgtat attattgtgc gcgctcttct 360
tactacggtt cttactactc tattgactat tggggccagg gaaccctggt caccgtctcc 420
tcaggcggcg gcggcagcgg cggcggcggc agcggcggcg gaggctccgg cggcggcggc 480
agcgacatcc agatgaccca gtctccatcc tccctgagcg catctgtagg agaccgcgtc 540
accatcactt gccgggcaag tcagagcatt agcagctatt taaattggta tcagcagaaa 600
ccagggaaag cccctaagct cctgatctat gctgcatcca gtttgcaaag tggggtccca 660
tcacgtttca gtggcagtgg aagcgggaca gatttcactc tcaccatcag cagtctgcaa 720
cctgaagatt ttgcaactta ttactgtcaa cagtactacg acaacctgcc cacttttggc 780
caggggacca agctggagat caaatcctcg agtgagccca aatcttctga caaaactcac 840
acatgcccac cgtgcccagc acctgaagcc gcgggtgcac cgtcagtctt cctcttcccc 900
ccaaaaccca aggacaccct catgatctcc cggacccctg aggtcacatg cgtggtggtg 960
gacgtgagcc acgaagaccc tgaggtcaag ttcaactggt acgtggacgg cgtggaggtg 1020
cataatgcca agacaaagcc gcgggaggag cagtacaaca gcacgtaccg tgtggtcagc 1080
gtcctcaccg tcctgcacca ggactggctg aatggcaagg aatacaagtg cgcggtctcc 1140
aacaaagccc tcccagcccc catcgagaaa accatctcca aagccaaagg gcagccccga 1200
gaaccacagg tgtacaccct gcccccatcc cgggatgagc tgaccaagaa ccaggtcagc 1260
ctgacctgcc tggtcaaagg cttctatcca agcgacatcg ccgtggagtg ggagagcaat 1320
gggcagccgg agaacaacta caagaccacg cctcccgtgc tggactccga cggctccttc 1380
ttcctctaca gcaagctcac cgtggacaag agcaggtggc agcaggggaa cgtcttctca 1440
tgctccgtga tgcatgaggc tctgcacaac cactacacgc agaagagcct ctccctgtct 1500
ccgggttccg gaggtggcgg ttcgggaggt ggcgggtcag gaggtggggg atccccttca 1560
gaggtgcagc tgttggagag cgggggaggc ttggtacagc ctggggggtc cctgcgcctc 1620
tcctgtgcag ccagcggatt cacctttagc agctatgcca tgagctgggt ccgccaggct 1680
ccagggaagg ggctggagtg ggtctcagct attagtggta gtggtggtag cacatactat 1740
gcagactccg tgaagggccg gttcaccatc tcccgtgaca attccaagaa cacgctgtat 1800
ctgcaaatga acagcctgcg tgccgaggac acggctgtat attattgtgc gcgctactac 1860
ggtggttact actctgcttg gatggactat tggggccagg gaaccctggt caccgtctcc 1920

```
tcaggcggtg gaggcagcgg tgggggtggg tctggaggcg gtggcagtgg cggcggaggc   1980

tctgacatcc agatgaccca gtctccatcc tccctgagcg catctgtagg agaccgcgtc   2040

accatcactt gccgggcaag tcagagcatt agcagctatt taaattggta tcagcagaaa   2100

ccagggaaag cccctaagct cctgatctat gctgcatcca gtttgcaaag tggggtccca   2160

tcacgtttca gtggcagtgg aagcgggaca gatttcactc tcaccatcag cagtctgcaa   2220

cctgaagatt ttgcaactta ttactgtcaa cagacttacg gttacctgca cacttttggc   2280

caggggacca agctggagat caaatca                                       2307


<210> SEQ ID NO 150
<211> LENGTH: 769
<212> TYPE: PRT
<213> ORGANISM: Artificial Sequence
<220> FEATURE:
<223> OTHER INFORMATION: Made in Lab - anti-5T4 x anti-4-1BB polypeptide
      construct

<400> SEQUENCE: 150

Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Tyr Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Ser Ser Ser Glu
            260                 265                 270

Pro Lys Ser Ser Asp Lys Thr His Thr Cys Pro Pro Cys Pro Ala Pro
        275                 280                 285
```

```
Glu Ala Ala Gly Ala Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Ala Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Ser Gly Gly Gly Gly Ser Gly Gly Gly Gly
            500                 505                 510

Ser Gly Gly Gly Gly Ser Pro Ser Glu Val Gln Leu Leu Glu Ser Gly
        515                 520                 525

Gly Gly Leu Val Gln Pro Gly Gly Ser Leu Arg Leu Ser Cys Ala Ala
    530                 535                 540

Ser Gly Phe Thr Phe Ser Ser Tyr Ala Met Ser Trp Val Arg Gln Ala
545                 550                 555                 560

Pro Gly Lys Gly Leu Glu Trp Val Ser Ala Ile Ser Gly Ser Gly Gly
                565                 570                 575

Ser Thr Tyr Tyr Ala Asp Ser Val Lys Gly Arg Phe Thr Ile Ser Arg
            580                 585                 590

Asp Asn Ser Lys Asn Thr Leu Tyr Leu Gln Met Asn Ser Leu Arg Ala
        595                 600                 605

Glu Asp Thr Ala Val Tyr Tyr Cys Ala Arg Tyr Tyr Gly Gly Tyr Tyr
    610                 615                 620

Ser Ala Trp Met Asp Tyr Trp Gly Gln Gly Thr Leu Val Thr Val Ser
625                 630                 635                 640

Ser Gly Gly Gly Gly Ser Gly Gly Gly Gly Ser Gly Gly Gly Gly Ser
                645                 650                 655

Gly Gly Gly Gly Ser Asp Ile Gln Met Thr Gln Ser Pro Ser Ser Leu
            660                 665                 670

Ser Ala Ser Val Gly Asp Arg Val Thr Ile Thr Cys Arg Ala Ser Gln
        675                 680                 685

Ser Ile Ser Ser Tyr Leu Asn Trp Tyr Gln Gln Lys Pro Gly Lys Ala
    690                 695                 700
```

```
Pro Lys Leu Leu Ile Tyr Ala Ala Ser Ser Leu Gln Ser Gly Val Pro
705                 710                 715                 720

Ser Arg Phe Ser Gly Ser Gly Ser Gly Thr Asp Phe Thr Leu Thr Ile
                725                 730                 735

Ser Ser Leu Gln Pro Glu Asp Phe Ala Thr Tyr Tyr Cys Gln Gln Thr
            740                 745                 750

Tyr Gly Tyr Leu His Thr Phe Gly Gln Gly Thr Lys Leu Glu Ile Lys
        755                 760                 765

Ser


<210> SEQ ID NO 151
<211> LENGTH: 2304
<212> TYPE: DNA
<213> ORGANISM: Artificial Sequence
<220> FEATURE:
<223> OTHER INFORMATION: Made in Lab - anti-5T4 x anti-4-1BB
      polynucleotide construct

<400> SEQUENCE: 151

atggaagcac cagcgcagct tctcttcctc ctgctactct ggctcccaga taccaccggt     60

gaggtgcagc tgttggagag cgggggaggc ttggtacagc ctggggggtc cctgcgcctc    120

tcctgtgcag ccagcggatt caccttttct tacggttcta tgtactgggt ccgccaggct    180

ccagggaagg ggctggagtg ggtctcatct atttcttctg gttctggttc tacatactat    240

gcagactccg tgaagggccg gttcaccatc tcccgtgaca attccaagaa cacgctgtat    300

ctgcaaatga acagcctgcg tgccgaggac acggctgtat attattgtgc gcgctcttct    360

tactacggtt cttactactc tattgactat tggggccagg gaaccctggt caccgtctcc    420

tcaggcggcg gcggcagcgg cggcggcggc agcggcggcg gaggctccgg cggcggcggc    480

agcgacatcc agatgaccca gtctccatcc tccctgagcg catctgtagg agaccgcgtc    540

accatcactt gccgggcaag tcagagcatt agcagctatt taaattggta tcagcagaaa    600

ccagggaaag cccctaagct cctgatctat gctgcatcca gtttgcaaag tggggtccca    660

tcacgtttca gtggcagtgg aagcgggaca gatttcactc tcaccatcag cagtctgcaa    720

cctgaagatt ttgcaactta ttactgtcaa cagtactacg acaacctgcc cacttttggc    780

caggggacca agctggagat caaatcctcg agtgagccca aatcttctga caaaactcac    840

acatgcccac cgtgcccagc acctgaagcc gcgggtgcac cgtcagtctt cctcttcccc    900

ccaaaaccca aggacaccct catgatctcc cggacccctg aggtcacatg cgtggtggtg    960

gacgtgagcc acgaagaccc tgaggtcaag ttcaactggt acgtggacgg cgtggaggtg   1020

cataatgcca agacaaagcc gcgggaggag cagtacaaca gcacgtaccg tgtggtcagc   1080

gtcctcaccg tcctgcacca ggactggctg aatggcaagg aatacaagtg cgcggtctcc   1140

aacaaagccc tcccagcccc catcgagaaa accatctcca aagccaaagg gcagccccga   1200

gaaccacagg tgtacaccct gcccccatcc cgggatgagc tgaccaagaa ccaggtcagc   1260

ctgacctgcc tggtcaaagg cttctatcca agcgacatcg ccgtggagtg ggagagcaat   1320

gggcagccgg agaacaacta caagaccacg cctcccgtgc tggactccga cggctccttc   1380

ttcctctaca gcaagctcac cgtggacaag agcaggtggc agcaggggaa cgtcttctca   1440

tgctccgtga tgcatgaggc tctgcacaac cactacacgc agaagagcct ctccctgtct   1500

ccgggttccg gaggtggcgg ttcgggaggt ggcgggtcag gaggtggggg atccccttca   1560

gacatccaga tgacccagtc tccatcctcc ctgagcgcat ctgtaggaga ccgcgtcacc   1620
```

```
atcacttgcc gggcaagtca gagcattagc agctatttaa attggtatca gcagaaacca   1680

gggaaagccc ctaagctcct gatctatgct gcatccagtt tgcaaagtgg ggtcccatca   1740

cgtttcagtg gcagtggaag cgggacagat ttcactctca ccatcagcag tctgcaacct   1800

gaagattttg caacttatta ctgtcaacag acttacggtt acctgcacac ttttggccag   1860

gggaccaagc tggagatcaa aggcggtgga ggcagcggtg gggtgggtc tggaggcggt   1920

ggcagtggcg gcggaggctc tgaggtgcag ctgttggaga gcgggggagg cttggtacag   1980

cctgggggt ccctgcgcct ctcctgtgca gccagcggat tcacctttag cagctatgcc   2040

atgagctggg tccgccaggc tccagggaag gggctggagt gggtctcagc tattagtggt   2100

agtggtggta gcacatacta tgcagactcc gtgaagggcc ggttcaccat ctcccgtgac   2160

aattccaaga acacgctgta tctgcaaatg aacagcctgc gtgccgagga cacggctgta   2220

tattattgtg cgcgctacta cggtggttac tactctgctt ggatggacta ttggggccag   2280

ggaaccctgg tcaccgtctc ctca                                          2304
```

```
<210> SEQ ID NO 152
<211> LENGTH: 768
<212> TYPE: PRT
<213> ORGANISM: Artificial Sequence
<220> FEATURE:
<223> OTHER INFORMATION: Made in Lab - anti-5T4 x anti-4-1BB polypeptide
      construct

<400> SEQUENCE: 152

Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Tyr Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240
```

```
Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Ser Ser Ser Glu
            260                 265                 270

Pro Lys Ser Ser Asp Lys Thr His Thr Cys Pro Pro Cys Pro Ala Pro
        275                 280                 285

Glu Ala Ala Gly Ala Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Ala Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Ser Gly Gly Gly Gly Ser Gly Gly Gly Gly
            500                 505                 510

Ser Gly Gly Gly Gly Ser Pro Ser Asp Ile Gln Met Thr Gln Ser Pro
        515                 520                 525

Ser Ser Leu Ser Ala Ser Val Gly Asp Arg Val Thr Ile Thr Cys Arg
    530                 535                 540

Ala Ser Gln Ser Ile Ser Ser Tyr Leu Asn Trp Tyr Gln Gln Lys Pro
545                 550                 555                 560

Gly Lys Ala Pro Lys Leu Leu Ile Tyr Ala Ala Ser Ser Leu Gln Ser
                565                 570                 575

Gly Val Pro Ser Arg Phe Ser Gly Ser Gly Ser Gly Thr Asp Phe Thr
            580                 585                 590

Leu Thr Ile Ser Ser Leu Gln Pro Glu Asp Phe Ala Thr Tyr Tyr Cys
        595                 600                 605

Gln Gln Thr Tyr Gly Tyr Leu His Thr Phe Gly Gln Gly Thr Lys Leu
    610                 615                 620

Glu Ile Lys Gly Gly Gly Gly Ser Gly Gly Gly Gly Ser Gly Gly Gly
625                 630                 635                 640

Gly Ser Gly Gly Gly Gly Ser Glu Val Gln Leu Leu Glu Ser Gly Gly
                645                 650                 655
```

```
Gly Leu Val Gln Pro Gly Gly Ser Leu Arg Leu Ser Cys Ala Ala Ser
            660                 665                 670

Gly Phe Thr Phe Ser Ser Tyr Ala Met Ser Trp Val Arg Gln Ala Pro
        675                 680                 685

Gly Lys Gly Leu Glu Trp Val Ser Ala Ile Ser Gly Ser Gly Gly Ser
    690                 695                 700

Thr Tyr Tyr Ala Asp Ser Val Lys Gly Arg Phe Thr Ile Ser Arg Asp
705                 710                 715                 720

Asn Ser Lys Asn Thr Leu Tyr Leu Gln Met Asn Ser Leu Arg Ala Glu
                725                 730                 735

Asp Thr Ala Val Tyr Tyr Cys Ala Arg Tyr Tyr Gly Gly Tyr Tyr Ser
            740                 745                 750

Ala Trp Met Asp Tyr Trp Gly Gln Gly Thr Leu Val Thr Val Ser Ser
        755                 760                 765
```

<210> SEQ ID NO 153
<211> LENGTH: 2307
<212> TYPE: DNA
<213> ORGANISM: Artificial Sequence
<220> FEATURE:
<223> OTHER INFORMATION: Made in Lab - anti-5T4 x anti-4-1BB polynucleotide construct

<400> SEQUENCE: 153

```
atggaagcac cagcgcagct tctcttcctc ctgctactct ggctcccaga taccaccggt      60

gaggtgcagc tgttggagag cgggggaggc ttggtacagc ctggggggtc cctgcgcctc     120

tcctgtgcag ccagcggatt caccttttct tacggttcta tgtactgggt ccgccaggct     180

ccagggaagg ggctggagtg ggtctcatct atttcttctg gttctggttc tacatactat     240

gcagactccg tgaagggccg gttcaccatc tcccgtgaca attccaagaa cacgctgtat     300

ctgcaaatga acagcctgcg tgccgaggac acggctgtat attattgtgc gcgctcttct     360

tactacggtt cttactactc tattgactat tggggccagg gaaccctggt caccgtctcc     420

tcaggcggcg gcggcagcgg cggcggcggc agcggcggcg gaggctccgg cggcggcggc     480

agcgacatcc agatgaccca gtctccatcc tccctgagcg catctgtagg agaccgcgtc     540

accatcactt gccgggcaag tcagagcatt agcagctatt taaattggta tcagcagaaa     600

ccagggaaag cccctaagct cctgatctat gctgcatcca gtttgcaaag tggggtccca     660

tcacgtttca gtggcagtgg aagcgggaca gatttcactc tcaccatcag cagtctgcaa     720

cctgaagatt ttgcaactta ttactgtcaa cagtactacg acaacctgcc cacttttggc     780

caggggacca agctggagat caaatcctcg agtgagccca aatcttctga caaaactcac     840

acatgcccac cgtgcccagc acctgaagcc gcgggtgcac cgtcagtctt cctcttcccc     900

ccaaaaccca aggacaccct catgatctcc cggacccctg aggtcacatg cgtggtggtg     960

gacgtgagcc acgaagaccc tgaggtcaag ttcaactggt acgtggacgg cgtggaggtg    1020

cataatgcca agacaaagcc gcgggaggag cagtacaaca gcacgtaccg tgtggtcagc    1080

gtcctcaccg tcctgcacca ggactggctg aatggcaagg aatacaagtg cgcggtctcc    1140

aacaaagccc tcccagcccc catcgagaaa accatctcca aagccaaagg gcagccccga    1200

gaaccacagg tgtacaccct gcccccatcc cgggatgagc tgaccaagaa ccaggtcagc    1260

ctgacctgcc tggtcaaagg cttctatcca agcgacatcg ccgtggagtg ggagagcaat    1320

gggcagccgg agaacaacta caagaccacg cctcccgtgc tggactccga cggctccttc    1380

ttcctctaca gcaagctcac cgtggacaag agcaggtggc agcaggggaa cgtcttctca    1440
```

-continued tgctccgtga tgcatgaggc tctgcacaac cactacacgc agaagagcct ctccctgtct 1500
ccgggttccg gaggtggcgg ttcgggaggt ggcgggtcag gaggtggggg atccccttca 1560
gaggtgcagc tgttggagag cgggggaggc ttggtacagc ctggggggtc cctgcgcctc 1620
tcctgtgcag ccagcggatt cacctttagc agctatgcca tgagctgggt ccgccaggct 1680
ccagggaagt gcctggagtg ggtctcagct attagtggta gtggtggtag cacatactat 1740
gcagactccg tgaagggccg gttcaccatc tcccgtgaca attccaagaa cacgctgtat 1800
ctgcaaatga acagcctgcg tgccgaggac acggctgtat attattgtgc gcgctactac 1860
ggtggttact actctgcttg gatggactat tggggccagg gaaccctggt caccgtctcc 1920
tcaggcggtg gaggcagcgg tgggggtggg tctggaggcg gtggcagtgg cggcggaggc 1980
tctgacatcc agatgaccca gtctccatcc tccctgagcg catctgtagg agaccgcgtc 2040
accatcactt gccgggcaag tcagagcatt agcagctatt taaattggta tcagcagaaa 2100
ccagggaaag cccctaagct cctgatctat gctgcatcca gtttgcaaag tggggtccca 2160
tcacgtttca gtggcagtgg aagcgggaca gatttcactc tcaccatcag cagtctgcaa 2220
cctgaagatt ttgcaactta ttactgtcaa cagacttacg gttacctgca cacttttggc 2280
tgcgggacca agctggagat caaatca 2307

<210> SEQ ID NO 154
<211> LENGTH: 769
<212> TYPE: PRT
<213> ORGANISM: Artificial Sequence
<220> FEATURE:
<223> OTHER INFORMATION: Made in Lab - anti-5T4 x anti-4-1BB polypeptide construct

<400> SEQUENCE: 154

Met Glu Ala Pro Ala Gln Leu Leu Phe Leu Leu Leu Leu Trp Leu Pro
1 5 10 15

Asp Thr Thr Gly Glu Val Gln Leu Leu Glu Ser Gly Gly Gly Leu Val
20 25 30

Gln Pro Gly Gly Ser Leu Arg Leu Ser Cys Ala Ala Ser Gly Phe Thr
35 40 45

Phe Ser Tyr Gly Ser Met Tyr Trp Val Arg Gln Ala Pro Gly Lys Gly
50 55 60

Leu Glu Trp Val Ser Ser Ile Ser Ser Gly Ser Gly Ser Thr Tyr Tyr
65 70 75 80

Ala Asp Ser Val Lys Gly Arg Phe Thr Ile Ser Arg Asp Asn Ser Lys
85 90 95

Asn Thr Leu Tyr Leu Gln Met Asn Ser Leu Arg Ala Glu Asp Thr Ala
100 105 110

Val Tyr Tyr Cys Ala Arg Ser Ser Tyr Tyr Gly Ser Tyr Tyr Ser Ile
115 120 125

Asp Tyr Trp Gly Gln Gly Thr Leu Val Thr Val Ser Ser Gly Gly Gly
130 135 140

Gly Ser Gly Gly Gly Gly Ser Gly Gly Gly Gly Ser Gly Gly Gly Gly
145 150 155 160

Ser Asp Ile Gln Met Thr Gln Ser Pro Ser Ser Leu Ser Ala Ser Val
165 170 175

Gly Asp Arg Val Thr Ile Thr Cys Arg Ala Ser Gln Ser Ile Ser Ser
180 185 190

Tyr Leu Asn Trp Tyr Gln Gln Lys Pro Gly Lys Ala Pro Lys Leu Leu

```
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Ser Ser Ser Glu
            260                 265                 270

Pro Lys Ser Ser Asp Lys Thr His Thr Cys Pro Pro Cys Pro Ala Pro
        275                 280                 285

Glu Ala Ala Gly Ala Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Ala Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Ser Gly Gly Gly Gly Ser Gly Gly Gly Gly
            500                 505                 510

Ser Gly Gly Gly Gly Ser Pro Ser Glu Val Gln Leu Leu Glu Ser Gly
        515                 520                 525

Gly Gly Leu Val Gln Pro Gly Gly Ser Leu Arg Leu Ser Cys Ala Ala
    530                 535                 540

Ser Gly Phe Thr Phe Ser Ser Tyr Ala Met Ser Trp Val Arg Gln Ala
545                 550                 555                 560

Pro Gly Lys Cys Leu Glu Trp Val Ser Ala Ile Ser Gly Ser Gly Gly
                565                 570                 575

Ser Thr Tyr Tyr Ala Asp Ser Val Lys Gly Arg Phe Thr Ile Ser Arg
            580                 585                 590

Asp Asn Ser Lys Asn Thr Leu Tyr Leu Gln Met Asn Ser Leu Arg Ala
        595                 600                 605

Glu Asp Thr Ala Val Tyr Tyr Cys Ala Arg Tyr Tyr Gly Gly Tyr Tyr
    610                 615                 620
```

```
Ser Ala Trp Met Asp Tyr Trp Gly Gln Gly Thr Leu Val Thr Val Ser
625                 630                 635                 640

Ser Gly Gly Gly Gly Ser Gly Gly Gly Gly Ser Gly Gly Gly Gly Ser
                645                 650                 655

Gly Gly Gly Gly Ser Asp Ile Gln Met Thr Gln Ser Pro Ser Ser Leu
            660                 665                 670

Ser Ala Ser Val Gly Asp Arg Val Thr Ile Thr Cys Arg Ala Ser Gln
        675                 680                 685

Ser Ile Ser Ser Tyr Leu Asn Trp Tyr Gln Gln Lys Pro Gly Lys Ala
    690                 695                 700

Pro Lys Leu Leu Ile Tyr Ala Ala Ser Ser Leu Gln Ser Gly Val Pro
705                 710                 715                 720

Ser Arg Phe Ser Gly Ser Gly Ser Gly Thr Asp Phe Thr Leu Thr Ile
                725                 730                 735

Ser Ser Leu Gln Pro Glu Asp Phe Ala Thr Tyr Tyr Cys Gln Gln Thr
            740                 745                 750

Tyr Gly Tyr Leu His Thr Phe Gly Cys Gly Thr Lys Leu Glu Ile Lys
        755                 760                 765

Ser
```

<210> SEQ ID NO 155
<211> LENGTH: 2304
<212> TYPE: DNA
<213> ORGANISM: Artificial Sequence
<220> FEATURE:
<223> OTHER INFORMATION: Made in Lab - anti-5T4 x anti-4-1BB
      polynucleotide construct

<400> SEQUENCE: 155

```
atggaagcac cagcgcagct tctcttcctc ctgctactct ggctcccaga taccaccggt      60

gaggtgcagc tgttggagag cgggggaggc ttggtacagc ctggggggtc cctgcgcctc     120

tcctgtgcag ccagcggatt caccttttct tacggttcta tgtactgggt ccgccaggct     180

ccagggaagg ggctggagtg ggtctcatct atttcttctg gttctggttc tacatactat     240

gcagactccg tgaagggccg gttcaccatc tcccgtgaca attccaagaa cacgctgtat     300

ctgcaaatga acagcctgcg tgccgaggac acggctgtat attattgtgc gcgctcttct     360

tactacggtt cttactactc tattgactat tggggccagg gaaccctggt caccgtctcc     420

tcaggcggcg gcggcagcgg cggcggcggc agcggcggcg gaggctccgg cggcggcggc     480

agcgacatcc agatgaccca gtctccatcc tccctgagcg catctgtagg agaccgcgtc     540

accatcactt gccgggcaag tcagagcatt agcagctatt taaattggta tcagcagaaa     600

ccagggaaag cccctaagct cctgatctat gctgcatcca gtttgcaaag tggggtccca     660

tcacgtttca gtggcagtgg aagcgggaca gatttcactc tcaccatcag cagtctgcaa     720

cctgaagatt ttgcaactta ttactgtcaa cagtactacg acaacctgcc cacttttggc     780

caggggacca agctggagat caaatcctcg agtgagccca aatcttctga caaaactcac     840

acatgcccac cgtgcccagc acctgaagcc gcgggtgcac cgtcagtctt cctcttcccc     900

ccaaaaccca aggacaccct catgatctcc cggacccctg aggtcacatg cgtggtggtg     960

gacgtgagcc acgaagaccc tgaggtcaag ttcaactggt acgtggacgg cgtggaggtg    1020

cataatgcca agacaaagcc gcgggaggag cagtacaaca gcacgtaccg tgtggtcagc    1080

gtcctcaccg tcctgcacca ggactggctg aatggcaagg aatacaagtg cgcggtctcc    1140
```

```
aacaaagccc tcccagcccc catcgagaaa accatctcca aagccaaagg gcagccccga   1200

gaaccacagg tgtacaccct gcccccatcc cgggatgagc tgaccaagaa ccaggtcagc   1260

ctgacctgcc tggtcaaagg cttctatcca agcgacatcg ccgtggagtg ggagagcaat   1320

gggcagccgg agaacaacta caagaccacg cctcccgtgc tggactccga cggctccttc   1380

ttcctctaca gcaagctcac cgtggacaag agcaggtggc agcaggggaa cgtcttctca   1440

tgctccgtga tgcatgaggc tctgcacaac cactacacgc agaagagcct ctccctgtct   1500

ccgggttccg gaggtggcgg ttcgggaggt ggcgggtcag gaggtggggg atccccttca   1560

gacatccaga tgacccagtc tccatcctcc ctgagcgcat ctgtaggaga ccgcgtcacc   1620

atcacttgcc gggcaagtca gagcattagc agctatttaa attggtatca gcagaaacca   1680

gggaaagccc ctaagctcct gatctatgct gcatccagtt tgcaaagtgg ggtcccatca   1740

cgtttcagtg gcagtggaag cgggacagat ttcactctca ccatcagcag tctgcaacct   1800

gaagattttg caacttatta ctgtcaacag acttacggtt acctgcacac ttttggctgc   1860

gggaccaagc tggagatcaa aggcggtgga ggcagcggtg gggggtgggtc tggaggcggt   1920

ggcagtggcg gcggaggctc tgaggtgcag ctgttggaga gcgggggagg cttggtacag   1980

cctggggggt ccctgcgcct ctcctgtgca gccagcggat tcacctttag cagctatgcc   2040

atgagctggg tccgccaggc tccagggaag tgcctggagt gggtctcagc tattagtggt   2100

agtggtggta gcacatacta tgcagactcc gtgaagggcc ggttcaccat ctcccgtgac   2160

aattccaaga acacgctgta tctgcaaatg aacagcctgc gtgccgagga cacggctgta   2220

tattattgtg cgcgctacta cggtggttac tactctgctt ggatggacta ttggggccag   2280

ggaaccctgg tcaccgtctc ctca                                          2304
```

```
<210> SEQ ID NO 156
<211> LENGTH: 768
<212> TYPE: PRT
<213> ORGANISM: Artificial Sequence
<220> FEATURE:
<223> OTHER INFORMATION: Made in Lab - anti-5T4 x anti-4-1BB polypeptide
      construct

<400> SEQUENCE: 156

Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Tyr Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
```

-continued

```
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Ser Ser Ser Glu
            260                 265                 270

Pro Lys Ser Ser Asp Lys Thr His Thr Cys Pro Pro Cys Pro Ala Pro
        275                 280                 285

Glu Ala Ala Gly Ala Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Ala Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Ser Gly Gly Gly Gly Ser Gly Gly Gly Gly
            500                 505                 510

Ser Gly Gly Gly Gly Ser Pro Ser Asp Ile Gln Met Thr Gln Ser Pro
        515                 520                 525

Ser Ser Leu Ser Ala Ser Val Gly Asp Arg Val Thr Ile Thr Cys Arg
    530                 535                 540

Ala Ser Gln Ser Ile Ser Ser Tyr Leu Asn Trp Tyr Gln Gln Lys Pro
545                 550                 555                 560

Gly Lys Ala Pro Lys Leu Leu Ile Tyr Ala Ala Ser Ser Leu Gln Ser
                565                 570                 575
```

```
Gly Val Pro Ser Arg Phe Ser Gly Ser Gly Ser Gly Thr Asp Phe Thr
            580                 585                 590

Leu Thr Ile Ser Ser Leu Gln Pro Glu Asp Phe Ala Thr Tyr Tyr Cys
        595                 600                 605

Gln Gln Thr Tyr Gly Tyr Leu His Thr Phe Gly Cys Gly Thr Lys Leu
    610                 615                 620

Glu Ile Lys Gly Gly Gly Gly Ser Gly Gly Gly Gly Ser Gly Gly Gly
625                 630                 635                 640

Gly Ser Gly Gly Gly Gly Ser Glu Val Gln Leu Leu Glu Ser Gly Gly
            645                 650                 655

Gly Leu Val Gln Pro Gly Gly Ser Leu Arg Leu Ser Cys Ala Ala Ser
            660                 665                 670

Gly Phe Thr Phe Ser Ser Tyr Ala Met Ser Trp Val Arg Gln Ala Pro
        675                 680                 685

Gly Lys Cys Leu Glu Trp Val Ser Ala Ile Ser Gly Ser Gly Gly Ser
    690                 695                 700

Thr Tyr Tyr Ala Asp Ser Val Lys Gly Arg Phe Thr Ile Ser Arg Asp
705                 710                 715                 720

Asn Ser Lys Asn Thr Leu Tyr Leu Gln Met Asn Ser Leu Arg Ala Glu
            725                 730                 735

Asp Thr Ala Val Tyr Tyr Cys Ala Arg Tyr Tyr Gly Gly Tyr Tyr Ser
            740                 745                 750

Ala Trp Met Asp Tyr Trp Gly Gln Gly Thr Leu Val Thr Val Ser Ser
        755                 760                 765
```

```
<210> SEQ ID NO 157
<211> LENGTH: 699
<212> TYPE: DNA
<213> ORGANISM: Artificial Sequence
<220> FEATURE:
<223> OTHER INFORMATION: Made in Lab - antibody fragment

<400> SEQUENCE: 157

tcgagtgagc ccaaatcttc tgacaaaact cacacatgcc caccgtgccc agcacctgaa     60

gccgcgggtg caccgtcagt cttcctcttc cccccaaaac ccaaggacac cctcatgatc    120

tcccggaccc ctgaggtcac atgcgtggtg gtggacgtga gccacgaaga ccctgaggtc    180

aagttcaact ggtacgtgga cggcgtggag gtgcataatg ccaagacaaa gccgcgggag    240

gagcagtaca acagcacgta ccgtgtggtc agcgtcctca ccgtcctgca ccaggactgg    300

ctgaatggca aggaatacaa gtgcgcggtc tccaacaaag ccctcccagc ccccatcgag    360

aaaaccatct ccaaagccaa agggcagccc cgagaaccac aggtgtacac cctgccccca    420

tcccgggatg agctgaccaa gaaccaggtc agcctgacct gcctggtcaa aggcttctat    480

ccaagcgaca tcgccgtgga gtgggagagc aatgggcagc cggagaacaa ctacaagacc    540

acgcctcccg tgctggactc cgacggctcc ttcttcctct acagcaagct caccgtggac    600

aagagcaggt ggcagcaggg gaacgtcttc tcatgctccg tgatgcatga ggctctgcac    660

aaccactaca cgcagaagag cctctccctg tctccgggt                           699

<210> SEQ ID NO 158
<211> LENGTH: 233
<212> TYPE: PRT
<213> ORGANISM: Artificial Sequence
<220> FEATURE:
<223> OTHER INFORMATION: Made in Lab - antibody fragment
```

<400> SEQUENCE: 158

```
Ser Ser Glu Pro Lys Ser Ser Asp Lys Thr His Thr Cys Pro Pro Cys
1               5                   10                  15

Pro Ala Pro Glu Ala Ala Gly Ala Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Ala Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly
225                 230
```

<210> SEQ ID NO 159
<211> LENGTH: 693
<212> TYPE: DNA
<213> ORGANISM: Artificial Sequence
<220> FEATURE:
<223> OTHER INFORMATION: Made in Lab - antibody fragment

<400> SEQUENCE: 159

```
gagcccaaat cttctgacaa aactcacaca tgcccaccgt gcccagcacc tgaagccgcg     60

ggtgcaccgt cagtcttcct cttcccccca aaacccaagg acaccctcat gatctcccgg    120

acccctgagg tcacatgcgt ggtggtggac gtgagccacg aagaccctga ggtcaagttc    180

aactggtacg tggacggcgt ggaggtgcat aatgccaaga caaagccgcg ggaggagcag    240

tacaacagca cgtaccgtgt ggtcagcgtc ctcaccgtcc tgcaccagga ctggctgaat    300

ggcaaggaat acaagtgcgc ggtctccaac aaagccctcc cagcccccat cgagaaaacc    360

atctccaaag ccaaagggca gccccgagaa ccacaggtgt acaccctgcc cccatcccgg    420

gatgagctga ccaagaacca ggtcagcctg acctgcctgg tcaaaggctt ctatccaagc    480

gacatcgccg tggagtggga gagcaatggg cagccggaga acaactacaa gaccacgcct    540

cccgtgctgg actccgacgg ctccttcttc ctctacagca agctcaccgt ggacaagagc    600

aggtggcagc aggggaacgt cttctcatgc tccgtgatgc atgaggctct gcacaaccac    660
```

tacacgcaga agagcctctc cctgtctccg ggt 693

<210> SEQ ID NO 160
<211> LENGTH: 231
<212> TYPE: PRT
<213> ORGANISM: Artificial Sequence
<220> FEATURE:
<223> OTHER INFORMATION: Made in Lab - antibody fragment

<400> SEQUENCE: 160

Glu Pro Lys Ser Ser Asp Lys Thr His Thr Cys Pro Pro Cys Pro Ala
1 5 10 15

Pro Glu Ala Ala Gly Ala Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Ala Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 161
<211> LENGTH: 768
<212> TYPE: DNA
<213> ORGANISM: Homo sapiens

<400> SEQUENCE: 161
atgggaaaca gctgttacaa catagtagcc actctgttgc tggtcctcaa ctttgagagg 60
acaagatcat tgcaggatcc ttgtagtaac tgcccagctg gtacattctg tgataataac 120
aggaatcaga tttgcagtcc ctgtcctcca aatagtttct ccagcgcagg tggacaaagg 180
acctgtgaca tatgcaggca gtgtaaaggt gttttcagga ccaggaagga gtgttcctcc 240
accagcaatg cagagtgtga ctgcactcca gggtttcact gcctgggggc aggatgcagc 300
atgtgtgaac aggattgtaa acaaggtcaa gaactgacaa aaaaaggttg taaagactgt 360
tgctttggga catttaacga tcagaaacgt ggcatctgtc gaccctggac aaactgttct 420

-continued

```
ttggatggaa agtctgtgct tgtgaatggg acgaaggaga gggacgtggt ctgtggacca    480

tctccagccg acctctctcc gggagcatcc tctgtgaccc cgcctgcccc tgcgagagag    540

ccaggacact ctccgcagat catctccttc tttcttgcgc tgacgtcgac tgcgttgctc    600

ttcctgctgt tcttcctcac gctccgtttc tctgttgtta aacggggcag aaagaaactc    660

ctgtatatat tcaaacaacc atttatgaga ccagtacaaa ctactcaaga ggaagatggc    720

tgtagctgcc gatttccaga agaagaagaa ggaggatgtg aactgtga                768
```

```
<210> SEQ ID NO 162
<211> LENGTH: 255
<212> TYPE: PRT
<213> ORGANISM: Homo sapiens

<400> SEQUENCE: 162

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

```
<210> SEQ ID NO 163
<211> LENGTH: 1263
<212> TYPE: DNA
<213> ORGANISM: Homo sapiens

<400> SEQUENCE: 163

atgcctgggg ggtgctcccg ggcccccgcc gccggggacg ggcgtctgcg gctggcgcga     60

ctagcgctgg tactcctggg ctgggtctcc tcgtcttctc ccacctcctc ggcatcctcc    120
```

```
ttctcctcct cggcgccgtt cctggcttcc gccgtgtccg cccagccccc gctgccggac    180
cagtgccccg cgctgtgcga gtgctccgag gcagcgcgca cagtcaagtg cgttaaccgc    240
aatctgaccg aggtgcccac ggacctgccc gcctacgtgc gcaacctctt ccttaccggc    300
aaccagctgg ccgtgctccc tgccggcgcc ttcgcccgcc ggccgccgct ggcggagctg    360
gccgcgctca acctcagcgg cagccgcctg gacgaggtgc gcgcgggcgc cttcgagcat    420
ctgcccagcc tgcgccagct cgacctcagc cacaacccac tggccgacct cagtcccttc    480
gctttctcgg gcagcaatgc cagcgtctcg gcccccagtc cccttgtgga actgatcctg    540
aaccacatcg tgcccccctga agatgagcgg cagaaccgga gcttcgaggg catggtggtg    600
gcggccctgc tggcgggccg tgcactgcag gggctccgcc gcttggagct ggccagcaac    660
cacttccttt acctgccgcg ggatgtgctg gcccaactgc ccagcctcag gcacctggac    720
ttaagtaata attcgctggt gagcctgacc tacgtgtcct tccgcaacct gacacatcta    780
gaaagcctcc acctggagga caatgccctc aaggtccttc acaatggcac cctggctgag    840
ttgcaaggtc taccccacat tagggttttc ctggacaaca atccctgggt ctgcgactgc    900
cacatggcag acatggtgac ctggctcaag gaaacagagg tagtgcaggg caaagaccgg    960
ctcacctgtg catatccgga aaaaatgagg aatcgggtcc tcttggaact caacagtgct   1020
gacctggact gtgacccgat tcttccccca tccctgcaaa cctcttatgt cttcctgggt   1080
attgttttag ccctgatagg cgctattttc ctcctggttt tgtatttgaa ccgcaagggg   1140
ataaaaaagt ggatgcataa catcagagat gcctgcaggg atcacatgga agggtatcat   1200
tacagatatg aaatcaatgc ggaccccaga ttaacgaacc tcagttctaa ctcggatgtc   1260
tga                                                                 1263
```

<210> SEQ ID NO 164
<211> LENGTH: 420
<212> TYPE: PRT
<213> ORGANISM: Homo sapiens

<400> SEQUENCE: 164

```
Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160
```

```
Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Tyr Val Phe Leu Gly Ile Val Leu Ala Leu Ile Gly Ala
        355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420
```

<210> SEQ ID NO 165
<211> LENGTH: 558
<212> TYPE: DNA
<213> ORGANISM: Homo sapiens

<400> SEQUENCE: 165

```
atgggaaaca gctgttacaa catagtagcc actctgttgc tggtcctcaa ctttgagagg      60

acaagatcat tgcaggatcc ttgtagtaac tgcccagctg gtacattctg tgataataac     120

aggaatcaga tttgcagtcc ctgtcctcca aatagtttct ccagcgcagg tggacaaagg     180

acctgtgaca tatgcaggca gtgtaaaggt gttttcagga ccaggaagga gtgttcctcc     240

accagcaatg cagagtgtga ctgcactcca gggtttcact gcctgggggc aggatgcagc     300

atgtgtgaac aggattgtaa acaaggtcaa gaactgacaa aaaaaggttg taaagactgt     360

tgctttggga catttaacga tcagaaacgt ggcatctgtc gaccctggac aaactgttct     420

ttggatggaa agtctgtgct tgtgaatggg acgaaggaga gggacgtggt ctgtggacca     480

tctccagccg acctctctcc gggagcatcc tctgtgaccc cgcctgcccc tgcgagagag     540

ccaggacact ctccgcag                                                   558
```

<210> SEQ ID NO 166
<211> LENGTH: 186
<212> TYPE: PRT
<213> ORGANISM: Homo sapiens

<400> SEQUENCE: 166

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln
            180                 185
```

<210> SEQ ID NO 167
<211> LENGTH: 1065
<212> TYPE: DNA
<213> ORGANISM: Homo sapiens

<400> SEQUENCE: 167

```
atgcctgggg ggtgctcccg gggccccgcc gccggggacg ggcgtctgcg gctggcgcga     60

ctagcgctgg tactcctggg ctgggtctcc tcgtcttctc ccacctcctc ggcatcctcc    120

ttctcctcct cggcgccgtt cctggcttcc gccgtgtccg cccagccccc gctgccggac    180

cagtgccccg cgctgtgcga gtgctccgag gcagcgcgca cagtcaagtg cgttaaccgc    240

aatctgaccg aggtgcccac ggacctgccc gcctacgtgc gcaacctctt ccttaccggc    300

aaccagctgg ccgtgctccc tgccggcgcc ttcgcccgcc ggccgccgct ggcggagctg    360

gccgcgctca acctcagcgg cagccgcctg gacgaggtgc gcgcgggcgc cttcgagcat    420

ctgcccagcc tgcgccagct cgacctcagc cacaacccac tggccgacct cagtcccttc    480

gctttctcgg gcagcaatgc cagcgtctcg gcccccagtc cccttgtgga actgatcctg    540

aaccacatcg tgccccctga agatgagcgg cagaaccgga gcttcgaggg catggtggtg    600

gcggccctgc tggcgggccg tgcactgcag gggctccgcc gcttggagct ggccagcaac    660

cacttccttt acctgccgcg ggatgtgctg gcccaactgc ccagcctcag gcacctggac    720

ttaagtaata attcgctggt gagcctgacc tacgtgtcct tccgcaacct gacacatcta    780

gaaagcctcc acctggagga caatgccctc aaggtccttc acaatggcac cctggctgag    840
```

```
ttgcaaggtc taccccacat tagggttttc ctggacaaca atccctgggt ctgcgactgc    900

cacatggcag acatggtgac ctggctcaag gaaacagagg tagtgcaggg caaagaccgg    960

ctcacctgtg catatccgga aaaaatgagg aatcgggtcc tcttggaact caacagtgct   1020

gacctggact gtgacccgat tcttccccca tccctgcaaa cctct                   1065
```

<210> SEQ ID NO 168
<211> LENGTH: 355
<212> TYPE: PRT
<213> ORGANISM: Homo sapiens

<400> SEQUENCE: 168

```
Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335
```

```
Leu Asn Ser Ala Asp Leu Asp Cys Asp Pro Ile Leu Pro Pro Ser Leu
            340                 345                 350

Gln Thr Ser
        355


<210> SEQ ID NO 169
<211> LENGTH: 744
<212> TYPE: DNA
<213> ORGANISM: ARTIFICIAL SEQUENCE
<220> FEATURE:
<223> OTHER INFORMATION: Made in Lab - Synthesized scFv sequence

<400> SEQUENCE: 169

gacatccaga tgacccagtc tccatcctcc ctgagcgcat ctgtaggaga ccgcgtcacc      60

atcacttgcc gggcaagtca gagcattagc agctatttaa attggtatca gcagaaacca     120

gggaaagccc ctaagctcct gatctatgct gcatccagtt tgcaaagtgg ggtcccatca     180

cgtttcagtg gcagtggaag cgggacagat ttcactctca ccatcagcag tctgcaacct     240

gaagattttg caacttatta ctgtcaacag acttacggtt acctgcacac ttttggccag     300

gggaccaagc tggagatcaa aggcggtgga ggcagcggtg gggtgggtc tggaggcggt      360

ggcagtggcg gcggaggctc tgaggtgcag ctgttggaga gcgggggagg cttggtacag     420

cctgggggt ccctgcgcct ctcctgtgca gccagcggat tcacctttag cagctatgcc      480

atgagctggg tccgccaggc tccagggaag gggctggagt gggtctcagc tattagtggt     540

agtggtggta gcacatacta tgcagactcc gtgaagggcc ggttcaccat ctcccgtgac     600

aattccaaga acacgctgta tctgcaaatg aacagcctgc gtgccgagga cacggctgta     660

tattattgtg cgcgctacta cggtggttac tactctgctt ggatggacta ttggggccag     720

ggaaccctgg tcaccgtctc ctca                                            744


<210> SEQ ID NO 170
<211> LENGTH: 248
<212> TYPE: PRT
<213> ORGANISM: ARTIFICIAL SEQUENCE
<220> FEATURE:
<223> OTHER INFORMATION: Made in Lab - Synthesized scFv sequence

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Leu Glu Ser Gly Gly Gly Leu Val Gln Pro Gly Gly Ser
    130                 135                 140
```

Leu Arg Leu Ser Cys Ala Ala Ser Gly Phe Thr Phe Ser Ser Tyr Ala
145 150 155 160

Met Ser Trp Val Arg Gln Ala Pro Gly Lys Gly Leu Glu Trp Val Ser
165 170 175

Ala Ile Ser Gly Ser Gly Gly Ser Thr Tyr Tyr Ala Asp Ser Val Lys
180 185 190

Gly Arg Phe Thr Ile Ser Arg Asp Asn Ser Lys Asn Thr Leu Tyr Leu
195 200 205

Gln Met Asn Ser Leu Arg Ala Glu Asp Thr Ala Val Tyr Tyr Cys Ala
210 215 220

Arg Tyr Tyr Gly Gly Tyr Tyr Ser Ala Trp Met Asp Tyr Trp Gly Gln
225 230 235 240

Gly Thr Leu Val Thr Val Ser Ser
245

<210> SEQ ID NO 171
<211> LENGTH: 2298
<212> TYPE: DNA
<213> ORGANISM: Artificial Sequence
<220> FEATURE:
<223> OTHER INFORMATION: Made in Lab - anti-5T4 x anti-4-1BB
polynucleotide construct

<400> SEQUENCE: 171
atggaagcac cagcgcagct tctcttcctc ctgctactct ggctcccaga taccaccggt 60
gaggtgcagc tgttggagag cgggggaggc ttggtacagc ctgggggtc cctgcgcctc 120 tcctgtgcag ccagcggatt caccttttct cacggttcta tgtactgggt ccgccaggct 180
ccagggaagg ggctggagtg ggtctcatct atttcttctg gttctggttc tacatactat 240
gcagactccg tgaagggccg gttcaccatc tcccatgaca attccaagaa cacgctgtat 300
ctgcaaatga acagcctgcg tgccgaggac acggctgtat attattgtgc gcgctcttct 360
tactacggtt cttactactc tattgactat tggggccagg gaaccctggt caccgtctcc 420
tcaggtggag gtggctccgg gggtggaggt tccggaggag gcggatcagg tggaggcgga 480
agcgacatcc agatgaccca gtctccatcc tccctgagcg catctgtagg agaccgcgtc 540
accatcactt gccgggcaag tcagagcatt agcagctatt taaattggta tcagcagaaa 600
ccagggaaag cccctaagct cctgatctat gctgcatcca gtttgcaaag tggggtccca 660
tcacgtttca gtggcagtgg aagcgggaca gatttcactc tcaccatcag cagtctacaa 720
cctgaagatt ttgcaactta ttactgtcaa cagtactacg acaacctgcc cacttttggc 780
caggggacca agctggagat caaagagccc aaatcttctg acaaaactca cacatgccca 840
ccgtgcccag cacctgaagc cgcgggtgca ccgtcagtct tcctcttccc cccaaaaccc 900
aaggacaccc tcatgatctc ccggacccct gaggtcacat gcgtggtggt ggacgtgagc 960
cacgaagacc ctgaggtcaa gttcaactgg tacgtggacg gcgtggaggt gcataatgcc 1020
aagacaaagc cgcgggagga gcagtacaac agcacgtacc gtgtggtcag cgtcctcacc 1080
gtcctgcacc aggactggct gaatggcaag gaatacaagt gcgcggtctc caacaaagcc 1140
ctcccagccc ccatcgagaa aaccatctcc aaagccaaag ggcagccccg agaaccacag 1200
gtgtacaccc tgcccccatc ccgggatgag ctgaccaaga accaggtcag cctgacctgc 1260
ctggtcaaag gcttctatcc aagcgacatc gccgtggagt gggagagcaa tgggcagccg 1320
gagaacaact acaagaccac gcctcccgtg ctggactccg acggctcctt cttcctctac 1380

```
agcaagctca ccgtggacaa gagcaggtgg cagcagggga acgtcttctc atgctccgtg   1440

atgcatgagg ctctgcacaa ccactacacg cagaagagcc tctccctgtc tccgggttcc   1500

ggaggtggcg gttcgggagg tggcgggtca ggaggtgggg gatccccttc agaagtgcag   1560

ctgctggagt ccggaggagg actggtgcag cctggcggaa gcctgaggct gagctgcgct   1620

gcctccggct tcacattcag cagctatgct atgagctggg tgaggcaagc ccctggaaag   1680

ggcctggagt gggtgtccgc tatctccggc agcggcggaa gcacctacta cgctgactcc   1740

gtcaagggca ggttcaccat cagccgggac aacagcaaga acaccctgta cctgcagatg   1800

aatagcctca gggctgaaga caccgctgtg tactactgcg ccaggtacta tggcggctac   1860

tactccgcct ggatggacta ctggggacag ggcacactgg tgaccgtgtc cagcggcgga   1920

ggcggctccg gaggcggtgg ctccggagga ggcggaagcg gaggaggagg ctccgatatt   1980

cagatgacac agtcccctag ctccctgtcc gccagcgtgg gagatcgggt gaccatcacc   2040

tgcagggcca gccagtccat ctccagcttc ttaaactggt accagcagaa gcctggaaag   2100

gctcccaagc tgctgatcta cgccgcttcc agcctccaga gcggcgtgcc tagcaggttc   2160

tccggctccg gaagcggaac agacttcacc ctgaccatca gctccctgca gcccgaggac   2220

tccgctacct actactgcca gcagacctat ggctacctgc acaccttcgg ccagggcaca   2280

aagctggaga tcaagcgc                                                 2298
```

<210> SEQ ID NO 172
<211> LENGTH: 766
<212> TYPE: PRT
<213> ORGANISM: Artificial Sequence
<220> FEATURE:
<223> OTHER INFORMATION: Made in Lab - anti-5T4 x anti-4-1BB polypeptide construct

<400> SEQUENCE: 172

```
Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser His Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser His Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190
```

```
Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Glu Pro Lys Ser
            260                 265                 270

Ser Asp Lys Thr His Thr Cys Pro Pro Cys Pro Ala Pro Glu Ala Ala
        275                 280                 285

Gly Ala Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Ala Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Ser Gly Gly Gly Gly Ser Gly Gly Gly Gly Ser Gly Gly
            500                 505                 510

Gly Gly Ser Pro Ser Glu Val Gln Leu Leu Glu Ser Gly Gly Gly Leu
        515                 520                 525

Val Gln Pro Gly Gly Ser Leu Arg Leu Ser Cys Ala Ala Ser Gly Phe
    530                 535                 540

Thr Phe Ser Ser Tyr Ala Met Ser Trp Val Arg Gln Ala Pro Gly Lys
545                 550                 555                 560

Gly Leu Glu Trp Val Ser Ala Ile Ser Gly Ser Gly Gly Ser Thr Tyr
                565                 570                 575

Tyr Ala Asp Ser Val Lys Gly Arg Phe Thr Ile Ser Arg Asp Asn Ser
            580                 585                 590

Lys Asn Thr Leu Tyr Leu Gln Met Asn Ser Leu Arg Ala Glu Asp Thr
        595                 600                 605

Ala Val Tyr Tyr Cys Ala Arg Tyr Tyr Gly Gly Tyr Tyr Ser Ala Trp
```

```
    610                 615                 620

Met Asp Tyr Trp Gly Gln Gly Thr Leu Val Thr Val Ser Ser Gly Gly
625                 630                 635                 640

Gly Gly Ser Gly Gly Gly Gly Ser Gly Gly Gly Gly Ser Gly Gly Gly
                645                 650                 655

Gly Ser Asp Ile Gln Met Thr Gln Ser Pro Ser Ser Leu Ser Ala Ser
            660                 665                 670

Val Gly Asp Arg Val Thr Ile Thr Cys Arg Ala Ser Gln Ser Ile Ser
        675                 680                 685

Ser Phe Leu Asn Trp Tyr Gln Gln Lys Pro Gly Lys Ala Pro Lys Leu
    690                 695                 700

Leu Ile Tyr Ala Ala Ser Ser Leu Gln Ser Gly Val Pro Ser Arg Phe
705                 710                 715                 720

Ser Gly Ser Gly Ser Gly Thr Asp Phe Thr Leu Thr Ile Ser Ser Leu
                725                 730                 735

Gln Pro Glu Asp Ser Ala Thr Tyr Tyr Cys Gln Gln Thr Tyr Gly Tyr
            740                 745                 750

Leu His Thr Phe Gly Gln Gly Thr Lys Leu Glu Ile Lys Arg
        755                 760                 765


<210> SEQ ID NO 173
<211> LENGTH: 2298
<212> TYPE: DNA
<213> ORGANISM: Artificial Sequence
<220> FEATURE:
<223> OTHER INFORMATION: Made in Lab - anti-5T4 x anti-4-1BB
      polynucleotide construct

<400> SEQUENCE: 173

atggaagcac cagcgcagct tctcttcctc ctgctactct ggctcccaga taccaccggt      60

gaggtgcagc tgttggagag cgggggaggc ttggtacagc ctgggggtc cctgcgcctc     120

tcctgtgcag ccagcggatt caccttttct cacggttcta tgtactgggt ccgccaggct     180

ccagggaagg ggctggagtg ggtctcatct atttcttctg gttctggttc tacatactat     240

gcagactccg tgaagggccg gttcaccatc tcccatgaca attccaagaa cacgctgtat     300

ctgcaaatga acagcctgcg tgccgaggac acggctgtat attattgtgc gcgctcttct     360

tactacggtt cttactactc tattgactat tggggccagg gaaccctggt caccgtctcc     420

tcaggtggag gtggctccgg gggtggaggt tccggaggag gcggatcagg tggaggcgga     480

agcgacatcc agatgaccca gtctccatcc tccctgagcg catctgtagg agaccgcgtc     540

accatcactt gccgggcaag tcagagcatt agcagctatt taaattggta tcagcagaaa     600

ccagggaaag cccctaagct cctgatctat gctgcatcca gtttgcaaag tggggtccca     660

tcacgtttca gtggcagtgg aagcgggaca gatttcactc tcaccatcag cagtctacaa     720

cctgaagatt ttgcaactta ttactgtcaa cagtactacg acaacctgcc cacttttggc     780

caggggacca agctggagat caaagagccc aaatcttctg acaaaactca cacatgccca     840

ccgtgcccag cacctgaagc cgcgggtgca ccgtcagtct tcctcttccc cccaaaaccc     900

aaggacaccc tcatgatctc ccggacccct gaggtcacat gcgtggtggt ggacgtgagc     960

cacgaagacc ctgaggtcaa gttcaactgg tacgtggacg gcgtggaggt gcataatgcc    1020

aagacaaagc cgcgggagga gcagtacaac agcacgtacc gtgtggtcag cgtcctcacc    1080

gtcctgcacc aggactggct gaatggcaag gaatacaagt gcgcggtctc caacaaagcc    1140

ctcccagccc ccatcgagaa aaccatctcc aaagccaaag ggcagccccg agaaccacag    1200
```

```
gtgtacaccc tgcccccatc ccgggatgag ctgaccaaga accaggtcag cctgacctgc   1260

ctggtcaaag gcttctatcc aagcgacatc gccgtggagt gggagagcaa tgggcagccg   1320

gagaacaact acaagaccac gcctcccgtg ctggactccg acggctcctt cttcctctac   1380

agcaagctca ccgtggacaa gagcaggtgg cagcagggga acgtcttctc atgctccgtg   1440

atgcatgagg ctctgcacaa ccactacacg cagaagagcc tctccctgtc tccgggttcc   1500

ggaggtggcg gttcgggagg tggcgggtca ggaggtgggg gatccccttc agaagtgcag   1560

ctgctggagt ccggaggagg actggtgcag cctggcggaa gcctgaggct gagctgcgct   1620

gcctccggct tcacattcag cagctatgct atgagctggg tgaggcaagc ccctggaaag   1680

tgcctggagt gggtgtccgc tatctccggc agcggcggaa gcacctacta cgctgactcc   1740

gtcaagggca ggttcaccat cagccgggac aacagcaaga acaccctgta cctgcagatg   1800

aatagcctca gggctgaaga caccgctgtg tactactgcg ccaggtacta tggcggctac   1860

tactccgcct ggatggacta ctggggacag ggcacactgg tgaccgtgtc cagcggcgga   1920

ggcggctccg gaggcggtgg ctccggagga ggcggaagcg gaggaggagg ctccgatatt   1980

cagatgacac agtcccctag ctccctgtcc gccagcgtgg gagatcgggt gaccatcacc   2040

tgcagggcca gccagtccat ctccagcttc ttaaactggt accagcagaa gcctggaaag   2100

gctcccaagc tgctgatcta cgccgcttcc agcctccaga gcggcgtgcc tagcaggttc   2160

tccggctccg gaagcggaac agacttcacc ctgaccatca gctccctgca gcccgaggac   2220

tccgctacct actactgcca gcagacctat ggctacctgc acaccttcgg ctgcggcaca   2280

aagctggaga tcaagcgc                                                 2298
```

<210> SEQ ID NO 174
<211> LENGTH: 766
<212> TYPE: PRT
<213> ORGANISM: Artificial Sequence
<220> FEATURE:
<223> OTHER INFORMATION: Made in Lab - anti-5T4 x anti-4-1BB polypeptide construct

<400> SEQUENCE: 174

```
Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser His Gly Ser Met Tyr Trp Val Arg Gln Ala Pro Gly Lys Gly
    50                  55                  60

Leu Glu Trp Val Ser Ser Ile Ser Ser Gly Ser Gly Ser Thr Tyr Tyr
65                  70                  75                  80

Ala Asp Ser Val Lys Gly Arg Phe Thr Ile Ser His Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Ser Tyr Tyr Gly Ser Tyr Tyr Ser Ile
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160
```

Ser Asp Ile Gln Met Thr Gln Ser Pro Ser Ser Leu Ser Ala Ser Val
165 170 175

Gly Asp Arg Val Thr Ile Thr Cys Arg Ala Ser Gln Ser Ile Ser Ser
180 185 190

Tyr Leu Asn Trp Tyr Gln Gln Lys Pro Gly Lys Ala Pro Lys Leu Leu
195 200 205

Ile Tyr Ala Ala Ser Ser Leu Gln Ser Gly Val Pro Ser Arg Phe Ser
210 215 220

Gly Ser Gly Ser Gly Thr Asp Phe Thr Leu Thr Ile Ser Ser Leu Gln
225 230 235 240

Pro Glu Asp Phe Ala Thr Tyr Tyr Cys Gln Gln Tyr Tyr Asp Asn Leu
245 250 255

Pro Thr Phe Gly Gln Gly Thr Lys Leu Glu Ile Lys Glu Pro Lys Ser
260 265 270

Ser Asp Lys Thr His Thr Cys Pro Pro Cys Pro Ala Pro Glu Ala Ala
275 280 285

Gly Ala Pro Ser Val Phe Leu Phe Pro Pro Lys Pro Lys Asp Thr Leu
290 295 300

Met Ile Ser Arg Thr Pro Glu Val Thr Cys Val Val Val Asp Val Ser
305 310 315 320

His Glu Asp Pro Glu Val Lys Phe Asn Trp Tyr Val Asp Gly Val Glu
325 330 335

Val His Asn Ala Lys Thr Lys Pro Arg Glu Glu Gln Tyr Asn Ser Thr
340 345 350

Tyr Arg Val Val Ser Val Leu Thr Val Leu His Gln Asp Trp Leu Asn
355 360 365

Gly Lys Glu Tyr Lys Cys Ala Val Ser Asn Lys Ala Leu Pro Ala Pro
370 375 380

Ile Glu Lys Thr Ile Ser Lys Ala Lys Gly Gln Pro Arg Glu Pro Gln
385 390 395 400

Val Tyr Thr Leu Pro Pro Ser Arg Asp Glu Leu Thr Lys Asn Gln Val
405 410 415

Ser Leu Thr Cys Leu Val Lys Gly Phe Tyr Pro Ser Asp Ile Ala Val
420 425 430

Glu Trp Glu Ser Asn Gly Gln Pro Glu Asn Asn Tyr Lys Thr Thr Pro
435 440 445

Pro Val Leu Asp Ser Asp Gly Ser Phe Phe Leu Tyr Ser Lys Leu Thr
450 455 460

Val Asp Lys Ser Arg Trp Gln Gln Gly Asn Val Phe Ser Cys Ser Val
465 470 475 480

Met His Glu Ala Leu His Asn His Tyr Thr Gln Lys Ser Leu Ser Leu
485 490 495

Ser Pro Gly Ser Gly Gly Gly Gly Ser Gly Gly Gly Gly Ser Gly Gly
500 505 510

Gly Gly Ser Pro Ser Glu Val Gln Leu Leu Glu Ser Gly Gly Gly Leu
515 520 525

Val Gln Pro Gly Gly Ser Leu Arg Leu Ser Cys Ala Ala Ser Gly Phe
530 535 540

Thr Phe Ser Ser Tyr Ala Met Ser Trp Val Arg Gln Ala Pro Gly Lys
545 550 555 560

Cys Leu Glu Trp Val Ser Ala Ile Ser Gly Ser Gly Gly Ser Thr Tyr
565 570 575

```
Tyr Ala Asp Ser Val Lys Gly Arg Phe Thr Ile Ser Arg Asp Asn Ser
            580                 585                 590

Lys Asn Thr Leu Tyr Leu Gln Met Asn Ser Leu Arg Ala Glu Asp Thr
        595                 600                 605

Ala Val Tyr Tyr Cys Ala Arg Tyr Tyr Gly Gly Tyr Tyr Ser Ala Trp
    610                 615                 620

Met Asp Tyr Trp Gly Gln Gly Thr Leu Val Thr Val Ser Ser Gly Gly
625                 630                 635                 640

Gly Gly Ser Gly Gly Gly Gly Ser Gly Gly Gly Gly Ser Gly Gly Gly
                645                 650                 655

Gly Ser Asp Ile Gln Met Thr Gln Ser Pro Ser Ser Leu Ser Ala Ser
            660                 665                 670

Val Gly Asp Arg Val Thr Ile Thr Cys Arg Ala Ser Gln Ser Ile Ser
        675                 680                 685

Ser Phe Leu Asn Trp Tyr Gln Gln Lys Pro Gly Lys Ala Pro Lys Leu
    690                 695                 700

Leu Ile Tyr Ala Ala Ser Ser Leu Gln Ser Gly Val Pro Ser Arg Phe
705                 710                 715                 720

Ser Gly Ser Gly Ser Gly Thr Asp Phe Thr Leu Thr Ile Ser Ser Leu
                725                 730                 735

Gln Pro Glu Asp Ser Ala Thr Tyr Tyr Cys Gln Gln Thr Tyr Gly Tyr
            740                 745                 750

Leu His Thr Phe Gly Cys Gly Thr Lys Leu Glu Ile Lys Arg
        755                 760                 765
```

<210> SEQ ID NO 175
<211> LENGTH: 2298
<212> TYPE: DNA
<213> ORGANISM: Artificial Sequence
<220> FEATURE:
<223> OTHER INFORMATION: Made in Lab - anti-5T4 x anti-4-1BB
      polynucleotide construct

<400> SEQUENCE: 175

```
atggaagcac cagcgcagct tctcttcctc ctgctactct ggctcccaga taccaccggt     60

gaggtgcagc tgttggagag cgggggaggc ttggtacagc ctggggggtc cctgcgcctc    120

tcctgtgcag ccagcggatt caccttttct cacggttcta tgtactgggt ccgccaggct    180

ccagggaagg ggctggagtg ggtctcatct atttcttctg gttctggttc tacatactat    240

gcagactccg tgaagggccg gttcaccatc tcccatgaca attccaagaa cacgctgtat    300

ctgcaaatga acagcctgcg tgccgaggac acggctgtat attattgtgc gcgctcttct    360

tactacggtt cttactactc tattgactat tggggccagg gaaccctggt caccgtctcc    420

tcaggtggag gtggctccgg gggtggaggt tccggaggag gcggatcagg tggaggcgga    480

agcgacatcc agatgaccca gtctccatcc tccctgagcg catctgtagg agaccgcgtc    540

accatcactt gccgggcaag tcagagcatt agcagctatt taaattggta tcagcagaaa    600

ccagggaaag cccctaagct cctgatctat gctgcatcca gtttgcaaag tggggtccca    660

tcacgtttca gtggcagtgg aagcgggaca gatttcactc tcaccatcag cagtctacaa    720

cctgaagatt ttgcaactta ttactgtcaa cagtactacg acaacctgcc cacttttggc    780

caggggacca agctggagat caaagagccc aaatcttctg acaaaactca cacatgccca    840

ccgtgcccag cacctgaagc cgcgggtgca ccgtcagtct tcctcttccc cccaaaaccc    900

aaggacaccc tcatgatctc ccggacccct gaggtcacat gcgtggtggt ggacgtgagc    960
```

cacgaagacc ctgaggtcaa gttcaactgg tacgtggacg gcgtggaggt gcataatgcc 1020
aagacaaagc cgcgggagga gcagtacaac agcacgtacc gtgtggtcag cgtcctcacc 1080
gtcctgcacc aggactggct gaatggcaag gaatacaagt gcgcggtctc caacaaagcc 1140
ctcccagccc ccatcgagaa aaccatctcc aaagccaaag ggcagccccg agaaccacag 1200
gtgtacaccc tgcccccatc ccgggatgag ctgaccaaga accaggtcag cctgacctgc 1260
ctggtcaaag gcttctatcc aagcgacatc gccgtggagt gggagagcaa tgggcagccg 1320
gagaacaact acaagaccac gcctcccgtg ctggactccg acggctcctt cttcctctac 1380
agcaagctca ccgtggacaa gagcaggtgg cagcagggga acgtcttctc atgctccgtg 1440
atgcatgagg ctctgcacaa ccactacacg cagaagagcc tctccctgtc tccgggttcc 1500
ggaggtggcg gttcgggagg tggcgggtca ggaggtgggg gatccccttc agaagtgcag 1560
ctgctggagt ccggaggagg actggtgcag cctggcggaa gcctgaggct gagctgcgct 1620
gcctccggct tcacattcag cagctatgct atgagctggg tgaggcaagc ccctggaaag 1680
ggcctggagt gggtgtccgc tatctccggc agcggcggaa gcacctacta cgctgactcc 1740
gtcaagggca ggttcaccat cagccgggac aacagcaaga acaccctgta cctgcagatg 1800
aatagcctca gggctgaaga caccgctgtg tactactgcg ccaggtacta tggcggctac 1860
tactccgcct ggatggacta ctggggacag ggcacactgg tgaccgtgtc cagcggcgga 1920
ggcggctccg gaggcggtgg ctccggagga ggcggaagcg gaggaggagg ctccgatatt 1980
cagatgacac agtcccctag ctccctgtcc gccagcgtgg gagatcgggt gaccatcacc 2040
tgcagggcca gccagtccat ctccagctat ttaaactggt accagcagaa gcctggaaag 2100
gctcccaagc tgctgatcta cgccgcttcc agcctccaga gcggcgtgcc tagcaggttc 2160
tccggctccg gaagcggaac agacttcacc ctgaccatca gctccctgca gcccgaggac 2220
tccgctacct actactgcca gcagacctat ggctacctgc acaccttcgg ccagggcaca 2280
aagctggaga tcaagcgc 2298

<210> SEQ ID NO 176
<211> LENGTH: 766
<212> TYPE: PRT
<213> ORGANISM: Artificial Sequence
<220> FEATURE:
<223> OTHER INFORMATION: Made in Lab - anti-5T4 x anti-4-1BB polypeptide construct

<400> SEQUENCE: 176

Met Glu Ala Pro Ala Gln Leu Leu Phe Leu Leu Leu Leu Trp Leu Pro
1 5 10 15

Asp Thr Thr Gly Glu Val Gln Leu Leu Glu Ser Gly Gly Gly Leu Val
20 25 30

Gln Pro Gly Gly Ser Leu Arg Leu Ser Cys Ala Ala Ser Gly Phe Thr
35 40 45

Phe Ser His Gly Ser Met Tyr Trp Val Arg Gln Ala Pro Gly Lys Gly
50 55 60

Leu Glu Trp Val Ser Ser Ile Ser Ser Gly Ser Gly Ser Thr Tyr Tyr
65 70 75 80

Ala Asp Ser Val Lys Gly Arg Phe Thr Ile Ser His Asp Asn Ser Lys
85 90 95

Asn Thr Leu Tyr Leu Gln Met Asn Ser Leu Arg Ala Glu Asp Thr Ala
100 105 110

Val Tyr Tyr Cys Ala Arg Ser Ser Tyr Tyr Gly Ser Tyr Tyr Ser Ile

-continued

```
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Ser Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Tyr Tyr Asp Asn Leu
                245                 250                 255

Pro Thr Phe Gly Gln Gly Thr Lys Leu Glu Ile Lys Glu Pro Lys Ser
            260                 265                 270

Ser Asp Lys Thr His Thr Cys Pro Pro Cys Pro Ala Pro Glu Ala Ala
        275                 280                 285

Gly Ala Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Ala Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Ser Gly Gly Gly Gly Ser Gly Gly Gly Gly Ser Gly Gly
            500                 505                 510

Gly Gly Ser Pro Ser Glu Val Gln Leu Leu Glu Ser Gly Gly Gly Leu
        515                 520                 525

Val Gln Pro Gly Gly Ser Leu Arg Leu Ser Cys Ala Ala Ser Gly Phe
    530                 535                 540
```

Thr Phe Ser Ser Tyr Ala Met Ser Trp Val Arg Gln Ala Pro Gly Lys
545 550 555 560

Gly Leu Glu Trp Val Ser Ala Ile Ser Gly Ser Gly Gly Ser Thr Tyr
565 570 575

Tyr Ala Asp Ser Val Lys Gly Arg Phe Thr Ile Ser Arg Asp Asn Ser
580 585 590

Lys Asn Thr Leu Tyr Leu Gln Met Asn Ser Leu Arg Ala Glu Asp Thr
595 600 605

Ala Val Tyr Tyr Cys Ala Arg Tyr Tyr Gly Gly Tyr Tyr Ser Ala Trp
610 615 620

Met Asp Tyr Trp Gly Gln Gly Thr Leu Val Thr Val Ser Ser Gly Gly
625 630 635 640

Gly Gly Ser Gly Gly Gly Gly Ser Gly Gly Gly Gly Ser Gly Gly Gly
645 650 655

Gly Ser Asp Ile Gln Met Thr Gln Ser Pro Ser Ser Leu Ser Ala Ser
660 665 670

Val Gly Asp Arg Val Thr Ile Thr Cys Arg Ala Ser Gln Ser Ile Ser
675 680 685

Ser Tyr Leu Asn Trp Tyr Gln Gln Lys Pro Gly Lys Ala Pro Lys Leu
690 695 700

Leu Ile Tyr Ala Ala Ser Ser Leu Gln Ser Gly Val Pro Ser Arg Phe
705 710 715 720

Ser Gly Ser Gly Ser Gly Thr Asp Phe Thr Leu Thr Ile Ser Ser Leu
725 730 735

Gln Pro Glu Asp Ser Ala Thr Tyr Tyr Cys Gln Gln Thr Tyr Gly Tyr
740 745 750

Leu His Thr Phe Gly Gln Gly Thr Lys Leu Glu Ile Lys Arg
755 760 765

<210> SEQ ID NO 177
<211> LENGTH: 10
<212> TYPE: PRT
<213> ORGANISM: Artificial Sequence
<220> FEATURE:
<223> OTHER INFORMATION: ACN017 CDRH1 Sequence

<400> SEQUENCE: 177

Ala Lys Gly Ser Gly Ser Tyr Phe Asp Leu
1 5 10

<210> SEQ ID NO 178
<211> LENGTH: 9
<212> TYPE: PRT
<213> ORGANISM: Artificial Sequence
<220> FEATURE:
<223> OTHER INFORMATION: ACN017 CDRL3

<400> SEQUENCE: 178

Gln Gln Tyr Ser Gly Tyr Pro Tyr Thr
1 5

<210> SEQ ID NO 179
<211> LENGTH: 117
<212> TYPE: PRT
<213> ORGANISM: Artificial Sequence
<220> FEATURE:
<223> OTHER INFORMATION: ACN017 VH

<400> SEQUENCE: 179

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Ser Gly Ser Tyr Phe Asp Leu Trp Gly Gln Gly Thr Leu
100 105 110

Val Thr Val Ser Ser
115

<210> SEQ ID NO 180
<211> LENGTH: 107
<212> TYPE: PRT
<213> ORGANISM: Artificial Sequence
<220> FEATURE:
<223> OTHER INFORMATION: ACN017 VL

<400> SEQUENCE: 180

Asp Ile Gln Met Thr Gln Ser Pro Ser Phe Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Ser Gly Tyr Pro Tyr
85 90 95

Thr Phe Gly Gln Gly Thr Lys Leu Glu Ile Lys
100 105

<210> SEQ ID NO 181
<211> LENGTH: 741
<212> TYPE: PRT
<213> ORGANISM: Artificial Sequence
<220> FEATURE:
<223> OTHER INFORMATION: ACN017 Full

<400> SEQUENCE: 181

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

-continued

```
Leu Gln Met Asn Ser Leu Arg Ala Glu Asp Thr Ala Val Tyr Tyr Cys
                85                  90                  95

Ala Lys Gly Ser Gly Ser Tyr Phe Asp Leu Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Phe Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Tyr Ser Gly Tyr Pro Tyr Thr Phe Gly Gln Gly Thr Lys
225                 230                 235                 240

Leu Glu Ile Lys Ser Ser Glu Pro Lys Ser Ser Asp Lys Thr His Thr
                245                 250                 255

Cys Pro Pro Cys Pro Ala Pro Glu Ala Ala Gly Ala Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Ala Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Ser Gly Gly
465                 470                 475                 480

Gly Gly Ser Gly Gly Gly Gly Ser Gly Gly Gly Gly Ser Pro Ser Glu
                485                 490                 495
```

-continued

```
Val Gln Leu Leu Glu Ser Gly Gly Gly Leu Val Gln Pro Gly Gly Ser
            500                 505                 510

Leu Arg Leu Ser Cys Ala Ala Ser Gly Phe Thr Phe Ser Ser Tyr Ala
        515                 520                 525

Met Ser Trp Val Arg Gln Ala Pro Gly Lys Gly Leu Glu Trp Val Ser
    530                 535                 540

Ala Ile Ser Gly Ser Gly Gly Ser Thr Tyr Tyr Ala Asp Ser Val Lys
545                 550                 555                 560

Gly Arg Phe Thr Ile Ser Arg Asp Asn Ser Lys Asn Thr Leu Tyr Leu
                565                 570                 575

Gln Met Asn Ser Leu Arg Ala Glu Asp Thr Ala Val Tyr Tyr Cys Ala
            580                 585                 590

Lys Gly Ser Gly Ser Tyr Phe Asp Leu Trp Gly Gln Gly Thr Leu Val
        595                 600                 605

Thr Val Ser Ser Gly Gly Gly Gly Ser Gly Gly Gly Gly Ser Gly Gly
    610                 615                 620

Gly Gly Ser Gly Gly Gly Gly Ser Asp Ile Gln Met Thr Gln Ser Pro
625                 630                 635                 640

Ser Phe Leu Ser Ala Ser Val Gly Asp Arg Val Thr Ile Thr Cys Arg
                645                 650                 655

Ala Ser Gln Ser Ile Ser Ser Tyr Leu Asn Trp Tyr Gln Gln Lys Pro
            660                 665                 670

Gly Lys Ala Pro Lys Leu Leu Ile Tyr Ala Ala Ser Ser Leu Gln Ser
        675                 680                 685

Gly Val Pro Ser Arg Phe Ser Gly Ser Gly Ser Gly Thr Asp Phe Thr
    690                 695                 700

Leu Thr Ile Ser Ser Leu Gln Pro Glu Asp Phe Ala Thr Tyr Tyr Cys
705                 710                 715                 720

Gln Gln Tyr Ser Gly Tyr Pro Tyr Thr Phe Gly Gln Gly Thr Lys Leu
                725                 730                 735

Glu Ile Lys Arg Ser
            740
```

ONCOFETAL ANTIGEN BINDING PROTEINS AND RELATED COMPOSITIONS AND METHODS

CROSS-REFERENCE TO RELATED APPLICATIONS

This application claims priority to U.S. Provisional Application Nos. 62/535,107, filed on Jul. 20, 2017; 62/575,820, filed on Oct. 23, 2017; and 62/648,072, filed on Mar. 26, 2018, the contents of which are each incorporated herein by reference in their entireties.

DESCRIPTION OF THE TEXT FILE SUBMITTED ELECTRONICALLY

The contents of the text file submitted electronically herewith are incorporated herein by reference in their entirety. A computer readable format copy of the Sequence Listing (filename: APVO_057_03US_SeqList_ST25.txt, date recorded: Jul. 20, 2018, file size: 260 kilobytes).

FIELD OF THE DISCLOSURE

The present disclosure relates to molecules that specifically bind to trophoblast glycoprotein (5T4). The molecules may have at least one humanized 5T4-binding domain. These molecules are useful for the characterization or treatment of disorders characterized by expression of 5T4, such as cancer. A protein therapeutic binding to 5T4 may be a monospecific protein therapeutic or a multispecific protein therapeutic. The disclosure also relates to protein therapeutics that specifically bind to tumor necrosis factor receptor superfamily member 9 (4-1BB or CD137). A multispecific protein therapeutic may bind both 5T4-expressing cells and 4-1BB expressed on effector cells to enhance effector cell activation, proliferation, and/or effector-cell mediated cytotoxicity.

BACKGROUND OF THE DISCLOSURE

5T4 (also designated trophoblast glycoprotein, TPBG, M6P1 and Waif1) is a well-defined tumor-associated antigen (TAA) originally identified by Professor Peter Stern, University of Manchester (Hole and Stern, 1988). It is an oncofetal antigen expressed in a high proportion of patients in a variety of malignancies, including non-small cell lung, renal, pancreas, prostate, breast, colorectal, gastric, ovarian and cervix cancers as well as in acute lymphocytic leukemia, and has also been shown to be expressed in tumor-initiating cells (Castro et al., 2012; Damelin et al., 2011; Elkord et al., 2009; Southall et al., 1990).

Although low levels of 5T4 expression have been detected in some healthy tissue, such as the placenta and specialized epithelia, expression levels in tumors are considerably higher.

Data suggest that 5T4 regulates the functional activity of CXCR4 (Castro et al., 2012; Southgate et al., 2010). 5T4 binding antibodies or 5T4 knock-down resulted in inhibition of CXCR4-mediated cellular migration, a pathway involved in tumor growth and metastasis. Therefore, targeting 5T4 may provide therapeutic benefits in the treatment of various cancers. Currently there are no FDA approved therapeutics that specifically target or bind 5T4. There is a need for new therapeutics to treat malignancies in which 5T4 is expressed.

4-1BB (also known as CD137 or TNFRSF9) is a tumor necrosis factor (TNF) receptor (TNFR) superfamily member. 4-1BB is expressed on various cell populations including activated $CD4^+$ and $CD8^+$ T cells, regulatory T cells (Treg), dendritic cells (DC), monocytes, mast cells, eosinophils and tumor endothelial cells. Activation of 4-1BB is dependent on receptor oligomerization (Rabu et al., 2005; Wyzgol et al., 2009) induced by binding to 4-1BBL (also known as CD137L), which is expressed as a trimer on the cell surface of antigen presenting cells (APCs) and other cell types. 4-1BB activation on $CD8^+$ T cells sustains and augments $CD8^+$ T cell effector functions and preferentially supports Th1 cytokine production (Shuford et al., 1997; Lee et al., 2002; Pulle et al., 2006). 4-1BB activation on $CD4^+$ T cells, 4-1BB stimulation initially results in activation and later in activation-induced cell death, which is thought to explain why 4-1BB agonistic antibodies have shown therapeutic effect in tumor immunity as well as in autoimmunity (Zhang, J C I, 2007; Sun, Trends Mol Med, 2003). 4-1BB activation has also been reported to suppress Treg function or convert Tregs to cytotoxic $CD4^+$ T-cells (Akhmetzyanova et al., 2016; So et al., 2008).

In addition to expression on and modulation of T cell effector function, 4-1BB is upregulated on CD16- and cytokine-activated natural killer (NK) cells. Activation of 4-1BB has been shown to increase antibody-dependent cellular cytotoxicity (ADCC) activity of NK cells in both murine and human cells (Kohrt 2012 and 2014 J Clin Invest, reviewed by Hout 2012, Oncoimm). Further, activation of 4-1BB expressed on APCs, such as DCs and macrophages may also induce and/or modulate immune activation.

The role of 4-1BB in the modulation of immune cell activation suggests that it may be a desirable immunotherapy target in the treatment of multiple cancer types. Indeed, two 4-1BB antibodies are in clinical development: Urelumab (BMS-66513) developed by Bristol-Myers Squibb and PF-05082566 developed by Pfizer. Phase I and II studies in various indications are ongoing for each of the antibodies. However, liver and skin toxicities have been observed in patients and murine models upon 4-1BB activation (Ascierto et al., 2010; Dubrot et al., 2010; Niu et al., 2007). Further, a Phase II study with Urelumab as a second line therapy in metastatic melanoma was terminated in 2009 due to liver toxicity (Garber et al., 2011; Li and Liu, 2013).

Therefore, there remains a need in the art for therapeutics that safely and effectively activate 4-1BB for use in the treatment of oncologic indications.

SUMMARY OF THE DISCLOSURE

In some aspects, the disclosure relates to multispecific polypeptides that specifically bind to 5T4 and/or 4-1BB. In some embodiments, a 5T4-binding domain of the disclosure binds to an extracellular domain of human 5T4. In certain embodiments, a 4-1BB-binding domain of the disclosure binds to an extracellular domain of human 4-1BB. In some embodiments, the disclosure provides a multispecific polypeptide comprising a 5T4-binding domain that specifically binds to human 5T4 and a 4-1BB-binding domain, wherein said 5T4-binding domain comprises: (i) an immunoglobulin heavy chain variable region comprising HCDR1, HCDR2, and HCDR3, and (ii) an immunoglobulin light chain variable region comprising LCDR1, LCDR2, and LCDR3, wherein (a) the HCDR1 comprises an amino acid sequence of SEQ ID NO: 30; (b) the HCDR2 comprises an amino acid sequence of SEQ ID NO: 32; (c) the HCDR3 comprises an amino acid sequence of SEQ ID NO: 34; (d) the LCDR1 comprises an amino acid sequence of SEQ ID NO: 42; (e) the LCDR2 comprises an amino acid sequence of SEQ ID NO: 10; and (f) the LCDR3 comprises an amino acid sequence of SEQ ID NO: 36. In some embodiments, the 5T4-binding domain comprising the CDR sequences recited above comprises a heavy chain variable region comprising an amino acid sequence having at least 90%, at least 95%, or at least 97% identity to a sequence selected from the group consisting of SEQ ID NOs: 38 and 46. In certain embodiments, the 5T4-binding domain comprises a heavy chain variable region comprising an amino acid sequence selected from the group consisting of SEQ ID NOs: 38 and 46. In other embodiments, the 5T4-binding domain comprising the CDR sequences recited above comprises a light chain variable region comprising an amino acid sequence having at least 90%, at least 95%, or at least 97% identity to a sequence selected from the group consisting of SEQ ID NOs: 44, 48, and 50. In some embodiments, the 5T4-binding domain comprises a light chain variable region comprising an amino acid sequence selected from the group consisting of SEQ ID NOs: 44, 48, and 50. In other embodiments, the 5T4-binding domain comprising the CDR sequences recited above comprises i) a heavy chain variable region comprising an amino acid sequence having at least 90%, at least 95%, or at least 97% identity to SEQ ID NO: 38 and a light chain variable region comprising an amino acid sequence having at least 90%, at least 95%, or at least 97% identity to SEQ ID NO: 44; or ii) a heavy chain variable region comprising an amino acid sequence having at least 90%, at least 95%, or at least 97% identity to SEQ ID NO: 46 and a light chain variable region comprising an amino acid sequence having at least 90%, at least 95%, or at least 97% identity to SEQ ID NO: 48; or iii) a heavy chain variable region comprising an amino acid sequence having at least 90%, at least 95%, or at least 97% identity to SEQ ID NO: 46 and a light chain variable region comprising an amino acid sequence having at least 90%, at least 95%, or at least 97% identity to SEQ ID NO: 5. In some embodiments, the 5T4-binding domain comprises i) a heavy chain variable region comprising an amino acid sequence of SEQ ID NO: 38 and a light chain variable region comprising an amino acid sequence of SEQ ID NO: 44; or ii) a heavy chain variable region comprising an amino acid sequence of SEQ ID NO: 46 and a light chain variable region comprising an amino acid sequence of SEQ ID NO: 48; or iii) a heavy chain variable region comprising an amino acid sequence of SEQ ID NO: 46 and a light chain variable region comprising an amino acid sequence of SEQ ID NO: 50.

In certain aspects, the disclosure includes a multispecific polypeptide comprising a 5T4-binding domain that specifically binds to human 5T4 and a 4-1BB-binding domain that specifically binds to human 4-1BB, wherein each of the 4-1BB-binding domain and 5T4 binding domain comprise (i) an immunoglobulin heavy chain variable region (VH) comprising HCDR1, HCDR2, and HCDR3; and (ii) an immunoglobulin light chain variable region (VL) comprising LCDR1, LCDR2, and LCDR3, wherein the VH and/or the VL region of the 5T4-binding domain comprise one or more mutations in the framework region; and wherein the 5T4-binding domain comprises (a) the HCDR1 comprising an amino acid sequence of SEQ ID NO: 30; (b) the HCDR2 comprising an amino acid sequence of SEQ ID NO: 32; (c) the HCDR3 comprising an amino acid sequence of SEQ ID NO: 34; (d) the LCDR1 comprising an amino acid sequence of SEQ ID NO: 8; (e) the LCDR2 comprising an amino acid sequence of SEQ ID NO: 10; and (f) the LCDR3 comprising an amino acid sequence of SEQ ID NO: 36. In some embodiments, the 5T4-binding domain comprising the CDR sequences recited above comprises a heavy chain variable region comprising an amino acid sequence having at least 90%, at least 95%, or at least 97% identity to SEQ ID NOs: 38. In one embodiment, the 5T4-binding domain comprises a heavy chain variable region comprising an amino acid sequence of SEQ ID NO: 38. In some embodiments, the 5T4-binding domain comprising the CDR sequences recited above comprises a light chain variable region comprising an amino acid sequence having at least 90%, at least 95%, or at least 97% identity to SEQ ID NO: 40. In certain embodiments, the 5T4-binding domain comprises a light chain variable region comprising an amino acid sequence of SEQ ID NO: 40. In some embodiments, the 5T4-binding domain comprising the CDR sequences recited above comprises a heavy chain variable region comprising an amino acid sequence having at least 90%, at least 95%, or at least 97% identity to SEQ ID NO: 38 and a light chain variable region comprising an amino acid sequence having at least 90%, at least 95%, or at least 97% identity to SEQ ID NO: 40. In some embodiments, 5T4-binding domain comprises a heavy chain variable region comprising an amino acid sequence of SEQ ID NO: 38 and a light chain variable region comprising an amino acid sequence of SEQ ID NO: 40.

The disclosure further provides a multispecific polypeptide comprising a 5T4-binding domain that specifically binds to human 5T4 and a 4-1BB-binding domain that specifically binds to human 4-1BB, wherein each of the 4-1BB-binding domain and 5T4 binding domain comprise (i) an immunoglobulin heavy chain variable region (VH) comprising HCDR1, HCDR2, and HCDR3; and (ii) an immunoglobulin light chain variable region (VL) comprising LCDR1, LCDR2, and LCDR3, wherein the VH and/or the VL region of the 4-1BB-binding domain comprise one or more mutations in the framework region; and wherein the 5T4-binding domain comprises (a) the HCDR1 comprising an amino acid sequence of SEQ ID NO: 30; (b) the HCDR2 comprising an amino acid sequence of SEQ ID NO: 32; c) the HCDR3 comprising an amino acid sequence of SEQ ID NO: 34; (d) the LCDR1 comprising an amino acid sequence of SEQ ID NO: 42; (e) the LCDR2 comprising an amino acid sequence of SEQ ID NO: 10; and (f) the LCDR3 comprising an amino acid sequence of SEQ ID NO: 36. In some embodiments, the 5T4-binding domain comprising the CDR sequences recited above comprises a heavy chain variable region comprising an amino acid sequence having at least 90%, at least 95%, or at least 97% identity to a sequence selected from the group consisting of SEQ ID NOs: 38 and 46. In certain embodiments, the 5T4-binding domain comprises a heavy chain variable region comprising an amino acid sequence selected from the group consisting of SEQ ID NOs: 38 and 46. In some embodiments, the 5T4-binding domain comprising the CDR sequences recited above comprises a light chain variable region comprising an amino acid sequence having at least 90%, at least 95%, or at least 97% identity to a sequence selected from the group consisting of SEQ ID NOs: 44, 48, and 50. In some aspects, the 5T4-binding domain comprises a light chain variable region comprising an amino acid sequence selected from the group consisting of SEQ ID NOs: 44, 48, and 50. In certain embodiments, the 5T4-binding domain comprising the CDR sequences recited above comprises i) a heavy chain variable region comprising an amino acid sequence having at least 90%, at least 95%, or at least 97% identity to SEQ ID NO: 38 and a light chain variable region comprising an amino acid sequence having at least 90%, at least 95%, or at least 97% identity to SEQ ID NO: 44; or ii) a heavy chain variable region comprising an amino acid sequence having at least 90%, at least 95%, or at least 97% identity to SEQ ID NO:

46 and a light chain variable region comprising an amino acid sequence having at least 90%, at least 95%, or at least 97% identity to SEQ ID NO: 48; or iii) a heavy chain variable region comprising an amino acid sequence having at least 90%, at least 95%, or at least 97% identity to SEQ ID NO: 46 and a light chain variable region comprising an amino acid sequence having at least 90%, at least 95%, or at least 97% identity to SEQ ID NO: 50. In some embodiments, the 5T4-binding domain comprises i) a heavy chain variable region comprising an amino acid sequence of SEQ ID NO: 38 and a light chain variable region comprising an amino acid sequence of SEQ ID NO: 44; or ii) a heavy chain variable region comprising an amino acid sequence of SEQ ID NO: 46 and a light chain variable region comprising an amino acid sequence of SEQ ID NO: 48; or iii) a heavy chain variable region comprising an amino acid sequence of SEQ ID NO: 46 and a light chain variable region comprising an amino acid sequence of SEQ ID NO: 50.

In some aspects, the disclosure provides a multispecific polypeptide comprising a 5T4-binding domain that specifically binds to human 5T4 and a 4-1BB-binding domain that specifically binds to human 4-1BB, wherein each of the 4-1BB-binding domain and 5T4 binding domain comprise (i) an immunoglobulin heavy chain variable region (VH) comprising HCDR1, HCDR2, and HCDR3; and (ii) an immunoglobulin light chain variable region (VL) comprising LCDR1, LCDR2, and LCDR3, wherein the VH and/or the VL region of the 4-1BB-binding domain comprise one or more mutations in the framework region; and wherein the 5T4-binding domain comprises (a) the HCDR1 comprising an amino acid sequence of SEQ ID NO: 52; (b) the HCDR2 comprising an amino acid sequence of SEQ ID NO: 32; (c) the HCDR3 comprising an amino acid sequence of SEQ ID NO: 34; (d) the LCDR1 comprising an amino acid sequence of SEQ ID NO: 54; (e) the LCDR2 comprising an amino acid sequence of SEQ ID NO: 10; and (f) the LCDR3 comprising an amino acid sequence of SEQ ID NO: 36. In certain embodiments, the 5T4-binding domain comprising the CDR sequences recited above comprises a heavy chain variable region comprising an amino acid sequence having at least 90%, at least 95%, or at least 97% identity to SEQ ID NO: 56. In some aspects, the 5T4-binding domain comprises a heavy chain variable region comprising an amino acid sequence of SEQ ID NO: 56. In certain embodiments, the 5T4-binding domain comprising the CDR sequences recited above comprises a light chain variable region comprising an amino acid sequence having at least 90%, at least 95%, or at least 97% identity to SEQ ID NOs: 58. In some embodiments, the 5T4-binding domain comprises a light chain variable region comprising an amino acid sequence of SEQ ID NOs: 58. In certain embodiments, the 5T4-binding domain comprising the CDR sequences recited above comprises a heavy chain variable region comprising an amino acid sequence having at least 90%, at least 95%, or at least 97% identity to SEQ ID NO: 56 and a light chain variable region comprising an amino acid sequence having at least 90%, at least 95%, or at least 97% identity to SEQ ID NO: 58. In some embodiments, the 5T4-binding domain comprises a heavy chain variable region comprising an amino acid sequence of SEQ ID NO: 56 and a light chain variable region comprising an amino acid sequence of SEQ ID NO: 58.

The disclosure also provides a multispecific polypeptide comprising a 5T4-binding domain that specifically binds to human 5T4 and a 4-1BB-binding domain that specifically binds to human 4-1BB, wherein each of the 4-1BB-binding domain and 5T4 binding domain comprise (i) an immunoglobulin heavy chain variable region (VH) comprising HCDR1, HCDR2, and HCDR3; and (ii) an immunoglobulin light chain variable region (VL) comprising LCDR1, LCDR2, and LCDR3, wherein the VH and/or the VL region of the 4-1BB-binding domain comprise one or more mutations in the framework region; and wherein the 5T4-binding domain comprises (a) the HCDR1 comprising an amino acid sequence of SEQ ID NO: 60; (b) the HCDR2 comprising an amino acid sequence of SEQ ID NO: 62; (c) the HCDR3 comprising an amino acid sequence of SEQ ID NO: 34; (d) the LCDR1 comprising an amino acid sequence of SEQ ID NO: 54; (e) the LCDR2 comprising an amino acid sequence of SEQ ID NO: 10; and (f) the LCDR3 comprising an amino acid sequence of SEQ ID NO: 36. In certain embodiments, the 5T4-binding domain comprising the CDR sequences recited above comprises a heavy chain variable region comprising an amino acid sequence having at least 90%, at least 95%, or at least 97% identity to SEQ ID NO: 64. In some embodiments, the 5T4-binding domain comprises a heavy chain variable region comprising an amino acid sequence of SEQ ID NO: 64. In certain aspects, the 5T4-binding domain comprising the CDR sequences recited above comprises a light chain variable region comprising an amino acid sequence having at least 90%, at least 95%, or at least 97% identity to SEQ ID NOs: 58. In some embodiments, the 5T4-binding domain comprises a light chain variable region comprising an amino acid sequence of SEQ ID NOs: 58. In certain embodiments, the 5T4-binding domain comprising the CDR sequences recited above comprises a heavy chain variable region comprising an amino acid sequence having at least 90%, at least 95%, or at least 97% identity to SEQ ID NO: 64 and a light chain variable region comprising an amino acid sequence having at least 90%, at least 95%, or at least 97% identity to SEQ ID NO: 58. In some embodiments, the 5T4-binding domain comprises a heavy chain variable region comprising an amino acid sequence of SEQ ID NO: 64 and a light chain variable region comprising an amino acid sequence of SEQ ID NO: 58.

In certain aspects, the disclosure provides a multispecific polypeptide comprising a 4-1BB-binding domain that specifically binds to human 4-1BB. The disclosure also provides a multispecific polypeptide comprising a 4-1BB-binding domain and a 5T4-binding domain, wherein the 4-1BB-binding domain is linked to the 5T4-binding domain via a binding domain linker. In some embodiments, a multispecific polypeptide comprises, from amino-terminus to carboxyl-terminus, (i) a 5T4-binding domain, (ii) a binding domain linker, and (iii) a 4-1BB-binding domain. In certain aspects, the 5T4-binding domain is a single chain variable fragment (scFv). In some embodiments, the light chain variable region of said scFv is carboxy-terminal to the heavy chain variable region of said scFv. In other embodiments, the light chain variable region of said scFv is amino-terminal to the heavy chain variable region of said scFv. In certain aspects, the scFv comprises a linker polypeptide. In some examples, the linker polypeptide is between the light chain variable region and the heavy chain variable region of said scFv. In certain embodiments, the linker polypeptide comprises a $Gly_4Ser$ linker. In some embodiments, the linker polypeptide comprises the formula $(Gly_4Ser)_n$, wherein n=1-5. In some aspects, the linker polypeptide comprises an amino acid sequence selected from SEQ ID NOs: 85-108. In certain embodiments, the linker polypeptide comprises an amino acid sequence set forth in SEQ ID NO: 98 (GGGGSGGGGSGGGGSGGGGS).

In certain embodiments, an scFv comprising the CDR sequences recited above comprises a sequence having at least 80%, at least 85%, at least 90%, or at least 95% identity to an amino acid sequence selected from the group consisting of SEQ ID NOs: 118, 120, 122, 124, 126, 128, 130, 132, 134, and 170. In some embodiments, an scFv comprises an amino acid sequence selected from the group consisting of SEQ ID NOs: 118, 120, 122, 124, 126, 128, 130, 132, 134, and 170.

In some aspects, the disclosure provides a multispecific polypeptide comprising a 4-1BB-binding domain that specifically binds to human 4-1BB and a 5T4-binding domain, wherein said 4-1BB-binding domain comprises: (i) an immunoglobulin heavy chain variable region (VH) comprising HCDR1, HCDR2, and HCDR3, and (ii) an immunoglobulin light chain variable region (VL) comprising LCDR1, LCDR2, and LCDR3, wherein (a) the HCDR1 comprises an amino acid sequence of SEQ ID NO: 2; (b) the HCDR2 comprises an amino acid sequence of SEQ ID NO: 4; (c) the HCDR3 comprises an amino acid sequence of SEQ ID NO: 6; (d) the LCDR1 comprises an amino acid sequence of SEQ ID NO: 8; (e) the LCDR2 comprises an amino acid sequence of SEQ ID NO: 10; and (f) the LCDR3 comprises an amino acid sequence of SEQ ID NO: 12. In certain embodiments, the 4-1BB-binding domain comprising the CDR sequences recited above comprises a heavy chain variable region comprising an amino acid sequence having at least 90%, at least 95%, or at least 97% identity to SEQ ID NO: 14. In some embodiments, the 4-1BB-binding domain comprises a heavy chain variable region comprising an amino acid sequence of SEQ ID NO: 14. In certain embodiments, the 4-1BB-binding domain comprising the CDR sequences recited above comprises a light chain variable region comprising an amino acid sequence having at least 90%, at least 95%, or at least 97% identity to SEQ ID NO: 16. In some embodiments, the 4-1BB-binding domain comprises a light chain variable region comprising an amino acid sequence of SEQ ID NO: 16. In certain embodiments, the 4-1BB-binding domain comprising the CDR sequences recited above comprises a heavy chain variable region comprising an amino acid sequence having at least 90%, at least 95%, or at least 97% identity to SEQ ID NO: 14 and a light chain variable region comprising an amino acid sequence having at least 90%, at least 95%, or at least 97% identity to SEQ ID NO: 16. In some aspects, the 4-1BB-binding domain comprises a heavy chain variable region comprising an amino acid sequence of SEQ ID NO: 14 and a light chain variable region comprising an amino acid sequence of SEQ ID NO: 16.

The disclosure further provides a multispecific polypeptide comprising a 5T4-binding domain that specifically binds to human 5T4 and a 4-1BB-binding domain, wherein the 4-1BB-binding domain comprises (i) an immunoglobulin heavy chain variable region (VH) comprising HCDR1, HCDR2, and HCDR3; and (ii) an immunoglobulin light chain variable region (VL) comprising LCDR1, LCDR2, and LCDR3, and wherein the VH and/or the VL region of the 4-1BB-binding domain comprise one or more mutations in the framework region, and wherein the 4-1BB-binding domain comprises (a) the HCDR1 comprising an amino acid sequence of SEQ ID NO: 18; (b) the HCDR2 comprising an amino acid sequence of SEQ ID NO: 4; (c) the HCDR3 comprising an amino acid sequence of SEQ ID NO: 6; (d) the LCDR1 comprising an amino acid sequence of SEQ ID NO: 8; (e) the LCDR2 comprising an amino acid sequence of SEQ ID NO: 10; and (f) the LCDR3 comprising an amino acid sequence of SEQ ID NO: 12. In certain embodiments, the 4-1BB-binding domain comprising the CDR sequences recited above comprises a heavy chain variable region comprising an amino acid sequence having at least 90%, at least 95%, or at least 97% identity to SEQ ID NO: 20. In some embodiments, the 4-1BB-binding domain comprises a heavy chain variable region comprising an amino acid sequence of SEQ ID NO: 20. In certain embodiments, the 4-1BB-binding domain comprising the CDR sequences recited above comprises a light chain variable region comprising an amino acid sequence having at least 90%, at least 95%, or at least 97% identity to SEQ ID NO: 22. In some embodiments, the 4-1BB-binding domain comprises a light chain variable region comprising an amino acid sequence of SEQ ID NO: 22. In certain embodiments, the 4-1BB-binding domain comprising the CDR sequences recited above comprises a heavy chain variable region comprising an amino acid sequence having at least 90%, at least 95%, or at least 97% identity to SEQ ID NO: 20 and a light chain variable region comprising an amino acid sequence having at least 90%, at least 95%, or at least 97% identity to SEQ ID NO: 22. In some embodiments, the 4-1BB-binding domain comprises a heavy chain variable region comprising an amino acid sequence of SEQ ID NO: 20 and a light chain variable region comprising an amino acid sequence of SEQ ID NO: 22.

The disclosure also provides a multispecific polypeptide comprising a 5T4-binding domain that specifically binds to human 5T4 and a 4-1BB-binding domain, wherein the 4-1BB-binding domain comprises (i) an immunoglobulin heavy chain variable region ($V_H$) comprising HCDR1, HCDR2, and HCDR3; and (ii) an immunoglobulin light chain variable region ($V_L$) comprising LCDR1, LCDR2, and LCDR3, and wherein the $V_H$ and/or the $V_L$ region of the 4-1BB-binding domain comprise one or more mutations in the framework region, and wherein the 4-1BB-binding domain comprises (a) the HCDR1 comprising an amino acid sequence of SEQ ID NO: 24; (b) the HCDR2 comprising an amino acid sequence of SEQ ID NO: 4; (c) the HCDR3 comprising an amino acid sequence of SEQ ID NO: 6; (d) the LCDR1 comprising an amino acid sequence of SEQ ID NO: 8; (e) the LCDR2 comprising an amino acid sequence of SEQ ID NO: 10; and (f) the LCDR3 comprising an amino acid sequence of SEQ ID NO: 12. In certain embodiments, the 4-1BB-binding domain comprising the CDR sequences recited above comprises a heavy chain variable region comprising an amino acid sequence having at least 90%, at least 95%, or at least 97% identity to SEQ ID NO: 26. In some embodiments, the 4-1BB-binding domain comprises a heavy chain variable region comprising an amino acid sequence of SEQ ID NO: 26. In certain embodiments, the 4-1BB-binding domain comprising the CDR sequences recited above comprises a light chain variable region comprising an amino acid sequence having at least 90%, at least 95%, or at least 97% identity to SEQ ID NO: 16. In some embodiments, the 4-1BB-binding domain comprises a light chain variable region comprising an amino acid sequence of SEQ ID NO: 16. In certain embodiments, the 4-1BB-binding domain comprising the CDR sequences recited above comprises a heavy chain variable region comprising an amino acid sequence having at least 90%, at least 95%, or at least 97% identity to SEQ ID NO: 26 and a light chain variable region comprising an amino acid sequence having at least 90%, at least 95%, or at least 97% identity to SEQ ID NO: 16. In some embodiments, the 4-1BB-binding domain comprises a heavy chain variable region comprising an amino acid sequence of SEQ ID NO: 26 and a light chain variable region comprising an amino acid sequence of SEQ ID NO: 16.

In certain embodiments, the disclosure provides a multispecific polypeptide comprising a 4-1BB-binding domain wherein the 4-1BB-binding domain is a single chain variable fragment (scFv). In some aspects, the light chain variable region of said scFv is carboxy-terminal to the heavy chain variable region of said scFv. In other aspects, the light chain variable region of said scFv is amino-terminal to the heavy chain variable region of said scFv. In certain aspects, the scFv comprises a linker polypeptide. In some examples, the linker polypeptide is between the light chain variable region and the heavy chain variable region of said scFv. In certain embodiments, the linker polypeptide comprises a $Gly_4Ser$ linker. In some embodiments, the linker polypeptide comprises the formula $(Gly_4Ser)_n$, wherein n=1-5. In some aspects, the linker polypeptide comprises an amino acid sequence selected from SEQ ID NOs: 85-108. In certain embodiments, the linker polypeptide comprises an amino acid sequence set forth in SEQ ID NO: 98 (GGGGSGGGGSGGGGSGGGGS). In certain aspects, a multispecific polypeptide of the disclosure comprises a 4-1BB-binding domain that is linked to a 5T4-binding domain via a binding domain linker. In some embodiments, a multispecific polypeptide comprises, from amino-terminus to carboxyl-terminus, (i) the 5T4-binding domain, (ii) a binding domain linker, and (iii) the 4-1BB-binding domain.

In some embodiments, the 4-1BB-binding domain comprising the CDR sequences recited above comprises a sequence having at least 80%, at least 85%, at least 90%, or at least 95% identity to an amino acid sequence selected from the group consisting of SEQ ID NOs: 110, 112, 114, and 116. In certain embodiments, the 4-1BB-binding domain comprises a sequence selected from the group consisting of SEQ ID NOs: 110, 112, 114, and 116.

In certain aspects, a multispecific polypeptide of the disclosure comprises a 4-1BB-binding domain that is conjugated to a drug or a toxin.

The disclosure further provides a multispecific polypeptide comprising a 5T4-binding domain that is fused or conjugated to an immunoglobulin constant region. An immunoglobulin constant region may be a human Fc domain. In some embodiments, the human Fc domain comprises a sequence set forth in SEQ ID NO: 158 or SEQ ID NO: 160. In certain embodiments, the disclosure provides a multispecific polypeptide that comprises, from amino-terminus to carboxyl-terminus, (i) a 5T4-binding domain, (ii) a hinge region, (iii) an immunoglobulin constant region, (iv) a binding domain linker, and (v) a 4-1BB-binding domain. In some embodiments, the binding domain linker comprises a $Gly_4Ser$ sequence. In some examples, the binding domain linker comprises the formula $(Gly_4Ser)_n$, wherein n=1-5. In some aspects, the binding domain linker comprises an amino acid sequence selected from SEQ ID NOs: 85-108. In certain embodiments, the binding domain linker comprises an amino acid sequence set forth in SEQ ID NO: 107 (SGGGGSGGGGSGGGGSPS).

In some aspects, the disclosure also provides a multispecific polypeptide comprising a first scFv domain and a second scFv domain, wherein the first and second scFv domains are linked together by a binding domain linker or a binding domain linker and an immunoglobulin Fc domain, wherein the immunoglobulin Fc domain comprises a hinge region and an immunoglobulin constant region; and wherein the second scFv domain specifically binds to human 4-1BB and comprises: (i) an immunoglobulin heavy chain variable region comprising an HCDR1 amino acid sequence selected from the group consisting of SEQ ID NOs: 2, 18, 24, an HCDR2 amino acid sequence of SEQ ID NO: 4, and an HCDR3 amino acid sequence of SEQ ID NOs: 6; and (ii) an immunoglobulin light chain variable region comprising an LCDR1 amino acid sequence of SEQ ID NOs: 8, an LCDR2 amino acid sequence of SEQ ID NO: 10, and an LCDR3 amino acid sequence of SEQ ID NO: 12, wherein the first and second scFv domains are linked together by a binding domain linker or a binding domain linker and an immunoglobulin Fc domain, wherein the immunoglobulin Fc domain comprises a hinge region and an immunoglobulin constant region. In certain embodiments, this polypeptide comprises an amino acid sequence comprising at least 80%, at least 85%, at least 90%, or at least 95% sequence identity to a sequence selected from the group consisting of SEQ ID NOs: 136, 138, 140, 142, 144, 146, 148, 150, 152, 154, and 156. In some aspects, the polypeptide comprises an amino acid sequence selected from the group consisting of SEQ ID NOs: 136, 138, 140, 142, 144, 146, 148, 150, 152, 154, and 156. In some embodiments, the polypeptide comprises an amino acid sequence selected from the group consisting of SEQ ID NOs: 136, 138, and 146.

In some embodiments, the multispecific polypeptide comprises, from amino-terminus to carboxyl-terminus, (i) the first scFv domain, (ii) a binding domain linker, and (iii) the second binding domain. In other embodiments, the multispecific polypeptide comprises, from amino-terminus to carboxyl-terminus, (i) the second scFv domain, (ii) a binding domain linker, and (iii) the first scFv domain. In certain aspects, the multispecific polypeptide comprises, from amino-terminus to carboxyl-terminus, (i) the first scFv domain, (ii) a hinge region, (iii) an immunoglobulin constant region, (iv) a binding domain linker, and (v) the second scFv domain. In some embodiments, the binding domain linker comprises a $Gly_4Ser$ sequence. In some embodiments, the binding domain linker comprises the formula $(Gly_4Ser)_n$, wherein n=1-5. In certain aspects, the binding domain linker comprises an amino acid sequence selected from SEQ ID NOs: 85-108. In certain embodiments, the binding domain linker comprises an amino acid sequence set forth in SEQ ID NO: 107 (SGGGGSGGGGSGGGGSPS). In some embodiments, the second scFv domain of a multispecific polypeptide comprises: (a) the HCDR1 amino acid sequence set forth in SEQ ID NO: 2; (b) the HCDR2 amino acid sequence set forth in SEQ ID NO: 4; (c) the HCDR3 amino acid sequence set forth in SEQ ID NO: 6; (d) the LCDR1 amino acid sequence set forth in SEQ ID NO: 8; (e) the LCDR2 amino acid sequence set forth in SEQ ID NO: 10; and (f) the LCDR3 amino acid sequence set forth in SEQ ID NO: 12. In other embodiments, the second scFv domain of a multispecific polypeptide comprises: (a) the HCDR1 amino acid sequence set forth in SEQ ID NO: 24; (b) the HCDR2 amino acid sequence set forth in SEQ ID NO: 4; (c) the HCDR3 amino acid sequence set forth in SEQ ID NO: 6; (d) the LCDR1 amino acid sequence set forth in SEQ ID NO: 8; (e) the LCDR2 amino acid sequence set forth in SEQ ID NO: 10; and (f) the LCDR3 amino acid sequence set forth in SEQ ID NO: 12. In some embodiments, the second scFv domain of a multispecific polypeptide comprises a heavy chain variable region comprising an amino acid sequence of SEQ ID NO: 14 and a light chain variable region of SEQ ID NO: 16. In other embodiments, the second scFv domain of a multispecific polypeptide comprises a heavy chain variable region comprising an amino acid sequence of SEQ ID NO: 20 and a light chain variable region of SEQ ID NO: 22. In some embodiments, the second scFv domain of a multispecific polypeptide comprises a heavy chain variable region comprising an amino acid sequence of SEQ ID NO: 26 and a light chain variable region of SEQ ID NO: 16. In other embodiments, the second scFv domain of a multispecific polypeptide comprises a heavy chain variable region comprising an amino acid sequence of SEQ ID NO: 28 and a light chain variable region of SEQ ID NO: 16.

The disclosure further provides a multispecific polypeptide comprising a first scFv domain and a second scFv domain, wherein the first and second scFv domains are linked together by a binding domain linker or a binding domain linker and an immunoglobulin Fc domain, wherein the immunoglobulin Fc domain comprises a hinge region and an immunoglobulin constant region; wherein the second scFv domain specifically binds to human 4-1BB; and wherein the first scFv domain comprises (i) an immunoglobulin heavy chain variable region comprising an HCDR1 amino acid sequence selected from the group consisting of SEQ ID NOs: 30, 52, and 60, an HCDR2 amino acid sequence selected from the group consisting of SEQ ID NOs: 32 and 62, and an HCDR3 amino acid sequence of SEQ ID NO: 34; and (ii) an immunoglobulin light chain variable region comprising an LCDR1 amino acid sequence selected from the group consisting of SEQ ID NOs: 8, 42, and 54, an LCDR2 amino acid sequence of SEQ ID NOs: 10, and an LCDR3 amino acid sequence of SEQ ID NOs: 36; and wherein the second scFv domain comprises (i) an immunoglobulin heavy chain variable region comprising an HCDR1 amino acid sequence selected from the group consisting of SEQ ID NOs: 2, 18, 24, an HCDR2 amino acid sequence selected of SEQ ID NO: 4, and an HCDR3 amino acid sequence of SEQ ID NO: 6; and (ii) an immunoglobulin light chain variable region comprising an LCDR1 amino acid sequence of SEQ ID NO: 8, an LCDR2 amino acid sequence of SEQ ID NO: 10, and an LCDR3 amino acid sequence of SEQ ID NO: 12, wherein the first and second scFv domains are linked together by a binding domain linker or a binding domain linker and an immunoglobulin Fc domain, wherein the immunoglobulin Fc domain comprises a hinge region and an immunoglobulin constant region. In some embodiments, the second scFv domain comprises (a) the HCDR1 amino acid sequence set forth in SEQ ID NO: 2; (b) the HCDR2 amino acid sequence set forth in SEQ ID NO: 4; (c) the HCDR3 amino acid sequence set forth in SEQ ID NO: 6; (d) the LCDR1 amino acid sequence set forth in SEQ ID NO: 8; (e) the LCDR2 amino acid sequence set forth in SEQ ID NO: 10; and (f) the LCDR3 amino acid sequence set forth in SEQ ID NO: 12. In certain embodiments, the first scFv domain comprises: (a) the HCDR1 amino acid sequence set forth in SEQ ID NO: 30; (b) the HCDR2 amino acid sequence set forth in SEQ ID NO: 32; (c) the HCDR3 amino acid sequence set forth in SEQ ID NO: 34; (d) the LCDR1 amino acid sequence set forth in SEQ ID NO: 8; (e) the LCDR2 amino acid sequence set forth in SEQ ID NO: 10; and (f) the LCDR3 amino acid sequence set forth in SEQ ID NO: 36. In some embodiments, the first scFv domain comprises: (a) the HCDR1 amino acid sequence set forth in SEQ ID NO: 30; (b) the HCDR2 amino acid sequence set forth in SEQ ID NO: 32; (c) the HCDR3 amino acid sequence set forth in SEQ ID NO: 34; (d) the LCDR1 amino acid sequence set forth in SEQ ID NO: 42; (e) the LCDR2 amino acid sequence set forth in SEQ ID NO: 10; and (f) the LCDR3 amino acid sequence set forth in SEQ ID NO: 36. In certain aspects, the first scFv domain comprises: (a) the HCDR1 amino acid sequence set forth in SEQ ID NO: 30; (b) the HCDR2 amino acid sequence set forth in SEQ ID NO: 32; (c) the HCDR3 amino acid sequence set forth in SEQ ID NO: 34; (d) the LCDR1 amino acid sequence set forth in SEQ ID NO: 42; (e) the LCDR2 amino acid sequence set forth in SEQ ID NO: 10; and (f) the LCDR3 amino acid sequence set forth in SEQ ID NO: 36. In some embodiments, the first scFv domain comprises: (a) the HCDR1 amino acid sequence set forth in SEQ ID NO: 52; (b) the HCDR2 amino acid sequence set forth in SEQ ID NO: 32; (c) the HCDR3 amino acid sequence set forth in SEQ ID NO: 34; (d) the LCDR1 amino acid sequence set forth in SEQ ID NO: 54; (e) the LCDR2 amino acid sequence set forth in SEQ ID NO: 10; and (f) the LCDR3 amino acid sequence set forth in SEQ ID NO: 36. In some embodiments, the first scFv domain comprises: (a) the HCDR1 amino acid sequence set forth in SEQ ID NO: 60; (b) the HCDR2 amino acid sequence set forth in SEQ ID NO: 62; (c) the HCDR3 amino acid sequence set forth in SEQ ID NO: 34; (d) the LCDR1 amino acid sequence set forth in SEQ ID NO: 54; (e) the LCDR2 amino acid sequence set forth in SEQ ID NO: 10; and (f) the LCDR3 amino acid sequence set forth in SEQ ID NO: 36. In certain embodiments, the second scFv domain comprises: (a) the HCDR1 amino acid sequence set forth in SEQ ID NO: 18; (b) the HCDR2 amino acid sequence set forth in SEQ ID NO: 4; (c) the HCDR3 amino acid sequence set forth in SEQ ID NO: 6; (d) the LCDR1 amino acid sequence set forth in SEQ ID NO: 8; (e) the LCDR2 amino acid sequence set forth in SEQ ID NO: 10; and (f) the LCDR3 amino acid sequence set forth in SEQ ID NO: 12. In some embodiments, the first scFv domain comprises: (a) the HCDR1 amino acid sequence set forth in SEQ ID NO: 30; (b) the HCDR2 amino acid sequence set forth in SEQ ID NO: 32; (c) the HCDR3 amino acid sequence set forth in SEQ ID NO: 34; (d) the LCDR1 amino acid sequence set forth in SEQ ID NO: 42; (e) the LCDR2 amino acid sequence set forth in SEQ ID NO: 10; and (f) the LCDR3 amino acid sequence set forth in SEQ ID NO: 36. In some embodiments, the second scFv domain comprises: (a) the HCDR1 amino acid sequence set forth in SEQ ID NO: 24; (b) the HCDR2 amino acid sequence set forth in SEQ ID NO: 4; (c) the HCDR3 amino acid sequence set forth in SEQ ID NO: 6; (d) the LCDR1 amino acid sequence set forth in SEQ ID NO: 8; (e) the LCDR2 amino acid sequence set forth in SEQ ID NO: 10; and (f) the LCDR3 amino acid sequence set forth in SEQ ID NO: 12. In some embodiments, the first scFv domain comprises: (a) the HCDR1 amino acid sequence set forth in SEQ ID NO: 52; (b) the HCDR2 amino acid sequence set forth in SEQ ID NO: 32; (c) the HCDR3 amino acid sequence set forth in SEQ ID NO: 34; (d) the LCDR1 amino acid sequence set forth in SEQ ID NO: 54; (e) the LCDR2 amino acid sequence set forth in SEQ ID NO: 10; and (f) the LCDR3 amino acid sequence set forth in SEQ ID NO: 36. In some embodiments, the second scFv domain comprises: (a) the HCDR1 amino acid sequence set forth in SEQ ID NO: 24; (b) the HCDR2 amino acid sequence set forth in SEQ ID NO: 4; (c) the HCDR3 amino acid sequence set forth in SEQ ID NO: 6; (d) the LCDR1 amino acid sequence set forth in SEQ ID NO: 8; (e) the LCDR2 amino acid sequence set forth in SEQ ID NO: 10; and (f) the LCDR3 amino acid sequence set forth in SEQ ID NO: 12, and, optionally, the first scFv domain comprises: (a) the HCDR1 amino acid sequence set forth in SEQ ID NO: 30; (b) the HCDR2 amino acid sequence set forth in SEQ ID NO: 32; (c) the HCDR3 amino acid sequence set forth in SEQ ID NO: 34; (d) the LCDR1 amino acid sequence set forth in SEQ ID NO: 8; (e) the LCDR2 amino acid sequence set forth in SEQ ID NO: 10; and (f) the LCDR3 amino acid sequence set forth in SEQ ID NO: 36.

The disclosure also provides a multispecific polypeptide wherein a first scFv domain comprises i) a heavy chain variable region comprising an amino acid sequence of SEQ ID NO: 38 and a light chain variable region comprising an amino acid of SEQ ID NO: 40, and wherein a second scFv domain comprises ii) a heavy chain variable region comprising an amino acid of SEQ ID NO: 14 and a light chain variable region of SEQ ID NO: 16. In some embodiments, the first scFv domain comprises i) a heavy chain variable region comprising an amino acid sequence of SEQ ID NO: 38 and a light chain variable region comprising an amino acid of SEQ ID NO: 44, and the second scFv domain comprises ii) a heavy chain variable region comprising an amino acid of SEQ ID NO: 14 and a light chain variable region of SEQ ID NO: 16. In certain embodiments, the first scFv domain comprises i) a heavy chain variable region comprising an amino acid sequence of SEQ ID NO: 46 and a light chain variable region comprising an amino acid of SEQ ID NO: 48, and the second scFv domain comprises ii) a heavy chain variable region comprising an amino acid of SEQ ID NO: 14 and a light chain variable region of SEQ ID NO: 16. In other embodiments, the first scFv domain comprises i) a heavy chain variable region comprising an amino acid sequence of SEQ ID NO: 56 and a light chain variable region comprising an amino acid of SEQ ID NO: 58, and the second scFv domain comprises ii) a heavy chain variable region comprising an amino acid of SEQ ID NO: 14 and a light chain variable region of SEQ ID NO: 16. In certain embodiments, the first scFv domain comprises i) a heavy chain variable region comprising an amino acid sequence of SEQ ID NO: 64 and a light chain variable region comprising an amino acid of SEQ ID NO: 58, and the second scFv domain comprises ii) a heavy chain variable region comprising an amino acid of SEQ ID NO: 14 and a light chain variable region of SEQ ID NO: 16. In other embodiments, the first scFv domain comprises i) a heavy chain variable region comprising an amino acid sequence of SEQ ID NO: 46 and a light chain variable region comprising an amino acid of SEQ ID NO: 50, and the second scFv domain comprises ii) a heavy chain variable region comprising an amino acid of SEQ ID NO: 20 and a light chain variable region of SEQ ID NO: 22. In yet other embodiments, the first scFv domain comprises i) a heavy chain variable region comprising an amino acid sequence of SEQ ID NO: 56 and a light chain variable region comprising an amino acid of SEQ ID NO: 58, and the second scFv domain comprises ii) a heavy chain variable region comprising an amino acid of SEQ ID NO: 26 and a light chain variable region of SEQ ID NO: 16. In some embodiments, the first scFv domain comprises i) a heavy chain variable region comprising an amino acid sequence of SEQ ID NO: 38 and a light chain variable region comprising an amino acid of SEQ ID NO: 68, and the second scFv domain comprises ii) a heavy chain variable region comprising an amino acid of SEQ ID NO: 28 and a light chain variable region of SEQ ID NO: 16. In some embodiments, the first scFv domain comprises i) a heavy chain variable region comprising an amino acid sequence of SEQ ID NO: 46 and a light chain variable region comprising an amino acid of SEQ ID NO: 70, and the second scFv domain comprises ii) a heavy chain variable region comprising an amino acid of SEQ ID NO: 28 and a light chain variable region of SEQ ID NO: 16.

In some embodiments, the present disclosure provides a multispecific polypeptide comprising a first scFv domain and a second scFv domain, wherein the first and second scFv domains are linked together by a binding domain linker or a binding domain linker and an immunoglobulin Fc domain, wherein the immunoglobulin Fc domain comprises a hinge region and an immunoglobulin constant region; and wherein the first scFv domain specifically binds to human 5T4 and comprises: (i) an immunoglobulin heavy chain variable region comprising an HCDR1 amino acid sequence of SEQ ID NO: 30, an HCDR2 amino acid sequence of SEQ ID NO: 32, and an HCDR3 amino acid sequence of SEQ ID NO: 34; and (ii) an immunoglobulin light chain variable region comprising an LCDR1 amino acid sequence of SEQ ID NO: 42, an LCDR2 amino acid sequence of SEQ ID NO: 10, and an LCDR3 amino acid sequence of SEQ ID NO: 36.

In some embodiments, the first scFv domain comprises: i) a heavy chain variable region comprising an amino acid sequence of SEQ ID NO: 38 and a light chain variable region comprising an amino acid sequence of SEQ ID NO: 44; or ii) a heavy chain variable region comprising an amino acid sequence of SEQ ID NO: 46 and a light chain variable region comprising an amino acid sequence of SEQ ID NO: 48; or iii) a heavy chain variable region comprising an amino acid sequence of SEQ ID NO: 46 and a light chain variable region comprising an amino acid sequence of SEQ ID NO: 50.

In some embodiments, the present disclosure provides a multispecific polypeptide comprising a first scFv domain and a second scFv domain, wherein the first and second scFv domains are linked together by a binding domain linker or a binding domain linker and an immunoglobulin Fc domain, wherein the immunoglobulin Fc domain comprises a hinge region and an immunoglobulin constant region; and wherein the first scFv domain specifically binds to human 5T4, wherein the VH and/or the VL region of the second scFv domain comprise one or more mutations in the framework region; and wherein the first scFv domain comprises: (a) the HCDR1 comprising an amino acid sequence of SEQ ID NO: 30; (b) the HCDR2 comprising an amino acid sequence of SEQ ID NO: 32; (c) the HCDR3 comprising an amino acid sequence of SEQ ID NO: 34; (d) the LCDR1 comprising an amino acid sequence of SEQ ID NO: 42; (e) the LCDR2 comprising an amino acid sequence of SEQ ID NO: 10; and (f) the LCDR3 comprising an amino acid sequence of SEQ ID NO: 36. In some embodiments, the first scFv domain comprises i) a heavy chain variable region comprising an amino acid sequence of SEQ ID NO: 38 and a light chain variable region comprising an amino acid sequence of SEQ ID NO: 44; or ii) a heavy chain variable region comprising an amino acid sequence of SEQ ID NO: 46 and a light chain variable region comprising an amino acid sequence of SEQ ID NO: 48; or iii) a heavy chain variable region comprising an amino acid sequence of SEQ ID NO: 46 and a light chain variable region comprising an amino acid sequence of SEQ ID NO: 50.

In some embodiments, the multispecific polypeptides described herein comprise, from amino-terminus to carboxyl-terminus, (i) the first scFv domain, (ii) a binding domain linker, and (iii) the second binding domain. In some embodiments, the multispecific polypeptides comprise, from amino-terminus to carboxyl-terminus, (i) the second scFv domain, (ii) a binding domain linker, and (iii) the first scFv domain. In some embodiments, the multispecific polypeptides comprise, from amino-terminus to carboxyl-terminus, (i) the first scFv domain, (ii) a hinge region, (iii) an immunoglobulin constant region, (iv) a binding domain linker, and (v) the second scFv domain. In some embodiments, the binding domain linker comprises a $Gly_4Ser$ sequence. In some embodiments, the binding domain linker comprises the formula $(Gly_4Ser)_n$, wherein n=1-5. In some embodiments, the binding domain linker comprises an amino acid sequence selected from SEQ ID NOs: 85-108. In some embodiments, the binding domain linker comprises an amino acid sequence set forth in SEQ ID NO: 107 (SGGGGSGGGGSGGGGSPS).

In certain aspects, the first scFv domain of a multispecific polypeptide of the disclosure specifically binds to human 5T4 and comprises an amino acid sequence selected from the group consisting of SEQ ID NOs: 118, 120, 122, 124, 126, 128, 130, 132, 134, and 170; and the second scFv domain specifically binds to human 4-1BB and comprises an amino acid sequence selected from the group consisting of SEQ ID NO: 110, 112, 114, and 116. In some embodiments, the first scFv domain comprises an amino acid sequence set forth in SEQ ID NO: 118 and the second scFv domain comprises an amino acid sequence set forth in SEQ ID NO: 110. In other embodiments, the first scFv domain comprises an amino acid sequence set forth in SEQ ID NO: 120 and the second scFv domain comprises an amino acid sequence set forth in SEQ ID NO: 110. In certain embodiments, the first scFv domain comprises an amino acid sequence set forth in SEQ ID NO: 122 and the second scFv domain comprises an amino acid sequence set forth in SEQ ID NO: 110. In some embodiments, the first scFv domain comprises an amino acid sequence set forth in SEQ ID NO: 124 and the second scFv domain comprises an amino acid sequence set forth in SEQ ID NO: 112. In some embodiments, the first scFv domain comprises an amino acid sequence set forth in SEQ ID NO: 126 and the second scFv domain comprises an amino acid sequence set forth in SEQ ID NO: 114. In other embodiments, the first scFv domain comprises an amino acid sequence set forth in SEQ ID NO: 126 and the second scFv domain comprises an amino acid sequence set forth in SEQ ID NO: 110. In certain embodiments, the first scFv domain comprises an amino acid sequence set forth in SEQ ID NO: 128 and the second scFv domain comprises an amino acid sequence set forth in SEQ ID NO: 110. In some embodiments, the first scFv domain comprises an amino acid sequence set forth in SEQ ID NO: 170 and the second scFv domain comprises an amino acid sequence set forth in SEQ ID NO: 116. In some embodiments, the first scFv domain comprises an amino acid sequence set forth in SEQ ID NO: 130 and the second scFv domain comprises an amino acid sequence set forth in SEQ ID NO: 116. In some embodiments, the first scFv domain comprises an amino acid sequence set forth in SEQ ID NO: 132 and the second scFv domain comprises an amino acid sequence set forth in SEQ ID NO: 116. In other embodiments, the first scFv domain comprises an amino acid sequence set forth in SEQ ID NO: 134 and the second scFv domain comprises an amino acid sequence set forth in SEQ ID NO: 116. In some embodiments, the disclosure provides a multispecific polypeptide, wherein the polypeptide comprises an amino acid sequence comprising at least 80%, at least 85%, at least 90%, or at least 95% sequence identity to a sequence selected from the group consisting of SEQ ID NOs: 136, 138, 140, 142, 144, 146, 148, 150, 152, 154, 156, 172, 174, and 176. In some embodiments, the polypeptide comprises an amino acid sequence selected from the group consisting of SEQ ID NOs: 136, 138, 140, 142, 144, 146, 148, 150, 152, 154, 156, 172, 174, and 176.

In some embodiments, the disclosure provides a multispecific polypeptide that specifically binds to 5T4 and 4-1BB, wherein the polypeptide comprises an amino acid sequence comprising at least 80%, at least 85%, at least 90%, or at least 95% sequence identity to a sequence selected from the group consisting of SEQ ID NOs: 136, 138, 140, 142, 144, 146, 148, 150, 152, 154, 156, 172, 174, and 176. In certain embodiments, the polypeptide that specifically binds to 5T4 and 4-1BB comprises an amino acid sequence comprising at least 80%, at least 85%, at least 90%, or at least 95% sequence identity to a sequence selected from the group consisting of SEQ ID NOs: 136, 138, 140, 142, 144, 146, 148, 150, 152, 154, 156, 172, 174, and 176, wherein the polypeptide comprises the same CDR amino acid sequences as the respective SEQ ID NO or the polypeptide comprises CDR amino acid sequences that deviate by no more than one amino acid as compared to the respective SEQ ID NO. In some embodiments, the polypeptide comprises an amino acid sequence selected from the group consisting of SEQ ID NOs: 136, 138, 140, 142, 144, 146, 148, 150, 152, 154, 156, 172, 174, and 176.

The disclosure further provides a multispecific polypeptide wherein the first scFv domain binds to an extracellular domain of 5T4 and wherein the second scFv domain binds to an extracellular domain of 4-1BB. In some aspects, the polypeptide results in enhanced effector cell activation. In some aspects, a multispecific polypeptide of the disclosure increases effector cell activation and/or effector cell proliferation. In other aspects, a multispecific polypeptide enhances effector cell-dependent lysis of 5T4-expressing cells. In some embodiments, a 5T4-binding domain of the disclosure is capable of binding 5T4 with a kD value of less than 50 nM. In some aspects, the light chain variable region and/or the heavy chain variable region of the 5T4-binding domain and/or the 4-1BB-binding domain is humanized.

In some embodiments, the present disclosure provides a multispecific polypeptide comprising a first single chain variable fragment (scFv) domain and a second scFv domain linked together by a binding domain linker and an immunoglobulin Fc domain, wherein the immunoglobulin Fc domain comprises a hinge region and an immunoglobulin constant region; wherein the multispecific polypeptide is capable of forming a homodimer by association with a second identical multispecific polypeptide; wherein the first scFv domain specifically binds to human 5T4 and comprises: (i) an immunoglobulin heavy chain variable region comprising a heavy chain complementarity determining region (HCDR)-1 amino acid sequence of SEQ ID NO: 30, an HCDR2 amino acid sequence of SEQ ID NO: 32, and an HCDR3 amino acid sequence of SEQ ID NO: 34; and (ii) an immunoglobulin light chain variable region comprising a light chain complementarity determining region (LCDR)-1 amino acid sequence of SEQ ID NO: 42, an LCDR2 amino acid sequence of SEQ ID NO: 10, and an LCDR3 amino acid sequence of SEQ ID NOs: 36; and wherein the second scFv domain specifically binds to human 4-1BB and comprises: (i) an immunoglobulin heavy chain variable region comprising an HCDR1 amino acid sequence of SEQ ID NO: 2, an HCDR2 amino acid sequence of SEQ ID NO: 4, and an HCDR3 amino acid sequence of SEQ ID NO: 6; and (ii) an immunoglobulin light chain variable region comprising an LCDR1 amino acid sequence of SEQ ID NO: 8, an LCDR2 amino acid sequence of SEQ ID NO: 10, and an LCDR3 amino acid sequence of SEQ ID NO: 12. 2. The multispecific polypeptide of claim 1, wherein the multispecific polypeptide comprises, from amino-terminus to carboxyl-terminus: (i) the first scFv domain, (ii) the hinge region, (iii) the immunoglobulin constant region, (iv) the binding domain linker, and (v) the second scFv domain. In some embodiments, the first scFv domain comprises a mutation in the framework region compared to the framework region of SEQ ID NOs: 130 or 170. In some embodiments, the mutation introduces a stabilizing disulfide bond.

In some embodiments, the first scFv domain of the multispecific polypeptide comprises the immunoglobulin heavy chain variable region of SEQ ID NO: 38 and the immunoglobulin light chain variable region of SEQ ID NO: 44. In some embodiments, the first scFv domain of the multispecific polypeptide comprises the immunoglobulin heavy chain variable region of SEQ ID NO: 46 and the immunoglobulin light chain variable region of SEQ ID NO:48. In some embodiments, the second scFv domain of the multispecific polypeptide comprises immunoglobulin heavy chain variable region of SEQ ID NO: 14 and the immunoglobulin light chain variable region of SEQ ID NO: 16. In some embodiments, the first scFv domain of the multispecific polypeptide comprises the immunoglobulin heavy chain variable region of SEQ ID NO: 46 and the immunoglobulin light chain variable region of SEQ ID NO: 48, and the second scFv domain comprises the immunoglobulin heavy chain variable region of SEQ ID NO: 14 and the immunoglobulin light chain variable region of SEQ ID NO: 16. In some embodiments, the amino acid sequence of the first scFv domain is at least 97% identical to SEQ ID NO: 120, and the amino acid sequence of the second scFv domain is at least 97% identical to SEQ ID NO: 110. In some embodiments, the polypeptide comprises an amino acid sequence at least 95% identical to SEQ ID NO: 172 or comprises an amino acid sequence identical to SEQ ID NO: 172. In some embodiments, the amino acid sequence of the first scFv domain is at least 97% identical to SEQ ID NO: 122 and the amino acid sequence of the second scFv domain is at least 97% identical to SEQ ID NO: 110. In some embodiments, the polypeptide comprises an amino acid sequence at least 95% identical to SEQ ID NO: 174 or comprises an amino acid sequence of SEQ ID NO: 174.

In some embodiments, binding of the multispecific polypeptide to an effector cell results in increased effector cell activation, increased effector cell proliferation, or wherein binding of the multispecific polypeptide to an effector cell an a 5T4-expressing cell results in enhanced effector cell-dependent lysis of the 5T4-expressing cell.

The disclosure also encompasses a dimer comprising two identical polypeptides, wherein the two polypeptides are each the multispecific polypeptide described in the disclosure.

In certain aspects, the disclosure provides a pharmaceutical composition comprising a polypeptide or a protein described in the disclosure, and a pharmaceutically acceptable carrier, diluent, or excipient. In some embodiments, a pharmaceutical composition may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. Non-limiting examples of an oral unit dosage form include tablets, pills, pellets, capsules, powders, lozenges, granules, solutions, suspensions, emulsions, syrups, elixirs, sustained-release formulations, aerosols, and sprays.

The disclosure further encompasses a method for enhancing effector cell activation against a cell expressing 5T4, the method comprising: contacting said 5T4-expressing cell with a polypeptide or a protein of the disclosure, wherein said contacting is under conditions whereby enhanced effector cell activation against the 5T4-expressing cell is induced. In some aspects, the disclosure provides a method for treating a disorder in a subject, wherein said disorder is characterized by expression of 5T4, the method comprising administering to the subject a therapeutically effective amount of a polypeptide or a protein or a pharmaceutical composition of the disclosure. The disclosure also encompasses a use of a polypeptide or a protein of the disclosure for the manufacture of a medicament for treatment of a disorder in a subject, wherein said disorder is characterized by expression of 5T4. In some embodiments, the disclosure is related to a polypeptide or a protein of the disclosure for use in treating a disorder in a subject, wherein said disorder is characterized by expression of 5T4. In some embodiments, the disorder is a cancer. In certain aspects, the cancer is breast cancer, pancreatic cancer, ovarian cancer, non-small cell lung cancer, mesothelioma, chronic lymphocytic leukemia (CLL), mantle cell leukemia (MCL), acute lymphoblastic leukemia (ALL), squamous cell carcinoma, melanoma, adrenal cancer, bladder cancer, cervical cancer, renal cancer, gastric cancer, prostate cancer, thyroid cancer, liver cancer, uterine cancer, neurofibroma, sarcoma or head and neck cancer.

In some embodiments, the multispecific polypeptide for use in such methods comprises, from amino-terminus to carboxyl-terminus: (i) the first scFv domain, (ii) the hinge region, (iii) the immunoglobulin constant region, (iv) the binding domain linker, and (v) the second scFv domain. In some embodiments, the multispecific polypeptide for use in such methods comprisines a second scFv domain comprising an immunoglobulin heavy chain variable region of SEQ ID NO: 14 and an immunoglobulin light chain variable region of SEQ ID NO: 16, and a first scFv domain comprising (i) the immunoglobulin heavy chain variable region of SEQ ID NO: 38 and the immunoglobulin light chain variable region of SEQ ID NO: 44; or (ii) the immunoglobulin heavy chain variable region of SEQ ID NO: 46 and the immunoglobulin light chain variable region of SEQ ID NO: 48. In some embodiments, the amino acid sequence of the second scFv domain of the multispecific polypeptide is at least 97% identical to SEQ ID NO: 110, and the amino acid sequence of the first scFv domain of the multispecific polypeptide is at least 97% identical to SEQ ID NO: 120 (anti-5T4 scFv for 209) or SEQ ID NO: 122. In some embodiments, said polypeptide exhibits statistically significant enhanced effector cell activation compared to a second multispecific polypeptide, wherein the second multispecific polypeptide is an IgG-scFv structure comprising an anti-4-1BB antibody comprising a variable heavy chain comprising SEQ ID NO: 28 and a variable light chain comprising SEQ ID NO: 16 and an anti-5T4 scFv comprising a variable heavy chain comprising SEQ ID NO: 46 and a variable light chain comprising SEQ ID NO: 66. In some embodiments, said polypeptide induces statistically significant increased effector cell proliferation compared to a second multispecific polypeptide, wherein the second multispecific polypeptide is an IgG-scFv structure comprising an anti-4-1BB antibody comprising a variable heavy chain comprising SEQ ID NO: 28 and a variable light chain comprising SEQ ID NO: 16 and an anti-5T4 scFv comprising a variable heavy chain comprising SEQ ID NO: 46 and a variable light chain comprising SEQ ID NO: 66.

Some aspects of the disclosure include an isolated nucleic acid molecule encoding a polypeptide of the disclosure. In some embodiments, a nucleic acid molecule comprises a nucleotide sequence selected from the group consisting of SEQ ID NOs: 109, 111, 113, 115, 117, 119, 121, 123, 125, 127, 129, 131, 133, 135, 137, 139, 141, 143, 145, 147, 149, 151, 153, 155, 171, 173, and 175. The disclosure encompasses an expression vector comprising an isolated nucleic acid molecule described herein. In some embodiments, the nucleic acid molecule in an expression vector is operatively linked to regulatory sequences suitable for expression of the nucleic acid segment in a host cell. The disclosure provides a recombinant host cell comprising an expression vector described herein. In some aspects, the disclosure provides a method for producing a polypeptide comprising a 5T4-binding domain, the method comprising culturing a recombinant host cell comprising an expression vector described herein under conditions whereby the nucleic acid segment is expressed, thereby producing the polypeptide comprising a 5T4-binding domain.

BRIEF DESCRIPTION OF THE DRAWINGS

FIG. 11A shows T cell responses when cultured in plates coated with 5T4-Fc antigen. FIG. 11B shows T cell responses when cultured without 5T4-Fc antigen. The figure displays mean values from two donors.

FIG. 22C shows the normalized pooled data for ALG.APV-210 from the 2 independent experiments. n=3 donors/group/exp.

FIG. 23C shows the normalized pooled data from experiment 1 and 2. n=3 donors/group/exp.

DETAILED DESCRIPTION OF THE DISCLOSURE

Figure 1:
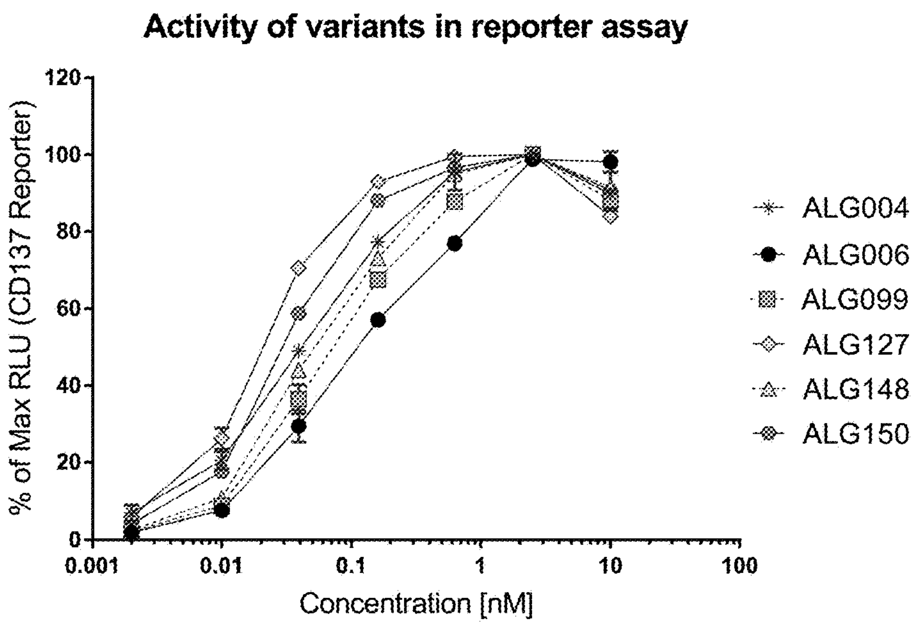
FIG. 1 illustrates the agonistic function of seven constructs (ALG.APV-004, ALG.APV-006, ALG.APV-099, ALG.APV-127, ALG.APV-148, and ALG.APV-150) in the presence of 5T4(+) cells.

The disclosure provides polypeptides comprising binding domains that specifically bind to trophoblast glycoprotein (5T4) and polypeptides that specifically bind to 5T4. In some embodiments, the polypeptides are multi specific polypeptides that may bind specifically to 5T4 and to another target. In some embodiments, the polypeptides described herein are multispecific polypeptides that bind specifically to 5T4 and also bind specifically to a target on an effector cell. The disclosure also provides polypeptides comprising binding domains that specifically bind to tumor necrosis factor receptor superfamily member 9 (41BB or CD137) and polypeptides that specifically bind to 4-1BB. In some embodiments, the polypeptides are multispecific polypeptides that may bind specifically to 4-1BB and to another target (e.g., a tumor-associated antigen). In some embodiments, the polypeptides described herein are multispecific polypeptides that bind specifically to 4-1BB and also bind specifically to a target on a target cell. In some embodiments, the multispecific polypeptides are bispecific polypeptides that bind specifically to 5T4 and bind specifically to 4-1BB. In some embodiments, the bispecific polypeptides bind to 5T4 expressed on a target cell and 4-1BB expressed on an effector cell, thereby resulting in amplification of effector cell activation and enhancing effector cell-mediated cytotoxicity of a target cell.

In some embodiments, the present disclosure provides 5T4-binding domains and/or 4-1BB-binding domains (and polypeptides or proteins comprising such binding domains) that exhibit less off-target binding relative to previously known 5T4-binding domains and/or 4-1BB-binding domains. In certain aspects, the binding domains and/or polypeptides comprising the binding domains described herein bind to 5T4 and/or 4-1BB more effectively in certain formats and/or certain orientations (e.g., $V_H$-$V_L$ compared to $V_L$-$V_H$), leading to higher potency and/or improved utility in treating disorders associated with expression of 5T4.

In some embodiments, administration of a therapeutically effective amount of a polypeptide or protein described herein to a patient in need thereof is useful for treatment of certain disorders associated with the expression of 5T4, including certain cancers. In one embodiment, the polypeptide or protein binds both a target cell expressing 5T4 and an effector-cell, thereby "cross-linking" the target cell expressing 5T4 and the effector cell. The binding of both domains to their targets enhances the activation of the effector cells, leading to a prolonged and/or more robust effector cell response (e.g., effector cell-mediated cytotoxicity). The polypeptides and proteins of the present disclosure offer various advantages in treating patients, for example, effective binding to 5T4, efficient enhancement of effector cell activity, reduced levels of cytokine release, and/or a lower risk of adverse events (e.g., toxicity). In some embodiments, a target cell expresses 5T4 at a higher level than a non-target cell (e.g., normal cell or non-cancerous cell in the same subject, organ, or tissue) expresses 5T4. In other embodiments, a target cell expresses 5T4 while a non-target cell (e.g., normal cell or non-cancerous cell in the same subject, organ, or tissue) does not express 5T4.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. In addition, it should be understood that the polypeptides comprising the various combinations of the components (e.g., domains or regions) and substituents described herein, are disclosed by the present application to the same extent as if each polypeptide was set forth individually. Thus, selection of particular components of individual polypeptides is within the scope of the present disclosure.

Definitions

As used herein, the term "binding domain" or "binding region" refers to the domain, region, portion, or site of a protein, polypeptide, oligopeptide, peptide, antibody, or binding domain derived from an antibody that possesses the ability to specifically recognize and bind to a target molecule, such as an antigen, ligand, receptor, substrate, or inhibitor (e.g., 5T4 or 4-1BB). Exemplary binding domains include, antibodies and antibody-like proteins or domains, antibody heavy and light chain variable regions, and single-chain antibody variable regions (e.g., domain antibodies, sFv, scFv, scFab). In certain embodiments, the binding domain comprises or consists of an antigen binding site (e.g., comprising a variable heavy chain sequence and variable light chain sequence or three light chain complementary determining regions (CDRs) and three heavy chain CDRs from an antibody placed into alternative framework regions (FRs) (e.g., human FRs optionally comprising one or more amino acid substitutions). A variety of assays are known for identifying binding domains of the present disclosure that specifically bind a particular target, including Western blot, ELISA, phage display library screening, and BIACORE® interaction analysis. In some embodiments, the polypeptides of the present invention comprise a binding domain that specifically binds to a target antigen expressed by a target cell (e.g., a tumor associated antigen, such as 5T4). In some embodiments, the polypeptides of the present invention comprise a binding domain that specifically binds to a target antigen expressed by an effector cell (e.g., 4-1BB). In some embodiments, the polypeptides of the present invention are multispecific polypeptides and comprise two or more binding domains.

A binding domain or protein comprising a binding domain "specifically binds" a target if it binds the target with an affinity or $K_a$ (i.e., an equilibrium association constant of a particular binding interaction with units of 1/M) equal to or greater than $10^5$ $M^{-1-}$, while not significantly binding other components present in a test sample. Binding domains can be classified as "high affinity" binding domains and "low affinity" binding domains. "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}M^{-1}$, at least $10^{12}$ $M^{-1}$ or at least $10^{13}M^{-1}$. "Low affinity" binding domains refer to those binding domains with a $K_a$ of up to $10^7$ $M^{-1}$, up to $10^6$ $M^{-1}$, up to $10^5$ $M^{-1}$. Alternatively, affinity can be defined as an equilibrium dissociation constant ($K_d$) of a particular binding interaction with units of M (e.g., $10^{-5}$ M to $10^{-13}$, or about 500 nM, about 300 nM, about 250 nM, about 200 nM, about 150 nM, about 100 nM, about 50 nM, about 25 nM, about 10 nM, or about 5 nM). Affinities of binding domain polypeptides and single chain polypeptides according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

As used herein, a "conservative substitution" is recognized in the art as a substitution of one amino acid for another amino acid that has similar properties. Exemplary conservative substitutions are well-known in the art (see, e.g., PCT Application Publication No. WO 97/09433, page 10, published Mar. 13, 1997; Lehninger, Biochemistry, Second Edition; Worth Publishers, Inc. NY:NY (1975), pp. 71-'7'7; Lewin, Genes IV, Oxford University Press, NY and Cell Press, Cambridge, Mass. (1990), p. 8).

As used herein, the term "derivative" refers to a modification of one or more amino acid residues of a peptide by chemical or biological means, either with or without an enzyme, e.g., by glycosylation, alkylation, acylation, ester formation, or amide formation.

As used herein, a polypeptide or amino acid sequence "derived from" a designated polypeptide or protein refers to the origin of the polypeptide. In certain embodiments, the polypeptide or amino acid sequence which is derived from a particular sequence (sometimes referred to as the "parent" or "parental" sequence) and has an amino acid sequence that is essentially identical to the parent sequence or a portion thereof, wherein the portion consists of at least 10-20 amino acids, at least 20-30 amino acids, or at least 30-50 amino acids, or at least 50-150 amino acids, or which is otherwise identifiable to one of ordinary skill in the art as having its origin in the parent sequence. For example, a binding domain (e.g., a Fab, F(ab')2, Fab', scFv, single domain antibody (sdAb), etc.) can be derived from an antibody. In some embodiments, a binding domain sequence (e.g., a 5T4- or 4-1BB-binding domain) is derived from an antibody or protein by means of a computer algorithm or in silico.

Polypeptides derived from another polypeptide can have one or more mutations or alterations relative to the parent polypeptide, e.g., one or more amino acid residues which have been substituted with another amino acid residue or which has one or more amino acid insertions or deletions. In such embodiments, polypeptides derived from a parent polypeptide and comprising one or more mutations or alteration are referred to as "variants." As used herein, the term "variant" or "variants" refers to a polynucleotide or polypeptide with a sequence differing from that of a reference polynucleotide or polypeptide, but retaining essential properties thereof. Generally, variant polynucleotide or polypeptide sequences are overall closely similar, and, in many regions, identical to the reference polynucleotide or polypeptide. For instance, a variant polynucleotide or polypeptide may exhibit at least about 70%, at least about 80%, at least about 90%, at least about 91%, at least about 92%, at least about 93%, at least about 94%, at least about 95%, at least about 96%, at least about 97%, at least about 98% or at least about 99% sequence identity compared to the active portion or full length reference polynucleotide or polypeptide. The polypeptide can comprise an amino acid sequence which is not naturally occurring. Such variations necessarily have less than 100% sequence identity or similarity with the parent polypeptide. In one embodiment, the variant will have an amino acid sequence from about 60% to less than 100% amino acid sequence identity or similarity with the amino acid sequence of the parent polypeptide. In another embodiment, the variant will have an amino acid sequence from about 75% to less than 100%, from about 80% to less than 100%, from about 85% to less than 100%, from about 90% to less than 100%, from about 95% to less than 100% amino acid sequence identity or similarity with the amino acid sequence of the parent polypeptide.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage sequence identity is calculated by determining the number of positions at which the identical nucleic acid base or amino acid residue occurs in both sequences to yield the number of identical positions. The number of identical positions is then divided by the total number of positions in the comparison window and multiplied by 100 to yield the percentage of sequence identity. Percentage of sequence identity is determined by comparing two optimally aligned sequences over a comparison window. The comparison window for polynucleotide sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

As used herein, unless otherwise provided, a position of an amino acid residue in a variable region of an immunoglobulin molecule is numbered according to either the IMGT criteria (Brochet et al, Nucl. Acids Res. (2008) 36, W503-508) or according to EU nomenclature (Ward et al., 1995 *Therap. Immunol.* 2:77-94), and a position of an amino acid residue in a constant region of an immunoglobulin molecule is numbered according to EU nomenclature (Ward et al., 1995 *Therap. Immunol.* 2:77-94). The Kabat numbering convention (Kabat, Sequences of Proteins of Immunological Interest, $5^{th}$ ed. Bethesda, Md.: Public Health Service, National Institutes of Health (1991)) is an alternative system used to refer to a position of an amino acid residue in a variable region of an immunoglobulin molecule and is sometimes used to refer to a position of an amino acid residue in a variable region of an immunoglobulin molecule herein.

As used herein, the term "dimer" refers to a biological entity that consists of two subunits associated with each other via one or more forms of intramolecular forces, including covalent bonds (e.g., disulfide bonds) and other interactions (e.g., electrostatic interactions, salt bridges, hydrogen bonding, and hydrophobic interactions), and is stable under appropriate conditions (e.g., under physiological conditions, in an aqueous solution suitable for expressing, purifying, and/or storing recombinant proteins, or under conditions for non-denaturing and/or non-reducing electrophoresis). The terms "heterodimer" or "heterodimeric protein," as used herein, refers to a dimer formed from two different polypeptides. A heterodimer may comprise an anti-5T4×anti-4-1BB molecule as described herein. A heterodimer does not include an antibody formed from four polypeptides (i.e., two light chains and two heavy chains). The terms "homodimer" or "homodimeric protein," as used herein, refers to a dimer formed from two identical polypeptides.

"Fc region" or "Fc domain" refers to a polypeptide sequence corresponding to or derived from the portion of a source antibody that is capable of binding to Fc receptors on cells and/or the C1q component of complement, thereby mediating the effector function of an antibody. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc region is a homodimeric protein comprising two polypeptides that are associated by disulfide bonds, and each comprising a hinge region, a CH2 domain, and a CH3 domain. However, more recently the term has been applied to the single chain monomer component consisting of CH3, CH2, and at least a portion of the hinge sufficient to form a disulfide-linked dimer with a second such chain. As such, and depending on the context, use of the terms "Fc region" or "Fc domain" will refer herein to either the dimeric form or the individual monomers that associate to form the dimeric protein. For a review of immunoglobulin structure and function, see Putnam, *The Plasma Proteins*, Vol. V (Academic Press, Inc., 1987), pp. 49-140; and Padlan, *Mol. Immunol.* 31:169-217, 1994. As used herein, the term Fc includes variants of naturally occurring sequences.

An "immunoglobulin constant region" or "constant region" is a term defined herein to refer to a peptide or polypeptide sequence that corresponds to or is derived from part or all of one or more constant domains of an immunoglobulin. In certain embodiments, the constant region comprises IgG CH2 and CH3 domains, e.g., IgG1 CH2 and CH3 domains. In certain embodiments, the constant region does not comprise a CH1 domain. In certain embodiments, the constant domains making up the constant region are human. In some embodiments (for example, in certain variations of a 41BB-binding polypeptide, 5T4-binding polypeptide or multispecific polypeptides thereof), the constant region of a fusion protein of this disclosure lacks or has minimal effector functions while retaining the ability to bind some Fc receptors such as the neonatal Fc receptor (FcRn) and retaining a relatively long half-life in vivo. For example, the constant region of a fusion protein of this disclosure do not result in, or substantially reduce the induction of antibody-dependent cell-mediated cytotoxicity (ADCC), antibody-dependent cell-mediated phagocytosis (ADCP), complement activation, and/or complement-dependent cytotoxicity (CDC). In other variations, a fusion protein of this disclosure comprises constant domains that retain one or more effector functions, such as of one or both of ADCC and CDC. In certain embodiments, a binding domain of this disclosure is fused to a human IgG1 constant region, wherein the IgG1 constant region has one or more of the following amino acids mutated: leucine at position 234 (L234), leucine at position 235 (L235), glycine at position 237 (G237), glutamate at position 318 (E318), lysine at position 320 (K320), lysine at position 322 (K322), or any combination thereof (numbering according to EU). For example, any one or more of these amino acids can be changed to alanine. In a further embodiment, an IgG1 Fc domain has each of L234, L235, G237, E318, K320, and K322 (according to EU numbering) mutated to an alanine (i.e., L234A, L235A, G237A, E318A, K320A, and K322A, respectively), and optionally an N297A mutation as well (i.e., essentially eliminating glycosylation of the CH2 domain).

The terms "light chain variable region" (also referred to as "light chain variable domain" or "$V_L$") and "heavy chain variable region" (also referred to as "heavy chain variable domain" or "$V_H$") refer to the variable binding region from an antibody light and heavy chain, respectively. The variable binding regions are made up of discrete, well-defined sub-regions known as "complementarity determining regions" (CDRs) and "framework regions" (FRs). In one embodiment, the FRs are humanized. The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 domain of the heavy chain linked to the light chain via an inter-chain disulfide bond.

As used herein, the term "linker" generally refers to a short polypeptide sequence connecting two sub-domains of a polypeptide. Non-limiting examples of linkers include flexible linkers comprising glycine-serine repeats, and linkers derived from (a) an interdomain region of a transmembrane protein (e.g., a type I transmembrane protein); (b) a stalk region of a type II C-lectin; or (c) an immunoglobulin hinge. In some embodiments, a linker provides a spacer function compatible with interaction of the two sub-binding domains so that the resulting polypeptide retains a specific binding affinity to the same target molecule as an antibody that comprises the same light and heavy chain variable regions. In certain embodiments, a linker is comprised of five to about 35 amino acids, for instance, about 15 to about 25 amino acids. As used herein, the phrase a "linker between CH3 and CH1 or CL" refers to one or more amino acid residues (e.g., about 2-12, about 2-10, about 4-10, about 5-10, about 6-10, about 7-10, about 8-10, about 9-10, about 8-12, about 9-12, or about 10-12) between the C-terminus of a CH3 domain (e.g., a wild type CH3 or a mutated CH3) and the N-terminus of a CH1 domain or CL domain (e.g., Cκ).

In some embodiments, depending on context, a linker may refer to (1) a polypeptide region between $V_H$ and $V_L$ regions in a single-chain Fv (scFv) or (2) a polypeptide region between a first binding domain and a second binding domain in a multispecific polypeptide comprising two binding domains. In the later example, wherein a linker connects two or more binding domains, such a linker is referred to herein as a "binding domain linker." In some embodiments, a binding domain linker may directly link or connect two or more binding domains, resulting in a construct comprising the following structure: binding domain-binding domain linker-binding domain. In some embodiments, the multispecific polypeptides described herein comprise, in order from amino-terminus to carboxyl-terminus (i) a first binding domain, (ii) a binding domain linker, and (iii) a second binding domain. In some embodiments, a multispecific polypeptide comprises, in order from amino-terminus to carboxyl-terminus (i) a second binding domain, (ii) a binding domain linker, and (iii) a first binding domain. In some embodiments, a binding domain linker may link or connect two or more binding domains by linking at least one binding domain to a non-binding domain polypeptide, such as an immunoglobulin Fc domain (i.e., a polypeptide comprising the structure: Ig hinge—Ig constant region). In such embodiments, the resulting constructs may comprise the following structure: binding domain—Fc domain—binding domain linker—binding domain. In some embodiments, the multispecific polypeptides described herein comprise, in order from amino-terminus to carboxyl-terminus: (i) a first binding domain, (ii) a hinge region, (iii) an immunoglobulin constant region, (iv) a binding domain linker, and (v) a second binding domain. In some embodiments, a multispecific polypeptide comprises, in order from amino-terminus to carboxyl-terminus (i) a second binding domain, (ii) a binding domain linker, (iii) an immunoglobulin constant region, (iv) a hinge region, and (v) a first binding domain. A polypeptide region between an immunoglobulin constant region and a second binding domain in a multispecific polypeptide comprising two binding domains (e.g., a binding domain linker) may also be referred to as a "carboxyl-terminus linker" or an "amino-terminus linker" depending on the orientation of the domains within the multispecific polypeptide. Non-limiting examples of linkers are provided in Table 1.

In some embodiments, a "hinge" or a "hinge region" refers to a polypeptide derived from an immunoglobulin hinge region and located between a binding domain (e.g., a 5T4-binding domain or a 4-1BB-binding domain) and an immunoglobulin constant region in a polypeptide described herein. A "wild-type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a wild type immunoglobulin hinge region sequence is human, and can comprise a human IgG hinge region (e.g., and IgG1, IgG2, IgG3, or IgG4 hinge region).

An "altered immunoglobulin hinge region" or "variant immunoglobulin hinge region" refers to a hinge region polypeptide with one or more mutations, substitutions, insertions, or deletions compared to a corresponding parental wild-type immunoglobulin hinge region. In certain embodiments, an altered immunoglobulin hinge region is at least 70% homologous to a wild-type immunoglobulin hinge region (e.g., at least 70%, 75%, 80%, 85%, 90%, 95%, 97%, 98%, or 99% homologous). In certain embodiments, an altered immunoglobulin hinge region is a fragment of a wild type immunoglobulin hinge region that has a length of about 5 amino acids (e.g., about 5, 6, 7, 8, 9, 10, 11, 12, 13, 14, 15, 16, 17, 18, 19, 20, or more amino acids) up to about 120 amino acids (for instance, having a length of about 10 to about 40 amino acids or about 15 to about 30 amino acids or about 15 to about 20 amino acids or about 20 to about 25 amino acids). Typically, an altered immunoglobulin hinge region that is a fragment of a wild type immunoglobulin hinge region comprises an IgG core hinge region (e.g., a polypeptide comprising the sequence C-X-X-C, wherein X is any amino acid) as disclosed in U.S. Patent Application Publication Nos. 2013/0129723 and 2013/0095097. Non-limiting examples of hinges are provided in Table 1.

As used herein, the term "humanized" refers to a process of making an antibody or immunoglobulin binding proteins and polypeptides derived from a non-human species (e.g., mouse or rat) less immunogenic to humans, while still retaining antigen-binding properties of the original antibody, using genetic engineering techniques. In some embodiments, the binding domain(s) of an antibody or immunoglobulin binding proteins and polypeptides (e.g., light and heavy chain variable regions, Fab, scFv) are humanized. Non-human binding domains can be humanized using techniques known as CDR grafting (Jones et al., Nature 321:522 (1986)) and variants thereof, including "reshaping" (Verhoeyen, et al., 1988 Science 239:1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312). If derived from a non-human source, other regions of the antibody or immunoglobulin binding proteins and polypeptides, such as the hinge region and constant region domains, can also be humanized. Knowledge about humanized antibodies in the art is applicable to the polypeptides according to the disclosure, even if these polypeptides are not antibodies.

As used herein, the term "patient in need" refers to a patient at risk of, or suffering from, a disease, disorder or condition that is amenable to treatment or amelioration with a 5T4-binding protein or multispecific polypeptide or a composition thereof provided herein.

As used herein, the term "pharmaceutically acceptable" refers to molecular entities and compositions that do not generally produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

As used herein, the term "promoter" refers to a region of DNA involved in binding RNA polymerase to initiate transcription.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Cassol et al. (1992); Rossolini et al. (1994) *Mol. Cell. Probes* 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

The term "expression" refers to the biosynthesis of a product encoded by a nucleic acid. For example, in the case of nucleic acid segment encoding a polypeptide of interest, expression involves transcription of the nucleic acid segment into mRNA and the translation of mRNA into one or more polypeptides.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. In addition to a transcriptional promoter and terminator, an expression unit can further include other nucleic acid segments such as, e.g., an enhancer or a polyadenylation signal.

The term "expression vector," as used herein, refers to a nucleic acid molecule, linear or circular, comprising one or more expression units. In addition to one or more expression units, an expression vector can also include additional nucleic acid segments such as, for example, one or more origins of replication or one or more selectable markers. Expression vectors are generally derived from plasmid or viral DNA, or can contain elements of both.

As used herein, a "polypeptide," "polypeptide chain," or "protein" refers to a single, linear and contiguous arrangement of covalently linked amino acids. Polypeptides can form one or more intrachain disulfide bonds. With regard to polypeptides as described herein, reference to modifications or alterations of amino acid residues corresponding to those specified by SEQ ID NO includes post-translational modifications of such residues. The terms polypeptide and protein also encompass embodiments where two polypeptide chains link together in a non-linear fashion, such as via an interchain disulfide bond. For example, a native immunoglobulin molecule is comprised of two heavy chain polypeptides and two light chain polypeptides. Each of the heavy chain polypeptides associate with a light chain polypeptide by virtue of interchain disulfide bonds between the heavy and light chain polypeptides to form two heterodimeric proteins or polypeptides (i.e., a protein comprised of two heterologous polypeptide chains). The two heterodimeric proteins then associate by virtue of additional interchain disulfide bonds between the heavy chain polypeptides to form an immunoglobulin protein or polypeptide. Herein, a protein or polypeptide may be an antibody or an antigen-binding fragment of an antibody. In some embodiments, a protein may be an scFv-Fc-scFv protein, scFv-scFv dimer, or a diabody.

As will be appreciated by one of skill in the art, proteins and polypeptides are defined herein in terms of the amino acid sequences of the individual polypeptide chains, which are indicated by the SEQ ID NOs reference throughout this disclosure. For example, in some embodiments an scFv-Fc-scFv protein or polypeptide described herein is comprised of two scFv-Fc-scFv polypeptide chains associated by interchain bonds (e.g., interchain disulfide bonds) to form a dimeric scFv-Fc-scFv protein (e.g., a homodimeric or heterodimeric scFv-Fc-scFv protein) (See, for example, FIG. 10). In such embodiments, the scFv-Fc-scFv protein is defined by the amino acid sequences of the individual scFv-Fc-scFv polypeptide chains. Polypeptides and proteins can also comprise non-peptidic components, such as carbohydrate groups. Carbohydrates and other non-peptidic substituents can be added to a protein or polypeptide by the cell in which the protein is produced, and will vary with the type of cell. Proteins and polypeptides are defined herein in terms of their amino acid backbone structures; substituents such as carbohydrate groups are generally not specified, but may be present nonetheless.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl-terminus of the reference sequence, but is not necessarily at the carboxyl-terminus of the complete polypeptide.

As used herein, the term "transformation," "transfection," and "transduction" refer to the transfer of nucleic acid (i.e., a nucleotide polymer) into a cell. As used herein, the term "genetic transformation" refers to the transfer and incorporation of DNA, especially recombinant DNA, into a cell. The transferred nucleic acid can be introduced into a cell via an expression vector.

"Antibody-dependent cell-mediated cytotoxicity" and "ADCC," as used herein, refer to a cell-mediated process in which nonspecific cytotoxic cells that express FcγRs (e.g., monocytic cells such as natural killer (NK) cells and macrophages) recognize bound antibody (or other protein capable of binding FcγRs) on a target cell and subsequently cause lysis of the target cell. In principle, any effector cell with an activating FcγR can be triggered to mediate ADCC. The primary cells for mediating ADCC are NK cells, which express only FcγRIII, whereas monocytes, depending on their state of activation, localization, or differentiation, can express FcγRI, FcγRII, and FcγRIII For a review of FcγR expression on hematopoietic cells, see, e.g., Ravetch et al., 1991, Annu. Rev. Immunol., 9:457-92.

The term "having ADCC activity," as used herein in reference to a polypeptide or protein, means that the polypeptide or protein, for example, one comprising an Fc domain (e.g., an immunoglobulin hinge region and an immunoglobulin constant region having CH2 and CH3 domains) such as derived from IgG (e.g., IgG1), is capable of mediating antibody-dependent cell-mediated cytotoxicity (ADCC) through binding of a cytolytic Fc receptor (e.g., FcγRIII) on a cytolytic immune effector cell expressing the Fc receptor (e.g., an NK cell). In some embodiments, a multispecific polypeptide or protein (e.g., an anti-5T4×anti-4-1BB molecule as described herein) comprising an Fc domain may lack effector function (e.g., null ADCC activity) as the result of mutations in the CH2 and/or CH3 domain.

"Complement-dependent cytotoxicity" and "CDC," as used herein, refer to a process in which components in normal serum ("complement"), together with an antibody or other C1q-complement-binding protein bound to a target antigen, exhibit lysis of a target cell expressing the target antigen. Complement consists of a group of serum proteins that act in concert and in an orderly sequence to exert their effect.

The terms "classical complement pathway" and "classical complement system," as used herein, are synonymous and refer to a particular pathway for the activation of complement. The classical pathway requires antigen-antibody complexes for initiation and involves the activation, in an orderly fashion, of nine major protein components designated C1 through C9. For several steps in the activation process, the product is an enzyme that catalyzes the subsequent step. This cascade provides amplification and activation of large amounts of complement by a relatively small initial signal.

The term "having CDC activity," as used herein in reference to a polypeptide or protein, means that the polypeptide or protein, for example, one comprising an Fc domain (e.g., an immunoglobulin hinge region and an immunoglobulin constant region having CH2 and CH3 domains) such as derived from IgG (e.g., IgG1) is capable of mediating complement-dependent cytotoxicity (CDC) through binding of C1q complement protein and activation of the classical complement system. In some embodiments, a multispecific polypeptide or protein (e.g., an anti-5T4×anti-4-1BB molecule as described herein) may have lack effector function (e.g., null CDC activity) as the result of one or more mutations in the CH2 and/or CH3 domains.

"Enhanced effector cell activation" as used herein, refers to the increase, prolonging, and/or potentiation of an effector cell response by the polypeptides or proteins described herein. In some embodiments, enhanced effector cell activation refers to an increase in the cytotoxic activity of an effector cell. In some embodiments, enhanced effector cell activation refers to an increase in cytokine production, cell proliferation, or a change in cell-surface molecule expression such that the ability of the effector cell to lyse a target cell is enhanced. In certain embodiments, the polypeptides and proteins described herein enhance effector cell activation by modulating Wnt/β-catenin signaling.

As used herein, the term "effector cell" refers to a cell of the immune system that is capable of lysing or killing a target cell, such as a tumor cell. Herein, an effector cell may refer to a lymphocyte, such as a T cell, a natural killer (NK) cell, or an NKT cell, a monocyte, a macrophage, a dendritic cell, or a granulocyte. In particular embodiments, the term effector cell refers to a T cell, an NK cell, or an NKT cell.

As used herein, the terms "treatment," "treating," or "ameliorating" refers to either a therapeutic treatment or prophylactic/preventative treatment. A treatment is therapeutic if at least one symptom of disease in an individual receiving treatment improves or a treatment can delay worsening of a progressive disease in an individual, or prevent onset of additional associated diseases.

As used herein, the term "therapeutically effective amount (or dose)" or "effective amount (or dose)" of a polypeptide or protein described herein or a composition thereof refers to that amount of the compound sufficient to result in amelioration of one or more symptoms of the disease being treated in a statistically significant manner or a statistically significant improvement in organ function. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially or simultaneously (in the same formulation or concurrently in separate formulations).

Herein, the term "statistical significance" refers the probability of obtaining a test result that occurs by chance. For example, an observation or test result is said to be statistically significant if the probability of it occurring purely by chance (p) is less than the predetermined statistical threshold (α), or $p<\alpha$. The statistical threshold for a particular test may be set according to the characteristics of the data and conventions known in the art. For example, a is conventionally set to 5% (0.05), such that, for a given result, $p<0.05$ in order for said result to be considered statistically significant.

As used herein, a "5T4-binding domain" refers to a domain of a polypeptide described herein that specifically bind to oncofetal trophoblast glycoprotein (5T4) (e.g., human 5T4), also known as TPBG and Wnt-activated inhibitory factor 1 (WAIF1). 5T4 is a 72 kD oncofetal glycoprotein that is heavily N-glycosylated proteins with several leucine-rich repeats associated with protein-protein interactions. The term "5T4" may refer to any isoform of 5T4. Exemplary human 5T4 nucleotide sequences are shown in Table 1 below and provided in SEQ ID NOs: 163 and 167 and exemplary human 5T4 amino acid sequences are provided in SEQ ID NOs: 164 and 168.

As used herein, "4-1BB-binding domain" refers to a binding domain of a protein or polypeptide described herein that is capable of specifically binding to human 4-1BB (also known as CD137). The term "4-1BB" may refer to any isoform of 4-1BB. Exemplary human 4-1BB nucleotide sequences are shown in Table 1 below and provided in SEQ ID NOs: 161 and 165, and exemplary human 4-1BB amino acid sequences are provided in SEQ ID NOs: 162 and 166.

TABLE 1

Exemplary 4-1BB and 5T4 DNA and amino acid sequences

| Protein Name | DNA Sequence | DNA SEQ ID | AA Sequence | AA SEQ ID |
|---|---|---|---|---|
| Full length human 4-1BB | ATGGGAAACAGCTGTTACAACATAGTAGCCACTCT<br>GTTGCTGGTCCTCAACTTTGAGAGGACAAGATCAT<br>TGCAGGATCCTTGTAGTAACTGCCCAGCTGGTACA<br>TTCTGTGATAATAACAGGAATCAGATTTGCAGTCC<br>CTGTCCTCCAAATAGTTTCTCCAGCGCAGGTGGAC<br>AAAGGACCTGTGACATATGCAGGCAGTGTAAAGGT<br>GTTTTCAGGACCAGGAAGGAGTGTTCCTCCACCAG<br>CAATGCAGAGTGTGACTGCACTCCAGGGTTTCACT<br>GCCTGGGGGCAGGATGCAGCATGTGTGAACAGGAT<br>TGTAAACAAGGTCAAGAACTGACAAAAAAAGGTTG<br>TAAAGACTGTTGCTTTGGGACATTTAACGATCAGA<br>AACGTGGCATCTGTCGACCCTGGACAAACTGTTCT<br>TTGGATGGAAAGTCTGTGCTTGTGAATGGGACGAA<br>GGAGAGGGACGTGGTCTGTGGACCATCTCCAGCCG<br>ACCTCTCTCCGGGAGCATCCTCTGTGACCCCGCCT<br>GCCCCTGCGAGAGAGCCAGGACACTCTCCGCAGAT<br>CATCTCCTTCTTTCTTGCGCTGACGTCGACTGCGT<br>TGCTCTTCCTGCTGTTCTTCCTCACGCTCCGTTTC<br>TCTGTTGTTAAACGGGGCAGAAAGAAACTCCTGTA<br>TATATTCAAACAACCATTTATGAGACCAGTACAAA<br>CTACTCAAGAGGAAGATGGCTGTAGCTGCCGATTT<br>CCAGAAGAAGAAGAAGGAGGATGTGAACTGTGA | 161 | MGNSCYNIVATLLLVLNF<br>ERTRSLQDPCSNCPAGTF<br>CDNNRNQICSPCPPNSFS<br>SAGGQRTCDICRQCKGVF<br>RTRKECSSTSNAECDCTP<br>GFHCLGAGCSMCEQDCKQ<br>GQELTKKGCKDCCFGTFN<br>DQKRGICRPWTNCSLDGK<br>SVLVNGTKERDVVCGPSP<br>ADLSPGASSVTPPAPARE<br>PGHSPQIISFFLALTSTA<br>LLFLLFFLTLRFSVVKRG<br>RKKLLYIFKQPFMRPVQT<br>TQEEDGCSCRFPEEEEGG<br>CEL | 162 |
| Full length human 5T4 | ATGCCTGGGGGGTGCTCCCGGGGCCCCGCCGCCGG<br>GGACGGGCGTCTGCGGCTGGCGCGACTAGCGCTGG<br>TACTCCTGGGCTGGGTCTCCTCGTCTTCTCCCACC<br>TCCTCGGCATCCTCCTTCTCCTCCTCGGCGCCGTT<br>CCTGGCTTCCGCCGTGTCCGCCCAGCCCCCGCTGC<br>CGGACCAGTGCCCCGCGCTGTGCGAGTGCTCCGAG<br>GCAGCGCGCACAGTCAAGTGCGTTAACCGCAATCT<br>GACCGAGGTGCCCACGGACCTGCCCGCCTACGTGC<br>GCAACCTCTTCCTTACCGGCAACCAGCTGGCCGTG<br>CTCCCTGCCGGCGCCTTCGCCCGCCGGCCGCCGCT<br>GGCGGAGCTGGCCGCGCTCAACCTCAGCGGCAGCC<br>GCCTGGACGAGGTGCGCGCGGGCGCCTTCGAGCAT<br>CTGCCCAGCCTGCGCCAGCTCGACCTCAGCCACAA<br>CCCACTGGCCGACCTCAGTCCCTTCGCTTTCTCGG<br>GCAGCAATGCCAGCGTCTCGGCCCCCAGTCCCCTT<br>GTGGAACTGATCCTGAACCACATCGTGCCCCCTGA<br>AGATGAGCGGCAGAACCGGAGCTTCGAGGGCATGG<br>TGGTGGCGGCCCTGCTGGCGGGCCGTGCACTGCAG<br>GGGCTCCGCCGCTTGGAGCTGGCCAGCAACCACTT<br>CCTTTACCTGCCGCGGGATGTGCTGGCCCAACTGC<br>CCAGCCTCAGGCACCTGGACTTAAGTAATAATTCG<br>CTGGTGAGCCTGACCTACGTGTCCTTCCGCAACCT<br>GACACATCTAGAAAGCCTCCACCTGGAGGACAATG<br>CCCTCAAGGTCCTTCACAATGGCACCCTGGCTGAG<br>TTGCAAGGTCTACCCCACATTAGGGTTTTCCTGGA<br>CAACAATCCCTGGGTCTGCGACTGCCACATGGCAG<br>ACATGGTGACCTGGCTCAAGGAAACAGAGGTAGTG<br>CAGGGCAAAGACCGGCTCACCTGTGCATATCCGGA<br>AAAAATGAGGAATCGGGTCCTCTTGGAACTCAACA<br>GTGCTGACCTGGACTGTGACCCGATTCTTCCCCCA<br>TCCCTGCAAACCTCTTATGTCTTCCTGGGTATTGT<br>TTTAGCCCTGATAGGCGCTATTTTCCTCCTGGTTT<br>TGTATTTGAACCGCAAGGGGATAAAAAAGTGGATG<br>CATAACATCAGAGATGCCTGCAGGGATCACATGGA<br>AGGGTATCATTACAGATATGAAATCAATGCGGACC<br>CCAGATTAACGAACCTCAGTTCTAACTCGGATGTC<br>TGA | 163 | MPGGCSRGPAAGDGRLRL<br>ARLALVLLGWVSSSSPTS<br>SASSFSSSAPFLASAVSA<br>QPPLPDQCPALCECSEAA<br>RTVKCVNRNLTEVPTDLP<br>AYVRNLFLTGNQLAVLPA<br>GAFARRPPLAELAALNLS<br>GSRLDEVRAGAFEHLPSL<br>RQLDLSHNPLADLSPFAF<br>SGSNASVSAPSPLVELIL<br>NHIVPPEDERQNRSFEGM<br>VVAALLAGRALQGLRRLE<br>LASNHFLYLPRDVLAQLP<br>SLRHLDLSNNSLVSLTYV<br>SFRNLTHLESLHLEDNAL<br>KVLHNGTLAELQGLPHIR<br>VFLDNNPWVCDCHMADMV<br>TWLKETEVVQGKDRLTCA<br>YPEKMRNRVLLELNSADL<br>DCDPILPPSLQTSYVFLG<br>IVLALIGAIFLLVLYLNR<br>KGIKKWMHNIRDACRDHM<br>EGYHYRYEINADPRLTNL<br>SSNSDV | 164 |

TABLE 1-continued

Exemplary 4-1BB and 5T4 DNA and amino acid sequences

| Protein Name | DNA Sequence | DNA SEQ ID | AA Sequence | AA SEQ ID |
|---|---|---|---|---|
| human 4-1BB (ECD*) | ATGGGAAACAGCTGTTACAACATAGTAGCCACTCT<br>GTTGCTGGTCCTCAACTTTGAGAGGACAAGATCAT<br>TGCAGGATCCTTGTAGTAACTGCCCAGCTGGTACA<br>TTCTGTGATAATAACAGGAATCAGATTTGCAGTCC<br>CTGTCCTCCAAATAGTTTCTCCAGCGCAGGTGGAC<br>AAAGGACCTGTGACATATGCAGGCAGTGTAAAGGT<br>GTTTTCAGGACCAGGAAGGAGTGTTCCTCCACCAG<br>CAATGCAGAGTGTGACTGCACTCCAGGGTTTCACT<br>GCCTGGGGGCAGGATGCAGCATGTGTGAACAGGAT<br>TGTAAACAAGGTCAAGAACTGACAAAAAAAGGTTG<br>TAAAGACTGTTGCTTTGGGACATTTAACGATCAGA<br>AACGTGGCATCTGTCGACCCTGGACAAACTGTTCT<br>TTGGATGGAAAGTCTGTGCTTGTGAATGGGACGAA<br>GGAGAGGGACGTGGTCTGTGGACCATCTCCAGCCG<br>ACCTCTCTCCGGGAGCATCCTCTGTGACCCCGCCT<br>GCCCCTGCGAGAGAGCCAGGACACTCTCCGCAG | 165 | MGNSCYNIVATLLLVLNF<br>ERTRSLQDPCSNCPAGTF<br>CDNNRNQICSPCPPNSFS<br>SAGGQRTCDICRQCKGVF<br>RTRKECSSTSNAECDCTP<br>GFHCLGAGCSMCEQDCKQ<br>GQELTKKGCKDCCFGTFN<br>DQKRGICRPWTNCSLDGK<br>SVLVNGTKERDVVCGPSP<br>ADLSPGASSVTPPAPARE<br>PGHSPQ | 166 |
| human 5T4 (ECD*) | ATGCCTGGGGGGTGCTCCCGGGGCCCCGCCGCCGG<br>GGACGGGCGTCTGCGGCTGGCGCGACTAGCGCTGG<br>TACTCCTGGGCTGGGTCTCCTCGTCTTCTCCCACC<br>TCCTCGGCATCCTCCTTCTCCTCCTCGGCGCCGTT<br>CCTGGCTTCCGCCGTGTCCGCCCAGCCCCCGCTGC<br>CGGACCAGTGCCCCGCGCTGTGCGAGTGCTCCGAG<br>GCAGCGCGCACAGTCAAGTGCGTTAACCGCAATCT<br>GACCGAGGTGCCCACGGACCTGCCCGCCTACGTGC<br>GCAACCTCTTCCTTACCGGCAACCAGCTGGCCGTG<br>CTCCCTGCCGGCGCCTTCGCCCGCCGGCCGCCGCT<br>GGCGGAGCTGGCCGCGCTCAACCTCAGCGGCAGCC<br>GCCTGGACGAGGTGCGCGCGGGCGCCTTCGAGCAT<br>CTGCCCAGCCTGCGCCAGCTCGACCTCAGCCACAA<br>CCCACTGGCCGACCTCAGTCCCTTCGCTTTCTCGG<br>GCAGCAATGCCAGCGTCTCGGCCCCCAGTCCCCTT<br>GTGGAACTGATCCTGAACCACATCGTGCCCCCTGA<br>AGATGAGCGGCAGAACCGGAGCTTCGAGGGCATGG<br>TGGTGGCGGCCCTGCTGGCGGGCCGTGCACTGCAG<br>GGGCTCCGCCGCTTGGAGCTGGCCAGCAACCACTT<br>CCTTTACCTGCCGCGGGATGTGCTGGCCCAACTGC<br>CCAGCCTCAGGCACCTGGACTTAAGTAATAATTCG<br>CTGGTGAGCCTGACCTACGTGTCCTTCCGCAACCT<br>GACACATCTAGAAAGCCTCCACCTGGAGGACAATG<br>CCCTCAAGGTCCTTCACAATGGCACCCTGGCTGAG<br>TTGCAAGGTCTACCCCACATTAGGGTTTTCCTGGA<br>CAACAATCCCTGGGTCTGCGACTGCCACATGGCAG<br>ACATGGTGACCTGGCTCAAGGAAACAGAGGTAGTG<br>CAGGGCAAAGACCGGCTCACCTGTGCATATCCGGA<br>AAAAATGAGGAATCGGGTCCTCTTGGAACTCAACA<br>GTGCTGACCTGGACTGTGACCCGATTCTTCCCCCA<br>TCCCTGCAAACCTCT | 167 | MPGGCSRGPAAGDGRLRL<br>ARLALVLLGWVSSSSPTS<br>SASSFSSSAPFLASAVSA<br>QPPLPDQCPALCECSEAA<br>RTVKCVNRNLTEVPTDLP<br>AYVRNLFLTGNQLAVLPA<br>GAFARRPPLAELAALNLS<br>GSRLDEVRAGAFEHLPSL<br>RQLDLSHNPLADLSPFAF<br>SGSNASVSAPSPLVELIL<br>NHIVPPEDERQNRSFEGM<br>VVAALLAGRALQGLRRLE<br>LASNHFLYLPRDVLAQLP<br>SLRHLDLSNNSLVSLTYV<br>SFRNLTHLESLHLEDNAL<br>KVLHNGTLAELQGLPHIR<br>VFLDNNPWVCDCHMADMV<br>TWLKETEVVQGKDRLTCA<br>YPEKMRNRVLLELNSADL<br>DCDPILPPSLQTS | 168 |

*ECD = Extracellular domain

As used herein, a "multispecific polypeptide" refers to a polypeptide comprising two or more binding domains each capable of specifically binding to a target antigen. For example, the polypeptides described herein may comprise 2, 3, 4, or more binding domains and may be able to bind 2, 3, 4, or more target antigens. In some embodiments, a multispecific polypeptide is a bispecific polypeptide. Herein, a "bispecific polypeptide" comprises two binding domains and capable of binding to two distinct target antigens. In some embodiments, the bispecific polypeptides described herein comprise a first binding domain that specifically binds to a cell surface antigen expressed on a target cell, such as 5T4. In some embodiments, the bispecific polypeptides described herein comprise a binding domain that specifically binds to a cell surface antigen expressed on an effector cell, such as 4-1BB. In particular embodiments, the multispecific polypeptide is an ADAPTIR™ homodimer bispecific polypeptide in the format scFv-Fc-scFv.

Figure 10:
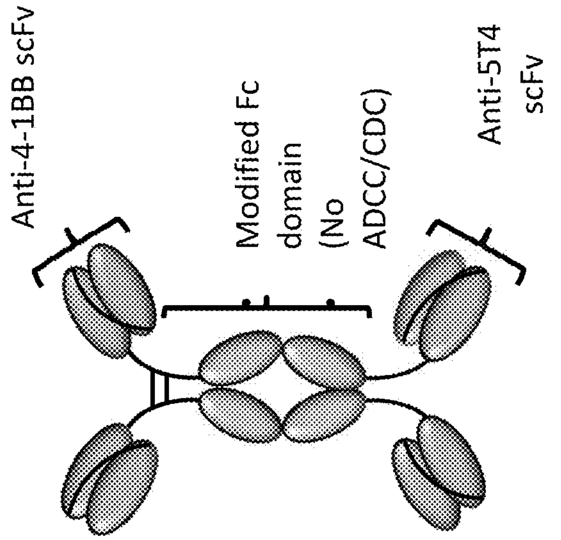
FIG. 10 illustrates an exemplary embodiment of a protein with an scFv-Fc-scFv format (ADAPTIR™ format).

Multispecific polypeptides using scaffolds are disclosed, for instance, in PCT Publication Nos. WO 2007/146968; WO 2010/040105; WO 2010/003108; WO 2016/094873; WO 2017/053469; U.S. Patent Application Publication No. 2006/0051844; and U.S. Pat. Nos. 7,166,707; and 8,409,577, which are each incorporated herein by reference in their entirety. In certain embodiments, the multispecific polypeptides described herein are bispecific polypeptides and may comprise an scFv-Fc-scFv structure, also referred to herein as an ADAPTIR™ polypeptide, or Format 1, an exemplary embodiment of which is shown in FIG. 10. The structure of a polypeptide comprising a Format 1 structure comprises, from N-terminus to C-terminus: a first scFv binding domain—an immunoglobulin (Ig) hinge region—an Ig constant region—a second scFv binding domain (FIG. 10). In certain embodiments, the multispecific polypeptides described herein may comprise an IgG-scFv structure (also referred to herein as the Morrison format, or Format 2). The structure of a polypeptide comprising a Format 2 structure comprises, from N-terminus to C-terminus: an scFv binding domain—an Ig constant region—an Ig hinge region—an Ig variable region. Format 2 is, essentially, an intact Ig molecule comprising a C-terminal scFv domain.

Binding Polypeptides and Proteins

In some embodiments, the present disclosure describes polypeptides capable of specifically binding to 5T4 (e.g., 5T4-binding polypeptides), as well as multispecific polypeptides and proteins comprising these binding domains. Such embodiments may be referred to as 5T4-binding polypeptides. In particular embodiments, the present invention provides multispecific binding proteins comprising a 5T4-binding domain and a second binding domain capable of binding to a cell-surface molecule on an effector cell. In particular embodiments, the present invention provides bispecific binding proteins comprising a 5T4-binding domain and a second binding domain capable of binding to 4-1BB (e.g., a 4-1BB-binding domain). In some embodiments, the 5T4-binding polypeptides comprise the structure, from N-terminus to C-terminus: a 5T4-binding domain—Fc domain.

In some embodiments, the present disclosure describes polypeptides capable of specifically binding to 4-1BB, as well as multispecific polypeptides and proteins comprising these binding domains. Such embodiments may be referred to as 4-1BB-binding polypeptides. In particular embodiments, the present invention provides multispecific polypeptides comprising a 4-1BB-binding domain and a second binding domain capable of binding to a cell-surface molecule on a target cell. In particular embodiments, the present invention provides bispecific polypeptides comprising a 4-1BB-binding domain and a second binding domain capable of binding to 5T4 (e.g., a 5T4-binding domain). In some embodiments, the 4-1BB-binding polypeptides comprise the structure, from N-terminus to C-terminus: a 4-1BB-binding domain—Fc domain.

In some embodiments, the polypeptides described herein can further comprise immunoglobulin constant regions, linker peptides, hinge regions, immunoglobulin dimerization/heterodimerization domains, junctional amino acids, tags, etc. These components of the disclosed polypeptides and proteins are described in further detail below.

The polypeptides and proteins described herein (e.g., 5T4-binding polypeptides, 4-1BB-binding polypeptides, and/or multispecific binding proteins thereof) comprise one or more binding domains capable of specifically binding a target antigen. The binding domains described herein can be in the form of an antibody or a fusion protein of any of a variety of different formats (e.g., the fusion protein can be in the form of a bispecific or multispecific molecule). Non-limiting examples of bispecific molecules include an scFv-Fc-scFv molecule (e.g. a bispecific protein comprising the structure of Format 1), an scFv-Ig molecule (e.g. a bispecific protein comprising the structure of Format 2) and an scFv-scFv molecule. In some embodiments, the bispecific molecules described herein comprise or consist of a first binding domain scFv linked to a second binding domain scFv and do not include other sequences such as an immunoglobulin constant region. In other embodiments, the bispecific protein described herein are diabodies.

In some embodiments, the polypeptides and proteins described herein are conjugated to a drug or a toxic moiety.

In some embodiments, the polypeptides and proteins described herein (e.g., 5T4-binding polypeptides, 4-1BB-binding polypeptides, and/or multispecific binding proteins thereof) may comprise sequences amino acid and/or nucleic acid shown in Tables 2-10. In certain embodiments, the binding domains of the polypeptides described herein comprise (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some embodiments, amino acid sequences provided for polypeptide constructs do not include the human immunoglobulin leader sequences. CDR sequences and amino acid substitution positions shown are those defined using the IMGT criteria (Brochet et al, Nucl. Acids Res. (2008) 36, W503-508). In some cases, the sequences shown in the disclosure, including in Tables 2-10, contain amino acid substitutions relative to a parent sequence (e.g. an anti-4-1BB antibody or binding fragment thereof such as clone 1618/1619, which is disclosed in PCT Application Publication No. WO 2016/185016, or an anti-5T4 antibody or binding fragment thereof such as those disclosed in PCT Application Publication No. WO 2016/185016). In some embodiments, the parent sequence of an anti-5T4 binding domain comprises the amino acid sequence provided in SEQ ID NOs: 38 and 68. In some embodiments, the parent sequence of an anti-4-1BB binding domain comprises the amino acid sequence provided in SEQ ID NOs: 28 and 16. Exemplary parental sequences for the anti-4-1BB and anti-5T4 binding domains described herein are shown below in Table 2. Underlined text indicates CDR sequences.

TABLE 2

Exemplary Binding Domain Parental Sequences

| Parental Sequence | Amino Acid Sequence | SEQ ID NO: |
|---|---|---|
| 1618 anti-4-1BB $V_H$ | EVQLLESGGGLVQPGGSLRLSCAASGFTF**SY**GSMYWVRQAPGKGLEWVSSISSGSGSTYYADSVKGRFTIS**R**DNSKNTLYLQMNSLRAEDTAVYYCARSSYYGSYYSIDYWGQGTLVTVSS | 28 |
| 1618 anti-4-1BB $V_L$ | DIQMTQSPSSLSASVGDRVTITCRASQSISSYLNWYQQKPGKAPKLLIYAASSLQSGVPSRFSGSGSGTDFTLTISSLQPEDFATYYCQQYYDNLPTFGQGTKLEIK | 16 |
| 1210 anti-5T4 $V_H$ | EVQLLESGGGLVQPGGSLRLSCAASGF**T**F**S**SYAMSWVRQAPGK**G**LEWVSAISGSGGSTYYADSVKGRFTISRDNSKNTLYLQMNSLRAEDTAVYYCARYYGGYYSAWMDYWGQGTLVTVSS | 38 |

TABLE 2-continued

| Exemplary Binding Domain Parental Sequences | | |
| --- | --- | --- |
| Parental Sequence | Amino Acid Sequence | SEQ ID NO: |
| 1210 anti-5T4 $V_L$ | DIQMTQSPSSLSASVGDRVTITCRASQSISSYLNWYQQKPGKAPKLLIYAASSLQ SGVPSRFSGSGSGTDFTLTISSLQPEDFATYYCQQTYGYLHTFGQGTKLEIK | 68 |

In certain embodiments, a binding domain $V_L$ and/or $V_H$ region of the present disclosure is derived from a $V_L$ and/or $V_H$ of a parent $V_L$ and/or $V_H$ region (e.g., 1618/1619 as described in PCT Application Publication No. WO 2016/185016) and optionally contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the $V_L$ and/or $V_H$ sequence of a known monoclonal antibody. The insertion(s), deletion(s) or substitution(s) can be anywhere in the $V_L$ and/or $V_H$ region, including at the amino- or carboxyl-terminus or both ends of this region, provided that each CDR comprises zero changes or at most one, two, or three changes. In some embodiments, the binding domain containing the modified $V_L$ and/or $V_H$ region can still specifically bind its target with an affinity similar to or greater than the parent binding domain.

In some embodiments, a binding domain described herein is derived from an antibody and comprises a variable heavy chain ($V_H$) and a variable light chain ($V_L$). For example, an scFv comprising a $V_H$ and $V_L$ chain. These binding domains and variable chains may be arranged in any order that still retains some binding to the target(s). For example, the variable domains may be arranged in the order such as $V_H$ 5T4-$V_L$ 5T4-$V_H$ 4-1BB-$V_L$ 4-1BB; $V_L$ 5T4-$V_H$ 5T4-$V_H$ 4-1BB-$V_L$ 4-1BB; $V_H$ 5T4-$V_L$ 5T4-$V_L$ 4-1BB-$V_H$ 4-1BB; $V_L$ 5T4- $V_H$ 5T4-$V_L$ 4-1BB-$V_H$ 4-1BB; $V_H$ 4-1BB-$V_L$ 4-1BB-$V_H$ 5T4-$V_L$ 5T4; $V_L$ 4-1BB-$V_H$ 4-1BB-$V_L$ 5T4-$V_H$ 5T4; $V_H$ 4-1BB-$V_L$ 4-1BB-$V_L$ 5T4-$V_H$ 5T4; or $V_L$ 4-1BB-$V_H$ 4-1BB-$V_H$ 5T4-$V_L$ 5T4. The pairs of $V_H$ regions and $V_L$ regions in the binding domain binding to 4-1BB and/or the binding domain binding to 5T4 may be in the format of a single chain antibody (scFv).

In some embodiments, the polypeptides and proteins described herein (e.g., 5T4-binding polypeptides, 4-1BB-binding polypeptides, and/or multispecific binding proteins thereof) comprise binding domains that are scFvs. In such embodiments, the binding domains may be referred to as scFv domains. In some embodiments, a binding domain is a single-chain Fv fragment (scFv) that comprises $V_H$ and $V_L$ regions specific for a target of interest. In certain embodiments, the $V_H$ and $V_L$ regions are human or humanized. In some variations, a binding domain is a single-chain Fv (scFv) comprising $V_L$ and $V_H$ regions joined by a peptide linker.

The use of peptide linkers for joining $V_L$ and $V_H$ regions is well-known in the art, and a large number of publications exist within this particular field. In some embodiments, a peptide linker is a 15mer consisting of three repeats of a Gly-Gly-Gly-Gly-Ser amino acid sequence ($(Gly_4Ser)_3$) (SEQ ID NO: 96). Other linkers have been used, and phage display technology, as well as selective infective phage technology, has been used to diversify and select appropriate linker sequences (Tang et al., *J. Biol. Chem.* 271, 15682-15686, 1996; Hennecke et al., *Protein Eng.* 11, 405-410, 1998). In certain embodiments, the $V_L$ and $V_H$ regions are joined by a peptide linker having an amino acid sequence comprising the formula $(Gly_4Ser)_n$, wherein n=1-5. For instance, in one embodiment of the invention, the linker comprises $(Gly_4Ser)_4$. Other suitable linkers can be obtained by optimizing a simple linker (e.g., $(Gly_4Ser)_n$) through random mutagenesis. In some embodiments, the $V_H$ region of the scFv described herein may be positioned N-terminally to a linker sequence. In some embodiments, the $V_L$ region of the scFvs described herein may be positioned C-terminally to the linker sequence. In some embodiments, the scFv may bind to 5T4 and/or 4-1BB more effectively than the antibody comprising the same $V_H$ and $V_L$ region sequences in the same orientation. In certain embodiments, the scFv may bind more effectively to 5T4 and/or 4-1BB in the $V_L$-$V_H$ orientation than in the $V_H$-$V_L$ orientation, or vice versa.

In some embodiments, the polypeptide comprises a binding domain linker linking the binding domains (e.g., linking the scFv domains). In some embodiments, the binding domain linker is a $Gly_4Ser$ linker. In some embodiments, the binding domain linker is a 20mer consisting of four repeats of a Gly-Gly-Gly-Gly-Ser amino acid sequence ($(Gly_4Ser)_3$) (SEQ ID NO: 98). In some embodiments, the binding domain linker comprises an amino acid sequence selected from SEQ ID NOs 86-108. Other linkers have been used, and phage display technology, as well as selective infective phage technology, has been used to diversify and select appropriate linker sequences (Tang et al., *J. Biol. Chem.* 271, 15682-15686, 1996; Hennecke et al., *Protein Eng.* 11, 405-410, 1998). In certain embodiments, the $V_L$ and $V_H$ regions are joined by a peptide linker having an amino acid sequence comprising the formula $(Gly_4Ser)_n$, wherein n=1-5. Other suitable linkers can be obtained by optimizing a simple linker (e.g., $(Gly_4Ser)_n$) through random mutagenesis. In some instances, a bispecific molecule may comprise an scFv binding to 5T4 linked to an scFv binding to 4-1BB. In some embodiments, bispecific molecules do not comprise a hinge region or a constant region.

In some embodiments, the polypeptides and proteins described herein (e.g., 5T4-binding polypeptides, 4-1BB-binding polypeptides, and/or multispecific binding proteins thereof) further comprise a hinge. In some embodiments, the hinge is an altered immunoglobulin hinge in which one or more cysteine residues in a wild type immunoglobulin hinge region is substituted with one or more other amino acid residues (e.g., serine or alanine). Exemplary altered immunoglobulin hinges, carboxyl-terminus linkers, and amino-terminus linkers include an immunoglobulin human IgG1 hinge region having one, two or three cysteine residues found in a wild type human IgG1 hinge substituted by one, two or three different amino acid residues (e.g., serine or alanine). An altered immunoglobulin hinge can additionally have a proline substituted with another amino acid (e.g., serine or alanine). For example, the above-described altered human IgG1 hinge can additionally have a proline located carboxyl-terminal to the three cysteines of wild type human IgG1 hinge region substituted by another amino acid residue (e.g., serine, alanine). In one embodiment, the prolines of the core hinge region are not substituted. In certain embodiments, a hinge, a carboxyl-terminus linker, or an amino-terminus linker polypeptide comprises or is a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a wild type immunoglobulin hinge region, such as a wild type human IgG1 hinge, a wild type human IgG2 hinge, or a wild type human IgG4 hinge.

In certain embodiments, a hinge present in a polypeptide that forms a heterodimer with another polypeptide chain can be an immunoglobulin hinge, such as a wild-type immunoglobulin hinge region or an altered immunoglobulin hinge region thereof. In certain embodiments, a hinge of one polypeptide chain of a heterodimeric protein is identical to a corresponding hinge of the other polypeptide chain of the heterodimer. In certain other embodiments, a hinge of one chain is different from that of the other chain (in their length or sequence). The different hinges in the different chains allow different manipulation of the binding affinities of the binding domains to which the hinges are connected, so that the heterodimer is able to preferentially bind to the target of one binding domain over the target of the other binding domain. For example, in certain embodiments, a heterodimeric protein has a 4-1BB-binding domain in one chain and a 5T4-binding domain in another chain. Having two different hinges in the two chains may allow the heterodimer to bind to the 5T4 first, and then to 4-1BB second. Thus, the heterodimer may recruit 4-1BB-expressing effector cells to 5T4-expressing target cells (e.g., 5T4-expressing tumor or cancer cells), which in turn may damage or destroy the 5T4-expressing cells.

In certain embodiments, a carboxyl-terminus linker or an amino-terminus linker is a flexible linker sequence comprising glycine-serine (e.g., $Gly_4Ser$) repeats. In certain embodiments, the linker comprises three $Gly_4Ser$ repeats (SEQ ID NO: 96) followed by a proline residue. In certain embodiments the proline residue is followed by an amino acid selected from the group consisting of glycine, arginine and serine. In some embodiments, a carboxyl-terminus linker or an amino-terminus linker comprises or consists of a sequence selected from SEQ ID NO: 86-108.

Some exemplary hinge, carboxyl-terminus linker, and amino-terminus linker sequences suitable for use in accordance with the present disclosure are Table 3 below. Additional exemplary hinge and linker regions are set forth in SEQ ID NOs: 241-244, 601, 78, 763-791, 228, 379-434, 618-749 of U.S. Patent Publication No. 2013/0129723 (said sequences incorporated by reference herein).

TABLE 3

Exemplary hinges and linkers

| Hinge Region | Amino Acid Sequence | SEQ ID |
|---|---|---|
| sss(s)-hIgG1 hinge | EPKSSDKTHTSPPSS | 71 |
| csc(s)-hIgG1 hinge | EPKSCDKTHTSPPCS | 72 |
| ssc(s)-hIgG1 hinge | EPKSSDKTHTSPPCS | 73 |
| scc(s)-hIgG1 hinge | EPKSSDKTHTCPPCS | 74 |
| css(s)-hIgG1 hinge | EPKSCDKTHTSPPSS | 75 |
| scs(s)-hIgG1 hinge | EPKSSDKTHTCPPSS | 76 |
| ccc(s)-hIgG1 hinge | EPKSCDKTHTSPPCS | 77 |
| ccc(p)-hIgG1 hinge | EPKSCDKTHTSPPCP | 78 |
| sss(p)-hIgG1 hinge | EPKSSDKTHTSPPSP | 79 |
| csc(p)-hIgG1 hinge | EPKSCDKTHTSPPCP | 80 |
| ssc(p)-hIgG1 hinge | EPKSSDKTHTSPPCP | 81 |
| scc(p)-hIgG1 hinge | EPKSSDKTHTCPPCP | 82 |
| css(p)-hIgG1 hinge | EPKSCDKTHTSPPSP | 83 |
| scs(p)-hIgG1 hinge | EPKSSDKTHTCPPSP | 84 |
| Scppcp | SCPPCP | 85 |
| STD1 | NYGGGGSGGGGSGGGGSGNS | 86 |
| STD2 | NYGGGGSGGGGSGGGGSGNY GGGGSGGGGSGGGGSGNS | 87 |
| H1 | NS | 88 |
| H2 | GGGGSGNS | 89 |
| H3 | NYGGGGSGNS | 90 |
| H4 | GGGGSGGGGSGNS | 91 |
| H5 | NYGGGGSGGGGSGNS | 92 |
| H6 | GGGGSGGGGSGGGGSGNS | 93 |
| H7 | GCPPCPNS | 94 |
| $Gly_4Ser$ | GGGGS | 95 |
| $(G_4S)_3$ | GGGGSGGGGSGGGGS | 96 |
| H105 | SGGGGSGGGGSGGGGS | 97 |
| $(G_4S)_4$ | GGGGSGGGGSGGGGSGGGGS | 98 |
| H75 (NKG2A quadruple mutant) | QRHNNSSLNTGTQMAGHSPNS | 99 |
| H83 (NKG2A derived) | SSLNTGTQMAGHSPNS | 100 |
| H106 (NKG2A derived) | QRHNNSSLNTGTQMAGHS | 101 |
| H81 (NKG2D derived) | EVQIPLTESYSPNS | 102 |
| H91 (NKG2D derived) | NSLANQEVQIPLTESYSPNS | 103 |
| H94 | SGGGGSGGGGSGGGGSPNS | 104 |
| H111 | SGGGGSGGGGSGGGGSPGS | 105 |
| H113 | SGGGGSGGGGSGGGGSPAS | 106 |
| H114 | SGGGGSGGGGSGGGGSPS | 107 |
| H115 | SGGGGSGGGGSGGGGSPSS | 108 |

In other embodiments, the polypeptides and proteins described herein include a heterodimerization domain that is capable of heterodimerization with a different heterodimerization domain in a second, non-identical polypeptide chain. In certain variations, the second polypeptide chain for heterodimerization includes a second binding domain. Accordingly, in certain embodiments of the present disclosure, two non-identical polypeptide chains, one comprising the polypeptide comprising a first binding domain and the second optionally comprising a second binding domain, dimerize to form a heterodimeric binding protein. Dimerization/heterodimerization domains can be used where it is desired to form heterodimers from two non-identical polypeptide chains, where one or both polypeptide chains comprise a binding domain. In certain embodiments, one polypeptide chain member of certain heterodimers described herein does not contain a binding domain. Examples of types of heterodimers include those described in U.S. Patent Application Publication Nos. 2013/0095097 and 2013/0129723, and International PCT Publication No. WO 2016/094873.

In certain embodiments, the first and second polypeptide chains dimerize via the inclusion of an "immunoglobulin dimerization domain" or "immunoglobulin heterodimerization domain." An "immunoglobulin dimerization domain" or "immunoglobulin heterodimerization domain" refers herein to an immunoglobulin domain of a first polypeptide chain that preferentially interacts or associates with a different immunoglobulin domain of a second polypeptide chain, wherein the interaction of the different immunoglobulin domains substantially contributes to or efficiently promotes heterodimerization of the first and second polypeptide chains (i.e., the formation of a dimer between two different polypeptide chains, which is also referred to as a "heterodimer"). The immunoglobulin heterodimerization domains in the polypeptide chains of a heterodimer are different from each other and thus can be differentially modified to facilitate heterodimerization of both chains and to minimize homodimerization of either chain. Immunoglobulin heterodimerization domains provided herein allow for efficient heterodimerization between different polypeptides and facilitate purification of the resulting heterodimeric protein.

As provided herein, immunoglobulin heterodimerization domains useful for promoting heterodimerization of two different polypeptide chains according to the present disclosure include wild-type and altered immunoglobulin CH1 and CL domains, for instance, human CH1 and CL domains. In certain embodiments, an immunoglobulin heterodimerization domain is a wild-type CH1 domain, such as a wild type IgG1, IgG2, IgG3, IgG4, IgA1, IgA2, IgD, IgE, or IgM CH1 domain, for example, as set forth in SEQ ID NOs: 114, 186-192 and 194, respectively, of U.S. Patent Application Publication No. 2013/0129723 or SEQ ID NO: 114 of U.S. Patent Application Publication No. 2013/0129723 (said sequence incorporated by reference herein). In further embodiments, a cysteine residue of a wild-type CH1 domain (e.g., a human CH1) involved in forming a disulfide bond with a wild type immunoglobulin CL domain (e.g., a human CL) is deleted or substituted in the altered immunoglobulin CH1 domain such that a disulfide bond is not formed between the altered CH1 domain and the wild-type CL domain.

In certain embodiments, an immunoglobulin heterodimerization domain is a wild-type CL domain, such as a wild type Cκ domain or a wild type Cλ, domain, for example, as set forth in SEQ ID NOs: 112 and 113, respectively, of U.S. Patent Application Publication No. 2013/0129723 (said sequences incorporated by reference herein). In further embodiments, an immunoglobulin heterodimerization domain is an altered immunoglobulin CL domain, such as an altered Cκ or Cλ, domain, for instance, an altered human Cκ or human Cλ, domain. In certain embodiments, a cysteine residue of a wild-type CL domain involved in forming a disulfide bond with a wild type immunoglobulin CH1 domain is deleted or substituted in the altered immunoglobulin CL domain, for example a Cκ domain as set forth in SEQ ID NO: 141 of U.S. Patent Application Publication No. 2013/0129723 or a Cλ, domain as set forth in SEQ ID NO: 140 of U.S. Patent Application Publication No. 2013/0129723 (said sequences incorporated by reference herein). In certain embodiments, only the last cysteine of the wild type human Cκ domain is deleted in the altered Cκ domain because the first arginine deleted from the wild type human Cκ domain can be provided by a linker that has an arginine at its carboxyl-terminus and links the amino-terminus of the altered Cκ domain with another domain (e.g., an immunoglobulin sub-region, such as a sub-region comprising immunoglobulin CH2 and CH3 domains).

In further embodiments, an immunoglobulin heterodimerization domain is an altered Cκ domain that contains one or more amino acid substitutions, as compared to a wild type Cκ domain, at positions that may be involved in forming the interchain-hydrogen bond network at a Cκ-Cκ interface. For example, in certain embodiments, an immunoglobulin heterodimerization domain is an altered human Cκ domain having one or more amino acids at positions N29, N30, Q52, V55, T56, S68 or T70 that are substituted with a different amino acid. The numbering of the amino acids is based on their positions in the altered human Cκ sequence as set forth in SEQ ID NO: 141 of U.S. Patent Application Publication No. 2013/0129723 (said sequence incorporated by reference herein). In certain embodiments, an immunoglobulin heterodimerization domain is an altered human Cκ domain having one, two, three or four amino acid substitutions at positions N29, N30, V55, or T70. The amino acid used as a substitute at the above-noted positions can be an alanine, or an amino acid residue with a bulk side chain moiety such as arginine, tryptophan, tyrosine, glutamate, glutamine, lysine aspartate, methionine, serine or phenylalanine. Altered human Cκ domains are those that facilitate heterodimerization with a CH1 domain, but minimize homodimerization with another Cκ domain. Representative altered human Cκ domains are set forth in SEQ ID NOs: 142-178 of U.S. Patent Application Publication No. 2013/0129723; SEQ ID NOs: 160 (N29W V55A T70A), 161 (N29Y V55A T70A), 202 (T70E N29A N30A V55A), 167 (N3OR V55A T70A), 168 (N3OK V55A T70A), 170 (N30E V55A T70A), 172 (V55R N29A N30A), 175 (N29W N30Y V55A T70E), 176 (N29Y N30Y V55A T70E), 177 (N30E V55A T70E), 178 (N30Y V55A T70E), 838 (N3OD V55A T70E), 839 (N30M V55A T70E), 840 (N305 V55A T70E), and 841 (N3OF V55A T70E) of U.S. Patent Application Publication No. 2013/0129723 (said sequences incorporated by reference herein).

In certain embodiments, in addition to or alternative to the mutations in Cκ domains described herein, both the immunoglobulin heterodimerization domains (i.e., immunoglobulin CH1 and CL domains) of a polypeptide heterodimer have mutations so that the resulting immunoglobulin heterodimerization domains form salt bridges (i.e., ionic interactions) between the amino acid residues at the mutated sites. For example, the immunoglobulin heterodimerization domains of a polypeptide heterodimer can be a mutated CH1 domain in combination with a mutated Cκ domain. In the mutated CH1 domain, valine at position 68 (V68) of the wild type human CH1 domain is substituted by an amino acid residue having a negative charge (e.g., aspartate or glutamate), whereas leucine at position 29 (L29) of a mutated human Cκ domain in which the first arginine and the last cysteine have been deleted is substituted by an amino acid residue having a positive charge (e.g., lysine, arginine or histidine). The charge-charge interaction between the amino acid residue having a negative charge of the resulting mutated CH1 domain and the amino acid residue having a positive charge of the resulting mutated Cκ domain forms a salt bridge, which stabilizes the heterodimeric interface between the mutated CH1 and Cκ domains. Alternatively, V68 of the wild type CH1 can be substituted by an amino acid residue having a positive charge, whereas L29 of a mutated human Cκ domain in which the first arginine and the last cysteine have been deleted can be substituted by an amino acid residue having a negative charge. Exemplary mutated CH1 sequences in which V68 is substituted by an amino acid with either a negative or positive charge are set forth in SEQ ID NOs: 844 and 845 of U.S. Patent Application Publication No. 2013/0129723 (said sequences incorporated by reference herein). Exemplary mutated Cκ sequences in which L29 is substituted by an amino acid with either a negative or positive charge are set forth in SEQ ID NOs: 842 and 843 of U.S. Patent Application Publication No. 2013/0129723 (said sequences incorporated by reference herein).

Positions other than V68 of human CH1 domain and L29 of human Cκ domain can be substituted with amino acids having opposite charges to produce ionic interactions between the amino acids in addition or alternative to the mutations in V68 of CH1 domain and L29 of Cκ domain.

Such positions can be identified by any suitable method, including random mutagenesis, analysis of the crystal structure of the CH1-Cκ pair to identify amino acid residues at the CH1-Cκ interface, and further identifying suitable positions among the amino acid residues at the CH1-Cκ interface using a set of criteria (e.g., propensity to engage in ionic interactions, proximity to a potential partner residue, etc.).

In certain embodiments, polypeptide heterodimers of the present disclosure contain only one pair of immunoglobulin heterodimerization domains. For example, a first chain of a polypeptide heterodimer can comprise a CH1 domain as an immunoglobulin heterodimerization domain, while a second chain can comprise a CL domain (e.g., a Cκ or Cλ) as an immunoglobulin heterodimerization domain. Alternatively, a first chain can comprise a CL domain (e.g., a Cκ or Cλ) as an immunoglobulin heterodimerization domain, while a second chain can comprise a CH1 domain as an immunoglobulin heterodimerization domain. As set forth herein, the immunoglobulin heterodimerization domains of the first and second chains are capable of associating to form a heterodimeric protein of this disclosure.

In certain other embodiments, heterodimeric proteins of the present disclosure can have two pairs of immunoglobulin heterodimerization domains. For example, a first chain of a heterodimer can comprise two CH1 domains, while a second chain can have two CL domains that associate with the two CH1 domains in the first chain. Alternatively, a first chain can comprise two CL domains, while a second chain can have two CH1 domains that associate with the two CL domains in the first chain. In certain embodiments, a first polypeptide chain comprises a CH1 domain and a CL domain, while a second polypeptide chain comprises a CL domain and a CH1 domain that associate with the CH1 domain and the CL domain, respectively, of the first polypeptide chain.

In the embodiments where a heterodimeric protein comprises only one heterodimerization pair (i.e., one immunoglobulin heterodimerization domain in each chain), the immunoglobulin heterodimerization domain of each chain can be located amino-terminal to the immunoglobulin constant region of that chain. Alternatively, the immunoglobulin heterodimerization domain in each chain can be located carboxyl-terminal to the immunoglobulin constant region of that chain.

In the embodiments where a heterodimeric protein comprises two heterodimerization pairs (i.e., two immunoglobulin heterodimerization domains in each chain), both immunoglobulin heterodimerization domains in each chain can be located amino-terminal to the immunoglobulin constant region of that chain. Alternatively, both immunoglobulin heterodimerization domains in each chain can be located carboxyl-terminal to the immunoglobulin constant region of that chain. In further embodiments, one immunoglobulin heterodimerization domain in each chain can be located amino-terminal to the immunoglobulin constant region of that chain, while the other immunoglobulin heterodimerization domain of each chain can be located carboxyl-terminal to the immunoglobulin constant region of that chain. In other words, in those embodiments, the immunoglobulin constant region is interposed between the two immunoglobulin heterodimerization domains of each chain.

As indicated herein, in some embodiments, the polypeptides and proteins (e.g., 5T4-binding polypeptides, 4-1BB-binding polypeptides, and/or multispecific binding proteins thereof) of the present disclosure further comprise an immunoglobulin constant region (also referred to herein as a constant region, Fc domain, Fc region, and the like) in a polypeptide chain. In some embodiments, the immunoglobulin constant region comprises an amino acid sequence according to SEQ ID NO: 158, 160, or a variant thereof. The inclusion of an immunoglobulin constant region slows clearance of the polypeptides and proteins of the present invention from circulation after administration to a subject. By mutations or other alterations, an immunoglobulin constant region further enables relatively easy modulation of polypeptide effector functions (e.g., ADCC, ADCP, CDC, complement fixation, and binding to Fc receptors), which can either be increased or decreased depending on the disease being treated, as known in the art and described herein. In certain embodiments, the polypeptides and proteins described herein comprise an immunoglobulin constant region capable of mediating one or more of these effector functions. In other embodiments, one or more of these effector functions are reduced or absent in an immunoglobulin constant region of a polypeptide or protein described herein present disclosure, as compared to a corresponding wild-type immunoglobulin constant region. For example, for dimeric 5T4-binding or 4-1BB-binding polypeptides designed to enhance effector cell activation, such as, e.g., via the inclusion of a 4-1BB-binding domain, an immunoglobulin constant region preferably has reduced or no effector function relative to a corresponding wild-type immunoglobulin constant region.

An immunoglobulin constant region present in the polypeptides and proteins of the present disclosure (e.g., 5T4-binding polypeptides, 4-1BB-binding polypeptides, and/or multispecific binding proteins thereof) can comprise or can be derived from part or all of: a CH2 domain, a CH3 domain, a CH4 domain, or any combination thereof. For example, an immunoglobulin constant region can comprise a CH2 domain, a CH3 domain, both CH2 and CH3 domains, both CH3 and CH4 domains, two CH3 domains, a CH4 domain, two CH4 domains, and a CH2 domain and part of a CH3 domain. In certain embodiments, the polypeptides or proteins described herein do not comprise a CH1 domain.

A polypeptide or protein described herein may comprise a wild type immunoglobulin CH2 domain or an altered immunoglobulin CH2 domain from certain immunoglobulin classes or subclasses (e.g., IgG1, IgG2, IgG3, IgG4, IgA1, IgA2, or IgD) and from various species (including human, mouse, rat, and other mammals). In certain embodiments, a CH2 domain of a polypeptide or a protein described herein is a wild type human immunoglobulin CH2 domain, such as wild type CH2 domains of human IgG1, IgG2, IgG3, IgG4, IgA1, IgA2, or IgD, as set forth in SEQ ID NOs: 115, 199-201 and 195-197, respectively, of U.S. Patent Application Publication No. 2013/0129723 (said sequences incorporated by reference herein). In certain embodiments, the CH2 domain is a wild type human IgG1 CH2 domain as set forth in SEQ ID NO: 115 of U.S. Patent Application Publication No. US 2013/0129723 (said sequence incorporated by reference herein).

In certain embodiments, an altered CH2 region in a polypeptide or a protein of the present disclosure comprises or is a sequence that is at least 90%, at least 91%, at least 92%, at least 93%, at least 94%, at least 95%, at least 96%, at least 97%, at least 98%, at least 99% identical to a wild type immunoglobulin CH2 region, such as the CH2 region of wild type human IgG1, IgG2, or IgG4, or mouse IgG2a (e.g., IGHG2c).

An altered immunoglobulin CH2 region in a polypeptide or protein of the present disclosure (e.g., 5T4-binding polypeptides, 4-1BB-binding polypeptides, and/or multispecific binding proteins thereof) can be derived from a CH2 region of various immunoglobulin isotypes, such as IgG1, IgG2, IgG3, IgG4, IgA1, IgA2, and IgD, from various species (including human, mouse, rat, and other mammals). In certain embodiments, an altered immunoglobulin CH2 region in a fusion protein of the present disclosure can be derived from a CH2 region of human IgG1, IgG2 or IgG4, or mouse IgG2a (e.g., IGHG2c), whose sequences are set forth in SEQ ID NOs: 115, 199, 201, and 320 of U.S. Patent Application Publication No. 2013/0129723 (said sequences incorporated by reference herein). In certain embodiments, an altered CH2 domain of a polypeptide or a protein described herein (e.g., 5T4-binding polypeptides, 4-1BB-binding polypeptides, and/or multispecific binding proteins thereof) is an altered human IgG1 CH2 domain with mutations known in the art that enhance or reduce immunological activities (i.e., effector functions) such as ADCC, ADCP, CDC, complement fixation, Fc receptor binding, or any combination thereof.

In certain embodiments, a CH2 domain of a polypeptide or a protein described herein is an altered immunoglobulin CH2 region (e.g., an altered human IgG1 CH2 domain) that comprises one or more amino acid deletions or substitutions. In some embodiments, the CH2 domain comprises an amino acid substitution at the asparagine of position 297 (e.g., asparagine to alanine). Such an amino acid substitution reduces or eliminates glycosylation at this site and abrogates efficient Fc binding to FcγR and C1q. The sequence of an altered human IgG1 CH2 domain with an Asn to Ala substitution at position 297 is set forth in SEQ ID NO: 324 of U.S. Patent Application Publication No. 2013/0129723 (said sequence incorporated by reference herein). In some embodiments, the altered CH2 domain comprises at least one substitution or deletion at positions 234 to 238. For example, an immunoglobulin CH2 region can comprise a substitution at position 234, 235, 236, 237 or 238; positions 234 and 235; positions 234 and 236; positions 234 and 237; positions 234 and 238; positions 234-236; positions 234, 235 and 237; positions 234, 236 and 238; positions 234, 235, 237, and 238; positions 236-238; or any other combination of two, three, four, or five amino acids at positions 234-238. In some embodiments, an altered CH2 region comprises one or more (e.g., two, three, four or five) amino acid deletions at positions 234-238, for instance, at one of position 236 or position 237 while the other position is substituted. In certain embodiments, the amino acid residues at one or more of positions 234-238 has been replaced with one or more alanine residues. In further embodiments, only one of the amino acid residues at positions 234-238 have been deleted while one or more of the remaining amino acids at positions 234-238 can be substituted with another amino acid (e.g., alanine or serine).

In some embodiments, the above-noted mutation(s) decrease or eliminate the ADCC activity or Fc receptor-binding capability of a polypeptide that comprises the altered CH2 domain.

In certain other embodiments, a CH2 domain of a polypeptide or a protein described herein is an altered immunoglobulin CH2 region (e.g., an altered human IgG1 CH2 domain) that comprises one or more amino acid substitutions at positions 253, 310, 318, 320, 322, and 331. For example, an immunoglobulin CH2 region can comprise a substitution at position 253, 310, 318, 320, 322, or 331, positions 318 and 320, positions 318 and 322, positions 318, 320 and 322, or any other combination of two, three, four, five or six amino acids at positions 253, 310, 318, 320, 322, and 331. In such embodiments, the above-noted mutation(s) decrease or eliminate the CDC activity of a polypeptide comprising the altered CH2 domain.

In certain other embodiments, in addition to the amino acid substitution at position 297, an altered CH2 region of a polypeptide or a protein described herein (e.g., an altered human IgG1 CH2 domain) can further comprise one or more (e.g., two, three, four, or five) additional substitutions at positions 234-238. For example, an immunoglobulin CH2 region can comprise a substitution at positions 234 and 297, positions 234, 235, and 297, positions 234, 236 and 297, positions 234-236 and 297, positions 234, 235, 237 and 297, positions 234, 236, 238 and 297, positions 234, 235, 237, 238 and 297, positions 236-238 and 297, or any combination of two, three, four, or five amino acids at positions 234-238 in addition to position 297. In addition or alternatively, an altered CH2 region can comprise one or more (e.g., two, three, four or five) amino acid deletions at positions 234-238, such as at position 236 or position 237. The additional mutation(s) decreases or eliminates the ADCC activity or Fc receptor-binding capability of a polypeptide comprising the altered CH2 domain. In certain embodiments, the amino acid residues at one or more of positions 234-238 have been replaced with one or more alanine residues. In further embodiments, only one of the amino acid residues at positions 234-238 has been deleted while one or more of the remaining amino acids at positions 234-238 can be substituted with another amino acid (e.g., alanine or serine).

In certain embodiments, in addition to one or more (e.g., 2, 3, 4, or 5) amino acid substitutions at positions 234-238, a mutated CH2 region of a polypeptide or a protein described herein (e.g., an altered human IgG1 CH2 domain) in a fusion protein of the present disclosure can contain one or more (e.g., 2, 3, 4, 5, or 6) additional amino acid substitutions (e.g., substituted with alanine) at one or more positions involved in complement fixation (e.g., at positions I253, H310, E318, K320, K322, or P331). Examples of mutated immunoglobulin CH2 regions include human IgG1, IgG2, IgG4 and mouse IgG2a CH2 regions with alanine substitutions at positions 234, 235, 237 (if present), 318, 320 and 322. An exemplary mutated immunoglobulin CH2 region is mouse IGHG2c CH2 region with alanine substitutions at L234, L235, G237, E318, K320, and K322.

In still further embodiments, in addition to the amino acid substitution at position 297 and the additional deletion(s) or substitution(s) at positions 234-238, an altered CH2 region of a polypeptide or a protein described herein (e.g., an altered human IgG1 CH2 domain) can further comprise one or more (e.g., two, three, four, five, or six) additional substitutions at positions 253, 310, 318, 320, 322, and 331. For example, an immunoglobulin CH2 region can comprise a (1) substitution at position 297, (2) one or more substitutions or deletions or a combination thereof at positions 234-238, and one or more (e.g., 2, 3, 4, 5, or 6) amino acid substitutions at positions I253, H310, E318, K320, K322, and P331, such as one, two, three substitutions at positions E318, K320 and K322. The amino acids at the above-noted positions can be substituted by alanine or serine.

In certain embodiments, an immunoglobulin CH2 region of a polypeptide or a protein described herein comprises: (i) an amino acid substitution at the asparagines of position 297 and one amino acid substitution at position 234, 235, 236 or 237; (ii) an amino acid substitution at the asparagine of position 297 and amino acid substitutions at two of positions 234-237; (iii) an amino acid substitution at the asparagine of position 297 and amino acid substitutions at three of positions 234-237; (iv) an amino acid substitution at the asparagine of position 297, amino acid substitutions at positions 234, 235 and 237, and an amino acid deletion at position 236; (v) amino acid substitutions at three of positions 234-237 and amino acid substitutions at positions 318, 320 and 322; or (vi) amino acid substitutions at three of positions 234-237, an amino acid deletion at position 236, and amino acid substitutions at positions 318, 320 and 322.

Exemplary altered immunoglobulin CH2 regions with amino acid substitutions at the asparagine of position 297 include: human IgG1 CH2 region with alanine substitutions at L234, L235, G237 and N297 and a deletion at G236 (SEQ ID NO: 325 of U.S. Patent Application Publication No. 2013/0129723, said sequence incorporated by reference herein), human IgG2 CH2 region with alanine substitutions at V234, G236, and N297 (SEQ ID NO: 326 of U.S. Patent Application Publication No. 2013/0129723, said sequence incorporated by reference herein), human IgG4 CH2 region with alanine substitutions at F234, L235, G237 and N297 and a deletion of G236 (SEQ ID NO: 322 of U.S. Patent Application Publication No. 2013/0129723, said sequence incorporated by reference herein), human IgG4 CH2 region with alanine substitutions at F234 and N297 (SEQ ID NO: 343 of U.S. Patent Application Publication No. US 2013/0129723, said sequence incorporated by reference herein), human IgG4 CH2 region with alanine substitutions at L235 and N297 (SEQ ID NO: 344 of U.S. Patent Application Publication No. 2013/0129723, said sequence incorporated by reference herein), human IgG4 CH2 region with alanine substitutions at G236 and N297 (SEQ ID NO: 345 of U.S. Patent Application Publication No. 2013/0129723, said sequence incorporated by reference herein), and human IgG4 CH2 region with alanine substitutions at G237 and N297 (SEQ ID NO: 346 of U.S. Patent Application Publication No. 2013/0129723, said sequence incorporated by reference herein). These CH2 regions can be used in a polypeptide of the present disclosure (e.g., a 5T4-binding polypeptide and/or a bispecific 4-1BB polypeptide).

In certain embodiments, in addition to the amino acid substitutions described above, an altered CH2 region of a polypeptide or a protein described herein (e.g., an altered human IgG1 CH2 domain) can contain one or more additional amino acid substitutions at one or more positions other than the above-noted positions. Such amino acid substitutions can be conservative or non-conservative amino acid substitutions. For example, in certain embodiments, P233 can be changed to E233 in an altered IgG2 CH2 region (see, e.g., SEQ ID NO: 326 of U.S. Patent Application Publication No. 2013/0129723, said sequence incorporated by reference herein). In addition or alternatively, in certain embodiments, the altered CH2 region can contain one or more amino acid insertions, deletions, or both. The insertion(s), deletion(s) or substitution(s) can be anywhere in an immunoglobulin CH2 region, such as at the N- or C-terminus of a wild type immunoglobulin CH2 region resulting from linking the CH2 region with another region (e.g., a binding domain or an immunoglobulin heterodimerization domain) via a hinge.

In certain embodiments, an altered CH2 domain of a polypeptide or protein described herein is a human IgG1 CH2 domain with alanine substitutions at positions 235, 318, 320, and 322 (i.e., a human IgG1 CH2 domain with L235A, E318A, K320A and K322A substitutions) (SEQ ID NO: 595 of U.S. Patent Application Publication No. 2013/0129723, said sequence incorporated by reference herein), and optionally an N297 mutation (e.g., to alanine). In certain other embodiments, an altered CH2 domain is a human IgG1 CH2 domain with alanine substitutions at positions 234, 235, 237, 318, 320 and 322 (i.e., a human IgG1 CH2 domain with L234A, L235A, G237A, E318A, K320A and K322A substitutions) (SEQ ID NO: 596 of U.S. Patent Application Publication No. 2013/0129723, said sequence incorporated by reference herein), and optionally an N297 mutation (e.g., to alanine).

In some embodiments, an immunoglobulin constant region of a polypeptide or a protein described herein (e.g., 5T4-binding polypeptides, 4-1BB-binding polypeptides, and/or multispecific binding proteins thereof) comprises a human IgG1 CH2 domain comprising the substitutions L234A, L235A, G237A, and K322A, according to the EU numbering system.

The CH3 domain that can form an immunoglobulin constant region of a polypeptide or a protein described herein (e.g., 5T4-binding polypeptides, 4-1BB-binding polypeptides, and/or multispecific binding proteins thereof) can be a wild type immunoglobulin CH3 domain or an altered immunoglobulin CH3 domain thereof from certain immunoglobulin classes or subclasses (e.g., IgG1, IgG2, IgG3, IgG4, IgA1, IgA2, IgD, IgE, IgM) of various species (including human, mouse, rat, and other mammals). In certain embodiments, a CH3 domain of a polypeptide described herein (e.g., 5T4-binding polypeptides, 4-1BB-binding polypeptides, and/or multispecific binding proteins thereof) is a wild type human immunoglobulin CH3 domain, such as wild type CH3 domains of human IgG1, IgG2, IgG3, IgG4, IgA1, IgA2, IgD, IgE, or IgM as set forth in SEQ ID NOs: 116, 208-210, 204-207, and 212, respectively of U.S. Patent Application Publication No. 2013/0129723 (said sequences incorporated by reference herein). In certain embodiments, the CH3 domain is a wild type human IgG1 CH3 domain as set forth in SEQ ID NO: 116 of U.S. Patent Application Publication No. 2013/0129723 (said sequence incorporated by reference herein).

In certain embodiments, a CH3 domain of a polypeptide described herein (e.g., 5T4-binding polypeptides, 4-1BB-binding polypeptides, and/or multispecific binding proteins thereof) is an altered human immunoglobulin CH3 domain, such as an altered CH3 domain based on or derived from a wild-type CH3 domain of human IgG1, IgG2, IgG3, IgG4, IgA1, IgA2, IgD, IgE, or IgM antibodies. For example, an altered CH3 domain can be a human IgG1 CH3 domain with one or two mutations at positions H433 and N434 (positions are numbered according to EU numbering). The mutations in such positions can be involved in complement fixation. In certain other embodiments, an altered CH3 domain of a polypeptide described herein (e.g., 5T4-binding polypeptides, 4-1BB-binding polypeptides, and/or multispecific binding proteins thereof) can be a human IgG1 CH3 domain but with one or two amino acid substitutions at position F405 or Y407. The amino acids at such positions are involved in interacting with another CH3 domain. In certain embodiments, an altered CH3 domain of polypeptide described herein can be an altered human IgG1 CH3 domain with its last lysine deleted. The sequence of this altered CH3 domain is set forth in SEQ ID NO: 761 of U.S. Patent Application Publication No. 2013/0129723 (said sequence incorporated by reference herein).

In certain embodiments, a polypeptide or a protein described herein (e.g., 5T4-binding polypeptides, 4-1BB-binding polypeptides, and/or multispecific binding proteins thereof) comprises a CH3 domain that comprises so called "knobs-into-holes" mutations (see, Marvin and Zhu, Acta Pharmacologica Sinica 26:649-58, 2005; Ridgway et al., Protein Engineering 9:617-21, 1966). More specifically, mutations can be introduced into each of the CH3 domains of each polypeptide chain so that the steric complementarity required for CH3/CH3 association obligates these two CH3 domains to pair with each other. For example, a CH3 domain in one single chain polypeptide of a polypeptide heterodimer can contain a T366W mutation (a "knob" mutation, which substitutes a small amino acid with a larger one), and a CH3 domain in the other single chain polypeptide of the polypeptide heterodimer can contain a Y407A mutation (a "hole" mutation, which substitutes a large amino acid with a smaller one). Other exemplary knobs-into-holes mutations include (1) a T366Y mutation in one CH3 domain and a Y407T in the other CH3 domain, and (2) a T366W mutation in one CH3 domain and T366S, L368A and Y407V mutations in the other CH3 domain.

The CH4 domain that can form an immunoglobulin constant region a polypeptide or a protein described herein (e.g., 5T4-binding polypeptides, 4-1BB-binding polypeptides, and/or multispecific binding proteins thereof) can be a wild type immunoglobulin CH4 domain or an altered immunoglobulin CH4 domain thereof from IgE or IgM molecules. In certain embodiments, the CH4 domain of a polypeptide described herein is a wild type human immunoglobulin CH4 domain, such as wild type CH4 domains of human IgE and IgM molecules as set forth in SEQ ID NOs: 213 and 214, respectively, of U.S. Patent Application Publication No. 2013/0129723 (said sequences incorporated by reference herein). In certain embodiments, a CH4 domain of a polypeptide described herein is an altered human immunoglobulin CH4 domain, such as an altered CH4 domain based on or derived from a CH4 domain of human IgE or IgM molecules, which have mutations that increase or decrease an immunological activity known to be associated with an IgE or IgM Fc region.

In certain embodiments, an immunoglobulin constant region of a polypeptide or a protein described herein (e.g., 5T4-binding polypeptides, 4-1BB-binding polypeptides, and/or multispecific binding proteins thereof) comprises a combination of CH2, CH3 or CH4 domains (i.e., more than one constant region domain selected from CH2, CH3 and CH4). For example, the immunoglobulin constant region can comprise CH2 and CH3 domains or CH3 and CH4 domains. In certain other embodiments, the immunoglobulin constant region can comprise two CH3 domains and no CH2 or CH4 domains (i.e., only two or more CH3). The multiple constant region domains that form an immunoglobulin constant region of the polypeptides described herein can be based on or derived from the same immunoglobulin molecule, or the same class or subclass immunoglobulin molecules. In certain embodiments, the immunoglobulin constant region is an IgG CH2-CH3 (e.g., IgG1 CH2-CH3, IgG2 CH2-CH3, and IgG4 CH2-CH3) and can be a human (e.g., human IgG1, IgG2, and IgG4) CH2CH3. For example, in certain embodiments, the immunoglobulin constant region of a polypeptide described herein comprises (1) wild type human IgG1 CH2 and CH3 domains, (2) human IgG1 CH2 with N297A substitution (i.e., CH2(N297A)) and wild type human IgG1 CH3, or (3) human IgG1 CH2(N297A) and an altered human IgG1 CH3 with the last lysine deleted. Alternatively, the multiple constant region domains of a polypeptide or a protein described herein (e.g., 5T4-binding polypeptides, 4-1BB-binding polypeptides, and/or multispecific binding proteins thereof) can be based on or derived from different immunoglobulin molecules, or different classes or subclasses immunoglobulin molecules. For example, in certain embodiments, an immunoglobulin constant region comprises both human IgM CH3 domain and human IgG1 CH3 domain. The multiple constant region domains that form an immunoglobulin constant region of a polypeptide described herein can be directly linked together or can be linked to each other via one or more (e.g., about 2-about 10) amino acids.

Exemplary immunoglobulin constant regions that can be used in a polypeptide or a protein described herein (e.g., 5T4-binding polypeptides, 4-1BB-binding polypeptides, and/or multispecific binding proteins thereof) are set forth in SEQ ID NOs: 305-309, 321, 323, 341, 342, and 762 of U.S. Patent Application Publication No. 2013/0129723 (said sequences incorporated by reference herein). Further exemplary immunoglobulin constant regions that can be used in a polypeptide or a protein described herein are provided in Table 4 below.

TABLE 4

Exemplary immunoglobulin constant regions

| Name | Amino Acid Sequence | SEQ ID NO: |
|---|---|---|
| SS-Fc domain | SSEPKSSDKTHTCPPCPAPEAAGAPSVFLEPPKPKDTLMISRTPEVTCVVVDVSHEDPE VKFNWYVDGVEVHNAKTKPREEQYNSTYRVVSVLTVLHQDWLNGKEYKCAVSNKALPAP IEKTISKAKGQPREPQVYTLPPSRDELTKNQVSLTCLVKGFYPSDIAVEWESNGQPENN YKTTPPVLDSDGSFELYSKLTVDKSRWQQGNVESCSVMHEALHNHYTQKSLSLSPG | 158 |
| Delta SS-Fc domain | EPKSSDKTHTCPPCPAPEAAGAPSVFLEPPKPKDTLMISRTPEVTCVVVDVSHEDPEVK FNWYVDGVEVHNAKTKPREEQYNSTYRVVSVLTVLHQDWLNGKEYKCAVSNKALPAPIE KTISKAKGQPREPQVYTLPPSRDELTKNQVSLTCLVKGFYPSDIAVEWESNGQPENNYK TTPPVLDSDGSFELYSKLTVDKSRWQQGNVESCSVMHEALHNHYTQKSLSLSPG | 160 |

In certain embodiments, the immunoglobulin constant regions of each polypeptide chain of a homodimeric or heterodimeric protein described herein (e.g., 5T4-binding polypeptides, 4-1BB-binding polypeptides, and/or multispecific binding proteins thereof) are identical to each other. In certain other embodiments, the immunoglobulin constant region of one polypeptide chain of a heterodimeric protein is different from the immunoglobulin constant region of the other polypeptide chain of the heterodimer. For example, one immunoglobulin constant region of a heterodimeric protein can contain a CH3 domain with a "knob" mutation, whereas the other immunoglobulin constant region of the heterodimeric protein can contain a CH3 domain with a "hole" mutation.

In some embodiments, the polypeptides of the present disclosure may comprise an immunoglobulin constant region comprising any of the above described mutations and a binding domain comprising one or more amino acid mutations compared to a parental binding domain amino acid sequence. For example, in some embodiments the polypeptides of the present disclosure may comprise an immunoglobulin constant region comprising one or more of the L234A, L235A, G237A, and K322A mutations in the human IgG1 CH2 domain and a 5T4-binding domain comprising a $V_H$ domain selected from the group consisting of SEQ ID NOs: 38 and 46 and a $V_L$ domain selected from the group consisting of SEQ ID NOs: 44, 48, and 50. In some embodiments, the polypeptides of the present disclosure may comprise an immunoglobulin constant region comprising one or more of the L234A, L235A, G237A, and K322A mutations in the human IgG1 CH2 domain and a 41BB-binding domain comprising a $V_H$ domain amino acid sequence of SEQ ID NO: 14 and a $V_L$ domain amino acid sequence of SEQ ID NO: 16. In some embodiments the polypeptides of the present disclosure may comprise an immunoglobulin constant region comprising one or more of the L234A, L235A, G237A, and K322A mutations in the human IgG1 CH2 domain and a 5T4-binding domain comprising a $V_H$ domain selected from the group consisting of SEQ ID NOs: 38 and 46 and a $V_L$ domain selected from the group consisting of SEQ ID NOs: 44, 48, and 50; and a 41BB-binding domain comprising a $V_H$ domain amino acid sequence of SEQ ID NO: 14, and a $V_L$ domain amino acid sequence of SEQ ID NO: 16.

Polypeptides and proteins described herein (e.g., 5T4-binding polypeptides, 4-1BB-binding polypeptides, and/or multispecific binding proteins thereof) may be made using scaffolding as generally disclosed in U.S. Patent Application Publication Nos. 2013/0129723 and 2013/0095097, which are each incorporated herein by reference in their entirety. The polypeptides described herein may comprise two non-identical polypeptide chains, each polypeptide chain comprising an immunoglobulin heterodimerization domain. The interfacing immunoglobulin heterodimerization domains are different. In one embodiment, the immunoglobulin heterodimerization domain comprises a CH1 domain or a derivative thereof. In another embodiment, the immunoglobulin heterodimerization domain comprises a CL domain or a derivative thereof. In one embodiment, the CL domain is a Cκ or Cλ, isotype or a derivative thereof.

In some embodiments, polypeptides and proteins described herein (e.g., 5T4-binding polypeptides, 4-1BB-binding polypeptides, and/or multispecific binding proteins thereof) may have improved characteristics compared to other 5T4-binding polypeptides or 4-1BB-binding polypeptides. For example, the 5T4-binding polypeptides, 4-1BB-binding polypeptides, or multispecific proteins thereof of the present invention may exhibit a reduced isoelectric point compared to the isoelectric point of a different 5T4-binding polypeptide and/or 4-1BB-binding polypeptide. "Isoelectric point" or "pI" is the pH at which net charge is zero. The isoelectric point of a protein may be measured by any suitable method, e.g., analytical capillary isoelectric focusing chromatography.

In some embodiments, polypeptides and proteins described herein (e.g., 5T4-binding polypeptides, 4-1BB-binding polypeptides, and/or multispecific binding proteins thereof) may bind to 5T4 (e.g., human 5T4) and/or 4-1BB with a higher affinity than a previously known 5T4- and/or 4-1BB-binding domains and/or a parent 5T4- and/or 4-1BB-binding domain or protein. In some embodiments, the dissociation constant of a 5T4- and/or 4-1BB-binding domain or polypeptide may be about 2-5 nM. In certain embodiments, the off rate of a 5T4- and/or 4-1BB-binding domain or polypeptide may be 4- to 10-fold reduced compared to the off rate of a previously known antibody or scFv construct or the parent 5T4- and/or 4-1BB-binding domain or protein.

In some embodiments, polypeptides and proteins described herein (e.g., 5T4-binding polypeptides, 4-1BB-binding polypeptides, and/or multispecific binding proteins thereof) may have a low level of high molecular weight aggregates produced during recombinant expression of the polypeptide or protein. In some embodiments, polypeptides and proteins described herein (e.g., 5T4-binding polypeptides, 4-1BB-binding polypeptides, and/or multispecific binding proteins thereof) may exhibit longer stability in human serum, depending on the combination of domains present in the polypeptide or protein.

5T4-Binding Domains and Proteins Comprising the Same

In some embodiments, the present invention provides 5T4-binding domains that specifically bind to 5T4 (e.g. human 5T4). In some embodiments, the present invention further provides polypeptides comprising a 5T4-binding domain (e.g., 5T4-binding polypeptides). In certain variations, the 5T4-binding polypeptide comprises a hinge region carboxyl-terminal to the 5T4-binding domain, and an immunoglobulin constant region. In further variations, the 5T4-binding polypeptide comprises a carboxyl-terminus binding domain linker carboxyl-terminal to the immunoglobulin constant region, and a second binding domain carboxyl-terminal to the carboxyl-terminus linker. In yet other variations, a 5T4-binding polypeptide comprises a hinge region amino-terminal to the polypeptide comprising the 5T4-binding domain, and an immunoglobulin constant amino-terminal to the hinge region.

In some embodiments, the 5T4-binding domains described herein binds an epitope located on the extracellular domain of 5T4 (e.g., an epitope comprised within SEQ ID NO: 168). In certain aspects, this epitope is a discontinuous and/or conformational epitope.

A 5T4-binding domain polypeptide may specifically bind to human 5T4 and comprise a heavy chain CDR1 (HCDR1), HCDR2, HCDR3, light chain CDR1 (LCDR1), LCDR2, and LCDR3, wherein the HCDR1 comprises an amino acid sequence selected from the group consisting of SEQ ID NOs: 30, 52, and 60; the HCDR2 comprises an amino acid sequence selected from the group consisting of SEQ ID NOs: 32 and 62; the HCDR3 comprises an amino acid sequence of SEQ ID NO: 34; the LCDR1 comprises an amino acid sequence selected from the group consisting of SEQ ID NOs: 8, 42, and 54; the LCDR2 comprises an amino acid sequence of SEQ ID NOs: 10; and the LCDR3 comprises an amino acid sequence of SEQ ID NO: 36.

In particular embodiments, a 5T4-binding domain polypeptide may specifically bind to human 5T4 and comprise an HCDR1, HCDR2, HCDR3, LCDR1, LCDR2, and LCDR3, wherein (a) the HCDR1 comprises an amino acid sequence set forth in SEQ ID NO: 30; (b) the HCDR2 comprises an amino acid sequence set forth in SEQ ID NO: 32; (c) the HCDR3 comprises an amino acid sequence set forth in SEQ ID NO: 34; (d) the LCDR1 comprises an amino acid sequence set forth in SEQ ID NO: 8; the LCDR2 comprises an amino acid sequence set forth in SEQ ID NO: 10; and (f) the LCDR3 comprises an amino acid sequence set forth in SEQ ID NO: 36. In other particular embodiments, a 5T4-binding domain polypeptide specifically binds to human 5T4 and comprises an HCDR1, HCDR2, HCDR3, LCDR1, LCDR2, and LCDR3, wherein (a) the HCDR1 comprises an amino acid sequence set forth in SEQ ID NO: 30; (b) the HCDR2 comprises an amino acid sequence set forth in SEQ ID NO: 32; (c) the HCDR3 comprises an amino acid sequence set forth in SEQ ID NO: 34; (d) the LCDR1 comprises an amino acid sequence set forth in SEQ ID NO: 42; (e) the LCDR2 comprises an amino acid sequence set forth in SEQ ID NO: 10; and (f) the LCDR3 comprises an amino acid sequence set forth in SEQ ID NO: 36. In other particular embodiments, a 5T4-binding domain polypeptide specifically binds to human 5T4 and comprises an HCDR1, HCDR2, HCDR3, LCDR1, LCDR2, and LCDR3, wherein (a) the HCDR1 comprises an amino acid sequence set forth in SEQ ID NO: 52; (b) the HCDR2 comprises an amino acid sequence set forth in SEQ ID NO: 32; (c) the HCDR3 comprises an amino acid sequence set forth in SEQ ID NO: 34; (d) the LCDR1 comprises an amino acid sequence set forth in SEQ ID NO: 54; (e) the LCDR2 comprises an amino acid sequence set forth in SEQ ID NO: 10; and (f) the LCDR3 comprises an amino acid sequence set forth in SEQ ID NO: 36. In other particular embodiments, a 5T4-binding domain polypeptide specifically binds to human 5T4 and comprises an HCDR1, HCDR2, HCDR3, LCDR1, LCDR2, and LCDR3, wherein (a) the HCDR1 comprises an amino acid sequence set forth in SEQ ID NO: 60; (b) the HCDR2 comprises an amino acid sequence set forth in SEQ ID NO: 62; (c) the HCDR3 comprises an amino acid sequence set forth in SEQ ID NO: 34; (d) the LCDR1 comprises an amino acid sequence set forth in SEQ ID NO: 54; (e) the LCDR2 comprises an amino acid sequence set forth in SEQ ID NO: 10; and (f) the LCDR3 comprises an amino acid sequence set forth in SEQ ID NO: 36.

In certain embodiments, a 5T4-binding domain polypeptide comprises or is a sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) selected from the group consisting of SEQ ID NOs: 40, 44, 48, 50, 58, 68, and 70, wherein the polypeptide is a multi-specific polypeptide in the format scFv-Fc-scFv and comprises a Y to F substitution in the LCDR1 at position 99 of the $V_L$ and/or a F to S substitution in the FR3 at position 148 of the $V_L$. In certain embodiments, a polypeptide comprising a 5T4-binding domain comprises an amino acid sequence of a light chain variable region ($V_L$) selected from the group consisting of SEQ ID NOs: 40, 44, 48, 50, 58, 68, and 70. In certain embodiments, a 5T4-binding domain polypeptide comprises an amino acid sequence of a heavy chain variable region ($V_H$) selected from the group consisting of SEQ ID NOs 38, 46, 56, and 64.

In certain embodiments, a 5T4-binding domain polypeptide comprises a $V_H$ region comprising the amino acid sequence of SEQ ID NO: 38 and a $V_L$ region comprising the amino acid sequence of SEQ ID NO: 40. In certain embodiments, a 5T4-binding domain polypeptide comprises a $V_H$ region comprising the amino acid sequence of SEQ ID NO: 38 and a $V_L$ region comprising the amino acid sequence of SEQ ID NO: 44. In certain embodiments, a 5T4-binding domain polypeptide comprises a $V_H$ region comprising the amino acid sequence of SEQ ID NO: 46 and a $V_L$ region comprising the amino acid sequence of SEQ ID NO: 48. In certain embodiments, a 5T4-binding domain polypeptide comprises a $V_H$ region comprising the amino acid sequence of SEQ ID NO: 46 and a $V_L$ region comprising the amino acid sequence of SEQ ID NO: 50. In certain embodiments, a 5T4-binding domain polypeptide comprises a $V_H$ region comprising the amino acid sequence of SEQ ID NO: 56 and a $V_L$ region comprising the amino acid sequence of SEQ ID NO: 58. In certain embodiments, a 5T4-binding domain polypeptide comprises a $V_H$ region comprising the amino acid sequence of SEQ ID NO: 64 and a $V_L$ region comprising the amino acid sequence of SEQ ID NO: 58. In certain embodiments, a 5T4-binding domain polypeptide comprises a $V_H$ region comprising the amino acid sequence of SEQ ID NO: 38 and a $V_L$ region comprising the amino acid sequence of SEQ ID NO: 68. In certain embodiments, a 5T4-binding domain polypeptide comprises a $V_H$ region comprising the amino acid sequence of SEQ ID NO: 46 and a $V_L$ region comprising the amino acid sequence of SEQ ID NO: 70.

Exemplary anti-5T4 binding domain sequences are shown in Table 5.

TABLE 5

5T4-binding domain polypeptide CDR and variable region amino acid and DNA sequences

| Construct | Component | DNA Sequence | DNA SEQID | AA sequence | AA SEQID |
|---|---|---|---|---|---|
| ALG.APV-178 ALG.APV-208 | HCDR1 | GGCTTCACATTCAGCAGCTATGCT | 29 | GFTFSSYA | 30 |
| | HCDR2 | ATCTCCGGCAGCGGCGGAAGCACC | 31 | ISGSGGST | 32 |
| | HCDR3 | GCCAGGTACTATGGCGGCTACTAC TCCGCCTGGATGGACTAC | 33 | ARYYGGYYSAWMDY | 34 |
| | LCDR1 | CAGTCCATCTCCAGCTAT | 7 | QSISSY | 8 |
| | LCDR2 | GCCGCTTCC | 9 | AAS | 10 |
| | LCDR3 | CAGCAGACCTATGGCTACCTGCAC ACC | 35 | QQTYGYLHT | 36 |
| | $V_H$ | GAAGTGCAGCTGCTGGAGTCCGGA GGAGGACTGGTGCAGCCTGGCGGA AGCCTGAGGCTGAGCTGCGCTGCC TCCGGCTTCACATTCAGCAGCTAT GCTATGAGCTGGGTGAGGCAAGCC CCTGGAAAGGGCCTGGAGTGGGTG TCCGCTATCTCCGGCAGCGGCGGA AGCACCTACTACGCTGACTCCGTC AAGGGCAGGTTCACCATCAGCCGG GACAACAGCAAGAACACCCTGTAC CTGCAGATGAATAGCCTCAGGGCT GAAGACACCGCTGTGTACTACTGC GCCAGGTACTATGGCGGCTACTAC TCCGCCTGGATGGACTACTGGGGA CAGGGCACACTGGTGACCGTGTCC AGC | 37 | EVQLLESGGGLVQPGGS LRLSCAASGFTFSSYAM SWVRQAPGKGLEWVSAI SGSGGSTYYADSVKGRF TISRDNSKNTLYLQMNS LRAEDTAVYYCARYYGG YYSAWMDYWGQGTLVTV SS | 38 |

TABLE 5-continued

5T4-binding domain polypeptide CDR and variable region amino acid and DNA sequences

| Construct | Component | DNA Sequence | DNA SEQID | AA sequence | AA SEQID |
|---|---|---|---|---|---|
| | $V_L$ | GATATTCAGATGACACAGTCCCCTAGCTCCCTGTCCGCCAGCGTGGGAGATCGGGTGACCATCACCTGCAGGGCCAGCCAGTCCATCTCCAGCTATTTAAACTGGTACCAGCAGAAGCCTGGAAAGGCTCCCAAGCTGCTGATCTACGCCGCTTCCAGCCTCCAGAGCGGCGTGCCTAGCAGGTTCTCCGGCTCCGGAAGCGGAACAGACTTCACCCTGACCATCAGCTCCCTGCAGCCCGAGGACTCCGCTACCTACTACTGCCAGCAGACCTATGGCTACCTGCACACCTTCGGCCAGGGCACAAAGCTGGAGATCAAG | 39 | DIQMTQSPSSLSASVGDRVTITCRASQSISSYLNWYQQKPGKAPKLLIYAASSLQSGVPSRFSGSGSGTDFTLTISSLQPEDSATYYCQQTYGYLHTFGQGTKLEIK | 40 |
| ALG.APV-179 | HCDR1 | GGCTTCACATTCAGCAGCTATGCT | 29 | GFTFSSYA | 30 |
| | HCDR2 | ATCTCCGGCAGCGGCGGAAGCACC | 31 | ISGSGGST | 32 |
| ALG.APV-209 | HCDR3 | GCCAGGTACTATGGCGGCTACTACTCCGCCTGGATGGACTAC | 33 | ARYYGGYYSAWMDY | 34 |
| ALG.APV-222 | LCDR1 | CAGTCCATCTCCAGCTTC | 41 | QSISSF | 42 |
| | LCDR2 | GCCGCTTCC | 9 | AAS | 10 |
| | LCDR3 | CAGCAGACCTATGGCTACCTGCACACC | 35 | QQTYGYLHT | 36 |
| | $V_H$ | GAAGTGCAGCTGCTGGAGTCCGGAGGAGGACTGGTGCAGCCTGGCGGAAGCCTGAGGCTGAGCTGCGCTGCCTCCGGCTTCACATTCAGCAGCTATGCTATGAGCTGGGTGAGGCAAGCCCCTGGAAAGGGCCTGGAGTGGGTGTCCGCTATCTCCGGCAGCGGCGGAAGCACCTACTACGCTGACTCCGTCAAGGGCAGGTTCACCATCAGCCGGGACAACAGCAAGAACACCCTGTACCTGCAGATGAATAGCCTCAGGGCTGAAGACACCGCTGTGTACTACTGCGCCAGGTACTATGGCGGCTACTACTCCGCCTGGATGGACTACTGGGGACAGGGCACACTGGTGACCGTGTCCAGC | 37 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARYYGGYYSAWMDYWGQGTLVTVSS | 38 |
| | $V_L$ | GATATTCAGATGACACAGTCCCCTAGCTCCCTGTCCGCCAGCGTGGGAGATCGGGTGACCATCACCTGCAGGGCCAGCCAGTCCATCTCCAGCTTCTTAAACTGGTACCAGCAGAAGCCTGGAAAGGCTCCCAAGCTGCTGATCTACGCCGCTTCCAGCCTCCAGAGCGGCGTGCCTAGCAGGTTCTCCGGCTCCGGAAGCGGAACAGACTTCACCCTGACCATCAGCTCCCTGCAGCCCGAGGACTCCGCTACCTACTACTGCCAGCAGACCTATGGCTACCTGCACACCTTCGGCCAGGGCACAAAGCTGGAGATCAAG | 43 | DIQMTQSPSSLSASVGDRVTITCRASQSISSFLNWYQQKPGKAPKLLIYAASSLQSGVPSRFSGSGSGTDFTLTISSLQPEDSATYYCQQTYGYLHTFGQGTKLEIK | 44 |
| ALG.APV-187 | HCDR1 | GGCTTCACATTCAGCAGCTATGCT | 29 | GFTFSSYA | 30 |
| | HCDR2 | ATCTCCGGCAGCGGCGGAAGCACC | 31 | ISGSGGST | 32 |
| ALG.APV-210 | HCDR3 | GCCAGGTACTATGGCGGCTACTACTCCGCCTGGATGGACTAC | 33 | ARYYGGYYSAWMDY | 34 |
| ALG.APV-223 | LCDR1 | CAGTCCATCTCCAGCTTC | 41 | QSISSF | 42 |
| | LCDR2 | GCCGCTTCC | 9 | AAS | 10 |
| LCDR3 | | CAGCAGACCTATGGCTACCTGCACACC | 35 | QQTYGYLHT | 36 |
| | V+HDH+L | GAAGTGCAGCTGCTGGAGTCCGGAGGAGGACTGGTGCAGCCTGGCGGAAGCCTGAGGCTGAGCTGCGCTGCCTCCGGCTTCACATTCAGCAGCTATGCTATGAGCTGGGTGAGGCAAGCCCCTGGAAAGTGCCTGGAGTGGGTGTCCGCTATCTCCGGCAGCGGCGGAAGCACCTACTACGCTGACTCCGTCAAGGGCAGGTTCACCATCAGCCGGGACAACAGCAAGAACACCCTGTACCTGCAGATGAATAGCCTCAGGGCTGAAGACACCGCTGTGTACTACTGC | 45 | EVQLLESGGGLVQPGGSLRLSCAASGFTFSSYAMSWVRQAPGKCLEWVSAISGSGGSTYYADSVKGRFTISRDNSKNTLYLQMNSLRAEDTAVYYCARYYGGYYSAWMDYWGQGTLVTVSS | 46 |

TABLE 5-continued

5T4-binding domain polypeptide CDR and variable region amino acid and DNA sequences

| Construct | Component | DNA Sequence | DNA SEQID | AA sequence | AA SEQID |
|---|---|---|---|---|---|
| | | GCCAGGTACTATGGCGGCTACTAC<br>TCCGCCTGGATGGACTACTGGGGA<br>CAGGGCACACTGGTGACCGTGTCC<br>AGC | | | |
| | $V_L$ | GATATTCAGATGACACAGTCCCCT<br>AGCTCCCTGTCCGCCAGCGTGGGA<br>GATCGGGTGACCATCACCTGCAGG<br>GCCAGCCAGTCCATCTCCAGCTTC<br>TTAAACTGGTACCAGCAGAAGCCT<br>GGAAAGGCTCCCAAGCTGCTGATC<br>TACGCCGCTTCCAGCCTCCAGAGC<br>GGCGTGCCTAGCAGGTTCTCCGGC<br>TCCGGAAGCGGAACAGACTTCACC<br>CTGACCATCAGCTCCCTGCAGCCC<br>GAGGACTCCGCTACCTACTACTGC<br>CAGCAGACCTATGGCTACCTGCAC<br>ACCTTCGGCTGCGGCACAAAGCTG<br>GAGATCAAG | 47 | DIQMTQSPSSLSASVGD<br>RVTITCRASQSISSFLN<br>WYQQKPGKAPKLLIYAA<br>SSLQSGVPSRFSGSGSG<br>TDFTLTISSLQPEDSAT<br>YYCQQTYGYLHTFGCGT<br>KLEIK | 48 |
| ALG.APV-<br>191 | HCDR1 | GGCTTCACATTCAGCAGCTATGCT | 29 | GFTFSSYA | 30 |
| | HCDR2 | ATCTCCGGCAGCGGCGGAAGCACC | 31 | ISGSGGST | 32 |
| | HCDR3 | GCCAGGTACTATGGCGGCTACTAC<br>TCCGCCTGGATGGACTAC | 33 | ARYYGGYYSAWMDY | 34 |
| | LCDR1 | CAGTCCATCTCCAGCTTC | 41 | QSISSF | 42 |
| | LCDR2 | GCCGCTTCC | 9 | AAS | 10 |
| | LCDR3 | CAGCAGACCTATGGCTACCTGCAC<br>ACC | 35 | QQTYGYLHT | 36 |
| | $V_H$ | GAAGTGCAGCTGCTGGAGTCCGGA<br>GGAGGACTGGTGCAGCCTGGCGGA<br>AGCCTGAGGCTGAGCTGCGCTGCC<br>TCCGGCTTCACATTCAGCAGCTAT<br>GCTATGAGCTGGGTGAGGCAAGCC<br>CCTGGAAAGTGCCTGGAGTGGGTG<br>TCCGCTATCTCCGGCAGCGGCGGA<br>AGCACCTACTACGCTGACTCCGTC<br>AAGGGCAGGTTCACCATCAGCCGG<br>GACAACAGCAAGAACACCCTGTAC<br>CTGCAGATGAATAGCCTCAGGGCT<br>GAAGACACCGCTGTGTACTACTGC<br>GCCAGGTACTATGGCGGCTACTAC<br>TCCGCCTGGATGGACTACTGGGGA<br>CAGGGCACACTGGTGACCGTGTCC<br>AGC | 45 | EVQLLESGGGLVQPGGS<br>LRLSCAASGFTFSSYAM<br>SWVRQAPGKCLEWVSAI<br>SGSGGSTYYADSVKGRF<br>TISRDNSKNTLYLQMNS<br>LRAEDTAVYYCARYYGG<br>YYSAWMDYWGQGTLVTV<br>SS | 46 |
| | $V_L$ | GATATTCAGATGACACAGTCCCCT<br>AGCTCCCTGTCCGCCAGCGTGGGA<br>GATCGGGTGACCATCACCTGCAGG<br>GCCAGCCAGTCCATCTCCAGCTTC<br>TTAAACTGGTACCAGCAGAAGCCT<br>GGAAAGGCTCCCAAGCTGCTGATC<br>TACGCCGCTTCCAGCCTCCAGAGC<br>GGCGTGCCTAGCAGGTTCTCCGGC<br>TCCGGAAGCGGAACAGACTTCACC<br>CTGACCATCAGCTCCCTGCAGCCC<br>GAGGACTTCGCTACCTACTACTGC<br>CAGCAGACCTATGGCTACCTGCAC<br>ACCTTCGGCTGCGGCACAAAGCTG<br>GAGATCAAG | 49 | DIQMTQSPSSLSASVGD<br>RVTITCRASQSISSFLN<br>WYQQKPGKAPKLLIYAA<br>SSLQSGVPSRFSGSGSG<br>TDFTLTISSLQPEDFAT<br>YYCQQTYGYLHTFGCGT<br>KLEIK | 50 |
| ALG.APV-<br>196<br>ALG.APV-<br>198 | HCDR1 | GGCTTCGACTTCGAGAGCTATGCT | 51 | GFDFESYA | 52 |
| | HCDR2 | ATCTCCGGCAGCGGCGGAAGCACC | 31 | ISGSGGST | 32 |
| | HCDR3 | GCCAGGTACTATGGCGGCTACTAC<br>TCCGCCTGGATGGACTAC | 33 | ARYYGGYYSAWMDY | 34 |
| | LCDR1 | CAGTCCATCAGGAGCGCC | 53 | QSIRSA | 54 |
| | LCDR2 | GCCGCTTCC | 9 | AAS | 10 |
| | LCDR3 | CAGCAGACCTATGGCTACCTGCAC<br>ACC | 35 | QQTYGYLHT | 36 |
| | $V_H$ | GAAGTGCAGCTGCTGGAGTCCGGA<br>GGAGGACTGGTGCAGCCTGGCGGA<br>AGCCTGAGGCTGAGCTGCGCTGCC<br>TCCGGCTTCGACTTCGAGAGCTAT<br>GCTATGAGCTGGGTGAGGCAAGCC<br>CCTGGAAAGTGCCTGGAGTGGGTG<br>TCCGCTATCTCCGGCAGCGGCGGA<br>AGCACCTACTACGCTGACTCCGTC | 55 | EVQLLESGGGLVQPGGS<br>LRLSCAASGFDFESYAM<br>SWVRQAPGKCLEWVSAI<br>SGSGGSTYYADSVKGRF<br>TISRDNSKNTLYLQMNS<br>LRAEDTAVYYCARYYGG<br>YYSAWMDYWGQGTLVTV<br>SS | 56 |

TABLE 5-continued

5T4-binding domain polypeptide CDR and variable region amino acid and DNA sequences

| Construct | Component | DNA Sequence | DNA SEQID | AA sequence | AA SEQID |
|---|---|---|---|---|---|
| | | AAGGGCAGGTTCACCATCAGCCGG | | | |
| | | GACAACAGCAAGAACACCCTGTAC | | | |
| | | CTGCAGATGAATAGCCTCAGGGCT | | | |
| | | GAAGACACCGCTGTGTACTACTGC | | | |
| | | GCCAGGTACTATGGCGGCTACTAC | | | |
| | | TCCGCCTGGATGGACTACTGGGGA | | | |
| | | CAGGGCACACTGGTGACCGTGTCC | | | |
| | | AGC | | | |
| | $V_L$ | GATATTCAGATGACACAGTCCCCT | 57 | DIQMTQSPSSLSASVGD | 58 |
| | | AGCTCCCTGTCCGCCAGCGTGGGA | | RVTITCRASQSIRSALN | |
| | | GATCGGGTGACCATCACCTGCAGG | | WYQQKPGKAPKLLIYAA | |
| | | GCCAGCCAGTCCATCAGGAGCGCC | | SSLQSGVPSRFSGSGSG | |
| | | CTGAACTGGTACCAGCAGAAGCCT | | TDFTLTISSLQPEDFAT | |
| | | GGAAAGGCTCCCAAGCTGCTGATC | | YYCQQTYGYLHTFGCGT | |
| | | TACGCCGCTTCCAGCCTCCAGAGC | | KLEIK | |
| | | GGCGTGCCTAGCAGGTTCTCCGGC | | | |
| | | TCCGGAAGCGGAACAGACTTCACC | | | |
| | | CTGACCATCAGCTCCCTGCAGCCC | | | |
| | | GAGGACTTCGCTACCTACTACTGC | | | |
| | | CAGCAGACCTATGGCTACCTGCAC | | | |
| | | ACCTTCGGCTGCGGCACAAAGCTG | | | |
| | | GAGATCAAG | | | |
| ALG.APV- | HCDR1 | GGCTTCGACTTCGACAGCTATGCT | 59 | GFDFDSYA | 60 |
| 199 | HCDR2 | ATCTCCGGCAGGGGCGGAAGCACC | 61 | ISGRGGST | 62 |
| | HCDR3 | GCCAGGTACTATGGCGGCTACTAC | 33 | ARYYGGYYSAWMDY | 34 |
| | | TCCGCCTGGATGGACTAC | | | |
| | LCDR1 | CAGTCCATCAGGAGCGCC | 53 | QSIRSA | 54 |
| | LCDR2 | GCCGCTTCC | 9 | AAS | 10 |
| | LCDR3 | CAGCAGACCTATGGCTACCTGCAC | 35 | QQTYGYLHT | 36 |
| | | ACC | | | |
| | $V_H$ | GAAGTGCAGCTGCTGGAGTCCGGA | 63 | EVQLLESGGGLVQPGGS | 64 |
| | | GGAGGACTGGTGCAGCCTGGCGGA | | LRLSCAASGFDFDSYAM | |
| | | AGCCTGAGGCTGAGCTGCGCTGCC | | SWVRQAPGKCLEWVSAI | |
| | | TCCGGCTTCGACTTCGACAGCTAT | | SGRGGSTYYADSVKGRF | |
| | | GCTATGAGCTGGGTGAGGCAAGCC | | TISRDNSKNTLYLQMNS | |
| | | CCTGGAAAGTGCCTGGAGTGGGTG | | LRAEDTAVYYCARYYGG | |
| | | TCCGCTATCTCCGGCAGGGGCGGA | | YYSAWMDYWGQGTLVTV | |
| | | AGCACCTACTACGCTGACTCCGTC | | SS | |
| | | AAGGGCAGGTTCACCATCAGCCGG | | | |
| | | GACAACAGCAAGAACACCCTGTAC | | | |
| | | CTGCAGATGAATAGCCTCAGGGCT | | | |
| | | GAAGACACCGCTGTGTACTACTGC | | | |
| | | GCCAGGTACTATGGCGGCTACTAC | | | |
| | | TCCGCCTGGATGGACTACTGGGGA | | | |
| | | CAGGGCACACTGGTGACCGTGTCC | | | |
| | | AGC | | | |
| | $V_L$ | GATATTCAGATGACACAGTCCCCT | 57 | DIQMTQSPSSLSASVGD | 58 |
| | | AGCTCCCTGTCCGCCAGCGTGGGA | | RVTITCRASQSIRSALN | |
| | | GATCGGGTGACCATCACCTGCAGG | | WYQQKPGKAPKLLIYAA | |
| | | GCCAGCCAGTCCATCAGGAGCGCC | | SSLQSGVPSRFSGSGSG | |
| | | CTGAACTGGTACCAGCAGAAGCCT | | TDFTLTISSLQPEDFAT | |
| | | GGAAAGGCTCCCAAGCTGCTGATC | | YYCQQTYGYLHTFGCGT | |
| | | TACGCCGCTTCCAGCCTCCAGAGC | | KLEIK | |
| | | GGCGTGCCTAGCAGGTTCTCCGGC | | | |
| | | TCCGGAAGCGGAACAGACTTCACC | | | |
| | | CTGACCATCAGCTCCCTGCAGCCC | | | |
| | | GAGGACTTCGCTACCTACTACTGC | | | |
| | | CAGCAGACCTATGGCTACCTGCAC | | | |
| | | ACCTTCGGCTGCGGCACAAAGCTG | | | |
| | | GAGATCAAG | | | |
| ALG.APV- | HCDR1 | GGATTCACCTTTAGCAGCTATGCC | 29 | GFTFSSYA | 30 |
| 004 | HCDR2 | ATTAGTGGTAGTGGTGGTAGCACA | 31 | ISGSGGST | 32 |
| | HCDR3 | GCGCGCTACTACGGTGGTTACTAC | 33 | ARYYGGYYSAWMDY | 34 |
| | | TCTGCTTGGATGGACTAT | | | |
| | LCDR1 | CAGAGCATTAGCAGCTAT | 7 | QSISSY | 8 |
| | LCDR2 | GCTGCATCC | 9 | AAS | 10 |
| | LCDR3 | CAACAGACTTACGGTTACCTGCAC | 35 | QQTYGYLHT | 36 |
| | | ACT | | | |
| | $V_H$ | GAGGTGCAGCTGCTCGAGAGCGGG | 45 | EVQLLESGGGLVQPGGS | 46 |
| | | GGAGGCTTGGTACAGCCTGGGGGG | | LRLSCAASGFTFSSYAM | |
| | | TCCCTGCGCCTCTCCTGTGCAGCC | | SWVRQAPGKCLEWVSAI | |
| | | AGCGGATTCACCTTTAGCAGCTAT | | SGSGGSTYYADSVKGRF | |

TABLE 5-continued

5T4-binding domain polypeptide CDR and variable region amino acid and DNA sequences

| Construct | Component | DNA Sequence | DNA SEQID | AA sequence | AA SEQID |
|---|---|---|---|---|---|
| | | GCCATGAGCTGGGTCCGCCAGGCTCCAGGGAAGTGTCTGGAGTGGGTCTCAGCTATTAGTGGTAGTGGTGGTAGCACATACTATGCAGACTCCGTGAAGGGCCGGTTCACCATCTCCCGTGACAATTCCAAGAACACGCTGTATCTGCAAATGAACAGCCTGCGTGCCGAGGACACGGCTGTATATTATTGTGCGCGCTACTACGGTGGTTACTACTCTGCTTGGATGGACTATTGGGGCCAGGGAACCCTGGTCACCGTCTCCTCA | | TISRDNSKNTLYLQMNSLRAEDTAVYYCARYYGGYYSAWMDYWGQGTLVTVSS | |
| | $V_L$ | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGACTTACGGTTACCTGCACACTTTTGGCTGTGGGACCAGGCTGGAGATCAAA | 65 | DIQMTQSPSSLSASVGDRVTITCRASQSISSYLNWYQQKPGKAPKLLIYAASSLQSGVPSRFSGSGSGTDFTLTISSLQPEDFATYYCQQTYGYLHTFGCGTRLEIK | 66 |
| ALG.APV-006 | HCDR1 | GGATTCACCTTTAGCAGCTATGCC | 29 | GFTFSSYA | 30 |
| | HCDR2 | ATTAGTGGTAGTGGTGGTAGCACA | 31 | ISGSGGST | 32 |
| ALG.APV-010 | HCDR3 | GCGCGCTACTACGGTGGTTACTACTCTGCTTGGATGGACTAT | 33 | ARYYGGYYSAWMDY | 34 |
| | LCDR1 | CAGAGCATTAGCAGCTAT | 7 | QSISSY | 8 |
| | LCDR2 | GCTGCATCC | 9 | AAS | 10 |
| | LCDR3 | CAACAGACTTACGGTTACCTGCACACT | 35 | QQTYGYLHT | 36 |
| | $V_H$ | GAGGTGCAGCTGTTGGAGAGCGGGGGAGGCTTGGTACAGCCTGGGGGGTCCCTGCGCCTCTCCTGTGCAGCCAGCGGATTCACCTTTAGCAGCTATGCCATGAGCTGGGTCCGCCAGGCTCCAGGGAAGGGGCTGGAGTGGGTCTCAGCTATTAGTGGTAGTGGTGGTAGCACATACTATGCAGACTCCGTGAAGGGCCGGTTCACCATCTCCCGTGACAATTCCAAGAACACGCTGTATCTGCAAATGAACAGCCTGCGTGCCGAGGACACGGCTGTATATTATTGTGCGCGCTACTACGGTGGTTACTACTCTGCTTGGATGGACTATTGGGGCCAGGGAACCCTGGTCACCGTCTCCTCA | 37 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARYYGGYYSAWMDYWGQGTLVTVSS | 38 |
| | $V_L$ | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGACTTACGGTTACCTGCACACTTTTGGCCAGGGGACCAAGCTGGAGATCAAA | 67 | DIQMTQSPSSLSASVGDRVTITCRASQSISSYLNWYQQKPGKAPKLLIYAASSLQSGVPSRFSGSGSGTDFTLTISSLQPEDFATYYCQQTYGYLHTFGQGTKLEIK | 68 |
| ALG.APV-014 | HCDR1 | GGATTCACCTTTAGCAGCTATGCC | 29 | GFTFSSYA | 30 |
| | HCDR2 | ATTAGTGGTAGTGGTGGTAGCACA | 31 | ISGSGGST | 32 |
| ALG.APV-018 | HCDR3 | GCGCGCTACTACGGTGGTTACTACTCTGCTTGGATGGACTAT | 33 | ARYYGGYYSAWMDY | 34 |
| | LCDR1 | CAGAGCATTAGCAGCTAT | 7 | QSISSY | 8 |
| | LCDR2 | GCTGCATCC | 9 | AAS | 10 |
| | LCDR3 | CAACAGACTTACGGTTACCTGCACACT | 35 | QQTYGYLHT | 36 |

TABLE 5-continued

5T4-binding domain polypeptide CDR and variable region amino acid and DNA sequences

| Construct | Component | DNA Sequence | DNA SEQID | AA sequence | AA SEQID |
|---|---|---|---|---|---|
| | $V_H$ | GAGGTGCAGCTGTTGGAGAGCGGG GGAGGCTTGGTACAGCCTGGGGGG TCCCTGCGCCTCTCCTGTGCAGCC AGCGGATTCACCTTTAGCAGCTAT GCCATGAGCTGGGTCCGCCAGGCT CCAGGGAAGTGCCTGGAGTGGGTC TCAGCTATTAGTGGTAGTGGTGGT AGCACATACTATGCAGACTCCGTG AAGGGCCGGTTCACCATCTCCCGT GACAATTCCAAGAACACGCTGTAT CTGCAAATGAACAGCCTGCGTGCC GAGGACACGGCTGTATATTATTGT GCGCGCTACTACGGTGGTTACTAC TCTGCTTGGATGGACTATTGGGGC CAGGGAACCCTGGTCACCGTCTCC TCA | 45 | EVQLLESGGGLVQPGGS LRLSCAASGFTFSSYAM SWVRQAPGKCLEWVSAI SGSGGSTYYADSVKGRF TISRDNSKNTLYLQMNS LRAEDTAVYYCARYYGG YYSAWMDYWGQGTLVTV SS | 46 |
| | $V_L$ | GACATCCAGATGACCCAGTCTCCA TCCTCCCTGAGCGCATCTGTAGGA GACCGCGTCACCATCACTTGCCGG GCAAGTCAGAGCATTAGCAGCTAT TTAAATTGGTATCAGCAGAAACCA GGGAAAGCCCCTAAGCTCCTGATC TATGCTGCATCCAGTTTGCAAAGT GGGGTCCCATCACGTTTCAGTGGC AGTGGAAGCGGGACAGATTTCACT CTCACCATCAGCAGTCTGCAACCT GAAGATTTTGCAACTTATTACTGT CAACAGACTTACGGTTACCTGCAC ACTTTTGGCTGCGGGACCAAGCTG GAGATCAAA | 69 | DIQMTQSPSSLSASVGD RVTITCRASQSISSYLN WYQQKPGKAPKLLIYAA SSLQSGVPSRFSGSGSG TDFTLTISSLQPEDFAT YYCQQTYGYLHTFGCGT KLEIK | 70 |

In some embodiments, the present invention provides for multispecific polypeptides (e.g., bispecific polypeptides) comprising a 5T4-binding domain. In such embodiments, a 5T4-binding protein or polypeptide can comprise one or more additional binding domains (e.g., second binding domain) that bind a target other than 5T4. These other binding domains can comprise, for example, a particular cytokine or a molecule that targets the binding domain polypeptide to, for example, a particular cell type, a toxin, an additional cell receptor, or an antibody. A multispecific 5T4-binding polypeptide or protein may comprise two binding domains (the domains can be designed to specifically bind the same or different targets), a hinge region, a linker (e.g., a carboxyl-terminus or an amino-terminus linker), and an immunoglobulin constant region. A multispecific 5T4-binding protein may be a homodimeric protein comprising two identical, disulfide-bonded polypeptides. In some embodiments the 5T4-binding domains may be derived from a monoclonal antibody that binds to 5T4.

In some embodiments of the disclosure, a 5T4-binding polypeptide is capable of forming a heterodimer with a second polypeptide chain and comprises a hinge region (a) immediately amino-terminal to an immunoglobulin constant region (e.g., amino-terminal to a CH2 domain wherein the immunoglobulin constant region includes CH2 and CH3 domains, or amino-terminal to a CH3 domain wherein the immunoglobulin sub-regions includes CH3 and CH4 domains), (b) interposed between and connecting a binding domain (e.g., scFv) and a immunoglobulin heterodimerization domain, (c) interposed between and connecting a immunoglobulin heterodimerization domain and an immunoglobulin constant region (e.g., wherein the immunoglobulin constant region includes CH2 and CH3 domains or CH3 and CH4 domains), (d) interposed between and connecting an immunoglobulin constant region and a binding domain, (e) at the amino-terminus of a polypeptide chain, or (f) at the carboxyl-terminus of a polypeptide chain. A polypeptide chain comprising a hinge region as described herein will be capable of associating with a different polypeptide chain to form a heterodimeric protein provided herein, and the heterodimer formed will contain a binding domain that retains its target specificity or its specific target binding affinity.

In some embodiments, the 5T4-binding polypeptide provided herein is a polypeptide comprising two scFvs. In some embodiments, the two scFvs comprise 5T4-binding domains. In certain embodiments, the two scFvs comprise identical 5T4-binding domains. In other embodiments, the two scFvs comprise different 5T4-binding domains. In other embodiments, the polypeptide comprises an 5T4-binding domain as a first scFv and an effector cell binding domain as a second scFv. For example, the effector cell binding domain may be an scFv specific for 4-1BB.

In some embodiments, a 5T4-binding polypeptide provided herein comprises an anti-5T4 scFv that is at least about 82%, at least about 85%, at least about 87%, at least about 90%, at least about 91%, at least about 92%, at least about 93%, at least about 94%, at least about 95%, at least about 96%, at least about 97%, at least about 98%, at least about 99%, or 100% identical to an amino acid sequence selected from the group consisting of SEQ ID NOs: 118, 120, 122, 124, 126, 128, 130, 132, 134, and 170, wherein the polypeptide is a multispecific polypeptide in the format scFv-Fc-scFv and comprises a Y to F substitution in the LCDR1 at position 99 of the anti-5T4 $V_L$ and/or a F to S substitution in the FR3 at position 148 of the anti-5T4 $V_L$. In some embodiments, a 5T4-binding polypeptide provided herein comprises an anti-5T4 scFv that comprises an amino acid sequence selected from the group consisting of SEQ ID NOs: 118, 120, 122, 124, 126, 128, 130, 132, 134, and 170. Amino acid and nucleic acid sequences for exemplary anti-5T4 scFvs are provided in Table 6 below.

TABLE 6

Amino Acid and DNA Sequences of Exemplary anti-5T4 scFvs

| Name | DNA Sequence | DNA SEQ ID | AA Sequence | AA SEQ ID |
|---|---|---|---|---|
| ALG.APV- | GAAGTGCAGCTGCTGGAGTCCGGAGGAGGAC | 117 | EVQLLESGGGLVQPGG | 118 |
| 178 | TGGTGCAGCCTGGCGGAAGCCTGAGGCTGAG | | SLRLSCAASGFTFSSY | |
| ALG.APV- | CTGCGCTGCCTCCGGCTTCACATTCAGCAGC | | AMSWVRQAPGKGLEWV | |
| 208 | TATGCTATGAGCTGGGTGAGGCAAGCCCCTG | | SAISGSGGSTYYADSV | |
| anti-5T4 | GAAAGGGCCTGGAGTGGGTGTCCGCTATCTC | | KGRFTISRDNSKNTLY | |
| | CGGCAGCGGCGGAAGCACCTACTACGCTGAC | | LQMNSLRAEDTAVYYC | |
| | TCCGTCAAGGGCAGGTTCACCATCAGCCGGG | | ARYYGGYYSAWMDYWG | |
| | ACAACAGCAAGAACACCCTGTACCTGCAGAT | | QGTLVTVSSGGGGSGG | |
| | GAATAGCCTCAGGGCTGAAGACACCGCTGTG | | GGSGGGGSGGGGSDIQ | |
| | TACTACTGCGCCAGGTACTATGGCGGCTACT | | MTQSPSSLSASVGDRV | |
| | ACTCCGCCTGGATGGACTACTGGGGACAGGG | | TITCRASQSISSYLNW | |
| | CACACTGGTGACCGTGTCCAGCGGCGGAGGC | | YQQKPGKAPKLLIYAA | |
| | GGCTCCGGAGGCGGTGGCTCCGGAGGAGGCG | | SSLQSGVPSRFSGSGS | |
| | GAAGCGGAGGAGGAGGCTCCGATATTCAGAT | | GTDFTLTISSLQPEDS | |
| | GACACAGTCCCCTAGCTCCCTGTCCGCCAGC | | ATYYCQQTYGYLHTFG | |
| | GTGGGAGATCGGGTGACCATCACCTGCAGGG | | QGTKLEIK | |
| | CCAGCCAGTCCATCTCCAGCTATTTAAACTG | | | |
| | GTACCAGCAGAAGCCTGGAAAGGCTCCCAAG | | | |
| | CTGCTGATCTACGCCGCTTCCAGCCTCCAGA | | | |
| | GCGGCGTGCCTAGCAGGTTCTCCGGCTCCGG | | | |
| | AAGCGGAACAGACTTCACCCTGACCATCAGC | | | |
| | TCCCTGCAGCCCGAGGACTCCGCTACCTACT | | | |
| | ACTGCCAGCAGACCTATGGCTACCTGCACAC | | | |
| | CTTCGGCCAGGGCACAAAGCTGGAGATCAAG | | | |
| ALG.APV- | GAAGTGCAGCTGCTGGAGTCCGGAGGAGGAC | 119 | EVQLLESGGGLVQPGG | 120 |
| 179 | TGGTGCAGCCTGGCGGAAGCCTGAGGCTGAG | | SLRLSCAASGFTFSSY | |
| ALG.APV. | CTGCGCTGCCTCCGGCTTCACATTCAGCAGC | | AMSWVRQAPGKGLEWV | |
| 209 | TATGCTATGAGCTGGGTGAGGCAAGCCCCTG | | SAISGSGGSTYYADSV | |
| ALG.APV | GAAAGGGCCTGGAGTGGGTGTCCGCTATCTC | | KGRFTISRDNSKNTLY | |
| 222 | CGGCAGCGGCGGAAGCACCTACTACGCTGAC | | LQMNSLRAEDTAVYYC | |
| anti-5T4 | TCCGTCAAGGGCAGGTTCACCATCAGCCGGG | | ARYYGGYYSAWMDYWG | |
| | ACAACAGCAAGAACACCCTGTACCTGCAGAT | | QGTLVTVSSGGGGSGG | |
| | GAATAGCCTCAGGGCTGAAGACACCGCTGTG | | GGSGGGGSGGGGSDIQ | |
| | TACTACTGCGCCAGGTACTATGGCGGCTACT | | MTQSPSSLSASVGDRV | |
| | ACTCCGCCTGGATGGACTACTGGGGACAGGG | | TITCRASQSISSFLNW | |
| | CACACTGGTGACCGTGTCCAGCGGCGGAGGC | | YQQKPGKAPKLLIYAA | |
| | GGCTCCGGAGGCGGTGGCTCCGGAGGAGGCG | | SSLQSGVPSRFSGSGS | |
| | GAAGCGGAGGAGGAGGCTCCGATATTCAGAT | | GTDFTLTISSLQPEDS | |
| | GACACAGTCCCCTAGCTCCCTGTCCGCCAGC | | ATYYCQQTYGYLHTFG | |
| | GTGGGAGATCGGGTGACCATCACCTGCAGGG | | QGTKLEIK | |
| | CCAGCCAGTCCATCTCCAGCTTCTTAAACTG | | | |
| | GTACCAGCAGAAGCCTGGAAAGGCTCCCAAG | | | |
| | CTGCTGATCTACGCCGCTTCCAGCCTCCAGA | | | |
| | GCGGCGTGCCTAGCAGGTTCTCCGGCTCCGG | | | |
| | AAGCGGAACAGACTTCACCCTGACCATCAGC | | | |
| | TCCCTGCAGCCCGAGGACTCCGCTACCTACT | | | |
| | ACTGCCAGCAGACCTATGGCTACCTGCACAC | | | |
| | CTTCGGCCAGGGCACAAAGCTGGAGATCAAG | | | |
| ALG.APV- | GAAGTGCAGCTGCTGGAGTCCGGAGGAGGAC | 121 | EVQLLESGGGLVQPGG | 122 |
| 187 | TGGTGCAGCCTGGCGGAAGCCTGAGGCTGAG | | SLRLSCAASGFTFSSY | |
| ALG.APV. | CTGCGCTGCCTCCGGCTTCACATTCAGCAGC | | AMSWVRQAPGKCLEWV | |
| 210 | TATGCTATGAGCTGGGTGAGGCAAGCCCCTG | | SAISGSGGSTYYADSV | |
| ALG.APV | GAAAGTGCCTGGAGTGGGTGTCCGCTATCTC | | KGRFTISRDNSKNTLY | |
| 223 | CGGCAGCGGCGGAAGCACCTACTACGCTGAC | | LQMNSLRAEDTAVYYC | |
| anti-5T4 | TCCGTCAAGGGCAGGTTCACCATCAGCCGGG | | ARYYGGYYSAWMDYWG | |
| | ACAACAGCAAGAACACCCTGTACCTGCAGAT | | QGTLVTVSSGGGGSGG | |
| | GAATAGCCTCAGGGCTGAAGACACCGCTGTG | | GGSGGGGSGGGGSDIQ | |
| | TACTACTGCGCCAGGTACTATGGCGGCTACT | | MTQSPSSLSASVGDRV | |
| | ACTCCGCCTGGATGGACTACTGGGGACAGGG | | TITCRASQSISSFLNW | |
| | CACACTGGTGACCGTGTCCAGCGGCGGAGGC | | YQQKPGKAPKLLIYAA | |
| | GGCTCCGGAGGCGGTGGCTCCGGAGGAGGCG | | SSLQSGVPSRFSGSGS | |
| | GAAGCGGAGGAGGAGGCTCCGATATTCAGAT | | GTDFTLTISSLQPEDS | |
| | GACACAGTCCCCTAGCTCCCTGTCCGCCAGC | | ATYYCQQTYGYLHTFG | |
| | GTGGGAGATCGGGTGACCATCACCTGCAGGG | | CGTKLEIK | |
| | CCAGCCAGTCCATCTCCAGCTTCTTAAACTG | | | |
| | GTACCAGCAGAAGCCTGGAAAGGCTCCCAAG | | | |
| | CTGCTGATCTACGCCGCTTCCAGCCTCCAGA | | | |
| | GCGGCGTGCCTAGCAGGTTCTCCGGCTCCGG | | | |
| | AAGCGGAACAGACTTCACCCTGACCATCAGC | | | |
| | TCCCTGCAGCCCGAGGACTCCGCTACCTACT | | | |
| | ACTGCCAGCAGACCTATGGCTACCTGCACAC | | | |
| | CTTCGGCTGCGGCACAAAGCTGGAGATCAAG | | | |

TABLE 6-continued

Amino Acid and DNA Sequences of Exemplary anti-5T4 scFvs

| Name | DNA Sequence | DNA SEQ ID | AA Sequence | AA SEQ ID |
|---|---|---|---|---|
| ALG.APV-191 anti-5T4 | GAAGTGCAGCTGCTGGAGTCCGGAGGAGGAC<br>TGGTGCAGCCTGGCGGAAGCCTGAGGCTGAG<br>CTGCGCTGCCTCCGGCTTCACATTCAGCAGC<br>TATGCTATGAGCTGGGTGAGGCAAGCCCCTG<br>GAAAGTGCCTGGAGTGGGTGTCCGCTATCTC<br>CGGCAGCGGCGGAAGCACCTACTACGCTGAC<br>TCCGTCAAGGGCAGGTTCACCATCAGCCGGG<br>ACAACAGCAAGAACACCCTGTACCTGCAGAT<br>GAATAGCCTCAGGGCTGAAGACACCGCTGTG<br>TACTACTGCGCCAGGTACTATGGCGGCTACT<br>ACTCCGCCTGGATGGACTACTGGGGACAGGG<br>CACACTGGTGACCGTGTCCAGCGGCGGAGGC<br>GGCTCCGGAGGCGGTGGCTCCGGAGGAGGCG<br>GAAGCGGAGGAGGAGGCTCCGATATTCAGAT<br>GACACAGTCCCCTAGCTCCCTGTCCGCCAGC<br>GTGGGAGATCGGGTGACCATCACCTGCAGGG<br>CCAGCCAGTCCATCTCCAGCTTCTTAAACTG<br>GTACCAGCAGAAGCCTGGAAAGGCTCCCAAG<br>CTGCTGATCTACGCCGCTTCCAGCCTCCAGA<br>GCGGCGTGCCTAGCAGGTTCTCCGGCTCCGG<br>AAGCGGAACAGACTTCACCCTGACCATCAGC<br>TCCCTGCAGCCCGAGGACTTCGCTACCTACT<br>ACTGCCAGCAGACCTATGGCTACCTGCACAC<br>CTTCGGCTGCGGCACAAAGCTGGAGATCAAG | 123 | EVQLLESGGGLVQPGG<br>SLRLSCAASGFTFSSY<br>AMSWVRQAPGKCLEWV<br>SAISGSGGSTYYADSV<br>KGRFTISRDNSKNTLY<br>LQMNSLRAEDTAVYYC<br>ARYYGGYYSAWMDYWG<br>QGTLVTVSSGGGGSGG<br>GGSGGGGSGGGGSDIQ<br>MTQSPSSLSASVGDRV<br>TITCRASQSISSFLNW<br>YQQKPGKAPKLLIYAA<br>SSLQSGVPSRFSGSGS<br>GTDFTLTISSLQPEDF<br>ATYYCQQTYGYLHTFG<br>CGTKLEIK | 124 |
| ALG.APV-196 anti-5T4 ALG.APV-198 anti-5T4 | GAAGTGCAGCTGCTGGAGTCCGGAGGAGGAC<br>TGGTGCAGCCTGGCGGAAGCCTGAGGCTGAG<br>CTGCGCTGCCTCCGGCTTCGACTTCGAGAGC<br>TATGCTATGAGCTGGGTGAGGCAAGCCCCTG<br>GAAAGTGCCTGGAGTGGGTGTCCGCTATCTC<br>CGGCAGCGGCGGAAGCACCTACTACGCTGAC<br>TCCGTCAAGGGCAGGTTCACCATCAGCCGGG<br>ACAACAGCAAGAACACCCTGTACCTGCAGAT<br>GAATAGCCTCAGGGCTGAAGACACCGCTGTG<br>TACTACTGCGCCAGGTACTATGGCGGCTACT<br>ACTCCGCCTGGATGGACTACTGGGGACAGGG<br>CACACTGGTGACCGTGTCCAGCGGCGGAGGC<br>GGCTCCGGAGGCGGTGGCTCCGGAGGAGGCG<br>GAAGCGGAGGAGGAGGCTCCGATATTCAGAT<br>GACACAGTCCCCTAGCTCCCTGTCCGCCAGC<br>GTGGGAGATCGGGTGACCATCACCTGCAGGG<br>CCAGCCAGTCCATCAGGAGCGCCCTGAACTG<br>GTACCAGCAGAAGCCTGGAAAGGCTCCCAAG<br>CTGCTGATCTACGCCGCTTCCAGCCTCCAGA<br>GCGGCGTGCCTAGCAGGTTCTCCGGCTCCGG<br>AAGCGGAACAGACTTCACCCTGACCATCAGC<br>TCCCTGCAGCCCGAGGACTTCGCTACCTACT<br>ACTGCCAGCAGACCTATGGCTACCTGCACAC<br>CTTCGGCTGCGGCACAAAGCTGGAGATCAAG | 125 | EVQLLESGGGLVQPGG<br>SLRLSCAASGFDFESY<br>AMSWVRQAPGKCLEWV<br>SAISGSGGSTYYADSV<br>KGRFTISRDNSKNTLY<br>LQMNSLRAEDTAVYYC<br>ARYYGGYYSAWMDYWG<br>QGTLVTVSSGGGGSGG<br>GGSGGGGSGGGGSDIQ<br>MTQSPSSLSASVGDRV<br>TITCRASQSIRSALNW<br>YQQKPGKAPKLLIYAA<br>SSLQSGVPSRFSGSGS<br>GTDFTLTISSLQPEDF<br>ATYYCQQTYGYLHTFG<br>CGTKLEIK | 126 |
| ALG.APV-199 anti-5T4 | GAAGTGCAGCTGCTGGAGTCCGGAGGAGGAC<br>TGGTGCAGCCTGGCGGAAGCCTGAGGCTGAG<br>CTGCGCTGCCTCCGGCTTCGACTTCGACAGC<br>TATGCTATGAGCTGGGTGAGGCAAGCCCCTG<br>GAAAGTGCCTGGAGTGGGTGTCCGCTATCTC<br>CGGCAGGGGCGGAAGCACCTACTACGCTGAC<br>TCCGTCAAGGGCAGGTTCACCATCAGCCGGG<br>ACAACAGCAAGAACACCCTGTACCTGCAGAT<br>GAATAGCCTCAGGGCTGAAGACACCGCTGTG<br>TACTACTGCGCCAGGTACTATGGCGGCTACT<br>ACTCCGCCTGGATGGACTACTGGGGACAGGG<br>CACACTGGTGACCGTGTCCAGCGGCGGAGGC<br>GGCTCCGGAGGCGGTGGCTCCGGAGGAGGCG<br>GAAGCGGAGGAGGAGGCTCCGATATTCAGAT<br>GACACAGTCCCCTAGCTCCCTGTCCGCCAGC<br>GTGGGAGATCGGGTGACCATCACCTGCAGGG<br>CCAGCCAGTCCATCAGGAGCGCCCTGAACTG<br>GTACCAGCAGAAGCCTGGAAAGGCTCCCAAG<br>CTGCTGATCTACGCCGCTTCCAGCCTCCAGA<br>GCGGCGTGCCTAGCAGGTTCTCCGGCTCCGG<br>AAGCGGAACAGACTTCACCCTGACCATCAGC<br>TCCCTGCAGCCCGAGGACTTCGCTACCTACT<br>ACTGCCAGCAGACCTATGGCTACCTGCACAC<br>CTTCGGCTGCGGCACAAAGCTGGAGATCAAG | 127 | EVQLLESGGGLVQPGG<br>SLRLSCAASGFDFDSY<br>AMSWVRQAPGKCLEWV<br>SAISGRGGSTYYADSV<br>KGRFTISRDNSKNTLY<br>LQMNSLRAEDTAVYYC<br>ARYYGGYYSAWMDYWG<br>QGTLVTVSSGGGGSGG<br>GGSGGGGSGGGGSDIQ<br>MTQSPSSLSASVGDRV<br>TITCRASQSIRSALNW<br>YQQKPGKAPKLLIYAA<br>SSLQSGVPSRFSGSGS<br>GTDFTLTISSLQPEDF<br>ATYYCQQTYGYLHTFG<br>CGTKLEIK | 128 |

TABLE 6-continued

| Amino Acid and DNA Sequences of Exemplary anti-5T4 scFvs | | | | |
|---|---|---|---|---|
| Name | DNA Sequence | DNA SEQ ID | AA Sequence | AA SEQ ID |
| ALG.APV-<br>006<br>anti-5T4 | GAGGTGCAGCTGTTGGAGAGCGGGGGAGGCT<br>TGGTACAGCCTGGGGGGTCCCTGCGCCTCTC<br>CTGTGCAGCCAGCGGATTCACCTTTAGCAGC<br>TATGCCATGAGCTGGGTCCGCCAGGCTCCAG<br>GGAAGGGGCTGGAGTGGGTCTCAGCTATTAG<br>TGGTAGTGGTGGTAGCACATACTATGCAGAC<br>TCCGTGAAGGGCCGGTTCACCATCTCCCGTG<br>ACAATTCCAAGAACACGCTGTATCTGCAAAT<br>GAACAGCCTGCGTGCCGAGGACACGGCTGTA<br>TATTATTGTGCGCGCTACTACGGTGGTTACT<br>ACTCTGCTTGGATGGACTATTGGGGCCAGGG<br>AACCCTGGTCACCGTCTCCTCAGGCGGTGGA<br>GGCAGCGGTGGGGGTGGGTCTGGAGGCGGTG<br>GCAGTGGCGGCGGAGGCTCTGACATCCAGAT<br>GACCCAGTCTCCATCCTCCCTGAGCGCATCT<br>GTAGGAGACCGCGTCACCATCACTTGCCGGG<br>CAAGTCAGAGCATTAGCAGCTATTTAAATTG<br>GTATCAGCAGAAACCAGGGAAAGCCCCTAAG<br>CTCCTGATCTATGCTGCATCCAGTTTGCAAA<br>GTGGGGTCCCATCACGTTTCAGTGGCAGTGG<br>AAGCGGGACAGATTTCACTCTCACCATCAGC<br>AGTCTGCAACCTGAAGATTTTGCAACTTATT<br>ACTGTCAACAGACTTACGGTTACCTGCACAC<br>TTTTGGCCAGGGGACCAAGCTGGAGATCAAA | 129 | EVQLLESGGGLVQPGG<br>SLRLSCAASGFTFSSY<br>AMSWVRQAPGKGLEWV<br>SAISGSGGSTYYADSV<br>KGRFTISRDNSKNTLY<br>LQMNSLRAEDTAVYYC<br>ARYYGGYYSAWMDYWG<br>QGTLVTVSSGGGGSGG<br>GGSGGGGSGGGGSDIQ<br>MTQSPSSLSASVGDRV<br>TITCRASQSISSYLNW<br>YQQKPGKAPKLLIYAA<br>SSLQSGVPSRFSGSGS<br>GTDFTLTISSLQPEDF<br>ATYYCQQTYGYLHTFG<br>QGTKLEIK | 130 |
| ALG.APV-<br>010<br>anti-5T4 | GACATCCAGATGACCCAGTCTCCATCCTCCC<br>TGAGCGCATCTGTAGGAGACCGCGTCACCAT<br>CACTTGCCGGGCAAGTCAGAGCATTAGCAGC<br>TATTTAAATTGGTATCAGCAGAAACCAGGGA<br>AAGCCCCTAAGCTCCTGATCTATGCTGCATC<br>CAGTTTGCAAAGTGGGGTCCCATCACGTTTC<br>AGTGGCAGTGGAAGCGGGACAGATTTCACTC<br>TCACCATCAGCAGTCTGCAACCTGAAGATTT<br>TGCAACTTATTACTGTCAACAGACTTACGGT<br>TACCTGCACACTTTTGGCCAGGGGACCAAGC<br>TGGAGATCAAAGGCGGTGGAGGCAGCGGTGG<br>GGGTGGGTCTGGAGGCGGTGGCAGTGGCGGC<br>GGAGGCTCTGAGGTGCAGCTGTTGGAGAGCG<br>GGGGAGGCTTGGTACAGCCTGGGGGGTCCCT<br>GCGCCTCTCCTGTGCAGCCAGCGGATTCACC<br>TTTAGCAGCTATGCCATGAGCTGGGTCCGCC<br>AGGCTCCAGGGAAGGGGCTGGAGTGGGTCTC<br>AGCTATTAGTGGTAGTGGTGGTAGCACATAC<br>TATGCAGACTCCGTGAAGGGCCGGTTCACCA<br>TCTCCCGTGACAATTCCAAGAACACGCTGTA<br>TCTGCAAATGAACAGCCTGCGTGCCGAGGAC<br>ACGGCTGTATATTATTGTGCGCGCTACTACG<br>GTGGTTACTACTCTGCTTGGATGGACTATTG<br>GGGCCAGGGAACCCTGGTCACCGTCTCCTCA | 169 | DIQMTQSPSSLSASVG<br>DRVTITCRASQSISSY<br>LNWYQQKPGKAPKLLI<br>YAASSLQSGVPSRFSG<br>SGSGTDFTLTISSLQP<br>EDFATYYCQQTYGYLH<br>TFGQGTKLEIKGGGGS<br>GGGGSGGGGSGGGGSE<br>VQLLESGGGLVQPGGS<br>LRLSCAASGFTFSSYA<br>MSWVRQAPGKGLEWVS<br>AlSGSGGSTYYADSVK<br>GRFTISRDNSKNTLYL<br>QMNSLRAEDTAVYYCA<br>RYYGGYYSAWMDYWGQ<br>GTLVTVSS | 170 |
| ALG.APV-<br>014<br>anti-5T4 | GAGGTGCAGCTGTTGGAGAGCGGGGGAGGCT<br>TGGTACAGCCTGGGGGGTCCCTGCGCCTCTC<br>CTGTGCAGCCAGCGGATTCACCTTTAGCAGC<br>TATGCCATGAGCTGGGTCCGCCAGGCTCCAG<br>GGAAGTGCCTGGAGTGGGTCTCAGCTATTAG<br>TGGTAGTGGTGGTAGCACATACTATGCAGAC<br>TCCGTGAAGGGCCGGTTCACCATCTCCCGTG<br>ACAATTCCAAGAACACGCTGTATCTGCAAAT<br>GAACAGCCTGCGTGCCGAGGACACGGCTGTA<br>TATTATTGTGCGCGCTACTACGGTGGTTACT<br>ACTCTGCTTGGATGGACTATTGGGGCCAGGG<br>AACCCTGGTCACCGTCTCCTCAGGCGGTGGA<br>GGCAGCGGTGGGGGTGGGTCTGGAGGCGGTG<br>GCAGTGGCGGCGGAGGCTCTGACATCCAGAT<br>GACCCAGTCTCCATCCTCCCTGAGCGCATCT<br>GTAGGAGACCGCGTCACCATCACTTGCCGGG<br>CAAGTCAGAGCATTAGCAGCTATTTAAATTG<br>GTATCAGCAGAAACCAGGGAAAGCCCCTAAG<br>CTCCTGATCTATGCTGCATCCAGTTTGCAAA<br>GTGGGGTCCCATCACGTTTCAGTGGCAGTGG<br>AAGCGGGACAGATTTCACTCTCACCATCAGC<br>AGTCTGCAACCTGAAGATTTTGCAACTTATT<br>ACTGTCAACAGACTTACGGTTACCTGCACAC<br>TTTTGGCTGCGGGACCAAGCTGGAGATCAAA | 131 | EVQLLESGGGLVQPGG<br>SLRLSCAASGFTFSSY<br>AMSWVRQAPGKCLEWV<br>SAISGSGGSTYYADSV<br>KGRFTISRDNSKNTLY<br>LQMNSLRAEDTAVYYC<br>ARYYGGYYSAWMDYWG<br>QGTLVTVSSGGGGSGG<br>GGSGGGGSGGGGSDIQ<br>MTQSPSSLSASVGDRV<br>TITCRASQSISSYLNW<br>YQQKPGKAPKLLIYAA<br>SSLQSGVPSRFSGSGS<br>GTDFTLTISSLQPEDF<br>ATYYCQQTYGYLHTFG<br>CGTKLEIK | 132 |

TABLE 6-continued

Amino Acid and DNA Sequences of Exemplary anti-5T4 scFvs

| Name | DNA Sequence | DNA SEQ ID | AA Sequence | AA SEQ ID |
|---|---|---|---|---|
| ALG.APV-018 anti-5T4 | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGACTTACGGTTACCTGCACACTTTTGGCTGCGGGACCAAGCTGGAGATCAAAGGCGGTGGAGGCAGCGGTGGGGGTGGGTCTGGAGGCGGTGGCAGTGGCGGCGGAGGCTCTGAGGTGCAGCTGTTGGAGAGCGGGGGAGGCTTGGTACAGCCTGGGGGGTCCCTGCGCCTCTCCTGTGCAGCCAGCGGATTCACCTTTAGCAGCTATGCCATGAGCTGGGTCCGCCAGGCTCCAGGGAAGTGCCTGGAGTGGGTCTCAGCTATTAGTGGTAGTGGTGGTAGCACATACTATGCAGACTCCGTGAAGGGCCGGTTCACCATCTCCCGTGACAATTCCAAGAACACGCTGTATCTGCAAATGAACAGCCTGCGTGCCGAGGACACGGCTGTATATTATTGTGCGCGCTACTACGGTGGTTACTACTCTGCTTGGATGGACTATTGGGGCCAGGGAACCCTGGTCACCGTCTCCTCA | 133 | DIQMTQSPSSLSASVGDRVTITCRASQSISSYLNWYQQKPGKAPKLLIYAASSLQSGVPSRFSGSGSGTDFTLTISSLQPEDFATYYCQQTYGYLHTFGCGTKLEIKGGGGSGGGGSGGGGSGGGGSEVQLLESGGGLVQPGGSLRLSCAASGFTFSSYAMSWVRQAPGKCLEWVSAISGSGGSTYYADSVKGRFTISRDNSKNTLYLQMNSLRAEDTAVYYCARYYGGYYSAWMDYWGQGTLVTVSS | 134 |

In some embodiments, a 5T4-binding polypeptide comprises, in order from amino-terminus to carboxyl-terminus (or in order from carboxyl-terminus to amino-terminus), (i) a 5T4-binding domain, (ii) a hinge region, (iii) an immunoglobulin constant region, (iv) a carboxyl-terminus linker (or an amino-terminus linker), and (v) a second binding domain. In further embodiments, the second binding domain is an scFv specific for 4-1BB. In some embodiments, a 5T4-binding polypeptide comprises, in order from amino-terminus to carboxyl-terminus (or in order from carboxyl-terminus to amino-terminus), (i) second binding domain, (ii) a hinge region, (iii) an immunoglobulin constant region, (iv) a carboxyl-terminus linker (or an amino-terminus linker), and (v) a 5T4-binding domain. In further embodiments, the second binding domain comprises or is a 4-1BB-binding domain. In certain embodiments, a 5T4-binding protein can comprise an effector-cell binding domain for recruitment of effector to target cells expressing 5T4. In certain embodiments, the effector-cell binding domain specifically binds to 4-1BB.

In some embodiments, the second binding domain of a 5T4-binding polypeptide described herein is a 4-1BB-binding domain and comprises one or more of the 4-1BB-binding sequences (e.g., CDRs or variable regions) disclosed in PCT Application Publication No WO 2016/185016; PCT Application No. PCT/EP2017/059656; Dubrot et al., 2010; Gauttier et al., 2014; Kim et al., 2001; McMillin et al., 2006; Melero et al., 1997; Miller et al., 2002; Sallin et al., 2014; Taraban et al., 2002; Uno et al., 2006; Vinay and Kwon, 2012; Wilcox et al., 2002, each of which is incorporated herein by reference in its entirety.

In some embodiments, the second binding domain specifically binds 4-1BB and comprises an immunoglobulin light chain variable region ($V_L$) and an immunoglobulin heavy chain variable region ($V_H$); wherein the $V_L$ comprises an amino acid sequence that is at least about 93% identical, at least about 95% identical, at least about 97% identical, at least about 98% identical, at least about 99% identical, or 100% identical to an amino acid sequence selected from the group consisting of SEQ ID NOs: 16 and 22; and wherein the $V_H$ comprises an amino acid sequence that is at least about 93% identical, at least about 95% identical, at least about 97% identical, at least about 98% identical, at least about 99% identical, or 100% identical to an amino acid sequence selected from the group consisting of SEQ ID NOs: 14, 20, 26, and 28, wherein the polypeptide is a multispecific polypeptide in the format scFv-Fc-scFv and comprises a Y to H substitution in the HCDR1 at position 150 of the $V_H$ and/or an R to H substitution in the FR3 at position 127 of the $V_H$. In some embodiments, the second binding domain specifically binds 4-1BB and comprises a $V_L$ and a $V_H$; wherein the $V_L$ comprises an amino acid sequence selected from the group consisting of SEQ ID NOs: 16 and 22; and wherein the $V_H$ comprises an amino acid sequence selected from the group consisting of SEQ ID NOs: 14, 20, 26, and 28.

In some embodiments, the second binding domain is a 4-1BB-binding domain polypeptide, wherein the polypeptide is an scFv comprising a sequence that is at least about 82%, at least about 85%, at least about 87%, at least about 90%, at least about 91%, at least about 92%, at least about 93%, at least about 94%, at least about 95%, at least about 96%, at least about 97%, at least about 98%, at least about 99%, or 100% identical to an amino acid sequence selected from the group consisting of SEQ ID NOs: 110, 112, 114, and 116. Exemplary anti-4-1BB binding domain sequences are shown in Tables 6 and 7 and are discussed further below.

4-1BB-Binding Domains and Proteins Comprising the Same

In some embodiments, the present invention provides 4-1BB-binding domains that specifically bind to 4-1BB (e.g. human 4-1BB). 4-1BB is also known as CD137 or TNFRSF9 and is a member of the tumor necrosis factor (TNF) receptor family. 4-1BB is expressed on multiple cell types, including activated subsets of T cell (e.g., CD4+ and CD8+ T cells and T regulatory cells (Tregs)), natural killer (NK) cells, dendritic cells, monocytes, mast cells, and eosinophils. 4-1BB activation on CD8+ T cells sustains and/or augments cellular activation, while 4-1BB activation on CD4+ T cells can initiate cell activation and, in some instance, lead to activation-induced cell death. 4-1BB activation on Tregs generally suppresses Treg function. Several studies have demonstrated induction of tumor immunity through the use of antagonists 4-1BB antibodies. Exemplary human 4-1BB nucleotide and amino acid sequences are provided in SEQ ID NOs: 163, 167 and SEQ ID NOs: 164 and 166, respectively.

In some embodiments, the present invention further provides polypeptides comprising a 4-1BB-binding domain (e.g., 4-1BB-binding polypeptides). In certain variations, the 4-1BB-binding polypeptide comprises a hinge region carboxyl-terminal to the 4-1BB-binding domain, and an immunoglobulin constant region. In further variations, the 4-1BB-binding polypeptide comprises a carboxyl-terminus binding domain linker carboxyl-terminal to the immunoglobulin constant region, and a second binding domain carboxyl-terminal to the carboxyl-terminus linker.

In yet other variations, a 4-1BB-binding polypeptide comprises a hinge region amino-terminal to the polypeptide comprising the 4-1BB-binding domain, and an immunoglobulin constant amino-terminal to the hinge region.

In some embodiments, the 4-1BB-binding domains described herein binds an epitope located on the extracellular domain of 4-1BB (e.g., an epitope comprised within SEQ ID NO: 166). In certain aspects, this epitope is a discontinuous and/or conformational epitope.

A 4-1BB-binding domain polypeptide may specifically bind to human 4-1BB and comprise a heavy chain CDR1 (HCDR1), HCDR2, HCDR3, light chain CDR1 (LCDR1), LCDR2, and LCDR3, wherein the HCDR1 comprises an amino acid sequence selected from the group consisting of SEQ ID NOs: 2, 18, 24; the HCDR2 comprises an amino acid sequence of SEQ ID NO: 4; the HCDR3 comprises an amino acid sequence of SEQ ID NO: 6; the LCDR1 comprises an amino acid sequence of SEQ ID NO: 8; the LCDR2 comprises an amino acid sequence of SEQ ID NO: 10; and the LCDR3 comprises an amino acid sequence of SEQ ID NO: 12, wherein the polypeptide is a multispecific polypeptide in the format scFv-Fc-scFv and comprises a Y to H substitution in the HCDR1 at position 150 of the anti-4-1BB $V_H$ and/or an R to H substitution in the FR3 at position 127 of the anti-4-1BB $V_H$.

In particular embodiments, a 4-1BB-binding domain polypeptide may specifically bind to human 4-1BB and comprise an HCDR1, HCDR2, HCDR3, LCDR1, LCDR2, and LCDR3, wherein (a) the HCDR1 comprises an amino acid sequence set forth in SEQ ID NO: 2; (b) the HCDR2 comprises an amino acid sequence set forth in SEQ ID NO: 4; (c) the HCDR3 comprises an amino acid sequence set forth in SEQ ID NO: 6; (d) the LCDR1 comprises an amino acid sequence set forth in SEQ ID NO: 8; the LCDR2 comprises an amino acid sequence set forth in SEQ ID NO: 10; and (f) the LCDR3 comprises an amino acid sequence set forth in SEQ ID NO: 12. In other particular embodiments, a 5T4-binding domain polypeptide specifically binds to human 5T4 and comprises an HCDR1, HCDR2, HCDR3, LCDR1, LCDR2, and LCDR3, wherein (a) the HCDR1 comprises an amino acid sequence set forth in SEQ ID NO: 18; (b) the HCDR2 comprises an amino acid sequence set forth in SEQ ID NO: 4; (c) the HCDR3 comprises an amino acid sequence set forth in SEQ ID NO: 6; (d) the LCDR1 comprises an amino acid sequence set forth in SEQ ID NO: 8; (e) the LCDR2 comprises an amino acid sequence set forth in SEQ ID NO: 10 and (f) the LCDR3 comprises an amino acid sequence set forth in SEQ ID NO: 12. In other particular embodiments, a 5T4-binding domain polypeptide specifically binds to human 5T4 and comprises an HCDR1, HCDR2, HCDR3, LCDR1, LCDR2, and LCDR3, wherein (a) the HCDR1 comprises an amino acid sequence set forth in SEQ ID NO: 24; (b) the HCDR2 comprises an amino acid sequence set forth in SEQ ID NO: 4; (c) the HCDR3 comprises an amino acid sequence set forth in SEQ ID NO: 6; (d) the LCDR1 comprises an amino acid sequence set forth in SEQ ID NO: 8; (e) the LCDR2 comprises an amino acid sequence set forth in SEQ ID NO: 10; and (f) the LCDR3 comprises an amino acid sequence set forth in SEQ ID NO: 12.

In certain embodiments, a 4-1BB-binding domain polypeptide comprises an amino acid sequence of a light chain variable region ($V_L$) selected from the group consisting of SEQ ID NOs: 16 and 22. In certain embodiments, a 4-1BB-binding domain polypeptide comprises an amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid of a heavy chain variable region ($V_H$) selected from the group consisting of SEQ ID NOs: 14, 20, 26, and 28, wherein the polypeptide is a multi specific polypeptide in the format scFv-Fc-scFv and comprises a Y to H substitution in the HCDR1 at position 150 of the anti-4-1BB $V_H$ and/or an R to H substitution in the FR3 at position 127 of the anti-4-1BB $V_H$. In certain embodiments, a 4-1BB-binding domain polypeptide comprises an amino acid sequence of a heavy chain variable region ($V_H$) selected from the group consisting of SEQ ID NOs: 14, 20, 26, and 28.

In certain embodiments, a 4-1BB-binding domain polypeptide comprises a $V_H$ region comprising the amino acid sequence of SEQ ID NO: 14 and a $V_L$ region comprising the amino acid sequence of SEQ ID NO: 16. In certain embodiments, a 4-1BB-binding domain polypeptide comprises a $V_H$ region comprising the amino acid sequence of SEQ ID NO: 20 and a $V_L$ region comprising the amino acid sequence of SEQ ID NO: 22. In certain embodiments, a 4-1BB-binding domain polypeptide comprises a $V_H$ region comprising the amino acid sequence of SEQ ID NO: 26 and a $V_L$ region comprising the amino acid sequence of SEQ ID NO: 16. In certain embodiments, a 4-1BB-binding domain polypeptide comprises a $V_H$ region comprising the amino acid sequence of SEQ ID NO: 28 and a $V_L$ region comprising the amino acid sequence of SEQ ID NO: 16.

Exemplary anti-4-1BB binding domain sequences are shown in Table 7.

TABLE 7

Exemplary 4-1BB binding domain polypeptide and nucleic acid sequences

| Construct | Component | DNA Sequence | DNA SEQ ID | AA sequence | AA SEQ ID |
|---|---|---|---|---|---|
| ALG.APV- | HCDR1 | GGATTCACCTTTTCTCACGGTTCT | 1 | GFTFSHGS | 2 |
| 178 | HCDR2 | ATTTCTTCTGGTTCTGGTTCTACA | 3 | ISSGSGST | 4 |

TABLE 7-continued

Exemplary 4-1BB binding domain polypeptide and nucleic acid sequences

| Construct | Component | DNA Sequence | DNA SEQ ID | AA sequence | AA SEQ ID |
|---|---|---|---|---|---|
| ALG.APV-179<br>ALG.APV-187<br>ALG.APV-198<br>ALG.APV-199<br>ALG.APV-208<br>ALG.APV-209<br>ALG.APV-210<br>ALG.APV-222<br>ALG.APV-223 | HCDR3 | GCGCGCTCTTCTTACTACGGTTCTTACTACTCTATTGACTAT | 5 | ARSSYYGSYYSIDY | 6 |
| | LCDR1 | CAGAGCATTAGCAGCTAT | 7 | QSISSY | 8 |
| | LCDR2 | GCTGCATCC | 9 | AAS | 10 |
| | LCDR3 | CAACAGTACTACGACAACCTGCCCACT | 11 | QQYYDNL PT | 12 |
| | $V_H$ | GAGGTGCAGCTGTTGGAGAGCGGGGGAGGCTTGGTACAGCCTGGGGGGTCCCTGCGCCTCTCCTGTGCAGCCAGCGGATTCACCTTTTCTCACGGTTCTATGTACTGGGTCCGCCAGGCTCCAGGGAAGGGGCTGGAGTGGGTCTCATCTATTTCTTCTGGTTCTGGTTCTACATACTATGCAGACTCCGTGAAGGGCCGGTTCACCATCTCCCATGACAATTCCAAGAACACGCTGTATCTGCAAATGAACAGCCTGCGTGCCGAGGACACGGCTGTATATTATTGTGCGCGCTCTTCTTACTACGGTTCTTACTACTCTATTGACTATTGGGGCCAGGGAACCCTGGTCACCGTCTCCTCA | 13 | EVQLLESGGGLVQPGGSLRLSCAASGFTFSHGSMYWVRQAPGKGLEWVSSISSGSGSTYYADSVKGRFTISHDNSKNTLYLQMNSLRAEDTAVYYCARSSYYGSYYSIDYWGQGTLVTVSS | 14 |
| | $V_L$ | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTACAACCTGAAGATTTTGCAACTTATTACTGTCAACAGTACTACGACAACCTGCCCACTTTTGGCCAGGGGACCAAGCTGGAGATCAAA | 15 | DIQMTQSPSSLSASVGDRVTITCRASQSISSYLNWYQQKPGKAPKLLIYAASSLQSGVPSRFSGSGSGTDFTLTISSLQPEDFATYYCQQYYDNLPTFGQGTKLEIK | 16 |
| ALG.APV-191 | HCDR1 | GGATTCACCTTTGATTACGGTTCT | 17 | GFTFDYGS | 18 |
| | HCDR2 | ATTTCTTCTGGTTCTGGTTCTACA | 3 | ISSGSGST | 4 |
| | HCDR3 | GCGCGCTCTTCTTACTACGGTTCTTACTACTCTATTGACTAT | 5 | ARSSYYGSYYSIDY | 6 |
| | LCDR1 | CAGAGCATTAGCAGCTAT | 7 | QSISSY | 8 |
| | LCDR2 | GCTGCATCC | 9 | AAS | 10 |
| | LCDR3 | CAACAGTACTACGACAACCTGCCCACT | 11 | QQYYDNLPT | 12 |
| | $V_H$ | GAGGTGCAGCTGTTGGAGAGCGGGGGAGGCTTGGTACAGCCTGGGGGGTCCCTGCGCCTCTCCTGTGCAGCCAGCGGATTCACCTTTGATTACGGTTCTATGTACTGGGTCCGCCAGGCTCCAGGGAAGGGGCTGGAGTGGGTCTCATCTATTTCTTCTGGTTCTGGTTCTACATACTATGCAGACTCCGTGAAGGGCCGGTTCACCATCTCCCACGACAATTCCAAGAACACGCTGTATCTGCAAATGAACAGCCTGCGTGCCGAGGACACGGCTGTATATTATTGTGCGCGCTCTTCTTACTACGGTTCTTACTACTCTATTGACTATTGGGGCCAGGGAACCCTGGTCACCGTCTCCTCA | 19 | EVQLLESGGGLVQPGGSLRLSCAASGFTFDYGSMYWVRQAPGKGLEWVSSISSGSGSTYYADSVKGRFTISHDNSKNTLYLQMNSLRAEDTAVYYCARSSYYGSYYSIDYWGQGTLVTVSS | 20 |
| | $V_L$ | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCACAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGTACTACGACAACCTGCCCACTTTTGGCCAGGGGACCAAGCTGGAGATCAAA | 21 | DIQMTQSPSSLSASVGDRVTITCRASQSISSYLNWYQQKPGKAPKLLIYAASSLHSGVPSRFSGSGSGTDFTLTISSLQPEDFATYYCQQYYDNLPTFGQGTKLEIK | 22 |

TABLE 7-continued

Exemplary 4-1BB binding domain polypeptide and nucleic acid sequences

| Construct | Component | DNA Sequence | DNA SEQ ID | AA sequence | AA SEQ ID |
|---|---|---|---|---|---|
| ALG.APV-196 | HCDR1 | GGATTCACCTTTTCTTACGGTTCT | 23 | GFTFSYGS | 24 |
| | HCDR2 | ATTTCTTCTGGTTCTGGTTCTACA | 3 | ISSGSGST | 4 |
| | HCDR3 | GCGCGCTCTTCTTACTACGGTTCTTACTACTCTATTGACTAT | 5 | ARSSYYGSYYSIDY | 6 |
| | LCDR1 | CAGAGCATTAGCAGCTAT | 7 | QSISSY | 8 |
| | LCDR2 | GCTGCATCC | 9 | AAS | 10 |
| | LCDR3 | CAACAGTACTACGACAACCTGCCCACT | 11 | QQYYDNLPT | 12 |
| | V$_H$ | GAGGTGCAGCTGTTGGAGAGCGGGGGAGGCTTGGTACAGCCTGGGGGGTCCCTGCGCCTCTCCTGTGCAGCCAGCGGATTCACCTTTTCTTACGGTTCTATGTACTGGGTCCGCCAGGCTCCAGGGAAGGGGCTGGAGTGGGTCTCATCTATTTCTTCTGGTTCTGGTTCTACATACTATGCAGACTCCGTGAAGGGCCGGTTCACCATCTCCCATGACAATTCCAAGAACACGCTGTATCTGCAAATGAACAGCCTGCGTGCCGAGGACACGGCTGTATATTATTGTGCGCGCTCTTCTTACTACGGTTCTTACTACTCTATTGACTATTGGGGCCAGGGAACCCTGGTCACCGTCTCCTCA | 25 | EVQLLESGGGLVQPGGSLRLSCAASGFTFSYGSMYWVRQAPGKGLEWVSSISSGSGSTYYADSVKGRFTISHDNSKNTLYLQMNSLRAEDTAVYYCARSSYYGSYYSIDYWGQGTLVTVSS | 26 |
| | V$_L$ | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGTACTACGACAACCTGCCCACTTTTGGCCAGGGGACCAAGCTGGAGATCAAA | 15 | DIQMTQSPSSLSASVGDRVTITCRASQSIISYLNWYQQKPGKAPKLLIYAASSLQSGVPSRFSGSGSGTDFTLTISSLQPEDFATYYCQQYYDNLPTFGQGTKLEIK | 16 |
| ALG.APV-004 ALG.APV-006 ALG.APV-010 ALG.APV-014 ALG.APV-018 | HCDR1 | GGATTCACCTTTTCTTACGGTTCT | 23 | GFTFSYGS | 24 |
| | HCDR2 | ATTTCTTCTGGTTCTGGTTCTACA | 3 | ISSGSGST | 4 |
| | HCDR3 | GCGCGCTCTTCTTACTACGGTTCTTACTACTCTATTGACTAT | 5 | ARSSYYGSYYSIDY | 6 |
| | LCDR1 | CAGAGCATTAGCAGCTAT | 7 | QSISSY | 8 |
| | LCDR2 | GCTGCATCC | 9 | AAS | 10 |
| | LCDR3 | CAACAGTACTACGACAACCTGCCCACT | 11 | QQYYDNLPT | 12 |
| | V$_H$ | GAGGTGCAGCTGTTGGAGAGCGGGGGAGGCTTGGTACAGCCTGGGGGGTCCCTGCGCCTCTCCTGTGCAGCCAGCGGATTCACCTTTTCTTACGGTTCTATGTACTGGGTCCGCCAGGCTCCAGGGAAGGGGCTGGAGTGGGTCTCATCTATTTCTTCTGGTTCTGGTTCTACATACTATGCAGACTCCGTGAAGGGCCGGTTCACCATCTCCCGTGACAATTCCAAGAACACGCTGTATCTGCAAATGAACAGCCTGCGTGCCGAGGACACGGCTGTATATTATTGTGCGCGCTCTTCTTACTACGGTTCTTACTACTCTATTGACTATTGGGGCCAGGGAACCCTGGTCACCGTCTCCTCA | 27 | EVQLLESGGGLVQPGGSLRLSCAASGFTFSYGSMYWVRQAPGKGLEWVSSISSGSGSTYYADSVKGRFTISRDNSKNTLYLQMNSLRAEDTAVYYCARSSYYGSYYSIDYWGQGTLVTVSS | 28 |
| | V$_L$ | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGTACTACGACAACCTGCCCACTTTTGGCCAGGGGACCAAGCTGGAGATCAAA | 15 | DIQMTQSPSSLSASVGDRVTITCRASQSIISYLNWYQQKPGKAPKLLIYAASSLQSGVPSRFSGSGSGTDFTLTISSLQPEDFATYYCQQYYDNLPTFGQGTKLEIK | 16 |

In some embodiments, the present invention provides for multispecific polypeptides (e.g., bispecific polypeptides) comprising a 4-1BB-binding domain. A multispecific 4-1BB-binding polypeptide or protein may comprise two binding domains (the domains can be designed to specifically bind the same or different targets), a hinge region, a linker (e.g., a carboxyl-terminus or an amino-terminus linker), and an immunoglobulin constant region. A multispecific 4-1BB-binding protein may be a homodimeric protein comprising two identical, disulfide-bonded polypeptides. In some embodiments the 4-1BB binding domains may be derived from a monoclonal antibody that binds to 4-1BB (e.g., Urelumab (BMS-66513) or PF-05082566 (Pfizer)), derived from a 4-1BB-binding domain described in PCT Application Publication No. WO 2016/185016, or derived from a 4-1BB-binding domain PCT Application No. PCT/EP2017/059656.

In some embodiments, a multispecific polypeptide comprising a 4-1BB binding domain may comprise, in order from amino-terminus to carboxyl-terminus: (i) a first binding domain; (ii) a hinge region; (iii) an immunoglobulin constant region; (iv) a binding domain linker; and (v) a 4-1BB-binding domain. In some embodiments, a multispecific polypeptide comprising a 4-1BB binding domain may comprise, in order from amino-terminus to carboxyl-terminus: (i) a 4-1BB-binding domain; (ii) a binding domain linker; (iii) an immunoglobulin constant region; (iv) a hinge region; and (v) a first binding domain. Amino acid and nucleic acid sequences for exemplary anti-4-1BB binding domain sequences are provided in Table 7.

In certain embodiments, a 4-1BB-binding protein or polypeptide can comprise one or more additional binding domains (e.g., second binding domain) that bind a target other than 4-1BB. These other binding domains can comprise, for example, a particular cytokine or a molecule that targets the binding domain polypeptide to, for example, a particular cell type, a toxin, an additional cell receptor, or an antibody.

In some embodiments of the disclosure, a 4-1BB-binding polypeptide is capable of forming a heterodimer with a second polypeptide chain and comprises a hinge region (a) immediately amino-terminal to an immunoglobulin constant region (e.g., amino-terminal to a CH2 domain wherein the immunoglobulin constant region includes CH2 and CH3 domains, or amino-terminal to a CH3 domain wherein the immunoglobulin sub-regions includes CH3 and CH4 domains), (b) interposed between and connecting a binding domain (e.g., scFv) and a immunoglobulin heterodimerization domain, (c) interposed between and connecting a immunoglobulin heterodimerization domain and an immunoglobulin constant region (e.g., wherein the immunoglobulin constant region includes CH2 and CH3 domains or CH3 and CH4 domains), (d) interposed between and connecting an immunoglobulin constant region and a binding domain, (e) at the amino-terminus of a polypeptide chain, or (f) at the carboxyl-terminus of a polypeptide chain. A polypeptide chain comprising a hinge region as described herein will be capable of associating with a different polypeptide chain to form a heterodimeric protein provided herein, and the heterodimer formed will contain a binding domain that retains its target specificity or its specific target binding affinity.

In certain embodiments, a 4-1BB-binding polypeptide can comprise a target cell binding domain for recruitment of target cells to effector cells expressing 4-1BB. In certain embodiments, the target cell binding domain specifically binds to 5T4. In certain embodiments, a 4-1BB-binding protein as described herein can comprise (i) a binding domain that specifically binds 4-1BB and (ii) another binding domain that specifically binds to 5T4. Non-limiting examples of anti-5T4 antibodies from which the 5T4 binding domain can be derived include those described in PCT Application Publication No. WO 2016/185016 and PCT Application No. PCT/EP2017/059656.

In some embodiments, the 4-1BB-binding polypeptide provided herein is a polypeptide comprising two scFvs. In some embodiments, the two scFvs comprise 4-1BB-binding domains. In certain embodiments, the two scFvs comprise identical 4-1BB-binding domains. In other embodiments, the two scFvs comprise different 4-1BB-binding domains. In other embodiments, the polypeptide comprises a 4-1BB-binding domain as a first scFv and an target cell binding domain as a second scFv. For example, the target cell binding domain may be an scFv specific for 5T4.

In some embodiments, the bispecific 4-1BB-binding polypeptides and proteins provided herein comprise an anti-4-1BB scFv that is at least about 82%, at least about 85%, at least about 87%, at least about 90%, at least about 91%, at least about 92%, at least about 93%, at least about 94%, at least about 95%, at least about 96%, at least about 97%, at least about 98%, at least about 99%, or 100% identical to an amino acid sequence selected from the group consisting of SEQ ID NOs: 110, 112, 114, and 116, wherein the polypeptide is a multispecific polypeptide in the format scFv-Fc-scFv and comprises a Y to H substitution in the HCDR1 at position 150 of the anti-4-1BB $V_H$ and/or an R to H substitution in the FR3 at position 127 of the anti-4-1BB $V_H$. In certain embodiments, the bispecific 4-1BB-binding polypeptides and proteins provided herein comprise an anti-4-1BB scFv that comprises an amino acid sequence selected from the group consisting of SEQ ID NOs: 110, 112, 114, and 116. Amino acid and nucleic acid sequences for exemplary anti-4-1BB scFvs are provided in Table 8 below.

TABLE 8

DNA and AA Sequences of Exemplary anti-4-1BB scFvs

| Construct | DNA Sequence | DNA SEQ ID | AA Sequence | AA SEQ ID |
|---|---|---|---|---|
| ALG.APV-<br>178-4-1BB<br>ALG.APV-<br>179-4-1BB<br>ALG.APV-<br>187-4-1BB<br>ALG.APV-<br>198-4-1BB<br>ALG.APV-<br>199-4-1BB | GAGGTGCAGCTGTTGGAGAGCGGGGGAGG<br>CTTGGTACAGCCTGGGGGGTCCCTGCGCC<br>TCTCCTGTGCAGCCAGCGGATTCACCTTT<br>TCTCACGGTTCTATGTACTGGGTCCGCCA<br>GGCTCCAGGGAAGGGGCTGGAGTGGGTCT<br>CATCTATTTCTTCTGGTTCTGGTTCTACA<br>TACTATGCAGACTCCGTGAAGGGCCGGTT<br>CACCATCTCCCATGACAATTCCAAGAACA<br>CGCTGTATCTGCAAATGAACAGCCTGCGT<br>GCCGAGGACACGGCTGTATATTATTGTGC | 109 | EVQLLESGGGLVQPGGSLRL<br>SCAASGFTFSHGSMYWVRQA<br>PGKGLEWVSSISSGSGSTYY<br>ADSVKGRFTISHDNSKNTLY<br>LQMNSLRAEDTAVYYCARSS<br>YYGSYYSIDYWGQGTLVTVS<br>SGGGGSGGGGSGGGGSGGGG<br>SDIQMTQSPSSLSASVGDRV<br>TITCRASQSISSYLNWYQQK<br>PGKAPKLLIYAASSLQSGVP | 110 |

TABLE 8-continued

DNA and AA Sequences of Exemplary anti-4-1BB scFvs

| Construct | DNA Sequence | DNA SEQ ID | AA Sequence | AA SEQ ID |
|---|---|---|---|---|
| ALG.APV- | GCGCTCTTCTTACTACGGTTCTTACTACT | | SRFSGSGSGTDFTLTISSLQ | |
| 208-4-1BB | CTATTGACTATTGGGGCCAGGGAACCCTG | | PEDFATYYCQQYYDNLPTFG | |
| ALGAPV- | GTCACCGTCTCCTCAGGTGGAGGTGGCTC | | QGTKLEIK | |
| 209-4-1BB | CGGGGGTGGAGGTTCCGGAGGAGGCGGAT | | | |
| ALGAPV- | CAGGTGGAGGCGGAAGCGACATCCAGATG | | | |
| 210-4-1BB | ACCCAGTCTCCATCCTCCCTGAGCGCATC | | | |
| ALGAPV- | TGTAGGAGACCGCGTCACCATCACTTGCC | | | |
| 222-4-1BB | GGGCAAGTCAGAGCATTAGCAGCTATTTA | | | |
| ALG.APV- | AATTGGTATCAGCAGAAACCAGGGAAAGC | | | |
| 223-4-1BB | CCCTAAGCTCCTGATCTATGCTGCATCCA | | | |
| | GTTTGCAAAGTGGGGTCCCATCACGTTTC | | | |
| | AGTGGCAGTGGAAGCGGGACAGATTTCAC | | | |
| | TCTCACCATCAGCAGTCTACAACCTGAAG | | | |
| | ATTTTGCAACTTATTACTGTCAACAGTAC | | | |
| | TACGACAACCTGCCCACTTTTGGCCAGGG | | | |
| | GACCAAGCTGGAGATCAAA | | | |
| ALG.APV- | GAGGTGCAGCTGTTGGAGAGCGGGGGAGG | 111 | EVQLLESGGGLVQPGGSLRL | 112 |
| 191-4-1BB | CTTGGTACAGCCTGGGGGGTCCCTGCGCC | | SCAASGFTFDYGSMYWVRQA | |
| | TCTCCTGTGCAGCCAGCGGATTCACCTTT | | PGKGLEWVSSISSGSGSTYY | |
| | GATTACGGTTCTATGTACTGGGTCCGCCA | | ADSVKGRFTISHDNSKNTLY | |
| | GGCTCCAGGGAAGGGGCTGGAGTGGGTCT | | LQMNSLRAEDTAVYYCARSS | |
| | CATCTATTTCTTCTGGTTCTGGTTCTACA | | YYGSYYSIDYWGQGTLVTVS | |
| | TACTATGCAGACTCCGTGAAGGGCCGGTT | | SGGGGSGGGGSGGGGSGGGG | |
| | CACCATCTCCCACGACAATTCCAAGAACA | | SDIQMTQSPSSLSASVGDRV | |
| | CGCTGTATCTGCAAATGAACAGCCTGCGT | | TITCRASQSISSYLNWYQQK | |
| | GCCGAGGACACGGCTGTATATTATTGTGC | | PGKAPKLLIYAASSLHSGVP | |
| | GCGCTCTTCTTACTACGGTTCTTACTACT | | SRFSGSGSGTDFTLTISSLQ | |
| | CTATTGACTATTGGGGCCAGGGAACCCTG | | PEDFATYYCQQYYDNLPTFG | |
| | GTCACCGTCTCCTCAGGTGGAGGTGGCTC | | QGTKLEIK | |
| | CGGGGGTGGAGGTTCCGGAGGAGGCGGAT | | | |
| | CAGGTGGAGGCGGAAGCGACATCCAGATG | | | |
| | ACCCAGTCTCCATCCTCCCTGAGCGCATC | | | |
| | TGTAGGAGACCGCGTCACCATCACTTGCC | | | |
| | GGGCAAGTCAGAGCATTAGCAGCTATTTA | | | |
| | AATTGGTATCAGCAGAAACCAGGGAAAGC | | | |
| | CCCTAAGCTCCTGATCTATGCTGCATCCA | | | |
| | GTTTGCACAGTGGGGTCCCATCACGTTTC | | | |
| | AGTGGCAGTGGAAGCGGGACAGATTTCAC | | | |
| | TCTCACCATCAGCAGTCTGCAACCTGAAG | | | |
| | ATTTTGCAACTTATTACTGTCAACAGTAC | | | |
| | TACGACAACCTGCCCACTTTTGGCCAGGG | | | |
| | GACCAAGCTGGAGATCAAA | | | |
| ALG.APV- | GAGGTGCAGCTGTTGGAGAGCGGGGGAGG | 113 | EVQLLESGGGLVQPGGSLRL | 114 |
| 196-4-1BB | CTTGGTACAGCCTGGGGGGTCCCTGCGCC | | SCAASGFTFSYGSMYWVRQA | |
| | TCTCCTGTGCAGCCAGCGGATTCACCTTT | | PGKGLEWVSSISSGSGSTYY | |
| | TCTTACGGTTCTATGTACTGGGTCCGCCA | | ADSVKGRFTISHDNSKNTLY | |
| | GGCTCCAGGGAAGGGGCTGGAGTGGGTCT | | LQMNSLRAEDTAVYYCARSS | |
| | CATCTATTTCTTCTGGTTCTGGTTCTACA | | YYGSYYSIDYWGQGTLVTVS | |
| | TACTATGCAGACTCCGTGAAGGGCCGGTT | | SGGGGSGGGGSGGGGSGGGG | |
| | CACCATCTCCCATGACAATTCCAAGAACA | | SDIQMTQSPSSLSASVGDRV | |
| | CGCTGTATCTGCAAATGAACAGCCTGCGT | | TITCRASQSISSYLNWYQQK | |
| | GCCGAGGACACGGCTGTATATTATTGTGC | | PGKAPKLLIYAASSLQSGVP | |
| | GCGCTCTTCTTACTACGGTTCTTACTACT | | SRFSGSGSGTDFTLTISSLQ | |
| | CTATTGACTATTGGGGCCAGGGAACCCTG | | PEDFATYYCQQYYDNLPTFG | |
| | GTCACCGTCTCCTCAGGTGGAGGTGGCTC | | QGTKLEIK | |
| | CGGGGGTGGAGGTTCCGGAGGAGGCGGAT | | | |
| | CAGGTGGAGGCGGAAGCGACATCCAGATG | | | |
| | ACCCAGTCTCCATCCTCCCTGAGCGCATC | | | |
| | TGTAGGAGACCGCGTCACCATCACTTGCC | | | |
| | GGGCAAGTCAGAGCATTAGCAGCTATTTA | | | |
| | AATTGGTATCAGCAGAAACCAGGGAAAGC | | | |
| | CCCTAAGCTCCTGATCTATGCTGCATCCA | | | |
| | GTTTGCAAAGTGGGGTCCCATCACGTTTC | | | |
| | AGTGGCAGTGGAAGCGGGACAGATTTCAC | | | |
| | TCTCACCATCAGCAGTCTACAACCTGAAG | | | |
| | ATTTTGCAACTTATTACTGTCAACAGTAC | | | |
| | TACGACAACCTGCCCACTTTTGGCCAGGG | | | |
| | GACCAAGCTGGAGATCAAA | | | |
| ALG.APV- | GAGGTGCAGCTGTTGGAGAGCGGGGGAGG | 115 | EVQLLESGGGLVQPGGSLRL | 116 |
| 006-4-1BB | CTTGGTACAGCCTGGGGGGTCCCTGCGCC | | SCAASGFTFSYGSMYWVRQA | |
| ALG.APV- | TCTCCTGTGCAGCCAGCGGATTCACCTTT | | PGKGLEWVSSISSGSGSTYY | |
| 010-4-1BB | TCTTACGGTTCTATGTACTGGGTCCGCCA | | ADSVKGRFTISRDNSKNTLY | |

TABLE 8-continued

| DNA and AA Sequences of Exemplary anti-4-1BB scFvs | | | | |
|---|---|---|---|---|
| Construct | DNA Sequence | DNA SEQ ID | AA Sequence | AA SEQ ID |
| ALG.APV-014-4-1BB ALG.APV-018-4-1BB | GGCTCCAGGGAAGGGGCTGGAGTGGGTCT CATCTATTTCTTCTGGTTCTGGTTCTACA TACTATGCAGACTCCGTGAAGGGCCGGTT CACCATCTCCCGTGACAATTCCAAGAACA CGCTGTATCTGCAAATGAACAGCCTGCGT GCCGAGGACACGGCTGTATATTATTGTGC GCGCTCTTCTTACTACGGTTCTTACTACT CTATTGACTATTGGGGCCAGGGAACCCTG GTCACCGTCTCCTCAGGCGGCGGCGGCAG CGGCGGCGGCGGCAGCGGCGGCGGAGGCT CCGGCGGCGGCGGCAGCGACATCCAGATG ACCCAGTCTCCATCCTCCCTGAGCGCATC TGTAGGAGACCGCGTCACCATCACTTGCC GGGCAAGTCAGAGCATTAGCAGCTATTTA AATTGGTATCAGCAGAAACCAGGGAAAGC CCCTAAGCTCCTGATCTATGCTGCATCCA GTTTGCAAAGTGGGGTCCCATCACGTTTC AGTGGCAGTGGAAGCGGGACAGATTTCAC TCTCACCATCAGCAGTCTGCAACCTGAAG ATTTTGCAACTTATTACTGTCAACAGTAC TACGACAACCTGCCCACTTTTGGCCAGGG GACCAAGCTGGAGATCAAA | | LQMNSLRAEDTAVYYCARSS YYGSYYSIDYWGQGTLVTVS SGGGGSGGGGSGGGGSGGGG SDIQMTQSPSSLSASVGDRV TITCRASQSISSYLNWYQQK PGKAPKLLIYAASSLQSGVP SRFSGSGSGTDFTLTISSLQ PEDFATYYCQQYYDNLPTFG QGTKLEIK | |

Bispecific Molecules

In some embodiments, the present invention provides multispecific 5T4-binding polypeptides comprising two binding domains wherein one binding domain is specific for 5T4 and the second binding domain is specific for a different target antigen. In some embodiments, the present invention provides bispecific 4-1BB-binding polypeptides comprising two binding domains wherein binding domain is specific for 4-1BB and the second binding domain is specific for a different target antigen. In particular embodiments, the present invention provides bispecific polypeptides comprising two binding domains, wherein one binding domain is specific for 4-1BB and wherein the other binding domain is specific for 5T4. Such embodiments are referred to herein as anti-5T4×anti-4-1BB molecules or anti-5T4×anti-4-1BB polypeptides or proteins. In particular embodiments, the 5T4 and 4-1BB binding domains of an anti-5T4×anti-4-1BB molecule are scFv domains that specifically bind to 5T4 and 4-1BB, respectively.

In some embodiments, the anti-5T4×anti-4-1BB molecules described herein comprise in order from amino-terminus to carboxyl-terminus (i) a 5T4-binding domain; (ii) a binding domain linker; and (iii) a 4-1BB-binding domain. In some embodiments, the anti-5T4× anti-4-1BB molecules described herein comprise in order from amino-terminus to carboxyl-terminus (i) a 4-1BB-binding domain; (ii) a binding domain linker; and (iii) a 5T4-binding domain. In some embodiments, the anti-5T4×anti-4-1BB molecules described herein comprise in order from amino-terminus to carboxyl-terminus (or in order from carboxyl-terminus to amino-terminus), (i) a 5T4-binding domain, (ii) a hinge region, (iii) an immunoglobulin constant region, (iv) a carboxyl-terminus linker (or an amino-terminus linker), and (v) a second binding domain.

The anti-5T4×anti-4-1BB molecules described herein may comprise any combination of the anti-5T4 and the anti-4-1BB binding domain sequences shown in Tables 4-7. In particular embodiments, the anti-5T4×anti-4-1BB molecules of the present invention comprise a 5T4-binding domain and a 4-1BB-binding domain that each comprise a HCDR1, HCDR2, HCDR3, LCDR1, LCDR2, and LCDR3. In some embodiments, the anti-5T4×anti-4-1BB molecules comprise (a) a first scFv domain comprising: (i) $V_H$ comprising an HCDR1 amino acid sequence selected from the group consisting of SEQ ID NOs: 30, 52, and 60, an HCDR2 amino acid sequence selected from the group consisting of SEQ ID NOs: 32 and 62, and an HCDR3 amino acid sequence of SEQ ID NO: 34; and (ii) a $V_L$ comprising an LCDR1 amino acid sequence selected from the group consisting of SEQ ID NOs: 8, 42, and 54, an LCDR2 amino acid sequence of SEQ ID NO: 10, and an LCDR3 amino acid sequence of SEQ ID NO: 36; and (b) a second scFv domain comprising (i) a $V_H$ comprising an HCDR1 amino acid sequence selected from the group consisting of SEQ ID NOs: 2, 18, and 24, an HCDR2 amino acid sequence of SEQ ID NO: 4, and an HCDR3 amino acid sequence of SEQ ID NO: 6; and (ii) a $V_L$ comprising an LCDR1 amino acid sequence of SEQ ID NO: 8, an LCDR2 amino acid sequence of SEQ ID NO: 10, and an LCDR3 amino acid sequence of SEQ ID NO: 12.

In some embodiments, the anti-5T4×anti-4-1BB molecules of the present invention comprise a 5T4-binding domain and a 4-1BB-binding domain that each comprise a $V_H$ and a $V_L$ domain. In some embodiments, the anti-5T4×anti-4-1BB molecules comprise a first scFv domain comprising i) a $V_H$ comprising an amino acid sequence selected from the group consisting of SEQ ID NO: 38, 46, 56, and 64 and a $V_L$ comprising an amino acid selected from the group consisting of SEQ ID NOs: 40, 44, 48, 50 58, 66, 68, and 70; and a second scFv domain comprising ii) a $V_H$ comprising an amino acid selected from the group consisting of SEQ ID NO: 14, 20, 26, and 28 and a $V_L$ comprising an amino acid selected from the group consisting of SEQ ID NO: 16 and 22.

In certain embodiments, the 5T4-binding domain of an anti-5T4×anti-4-1BB molecule comprises or is an scFv that is at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence selected from the group consisting of SEQ ID NOs: 118, 120, 122, 124, 126, 128, 130, 132, 134, and 170, wherein the molecule is a multispecific polypeptide in the format scFv-Fc-scFv and comprises a Y to F substitution in the LCDR1 at position 99 of the anti-5T4 $V_L$ and/or a F to S substitution in the FR3 at position 148 of the anti-5T4 $V_L$. In certain embodiments, the 5T4-binding domain of an anti-5T4×anti-4-1BB molecule comprises an scFv that comprises an amino acid sequence selected from the group consisting of SEQ ID NOs: 118, 120, 122, 124, 126, 128, 130, 132, 134, and 170.

In certain embodiments, the 4-1BB-binding domain of an anti-5T4×anti-4-1BB molecule comprises or is an scFv that is at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence selected from the group consisting of SEQ ID NOs: 110, 112, 114, and 116, wherein the molecule is a multispecific polypeptide in the format scFv-Fc-scFv and comprises a Y to H substitution in the HCDR1 at position 150 of the anti-4-1BB $V_H$ and/or an R to H substitution in the FR3 at position 127 of the anti-4-1BB $V_H$. In certain embodiments, the 4-1BB-binding domain of an anti-5T4×anti-4-1BB molecule comprises scFv that comprises an amino acid sequence selected from the group consisting of SEQ ID NOs: 110, 112, 114, and 116.

In particular embodiments, the anti-5T4×anti-4-1BB molecule comprises a combination of CDR sequences, $V_H$/$V_L$ sequences, and/or scFv sequences as shown in Table 9 below.

TABLE 9

Exemplary anti-5T4 and anti-4-1BB Binding Sequence Combinations

| 4-1BB Binding Domain | | 5T4 Binding Domain | |
|---|---|---|---|
| Component | SEQ ID NO: | Component | SEQ ID NO: |
| ALG.APV-178 (scFv-Fc-scFv Format) | | | |
| HCDR1 | 2 | HCDR1 | 30 |
| HCDR2 | 4 | HCDR2 | 32 |
| HCDR3 | 6 | HCDR3 | 34 |
| LCDR1 | 8 | LCDR1 | 8 |
| LCDR2 | 10 | LCDR2 | 10 |
| LCDR3 | 12 | LCDR3 | 36 |
| $V_H$ | 14 | $V_H$ | 38 |
| $V_L$ | 16 | $V_L$ | 40 |
| scFv | 110 | scFv | 118 |
| ALG.APV-179, ALG.APV-209, ALG.APV-222 (scFv-Fc-scFv Format) | | | |
| HCDR1 | 2 | HCDR1 | 30 |
| HCDR2 | 4 | HCDR2 | 32 |
| HCDR3 | 6 | HCDR3 | 34 |
| LCDR1 | 8 | LCDR1 | 42 |
| LCDR2 | 10 | LCDR2 | 10 |
| LCDR3 | 12 | LCDR3 | 36 |
| $V_H$ | 14 | $V_H$ | 38 |
| $V_L$ | 16 | $V_L$ | 44 |
| scFv | 110 | scFv | 120 |
| ALG.APV-187, ALG.APV-210, ALG.APV-223 (scFv-Fc-scFv Format) | | | |
| HCDR1 | 2 | HCDR1 | 30 |
| HCDR2 | 4 | HCDR2 | 32 |
| HCDR3 | 6 | HCDR3 | 34 |
| LCDR1 | 8 | LCDR1 | 42 |
| LCDR2 | 10 | LCDR2 | 10 |
| LCDR3 | 12 | LCDR3 | 36 |
| $V_H$ | 14 | $V_H$ | 46 |
| $V_L$ | 16 | $V_L$ | 48 |
| scFv | 110 | scFv | 122 |

TABLE 9-continued

Exemplary anti-5T4 and anti-4-1BB Binding Sequence Combinations

| 4-1BB Binding Domain | | 5T4 Binding Domain | |
|---|---|---|---|
| Component | SEQ ID NO: | Component | SEQ ID NO: |
| ALG.APV-191 (scFv-Fc-scFv Format) | | | |
| HCDR1 | 18 | HCDR1 | 30 |
| HCDR2 | 4 | HCDR2 | 32 |
| HCDR3 | 6 | HCDR3 | 34 |
| LCDR1 | 8 | LCDR1 | 42 |
| LCDR2 | 10 | LCDR2 | 10 |
| LCDR3 | 12 | LCDR3 | 36 |
| $V_H$ | 20 | $V_H$ | 46 |
| $V_L$ | 22 | $V_L$ | 50 |
| scFv | 112 | scFv | 124 |
| ALG.APV-196 (scFv-Fc-scFv Format) | | | |
| HCDR1 | 24 | HCDR1 | 52 |
| HCDR2 | 4 | HCDR2 | 32 |
| HCDR3 | 6 | HCDR3 | 34 |
| LCDR1 | 8 | LCDR1 | 54 |
| LCDR2 | 10 | LCDR2 | 10 |
| LCDR3 | 12 | LCDR3 | 36 |
| $V_H$ | 26 | $V_H$ | 56 |
| $V_L$ | 16 | $V_L$ | 58 |
| scFv | 114 | scFv | 126 |
| ALG.APV-198 (scFv-Fc-scFv Format) | | | |
| HCDR1 | 2 | HCDR1 | 52 |
| HCDR2 | 4 | HCDR2 | 32 |
| HCDR3 | 6 | HCDR3 | 34 |
| LCDR1 | 8 | LCDR1 | 54 |
| LCDR2 | 10 | LCDR2 | 10 |
| LCDR3 | 12 | LCDR3 | 36 |
| $V_H$ | 14 | $V_H$ | 56 |
| $V_L$ | 16 | $V_L$ | 58 |
| scFv | 110 | scFv | 126 |
| ALG.APV-199 (scFv-Fc-scFv Format) | | | |
| HCDR1 | 2 | HCDR1 | 60 |
| HCDR2 | 4 | HCDR2 | 62 |
| HCDR3 | 6 | HCDR3 | 34 |
| LCDR1 | 8 | LCDR1 | 54 |
| LCDR2 | 10 | LCDR2 | 10 |
| LCDR3 | 12 | LCDR3 | 36 |
| $V_H$ | 14 | $V_H$ | 64 |
| $V_L$ | 16 | $V_L$ | 58 |
| scFv | 110 | scFv | 128 |
| ALG.APV-006 (scFv-Fc-scFv Format) | | | |
| HCDR1 | 24 | HCDR1 | 30 |
| HCDR2 | 4 | HCDR2 | 32 |
| HCDR3 | 6 | HCDR3 | 34 |
| LCDR1 | 8 | LCDR1 | 8 |
| LCDR2 | 10 | LCDR2 | 10 |
| LCDR3 | 12 | LCDR3 | 36 |
| $V_H$ | 28 | $V_H$ | 38 |
| $V_L$ | 16 | $V_L$ | 68 |
| scFv | 116 | scFv | 130 |
| ALG.APV-010 (scFv-Fc-scFv Format) | | | |
| HCDR1 | 24 | HCDR1 | 30 |
| HCDR2 | 4 | HCDR2 | 32 |
| HCDR3 | 6 | HCDR3 | 34 |
| LCDR1 | 8 | LCDR1 | 8 |
| LCDR2 | 10 | LCDR2 | 10 |
| LCDR3 | 12 | LCDR3 | 36 |
| $V_H$ | 28 | $V_H$ | 38 |
| $V_L$ | 16 | $V_L$ | 68 |
| scFv | 116 | scFv | 170 |
| ALG.APV-014 (scFv-Fc-scFv Format) | | | |
| HCDR1 | 24 | HCDR1 | 30 |
| HCDR2 | 4 | HCDR2 | 32 |
| HCDR3 | 6 | HCDR3 | 34 |
| LCDR1 | 8 | LCDR1 | 8 |
| LCDR2 | 10 | LCDR2 | 10 |
| LCDR3 | 12 | LCDR3 | 36 |

TABLE 9-continued

| Exemplary anti-5T4 and anti-4-1BB Binding Sequence Combinations | | | |
|---|---|---|---|
| 4-1BB Binding Domain | | 5T4 Binding Domain | |
| Component | SEQ ID NO: | Component | SEQ ID NO: |
| $V_H$ | 28 | $V_H$ | 46 |
| $V_L$ | 16 | $V_L$ | 70 |
| scFv | 116 | scFv | 132 |
| ALG.APV-018 (scFv-Fc-scFv Format) | | | |
| HCDR1 | 24 | HCDR1 | 30 |
| HCDR2 | 4 | HCDR2 | 32 |
| HCDR3 | 6 | HCDR3 | 34 |
| LCDR1 | 8 | LCDR1 | 8 |
| LCDR2 | 10 | LCDR2 | 10 |
| LCDR3 | 12 | LCDR3 | 36 |
| $V_H$ | 28 | $V_H$ | 46 |
| $V_L$ | 16 | $V_L$ | 70 |
| scFv | 116 | scFv | 134 |

In some embodiments, the anti-5T4×anti-4-1BB molecules described herein may comprise an amino acid sequence that is at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence selected from the group consisting of SEQ ID NOs: 136, 138, 140, 142, 144, 146, 148, 150, 152, 154, 156, 172, 174, and 176. In some embodiments, the anti-5T4×anti-4-1BB molecules described herein may comprise an amino acid sequence selected from the group consisting of SEQ ID NOs: 136, 138, 140, 142, 144, 146, 148, 150, 152, 154, 156, 172, 174, and 176. Exemplary amino acid and nucleic acid sequences for the anti-5T4×anti-4-1BB molecules described herein are provided in Tables 10 and 11. In each of Tables 10 and 11, immunoglobulin Fc domains (hinge-CH1-CH2) are indicated in underlined text, and binding domain linker sequences are indicated in bolded text.

TABLE 10

| Exemplary anti-5T4 x anti-4-1BB Molecule DNA Sequences | | |
|---|---|---|
| Construct | DNA SEQ | DNA SEQ ID |
| ALG.APV-178 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTCACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCA<br>TGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGTGGAGGTGGCTCCGG<br>GGGTGGAGGTTCCGGAGGAGGCGGATCAGGTGGAGGCGGAAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCAAAGTGGGGTCCCA<br>TCACGTTTCAGTGGCAGTGGAAGCGGGACAGATTTCACTCTCACCATCAGCAGTC<br>TACAACCTGAAGATTTTGCAACTTATTACTGTCAACAGTACTACGACAACCTGCC<br>CACTTTTGGCCAGGGGACCAAGCTGGAGATCAAATCGAGTGAGCCCAAATCTTCT<br>GACAAAACTCACACATGCCCACCGTGCCCAGCACCTGAAGCCGCGGGTGCACCGT<br>CAGTCTTCCTCTTCCCCCCAAAACCCAAGGACACCCTCATGATCTCCCGGACCCC<br>TGAGGTCACATGCGTGGTGGTGGACGTGAGCCACGAAGACCCTGAGGTCAAGTTC<br>AACTGGTACGTGGACGGCGTGGAGGTGCATAATGCCAAGACAAAGCCGCGGGAGG<br>AGCAGTACAACAGCACGTACCGTGTGGTCAGCGTCCTCACCGTCCTGCACCAGGA<br>CTGGCTGAATGGCAAGGAATACAAGTGCGCGGTCTCCAACAAAGCCCTCCCAGCC<br>CCCATCGAGAAAACCATCTCCAAAGCCAAAGGGGAGCCCCGAGAACCACAGGTGT<br>ACACCCTGCCCCCATCCCGGGATGAGCTGACCAAGAACCAGGTCAGCCTGACCTG<br>CCTGGTCAAAGGCTTCTATCCAAGCGACATCGCCGTGGAGTGGGAGAGCAATGGG<br>CAGCCGGAGAACAACTACAAGACCACGCCTCCCGTGCTGGACTCCGACGGCTCCT<br>TCTTCCTCTACAGCAAGCTCACCGTGGACAAGAGCAGGTGGCAGCAGGGGAACGT<br>CTTCTCATGCTCCGTGATGCATGAGGCTCTGCACAACCACTAGACGCAGAAGAGC<br>CTCTCCCTGTCTCCGGGT**TCCGGAGGTGGCGGTTCGGGAGGTGGCGGGTCAGGAG**<br>**GTGGGGGATCCCCTTCA**GAAGTGCAGCTGCTGGAGTCCGGAGGAGGACTGGTGCA<br>GCCTGGCGGAAGCCTGAGGCTGAGCTGCGCTGCCTCCGGCTTCACATTCAGCAGC<br>TATGCTATGAGCTGGGTGAGGCAAGCCCCTGGAAAGGGCCTGGAGTGGGTGTCCG<br>CTATCTCCGGCAGCGGCGGAAGCACCTACTACGCTGACTCCGTCAAGGGCAGGTT<br>CACCATCAGCCGGGACAACAGCAAGAACACCCTGTACCTGCAGATGAATAGCCTC<br>AGGGCTGAAGACACCGCTGTGTACTACTGCGCCAGGTACTATGGCGGCTACTACT<br>CCGCCTGGATGGACTACTGGGGACAGGGCACACTGGTGACCGTGTCCAGCGGCGG<br>AGGCGGCTCCGGAGGCGGTGGCTCCGGAGGAGGCGGAAGCGGAGGAGGAGGCTCC<br>GATATTCAGATGACACAGTCCCCTAGCTCCCTGTCCGCCAGCGTGGGAGATCGGG<br>TGACCATCACCTGCAGGGCCAGCCAGTCCATCTCCAGCTATTTAAACTGGTACCA<br>GCAGAAGCCTGGAAAGGCTCCCAAGCTGCTGATCTACGCCGCTTCCAGCCTCCAG<br>AGCGGCGTGCCTAGCAGGTTCTCCGGCTCCGGAAGCGGAACAGACTTCACCCTGA<br>CCATCAGCTCCCTGCAGCCCGAGGACTCCGCTACCTACTACTGCCAGCAGACCTA<br>TGGCTACCTGCACACCTTCGGCCAGGGCACAAAGCTGGAGATCAAGCGC | 135 |
| ALG.APV-179 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTCACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCA<br>TGACAATTCCAAGAACACGCTGTATCTGCAAATGAACAGCCTGCGTGCCGAGGAC | 137 |

TABLE 10-continued

Exemplary anti-5T4 x anti-4-1BB Molecule DNA Sequences

| Construct | DNA SEQ | DNA SEQ ID |
|---|---|---|
| | ACGGCTGTATATTATTGTGCGCGCTCTTCTTACTACGGTTCTTACTACTCTATTG | |
| | ACTATTGGGGCCAGGGAACCCTGGTCACCGTCTCCTCAGGTGGAGGTGGCTCCGG | |
| | GGGTGGAGGTTCCGGAGGAGGCGGATCAGGTGGAGGCGGAAGCGACATCCAGATG | |
| | ACCCAGTCTCCATCCTCCCTGAGCGCATCTGTAGGAGACCGCGTCACCATCACTT | |
| | GCCGGGCAAGTCAGAGCATTAGCAGCTATTTAAATTGGTATCAGCAGAAACCAGG | |
| | GAAAGCCCCTAAGCTCCTGATCTATGCTGCATCCAGTTTGCAAAGTGGGGTCCCA | |
| | TCACGTTTCAGTGGCAGTGGAAGCGGGACAGATTTCACTCTCACCATCAGCAGTC | |
| | TACAACCTGAAGATTTTGCAACTTATTACTGTCAACAGTACTACGACAACCTGCC | |
| | CACTTTTGGCCAGGGGACCAAGCTGGAGATCAAATCGAGTGAGCCCAAATCTTCT | |
| | GACAAAACTCACACATGCCCACCGTGCCCAGCACCTGAAGCCGCGGGTGCACCGT | |
| | CAGTCTTCCTCTTCCCCCCAAAACCCAAGGACACCCTCATGATCTCCCGGACCCC | |
| | TGAGGTCACATGCGTGGTGGTGGACGTGAGCCACGAAGACCCTGAGGTCAAGTTC | |
| | AACTGGTACGTGGACGGCGTGGAGGTGCATAATGCCAAGACAAAGCCGCGGGAGG | |
| | AGCAGTACAACAGCACGTACCGTGTGGTCAGCGTCCTCACCGTCCTGCACCAGGA | |
| | CTGGCTGAATGGCAAGGAATACAAGTGCGCGGTCTCCAACAAAGCCCTCCCAGCC | |
| | CCCATCGAGAAAACCATCTCCAAAGCCAAAGGGCAGCCCCGAGAACCACAGGTGT | |
| | ACACCCTGCCCCCATCCCGGGATGAGCTGACCAAGAACCAGGTCAGCCTGACCTG | |
| | CCTGGTCAAAGGCTTCTATCCAAGCGACATCGCCGTGGAGTGGGAGAGCAATGGG | |
| | CAGCCGGAGAACAACTACAAGACCACGCCTCCCGTGCTGGACTCCGACGGCTCCT | |
| | TCTTCCTCTACAGCAAGCTCACCGTGGACAAGAGCAGGTGGCAGCAGGGGAACGT | |
| | CTTCTCATGCTCCGTGATGCATGAGGCTCTGCACAACCACTACACGCAGAAGAGC | |
| | CTCTCCCTGTCTCCGGGT**TCCGGAGGTGGCGGTTCGGGAGGTGGCGGGTCAGGAG** | |
| | **GTGGGGGATCCCCTTCA**GAAGTGCAGCTGCTGGAGTCCGGAGGAGGACTGGTGCA | |
| | GCCTGGCGGAAGCCTGAGGCTGAGCTGCGCTGCCTCCGGCTTCACATTCAGCAGC | |
| | TATGCTATGAGCTGGGTGAGGCAAGCCCCTGGAAAGGGCCTGGAGTGGGTGTCCG | |
| | CTATCTCCGGCAGCGGCGGAAGCACCTACTACGCTGACTCCGTCAAGGGCAGGTT | |
| | CACCATCAGCCGGGACAACAGCAAGAACACCCTGTACCTGCAGATGAATAGCCTC | |
| | AGGGCTGAAGACACCGCTGTGTACTACTGCGCCAGGTACTATGGCGGCTACTACT | |
| | CCGCCTGGATGGACTACTGGGGACAGGGCACACTGGTGACCGTGTCCAGCGGCGG | |
| | AGGCGGCTCCGGAGGCGGTGGCTCCGGAGGAGGCGGAAGCGGAGGAGGAGGCTCC | |
| | GATATTCAGATGACACAGTCCCCTAGCTCCCTGTCCGCCAGCGTGGGAGATCGGG | |
| | TGACCATCACCTGCAGGGCCAGCCAGTCCATCTCCAGCTTCTTAAACTGGTACCA | |
| | GCAGAAGCCTGGAAAGGCTCCCAAGCTGCTGATCTACGCCGCTTCCAGCCTCCAG | |
| | AGCGGCGTGCCTAGCAGGTTCTCCGGCTCCGGAAGCGGAACAGACTTCACCCTGA | |
| | CCATCAGCTCCCTGCAGCCCGAGGACTCCGCTACCTACTACTGCCAGCAGACCTA | |
| | TGGCTACCTGCACACCTTCGGCCAGGGCACAAAGCTGGAGATCAAGCGC | |
| ALG.APV-187 | ATGGAAGCACCAGCGCAGCTTCTCTTCCTCCTGCTACTCTGGCTCCCAGATACCA | 139 |
| | CCGGTGAGGTGCAGCTGTTGGAGAGCGGGGGAGGCTTGGTACAGCCTGGGGGGTC | |
| | CCTGCGCCTCTCCTGTGCAGCCAGCGGATTCACCTTTTCTCACGGTTCTATGTAC | |
| | TGGGTCCGCCAGGCTCCAGGGAAGGGGCTGGAGTGGGTCTCATCTATTTCTTCTG | |
| | GTTCTGGTTCTACATACTATGCAGACTCCGTGAAGGGCCGGTTCACCATCTCCCA | |
| | TGACAATTCCAAGAACACGCTGTATCTGCAAATGAACAGCCTGCGTGCCGAGGAC | |
| | ACGGCTGTATATTATTGTGCGCGCTCTTCTTACTACGGTTCTTACTACTCTATTG | |
| | ACTATTGGGGCCAGGGAACCCTGGTCACCGTCTCCTCAGGTGGAGGTGGCTCCGG | |
| | GGGTGGAGGTTCCGGAGGAGGCGGATCAGGTGGAGGCGGAAGCGACATCCAGATG | |
| | ACCCAGTCTCCATCCTCCCTGAGCGCATCTGTAGGAGACCGCGTCACCATCACTT | |
| | GCCGGGCAAGTCAGAGCATTAGCAGCTATTTAAATTGGTATCAGCAGAAACCAGG | |
| | GAAAGCCCCTAAGCTCCTGATCTATGCTGCATCCAGTTTGCAAAGTGGGGTCCCA | |
| | TCACGTTTCAGTGGCAGTGGAAGCGGGACAGATTTCACTCTCACCATCAGCAGTC | |
| | TACAACCTGAAGATTTTGCAACTTATTACTGTCAACAGTACTACGACAACCTGCC | |
| | CACTTTTGGCCAGGGGACCAAGCTGGAGATCAAATCGAGTGAGCCCAAATCTTCT | |
| | GACAAAACTCACACATGCCCACCGTGCCCAGCACCTGAAGCCGCGGGTGCACCGT | |
| | CAGTCTTCCTCTTCCCCCCAAAACCCAAGGACACCCTCATGATCTCCCGGACCCC | |
| | TGAGGTCACATGCGTGGTGGTGGACGTGAGCCACGAAGACCCTGAGGTCAAGTTC | |
| | AACTGGTACGTGGACGGCGTGGAGGTGCATAATGCCAAGACAAAGCCGCGGGAGG | |
| | AGCAGTACAACAGCACGTACCGTGTGGTCAGCGTCCTCACCGTCCTGCACCAGGA | |
| | CTGGCTGAATGGCAAGGAATACAAGTGCGCGGTCTCCAACAAAGCCCTCCCAGCC | |
| | CCCATCGAGAAAACCATCTCCAAAGCCAAAGGGCAGCCCCGAGAACCACAGGTGT | |
| | ACACCCTGCCCCCATCCCGGGATGAGCTGACCAAGAACCAGGTCAGCCTGACCTG | |
| | CCTGGTCAAAGGCTTCTATCCAAGCGACATCGCCGTGGAGTGGGAGAGCAATGGG | |
| | CAGCCGGAGAACAACTACAAGACCACGCCTCCCGTGCTGGACTCCGACGGCTCCT | |
| | TCTTCCTCTACAGCAAGCTCACCGTGGACAAGAGCAGGTGGCAGCAGGGGAACGT | |
| | CTTCTCATGCTCCGTGATGCATGAGGCTCTGCACAACCACTACACGCAGAAGAGC | |
| | CTCTCCCTGTCTCCGGGT**TCCGGAGGTGGCGGTTCGGGAGGTGGCGGGTCAGGAG** | |
| | **GTGGGGGATCCCCTTCA**GAAGTGCAGCTGCTGGAGTCCGGAGGAGGACTGGTGCA | |
| | GCCTGGCGGAAGCCTGAGGCTGAGCTGCGCTGCCTCCGGCTTCACATTCAGCAGC | |
| | TATGCTATGAGCTGGGTGAGGCAAGCCCCTGGAAAGTGCCTGGAGTGGGTGTCCG | |
| | CTATCTCCGGCAGCGGCGGAAGCACCTACTACGCTGACTCCGTCAAGGGCAGGTT | |
| | CACCATCAGCCGGGACAACAGCAAGAACACCCTGTACCTGCAGATGAATAGCCTC | |
| | AGGGCTGAAGACACCGCTGTGTACTACTGCGCCAGGTACTATGGCGGCTACTACT | |
| | CCGCCTGGATGGACTACTGGGGACAGGGCACACTGGTGACCGTGTCCAGCGGCGG | |
| | AGGCGGCTCCGGAGGCGGTGGCTCCGGAGGAGGCGGAAGCGGAGGAGGAGGCTCC | |
| | GATATTCAGATGACACAGTCCCCTAGCTCCCTGTCCGCCAGCGTGGGAGATCGGG | |
| | TGACCATCACCTGCAGGGCCAGCCAGTCCATCTCCAGCTTCTTAAACTGGTACCA | |

TABLE 10-continued

Exemplary anti-5T4 x anti-4-1BB Molecule DNA Sequences

| Construct | DNA SEQ | DNA SEQ ID |
|---|---|---|
| | GCAGAAGCCTGGAAAGGCTCCCAAGCTGCTGATCTACGCCGCTTCCAGCCTCCAG<br>AGCGGCGTGCCTAGCAGGTTCTCCGGCTCCGGAAGCGGAACAGACTTCACCCTGA<br>CCATCAGCTCCCTGCAGCCCGAGGACTCCGCTACCTACTACTGCCAGCAGACCTA<br>TGGCTACCTGCACACCTTCGGCTGCGGCACAAAGCTGGAGATCAAGCGC | |
| ALG.APV-191 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTGATTACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCA<br>CGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGTGGAGGTGGCTCCGG<br>GGGTGGAGGTTCCGGAGGAGGCGGATCAGGTGGAGGCGGAAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCACAGTGGGGTCCCA<br>TCACGTTTCAGTGGCAGTGGAAGCGGGACAGATTTCACTCTCACCATCAGCAGTC<br>TGCAACCTGAAGATTTTGCAACTTATTACTGTCAACAGTACTACGACAACCTGCC<br>CACTTTTGGCCAGGGGACCAAGCTGGAGATCAAATCCTCGGAGCCCAAATCTTCT<br>GACAAAACTCACACATGCCCACCGTGCCCAGCACCTGAAGCCGCGGGTGCACCGT<br>CAGTCTTCCTCTTCCCCCCAAAACCCAAGGACACCCTCATGATCTCCCGGACCCC<br>TGAGGTCACATGCGTGGTGGTGGACGTGAGCCACGAAGACCCTGAGGTCAAGTTC<br>AACTGGTACGTGGACGGCGTGGAGGTGCATAATGCCAAGACAAAGCCGCGGGAGG<br>AGCAGTACAACAGCACGTACCGTGTGGTCAGCGTCCTCACCGTCCTGCACCAGGA<br>CTGGCTGAATGGCAAGGAATACAAGTGCGCGGTCTCCAACAAAGCCCTCCCAGCC<br>CCCATCGAGAAAACCATCTCCAAAGCCAAAGGGCAGCCCCGAGAACCACAGGTGT<br>ACACCCTGCCCCCATCCCGGGATGAGCTGACCAAGAACCAGGTCAGCCTGACCTG<br>CCTGGTCAAAGGCTTCTATCCAAGCGACATCGCCGTGGAGTGGGAGAGCAATGGG<br>CAGCCGGAGAACAACTACAAGACCACGCCTCCCGTGCTGGACTCCGACGGCTCCT<br>TCTTCCTCTACAGCAAGCTCACCGTGGACAAGAGCAGGTGGCAGCAGGGGAACGT<br>CTTCTCATGCTCCGTGATGCATGAGGCTCTGCACAACCACTACACGCAGAAGAGC<br>CTCTCCCTGTCTCCGGGT**TCCGGAGGTGGCGGTTCGGGAGGTGGCGGGTCAGGAG**<br>**GTGGGGGATCCCCTTCA**GAAGTGCAGCTGCTGGAGTCCGGAGGAGGACTGGTGCA<br>GCCTGGCGGAAGCCTGAGGCTGAGCTGCGCTGCCTCCGGCTTCACATTCAGCAGC<br>TATGCTATGAGCTGGGTGAGGCAAGCCCCTGGAAAGTGCCTGGAGTGGGTGTCCG<br>CTATCTCCGGCAGCGGCGGAAGCACCTACTACGCTGACTCCGTCAAGGGCAGGTT<br>CACCATCAGCCGGGACAACAGCAAGAACACCCTGTACCTGCAGATGAATAGCCTC<br>AGGGCTGAAGACACCGCTGTGTACTACTGCGCCAGGTACTATGGCGGCTACTACT<br>CCGCCTGGATGGACTACTGGGGACAGGGCACACTGGTGACCGTGTCCAGCGGCGG<br>AGGCGGCTCCGGAGGCGGTGGCTCCGGAGGAGGCGGAAGCGGAGGAGGAGGCTCC<br>GATATTCAGATGACACAGTCCCCTAGCTCCCTGTCCGCCAGCGTGGGAGATCGGG<br>TGACCATCACCTGCAGGGCCAGCCAGTCCATCTCCAGCTTCTTAAACTGGTACCA<br>GCAGAAGCCTGGAAAGGCTCCCAAGCTGCTGATCTACGCCGCTTCCAGCCTCCAG<br>AGCGGCGTGCCTAGCAGGTTCTCCGGCTCCGGAAGCGGAACAGACTTCACCCTGA<br>CCATCAGCTCCCTGCAGCCCGAGGACTTCGCTACCTACTACTGCCAGCAGACCTA<br>TGGCTACCTGCACACCTTCGGCTGCGGCACAAAGCTGGAGATCAAGAGC | 141 |
| ALG.APV-196 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTTACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCA<br>TGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGTGGAGGTGGCTCCGG<br>GGGTGGAGGTTCCGGAGGAGGCGGATCAGGTGGAGGCGGAAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCAAAGTGGGGTCCCA<br>TCACGTTTCAGTGGCAGTGGAAGCGGGACAGATTTCACTCTCACCATCAGCAGTC<br>TACAACCTGAAGATTTTGCAACTTATTACTGTCAACAGTACTACGACAACCTGCC<br>CACTTTTGGCCAGGGGACCAAGCTGGAGATCAAATCCTCGGAGCCCAAATCTTCT<br>GACAAAACTCACACATGCCCACCGTGCCCAGCACCTGAAGCCGCGGGTGCACCGT<br>CAGTCTTCCTCTTCCCCCCAAAACCCAAGGACACCCTCATGATCTCCCGGACCCC<br>TGAGGTCACATGCGTGGTGGTGGACGTGAGCCACGAAGACCCTGAGGTCAAGTTC<br>AACTGGTACGTGGACGGCGTGGAGGTGCATAATGCCAAGACAAAGCCGCGGGAGG<br>AGCAGTACAACAGCACGTACCGTGTGGTCAGCGTCCTCACCGTCCTGCACCAGGA<br>CTGGCTGAATGGCAAGGAATACAAGTGCGCGGTCTCCAACAAAGCCCTCCCAGCC<br>CCCATCGAGAAAACCATCTCCAAAGCCAAAGGGCAGCCCCGAGAACCACAGGTGT<br>ACACCCTGCCCCCATCCCGGGATGAGCTGACCAAGAACCAGGTCAGCCTGACCTG<br>CCTGGTCAAAGGCTTCTATCCAAGCGACATCGCCGTGGAGTGGGAGAGCAATGGG<br>CAGCCGGAGAACAACTACAAGACCACGCCTCCCGTGCTGGACTCCGACGGCTCCT<br>TCTTCCTCTACAGCAAGCTCACCGTGGACAAGAGCAGGTGGCAGCAGGGGAACGT<br>CTTCTCATGCTCCGTGATGCATGAGGCTCTGCACAACCACTACACGCAGAAGAGC | 143 |

TABLE 10-continued

Exemplary anti-5T4 x anti-4-1BB Molecule DNA Sequences

| Construct | DNA SEQ | DNA SEQ ID |
|---|---|---|
| | CTCTCCCTGTCTCCGGGT**TCCGGAGGTGGCGGTTCGGGAGGTGGCGGGTCAGGAG**<br>**GTGGGGGATCCCCTTCA**GAAGTGCAGCTGCTGGAGTCCGGAGGAGGACTGGTGCA<br>GCCTGGCGGAAGCCTGAGGCTGAGCTGCGCTGCCTCCGGCTTCGACTTCGAGAGC<br>TATGCTATGAGCTGGGTGAGGCAAGCCCCTGGAAAGTGCCTGGAGTGGGTGTCCG<br>CTATCTCCGGCAGCGGCGGAAGCACCTACTACGCTGACTCCGTCAAGGGCAGGTT<br>CACCATCAGCCGGGACAACAGCAAGAACACCCTGTACCTGCAGATGAATAGCCTC<br>AGGGCTGAAGACACCGCTGTGTACTACTGCGCCAGGTACTATGGCGGCTACTACT<br>CCGCCTGGATGGACTACTGGGGACAGGGCACACTGGTGACCGTGTCCAGCGGCGG<br>AGGCGGCTCCGGAGGCGGTGGCTCCGGAGGAGGCGGAAGCGGAGGAGGAGGCTCC<br>GATATTCAGATGACACAGTCCCCTAGCTCCCTGTCCGCCAGCGTGGGAGATCGGG<br>TGACCATCACCTGCAGGGCCAGCCAGTCCATCAGGAGCGCCCTGAACTGGTACCA<br>GCAGAAGCCTGGAAAGGCTCCCAAGCTGCTGATCTACGCCGCTTCCAGCCTCCAG<br>AGCGGCGTGCCTAGCAGGTTCTCCGGCTCCGGAAGCGGAACAGACTTCACCCTGA<br>CCATCAGCTCCCTGCAGCCCGAGGACTTCGCTACCTACTACTGCCAGCAGACCTA<br>TGGCTACCTGCACACCTTCGGCTGCGGCACAAAGCTGGAGATCAAGCGC | |
| ALG.APV-198 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTCACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCA<br>TGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGTGGAGGTGGCTCCGG<br>GGGTGGAGGTTCCGGAGGAGGCGGATCAGGTGGAGGCGGAAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCAAAGTGGGGTCCCA<br>TCACGTTTCAGTGGCAGTGGAAGCGGGACAGATTTCACTCTCACCATCAGCAGTC<br>TACAACCTGAAGATTTTGCAACTTATTACTGTCAACAGTACTACGACAACCTGCC<br>CACTTTTGGCCAGGGGACCAAGCTGGAGATCAAATCGAGTGAGCCCAAATCTTCT<br>GACAAAACTCACACATGCCCACCGTGCCCAGCACCTGAAGCCGCGGGTGCACCGT<br>CAGTCTTCCTCTTCCCCCCAAAACCCAAGGACACCCTCATGATCTCCCGGACCCC<br>TGAGGTCACATGCGTGGTGGTGGACGTGAGCCACGAAGACCCTGAGGTCAAGTTC<br>AACTGGTACGTGGACGGCGTGGAGGTGCATAATGCCAAGACAAAGCCGCGGGAGG<br>AGCAGTACAACAGCACGTACCGTGTGGTCAGCGTCCTCACCGTCCTGCACCAGGA<br>CTGGCTGAATGGCAAGGAATACAAGTGCGCGGTCTCCAACAAAGCCCTCCCAGCC<br>CCCATCGAGAAAACCATCTCCAAAGCCAAAGGGCAGCCCCGAGAACCACAGGTGT<br>ACACCCTGCCCCCATCCCGGGATGAGCTGACCAAGAACCAGGTCAGCCTGACCTG<br>CCTGGTCAAAGGCTTCTATCCAAGCGACATCGCCGTGGAGTGGGAGAGCAATGGG<br>CAGCCGGAGAACAACTACAAGACCACGCCTCCCGTGCTGGACTCCGACGGCTCCT<br>TCTTCCTCTACAGCAAGCTCACCGTGGACAAGAGCAGGTGGCAGCAGGGGAACGT<br>CTTCTCATGCTCCGTGATGCATGAGGCTCTGCACAACCACTACACGCAGAAGAGC<br>CTCTCCCTGTCTCCGGGT**TCCGGAGGTGGCGGTTCGGGAGGTGGCGGGTCAGGAG**<br>**GTGGGGGATCCCCTTCA**GAAGTGCAGCTGCTGGAGTCCGGAGGAGGACTGGTGCA<br>GCCTGGCGGAAGCCTGAGGCTGAGCTGCGCTGCCTCCGGCTTCGACTTCGAGAGC<br>TATGCTATGAGCTGGGTGAGGCAAGCCCCTGGAAAGTGCCTGGAGTGGGTGTCCG<br>CTATCTCCGGCAGCGGCGGAAGCACCTACTACGCTGACTCCGTCAAGGGCAGGTT<br>CACCATCAGCCGGGACAACAGCAAGAACACCCTGTACCTGCAGATGAATAGCCTC<br>AGGGCTGAAGACACCGCTGTGTACTACTGCGCCAGGTACTATGGCGGCTACTACT<br>CCGCCTGGATGGACTACTGGGGACAGGGCACACTGGTGACCGTGTCCAGCGGCGG<br>AGGCGGCTCCGGAGGCGGTGGCTCCGGAGGAGGCGGAAGCGGAGGAGGAGGCTCC<br>GATATTCAGATGACACAGTCCCCTAGCTCCCTGTCCGCCAGCGTGGGAGATCGGG<br>TGACCATCACCTGCAGGGCCAGCCAGTCCATCAGGAGCGCCCTGAACTGGTACCA<br>GCAGAAGCCTGGAAAGGCTCCCAAGCTGCTGATCTACGCCGCTTCCAGCCTCCAG<br>AGCGGCGTGCCTAGCAGGTTCTCCGGCTCCGGAAGCGGAACAGACTTCACCCTGA<br>CCATCAGCTCCCTGCAGCCCGAGGACTTCGCTACCTACTACTGCCAGCAGACCTA<br>TGGCTACCTGCACACCTTCGGCTGCGGCACAAAGCTGGAGATCAAGCGC | 145 |
| ALG.APV-199 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTCACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCA<br>TGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGTGGAGGTGGCTCCGG<br>GGGTGGAGGTTCCGGAGGAGGCGGATCAGGTGGAGGCGGAAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCAAAGTGGGGTCCCA<br>TCACGTTTCAGTGGCAGTGGAAGCGGGACAGATTTCACTCTCACCATCAGCAGTC<br>TACAACCTGAAGATTTTGCAACTTATTACTGTCAACAGTACTACGACAACCTGCC<br>CACTTTTGGCCAGGGGACCAAGCTGGAGATCAAATCGAGTGAGCCCAAATCTTCT<br>GACAAAACTCACACATGCCCACCGTGCCCAGCACCTGAAGCCGCGGGTGCACCGT | 147 |

TABLE 10-continued

Exemplary anti-5T4 x anti-4-1BB Molecule DNA Sequences

| Construct | DNA SEQ | DNA SEQ ID |
| --- | --- | --- |
| | CAGTCTTCCTCTTCCCCCCAAAACCCAAGGACACCCTCATGATCTCCCGGACCCC<br>TGAGGTCACATGCGTGGTGGTGGACGTGAGCCACGAAGACCCTGAGGTCAAGTTC<br>AACTGGTACGTGGACGGCGTGGAGGTGCATAATGCCAAGACAAAGCCGCGGGAGG<br>AGCAGTACAACAGCACGTACCGTGTGGTCAGCGTCCTCACCGTCCTGCACCAGGA<br>CTGGCTGAATGGCAAGGAATACAAGTGCGCGGTCTCCAACAAAGCCCTCCCAGCC<br>CCCATCGAGAAAACCATCTCCAAAGCCAAAGGGCAGCCCCGAGAACCACAGGTGT<br>ACACCCTGCCCCCATCCCGGGATGAGCTGACCAAGAACCAGGTCAGCCTGACCTG<br>CCTGGTCAAAGGCTTCTATCCAAGCGACATCGCCGTGGAGTGGGAGAGCAATGGG<br>CAGCCGGAGAACAACTACAAGACCACGCCTCCCGTGCTGGACTCCGACGGCTCCT<br>TCTTCCTCTACAGCAAGCTCACCGTGGACAAGAGCAGGTGGCAGCAGGGGAACGT<br>CTTCTCATGCTCCGTGATGCATGAGGCTCTGCACAACCACTACACGCAGAAGAGC<br>CTCTCCCTGTCTCCGGGT**TCCGGAGGTGGCGGTTCGGGAGGTGGCGGGTCAGGAG**<br>**GTGGGGGATCCCCTTCA**GAAGTGCAGCTGCTGGAGTCCGGAGGAGGACTGGTGCA<br>GCCTGGCGGAAGCCTGAGGCTGAGCTGCGCTGCCTCCGGCTTCGACTTCGACAGC<br>TATGCTATGAGCTGGGTGAGGCAAGCCCCTGGAAAGTGCCTGGAGTGGGTGTCCG<br>CTATCTCCGGCAGGGGCGGAAGCACCTACTACGCTGACTCCGTCAAGGGCAGGTT<br>CACCATCAGCCGGGACAACAGCAAGAACACCCTGTACCTGCAGATGAATAGCCTC<br>AGGGCTGAAGACACCGCTGTGTACTACTGCGCCAGGTACTATGGCGGCTACTACT<br>CCGCCTGGATGGACTACTGGGGACAGGGCACACTGGTGACCGTGTCCAGCGGCGG<br>AGGCGGCTCCGGAGGCGGTGGCTCCGGAGGAGGCGGAAGCGGAGGAGGAGGCTCC<br>GATATTCAGATGACACAGTCCCCTAGCTCCCTGTCCGCCAGCGTGGGAGATCGGG<br>TGACCATCACCTGCAGGGCCAGCCAGTCCATCAGGAGCGCCCTGAACTGGTACCA<br>GCAGAAGCCTGGAAAGGCTCCCAAGCTGCTGATCTACGCCGCTTCCAGCCTCCAG<br>AGCGGCGTGCCTAGCAGGTTCTCCGGCTCCGGAAGCGGAACAGACTTCACCCTGA<br>CCATCAGCTCCCTGCAGCCCGAGGACTTCGCTACCTACTACTGCCAGCAGACCTA<br>TGGCTACCTGCACACCTTCGGCTGCGGCACAAAGCTGGAGATCAAGCGC | |
| ALG.APV-208 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTCACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCA<br>TGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGTGGAGGTGGCTCCGG<br>GGGTGGAGGTTCCGGAGGAGGCGGATCAGGTGGAGGCGGAAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCAAAGTGGGGTCCCA<br>TCACGTTTCAGTGGCAGTGGAAGCGGGACAGATTTCACTCTCACCATCAGCAGTC<br>TACAACCTGAAGATTTTGCAACTTATTACTGTCAACAGTACTACGACAACCTGCC<br>CACTTTTGGCCAGGGGACCAAGCTGGAGATCAAAGAGCCCAAATCTTCTGACAAA<br>ACTCACACATGCCCACCGTGCCCAGCACCTGAAGCCGCGGGTGCACCGTCAGTCT<br>TCCTCTTCCCCCCAAAACCCAAGGACACCCTCATGATCTCCCGGACCCCTGAGGT<br>CACATGCGTGGTGGTGGACGTGAGCCACGAAGACCCTGAGGTCAAGTTCAACTGG<br>TACGTGGACGGCGTGGAGGTGCATAATGCCAAGACAAAGCCGCGGGAGGAGCAGT<br>ACAACAGCACGTACCGTGTGGTCAGCGTCCTCACCGTCCTGCACCAGGACTGGCT<br>GAATGGCAAGGAATACAAGTGCGCGGTCTCCAACAAAGCCCTCCCAGCCCCCATC<br>GAGAAAACCATCTCCAAAGCCAAAGGGCAGCCCCGAGAACCACAGGTGTACACCC<br>TGCCCCCATCCCGGGATGAGCTGACCAAGAACCAGGTCAGCCTGACCTGCCTGGT<br>CAAAGGCTTCTATCCAAGCGACATCGCCGTGGAGTGGGAGAGCAATGGGCAGCCG<br>GAGAACAACTACAAGACCACGCCTCCCGTGCTGGACTCCGACGGCTCCTTCTTCC<br>TCTACAGCAAGCTCACCGTGGACAAGAGCAGGTGGCAGCAGGGGAACGTCTTCTC<br>ATGCTCCGTGATGCATGAGGCTCTGCACAACCACTACACGCAGAAGAGCCTCTCC<br>CTGTCTCCGGGT**TCCGGAGGTGGCGGTTCGGGAGGTGGCGGGTCAGGAGGTGGGG**<br>**GATCCCCTTCA**GAAGTGCAGCTGCTGGAGTCCGGAGGAGGACTGGTGCAGCCTGG<br>CGGAAGCCTGAGGCTGAGCTGCGCTGCCTCCGGCTTCACATTCAGCAGCTATGCT<br>ATGAGCTGGGTGAGGCAAGCCCCTGGAAAGGGCCTGGAGTGGGTGTCCGCTATCT<br>CCGGCAGCGGCGGAAGCACCTACTACGCTGACTCCGTCAAGGGCAGGTTCACCAT<br>CAGCCGGGACAACAGCAAGAACACCCTGTACCTGCAGATGAATAGCCTCAGGGCT<br>GAAGACACCGCTGTGTACTACTGCGCCAGGTACTATGGCGGCTACTACTCCGCCT<br>GGATGGACTACTGGGGACAGGGCACACTGGTGACCGTGTCCAGCGGCGGAGGCGG<br>CTCCGGAGGCGGTGGCTCCGGAGGAGGCGGAAGCGGAGGAGGAGGCTCCGATATT<br>CAGATGACACAGTCCCCTAGCTCCCTGTCCGCCAGCGTGGGAGATCGGGTGACCA<br>TCACCTGCAGGGCCAGCCAGTCCATCTCCAGCTATTTAAACTGGTACCAGCAGAA<br>GCCTGGAAAGGCTCCCAAGCTGCTGATCTACGCCGCTTCCAGCCTCCAGAGCGGC<br>GTGCCTAGCAGGTTCTCCGGCTCCGGAAGCGGAACAGACTTCACCCTGACCATCA<br>GCTCCCTGCAGCCCGAGGACTCCGCTACCTACTACTGCCAGCAGACCTATGGCTA<br>CCTGCACACCTTCGGCCAGGGCACAAAGCTGGAGATCAAGCGC | 175 |
| ALG.APV-209<br>ALG.APV-222 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTCACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCA | 171 |

TABLE 10-continued

Exemplary anti-5T4 x anti-4-1BB Molecule DNA Sequences

| Construct | DNA SEQ | DNA SEQ ID |
|---|---|---|
| | TGACAATTCCAAGAACACGCTGTATCTGCAAATGAACAGCCTGCGTGCCGAGGAC | |
| | ACGGCTGTATATTATTGTGCGCGCTCTTCTTACTACGGTTCTTACTACTCTATTG | |
| | ACTATTGGGGCCAGGGAACCCTGGTCACCGTCTCCTCAGGTGGAGGTGGCTCCGG | |
| | GGGTGGAGGTTCCGGAGGAGGCGGATCAGGTGGAGGCGGAAGCGACATCCAGATG | |
| | ACCCAGTCTCCATCCTCCCTGAGCGCATCTGTAGGAGACCGCGTCACCATCACTT | |
| | GCCGGGCAAGTCAGAGCATTAGCAGCTATTTAAATTGGTATCAGCAGAAACCAGG | |
| | GAAAGCCCCTAAGCTCCTGATCTATGCTGCATCCAGTTTGCAAAGTGGGGTCCCA | |
| | TCACGTTTCAGTGGCAGTGGAAGCGGGACAGATTTCACTCTCACCATCAGCAGTC | |
| | TACAACCTGAAGATTTTGCAACTTATTACTGTCAACAGTACTACGACAACCTGCC | |
| | CACTTTTGGCCAGGGGACCAAGCTGGAGATCAAAGAGCCCAAATCTTCTGACAAA | |
| | ACTCACACATGCCCACCGTGCCCAGCACCTGAAGCCGCGGGTGCACCGTCAGTCT | |
| | TCCTCTTCCCCCCAAAACCCAAGGACACCCTCATGATCTCCCGGACCCCTGAGGT | |
| | CACATGCGTGGTGGTGGACGTGAGCCACGAAGACCCTGAGGTCAAGTTCAACTGG | |
| | TACGTGGACGGCGTGGAGGTGCATAATGCCAAGACAAAGCCGCGGGAGGAGCAGT | |
| | ACAACAGCACGTACCGTGTGGTCAGCGTCCTCACCGTCCTGCACCAGGACTGGCT | |
| | GAATGGCAAGGAATACAAGTGCGCGGTCTCCAACAAAGCCCTCCCAGCCCCCATC | |
| | GAGAAAACCATCTCCAAAGCCAAAGGGCAGCCCCGAGAACCACAGGTGTACACCC | |
| | TGCCCCCATCCCGGGATGAGCTGACCAAGAACCAGGTCAGCCTGACCTGCCTGGT | |
| | CAAAGGCTTCTATCCAAGCGACATCGCCGTGGAGTGGGAGAGCAATGGGCAGCCG | |
| | GAGAACAACTACAAGACCACGCCTCCCGTGCTGGACTCCGACGGCTCCTTCTTCC | |
| | TCTACAGCAAGCTCACCGTGGACAAGAGCAGGTGGCAGCAGGGGAACGTCTTCTC | |
| | ATGCTCCGTGATGCATGAGGCTCTGCACAACCACTACACGCAGAAGAGCCTCTCC | |
| | CTGTCTCCGGGT**TCCGGAGGTGGCGGTTCGGGAGGTGGCGGGTCAGGAGGTGGGG** | |
| | **GATCCCCTTCA**GAAGTGCAGCTGCTGGAGTCCGGAGGAGGACTGGTGCAGCCTGG | |
| | CGGAAGCCTGAGGCTGAGCTGCGCTGCCTCCGGCTTCACATTCAGCAGCTATGCT | |
| | ATGAGCTGGGTGAGGCAAGCCCCTGGAAAGGGCCTGGAGTGGGTGTCCGCTATCT | |
| | CCGGCAGCGGCGGAAGCACCTACTACGCTGACTCCGTCAAGGGCAGGTTCACCAT | |
| | CAGCCGGGACAACAGCAAGAACACCCTGTACCTGCAGATGAATAGCCTCAGGGCT | |
| | GAAGACACCGCTGTGTACTACTGCGCCAGGTACTATGGCGGCTACTACTCCGCCT | |
| | GGATGGACTACTGGGGACAGGGCACACTGGTGACCGTGTCCAGCGGCGGAGGCGG | |
| | CTCCGGAGGCGGTGGCTCCGGAGGAGGCGGAAGCGGAGGAGGAGGCTCCGATATT | |
| | CAGATGACACAGTCCCCTAGCTCCCTGTCCGCCAGCGTGGGAGATCGGGTGACCA | |
| | TCACCTGCAGGGCCAGCCAGTCCATCTCCAGCTTCTTAAACTGGTACCAGCAGAA | |
| | GCCTGGAAAGGCTCCCAAGCTGCTGATCTACGCCGCTTCCAGCCTCCAGAGCGGC | |
| | GTGCCTAGCAGGTTCTCCGGCTCCGGAAGCGGAACAGACTTCACCCTGACCATCA | |
| | GCTCCCTGCAGCCCGAGGACTCCGCTACCTACTACTGCCAGCAGACCTATGGCTA | |
| | CCTGCACACCTTCGGCCAGGGCACAAAGCTGGAGATCAAGCGC | |
| ALG.APV-210 | ATGGAAGCACCAGCGCAGCTTCTCTTCCTCCTGCTACTCTGGCTCCCAGATACCA | 173 |
| ALG.APV-223 | CCGGTGAGGTGCAGCTGTTGGAGAGCGGGGGAGGCTTGGTACAGCCTGGGGGGTC | |
| | CCTGCGCCTCTCCTGTGCAGCCAGCGGATTCACCTTTTCTCACGGTTCTATGTAC | |
| | TGGGTCCGCCAGGCTCCAGGGAAGGGGCTGGAGTGGGTCTCATCTATTTCTTCTG | |
| | GTTCTGGTTCTACATACTATGCAGACTCCGTGAAGGGCCGGTTCACCATCTCCCA | |
| | TGACAATTCCAAGAACACGCTGTATCTGCAAATGAACAGCCTGCGTGCCGAGGAC | |
| | ACGGCTGTATATTATTGTGCGCGCTCTTCTTACTACGGTTCTTACTACTCTATTG | |
| | ACTATTGGGGCCAGGGAACCCTGGTCACCGTCTCCTCAGGTGGAGGTGGCTCCGG | |
| | GGGTGGAGGTTCCGGAGGAGGCGGATCAGGTGGAGGCGGAAGCGACATCCAGATG | |
| | ACCCAGTCTCCATCCTCCCTGAGCGCATCTGTAGGAGACCGCGTCACCATCACTT | |
| | GCCGGGCAAGTCAGAGCATTAGCAGCTATTTAAATTGGTATCAGCAGAAACCAGG | |
| | GAAAGCCCCTAAGCTCCTGATCTATGCTGCATCCAGTTTGCAAAGTGGGGTCCCA | |
| | TCACGTTTCAGTGGCAGTGGAAGCGGGACAGATTTCACTCTCACCATCAGCAGTC | |
| | TACAACCTGAAGATTTTGCAACTTATTACTGTCAACAGTACTACGACAACCTGCC | |
| | CACTTTTGGCCAGGGGACCAAGCTGGAGATCAAAGAGCCCAAATCTTCTGACAAA | |
| | ACTCACACATGCCCACCGTGCCCAGCACCTGAAGCCGCGGGTGCACCGTCAGTCT | |
| | TCCTCTTCCCCCCAAAACCCAAGGACACCCTCATGATCTCCCGGACCCCTGAGGT | |
| | CACATGCGTGGTGGTGGACGTGAGCCACGAAGACCCTGAGGTCAAGTTCAACTGG | |
| | TACGTGGACGGCGTGGAGGTGCATAATGCCAAGACAAAGCCGCGGGAGGAGCAGT | |
| | ACAACAGCACGTACCGTGTGGTCAGCGTCCTCACCGTCCTGCACCAGGACTGGCT | |
| | GAATGGCAAGGAATACAAGTGCGCGGTCTCCAACAAAGCCCTCCCAGCCCCCATC | |
| | GAGAAAACCATCTCCAAAGCCAAAGGGCAGCCCCGAGAACCACAGGTGTACACCC | |
| | TGCCCCCATCCCGGGATGAGCTGACCAAGAACCAGGTCAGCCTGACCTGCCTGGT | |
| | CAAAGGCTTCTATCCAAGCGACATCGCCGTGGAGTGGGAGAGCAATGGGCAGCCG | |
| | GAGAACAACTACAAGACCACGCCTCCCGTGCTGGACTCCGACGGCTCCTTCTTCC | |
| | TCTACAGCAAGCTCACCGTGGACAAGAGCAGGTGGCAGCAGGGGAACGTCTTCTC | |
| | ATGCTCCGTGATGCATGAGGCTCTGCACAACCACTACACGCAGAAGAGCCTCTCC | |
| | CTGTCTCCGGGT**TCCGGAGGTGGCGGTTCGGGAGGTGGCGGGTCAGGAGGTGGGG** | |
| | **GATCCCCTTCA**GAAGTGCAGCTGCTGGAGTCCGGAGGAGGACTGGTGCAGCCTGG | |
| | CGGAAGCCTGAGGCTGAGCTGCGCTGCCTCCGGCTTCACATTCAGCAGCTATGCT | |
| | ATGAGCTGGGTGAGGCAAGCCCCTGGAAAGTGCCTGGAGTGGGTGTCCGCTATCT | |
| | CCGGCAGCGGCGGAAGCACCTACTACGCTGACTCCGTCAAGGGCAGGTTCACCAT | |
| | CAGCCGGGACAACAGCAAGAACACCCTGTACCTGCAGATGAATAGCCTCAGGGCT | |
| | GAAGACACCGCTGTGTACTACTGCGCCAGGTACTATGGCGGCTACTACTCCGCCT | |
| | GGATGGACTACTGGGGACAGGGCACACTGGTGACCGTGTCCAGCGGCGGAGGCGG | |
| | CTCCGGAGGCGGTGGCTCCGGAGGAGGCGGAAGCGGAGGAGGAGGCTCCGATATT | |
| | CAGATGACACAGTCCCCTAGCTCCCTGTCCGCCAGCGTGGGAGATCGGGTGACCA | |

TABLE 10-continued

Exemplary anti-5T4 x anti-4-1BB Molecule DNA Sequences

| Construct | DNA SEQ | DNA SEQ ID |
|---|---|---|
| | TCACCTGCAGGGCCAGCCAGTCCATCTCCAGCTTCTTAAACTGGTACCAGCAGAA<br>GCCTGGAAAGGCTCCCAAGCTGCTGATCTACGCCGCTTCCAGCCTCCAGAGCGGC<br>GTGCCTAGCAGGTTCTCCGGCTCCGGAAGCGGAACAGACTTCACCCTGACCATCA<br>GCTCCCTGCAGCCCGAGGACTCCGCTACCTACTACTGCCAGCAGACCTATGGCTA<br>CCTGCACACCTTCGGCTGCGGCACAAAGCTGGAGATCAAGCGC | |
| ALG.APV-006 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTTACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCG<br>TGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGCGGCGGCGGCAGCGG<br>CGGCGGCGGCAGCGGCGGCGGAGGCTCCGGCGGCGGCGGCAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCAAAGTGGGGTCCCA<br>TCACGTTTCAGTGGCAGTGGAAGCGGGACAGATTTCACTCTCACCATCAGCAGTC<br>TGCAACCTGAAGATTTTGCAACTTATTACTGTCAACAGTACTACGACAACCTGCC<br>CACTTTTGGCCAGGGGACCAAGCTGGAGATCAAATCCTCGAGTGAGCCCAAATCT<br>TCTGACAAAACTCACACATGCCCACCGTGCCCAGCACCTGAAGCCGCGGGTGCAC<br>CGTCAGTCTTCCTCTTCCCCCCAAAACCCAAGGACACCCTCATGATCTCCCGGAC<br>CCCTGAGGTCACATGCGTGGTGGTGGACGTGAGCCACGAAGACCCTGAGGTCAAG<br>TTCAACTGGTACGTGGACGGCGTGGAGGTGCATAATGCCAAGACAAAGCCGCGGG<br>AGGAGCAGTACAACAGCACGTACCGTGTGGTCAGCGTCCTCACCGTCCTGCACCA<br>GGACTGGCTGAATGGCAAGGAATACAAGTGCGCGGTCTCCAACAAAGCCCTCCCA<br>GCCCCCATCGAGAAAACCATCTCCAAAGCCAAAGGGCAGCCCCGAGAACCACAGG<br>TGTACACCCTGCCCCCATCCCGGGATGAGCTGACCAAGAACCAGGTCAGCCTGAC<br>CTGCCTGGTCAAAGGCTTCTATCCAAGCGACATCGCCGTGGAGTGGGAGAGCAAT<br>GGGCAGCCGGAGAACAACTACAAGACCACGCCTCCCGTGCTGGACTCCGACGGCT<br>CCTTCTTCCTCTACAGCAAGCTCACCGTGGACAAGAGCAGGTGGCAGCAGGGGAA<br>CGTCTTCTCATGCTCCGTGATGCATGAGGCTCTGCACAACCACTACACGCAGAAG<br>AGCCTCTCCCTGTCTCCGGGT**TCCGGAGGTGGCGGTTCGGGAGGTGGCGGGTCAG**<br>**GAGGTGGGGGATCCCCTTCA**GAGGTGCAGCTGTTGGAGAGCGGGGGAGGCTTGGT<br>ACAGCCTGGGGGGTCCCTGCGCCTCTCCTGTGCAGCCAGCGGATTCACCTTTAGC<br>AGCTATGCCATGAGCTGGGTCCGCCAGGCTCCAGGGAAGGGGCTGGAGTGGGTCT<br>CAGCTATTAGTGGTAGTGGTGGTAGCACATACTATGCAGACTCCGTGAAGGGCCG<br>GTTCACCATCTCCCGTGACAATTCCAAGAACACGCTGTATCTGCAAATGAACAGC<br>CTGCGTGCCGAGGACACGGCTGTATATTATTGTGCGCGCTACTACGGTGGTTACT<br>ACTCTGCTTGGATGGACTATTGGGGCCAGGGAACCCTGGTCACCGTCTCCTCAGG<br>CGGTGGAGGCAGCGGTGGGGGTGGGTCTGGAGGCGGTGGCAGTGGCGGCGGAGGC<br>TCTGACATCCAGATGACCCAGTCTCCATCCTCCCTGAGCGCATCTGTAGGAGACC<br>GCGTCACCATCACTTGCCGGGCAAGTCAGAGCATTAGCAGCTATTTAAATTGGTA<br>TCAGCAGAAACCAGGGAAAGCCCCTAAGCTCCTGATCTATGCTGCATCCAGTTTG<br>CAAAGTGGGGTCCCATCACGTTTCAGTGGCAGTGGAAGCGGGACAGATTTCACTC<br>TCACCATCAGCAGTCTGCAACCTGAAGATTTTGCAACTTATTACTGTCAACAGAC<br>TTACGGTTACCTGCACACTTTTGGCCAGGGGACCAAGCTGGAGATCAAATCA | 149 |
| ALG.APV-010 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTTACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCG<br>TGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGCGGCGGCGGCAGCGG<br>CGGCGGCGGCAGCGGCGGCGGAGGCTCCGGCGGCGGCGGCAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCAAAGTGGGGTCCCA<br>TCACGTTTCAGTGGCAGTGGAAGCGGGACAGATTTCACTCTCACCATCAGCAGTC<br>TGCAACCTGAAGATTTTGCAACTTATTACTGTCAACAGTACTACGACAACCTGCC<br>CACTTTTGGCCAGGGGACCAAGCTGGAGATCAAATCCTCGAGTGAGCCCAAATCT<br>TCTGACAAAACTCACACATGCCCACCGTGCCCAGCACCTGAAGCCGCGGGTGCAC<br>CGTCAGTCTTCCTCTTCCCCCCAAAACCCAAGGACACCCTCATGATCTCCCGGAC<br>CCCTGAGGTCACATGCGTGGTGGTGGACGTGAGCCACGAAGACCCTGAGGTCAAG<br>TTCAACTGGTACGTGGACGGCGTGGAGGTGCATAATGCCAAGACAAAGCCGCGGG<br>AGGAGCAGTACAACAGCACGTACCGTGTGGTCAGCGTCCTCACCGTCCTGCACCA<br>GGACTGGCTGAATGGCAAGGAATACAAGTGCGCGGTCTCCAACAAAGCCCTCCCA<br>GCCCCCATCGAGAAAACCATCTCCAAAGCCAAAGGGCAGCCCCGAGAACCACAGG<br>TGTACACCCTGCCCCCATCCCGGGATGAGCTGACCAAGAACCAGGTCAGCCTGAC<br>CTGCCTGGTCAAAGGCTTCTATCCAAGCGACATCGCCGTGGAGTGGGAGAGCAAT<br>GGGCAGCCGGAGAACAACTACAAGACCACGCCTCCCGTGCTGGACTCCGACGGCT<br>CCTTCTTCCTCTACAGCAAGCTCACCGTGGACAAGAGCAGGTGGCAGCAGGGGAA | 151 |

TABLE 10-continued

Exemplary anti-5T4 x anti-4-1BB Molecule DNA Sequences

| Construct | DNA SEQ | DNA SEQ ID |
|---|---|---|
| | CGTCTTCTCATGCTCCGTGATGCATGAGGCTCTGCACAACCACTACACGCAGAAG<br>AGCCTCTCCCTGTCTCCGGGT**TCCGGAGGTGGCGGTTCGGGAGGTGGCGGGTCAG**<br>**GAGGTGGGGGATCCCCTTCA**GACATCCAGATGACCCAGTCTCCATCCTCCCTGAG<br>CGCATCTGTAGGAGACCGCGTCACCATCACTTGCCGGGCAAGTCAGAGCATTAGC<br>AGCTATTTAAATTGGTATCAGCAGAAACCAGGGAAAGCCCCTAAGCTCCTGATCT<br>ATGCTGCATCCAGTTTGCAAAGTGGGGTCCCATCACGTTTCAGTGGCAGTGGAAG<br>CGGGACAGATTTCACTCTCACCATCAGCAGTCTGCAACCTGAAGATTTTGCAACT<br>TATTACTGTCAACAGACTTACGGTTACCTGCACACTTTTGGCCAGGGGACCAAGC<br>TGGAGATCAAAGGCGGTGGAGGCAGCGGTGGGGGTGGGTCTGGAGGCGGTGGCAG<br>TGGCGGCGGAGGCTCTGAGGTGCAGCTGTTGGAGAGCGGGGGAGGCTTGGTACAG<br>CCTGGGGGGTCCCTGCGCCTCTCCTGTGCAGCCAGCGGATTCACCTTTAGCAGCT<br>ATGCCATGAGCTGGGTCCGCCAGGCTCCAGGGAAGGGGCTGGAGTGGGTCTCAGC<br>TATTAGTGGTAGTGGTGGTAGCACATACTATGCAGACTCCGTGAAGGGCCGGTTC<br>ACCATCTCCCGTGACAATTCCAAGAACACGCTGTATCTGCAAATGAACAGCCTGC<br>GTGCCGAGGACACGGCTGTATATTATTGTGCGCGCTACTACGGTGGTTACTACTC<br>TGCTTGGATGGACTATTGGGGCCAGGGAACCCTGGTCACCGTCTCCTCA | |
| ALG.APV-014 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTTACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCG<br>TGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGCGGCGGCGGCAGCGG<br>CGGCGGCGGCAGCGGCGGCGGAGGCTCCGGCGGCGGCGGCAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCAAAGTGGGGTCCCA<br>TCACGTTTCAGTGGCAGTGGAAGCGGGACAGATTTCACTCTCACCATCAGCAGTC<br>TGCAACCTGAAGATTTTGCAACTTATTACTGTCAACAGTACTACGACAACCTGCC<br>CACTTTTGGCCAGGGGACCAAGCTGGAGATCAAATCCTCGAGTGAGCCCAAATCT<br>TCTGACAAAACTCACACATGCCCACCGTGCCCAGCACCTGAAGCCGCGGGTGCAC<br>CGTCAGTCTTCCTCTTCCCCCCAAAACCCAAGGACACCCTCATGATCTCCCGGAC<br>CCCTGAGGTCACATGCGTGGTGGTGGACGTGAGCCACGAAGACCCTGAGGTCAAG<br>TTCAACTGGTACGTGGACGGCGTGGAGGTGCATAATGCCAAGACAAAGCCGCGGG<br>AGGAGCAGTACAACAGCACGTACCGTGTGGTCAGCGTCCTCACCGTCCTGCACCA<br>GGACTGGCTGAATGGCAAGGAATACAAGTGCGCGGTCTCCAACAAAGCCCTCCCA<br>GCCCCCATCGAGAAAACCATCTCCAAAGCCAAAGGGCAGCCCCGAGAACCACAGG<br>TGTACACCCTGCCCCCATCCCGGGATGAGCTGACCAAGAACCAGGTCAGCCTGAC<br>CTGCCTGGTCAAAGGCTTCTATCCAAGCGACATCGCCGTGGAGTGGGAGAGCAAT<br>GGGCAGCCGGAGAACAACTACAAGACCACGCCTCCCGTGCTGGACTCCGACGGCT<br>CCTTCTTCCTCTACAGCAAGCTCACCGTGGACAAGAGCAGGTGGCAGCAGGGGAA<br>CGTCTTCTCATGCTCCGTGATGCATGAGGCTCTGCACAACCACTACACGCAGAAG<br>AGCCTCTCCCTGTCTCCGGGT**TCCGGAGGTGGCGGTTCGGGAGGTGGCGGGTCAG**<br>**GAGGTGGGGGATCCCCTTCA**GAGGTGCAGCTGTTGGAGAGCGGGGGAGGCTTGGT<br>ACAGCCTGGGGGGTCCCTGCGCCTCTCCTGTGCAGCCAGCGGATTCACCTTTAGC<br>AGCTATGCCATGAGCTGGGTCCGCCAGGCTCCAGGGAAGTGCCTGGAGTGGGTCT<br>CAGCTATTAGTGGTAGTGGTGGTAGCACATACTATGCAGACTCCGTGAAGGGCCG<br>GTTCACCATCTCCCGTGACAATTCCAAGAACACGCTGTATCTGCAAATGAACAGC<br>CTGCGTGCCGAGGACACGGCTGTATATTATTGTGCGCGCTACTACGGTGGTTACT<br>ACTCTGCTTGGATGGACTATTGGGGCCAGGGAACCCTGGTCACCGTCTCCTCAGG<br>CGGTGGAGGCAGCGGTGGGGGTGGGTCTGGAGGCGGTGGCAGTGGCGGCGGAGGC<br>TCTGACATCCAGATGACCCAGTCTCCATCCTCCCTGAGCGCATCTGTAGGAGACC<br>GCGTCACCATCACTTGCCGGGCAAGTCAGAGCATTAGCAGCTATTTAAATTGGTA<br>TCAGCAGAAACCAGGGAAAGCCCCTAAGCTCCTGATCTATGCTGCATCCAGTTTG<br>CAAAGTGGGGTCCCATCACGTTTCAGTGGCAGTGGAAGCGGGACAGATTTCACTC<br>TCACCATCAGCAGTCTGCAACCTGAAGATTTTGCAACTTATTACTGTCAACAGAC<br>TTACGGTTACCTGCACACTTTTGGCTGCGGGACCAAGCTGGAGATCAAATCA | 153 |
| ALG.APV-018 | ATGGAAGCACCAGCGCAGCTTCTCTTCCTCCTGCTACTCTGGCTCCCAGATACCA<br>CCGGTGAGGTGCAGCTGTTGGAGAGCGGGGGAGGCTTGGTACAGCCTGGGGGGTC<br>CCTGCGCCTCTCCTGTGCAGCCAGCGGATTCACCTTTTCTTACGGTTCTATGTAC<br>TGGGTCCGCCAGGCTCCAGGGAAGGGGCTGGAGTGGGTCTCATCTATTTCTTCTG<br>GTTCTGGTTCTACATACTATGCAGACTCCGTGAAGGGCCGGTTCACCATCTCCCG<br>TGACAATTCCAAGAACACGCTGTATCTGCAAATGAACAGCCTGCGTGCCGAGGAC<br>ACGGCTGTATATTATTGTGCGCGCTCTTCTTACTACGGTTCTTACTACTCTATTG<br>ACTATTGGGGCCAGGGAACCCTGGTCACCGTCTCCTCAGGCGGCGGCGGCAGCGG<br>CGGCGGCGGCAGCGGCGGCGGAGGCTCCGGCGGCGGCGGCAGCGACATCCAGATG<br>ACCCAGTCTCCATCCTCCCTGAGCGCATCTGTAGGAGACCGCGTCACCATCACTT<br>GCCGGGCAAGTCAGAGCATTAGCAGCTATTTAAATTGGTATCAGCAGAAACCAGG<br>GAAAGCCCCTAAGCTCCTGATCTATGCTGCATCCAGTTTGCAAAGTGGGGTCCCA<br>TCACGTTTCAGTGGCAGTGGAAGCGGGACAGATTTCACTCTCACCATCAGCAGTC<br>TGCAACCTGAAGATTTTGCAACTTATTACTGTCAACAGTACTACGACAACCTGCC<br>CACTTTTGGCCAGGGGACCAAGCTGGAGATCAAATCCTCGAGTGAGCCCAAATCT | 155 |

TABLE 10-continued

Exemplary anti-5T4 x anti-4-1BB Molecule DNA Sequences

| Construct | DNA SEQ | DNA SEQ ID |
|---|---|---|
| | TCTGACAAAACTCACACATGCCCACCGTGCCCAGCACCTGAAGCCGCGGGTGCAC<br>CGTCAGTCTTCCTCTTCCCCCCAAAACCCAAGGACACCCTCATGATCTCCCGGAC<br>CCCTGAGGTCACATGCGTGGTGGTGGACGTGAGCCACGAAGACCCTGAGGTCAAG<br>TTCAACTGGTACGTGGACGGCGTGGAGGTGCATAATGCCAAGACAAAGCCGCGGG<br>AGGAGCAGTACAACAGCACGTACCGTGTGGTCAGCGTCCTCACCGTCCTGCACCA<br>GGACTGGCTGAATGGCAAGGAATACAAGTGCGCGGTCTCCAACAAAGCCCTCCCA<br>GCCCCCATCGAGAAAACCATCTCCAAAGCCAAAGGGCAGCCCCGAGAACCACAGG<br>TGTACACCCTGCCCCCATCCCGGGATGAGCTGACCAAGAACCAGGTCAGCCTGAC<br>CTGCCTGGTCAAAGGCTTCTATCCAAGCGACATCGCCGTGGAGTGGGAGAGCAAT<br>GGGCAGCCGGAGAACAACTACAAGACCACGCCTCCCGTGCTGGACTCCGACGGCT<br>CCTTCTTCCTCTACAGCAAGCTCACCGTGGACAAGAGCAGGTGGCAGCAGGGGAA<br>CGTCTTCTCATGCTCCGTGATGCATGAGGCTCTGCACAACCACTACACGCAGAAG<br>AGCCTCTCCCTGTCTCCGGGT**TCCGGAGGTGGCGGTTCGGGAGGTGGCGGGTCAG**<br>**GAGGTGGGGGATCCCCTTCA**GACATCCAGATGACCCAGTCTCCATCCTCCCTGAG<br>CGCATCTGTAGGAGACCGCGTCACCATCACTTGCCGGGCAAGTCAGAGCATTAGC<br>AGCTATTTAAATTGGTATCAGCAGAAACCAGGGAAAGCCCCTAAGCTCCTGATCT<br>ATGCTGCATCCAGTTTGCAAAGTGGGGTCCCATCACGTTTCAGTGGCAGTGGAAG<br>CGGGACAGATTTCACTCTCACCATCAGCAGTCTGCAACCTGAAGATTTTGCAACT<br>TATTACTGTCAACAGACTTACGGTTACCTGCACACTTTTGGCTGCGGGACCAAGC<br>TGGAGATCAAAGGCGGTGGAGGCAGCGGTGGGGGTGGGTCTGGAGGCGGTGGCAG<br>TGGCGGCGGAGGCTCTGAGGTGCAGCTGTTGGAGAGCGGGGGAGGCTTGGTACAG<br>CCTGGGGGGTCCCTGCGCCTCTCCTGTGCAGCCAGCGGATTCACCTTTAGCAGCT<br>ATGCCATGAGCTGGGTCCGCCAGGCTCCAGGGAAGTGCCTGGAGTGGGTCTCAGC<br>TATTAGTGGTAGTGGTGGTAGCACATACTATGCAGACTCCGTGAAGGGCCGGTTC<br>ACCATCTCCCGTGACAATTCCAAGAACACGCTGTATCTGCAAATGAACAGCCTGC<br>GTGCCGAGGACACGGCTGTATATTATTGTGCGCGCTACTACGGTGGTTACTACTC<br>TGCTTGGATGGACTATTGGGGCCAGGGAACCCTGGTCACCGTCTCCTCA | |

TABLE 11

Exemplary anti-5T4 x anti-4-1BB Molecule Amino Acid Sequences

| Construct | AA Sequence | AA SEQ ID |
|---|---|---|
| ALG.APV-178 | MEAPAQLLFLLLLWLPDTTGEVQLLESGGGLVQPGGSLRLSCAASGFTFSHGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSEPKSS<br>DKTHTCPPCPAPEAAGAPSVFLFPPKPKDTLMISRTPEVTCVVVDVSHEDPEVKF<br>NWYVDGVEVHNAKTKPREEQYNSTYRVVSVLTVLHQDWLNGKEYKCAVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPG**SGGGGSGGGGSGGGGSPS**EVQLLESGGGLVQPGGSLRLSCAASGFTFSS<br>YAMSWVRQAPGKGLEWVSAISGSGGSTYYADSVKGRFTISRDNSKNTLYLQMNSL<br>RAEDTAVYYCARYYGGYYSAWMDYWGQGTLVTVSSGGGGSGGGGSGGGGSGGGGS<br>DIQMTQSPSSLSASVGDRVTITCRASQSISSYLNWYQQKPGKAPKLLIYAASSLQ<br>SGVPSRFSGSGSGTDFTLTISSLQPEDSATYYCQQTYGYLHTFGQGTKLEIKR | 136 |
| ALG.APV-179 | MEAPAQLLFLLLLWLPDTTGEVQLLESGGGLVQPGGSLRLSCAASGFTFSHGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSEPKSS<br>DKTHTCPPCPAPEAAGAPSVFLFPPKPKDTLMISRTPEVTCVVVDVSHEDPEVKF<br>NWYVDGVEVHNAKTKPREEQYNSTYRVVSVLTVLHQDWLNGKEYKCAVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPG**SGGGGSGGGGSGGGGSPS**EVQLLESGGGLVQPGGSLRLSCAASGFTFSS<br>YAMSWVRQAPGKGLEWVSAISGSGGSTYYADSVKGRFTISRDNSKNTLYLQMNSL<br>RAEDTAVYYCARYYGGYYSAWMDYWGQGTLVTVSSGGGGSGGGGSGGGGSGGGGS<br>DIQMTQSPSSLSASVGDRVTITCRASQSISSFLNWYQQKPGKAPKLLIYAASSLQ<br>SGVPSRFSGSGSGTDFTLTISSLQPEDSATYYCQQTYGYLHTFGQGTKLEIKR | 138 |
| ALG.APV-187 | MEAPAQLLFLLLLWLPDTTGEVQLLESGGGLVQPGGSLRLSCAASGFTFSHGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSEPKSS<br>DKTHTCPPCPAPEAAGAPSVFLFPPKPKDTLMISRTPEVTCVVVDVSHEDPEVKF<br>NWYVDGVEVHNAKTKPREEQYNSTYRVVSVLTVLHQDWLNGKEYKCAVSNKALPA | 140 |

TABLE 11-continued

| Exemplary anti-5T4 x anti-4-1BB Molecule Amino Acid Sequences | | |
|---|---|---|
| Construct | AA Sequence | AA SEQ ID |
| | PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPG**SGGGGSGGGGSGGGGSPS**EVQLLESGGGLVQPGGSLRLSCAASGFTFSS<br>YAMSWVRQAPGKCLEWVSAISGSGGSTYYADSVKGRFTISRDNSKNTLYLQMNSL<br>RAEDTAVYYCARYYGGYYSAWMDYWGQGTLVTVSSGGGGSGGGGSGGGGSGGGGS<br>DIQMTQSPSSLSASVGDRVTITCRASQSISSFLNWYQQKPGKAPKLLIYAASSLQ<br>SGVPSRFSGSGSGTDFTLTISSLQPEDSATYYCQQTYGYLHTFGCGTKLEIKR | |
| ALG.APV-191 | MEAPAQLLFLLLLWLPDTTGEVQLLESGGGLVQPGGSLRLSCAASGFTFDYGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLHSGVP<br>SRFSGSGSGTDFTLTISSLQPEDFATYYCQQYYDNLPTFGQGTKLEIKSSEPKSS<br>DKTHTCPPCPAPEAAGAPSVFLFPPKPKDTLMISRTPEVTCVVVDVSHEDPEVKF<br>NWYVDGVEVHNAKTKPREEQYNSTYRVVSVLTVLHQDWLNGKEYKCAVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPG**SGGGGSGGGGSGGGGSPS**EVQLLESGGGLVQPGGSLRLSCAASGFTFSS<br>YAMSWVRQAPGKCLEWVSAISGSGGSTYYADSVKGRFTISRDNSKNTLYLQMNSL<br>RAEDTAVYYCARYYGGYYSAWMDYWGQGTLVTVSSGGGGSGGGGSGGGGSGGGGS<br>DIQMTQSPSSLSASVGDRVTITCRASQSISSFLNWYQQKPGKAPKLLIYAASSLQ<br>SGVPSRFSGSGSGTDFTLTISSLQPEDFATYYCQQTYGYLHTFGCGTKLEIKS | 142 |
| ALG.APV-196 | MEAPAQLLFLLLLWLPDTTGEVQLLESGGGLVQPGGSLRLSCAASGFTFSYGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSEPKSS<br>DKTHTCPPCPAPEAAGAPSVFLFPPKPKDTLMISRTPEVTCVVVDVSHEDPEVKF<br>NWYVDGVEVHNAKTKPREEQYNSTYRVVSVLTVLHQDWLNGKEYKCAVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPG**SGGGGSGGGGSGGGGSPS**EVQLLESGGGLVQPGGSLRLSCAASGFDFES<br>YAMSWVRQAPGKCLEWVSAISGSGGSTYYADSVKGRFTISRDNSKNTLYLQMNSL<br>RAEDTAVYYCARYYGGYYSAWMDYWGQGTLVTVSSGGGGSGGGGSGGGGSGGGGS<br>DIQMTQSPSSLSASVGDRVTITCRASQSIRSALNWYQQKPGKAPKLLIYAASSLQ<br>SGVPSRFSGSGSGTDFTLTISSLQPEDFATYYCQQTYGYLHTFGCGTKLEIKR | 144 |
| ALG.APV-198 | MEAPAQLLFLLLLWLPDTTGEVQLLESGGGLVQPGGSLRLSCAASGFTFSHGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSEPKSS<br>DKTHTCPPCPAPEAAGAPSVFLFPPKPKDTLMISRTPEVTCVVVDVSHEDPEVKF<br>NWYVDGVEVHNAKTKPREEQYNSTYRVVSVLTVLHQDWLNGKEYKCAVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPG**SGGGGSGGGGSGGGGSPS**EVQLLESGGGLVQPGGSLRLSCAASGFDFES<br>YAMSWVRQAPGKCLEWVSAISGSGGSTYYADSVKGRFTISRDNSKNTLYLQMNSL<br>RAEDTAVYYCARYYGGYYSAWMDYWGQGTLVTVSSGGGGSGGGGSGGGGSGGGGS<br>DIQMTQSPSSLSASVGDRVTITCRASQSIRSALNWYQQKPGKAPKLLIYAASSLQ<br>SGVPSRFSGSGSGTDFTLTISSLQPEDFATYYCQQTYGYLHTFGCGTKLEIKR | 146 |
| ALG.APV-199 | MEAPAQLLFLLLLWLPDTTGEVQLLESGGGLVQPGGSLRLSCAASGFTFSHGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSEPKSS<br>DKTHTCPPCPAPEAAGAPSVFLFPPKPKDTLMISRTPEVTCVVVDVSHEDPEVKF<br>NWYVDGVEVHNAKTKPREEQYNSTYRVVSVLTVLHQDWLNGKEYKCAVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPG**SGGGGSGGGGSGGGGSPS**EVQLLESGGGLVQPGGSLRLSCAASGFDFDS<br>YAMSWVRQAPGKCLEWVSAISGRGGSTYYADSVKGRFTISRDNSKNTLYLQMNSL<br>RAEDTAVYYCARYYGGYYSAWMDYWGQGTLVTVSSGGGGSGGGGSGGGGSGGGGS<br>DIQMTQSPSSLSASVGDRVTITCRASQSIRSALNWYQQKPGKAPKLLIYAASSLQ<br>SGVPSRFSGSGSGTDFTLTISSLQPEDFATYYCQQTYGYLHTFGCGTKLEIKR | 148 |
| ALG.APV-208 | MEAPAQLLFLLLLWLPDTTGEVQLLESGGGLVQPGGSLRLSCAASGFTFSHGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKEPKSSDK<br>THTCPPCPAPEAAGAPSVFLFPPKPKDTLMISRTPEVTCVVVDVSHEDPEVKFNW<br>YVDGVEVHNAKTKPREEQYNSTYRVVSVLTVLHQDWLNGKEYKCAVSNKALPAPI | 176 |

TABLE 11-continued

Exemplary anti-5T4 x anti-4-1BB Molecule Amino Acid Sequences

| Construct | AA Sequence | AA SEQ ID |
|---|---|---|
| | EKTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSLS<br>LSPG**SGGGGSGGGGSGGGGSPS**EVQLLESGGGLVQPGGSLRLSCAASGFTFSSYA<br>MSWVRQAPGKGLEWVSAISGSGGSTYYADSVKGRFTISRDNSKNTLYLQMNSLRA<br>EDTAVYYCARYYGGYYSAWMDYWGQGTLVTVSSGGGGSGGGGSGGGGSGGGGSDI<br>QMTQSPSSLSASVGDRVTITCRASQSISSYLNWYQQKPGKAPKLLIYAASSLQSG<br>VPSRFSGSGSGTDFTLTISSLQPEDSATYYCQQTYGYLHTFGQGTKLEIKR | |
| ALG.APV-209<br>ALG.APV-222 | MEAPAQLLFLLLLWLPDTTGEVQLLESGGGLVQPGGSLRLSCAASGFTFSHGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKEPKSSDK<br>THTCPPCPAPEAAGAPSVFLFPPKPKDTLMISRTPEVTCVVVDVSHEDPEVKFNW<br>YVDGVEVHNAKTKPREEQYNSTYRVVSVLTVLHQDWLNGKEYKCAVSNKALPAPI<br>EKTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSLS<br>LSPG**SGGGGSGGGGSGGGGSPS**EVQLLESGGGLVQPGGSLRLSCAASGFTFSSYA<br>MSWVRQAPGKGLEWVSAISGSGGSTYYADSVKGRFTISRDNSKNTLYLQMNSLRA<br>EDTAVYYCARYYGGYYSAWMDYWGQGTLVTVSSGGGGSGGGGSGGGGSGGGGSDI<br>QMTQSPSSLSASVGDRVTITCRASQSISSFLNWYQQKPGKAPKLLIYAASSLQSG<br>VPSRFSGSGSGTDFTLTISSLQPEDSATYYCQQTYGYLHTFGQGTKLEIKR | 172 |
| ALG.APV-210<br>ALG.APV-223 | MEAPAQLLFLLLLWLPDTTGEVQLLESGGGLVQPGGSLRLSCAASGFTFSHGSMY<br>WVRQAPGKGLEWVSSISSGSGSTYYADSVKGRFTISHDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKEPKSSDK<br>THTCPPCPAPEAAGAPSVFLFPPKPKDTLMISRTPEVTCVVVDVSHEDPEVKFNW<br>YVDGVEVHNAKTKPREEQYNSTYRVVSVLTVLHQDWLNGKEYKCAVSNKALPAPI<br>EKTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSLS<br>LSPG**SGGGGSGGGGSGGGGSPS**EVQLLESGGGLVQPGGSLRLSCAASGFTFSSYA<br>MSWVRQAPGKCLEWVSAISGSGGSTYYADSVKGRFTISRDNSKNTLYLQMNSLRA<br>EDTAVYYCARYYGGYYSAWMDYWGQGTLVTVSSGGGGSGGGGSGGGGSGGGGSDI<br>QMTQSPSSLSASVGDRVTITCRASQSISSFLNWYQQKPGKAPKLLIYAASSLQSG<br>VPSRFSGSGSGTDFTLTISSLQPEDSATYYCQQTYGYLHTFGCGTKLEIKR | 174 |
| ALG.APV-006 | MEAPAQLLFLLLLWLPDTTGEVQLLESGGGLVQPGGSLRLSCAASGFTFSYGSMY<br>WVRQAPGKGLEWVSSISSGSGSTYYADSVKGRFTISRDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSSEPKS<br>SDKTHTCPPCPAPEAAGAPSVFLFPPKPKDTLMISRTPEVTCVVVDVSHEDPEVK<br>FNWYVDGVEVHNAKTKPREEQYNSTYRVVSVLTVLHQDWLNGKEYKCAVSNKALP<br>APIEKTISKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEALHNHYTQK<br>SLSLSPG**SGGGGSGGGGSGGGGSPS**EVQLLESGGGLVQPGGSLRLSCAASGFTFS<br>SYAMSWVRQAPGKGLEWVSAISGSGGSTYYADSVKGRFTISRDNSKNTLYLQMNS<br>LRAEDTAVYYCARYYGGYYSAWMDYWGQGTLVTVSSGGGGSGGGGSGGGGSGGGG<br>SDIQMTQSPSSLSASVGDRVTITCRASQSISSYLNWYQQKPGKAPKLLIYAASSL<br>QSGVPSRFSGSGSGTDFTLTISSLQPEDFATYYCQQTYGYLHTFGQGTKLEIKS | 150 |
| ALG.APV-010 | MEAPAQLLFLLLLWLPDTTGEVQLLESGGGLVQPGGSLRLSCAASGFTFSYGSMY<br>WVRQAPGKGLEWVSSISSGSGSTYYADSVKGRFTISRDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSSEPKS<br>SDKTHTCPPCPAPEAAGAPSVFLFPPKPKDTLMISRTPEVTCVVVDVSHEDPEVK<br>FNWYVDGVEVHNAKTKPREEQYNSTYRVVSVLTVLHQDWLNGKEYKCAVSNKALP<br>APIEKTISKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEALHNHYTQK<br>SLSLSPG**SGGGGSGGGGSGGGGSPS**DIQMTQSPSSLSASVGDRVTITCRASQSIS<br>SYLNWYQQKPGKAPKLLIYAASSLQSGVPSRFSGSGSGTDFTLTISSLQPEDFAT<br>YYCQQTYGYLHTFGQGTKLEIKGGGGSGGGGSGGGGSGGGGSEVQLLESGGGLVQ<br>PGGSLRLSCAASGFTFSSYAMSWVRQAPGKGLEWVSAISGSGGSTYYADSVKGRF<br>TISRDNSKNTLYLQMNSLRAEDTAVYYCARYYGGYYSAWMDYWGQGTLVTVSS | 152 |
| ALG.APV-014 | MEAPAQLLFLLLLWLPDTTGEVQLLESGGGLVQPGGSLRLSCAASGFTFSYGSMY<br>WVRQAPGKGLEWVSSISSGSGSTYYADSVKGRFTISRDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSSEPKS<br>SDKTHTCPPCPAPEAAGAPSVFLFPPKPKDTLMISRTPEVTCVVVDVSHEDPEVK<br>FNWYVDGVEVHNAKTKPREEQYNSTYRVVSVLTVLHQDWLNGKEYKCAVSNKALP | 154 |

TABLE 11-continued

| Exemplary anti-5T4 x anti-4-1BB Molecule Amino Acid Sequences | | |
|---|---|---|
| Construct | AA Sequence | AA SEQ ID |
| | APIEKTISKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEALHNHYTQK<br>SLSLSPG**SGGGGSGGGGSGGGGSPS**EVQLLESGGGLVQPGGSLRLSCAASGFTFS<br>SYAMSWVRQAPGKCLEWVSAISGSGGSTYYADSVKGRFTISRDNSKNTLYLQMNS<br>LRAEDTAVYYCARYYGGYYSAWMDYWGQGTLVTVSSGGGGSGGGGSGGGGSGGGG<br>SDIQMTQSPSSLSASVGDRVTITCRASQSISSYLNWYQQKPGKAPKLLIYAASSL<br>QSGVPSRFSGSGSGTDFTLTISSLQPEDFATYYCQQTYGYLHTFGCGTKLEIKS | |
| ALG.APV-018 | MEAPAQLLFLLLLWLPDTTGEVQLLESGGGLVQPGGSLRLSCAASGFTFSYGSMY<br>WVRQAPGKGLEWVSSISSGSGSTYYADSVKGRFTISRDNSKNTLYLQMNSLRAED<br>TAVYYCARSSYYGSYYSIDYWGQGTLVTVSSGGGGSGGGGSGGGGSGGGGSDIQM<br>TQSPSSLSASVGDRVTITCRASQSISSYLNWYQQKPGKAPKLLIYAASSLQSGVP<br>SRFSGSGSGTDFTLTISSLQPEDFATYYCQQYYDNLPTFGQGTKLEIKSSSEPKS<br>SDKTHTCPPCPAPEAAGAPSVFLFPPKPKDTLMISRTPEVTCVVVDVSHEDPEVK<br>FNWYVDGVEVHNAKTKPREEQYNSTYRVVSVLTVLHQDWLNGKEYKCAVSNKALP<br>APIEKTISKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEALHNHYTQK<br>SLSLSPG**SGGGGSGGGGSGGGGSPS**DIQMTQSPSSLSASVGDRVTITCRASQSIS<br>SYLNWYQQKPGKAPKLLIYAASSLQSGVPSRFSGSGSGTDFTLTISSLQPEDFAT<br>YYCQQTYGYLHTFGCGTKLEIKGGGGSGGGGSGGGGSGGGGSEVQLLESGGGLVQ<br>PGGSLRLSCAASGFTFSSYAMSWVRQAPGKCLEWVSAISGSGGSTYYADSVKGRF<br>TISRDNSKNTLYLQMNSLRAEDTAVYYCARYYGGYYSAWMDYWGQGTLVTVSS | 156 |

Polynucleotides and Methods of Protein Expression

The disclosure also includes nucleic acids (e.g., DNA or RNA) encoding the polypeptides of the present disclosure (e.g., 5T4-binding polypeptides, 4-1BB-binding polypeptides, and/or multispecific binding proteins thereof) or one or more polypeptide chains of a polypeptide as described herein. Nucleic acids of the disclosure include nucleic acids having a region that is substantially identical to a polynucleotide as listed in Tables 1-10, infra. In certain embodiments, a nucleic acid in accordance with the present disclosure has at least 80%, typically at least about 90%, and more typically at least about 95% or at least about 98% identity to a polypeptide-encoding polynucleotide as listed in Tables 1-10, wherein the nucleic acid encodes a polypeptide that is a multispecific polypeptide in the format scFv-Fc-scFv and wherein the encoded polypeptide comprises one or more of (1) a Y to F substitution in the LCDR1 at position 99 of the anti-5T4 $V_L$; (2) a F to S substitution in the FR3 at position 148 of the anti-5T4 $V_L$; (3) a Y to H substitution in the HCDR1 at position 150 of the anti-4-1BB $V_H$; and (4) an R to H substitution in the FR3 at position 127 of the anti-4-1BB $V_H$. Nucleic acids of the disclosure also include complementary nucleic acids. In some instances, the sequences will be fully complementary (no mismatches) when aligned. In other instances, there can be up to about a 20% mismatch in the sequences. In some embodiments of the disclosure are provided nucleic acids encoding both first and second polypeptide chains of a bispecific protein of the disclosure. The nucleic acid sequences provided herein can be exploited using codon optimization, degenerate sequence, silent mutations, and other DNA techniques to optimize expression in a particular host, and the present disclosure encompasses such sequence modifications.

The disclosure relates to an isolated nucleic acid molecule encoding polypeptides of the present disclosure (e.g., 5T4-binding polypeptides, 4-1BB-binding polypeptides, and/or multispecific binding proteins thereof), wherein said nucleic acid molecule comprises a nucleotide sequence selected from SEQ ID NOs: 109, 111, 113, 115, 117, 119, 121, 123, 125, 127, 129, 131, 133, 135, 137, 139, 141, 143, 145, 147, 149, 151, 153, 155, 171, 173, and 175.

Polynucleotide molecules comprising a desired polynucleotide sequence are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a nucleic acid encoding a polypeptide disclosed herein, a nucleic acid molecule encoding the polypeptide, operably linked to regulatory sequences that control transcriptional expression in an expression vector, is introduced into a host cell. In addition to transcriptional regulatory sequences, such as promoters and enhancers, expression vectors can include translational regulatory sequences and a marker gene which is suitable for selection of cells that carry the expression vector. The gene product encoded by a polynucleotide of the disclosure is expressed in any convenient expression system, including, for example, bacterial, yeast, insect, amphibian and mammalian systems. In the expression vector, the polypeptide-encoding polynucleotide is linked to a regulatory sequence as appropriate to obtain the desired expression properties. These can include promoters, enhancers, terminators, operators, repressors, and inducers. The promoters can be regulated (e.g., the promoter from the steroid inducible pIND vector (Invitrogen)) or constitutive (e.g., promoters from CMV, SV40, Elongation Factor, or LTR sequences). These are linked to the desired nucleotide sequence using the techniques described above for linkage to vectors. Any techniques known in the art can be used. Accordingly, the expression vector will generally provide a transcriptional and translational initiation region, which can be inducible or constitutive, where the coding region is operably linked under the transcriptional control of the transcriptional initiation region, and a transcriptional and translational termination region.

An expression cassette ("expression unit") can be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors can provide for extrachromosomal maintenance, particularly as plasmids or viruses, or for integration into the host chromosome. Where extrachromosomal maintenance is desired, an origin sequence is provided for the replication of the plasmid, which can be low- or high copy-number. A wide variety of markers are available for selection, particularly those which protect against toxins, more particularly against antibiotics. The particular marker that is chosen is selected in accordance with the nature of the host, where, in some cases, complementation can be employed with auxotrophic hosts. Introduction of the DNA construct can use any convenient method, including, e.g., conjugation, bacterial transformation, calcium-precipitated DNA, electroporation, fusion, transfection, infection with viral vectors, biolistics, and the like. The disclosure relates to an expression vector comprising a nucleic acid segment, wherein said nucleic acid segment may comprise a nucleotide sequence selected from SEQ ID NOs: 109, 111, 113, 115, 117, 119, 121, 123, 125, 127, 129, 131, 133, 135, 137, 139, 141, 143, 145, 147, 149, 151, 153, 155, 171, 173, and 175.

Accordingly, proteins for use within the present disclosure can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, *Molecular Cloning: A Laboratory Manual* (3rd ed., Cold Spring Harbor Laboratory Press, Cold Spring Harbor, N.Y., 2001), and Ausubel et al., *Short Protocols in Molecular Biology* (4th ed., John Wiley & Sons, 1999).

For example, for recombinant expression of a homodimeric binding protein comprising two identical binding polypeptides as described herein, an expression vector will generally include a nucleic acid segment encoding the binding polypeptide, operably linked to a promoter. For recombinant expression of a heterodimeric binding protein comprising different first and second polypeptide chains, the first and second polypeptide chains can be co-expressed from separate vectors in the host cell for expression of the entire heterodimeric protein. Alternatively, for the expression of heterodimeric binding proteins the first and second polypeptide chains are co-expressed from separate expression units in the same vector in the host cell for expression of the entire heterodimeric protein. The expression vector(s) are transferred to a host cell by conventional techniques, and the transfected cells are then cultured by conventional techniques to produce the encoded polypeptide(s) to produce the corresponding binding proteins (e.g., 5T4-binding polypeptides, 4-1BB-binding polypeptides, and/or multi specific binding proteins thereof).

To direct a recombinant protein into the secretory pathway of a host cell, a secretory signal sequence (also known as a leader sequence) is provided in the expression vector. The secretory signal sequence can be that of the native form of the recombinant protein, or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., U.S. Pat. Nos. 5,037,743 and 5,143,830).

Cultured mammalian cells are suitable hosts for production of recombinant polypeptides and proteins of the present disclosure (e.g., 5T4-binding polypeptides, 4-1BB-binding polypeptides, and/or multispecific binding proteins thereof) for use within the present disclosure. Methods for introducing exogenous DNA into mammalian host cells include calcium phosphate-mediated transfection (Wigler et al., Cell 14:725, 1978; Corsaro and Pearson, Somatic Cell Genetics 7:603, 1981: Graham and Van der Eb, Virology 52:456, 1973), electroporation (Neumann et al., EMBO J. 1:841-845, 1982), DEAE-dextran mediated transfection (Ausubel et al., supra), and liposome-mediated transfection (Hawley-Nelson et al., Focus 15:73, 1993; Ciccarone et al., Focus 15:80, 1993). The production of recombinant polypeptides in cultured mammalian cells is disclosed by, for example, U.S. Pat. Nos. 4,713,339; 4,784,950; 4,579,821; and 4,656,134. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, Utah); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." Exemplary selectable markers include a gene encoding resistance to the antibiotic neomycin, which allows selection to be carried out in the presence of a neomycin-type drug, such as G-418 or the like; the gpt gene for xanthine-guanine phosphoribosyl transferase, which permits host cell growth in the presence of mycophenolic acid/xanthine; and markers that provide resistance to zeocin, bleomycin, blastocidin, and hygromycin (see, e.g., Gatignol et al., *Mol. Gen. Genet.* 207:342, 1987; Drocourt et al., *Nucl. Acids Res.* 18:4009, 1990). Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J Biosci.* (*Bangalore*) 11:47-58, 1987. Transformation of insect cells and production of foreign polypeptides therein is disclosed in U.S. Pat. No. 5,162,222 and PCT Publication No. WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press., New York 1994); and *Baculovirus Expression Protocols. Methods in Molecular Biology* (Richardson ed., Humana Press, Totowa, N.J., 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a protein-encoding DNA sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the protein or interest is subsequently produced. Recombinant viral stocks are made by methods commonly used in the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE™ cells; Invitrogen, Carlsbad, Calif.). See generally Glick and Pasternak, *Molecular Biotechnology, Principles & Applications of Recombinant DNA* (ASM Press, Washington, D.C., 1994). See also U.S. Pat. No. 5,300,435. Serum-free media are used to grow and maintain the cells. Suitable media formulations are known in the art and can be obtained from commercial suppliers. The cells are grown up from an inoculation density of approximately $2\text{-}5\times10^5$ cells to a density of $1\text{-}2\times10^6$ cells, at which time a recombinant viral stock is added at a multiplicity of infection (MOI) of 0.1 to 10, more typically near 3. Procedures used are generally described in available laboratory manuals (see, e.g., King and Possee, supra; O'Reilly et al., supra; Richardson, supra).

Fungal cells, including yeast cells, can also be used within the present disclosure to produce the polypeptides of the present disclosure (e.g., 5T4-binding polypeptides, 4-1BB-binding polypeptides, and/or multispecific binding proteins thereof). Yeast species of in this regard include, e.g., *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, U.S. Pat. Nos. 4,599,311; 4,931,373; 4,870,008; 5,037,743; and 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., U.S. Pat. Nos. 4,599,311; 4,615,974; and 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, e.g., Gleeson et al., *J. Gen. Microbiol.* 132:3459-3465, 1986; U.S. Pat. No. 4,882,279; and Raymond et al., *Yeast* 14:11-23, 1998. *Aspergillus* cells can be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus*, and other genera are also useful host cells within the present disclosure to produce, for example, 5T4-binding polypeptides, 4-1BB-binding polypeptides, and/or multispecific binding proteins thereof including anti-5T4×anti-4-1BB molecules. Techniques for transforming these hosts and expressing foreign DNA sequences cloned therein are well-known in the art (see, e.g., Sambrook and Russell, supra). When expressing a recombinant protein in bacteria such as *E. coli*, the protein can be retained in the cytoplasm, typically as insoluble granules, or can be directed to the periplasmic space by a bacterial secretion sequence. In the former case, the cells are lysed, and the granules are recovered and denatured using, for example, guanidine isothiocyanate or urea. The denatured protein can then be refolded and dimerized by diluting the denaturant, such as by dialysis against a solution of urea and a combination of reduced and oxidized glutathione, followed by dialysis against a buffered saline solution. In the alternative, the protein can be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted proteins can be recovered from the periplasmic space in a soluble and functional form by disrupting the cells (by, for example, sonication or osmotic shock) to release the contents of the periplasmic space and recovering the protein, thereby obviating the need for denaturation and refolding. Antibodies, including single-chain antibodies, can be produced in bacterial host cells according to known methods. See, e.g., Bird et al., *Science* 242:423-426, 1988; Huston et al., *Proc. Natl. Acad. Sci. USA* 85:5879-5883, 1988; and Pantoliano et al., *Biochem.* 30:10117-10125, 1991.

Transformed or transfected host cells to produce the polypeptides and proteins of the present disclosure (e.g., 5T4-binding polypeptides, 4-1BB-binding polypeptides, and/or multispecific binding proteins thereof) are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The proteins and polypeptides of the present disclosure (e.g., 5T4-binding polypeptides, 4-1BB-binding polypeptides, and/or multispecific binding proteins thereof) may be purified by conventional protein purification methods, typically by a combination of chromatographic techniques. See generally *Affinity Chromatography: Principles* & Methods (Pharmacia LKB Biotechnology, Uppsala, Sweden, 1988); Scopes, *Protein Purification: Principles and Practice* (Springer-Verlag, New York 1994). Proteins comprising an immunoglobulin Fc region can be purified by affinity chromatography on immobilized protein A or protein G. Additional purification steps, such as gel filtration, can be used to obtain the desired level of purity or to provide for desalting, buffer exchange, and the like.

Compositions and Methods of Use

The present disclosure provides methods for treating a subject with a disorder characterized by expression of 5T4. Generally, such methods include administering to a subject in need of such treatment a protein the present disclosure (e.g., 5T4-binding polypeptides, 4-1BB-binding polypeptides, and/or multispecific binding proteins thereof). In some embodiments, a 5T4-binding polypeptide, 4-1BB-binding polypeptide, and/or multispecific binding proteins thereof (e.g., an anti-5T4×anti-4-1BB molecule) does not induce or induces minimal antibody-dependent cell-mediated cytotoxicity (ADCC) activity and/or complement-dependent cytotoxicity (CDC) activity.

In other embodiments, where the binding proteins (e.g., multispecific binding proteins) comprise a second binding domain that specifically binds an effector cell (e.g., to 4-1BB), the binding proteins and/or multispecific binding proteins result in enhanced effector cell activation against 5T4-expressing cells in the subject. For example, in some embodiments, the binding proteins and/or multispecific binding proteins result in increased effector cell proliferation, increased effector cell production of one or more cytokines (e.g., IFNγ, TNFα, IL-6, IL-8, IL-12, IL-1α, etc.), or increased expression of one or more cell-surface activation markers (e.g., CD137, MHC-II, or CD69). Activation of effector cells can be measured by a variety of means known in the art including flow cytometry, immunofluorescence, and immunohistochemistry to assess changes in cell-surface marker expression, ELISA to assess production of cytokines and other factors, cell counts to assess proliferation, qPCR to assess changes in gene expression, and the like.

In some embodiments, the multi-specific binding proteins described herein exhibit enhanced effector cell activation compared to a second multispecific polypeptide of a different structure. For example, in some embodiments, the first multispecific polypeptide comprises a first scFv domain that specifically binds to 5T4 and a second scFv that specifically binds to 4-1BB, together by a binding domain linker and an immunoglobulin Fc domain in the following configuration, from amino-terminus to carboxyl-terminus: (i) the first scFv domain, (ii) the hinge region, (iii) the immunoglobulin constant region, (iv) the binding domain linker, and (v) the second scFv domain. In this example, a second multispecific binding protein comprises an IgG-scFv structure comprising an anti-4-1BB antibody and an anti-5T4 scFv. In some embodiments, the first multispecific binding protein exhibits a statistically significant enhancement of effector cell activation compared to the second multispecific polypeptide. For example, in some embodiments, the first multispecific binding protein exhibits a lower $EC_{50}$ value in a Jurkat/NF-κB reporter cell assay than observed for the second multispecific binding protein (See e.g., Example 10). In some embodiments, the $EC_{50}$ of the first multispecific binding protein is decreased by about 2 fold, about 3 fold, about 4 fold, about 5 fold, about 6 fold, about 7 fold, about 8 fold, about 9 fold, about 10 fold, or more compared to the $EC_{50}$ of the second multispecific binding protein. $EC_{50}$ values can be determined by non-linear regression analysis and other statistical methods known in the art.

In some embodiments, the first multispecific binding protein induces a statistically significant increase in effector cell proliferation compared to the second multispecific polypeptide. For example, in some embodiments, the first multispecific binding protein induces a statistically significant increase in proliferation of primed, human CD8+ T cells compared to the proliferation induced by the second multispecific binding protein (See e.g., Example 22). In some embodiments, the first multispecific binding protein induces an increase in effector cell proliferation of about 2 fold, about 3 fold, about 4 fold, about 5 fold, about 6 fold, about 7 fold, about 8 fold, about 9 fold, about 10 fold, or more compared to the effector cell proliferation induced by the second multispecific binding protein.

In certain variations of the method of treating a subject with a protein the present disclosure (e.g., 5T4-binding polypeptides, 4-1BB-binding polypeptides, and/or multispecific binding proteins thereof), the disorder is a cancer. Exemplary cancers amenable to treatment in accordance with a protein the present disclosure include, for example, breast cancer (e.g., triple negative breast cancer (TNBC)), pancreatic cancer, ovarian cancer, lung cancer (e.g., non-small cell lung cancer), hematologic malignancies (e.g., chronic lymphocytic leukemia (CLL), mantle cell leukemia (MCL) or acute lymphoblastic leukemia (ALL)), skin cancer (e.g., squamous cell carcinoma or melanoma), adrenal cancer, bladder cancer, cervical cancer, renal cancer, gastric cancer, prostate cancer, thyroid cancer, liver cancer, uterine cancer, a tumor formed on a nerve cell or nerve cell sheath (e.g., neurofibroma), sarcoma, carcinoma or head and neck cancer. TNBC is defined as breast cancer with the absence of staining for estrogen receptor, progesterone receptor, and HER2/neu. In some embodiments, a protein of the present disclosure can be administered to a subject to treat mesothelioma in the subject. In one embodiment, a protein of the present disclosure can be administered to a subject to treat a clear cell carcinoma in the subject. In one embodiment, a protein of the present disclosure can be administered to a subject to treat a striated muscle tumor in the subject.

In a further embodiment, the disclosure encompasses a method for enhancing effector cell activation against a cell expressing 5T4, the method comprising contacting said 5T4-expressing cell with a protein of the present disclosure (e.g., 5T4-binding polypeptides, 4-1BB-binding polypeptides, and/or multispecific binding proteins thereof), wherein said contacting is under conditions whereby enhanced effector cell activation against the 5T4-expressing cell is induced. In some embodiments, the disclosure relates to a method for enhancing effector cell activation against a cell expressing 5T4, the method comprising: contacting said 5T4-expressing cell with a protein of the present disclosure (e.g., 5T4-binding polypeptides, 4-1BB-binding polypeptides, and/or multispecific binding proteins thereof) comprising a first binding domain that specifically binds an epitope of human 5T4 and a second binding domain that specifically binds 4-1BB (e.g., an anti-5T4×anti-4-1BB molecule); wherein said contacting is under conditions whereby enhanced effector cell activation against the 5T4-expressing cell is induced. The disclosure encompasses a method for inducing effector cell dependent lysis of a cell expressing 5T4, the method comprising: contacting said 5T4-expressing cell with a protein of the present disclosure (e.g., 5T4-binding polypeptides, 4-1BB-binding polypeptides, and/or multispecific binding proteins thereof), wherein the second binding domain specifically binds 4-1BB (e.g., an anti-5T4×anti-4-1BB molecule); and wherein said contacting is under conditions whereby enhanced effector cell activation of the 5T4-expressing cell is induced, thereby resulting in the lysis of the 5T4-expressing cell. In some embodiments, the disclosure relates to a method for inducing effector cell dependent lysis of a cell expressing 5T4, the method comprising: contacting said 5T4-expressing cell with a protein of the present disclosure comprising a first binding domain that specifically binds an epitope of human 5T4 and a second binding domain that specifically binds 4-1BB (e.g., an anti-5T4×anti-4-1BB molecule); wherein said contacting is under conditions whereby enhanced effector cell activation of the 5T4-expressing cell is induced thereby resulting the lysis of the 5T4-expressing cell.

The disclosure also encompasses proteins and polypeptides (e.g., 5T4-binding polypeptides, 4-1BB-binding polypeptides, and/or multispecific binding proteins thereof) for the manufacture of a medicament for treatment of a disorder (e.g., cancer) characterized by expression of 5T4. In one embodiment, the protein or polypeptide comprises an anti-5T4 and anti-4-1BB binding domain (e.g., an anti-5T4×anti-4-1BB molecule) and has enhanced effector cell activation activity. In one embodiment, the disclosure provides proteins and polypeptides (e.g., an anti-5T4×anti-4-1BB molecule) for use in treating a disorder (e.g., cancer) characterized by expression of 5T4. In certain embodiments, the disclosure relates to a method for treating a disorder in a subject, wherein said disorder is characterized by expression of 5T4, the method comprising administering to the subject a therapeutically effective amount of a protein or polypeptide of the present disclosure comprising a 5T4 binding domain that specifically binds an epitope of human 5T4 (e.g., 5T4-binding polypeptides, 4-1BB-binding polypeptides, and/or multispecific binding proteins thereof).

In some embodiments, the disclosure provides a method of treating a patient with a cancer, comprising administering to the patient a polypeptide comprising amino acid sequence set forth in herein (e.g., an amino acid sequence selected from the group consisting of SEQ ID NOs: 136, 138, 140, 142, 144, 146, 148, 150, 152, 154, 156, 172, 174, and 176). In further embodiments, the polypeptide comprises an Fc. For example, in some embodiments, the disclosure provides a method of treating a patient with a cancer, comprising administering to the patient a polypeptide comprising a 5T4-binding domain and an Fc, wherein the polypeptide comprises an amino acid sequence selected from the group consisting of SEQ ID NOs: 136, 138, 140, 142, 144, 146, 148, 150, 152, 154, 156, 172, 174, and 176. In still further embodiments, the disclosure provides a method of treating a patient with a cancer comprising administering to the patient a polypeptide comprising a 5T4-binding domain and a 4-1BB-binding domain, wherein the polypeptide comprises an amino acid sequence selected from the group consisting of SEQ ID NOs: 136, 138, 140, 142, 144, 146, 148, 150, 152, 154, 156, 172, 174, and 176. In one embodiment, the disclosure provides a method of treating a patient with a cancer comprising administering to the patient a polypeptide comprising a 5T4-binding domain and a 4-1BB-binding domain, wherein the polypeptide comprises SEQ ID NO: 172. In one embodiment, the disclosure provides a method of treating a patient with a cancer comprising administering to the patient a polypeptide comprising a 5T4-binding domain and a 4-1BB-binding domain, wherein the polypeptide comprises SEQ ID NO: 174.

In some embodiments, for treatment methods and uses described herein, a protein or polypeptide described herein (e.g., 5T4-binding polypeptides, 4-1BB-binding polypeptides, and/or multispecific binding proteins thereof) is delivered in a manner consistent with conventional methodologies associated with management of the disease or disorder for which treatment is sought. In accordance with the disclosure herein, a therapeutically effective amount of the protein or polypeptide is administered to a subject in need of such treatment for a time and under conditions sufficient to prevent or treat the disease or disorder.

Subjects for administration of a protein of the present disclosure (e.g., 5T4-binding polypeptides, 4-1BB-binding polypeptides, and/or multispecific binding proteins thereof) include patients at high risk for developing a particular disorder characterized by 5T4 expression as well as patients presenting with an existing such disorder. Typically, the subject has been diagnosed as having the disorder for which treatment is sought. Further, subjects can be monitored during the course of treatment for any change in the disorder (e.g., for an increase or decrease in clinical symptoms of the disorder). Also, in some variations, the subject does not suffer from another disorder requiring treatment that involves targeting 5T4-expressing cells.

In prophylactic applications, pharmaceutical compositions or medicants comprising a protein of the present disclosure (e.g., 5T4-binding polypeptides, 4-1BB-binding polypeptides, and/or multispecific binding proteins thereof) are administered to a patient susceptible to, or otherwise at risk of, a particular disorder in an amount sufficient to eliminate or reduce the risk or delay the onset of the disorder. In therapeutic applications, compositions or medicants comprising a protein of the present disclosure are administered to a patient suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents are usually administered in several dosages until a sufficient response (e.g., inhibition of inappropriate angiogenesis activity) has been achieved. Typically, the response is monitored and repeated dosages are given if the desired response starts to fade.

To identify subject patients for treatment according to the methods of the disclosure (e.g., 5T4-binding polypeptides, 4-1BB-binding polypeptides, and/or multispecific binding proteins thereof), accepted screening methods can be employed to determine risk factors associated with specific disorders or to determine the status of an existing disorder identified in a subject. Such methods can include, for example, determining whether an individual has relatives who have been diagnosed with a particular disorder. Screening methods can also include, for example, conventional work-ups to determine familial status for a particular disorder known to have a heritable component. For example, various cancers are also known to have certain inheritable components. Inheritable components of cancers include, for example, mutations in multiple genes that are transforming (e.g., Ras, Raf, EGFR, cMet, and others), the presence or absence of certain HLA and killer inhibitory receptor (KIR) molecules, or mechanisms by which cancer cells are able to modulate immune suppression of cells like NK cells and T-cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disorder of interest. In addition, a wide variety of immunological methods are known in the art that are useful to identify markers for specific disorder. For example, various ELISA immunoassay methods are available and well-known in the art that employ monoclonal antibody probes to detect antigens associated with specific tumors. Screening can be implemented as indicated by known patient symptomology, age factors, related risk factors, etc. These methods allow the clinician to routinely select patients in need of the methods described herein for treatment. In accordance with these methods, targeting pathological, 5T4-expressing cells can be implemented as an independent treatment program or as a follow-up, adjunct, or coordinate treatment regimen to other treatments.

For administration, a protein of the present disclosure (e.g., 5T4-binding polypeptides, 4-1BB-binding polypeptides, and/or multispecific binding proteins thereof) may be formulated as a pharmaceutical composition. A pharmaceutical composition may comprise: (i) a 5T4-binding polypeptide, a 4-1BB-binding polypeptide, and/or multispecific binding protein thereof (e.g., an anti-5T4×anti-4-1BB molecule); and (ii) a pharmaceutically acceptable carrier, diluent or excipient. A pharmaceutical composition comprising a 5T4-binding polypeptide, a 4-1BB-binding polypeptide, and/or multispecific binding protein thereof (e.g., an anti-5T4×anti-4-1BB molecule) can be formulated according to known methods to prepare pharmaceutically useful compositions, whereby the therapeutic molecule is combined in a mixture with a pharmaceutically acceptable carrier, diluent or excipient. A carrier is said to be a "pharmaceutically acceptable carrier" if its administration can be tolerated by a recipient patient. Sterile phosphate-buffered saline is one example of a pharmaceutically acceptable carrier. Other suitable carriers, diluents or excipients are well-known to those in the art. (See, e.g., Gennaro (ed.), *Remington's Pharmaceutical Sciences* (Mack Publishing Company, 19th ed. 1995).) Formulations can further include one or more excipients, preservatives, solubilizers, buffering agents, albumin to prevent protein loss on vial surfaces, etc. In certain embodiments, a pharmaceutical composition comprises a 5T4-binding polypeptide, a 4-1BB-binding polypeptide, and/or multispecific binding protein thereof (e.g., an anti-5T4×anti-4-1BB molecule) that is a homodimer or a heterodimer. A "homodimer" may be a dimer formed from two identical polypeptides (e.g., an anti-5T4×anti-4-1BB molecule as described herein).

A pharmaceutical composition comprising a polypeptide or protein described herein may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. The oral unit dosage form may be selected from the group consisting of: tablets, pills, pellets, capsules, powders, lozenges, granules, solutions, suspensions, emulsions, syrups, elixirs, sustained-release formulations, aerosols, and sprays.

A pharmaceutical composition comprising polypeptide or protein described herein (e.g., 5T4-binding polypeptides, 4-1BB-binding polypeptides, and/or multispecific binding proteins thereof) may be administered to a subject in a therapeutically effective amount. According to the methods of the present disclosure, polypeptide or protein described herein (e.g., 5T4-binding polypeptides, 4-1BB-binding polypeptides, and/or multispecific binding proteins thereof) can be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, an agonist (e.g., 5T4-binding polypeptides, 4-1BB-binding polypeptides, and/or multispecific binding proteins thereof) can be administered to a subject in a single bolus delivery, via continuous delivery (e.g., continuous transdermal delivery) over an extended time period, or in a repeated administration protocol (e.g., on an hourly, daily, weekly, or monthly basis).

Determination of effective dosages in this context is typically based on animal model studies followed up by human clinical trials and is guided by determining effective dosages and administration protocols that significantly reduce the occurrence or severity of the subject disorder in model subjects. Effective doses of the compositions of the present disclosure vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically effective amount is also one in which any undesired collateral effects are outweighed by the beneficial effects of administering a 5T4-binding polypeptide, a 4-1BB-binding polypeptide, and/or a multispecific binding protein thereof (e.g., an anti-5T4×anti-4-1BB molecule) as described herein. For administration of a protein or polypeptide described herein, a dosage may range from about 0.1 μg to 100 mg/kg or 1 μg/kg to about 50 mg/kg, and more usually 10 μg to 5 mg/kg of the subject's body weight. In more specific embodiments, an effective amount of the agent is between about 1 μg/kg and about 20 mg/kg, between about 10 μg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring clinical symptoms of the disorder.

Dosage of the pharmaceutical composition comprising a polypeptide or protein described herein (e.g., 5T4-binding polypeptides, 4-1BB-binding polypeptides, and/or multispecific binding proteins thereof) can be varied by the attending clinician to maintain a desired concentration at a target site. For example, if an intravenous mode of delivery is selected, local concentration of the agent in the bloodstream at the target tissue can be between about 0.01-50 nanomoles of the composition per liter, sometimes between about 1.0 nanomole per liter and 10, 15, or 25 nanomoles per liter depending on the subject's status and projected measured response. Higher or lower concentrations can be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar.

The proteins and polypeptides described herein (e.g., 5T4-binding polypeptides, 4-1BB-binding polypeptides, and/or multispecific binding proteins thereof) (e.g., an anti-5T4×anti-4-1BB molecule) may also be administered at a daily dosage of from about 0.001 to about 10 milligrams (mg) per kilogram (mpk) of body weight, preferably given as a single daily dose or in divided doses about two to six times a day. For administration to a human adult patient, the therapeutically effective amount may be administered in doses in the range of 0.2 mg to 800 mg per dose, including but not limited to 0.2 mg per dose, 0.5 mg per dose, 1 mg per dose, 5 mg per dose, 10 mg per dose, 25 mg per dose, 100 mg per dose, 200 mg per dose, and 400 mg per dose, and multiple, usually consecutive daily doses may be administered in a course of treatment. The proteins and polypeptides described herein (e.g., 5T4-binding polypeptides, 4-1BB-binding polypeptides, and/or multispecific binding proteins thereof such as an anti-5T4×anti-4-1BB molecule) can be administered at different times of the day. In one embodiment the optimal therapeutic dose can be administered in the evening. In another embodiment the optimal therapeutic dose can be administered in the morning. The total daily dosage of the proteins and polypeptides described herein thus can in one embodiment range from about 1 mg to about 2 g, and often ranges from about 100 mg to about 1.5 g, and most often ranges from about 200 mg to about 1200 mg. In the case of a typical 70 kg adult human, the total daily dose of the anti-5T4 therapeutic can range from about 2 mg to about 1200 mg and will often range, as noted above, from about 0.2 mg to about 800 mg.

With particular regard to treatment of solid tumors, protocols for assessing endpoints and anti-tumor activity are well-known in the art. While each protocol may define tumor response assessments differently, the RECIST (Response evaluation Criteria in solid tumors) criteria is currently considered to be the recommended guidelines for assessment of tumor response by the National Cancer Institute (see Therasse et al., *J. Natl. Cancer Inst.* 92:205-216, 2000). According to the RECIST criteria tumor response means a reduction or elimination of all measurable lesions or metastases. Disease is generally considered measurable if it comprises lesions that can be accurately measured in at least one dimension as ≥20 mm with conventional techniques or ≥10 mm with spiral CT scan with clearly defined margins by medical photograph or X-ray, computerized axial tomography (CT), magnetic resonance imaging (MRI), or clinical examination (if lesions are superficial). Non-measurable disease means the disease comprises of lesions <20 mm with conventional techniques or <10 mm with spiral CT scan, and truly non-measurable lesions (too small to accurately measure). Non-measureable disease includes pleural effusions, ascites, and disease documented by indirect evidence.

The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (3) Progressive Disease (PD), defined as 20% increase in the sum of the longest diameter of target lesions or appearance of any new lesion; (4) Stable or No Response, defined as not qualifying for CR, PR, or Progressive Disease. (See Therasse et al., supra.)

Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer Drugs and Biologics*, April 2005, Center for Drug Evaluation and Research, FDA, Rockville, Md.)

Pharmaceutical compositions comprising the proteins and polypeptides described herein (e.g., 5T4-binding polypeptides, 4-1BB-binding polypeptides, and/or multispecific binding proteins thereof such as an anti-5T4×anti-4-1BB molecule) can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

The disclosure will be further clarified by the following examples, which are intended to be purely exemplary of the disclosure and in no way limiting.

EXAMPLES

Example 1: Conversion of "1618" Anti-CD137 Monoclonal Antibody to scFv Format and Generation of Bispecific Anti-CD137× Anti-5T4 Molecules in ADAPTIR™ Format (scFv-Fc-scFv)

In order to generate a nucleotide sequence encoding a 1618 scFv, nucleotide sequences encoding the variable domains of the heavy chain ($V_H$) and light chain ($V_L$) (SEQ ID NO: 28 and SEQ ID NO: 16, respectively) of the 1618 anti-4-1BB monoclonal antibody were synthesized and/or amplified from existing plasmid DNA and linked together by a (Gly)$_4$Ser-based linker using standard molecular biology techniques those described in, but not limited to e.g., PCT Application Publication Nos. WO 2007/146968, WO 2010/040105 and WO 2010/003108; U.S. Patent Application Publication Nos. 2006/0051844; and U.S. Pat. No. 7,166,707. The nucleotide sequence of the 1618 scFv was then fused to a modified human IgG1 Fc region sequence comprising point mutations to eliminate the effector function activities of the Fc region. Similarly, nucleotide sequences encoding the V$_H$ and V$_L$ domains of the 1210 anti-5T4 monoclonal antibody (SEQ ID NOs: 38 and 68, respectively) were linked together by an additional (Gly)$_4$Ser-based linker. The resulting bispecific molecules were expressed via transient transfection of HEK-293 or Chinese Hamster Ovary (CHO) cells and purified from conditioned media using Protein A affinity purification (ProA) and size exclusion chromatography (SEC). Protein purity was determined by analytical SEC after each of the Protein A and SEC purification steps. Endotoxin levels were determined by using the Endosafe PTS instrument according to the manufacturer's instructs to assure that the in vitro activity assay results would not be confounded by the presence of endotoxin. Each protein batch was buffer-exchanged into PBS as part of the SEC purification process, concentrated to 1 mg/mL, sterile-filtered, and stored at 4° C. until needed.

Protein concentration was determined from the absorbance at 280 nm and using the theoretical extinction coefficient.

In some instances, the bispecific molecules were comprised of 2 scFvs and 1 Fc domain (scFv-Fc-scFv) with the following structure, from N-terminus to C-terminus: 1618 scFv-Fc-1210 scFv. Additional bispecific molecules were generated in which the 1618 scFv was placed on the C-terminus of the construct and the 1210 scFv on the N-terminus (i.e., 1210 scFv-Fc-1618 scFv). However, molecules with this alternative orientation had less desirable properties when evaluated compared to the 1618 scFv-Fc-1210 scFv-Fc-scFv molecules.

HEK-293 cells compared to the Morrison format (i.e. ALG.APV-004). Table 12 contains representative data showing the improved expression levels of the ADAPTIR™ bispecific molecules (e.g., ALG.APV-006, ALG.APV-010, ALG.APV-014, and ALG.APV-018) versus the Morrison bispecific constructs (ALG.APV-004). This was an unexpected result, as the amino acid sequence of the 1618 and 1210 variable domains were not modified to obtain this improvement. These results indicate that the ADAPTIR™ bispecific molecules may be beneficial for manufacturing of therapeutic protein drugs; higher expression levels are generally considered beneficial for therapeutic protein drug manufacturing as this can provide lower cost of goods and other efficiencies in the manufacturing process, such as fewer production runs needed to meet market requirements.

In addition to the apparent improved expression in HEK-293, the aggregate levels quantified after Protein A purification of the bispecific molecule from conditioned media were significantly improved in the ADAPTIR™ bispecifics (ALG.APV-006, ALG.APV-010, ALG.APV-014 and ALG.APV-018) compared to the Morrison format bispecific (ALG.APV-004), as shown in Table 12.

TABLE 12

HEK-293 transient expression levels and post-Protein A purity of ADAPTIR ™ bispecifics vs. Morrison bispecifics

| Construct | Construct Distinction | Bispecific Format | Expression % Level µg/mL | Purity Analytical SEC |
|---|---|---|---|---|
| ALG.APV-004 | 1618 mAb-1210 V$_H$V$_L$ w/stabilizing disulfide | Morrison | 13.0 | 81.7 |
| ALG.APV-006 | 1618 V$_H$V$_L$-Fc-1210 V$_H$V$_L$ | ADAPTIR ™ | 25.5 | 94.4 |
| ALG.APV-010 | 1618 V$_H$V$_L$-Fc-1210 V$_L$V$_H$ | ADAPTIR ™ | 55.9 | 94.3 |
| ALG.APV-014 | 1618 V$_H$V$_L$-Fc-1210 V$_H$V$_L$ w/stabilizing disulfide | ADAPTIR ™ | 18.9 | 89.2 |
| ALG.APV-018 | 1618 V$_H$V$_L$-Fc-1210 V$_L$V$_H$ w/stabilizing disulfide | ADAPTIR ™ | 25.8 | 89.1 |

The order of the V$_H$ and V$_L$ domains was also evaluated with both the 1210 and 1618 scFvs (V$_H$-V$_L$ or V$_L$-V$_H$) and it was determined that the preferred orientation of the 1618 scFv was V$_H$-V$_L$, as the expression levels of scFv-Fc-scFv molecules were significantly reduced when the V$_L$-V$_H$ orientation was utilized. The preferred orientation of the 1210 scFv was V$_H$-V$_L$, which conferred improved binding to 5T4-expressing cells and in vitro activity in a CD137 reporter assay when compared to bispecific molecules that were comprised of the 1210 scFv in the V$_L$-V$_H$ format as shown in Table 13.

TABLE 13

Comparison of cell binding (EC$_{50}$) and in vitro activity in a CD137 reporter assay when the 1210 scFv is either in the V$_H$-V$_L$ or V$_L$-V$_H$ orientation

| Construct | Construct Distinction | Affinity to Human 5T4-expressing cells, EC$_{50}$ (nM), measured by flow cytometry | CD137 Reporter Assay EC$_{50}$ (nM) |
|---|---|---|---|
| ALG.APV-006 | 1618 V$_H$V$_L$-FC-1210 V$_H$V$_L$ | 15.7 | 0.23 |
| ALG.APV-010 | 1618 V$_H$V$_L$-FC-1210 V$_L$V$_H$ | 50.9 | 2.60 |

Most, but not all, of the 1618-Fc-1210 scFv-Fc-scFv ADAPTIR™ molecules (e.g., ALG.APV-006, ALG.APV-010, ALG.APV-014, and ALG.APV-018) had significantly improved expression levels when transiently transfected into The length of the linker between the V$_H$ and V$_L$ domains of the 1618 and 1210 scFvs was also evaluated. Changing the linker length connecting the V$_H$ and V$_L$ to either a 4× or 3× repeat of the Gly4Ser linker did not appear to result in a significant difference in activity or stability (data not shown), so the 4× repeat was generally used unless otherwise denoted.

Example 2: Optimization of the 1618 Anti-CD137 scFv and Anti-5T4 scFv Binding Domains After initial characterization of ADAPTIR™ bispecific (ALG.APV-006), it was desirable to increase 1) the binding affinities of the scFv binding domains to their respective targets; 2) the biophysical stability; and 3) the in vitro activity. Improvements in these parameters are expected to lead to improved cost of goods, ease of manufacturing and reduced clinical dosage amounts. For binding domain optimization, random mutagenesis phage libraries were generated for both the 1618 and 1210 scFV using error-prone PCR. Briefly, each scFv was used as template in an error-prone PCR reaction using a commercial mutagenesis kit (GeneMorph II Random Mutagenesis Kit, Agilent Technologies) following the manufacturer's protocol. The epPCR products were digested, ligated into the phagemid-scFV vector, and transformed into *E. coli* SS320/M13K07 competent cells to generate the phage libraries. Five rounds of panning were performed on each library, using biotinylated 4-1BB or 5T4 ECD as antigen (for the 1618 or 1210 binding domains, respectively). Increased stringency of panning was used for each successive round by decreasing the antigen concentration and increasing the wash times. Following the final round of panning, phage output was plated and prepared for a bulk cloning of the scFv pool into the prepared ADAPTIR™ expression vector. Approximately 400 individual colonies were picked, phagemids isolated and sequenced, and the purified DNA used in high-throughput small scale 293 transient transfections (~0.6 mL culture volume). 5-day clarified supernatants were assayed for binding by Flow Cytometry and SPR. The best performing variants were then carried forward through a battery of tests, including cell binding, in vitro activity and various stability assays. These bispecific ADAPTIR™ variants were produced with changes to either the 1210 or 1618 scFv, while keeping the other scFv as the unmodified parental sequence. This simplified the interpretation of the data and allowed us to assess the impact of these single changes on binding, activity and stability. Beneficial point mutations were identified, based on improvements to stability, affinity or bioactivity. These were then combined to produce an addition set of ADAPTIR DNA constructs. These constructs incorporated multiple changes in either the 1210 and/or 1618 scFv. Each construct was expressed by HEK-293 cells via transient transfection in 250 mL culture volume and purified using ProA and SEC steps. Final protein purity was verified by analytical SEC and the endotoxin levels was determined by using the Endosafe PTS instrument according to the manufacturer's instructs to assure that the in vitro activity assay results would not be confounded by the presence of endotoxin. The resulting protein was buffer-exchanged into PBS as part of the SEC purification process, concentrated to 1 mg/mL, sterile-filtered, and stored at 4° C. until needed. Protein concentration was determined from the absorbance at 280 nm and using the theoretical extinction coefficient.

Example 3. Evaluation of Phage-Derived Optimized Variants

Several beneficial amino acid changes to 1210 and 1618 scFvs were identified as part of the phage panning efforts, when compared to the parent ALG.APV-006 construct. One measure of protein colloidal stability is to examine the amount of protein that is precipitated out of solution when ammonium sulfate is added to a final concentration of ~1M. Under these conditions, the parent construct ALG.APV-006 lost nearly 89% of the protein in solution (Table 14). In comparison, the changes represented by ALG.APV-099, ALG.APV-127, ALG.APV-148 and ALG.APV-150 all show reduced protein loss under these conditions, suggesting that the individual amino acid changes made in these constructs improved the colloidal stability of the ADAPTIR™ bispecifics. Another measure of protein stability is to look at the impact of applying a shear force to a protein sample and examining that sample for loss due to precipitation or formation of soluble, aggregated forms of the bispecific. When assessed in a shear assay in which the protein solution was placed in a 96-well plate and shaken at 2,000 RPM for two hours, the ALG.APV-127 mutation significantly reduced the amount of protein loss, while the other variants had minimal effect or slightly exacerbated loss (Table 14). Another measure of thermostability can be determined by using differential scanning calorimetry (DSC) or differential scanning fluorimetry (DSF) to determine the mid-point temperature of the melting curve, otherwise known at Tm. Upon determination of the Tm of the 1618 and 1210 variants, we noted that the ALG.APV-127 and ALG.APV-150 variants increased the Tm of the 1618 scFv by three to four degrees, when compared to the ALG.APV-006 parental sequence (Table 14). An increase in the value of Tm can generally be interpreted as an improvement in a folded protein's stability, as it means that the protein is more resistant to heat-induced unfolding/denaturation. ALG.APV-148 increased the thermostability of the 1210 scFv, as the Tm was increased nearly three degrees compared to the parent 1210 sequence used in ALG.APV-006.

Various combinations of the ALG.APV-099, ALG.APV-127, ALG.APV-148, and ALG.APV-150 mutations were evaluated to see if combining mutations provided additive benefit to the biophysical stability of the ADAPTIR™ bispecfic constructs. These were expressed and purified using the same method and evaluated in the same assays as the individual point mutations. The results in Table 14 show that the combination of mutations included in ALG.APV-178 and ALG.APV-179, as representative examples, resulted in stability increases that were generally equivalent or better than that obtained from individual changes.

TABLE 14

Biophysical assessment data for non-optimized and optimized ADAPTIR ™ bispecific constructs

| Construct | Modified Domain | 1M Ammonium Sulfate Solubility, % Protein Loss | Shear Stress, % Protein Loss | Tm (° C.) 1618 scFv | Tm (° C.) 1210 scFv |
|---|---|---|---|---|---|
| ALG.APV-006 | Parent Sequence of 1210 and 1618 | 89 | 64 | 56.1 | 70.5 |
| ALG.APV-099 | 1210 | 67 | 80 | 57 | 70.5 |

TABLE 14-continued

Biophysical assessment data for non-optimized and optimized ADAPTIR ™ bispecific constructs

| Construct | Modified Domain | 1M Ammonium Sulfate Solubility, % Protein Loss | Shear Stress, % Protein Loss | Tm (° C.) 1618 scFv | Tm (° C.) 1210 scFv |
|---|---|---|---|---|---|
| ALG.APV-127 | 1618 | 55 | 32 | 60.4 | 71.0 |
| ALG.APV-148 | 1210 | 24 | 76 | 56.9 | 73.0 |
| ALG.APV-150 | 1618 | 56 | 71 | 58.9 | 70.8 |
| ALG.APV-178 | 1210 and 1618 | 18.7 | 24.5 | 61.7 | 72.3 |
| ALG.APV-179 | 1210 and 1618 | 28.9 | 26.5 | 61.7 | 72.3 |

In addition to the stability assessments that were performed, the binding affinity of ALG.APV-006 and the phage derived variants were determined by Surface Plasmon Resonance (SPR) using a Biacore T-200, using the recombinant extracellular domains of human 5T4 and human CD137. ALG.APV-127 and ALG.APV-150 modifications led to a significantly tighter binding affinity to CD137 (Table 15). Similarly, it was observed that ALG.APV-099 binds significantly more tightly than ALG.APV-006 (13 vs. 149 nM, respectively).

TABLE 15

Summary of binding and activity assessments for non-optimized and optimized ADAPTIR ™ bispecific constructs

| Construct | Modified Domain | Affinity to Human CD137 by SPR KD (nM) | Affinity to Human 5T4 by SPR KD (nM) | In vitro activity $EC_{50}$ (nM) |
|---|---|---|---|---|
| ALG.APV-006 | Parent Sequences | 128 | 149 | 0.23 |
| ALG.APV-099 | 1210 | N/A | 13 | 0.09 |
| ALG.APV-127 | 1618 | 58 | N/A | 0.03 |
| ALG.APV-148 | 1210 | N/A | 198 | 0.05 |
| ALG.APV-150 | 1618 | 97 | N/A | 0.03 |

The binding of the ALG.APV-099, ALG.APV-127, ALG.APV-148 and ALG.APV-150 variants to CD137 and 5T4 expressed on the surface of cells was compared to the binding of ALG.APV-006. In spite of the improved affinity for soluble CD137 or 5T4 displayed by some of these mutations, no appreciable difference was observed in on-cell binding experiments (data not shown). To compare the effectiveness of the phage-display derived variants at inducing target-dependent activation of CD137, the variants were compared in a CD137 reporter assay.

CD137 Reporter Assay:

Jurkat/CD137 transfectants carrying a luciferase reporter gene under the control of an NF-κB promoter (Promega) were cultured according to the manufacturer's protocols. Jurkat/NF-κB reporter cells were cultured with CHO-K1 cells transfected with human 5T4, at approximately 15,000 reporter cells to 30,000 target cells in 96-well plates. Concentrations of bispecific molecules with final concentration ranging from 10 nM to 0.002 nM were added. Cells were cultured in a total volume of 100 μL of RPMI 1640 media supplemented with 1% fetal bovine serum, sodium pyruvate, antibiotics and non-essential amino acids. Plates were incubated at 37° C., 5% $CO_2$ in humidified incubators for 5 to 6 hours. One hundred microliters of Bio-Glow buffer (Promega) was added to each well and incubated for 5 to 10 minutes before measuring fluorescence. Luminescence was measured in a MicroBeta$^2$ 2450 Microplate Counter (Perkin Elmer). Nonlinear regression analysis to determine $EC_{50}$ values was performed in GraphPad Prism 6® graphing and statistics software.

FIG. 1 shows that all the constructs displayed agonistic function in the presence of 5T4(+) cells; no reporter activity was observed in the absence of 5T4(+) cells (not shown). The constructs ALG.APV-099, ALG.APV-127, ALG.APV-148 and ALG.APV-150 displayed better agonist function (lower $EC_{50}$ values) than the original ALG.APV-006 construct. Every point in the curve represents the average of duplicate wells. The Morrison format molecule ALG.APV-004 was included for comparison. The y axis shows values in relative fluorescence units (RLU) represented as percent of maximum fluorescence.

Due to the improvements obtained with the single point mutations represented by ALG.APV-099, ALG.APV-127, ALG.APV-148 and ALG.APV-150, these were combined in various ways in order to determine if the characteristics of the individuals would have additive benefit when included in the same protein. These unique mutations were evaluated in combination to derive variants of 1618 and 1210 scFvs with significantly improved properties such as ALG.APV-178, ALG.APV-179, ALG.APV-187, ALG.APV-191, ALG.APV-196, ALG.APV-198 and ALG.APV-199. To generate the ALG.APV-191, ALG.APV-196, ALG.APV-198 and ALG.APV-199 constructs, the single point mutations were further combined with the LO1, LO2, and LO11 mutations described in Examples 22 and 23 of PCT Application No. PCT/EP2017/059656. Further, targeted phage libraries were created after analyzing regions of the 1618 and 1210 scFvs to identify regions that may contribute to instability. However, panning these libraries did not yield scFvs with improved properties (data not shown).

Example 4. Evaluation of Stabilizing Disulfide Bonds

Point mutations to incorporate an additional cysteine residue into the $V_H$ and $V_L$ domains of both the 1618 and 1210 scFvs were made. When these bispecific molecules are expressed, these cysteines react to form a disulfide bond and can act to increase the stability of the scFv and confer beneficial properties to improve the manufacturing and storage of these products. Experiments were performed showing that when optimized bispecific molecules with the stabilizing disulfide in the 1210 scFv are stored for one week at 4 or 25° C., or submitted to three freeze-thaw cycles between −80° C. and room temperature, they maintain their purity better than bispecific molecules without the disulfide. Representative data is shown in Table 16. Addition of a stabilizing disulfide bond to the 1618 scFv was also evaluated. While the disulfide appeared to confer a stability benefit, the Biacore binding data suggested that there was heterogeneity in the sample leading to atypical binding kinetics (data not shown).

TABLE 16

Improvement in storage and freeze-thaw stability in bispecific molecules containing a stabilizing disulfide bond in the 1210 scFv

| Construct | Is stabilizing disulfide in 1210 scFv? | Decrease in % Purity Day 7 @ 4° C. | Decrease in % Purity Day 7 @ 25° C. | Change in % Purity after 3 Freeze-Thaw Cycles from −80° C. to Room Temperature |
|---|---|---|---|---|
| ALG.APV-178 | No | 2.4 | 1.9 | 4 |
| ALG.APV-179 | No | 1.5 | 1.7 | 4 |
| ALG.APV-187 | Yes | 0.1 | 0.1 | 1 |
| ALG.APV-191 | Yes | 0.0 | 0.0 | 2 |
| ALG.APV-196 | Yes | 0.0 | 0.1 | 2 |
| ALG.APV-198 | Yes | 0.1 | 0.1 | 2 |
| ALG.APV-199 | Yes | 0.0 | 0.1 | 1 |

The improvement in bispecific molecule stability with the inclusion of a stabilizing disulfide bond in the 1210 scFv was also evident in a subsequent evaluation performed at 40° C. Two constructs, ALG.APV-209 and ALG.APV-210 differ by the addition of a stabilizing disulfide in the 1210 scFv of ALG.APV-210. After one week at this elevated temperature, ALG.APV-210 formed significantly less aggregated material (Table 17).

TABLE 17

Improved 40° C. stability data for a bispecific molecule with a stabilizing disulfide bond in the 1210 scFv

| Construct | Is stabilizing disulfide in 1210 scFv? | Decrease in % Purity Day 7 @ 40° C. |
|---|---|---|
| ALG.APV-209 | No | 2.6 |
| ALG.APV-210 | Yes | 0.2 |

While the inclusion of the disulfide bond in 1210 provided significant benefit in storage stability, the other stability parameters that were assessed did not detect a significant difference between the two constructs (Table 18). Both constructs performed significantly better in these assays as compared to the parent bispecific molecule ALG-006 (Table 14).

TABLE 18

Comparision of ALG.APV-209 to ALG.APV-210 stability data

| Construct | Is stabilizing disulfide in 1210 scFv? | Modified Domain | 1M Ammonium Sulfate Solubility, % Protein Loss | Shear Stress, % Protein Loss | Tm (° C.) 1618 scFv | Tm (° C.) 1210 scFv |
|---|---|---|---|---|---|---|
| ALG.APV-209 | No | 1210 and 1618 | 16.2 | 22.1 | 61.2 | 72.7 |
| ALG.APV-210 | Yes | 1210 and 1618 | 13.1 | 23.1 | 61.5 | 73.2 |

Example 5: Evaluation of Binding Affinity of Bispecific scFv2Fc Proteins to Human 5T4 and Human CD137

Methods

Expression and Purification of Recombinant Human 5T4 and Human CD137 Extracellular Domains (ECDs):

Using standard molecular biology techniques and starting with a vector encoding the full length sequence of the 5T4 and CD137 proteins, nucleotide primers were designed to amplify the extracellular regions of human 5T4 and human CD137. An additional peptide sequence was added to the c-terminus of ECD at the position where the native protein would be predicted to enter the membrane. This peptide contained recognition sequences that could be utilized for affinity purification purposes. The expression vectors were transiently transfected into HEK-293 cells. The recombinant ECD was purified from the conditioned media using immobilized metal affinity chromatography (IMAC) and size exclusion chromatography. Protein purity was verified using analytic SEC.

Surface Plasmon Resonance (SPR) Affinity Analyses of Bispecific Proteins to Recombinant CD137 and 5T4 Ecto-Domain:

SPR binding affinity studies of bispecific anti-5T4×anti-CD137 proteins to recombinant monomeric 5T4 and CD137 ectodomain (ECD) were conducted at 25° C. in HBS-EP$^+$ buffer on a Biacore T200 system. Goat anti-human IgG F(ab')2 fragment (Jackson ImmunoResearch) at 20 μg/mL in 10 mM sodium acetate (pH 4.5) was immobilized at a density of 2000 response units (RU) onto the flow cell of a CM5 research-grade sensor chip (GE) by standard amine coupling chemistry. Each bispecific variant at 200 nM in HBS-EP+ buffer was captured in the flow cell with the immobilized anti-human IgG at a flow rate of 50 μL/min for 60 sec to reach ~500 RU response, leaving one flow cell surface unmodified as the reference. Following a 30 sec stabilization period, four different concentrations of each ECD (0, 20, 60, and 180 nM) were injected at 50 μL/min for either 120 sec followed by a 240 sec dissociation period (for 5T4) or 90 sec followed by a 180 sec dissociation period (for 4-1BB). Regeneration was achieved by duplicate injections of 10 mM glycine (pH 1.5) at a flow rate of 50 μL/min for 30 sec followed by HBS-EP+ buffer stabilization for 1 min.

Sensorgrams obtained from kinetic SPR measurements were analyzed by the double subtraction method. The signal from the reference flow cell was subtracted from the analyte binding response obtained from flow cells with immobilized or captured ligands. Buffer reference responses were then averaged from multiple injections. The averaged buffer reference responses were then subtracted from analyte binding responses, and the final double-referenced data were analyzed with Biacore T200 Evaluation software (2.0, GE), globally fitting data to derive kinetic parameters. All sensorgrams were fitted using a simple one-to-one binding model.

Results

Table 19 shows the binding parameters determined by SPR for ADAPTIR™ bispecifics that bind to CD137 and 5T4. It should be noted that performing affinity measurements in this format, with the bispecific molecule captured on the chip and injecting recombinant monomeric CD137 or 5T4 ECD should result in true affinity values that are not confounded by avidity effects. As Table 19 illustrates, it was possible via careful screening of the randomized phage libraries to isolate binding domain variants that led to significant improvement in binding affinity either anti-CD137 and/or anti-5T4 scFv. A large reduction in the Hu CD137 KD value was achieved with the optimized ADAPTIR™ bispecifics ALG.APV-178, ALG.APV-179, ALG.APV-187, ALG.APV-209, and ALG.APV-210 in comparison to the unoptimized parent construct ALG.APV-006. Similarly, ALG.APV-179, ALG.APV-187, ALG.APV-209, and ALG.APV-210 exhibited improved affinity values for human 5T4 when compared to the unoptimized ALG.APV-006.

TABLE 19

Binding affinity ($K_D$), disassociation, and association constants for bispecific molecules binding to recombinant human CD137 or human 5T4

| | Affinity to Hu CD137 by SPR | | | Affinity to Hu 5T4 by SPR | | |
|---|---|---|---|---|---|---|
| Construct | KD (nM) | $k_a$ (1/Ms) | $k_d$ (1/s) | KD (nM) | $k_a$ (1/Ms) | $k_d$ (1/s) |
| ALG.APV-006 | 210 | 2.8E+05 | 5.9E−02 | 109 | 2.4E+04 | 2.6E−03 |
| ALG.APV-178 | 70 | 3.9E+05 | 2.7E−02 | 106 | 2.3E+04 | 2.5E−03 |
| ALG.APV-179 | 71 | 3.9E+05 | 2.8E−02 | 29 | 2.2E+04 | 6.2E−04 |
| ALG.APV-187 | 73 | 3.7E+05 | 2.7E−02 | 35 | 2.1E+04 | 7.2E−04 |
| ALG.APV-209 | 59 | 5.6E+05 | 3.3E−02 | 66 | 1.4E+04 | 9.4E−04 |
| ALG.APV-210 | 59 | 5.5E+05 | 3.3E−02 | 79 | 1.5E+04 | 1.2E−03 |

Example 6: Evaluation of Thermal Stability of Bispecific scFv-Fc-scFv Proteins to Human 5T4 and Human CD137

Differential Scanning calorimetry (DSC) and Differential Scanning Fluorimetry (DSF) are tools typically employed to measure assess the structural stability of recombinant proteins. By measuring the energy required to increase the temperature of a protein sample, it is possible to determine the midpoint temperature of melting (Tm) of individual protein domains. It is generally accepted that protein domains with higher Tm values are considered to be more stable. DSF analysis was performed with a set of optimized bispecific ADAPTIR™ bispecific proteins (ALG.APV-178, ALG.APV-179 and ALG.APV-187) and compared to the unoptimized ADAPTIR™ bispecific version (ALG.APV-006) (Table 20). A significant increase in Tm of the 1618 anti-CD137 and 1210 anti-5T4 was observed after incorporation of beneficial mutations that were identified by a random mutagenesis phage display approach described above.

TABLE 20

Midpoint of melting temperature, Tm, of optimized ADAPTIR ™ bispecifics versus unoptimized constructs

| Optimized? | Construct | Tm, Anti-CD137 scFv, ° C. | Tm, Anti-5T4 scFv, ° C. |
|---|---|---|---|
| N | ALG.APV-006 | 56.5 | 70.2 |
| Y | ALG.APV-178 | 60.7 | 73.0 |
| Y | ALG.APV-179 | 61.1 | 73.0 |
| Y | ALG.APV-187 | 61.1 | 73.5 |

Example 7: Binding of Bispecific scFv-Fc-scFv Proteins Molecules to Human and Non-Human Primate CD137(+) Cell Lines To confirm that binding to CD137 on the surface of cells was not lost upon scFv conversion of the variable domains or the mutations introduced, flow cytometry was used to quantitate binding of constructed bi-specific CD137×5T4 binding ADAPTIR™ molecules to cell lines expressing human or cynomolgus macaque CD137.

Binding studies on CHO-K1 cells lines expressing CD137 were performed by standard flow cytometry-based staining procedures. CHO-K1 cells (generated by Alligator) were transfected with human or cynomolgus macaque CD137. A typical experiment would label approximately 100,000 cells per well, in 96-well plates, with a range of 100 nM to 0.05 nM binding molecule in 50 μL of saline buffer with 2% BSA and 2 mM EDTA, for 30 min on ice, followed by washes and incubation with PE-labeled secondary antibody, goat anti-human IgG Fcγ (Jackson Laboratory), for 20 minutes on ice. Signal from bound molecules was detected using a LSR-II™ or a Symphony A3 flow cytometer (BD Biosciences) and analyzed by FlowJo flow cytometry analysis software. Median fluorescence intensity (MFI-median) of bound molecules on live cells was determined after exclusion of doublets cells. Nonlinear regression analysis to determine $EC_{50}$ values was performed in GraphPad Prism 6® graphing and statistics software.

Figure 2:
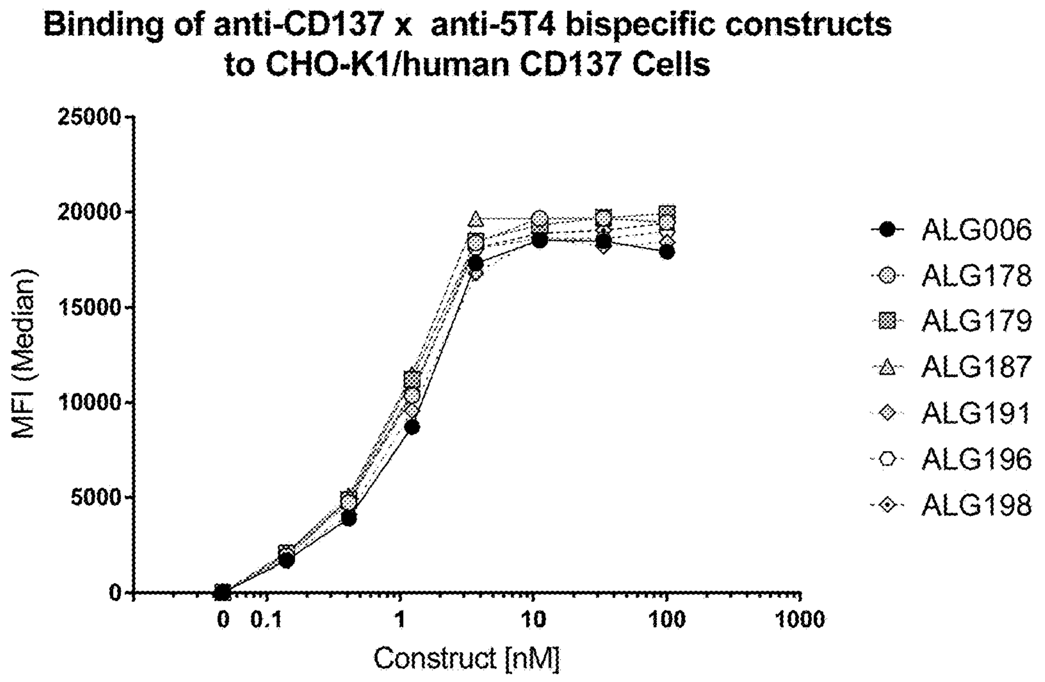
FIG. 2 illustrates binding curves of seven scFv-Fc-scFv molecules (ALG.APV-006, ALG.APV-178, ALG.APV-179, ALG.APV-187, ALG.APV-191, ALG.APV-196, and ALG.APV-198) to the CHO-K1 cell line expressing human 4-1BB.
Figure 3:
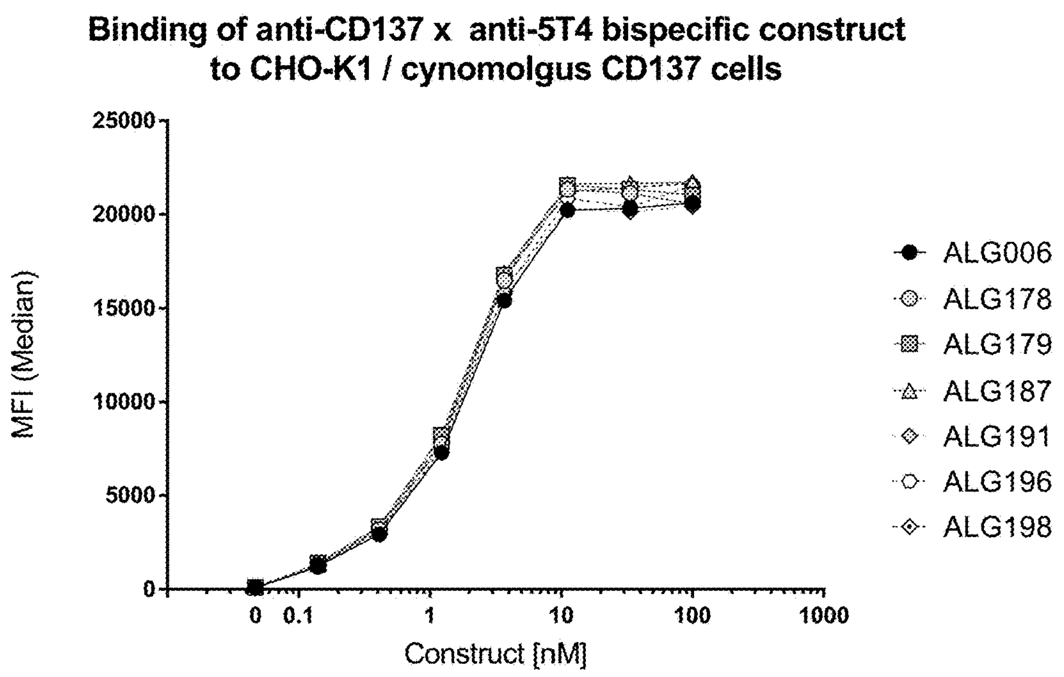
FIG. 3 illustrates binding curves of seven scFv-Fc-scFv molecules (ALG.APV-006, ALG.APV-178, ALG.APV-179, ALG.APV-187, ALG.APV-191, ALG.APV-196 and ALG.APV-198) to the CHO-K1 cell line expressing cynomolgus 4-1BB.
Figure 12:
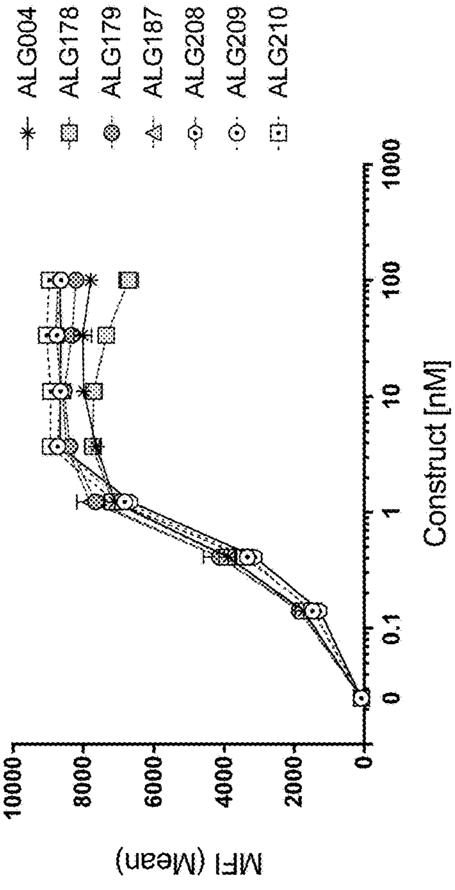
FIG. 12 shows the binding curves of ALG.APV-004, ALG.APV-178, ALG.APV-179, ALG.APV-187, ALG.APV-208, ALG.APV-209, and ALG.APV-210 to the CHO-K1/human CD137 cell line.

FIG. 2 shows the binding curves of seven ADAPTIR™ molecules (ALG.APV-006, ALG.APV-178, ALG.APV-179, ALG.APV-187, ALG.APV-191, ALG.APV-196 and ALG.APV-198) to the CHO-K1/human CD137 cell line. All the molecules showed similar levels of binding ($EC_{50}$ values) and saturation. FIG. 3 shows the binding curves of the same seven constructs to the CHO-K1/cynomolgus CD137 cell line. Similar levels of binding and saturation were observed by all seven constructs on the cynomolgus target. FIG. 12 shows the binding curves of six ADAPTIR™ molecules (ALG.APV-178, ALG.APV-179, ALG.APV-187, ALG.APV-208, ALG.APV-209, and ALG.APV-210) and the Morrison format control ALG.APV-004 to the CHO-K1/human CD137 cell line. All the molecules bound with similar $EC_{50}$ values in the range of 0.3 to 0.6 nM, and similar levels of saturation.

Example 8: Binding of Bispecific scFv-Fc-scFv Proteins to Human and Non-Human Primate 5T4(+) Cell Lines To compare the binding of the 5T4 on the surface of cancer cells after changes to the scFv domains were introduced, flow cytometry was used to quantitate binding of constructed bi-specific CD137×5T4 binding ADAPTIR™ molecules to cell lines expressing 5T4.

Binding of Bispecific CD137×5T4 Molecules to 5T4(+) Cell Lines:

Binding characteristics of the bispecific ADAPTIR™ molecules (ALG.APV-178, ALG.APV-179, ALG.APV-187, ALG.APV-196, ALG.APV-208, ALG.APV-209 and ALG.APV-210) were compared. Binding studies were performed by standard flow cytometry-based staining procedures two cell lines expressing 5T4:CHO-K1 cells (obtained from Alligator) transduced with human or cynomolgus macaque 5T4 and SKOV-3 human ovarian adenocarcinoma cells which express (human) 5T4. All labeling and washes were performed in U-bottom 96-well plates in saline buffer with 0.1% BSA and 2 mM EDTA. Cell were plated at approximately 100,000 cells per well and incubated with a range of 100 nM to 0.05 nM concentrations of test molecules in 50 μL volume/well, for 30 minutes on ice. Cells were washed three times then incubated for another 30 min on ice with fluorescently-labeled secondary polyclonal antibody, $F(ab')^2$ goat anti-human IgG (Jackson ImmunoResearch Laboratories). The cells were then washed twice and the samples acquired in a BD LSRII or a Symphony A3 flow cytometer. The sample files were analyzed using FlowJo software; the mean fluorescence intensity (MFI-mean) or median fluorescence intensity (MFI-median) of the live population of cells in each well was calculated after gating on live cells (forward vs side scatter). Nonlinear regression analysis to determine $EC_{50}$ values was performed in GraphPad Prism 6® graphing and statistics software.

Figure 4:
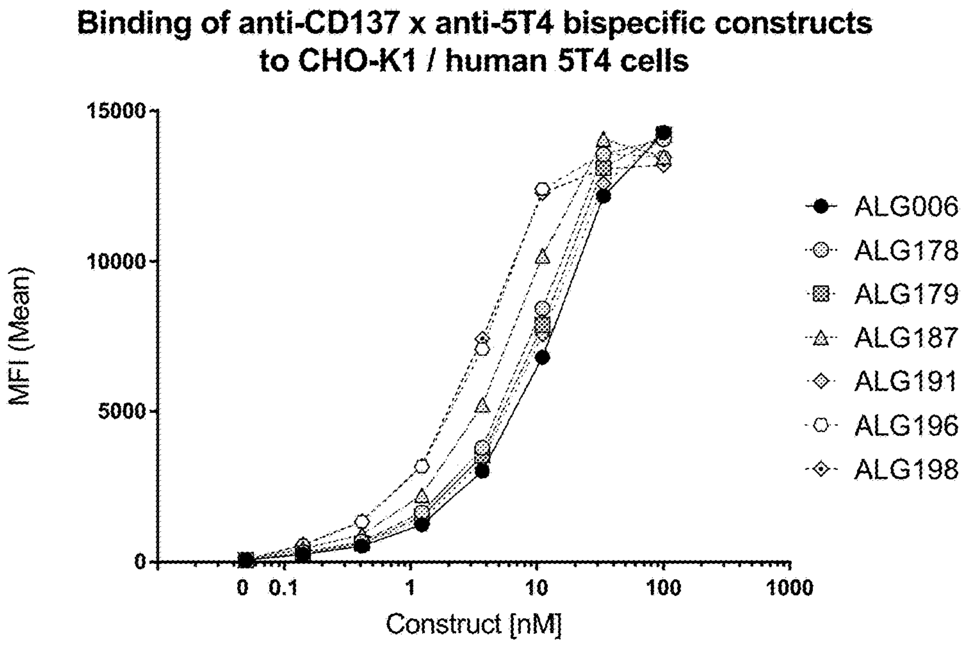
FIG. 4 illustrates the binding curves of seven scFv-Fc-scFv molecules (ALG.APV-006, ALG.APV-178, ALG.APV-179, ALG.APV-187, ALG.APV-191, ALG.APV-196, and ALG.APV-198) to the CHO-K1 cell line expressing human 5T4.
Figure 5:
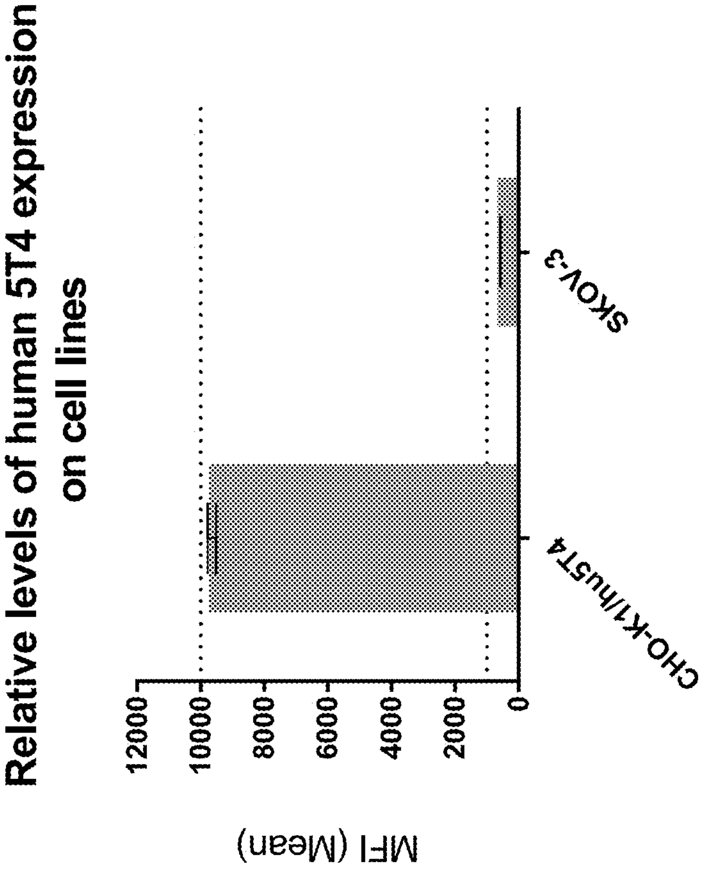
FIG. 5 illustrates the expression levels of human 5T4 in the CHO-K1 and SKOV-3 cell lines.
Figure 6:
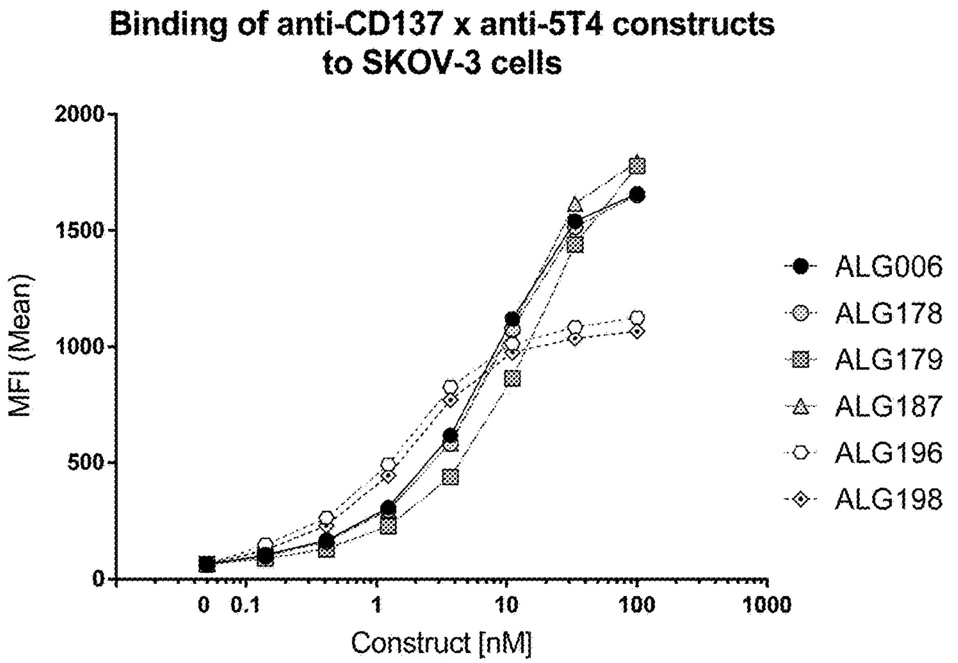
FIG. 6 illustrates the binding curves of the ALG.APV-006, ALG.APV-178, ALG.APV-179, ALG.APV-187, ALG.APV-196, and ALG.APV-198 constructs on SKOV-3 cells.
Figure 7:
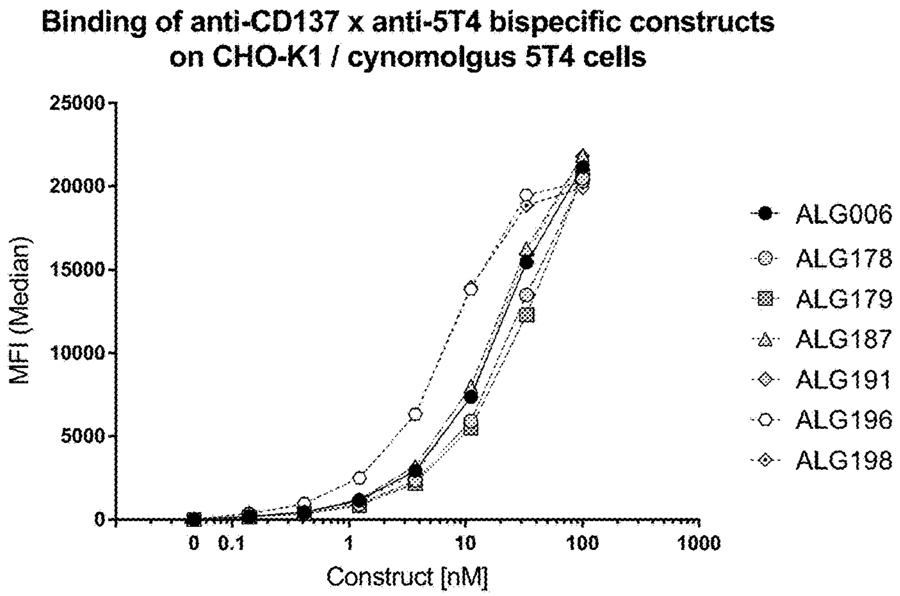
FIG. 7 illustrates the binding curves of ALG.APV-006, ALG.APV-178, ALG.APV-179, ALG.APV-187, ALG.APV-191, ALG.APV-196, and ALG.APV-198 on the CHO-K1 cell line expressing cynomolgus 5T4.

FIG. 4 shows the binding curves of seven ADAPTIR™ molecules (ALG.APV-006, ALG.APV-178, ALG.APV-179, ALG.APV-187, ALG.APV-191, ALG.APV-196, and ALG.APV-198) to the CHO-K1/human 5T4 cell line. The construct ALG.APV-006 bound with an $EC_{50}$ value >10 nM, while the remaining ADAPTIR™ constructs (ALG.APV-178, ALG.APV-179, ALG.APV-187, ALG.APV-191, ALG.APV-196, and ALG.APV-198) bound with $EC_{50}$ values in the range of 3 to 10 nM. The differences in $EC_{50}$ values between constructs were more evident when binding assays were conducted on SKOV-3 cells. SKOV-3 cells express approximately 10-fold lower levels of human 5T4 than the CHO-K1/human 5T4 transfectants (FIG. 5). FIG. 6 shows the binding curves of the ALG.APV-006, ALG.APV-178, ALG.APV-179, ALG.APV-187, ALG.APV-196, and ALG.APV-198 of constructs on SKOV-3 cells. The constructs ALG.APV-006, ALG.APV-078, ALG.APV-179, and ALG.APV-187 bound with slightly lower affinity (higher $EC_{50}$ values) and higher maximum binding levels than the ALG.APV-196 and ALG.APV-198 constructs. FIG. 7 shows the binding curves of ALG.APV-006, ALG.APV-178, ALG.APV-179, ALG.APV-187, ALG.APV-191, ALG.APV-196, and ALG.APV-198 on the CHO-K1/cynomolgus 5T4 transfectants. Similar to the binding profile on the human 5T4(+) cells, constructs ALG.APV-006, ALG.APV-178, ALG.APV-179, ALG.APV-187, ALG.APV-191, ALG.APV-196, and ALG.APV-198 displayed lower affinity and higher maximum binding levels than constructs ALG.APV-196 and ALG.APV-198.

Figure 13:
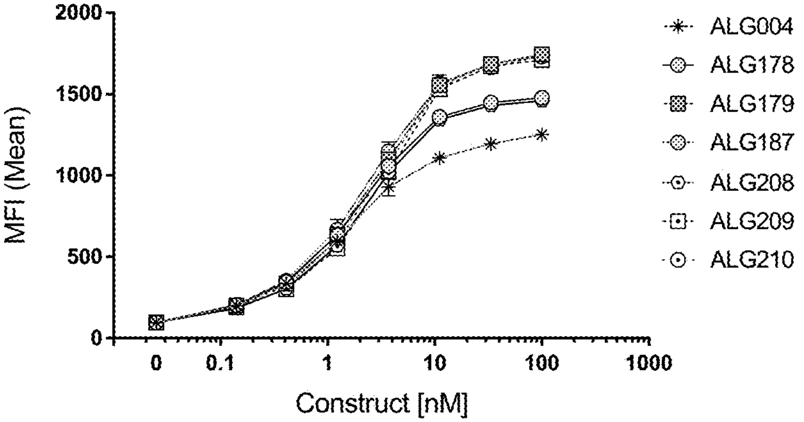
FIG. 13 shows the binding curves of ALG.APV-004, ALG.APV-178, ALG.APV-179, ALG.APV-187, ALG.APV-208, ALG.APV-209, and ALG.APV-210 to murine CT26 cells (ATCC) expressing human 5T4.
Figure 14:
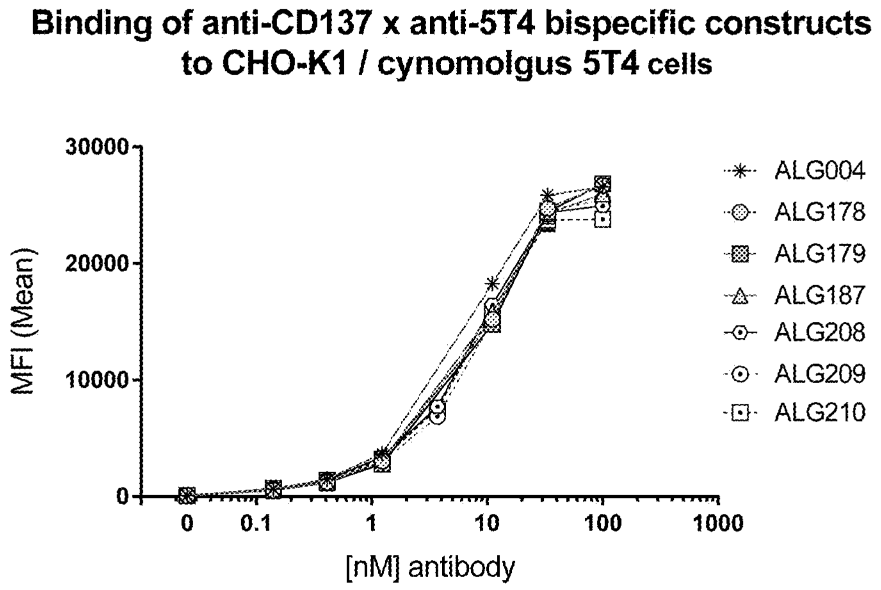
FIG. 14 shows the binding curves of ALG.APV-004, ALG.APV-178, ALG.APV-179, ALG.APV-187, ALG.APV-208, ALG.APV-209 and ALG.APV-210 on the CHO-K1/cynomolgus 5T4 transfectants.
Figure 15:
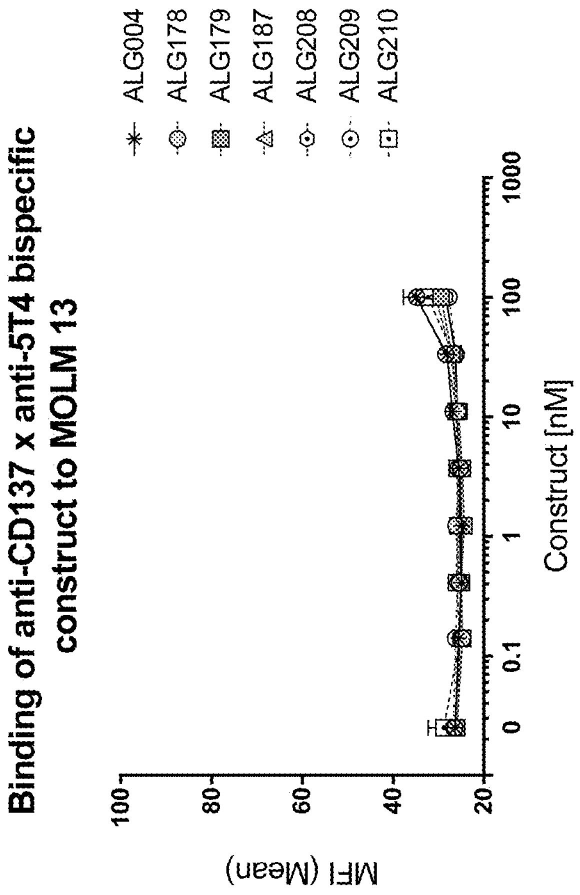
FIG. 15 shows the binding curves of ALG.APV-004, ALG.APV-178, ALG.APV-179, ALG.APV-187, ALG.APV-208, ALG.APV-209 and ALG.APV-210 on a human cell line expressing neither CD137 nor 5T4 (MOLM13 cells, ATCC).

FIG. 13 shows the binding curves of six ADAPTIR™ molecules (ALG.APV-178, ALG.APV-179, ALG.APV-187, ALG.APV-208, ALG.APV-209 and ALG.APV-210) and the Morrison format control ALG.APV-004 to murine CT26 cells (ATCC) expressing human 5T4. These cells express levels of human 5T4 comparable to those observed on SKOV-3 cells (FIG. 5). All the constructs bound with $EC_{50}$ values in the range of 1 to 3 nM. Constructs ALG.APV-179, ALG.APV-187, ALG.APV-209, and ALG.APV-210 showed higher levels of maximum binding than ALG.APV-178 and ALG.APV-208. The Morrison format control molecule ALG.APV-004 showed the lowest levels of maximum binding. FIG. 14 shows the binding curves of ALG.APV-004, ALG.APV-178, ALG.APV-179, ALG.APV-187, ALG.APV-208, ALG.APV-209, and ALG.APV-210 on the CHO-K1/cynomolgus 5T4 transfectants. All the molecules bound with similar $EC_{50}$ values, in the range of 6 to 10 nM, and similar levels of saturation. FIG. 15 shows the binding curves of ALG.APV-004, ALG.APV-178, ALG.APV-179, ALG.APV-187, ALG.APV-208, ALG.APV-209 and ALG.APV-210 on a human cell line expressing neither CD137 nor 5T4 (MOLM13 cells, ATCC). None of the molecules showed binding at any concentration.

Example 9: Binding of a 5T4-CD137 Bispecific Antibody to 5T4 Expressing Cell Lines Experiments were performed to determine the binding of ALG.APV-210 to human 5T4 expressed on cells at different receptor densities. Both human tumor cell lines with endogenous levels of 5T4 and cells transfected to produce 5T4 were assessed for target binding of ALG.APV-210.

Materials and Methods

Biotinylation:

In order to detect ALG.APV-210 binding to 5T4-expressing cell lines, ALG.APV-210 was first biotinylated. The quality of the biotinylated protein and the impact on binding to its targets was assessed using ELISA.

FACS Staining and Analysis of 5T4-Expressing Cell Lines:

Prior to the FACS staining, all cell lines were characterized for their 5T4 expression levels using a receptor density kit (Quantum Simply Cellular, anti-human IgG, Bangs Laboratories, Inc). Information on the cell lines used and their respective 5T4 expression densities are shown in Table 21. Adherent cell lines were cultured according to their supplier's instructions and were harvested from their cell culture flasks using Trypsin/EDTA, counted in R10 medium in a Burker chamber, and diluted in FACS buffer (PBS+0.5% BSA, 0.05% $NaN_3$) to a concentration of $4\times10^6$ cells/mL. 50 μL ($0.20\times10^6$) of cell solution was added to a 96-well FACS staining plate (Falcon #351190). Cells were incubated for 20 min in 4° C. with 50 μL of the biotinylated ALG.APV-210 (2× final concentration). The antibodies were added in a serial dilution starting at 20 μg/mL titrating down in a 12 step 1/2 dilution down to 0.010 μg/mL. Following 2× washing with FACS buffer, cells were incubated for 30 min in 4° C. with 100 μL of a secondary antibody (streptavidin-PE, BD #554061, diluted 1/500). Following 2× washing steps with FACS buffer, cells were re-suspended in 200 μL of cell fixation (BD CellFIX 10×BD, #340181, diluted in MQ H2O). Cells were analysed for ALG.APV-210 binding using flow cytometry (FACSVerse) by gating on single cells. MFI values (secondary antibody only subtracted) from 1 out of 2 independent experiments, as well as normalized data and $EC_{50}$-values of pooled data from 2 experiments were determined and plotted using GraphPad Prism 7, non-linear regression log (agonist) vs. normalized response-variable slope.

TABLE 21

Cell lines expressing 5T4 and receptor densities/cell

| Cells | Cancer type | 5T4 density/cell | $EC_{50}$ (nM) | 95% CI |
|---|---|---|---|---|
| HCT-116 | Human colon carcinoma | 62,000 | 16 | 15-17 |
| HT-29 | Human colon carcinoma | 30,000 | 12 | 11-14 |
| JAR | Human choriocarcinomas | 69,000 | 9 | 5-17 |
| JEG | Human choriocarcinomas | 66,000 | 8 | 5-12 |
| SKOV-3 | Human ovarian cancer | 60,000 | 15 | 12-18 |
| BxPC-3 | Pancreas cancer | 150,000 | 20 | 18-22 |
| B16-hu5T4 | Transfected mouse melanoma | 320,000 | 14 | 9-19 |
| CHO-hu5T4 | Transfected | 4,100,000 | 23 | 18-28 |
| CT26-hu5T4$^{high}$ | Transfected mouse colon carcinoma | 1,000,000 | 20 | 16-27 |
| CT26-hu5T4$^{int}$ | Transfected mouse colon carcinoma | 200,000 | 12 | 11-13 |
| CT26-hu5T4$^{low}$ | Transfected mouse colon carcinoma | 50,000 | 11 | 8-15 |

Results and Conclusions

Using ELISA, the binding of biotinylated ALG.APV-210 to 5T4 was determined to be similar to that of the non-biotinylated ALG.APV-210 (data not shown).

The binding ($EC_{50}$) of the biotinylated ALG.APV-210 to 5T4 when expressed on cells, either at endogenous levels on human tumor cells or on cells transfected to express 5T4 was assessed. As shown in FIG. 39 using MFI, ALG.APV-210 binds to both human tumor cells expressing endogenous levels of 5T4 and transfected cell lines in a dose-dependent manner.

Table 21 above shows the binding $EC_{50}$ of ALG.APV-210 to 5T4 positive human tumor cell line and to 5T4 transfected cells determined from normalized MFI values (background subtracted) from 2 pooled experiments plotted in a dose-response curve shown in FIG. 40. The mean $EC_{50}$ values ranged between 8-23 nM for the different 5T4 positive cell lines. In conclusion, ALG.APV-210 binds to 5T4-expressing cells at an $EC_{50}$ ranging between 8-23 nM.

Example 10: Agonistic Function of Bispecific scFv-Fc-scFv Proteins in Reporter Assays To compare the effectiveness of different bispecific CD137-binding molecules at inducing target-dependent activation of CD137, seven different bispecific anti-CD137× anti-5T4 molecules were compared in a CD137 reporter assay, as described in Example 3.

CD137 Reporter Assay

Jurkat/CD137 transfectants carrying a luciferase reporter gene under the control of an NF-κB promoter (Promega) were cultured according to the manufacturer's protocols. Jurkat/NF-κB reporter cells were cultured with human primary ductal breast carcinoma cells HCC1143 (ATCC), which express human 5T4, at approximately 15,000 reporter cells to 30,000 target cells in 96-well plates. Concentrations of bispecific molecules with final concentration ranging from 10 nM to 0.002 nM were added. Cells were cultured in a total volume of 100 μL of RPMI 1640 media supplemented with 10% fetal bovine serum, sodium pyruvate, antibiotics and non-essential amino acids. Plates were incubated at 37° C., 5% $CO_2$ in humidified incubators for 5 to 6 hours. One hundred microliters of Bio-Glow buffer (Promega) was added to each well and incubated for 5 to 10 minutes before measuring fluorescence. Luminescence was measured in a MicroBeta$^2$ 2450 Microplate Counter (Perkin Elmer). Non-linear regression analysis to determine $EC_{50}$ values was performed in GraphPad Prism 6® graphing and statistics software.

Results

Figure 8:
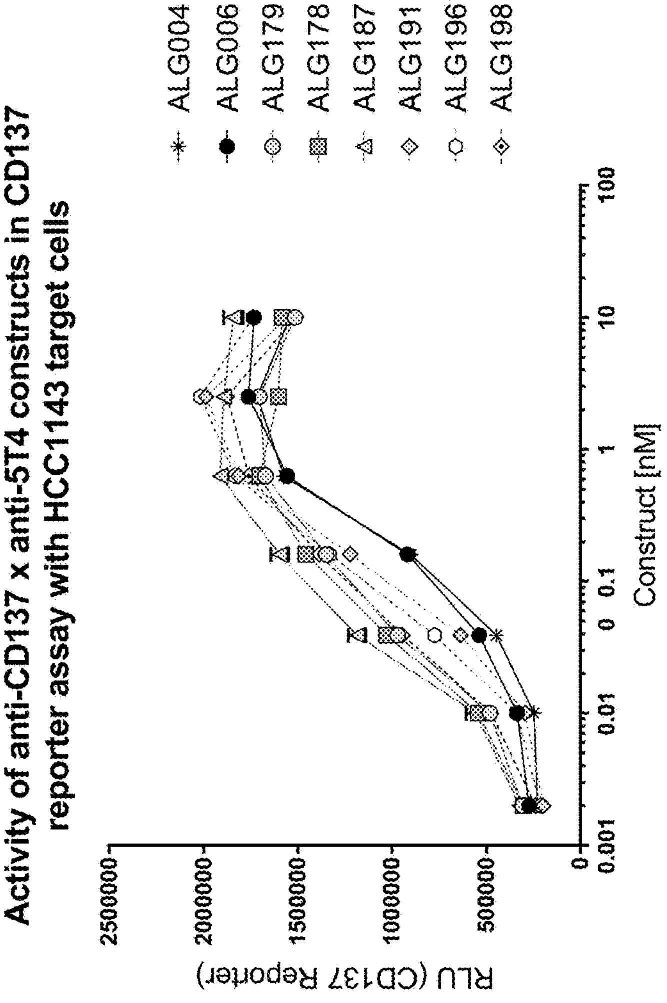
FIG. 8 illustrates the activity of anti-5T4×anti-4-1BB constructs in a 4-1BB reporter assay.
Figure 16A:
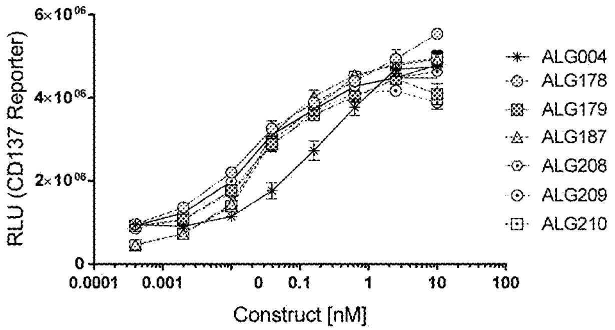
FIG. 16A-FIG. 16B show the activity of the bispecific constructs in Jurkat/NF-κB reporter cells, after 5 hours of incubation in the presence of 5T4(+) cells (HCC1143, FIG. 16A) or 5T4(−) cells (MOLM13, FIG. 16B). Every point in the curve represents the average of duplicate wells. The y-axis shows values in relative fluorescence units (RLU).
Figure 16B:
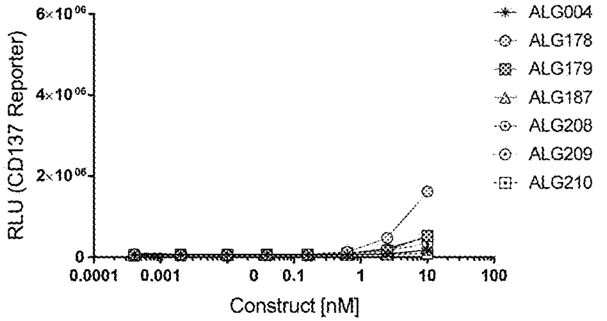

In FIG. 8, all the constructs display agonistic function in the presence of 5T4(+) cells; no reporter activity was observed in the absence of 5T4(+) cells (data not shown). The constructs ALG.APV-178, ALG.APV-179, ALG.APV-187, ALG.APV-191, ALG.APV-196 and ALG.APV-198 displayed better agonist function (up to 6-fold lower $EC_{50}$ values) than the non-optimized ADAPTIR™ construct, ALG.APV-006, and the Morrison format control, ALG.APV-004. Every point in the curve represents the average of duplicate wells. The y-axis shows values in relative fluorescence units (RLU). FIG. 16 shows the activity of the bispecific constructs in Jurkat/NF-κB reporter cells, after 5 hours of incubation in the presence of 5T4(+) cells (HCC1143) or 5T4(−) cells (MOLM13). The constructs ALG.APV-178, ALG.APV-179, ALG.APV-187, ALG.APV-208, ALG.APV-209 and ALG.APV-210 displayed better agonist function (10-fold lower $EC_{50}$ values) than the Morrison format control, ALG.APV-004. No reporter activity was observed in the presence of 5T4(−) cells (MOLM13). Every point in the curve represents the average of duplicate wells. The y-axis shows values in relative fluorescence units (RLU).

Example 11: Agonistic Function of Bispecific scFv-Fc-scFv Proteins in Primary T Cell Assays The agonistic function of different anti-CD137×anti-5T4 bispecific molecules at inducing target-dependent activation of CD137 was tested in cultures of peripheral blood mononuclear cells (PBMC). In order to test the function of the anti-CD137 bispecific constructs, primary PMBC were stimulated with anti-CD3 antibodies to upregulate CD137, which is not expressed on resting T cells. Co-stimulation of primary T cells through the TCR and CD137 enhances T-cell secretion of the cytokine interferon gamma (IFN-γ).

CD137 Stimulation of PBMC:

Peripheral blood mononuclear cells (PBMC) were isolated from human blood using standard ficoll gradients. The isolated cells were washed in saline buffer. PBMC were cultured with CHO-K1/human 5T4 cells, at approximately 120,000 PBMC to 30,000 5T4 (+) cells in 96-well plates. Anti-CD3 antibody OKT3 (eBioscience) was added to all the wells at a concentration of 0.1 μg/mL. Cells were cultured in a total volume of 200 μl of RPMI 1640 media supplemented with 1% fetal bovine serum, sodium pyruvate, antibiotics and non-essential amino acids. Plates were incubated at 37° C., 5% $CO_2$ in humidified incubators for 72 hours. One hundred microliters of media were collected at 72 hours. Levels of the IFN-γ were measured in the supernatant using Milliplex® kits (Millipore) using the manufacturer's instructions. Data was collected in a Bio-Plex Reader 200 System (Bio-Rad). Nonlinear regression analysis to determine $EC_{50}$ values was performed in GraphPad Prism 6® graphing and statistics software.

Figure 9:
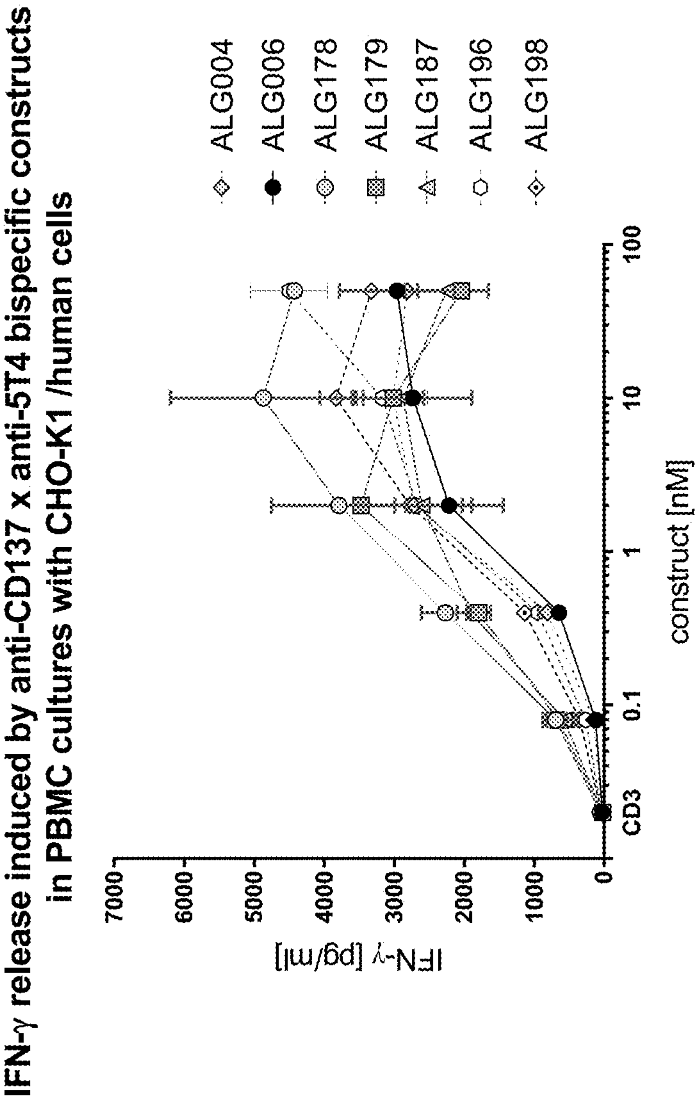
FIG. 9 illustrates the effect of anti-5T4×anti-4-1BB constructs on IFNγ release from PBMC and CHO-K1 co-cultures.
Figure 17:
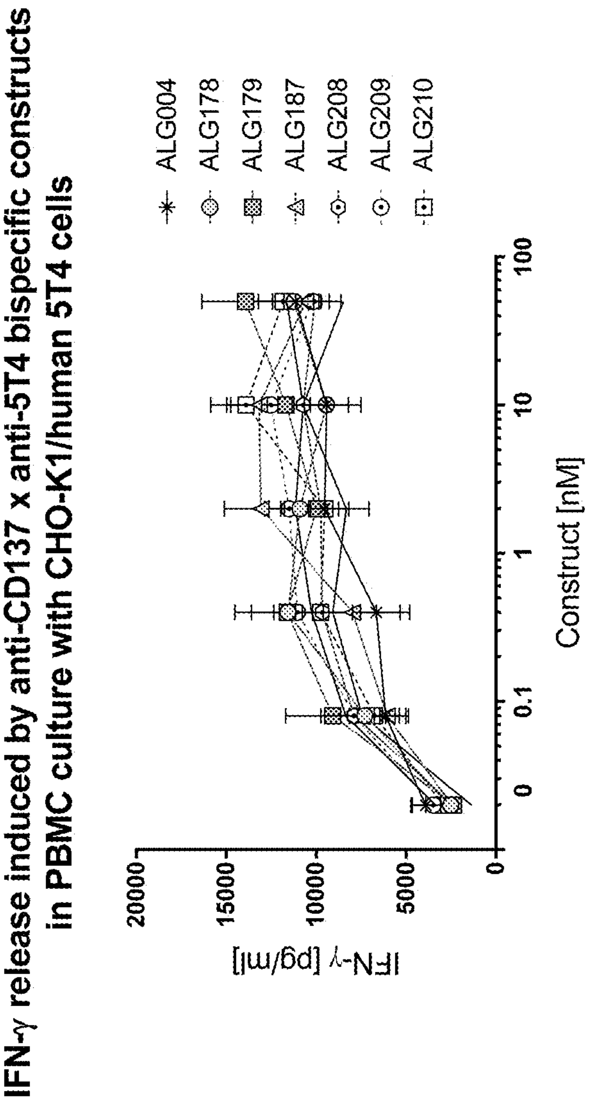
FIG. 17 shows the levels of IFN-γ induced in primary PBMC cultures at 72 by ALG.APV-178, ALG.APV-179, ALG.APV-187, ALG.APV-208, ALG.APV-209, ALG.APV-210, and the Morrison format control construct, ALG.APV-004. Every point in the curve represents the average of duplicate wells.

FIG. 9 shows the levels of IFN-γ induced by ALG.APV-006, ALG.APV-178, ALG.APV-179, ALG.APV-187, ALG.APV-196, ALG.APV-198 and the Morrison format control ALG.APV-004. All the constructs induced higher levels of IFN-γ than anti-CD3 alone, in a dose-dependent manner. Every point in the curve represents the average of duplicate wells. FIG. 17 shows the levels of IFN-γ induced in primary PBMC cultures at 72 by ALG.APV-178, ALG.APV-179, ALG.APV-187, ALG.APV-208, ALG.APV-209 and ALG.APV-210 and the Morrison format control construct ALG.APV-004 in the presence of CHO-K1/human 5T4 cells. All the constructs induced higher levels of IFN-γ than anti-CD3 alone, in a dose-dependent manner. Every point in the curve represents the average of duplicate wells.

The functional activity of anti-5T4×anti-CD137 bispecific constructs was also evaluated in a CD8+ T cell assay wherein cells were cultured in microtiter plates coated with a 5T4-Fc construct and an anti-CD3 antibody.

Figure 11A:
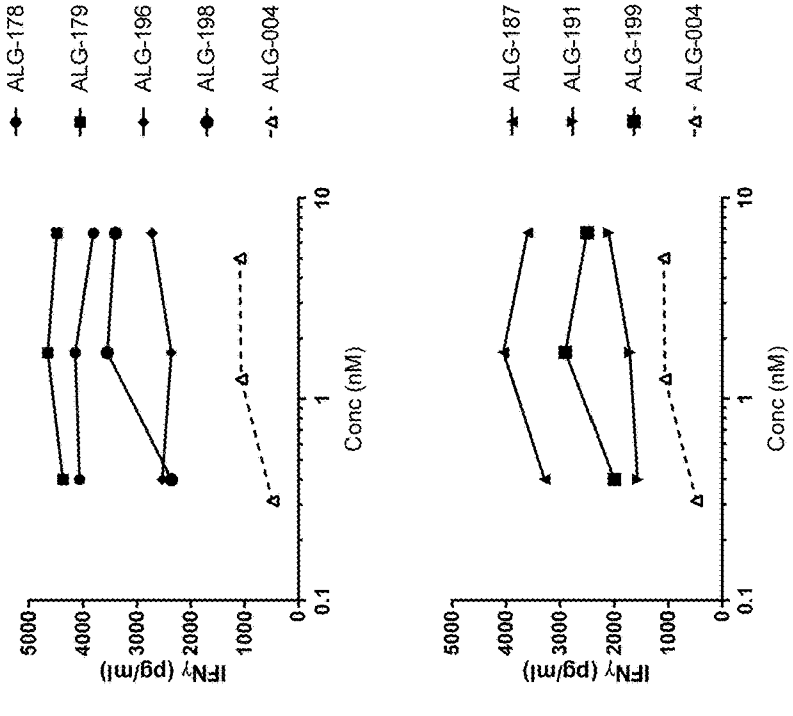
FIG. 11A-FIG. 11B show the interferon gamma (IFNγ) response in human CD8+ T cells cultured with bispecific scFv-Fc-scFv constructs.
Figure 11B:
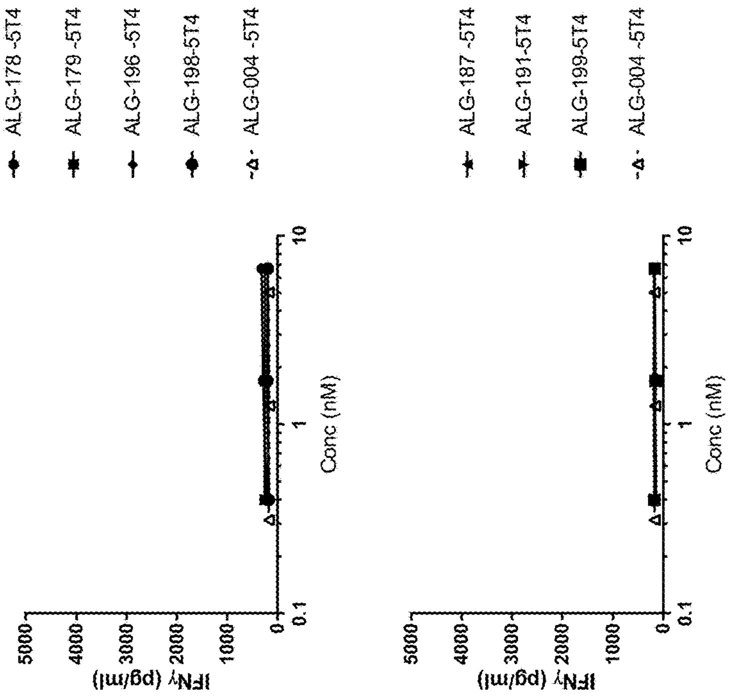

5T4 Stimulation of Purified T Cells:

PBMCs were isolated by density gradient centrifugation using Ficoll-Paque (ρ 1.077 g/mL) (GE Healthcare #17-1440-02) from leukocyte concentrates obtained from healthy donors (Clinical Immunology and Transfusion Medicine, Labmedicin Region Slane, Lund Sweden). CD8+ T cells were enriched by negative selection using the CD8+ T cell isolation kit (Miltenyi 130-096-495). Plates were coated overnight at 4° C. with 3 μg/mL α-CD3, clone OKT3 (Affymetrix eBioscience #16-0037-85), washed and coated with 5 μg/mL 5T4-Fc for 2 h at 37° C. After coating with 5T4-Fc, plates were washed and blocked for a minimum of 30 minutes with RPMI (Gibco #61870010) containing 10% FCS (Heat inactivated, Gibco #10270-106 lot 41Q9248K) and 10 mM Hepes (Gibco #15630056). Bispecific constructs were diluted in RPMI containing 10% FCS and 10 mM Hepes and added to the plates 30 minutes before addition of CD8+ T cells ($0.07\times10^6$ cells/well). Assay plates were incubated for 72 h at 37° C., after which culture supernatants were harvested. IFN-γ levels in the supernatants were measured by ELISA (BD OptiEIA #555142). The experiment was repeated twice with a total of 3 donors. Results from the first experiment are shown in FIG. 11A. Results of control samples, wherein cells and bispecific constructs were cultured in plates that were not coated with 5T4-Fc, are shown in FIG. 11B.

FIG. 11A shows that the ADAPTIR™ format anti-5T4×anti-CD137 bispecific constructs (ALG.APV-178, ALG.APV-179, ALG.APV-196, and ALG.APV-198) have increased functional activity compared to the Morrison format bispecific constructs (ALG.APV-004), demonstrated by an increase in the IFN-γ levels present in the culture supernatants in the presence of 5T4. In fact, the ADAPTIR™ format constructs induced IFN-γ levels that were 2-4.5 times higher than those induces by the Morrison format constructs (FIG. 11A).

Example 12: Antigen Dependent Localization of Bispecific Antibodies in 5T4 Positive Tumors In Vivo Antigen-dependent localization of the bispecific constructs targeting 5T4 and 4-1BB to 5T4-positive B16-5T4 tumors was evaluated in wild type C57BL/6 mice.

Materials and Methods

Mice:

8 week old, female C57BL/6 mice from Janvier, France were used for the experiments. All experiments were done by approval of the Malmö/Lund ethical committee.

Bispecific Constucts:

Two optimized 5T4- and CD137-targeting bispecific constructs in the ADAPTIR™ format, ALG.APV-209 and ALG.APV-210, were used. ALG.APV-004, a bispecific construct in the Morrison format, served as a positive control. Vehicle administration served as a negative control.

Cells:

B16.F10 WT (B16) cells were obtained from ATCC and cultivated according to their recommendations. B16 cells expressing human 5T4 (hereafter B16-5T4) were obtained from Professor Peter Stern and grown under 1.2 mg/mL of G418 selection medium.

Methods:

For the antigen dependent localization of bispecific constructs, a B16 melanoma twin tumor model was used, where each mouse received one 5T4 negative and one 5T4 positive tumor at each side of the hind flank/back. The tumor cell lines, growing in log phase, were injected subcutaneously ($1\times10^5$ cells in 100 μL) on day 0. Intraperitoneal construct treatments (100 μg) were given on day 6 and 13 and mice were sacrificed on day 14 (24 h after the final treatment).

FACS Analysis:

Tumors for flow cytometry analysis were mechanically and enzymatically digested using Liberase TL and DNase I (Roche) and passed through a 70 μm strainer. The resulting single cell suspension was stained for FACS analysis. Briefly, non-specific binding of the constructs was blocked using mouse IgG or Fc block. Dead cells were excluded using Fixable Viability Stain 450 (Molecular probes) according to manufacturer's instructions. Binding of the two ADAPTIR™ bispecific constructs or the control constructs to the tumor cells was analysed using a secondary antibody: goat-anti-human Fc-PE (Jackson Immunoresearch). Alternatively, detection of the bispecific constructs was performed using biotinylated 4-1BB antigen followed by streptavidin-PE/PerCP-Cy5.5. Samples were analyzed on a BD FACSVerse and data was analysed using FlowJo software. Statistical analysis was performed using Mann-Whitney non-parametric T-test, 2-tail and GraphPad prism program.

Immunohistochemistry:

Tumors for immunohistochemistry were snap frozen in isopropanol on dry ice. Cryosections (8 mm) were stained for 5T4 expression using a rabbit anti-human 5T4 (Abcam) or rabbit anti-human Fc (Jackson Immunoresearch) followed by anti-rabbit Brightvision—HRP (Immunologic) and DAPI staining. The immunohistochemical staining was assessed as follows; negative (0), weak staining (1+), moderate staining (2+), or strong staining (3+).

Results

Both bispecific constructs in the ADAPTIR™ format, ALG.APV-209 and ALG.APV-210, and the positive control, ALG.APV-004, localized to 5T4-expressing B16 tumors, but not to 5T4-negative tumors (B16.F10). This was demonstrated both by flow cytometry (FIGS. 18A and 18B) and immunohistochemistry (FIGS. 19A and 19B).

Figure 18A:
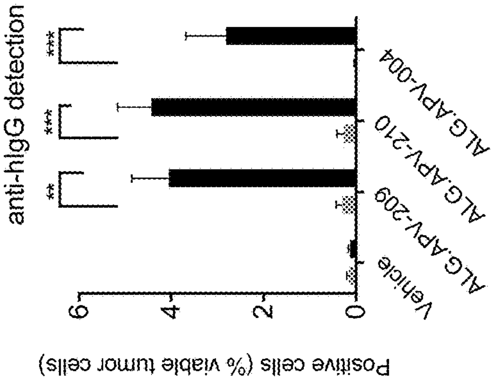
FIG. 18A-FIG. 18B illustrates FACS analysis of 5T4-dependent localization of bispecific constructs ALG.APV-209, ALG.APV-210, and ALG.APV-004 to antigen-expressing tumors. Localization was detected by staining with an anti-human Fc antibody (FIG. 18A) or biotinylated 4-1BB (FIG. 18B).
Figure 18B:
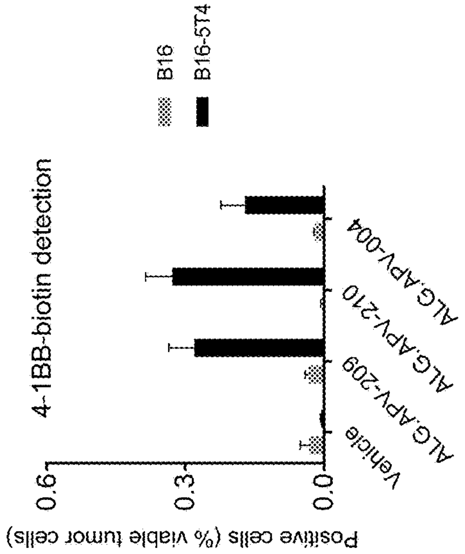

Both the bispecific constructs (ALG.APV-209, ALG.APV-210) and the positive control (ALG.APV-004) demonstrated statistically significant 5T4-dependent localization to antigen-positive tumors compared to the negative vehicle control as measured by flow cytometry (FIG. 18A). The binding to 5T4-expressing tumors could also be detected using biotinylated 4-1BB for detection (FIG. 18B), confirming that the bispecific molecules were intact.

Figure 19B:
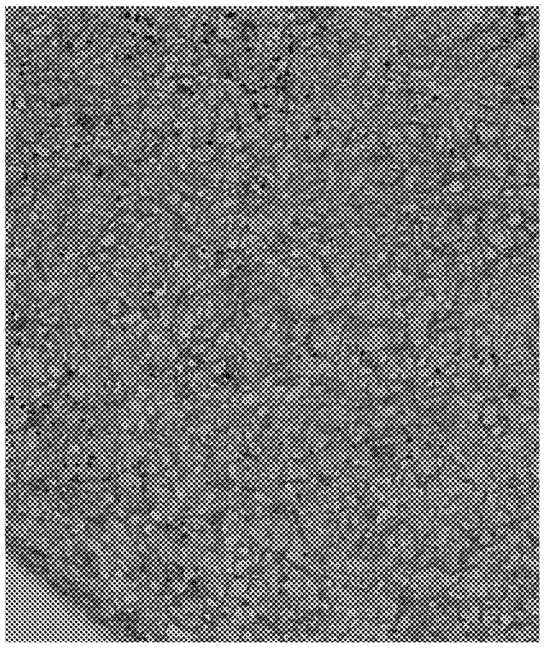
FIG. 19A-FIG. 19B illustrates immunohistochemical analysis of 5T4-dependent localization of bispecific constructs ALG.APV-209, ALG.APV-210, and ALG.APV-004 to 5T4+ (FIG. 19A) and 5T4− (FIG. 19B) tumors.
Figure 19A:
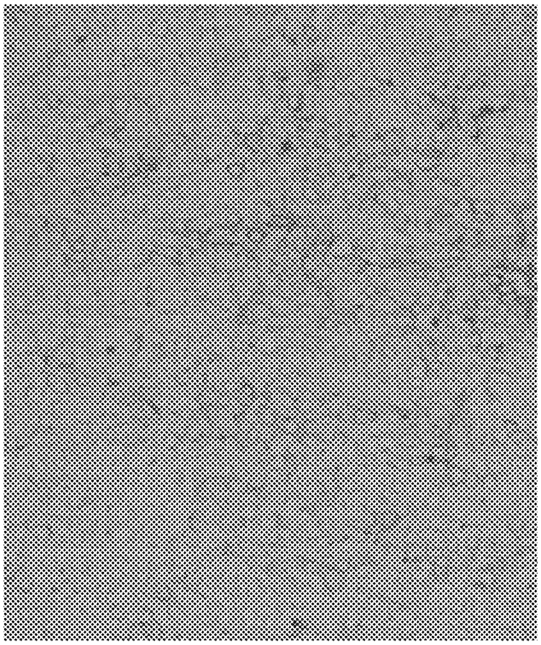

The localization was further demonstrated by immunohistochemistry (FIGS. 19A and 19B and Table 22). The bispecific antibodies bound strongly to 5T4 positive tumors (B16-5T4, FIG. 19A) but not to the 5T4 negative tumors (B16.F10, FIG. 19B).

TABLE 22

| In vivo localization of bispecific constructsand vehicle controls | | |
|---|---|---|
| Treatment | 5T4-negative tumors | 5T4-positive tumors |
| ALG.APV-209 | — | +++ |
| ALG.APV-210 | — | +++ |
| ALG.APV-004 | — | +++ |
| Vehicle | — | — |

Example 13: In Vitro Activity of a 5T4-CD137 Bispecific Antibody in an IFNγ Release Assay Using Human CD8 T Cells and 5T4-CT26 Tumor Cells The functional activity of the 5T4-CD137 bispecific antibody ALG.APV-210 was evaluated in a CD8 T cell assay, where CD8 T cells, stimulated with CD3 antibodies coated on beads, were co-cultured in plates with CT26 tumor cells expressing different levels of 5T4.

CT26 tumor cells, a murine colon carcinoma cell line (ATCC® CRL-2638) was previously transfected to express human 5T4 and then single cell sorted using flow cytometry to generate single cell clones expressing either high or low levels of human 5T4 (for receptor density, see Table 23). 5T4-CT26 tumor cells or non-transfected wildtype cells (CT26 wt) were UV irradiated using a UVB crosslinker (AnalytikJena, Lamp: 254 nm). After irradiation of the plate, the cells were washed once in medium and then resuspended at a concentration of $4\times10^6$ cells/ml in new growth medium R10 (RPMI, Gibco #61870010 containing 10% heat inactivated FBS, Hyclone #SV30160 lot RB35944 and 10 mM Hepes, Gibco #15630056). 50 μL ($2\times10^5$ cells/well) of the UV-irradiated CT26-h5T4$^{high}$, CT26-h5T4$^{low}$ or CT26 wt cells were added to TC treated assay plates (Eppendorf #0030 730.119) and incubated in 37° C. overnight.

TABLE 23

| 5T4 receptor density on human 5T4 transfected and single cell sorted CT26 cells | |
|---|---|
| CT26 cell clone | 5T4 receptor density/cell |
| CT26-h5T4$^{high}$ | $1 \times 10^6 \pm 2 \times 10^5$ |
| CT26-h5T4$^{low}$ | $5 \times 10^4 \pm 1 \times 10^4$ |
| CT26 wt | 0 |

The following day after UV irradiation of the CT26 cells, human PBMC were isolated by density gradient centrifugation using Ficoll-Paque (GE Healthcare #17-1440-02) from leucocyte concentrates obtained from healthy donors (Clinical Immunology and Transfusion Medicine, Labmedicin Region Slåne, Lund Sweden). CD8+ cells were enriched by negative selection using the CD8+ T cell isolation kit (Miltenyi 130-096-495).

The bispecific antibody ALG.APV-210 was diluted in a serial dilution in R10 medium and 50 μL was added to each well of the assay plates and incubated at 37° C. for 30 min, prior to the addition of 50 μL of αCD3 beads ($4\times10^8$/mL of anti-CD3 antibodies clone: OKT-3, Affymetrix eBioscience #16-0037-85, coated on beads, diluted to $2\times10^6$/mL) at a 1:1 CD8+ T cell to beads ratio, followed by the addition of 50 μL of the effector cells (enriched CD8+ cells, $2\times10^6$/mL or $1\times10^5$/well). The assay plates were incubated for 72 h at 37° C., and culture supernatant harvested. IFNγ levels in the supernatants were measured by ELISA (BD OptiEIA #555142). EC50 was determined by non-linear regression log (agonist) vs. Normalized response (variable slope) using GraphPad Prism 7. TOP value (maximal functional effect) was determined by calculating the mean of the two highest values of IFNγ production in the culture supernatant. The experiment was performed 5 times, including in total 12 donors.

Figure 20:
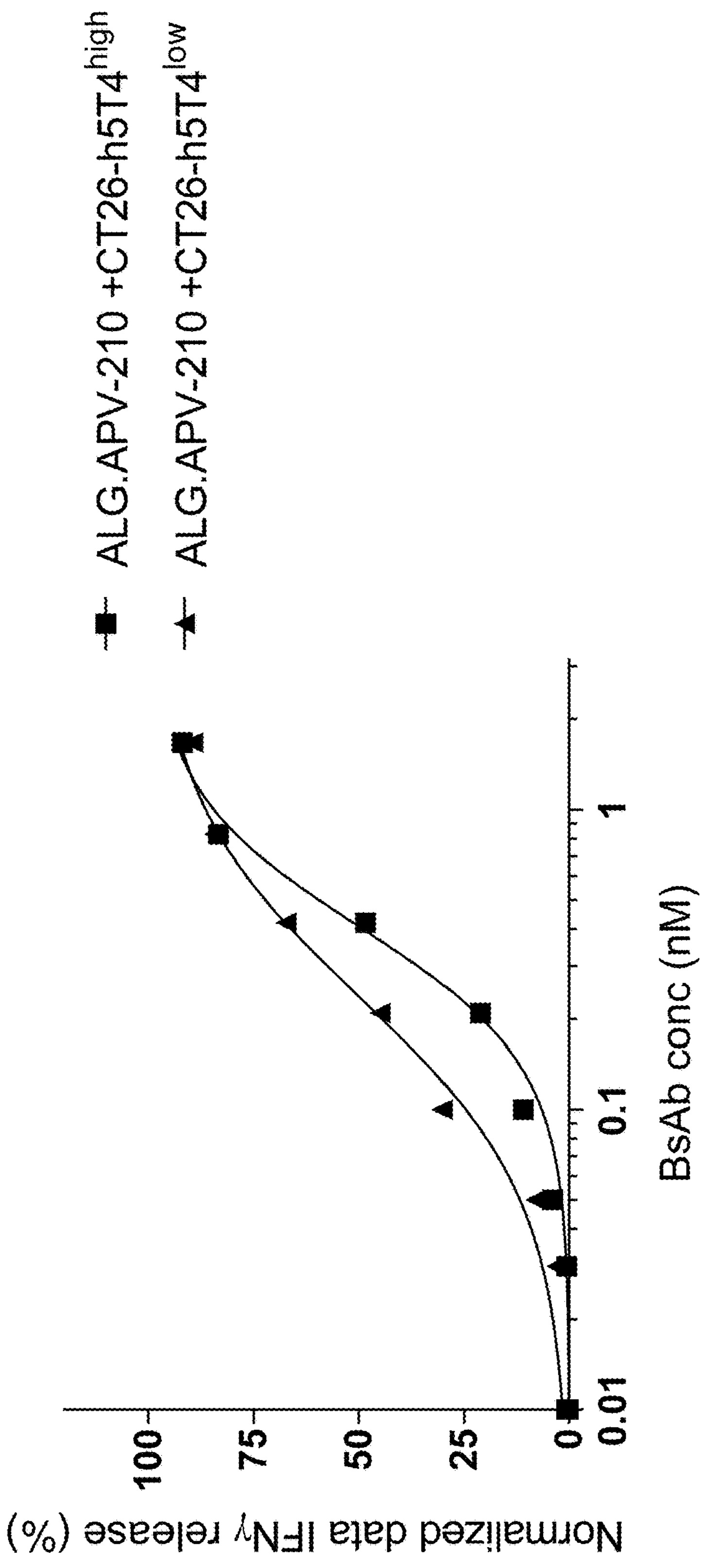
FIG. 20 shows the IFNγ response of human CD8 T cells cultured with the bispecific antibody ALG.APV-210 in the presence of CT26 cells expressing different levels of 5T4.

The study provided the functional effect of the CD137-5T4 bispecific antibody ALG.APV-210 using human CD8 T cells (the effector cells) co-cultured in plates with CT26 cells expressing different levels of 5T4 (for crosslinking of CD137 via binding to 5T4). As shown in FIG. 20, the bispecific CD137-5T4 antibody ALG.APV-210 induces a potent T cell activation, measured by IFNγ release, in a dose-dependent manner in the presence of CT26 cells expressing either high (CT26-h5T4$^{high}$) or low (CT26-h5T4$^{low}$) levels of 5T4. IFNγ release is presented in FIG. 20 as normalized data of ALG.APV-210; mean values of 12 donors from 5 pooled experiments are shown.

Figure 21B:
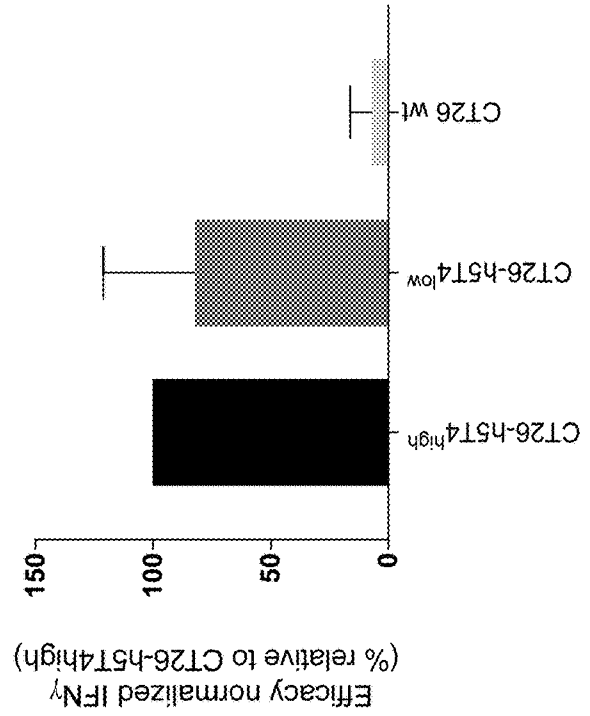
FIG. 21A-FIG. 21B show the maximum IFNγ release of human CD8 T cells cultured with the bispecific antibody ALG.APV-210 in the presence of CT26 cells expressing different levels of 5T4.
Figure 21A:
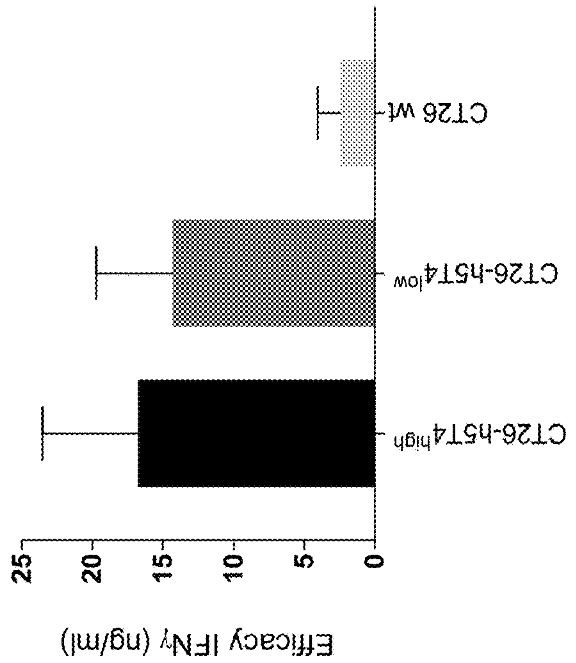

Table 24 shows the $EC_{50}$ of ALG.APV-210 in the CD8 T cell assay in the presence of human 5T4 expressing CT26 cells. Log (agonist) vs. Normalized response (variable slope) mean values and 95% CI of 12 donors from 5 pooled experiments is shown in the Table. As shown in FIGS. 21A and 21B, the maximal functional effect of ALG.APV-210 was dependent on the expression level of 5T4 on the CT26 cells, as illustrated by a slightly lower secretion of maximal IFNγ release in co-culture with CT26-h5T4$^{low}$ cells compared to co-cultures with CT26-h5T4$^{high}$ cells (the maximal effect of CT26-h5T4$^{low}$ was 82% of CT26-h5T4$^{high}$). In the absence of 5T4-induced crosslinking using CT26-wt cells there is no or very low T cell activity (7% of maximal effect of CT26-h5T4$^{high}$). Max IFNγ release is presented in FIG. 21 as absolute values (ng/mL) (FIG. 21A) or normalized values relative to CT26-h5T4$^{high}$ (FIG. 21B). Mean and SEM values of 12 donors from 5 pooled experiments are shown.

TABLE 24

| Binding ($EC_{50}$) of ALG.APV-210 in the presence of human 5T4+ CT26 cells | | |
|---|---|---|
| | ALG.APV-210-h5T4$^{high}$ | ALG.APV-210-h5T4$^{low}$ |
| $EC_{50}$ (nM) | 0.41 | 0.24 |
| 95% CI | 0.36 to 0.46 | 0.20 to 0.28 |

Example 14: Binding of a 5T4-CD137 Bispecific Antibody to CD137 on Human and Cynomolgus Primary CD3-Stimulated CD8 T Cells A study was conducted to compare the relative binding of ALG.APV-210 towards human and cynomolgus CD137 expressed on activated primary CD8 T cells (gated from CD3-stimulated PBMC).

Materials and Methods

In order to detect ALG.APV-210 binding to primary human and cynomolgus cells in FACS, ALG.APV-210 was first biotinylated. The quality of the biotinylated protein was assessed using HPLC and the impact on binding to its targets was assessed using ELISA. ANC017, an antibody in the ADAPTIR format with the same framework as ALG.APV-210 (germline CDRs) was used as a negative control and was also biotinylated.

Isolation and Stimulation of Human PBMC:

Human PBMC were isolated by density gradient centrifugation using Ficoll-Paque (GE Healthcare #17-1440-02) from leucocyte concentrates obtained from 3 human healthy donors (Clinical Immunology and Transfusion Medicine, Labmedicin Region Slåne, Lund Sweden). Non-tissue treated 96 well plates (Nunc #268200) were pre-coated overnight at 4° C. with 10 μg/mL αCD3, clone OKT3 (Affymetrix eBioscience #16-0037-85). The following day, plates were washed in PBS, and human PBMC diluted in R10 (RPMI, Gibco #61870010 containing 10% heat inactivated FBS, Hyclone #SV30160 lot RB35944 and 10 mM Hepes, Gibco #15630056), were added at a concentration of $0.2\times10^6$ cells/well and incubated in 37° C. in wells with or without CD3 stimulation for 48 h.

Isolation and Stimulation of Cynomolgus PBMC:

Cynomolgus PBMC were isolated from 20 mL of cynomolgus monkey blood from 3 different donors, obtained from Silabe, France by density gradient centrifugation using Lympholyte-mammal (Cedarlane labs) according to manufacturer's instructions. Non-tissue treated 96 well plates were pre-coated overnight at 4° C. with 3 μg/mL α-monkey CD3, clone FN-18 (Invitrogen #APS0301). The cynomolgus PBMC were then stimulated identically as the human PBMC described above FACS Staining and Analysis of CD8 T Cells:

Following 48 h of incubation with or without CD3, human and cynomolgus PBMC were harvested, pooled, recounted and diluted in FACS buffer (PBS+0.5% BSA, 0.05% $NaN_3$) to a concentration of $5\times10^6$ cells/mL. 50 μL ($0.25\times10^6$ cells) of cell solution was added to a 96-well FACS staining plate (Falcon #351190). Following 10 min of Fc-blocking in RT using Beriglobin (hIgG, 200 μg/mL), cells were washed in FACS buffer and then incubated for 1 h in 4° C. with 100 μL of the biotinylated ALG.APV-210 or negative control. The antibodies were added in a serial dilution starting either at 5 μg/mL titrating down in a 12 step 1/3 dilution down to 0.0003 μg/mL (exp 1) or 1 μg/mL titrating down in a 12 step 1/2 dilution down to 0.0005 μg/mL (exp 2). Following 2× washing with FACS buffer, cells were incubated for 30 min in 4° C. with 50 μL of a secondary antibody (streptavidin-APC, BD #554067) and 50 μL of fluorescent conjugated antibodies against different T cell surface markers (CD4-FITC #550628, CD3-PECy7 #557749 and CD8-APC-H7 #5601797, BD). Following washing in PBS, cells were stained in 15 min in 4° C. with 50 μL of fixable viability stain BV510 (in order to gate away non-viable cells), washed again and then re-suspended in 130 μL of cell fixation (BD CellFIX 10×BD, #340181, diluted in MQ H2O). Cells were analysed for ALG.APV-210 binding using flow cytometry by gating on viable, single cells expressing CD3 and CD8. MFI values (FMO subtracted) from 2 independent experiments as well as normalized pooled data from 2 experiments and $EC_{50}$-values were determined and plotted using GraphPad Prism 7, non-linear regression log (agonist) vs. normalized response-variable slope, n=6 donors/group.

Results

Figure 22A:
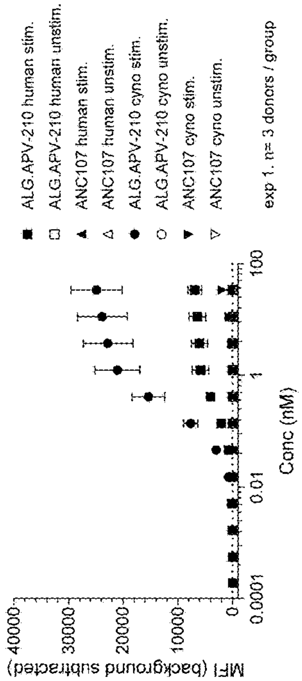
FIG. 22A-FIG. 22C show ALG.APV-210 or ANC107 (isotype control) binding to primary CD8 T cells gated from CD3-stimulated or unstimulated human and cynomolgus PBMC. The MFI (and SEM) from 2 independent experiments are shown in FIG. 22A and FIG. 22B.
Figure 22B:
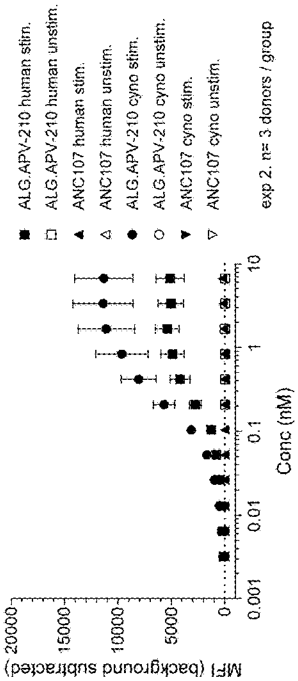
Figure 22C:
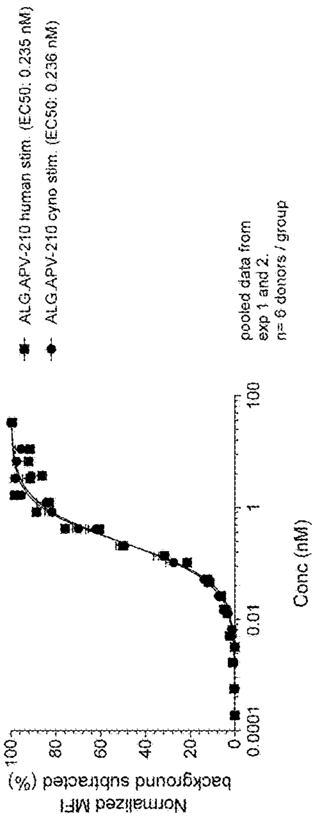

In ELISA tests, the binding of biotinylated ALG.APV-210 to CD137 was similar to that of the non-biotinylated ALG.APV-210 (0.6 nM vs. 0.7 nM). The binding ($EC_{50}$) of the biotinylated ALG.APV-210 to its immunomodulatory target CD137 when expressed on activated primary human and cynomolgus CD8 T cells from CD3 stimulated PBMC was assessed and compared between the two species as well as to unstimulated cells. As shown using MFI of all CD3+ CD8+ cells in FIGS. 22A, 22B, and 22C, and Table 25, ALG.APV-210 binds to both human and cynomolgus CD8 T cells in a dose-dependent manner, but not to unstimulated cells. Binding to the negative control, ANC107, was low/undetectable for CD3-stimulated or unstimulated human PBMC or cynomolgus PBMC cells. The maximum amount (MFI) of ALG.APV-210 bound to CD3-stimulated cynomolgus PBMC was higher in comparison to human PBMC, most likely due to a higher proportion of the CD3-stimulated cynomolgus PBMC expressing CD137, or due to a generally higher expression of CD137 on the cynomolgus CD8 T cells. It is uncertain whether the cynomolgus cells were more sensitive towards CD3 stimulation in comparison to the human cells, and therefore upregulated CD137 more, since the cells were stimulated with different clones of anti-CD3 due to lack of cross-reactivity of the anti-CD3 reagents between species.

TABLE 25

ALG.APV-210 binding ($EC_{50}$) to human and cynomolgus CD8 T cells

| ALG.APV-210 binding (nM) | Human CD8 T cells (gated from CD3 stim PBMC) | Cynomolgus CD8 T cells (gated from CD3 stim PBMC) |
|---|---|---|
| $EC_{50}$ (nM) | 0.235 | 0.236 |
| 95% CI (nM) | 0.21 to 0.26 | 0.22 to 0.25 |

Figure 23A:
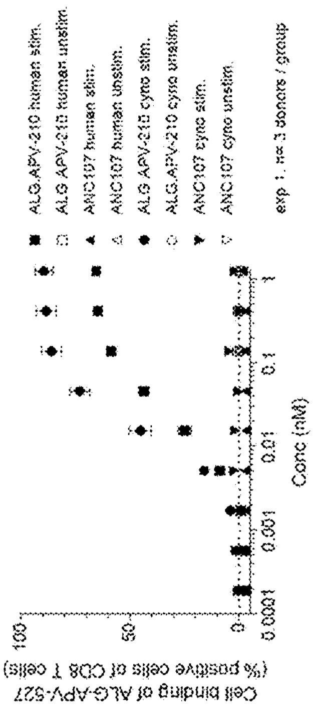
FIG. 23A-FIG. 23C show ALG.APV-210 or ANC107 (isotype control) binding to primary CD8 T cells gated from CD3-stimulated or unstimulated human and cynomolgus PBMC. Percentage and SEM of ALG.APV-210 binding to CD8 T cells from 2 independent experiments are shown in FIGS. 23A and 23B.
Figure 23B:
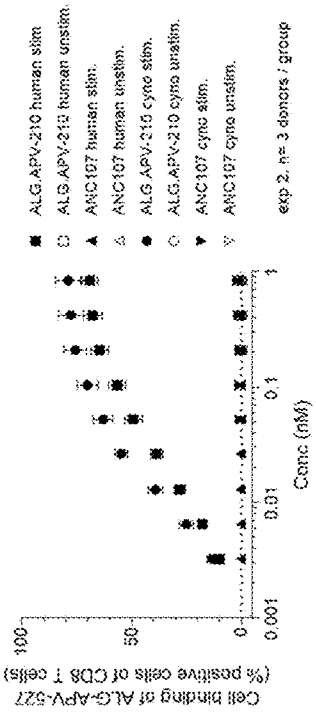
Figure 23C:
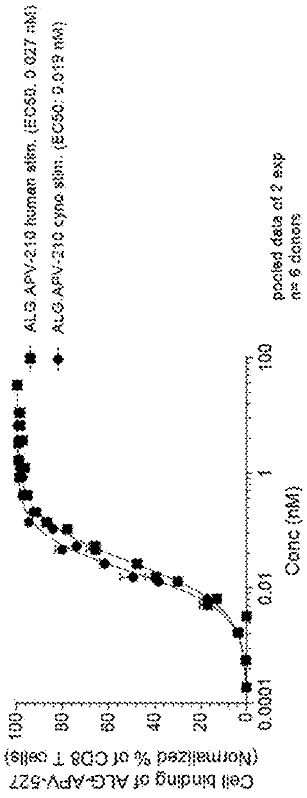

ALG.APV-210 binding was also assessed by looking at the percentage of CD8 T cells bound by ALG.APV-210. There was a larger percentage of cynomolgus CD8 T cells bound by ALG.APV-210 in comparison to the human CD8 T cells (71-96% for cynomolgus, 65-76% for human, see FIGS. 23A, 23B, and 23C). The binding $EC_{50}$ values were also calculated on the MFI of the CD137 positive cells, and the results was an $EC_{50}$ of 0.17 nM for binding to human CD137 and 0.20 nM for cynomolgus monkey CD137.

Taken together, the results of the study showed that ALG.APV-210 binds with a similar $EC_{50}$: 0.2 nM to CD3-stimulated primary CD8 T cells of human and cynomolgus, but not to unstimulated cells.

Example 15: In Vitro Activity of a 5T4-CD137 Bispecific Antibody in an IFNγ Release Assay Using Human or Cynomolgus CD8 T Cells in the Presence of 5T4

A study was conducted to compare the functional activity and determine $EC_{50}$ of ALG.APV-210 in an agonist assay using either human or cynomolgus monkey CD8 T cells in the presence of plate immobilized 5T4.

Materials and Methods

CD8 T cells were suboptimally stimulated with plate immobilized CD3 antibodies and activated by crosslinking of CD137 via ALG.APV-210 binding to plate immobilized 5T4-Fc. CD8 T cell activation was measured by determining IFNγ release in the cell culture supernatant.

Isolation and Assay Setup with Human CD8 T Cells:

Human PBMC were isolated by density gradient centrifugation using Ficoll-Paque (GE Healthcare #17-1440-02) from leucocyte concentrates obtained from healthy donors (Clinical Immunology and Transfusion Medicine, Labmedicin Region Slane, Lund Sweden). CD8+ cells were enriched by negative selection using the CD8+ T cell isolation kit (Miltenyi #130-096-495). Non-tissue treated 96-well assay plates were coated overnight at 4° C. with 3 μg/mL anti-CD3 antibody (clone: OKT-3, Affymetrix eBioscience #16-0037-85). The following day, plates were washed in PBS and coated with 5 μg/mL 5T4-Fc for 2 h at 37° C. After 5T4-Fc immobilization, assay plates were washed in PBS and blocked for a minimum of 30 minutes with R10 (RPMI, Gibco #61870010 containing 10% heat inactivated FBS, Hyclone #SV30160 lot RB35944 and 10 mM Hepes, Gibco #15630056). ALG.APV-210 were diluted in a serial dilution in R10 and 50 μL was added in triplicates to the assay plate 30 minutes prior to the addition of 50 μL of the effector cells (enriched CD8 T cells, $1.4\times10^6$ cells/mL or $0.07\times10^5$ cells/well). Assay plates were incubated for 72 h at 37° C., and culture supernatant harvested. IFNγ levels in the supernatant was measured by ELISA (BD OptiEIA #555142). The experiment was performed 4 times, including in total 8 donors.

Isolation and assay setup with cynomolgus CD8 T cells:

Cynomolgus (*Macaca fascicularis*, adult males, 3-15 years) whole blood obtained from Silabe, France was used. Red blood cells were removed by red blood cell lysis (BD Pharma lyse, BD Biosciences, #555899) according to the manufactures protocol. $CD8^+$ cells were enriched by positive selection using the CD8 MicroBead kit (Miltenyi Biotec, #130-091-112). Plates coated overnight at 4° C. with 1 μg/mL α-monkey CD3, clone FN-18 (Invitrogen, #APS0301), washed and coated with 5 μg/mL 5T4-Fc for 2 h at 37° C. After 5T4-Fc coating, plates were washed and blocked for a minimum of 30 minutes with R10. ALG.APV-210 was diluted in R10 and 50 μL was added in triplicates to the plates 30 minutes before addition of 50 μL of CD8 T cells ($0.07\times10^6$ cells/well). Assay plates were incubated for 72 h at 37° C., and culture supernatant harvested. IFNγ levels in the supernatants were measured by ELISA (Monkey IFNγ ELISA development kit, MABTECH, #3421M-1H-20). The experiment was performed 3 times, including in total 8 donors. Obtained IFNγ levels from each human and cynomolgus donor were normalized and means were calculated. The mean of the normalized IFNγ levels from all 8 human or cynomolgus donors were pooled and the $EC_{50}$ was determined by non-linear regression (log agonist vs normalized response, variable slope) using GraphPad 7.

Results

Figure 24:
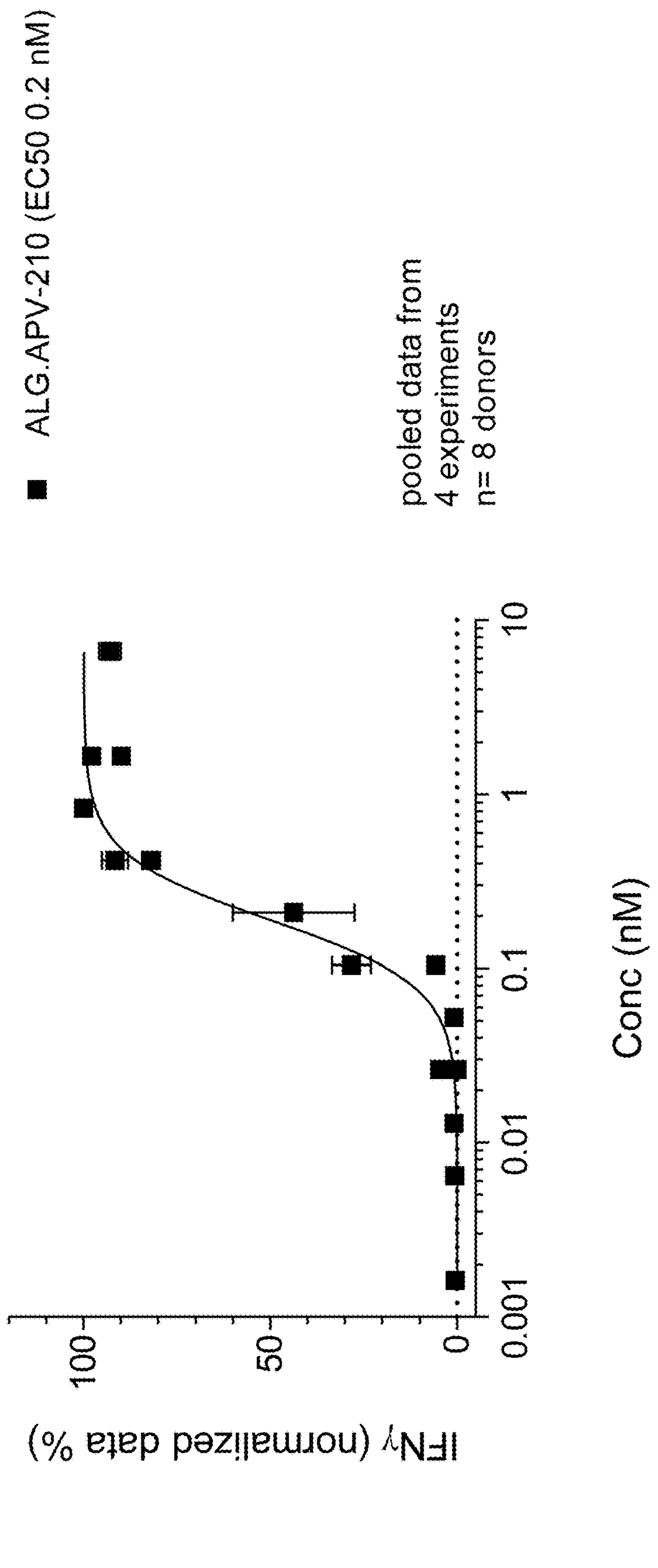
FIG. 24 shows the agonistic function of ALG.APV-210 on human CD8 T cells.
Figure 25A:
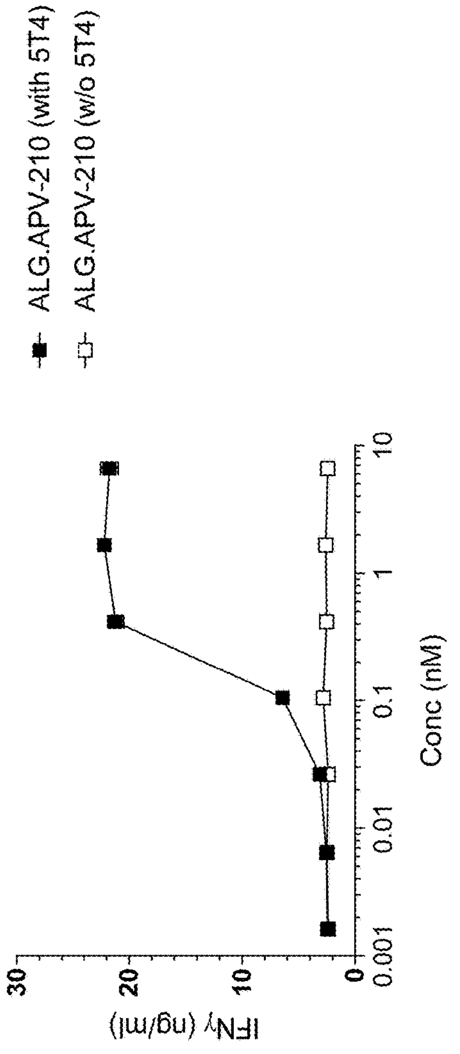
FIG. 25A-FIG. 25B show the agonistic function of ALG.APV-210 on human CD8 T cells from individual representative donors (FIG. 25A and FIG. 25B).
Figure 25B:
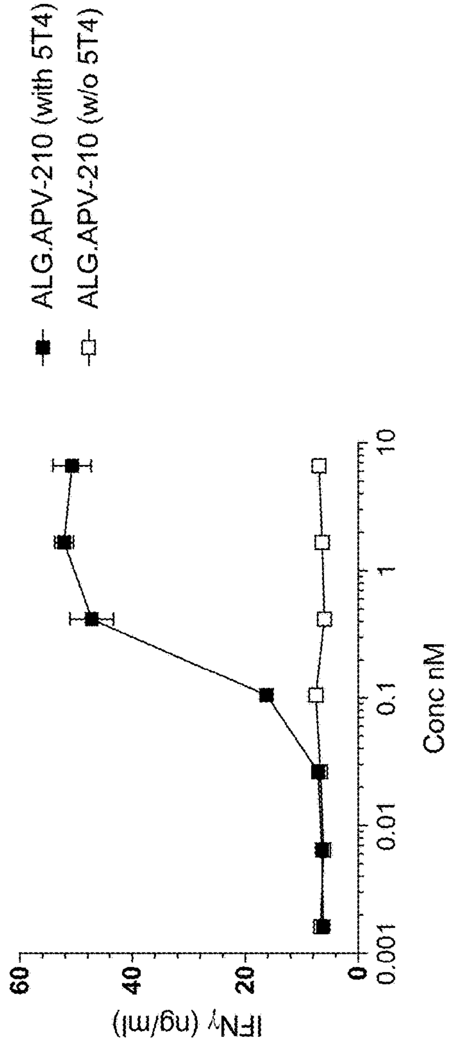

As shown in FIG. 24 and in Table 26, in the human CD8 T cell assay, the bispecific CD137-5T4 antibody ALG.APV-210 had a high functional activity with an $EC_{50}$ of 0.2 nM. Normalized IFNγ levels from 4 experiments and a total of 8 donors were pooled and the $EC_{50}$ determined by nonlinear regression using GraphPad 7. Mean and SEM are presented in FIG. 24. Absolute mean IFNγ values from two donors from one representative experiment is shown in FIGS. 25A and 25B. The top values of the anti-CD3 reagents as well as background IFNγ levels varies from donor to donor within one experiment. Due to the observed variations between donors the data was normalized prior to the analysis of the pooled data set. CD8 T cell activation of ALG.APV-210 was assessed both in the presence and absence of 5T4-Fc to verify a 5T4 crosslinking dependency. The results showed that the bispecific CD137-5T4 antibody ALG.APV-210 induces a potent T cell activation, measured by IFNγ release, when cross-linked by 5T4-; in the absence of 5T4 there is no T cell activity (FIGS. 25A and 25B).

Figure 26:
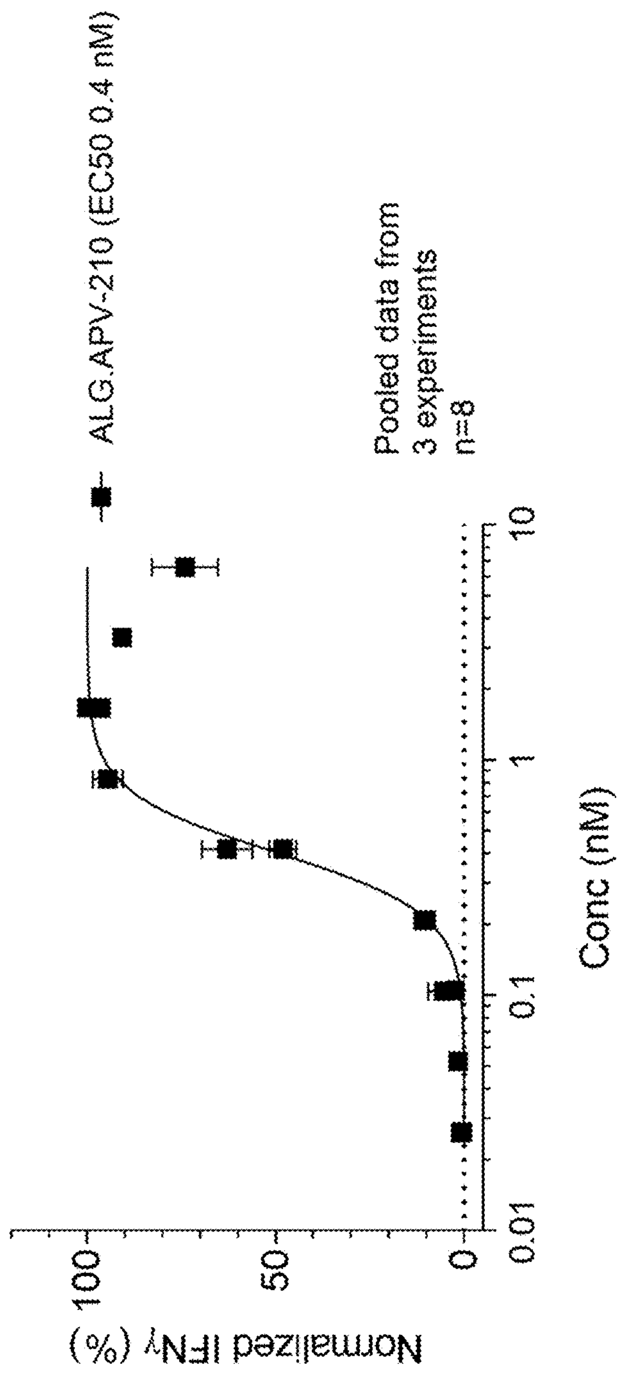
FIG. 26 shows the agonistic function of ALG.APV-210 on cynomolgus CD8 T cells.
Figure 27A:
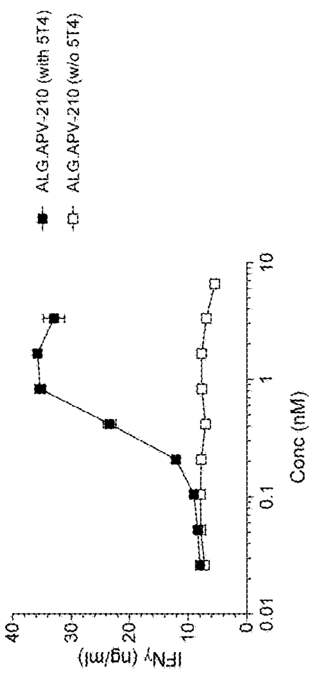
FIG. 27A-FIG. 27C show the agonistic function of ALG.APV-210 on cynomolgus CD8 T cells from individual representative donors (FIG. 27A, FIG. 27B, and FIG. 27C). The figures show a dose response dependent IFNγ production by cynomolgus CD8 T activated with ALG.APV-210 in the presence of 5T4-Fc.
Figure 27B:
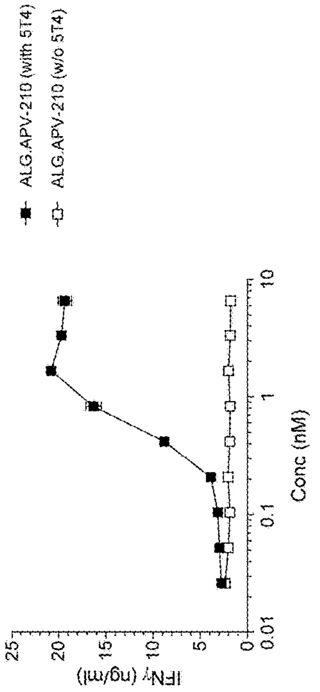
Figure 27C:
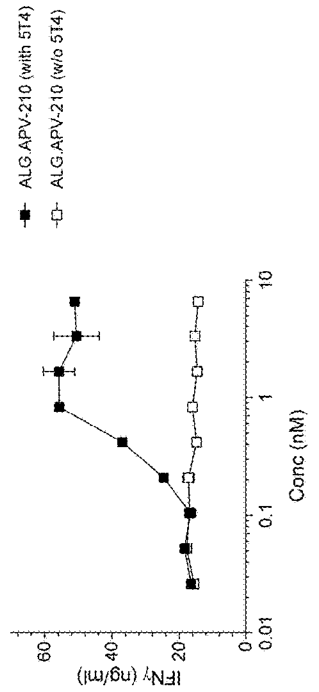

The functional effect of the CD137-5T4 bispecific antibody ALG.APV-210 when using cynomolgus CD8 T cells was also assessed. Based on pooled data from 3 experiments and a total of 8 donors, the $EC_{50}$ of ALG.APV-210 in the cynomolgus CD8 T cell assay was determined to be 0.4 nM (FIG. 26 and Table 26). Absolute mean values from 3 donors from one representative experiment is also shown in FIGS. 27A, 27B, and 27C. Similar to the human setting, the absolute values (including top values and background IFNγ levels) also vary between individual cynomolgus donors within one experiment. Therefore, the data was normalized prior to the $EC_{50}$ analysis of the pooled data set. CD8 T cell activation of ALG.APV-210 was assessed both in the presence and absence of 5T4-Fc, to verify a dependency of 5T4-induced crosslinking of CD137. As shown in FIGS. 27A-27C, the agonistic effect of ALG.APV-210 is 5T4-dependent in the cynomolgus CD8 T cell assay in a similar manner as observed in the human setting. Each of FIGS. 27A, 27B, and 27C show absolute mean and SEM values of IFNγ of 3 individual donors from one representative experiment. As negative control, wells without (w/o) 5T4 were included.

TABLE 26

Binding of ALG.APV-210 in human and cynomolgus CD8 T cell assay

| ALG.APV-210 binding (nM) | Human CD8 T cells | Cynomolgus CD8 T cells |
|---|---|---|
| $EC_{50}$ | 0.2 | 0.4 |
| 95% CI | 0.17-0.21 | 0.37-0.44 |
| HillSlope | 2.3 | 3.4 |

The study showed that the $EC_{50}$ of the CD137-5T4 bispecific antibody ALG.APV-210 in a functional CD8 T cell activation assay was comparable between human (0.2 nM) and cynomolgus monkey (0.4 nM). The T cell activation was mediated by crosslinking of CD137 which is dependent on 5T4 in both human and cynomolgus CD8 T cell assays.

Example 16: In Vitro Activity of a 5T4-CD137 Bispecific Antibody ALG.APV-210 in a T-Cell IFN-γ Secretion and T Cell Proliferation Assays The agonistic function of the 5T4-CD137 bispecific molecule ALG.APV-210 at inducing target-dependent activation of CD137 was evaluated in a T-cell IFN-γ secretion assay and a T-cell proliferation assay using unseparated peripheral blood mononuclear cells (PBMC). In order to test the function of the anti-CD137 bispecific constructs, primary PMBC were stimulated with anti-CD3 antibodies to upregulate CD137, which is not expressed, or is expressed at low levels, on resting T cells. Co-stimulation of primary T cells through the TCR and CD137 enhances T-cell secretion of the cytokine interferon gamma (IFN-γ).

Methods

IFN-γ Secretion Assay:

Peripheral blood mononuclear cells (PBMC) were isolated from healthy human blood using standard ficoll gradients. The isolated cells were washed in saline buffer to remove platelets. PBMC were cultured with CHO-K1 cells transfected with human 5T4 or empty vector, at approximately 120,000 PBMC to 30,000 CHO-K1 cells in 96-well plates. Anti-CD3 antibody OKT3 (eBioscience) was added to all the wells at a concentration of 1 ng/mL. Cells were cultured in a total volume of 200 μL of RPMI 1640 media supplemented with 10% fetal bovine serum, sodium pyruvate, antibiotics and non-essential amino acids. Plates were incubated at 37° C., 5% $CO_2$ in humidified incubators for 72 hours. 100 μL of media were collected after 72 hours of stimulation of PBMC cultures primed with a sub-optimal concentration of anti-CD3 antibodies to induce upregulation of CD137. Levels of the IFN-γ were measured in the supernatant using Milliplex® kits (Millipore) using the manufacturer's instructions. Data was collected in a Bio-Plex Reader 200 System (Bio-Rad). Nonlinear regression analysis to determine $EC_{50}$ values was performed in GraphPad Prism 6® graphing and statistics software.

T-Cell Proliferation Assay:

PBMC were isolated from healthy human blood using standard ficoll gradients. Once isolated, the cells were washed in saline buffer to remove platelets. PBMC were labeled with CellTrace™ Violet (Thermofisher), washed, and cultured with irradiated CHO-K1 cells transfected with human 5T4 at approximately 120,000 PBMC to 30,000 CHO-K1 cells in 96-well plates. CHO-K1 cells were irradiated (x-ray Cell Rad irradiator, Faxitron Bioptics, LLC), and washed in medium before plating with PBMC. Anti-CD3 antibody OKT3 (eBioscience) was added to all the wells at a concentration of 5 ng/mL. Cells were cultured in a total volume of 200 μL of RPMI 1640 media (GIBCO) supplemented with 10% human serum (SIGMA), sodium pyruvate, antibiotics and non-essential amino acids. Plates were incubated at 37° C., 5% $CO_2$ in humidified incubators for 96 hours.

Supernatants were removed and cells were labeled in the same assay plates with antibodies to CD4, CD8 and CD5 in PBS buffer with 2% BSA and 2 mM EDTA, for 30 min on ice. 7AAD (SIGMA) was added to enable exclusion of dead cells in the analysis. After washing, cells were resuspended at 120 μL/well, and 70 μL/well volumes were collected from each well and analyzed in a flow cytometer (a LSR-IITM, BD Biosciences). Data analysis was performed using Flowjo software in two ways: calculating the % of CD8+ live T cell events (CD4− CD8+ CD5+, 7AAD−) that had undergone at least one cell division, or by counting the number of CD8+ live T cell events (CD4− CD8+ CD5+, 7AAD−). In both cases the analysis was performed after gating on lymphocytes using FSC versus SSC parameters. Each condition was tested in duplicates and the averages of each duplicate set were graphed using GraphPad Prism 6® graphing and statistics software.

Results and Conclusions

Figure 32A:
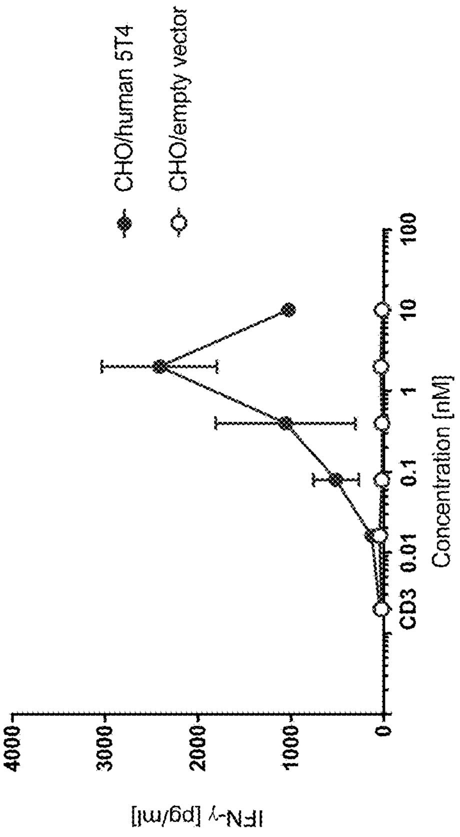
FIG. 32A-FIG. 32B show induction of IFN-γ secretion by the bispecific molecule ALG.APV-210 in whole PBMC cultures, from two different human PBMC donors (FIG. 32A and FIG. 32B).
Figure 32B:
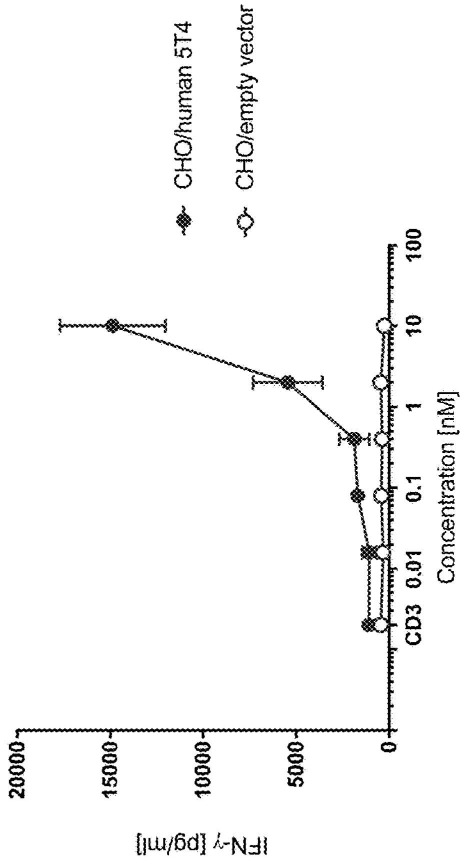

Results of the IFN-γ secretion experiments are shown in FIG. 32. Every data point in the graphs represents the average of duplicate wells. Addition of anti-CD3 alone, with no bispecific antibodies, induced very low levels of IFN-γ. The addition of the ALG.APV-210 bispecific molecule increased the secretion of IFN-γ in a dose-dependent manner. Baseline levels of IFN-γ induced by the anti-CD3 antibody, as well as the total amount of IFN-γ secretion induced by ALG.APV-210 varied by PBMC donor (FIG. 32A v. FIG. 32B). Enhanced secretion of IFN-γ was observed in the presence of CHO-K1 cells expressing 5T4, but not in the presence of CHO-K1 cells transfected with the empty vector control. Therefore, the bispecific molecule ALG.APV-210 requires engagement of 5T4 to stimulate CD137 function as measured by IFN-γ secretion.

Figure 33B:
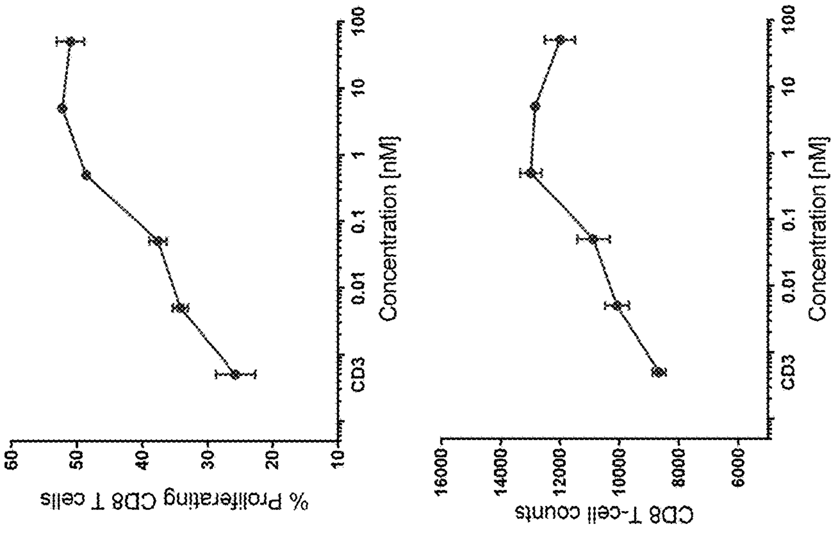
FIG. 33A-FIG. 33B show CD8+ T-cell proliferation induced by the bispecific molecule ALG.APV-210 in whole PBMC cultures, from two different human PBMC donors (FIG. 33A and FIG. 33B).
Figure 33A:
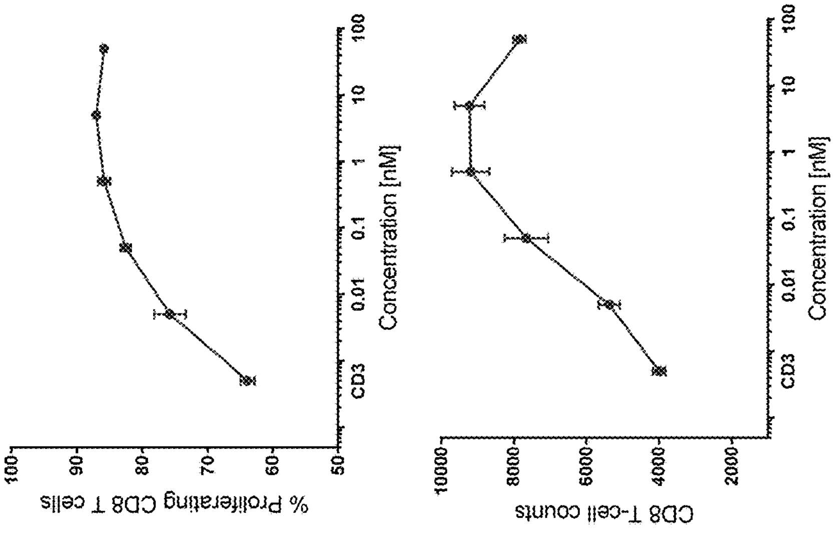

Results of the T cell proliferation experiments are shown in FIG. 33. Every data point in the graphs represents the average of duplicate wells. Polyclonal proliferation of CD8+ T cells was evaluated after 96 hours of stimulation with priming at a sub-optimal concentration of anti-CD3 antibody. Addition of anti-CD3 alone, with no bispecific antibody, induced low levels of CD8+ T-cell proliferation. The addition of ALG.APV-210 increased the proliferation of CD8+ T cells in a dose-dependent manner (FIG. 33A and FIG. 33B). Both the percentages of cells undergoing cell division (top panels) and the total cell counts (bottom panels) collected per well were consistent with robust cell division and accumulation of divided CD8+ T cells in the wells. The results were consistent across multiple donors.

Example 17: Functional Reporter Activity of ALG.APV-210 in the Presence of Various Human Tumor Lines Expressing a Range of 5T4 Protein Densities Experiments were conducted to determine whether the ALG.APV-210 construct has binding and functional reporter activity across multiple human tumor cell lines expressing 5T4 at a range of densities on the cell surface. The maximal binding capacity of ALG.APV-210 will vary depending on the cells' expression level of 5T4 tumor antigen. Binding of ALG.APV-210 was therefore tested on 3 tumor cells lines (MDA-MB-231, H1975, and TF-1) naturally expressing a range of 5T4 densities, as well as CHO-K1 cells stably transfected with 5T4 (CHO/5 T4).

Material and Methods

5T4 Binding Assay:

A 3-fold titration of ALG.APV-210 construct (ranging from 100 nM to 0.14 nM) was incubated with the human 5T4-expressing cell lines for 40 minutes in FACS buffer at 4° C., washed 3 times, and detected with PE-labeled, goat-anti-human Fc secondary antibody (Jackson ImmunoResearch). Binding of ALG.APV-210 was detected by flow cytometry. All samples were run in duplicates. Nonlinear regression analysis to determine $EC_{50}$ values was performed in GraphPad Prism 6® graphing and statistics software.

5T4 Protein Density:

The surface protein density of 5T4 present on each cell line was examined using Quantibrite™ Beads (BD Pharmingen). Quantibrite™ Beads were acquired using the exact cytometer settings used to acquire the cells for the binding curves with ALG.APV-210. The 4 bead populations were gated and the geometric mean fluorescence was determined for each peak. A linear regression $Log_{10}$ of PE molecules per bead was plotted against the $Log_{10}$ fluorescence using the equation y=mx+c, where y equals $Log_{10}$ fluorescence and x equals $Log_{10}$ PE molecules per bead. From that, the number of PE molecules (5T4) per cell could be calculated. For this particular assay the equation was y=1.036x−1.478. All fluorescence mean values were calculated using the geometric mean of the samples, as suggested by the manufacturer's protocol.

CD137 Reporter Assay:

Jurkat/CD137 transfectants carrying a luciferase reporter gene under the control of an NF-κB promoter (Promega) were cultured with H1975, TF-1, MDA-MB-231, or CHO/5T4 tumor cells at a ratio of 30,000 reporter cells to 60,000 target cells in 96-well plates. Five-fold concentrations of the ALG.APV-210 molecule, with final concentration ranging from 10 nM to 0.0006 nM, were added. Cells were cultured in a total volume of 100 μL of RPMI 1640 media supplemented with 1% fetal bovine serum, sodium pyruvate, antibiotics and non-essential amino acids. Plates were incubated at 37° C., 5% $CO_2$ in humidified incubators for 5 hours. 100 μL of Bio-Glow buffer (Promega) was added to each well, mixed, and incubated for 10 minutes before measuring luminescence. Luminescence was measured in a $MicroBeta^2$ 2450 Microplate Counter (Perkin Elmer). All data points represent duplicate samples. Nonlinear regression analysis to determine $EC_{50}$ values was performed in GraphPad Prism 6® graphing and statistics software. Every point in the curve represents the average of duplicate wells. The y-axis shows values in relative fluorescence units (RLU).

Results and Conclusions

Each of the tumor cell lines tested varied in the amount of 5T4 protein being expressed on the cell surface as determined using Quantibrite™ Beads. Thus, the ability of ALG.APV-210 to bind and be functionally active with a range of 5T4 expression could be examined.

Figure 34:
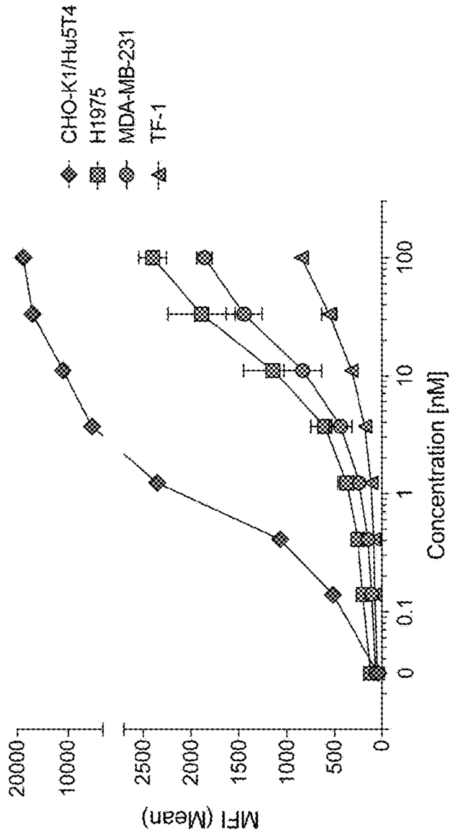
FIG. 34 shows binding of ALG.APV-210 to 5T4-expressing cell lines.

ALG.APV-210 bound to a range of 5T4 cell surface-expressing tumor cell lines. As shown in FIG. 34, CHO/5T4 have 10-fold higher 5T4 expression than the endogenously expressing 5T4 tumor cell lines. Of the three non-transfected tumor cell lines, H1975 had the highest 5T4 expression, whereas TF-1 cells had the lowest 5T4 protein density. MDA-MB-231 cells showed intermediate 5T4 expression. Surface 5T4 protein densities were calculated from the binding curves and show a range of molecules/cell from 17,000 to over 250,000. Table 27 shows 5T4 cell surface protein densities and binding $EC_{50}$ values generated from the binding curves. Density of 5T4 expression on tumor cell lines was calculated using a fluorescence standard.

TABLE 27

Summary of 5T4 densities and $EC_{50}$ ALG.APV-210

| Tumor line | 5T4 molecules/cell | $EC_{50}$ (nM) |
|---|---|---|
| CHO/5T4 | 278000 | 10 |
| H1975 | 43000 | 20 |
| MDA.MB-231 | 33000 | 21 |
| TF-1 | 18000 | 71 |

Figure 35:
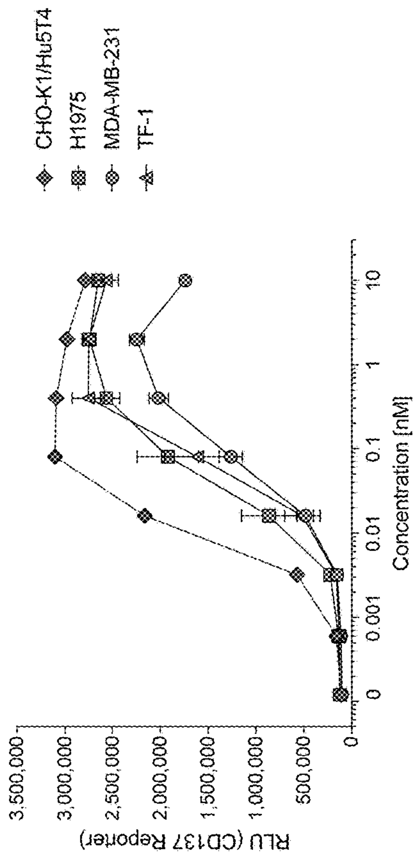
FIG. 35 shows agonist function of the bispecific construct ALG.APV-210 in Jurkat/NF-κB reporter cells after incubation in the presence of cells expressing a range of surface 5T4 protein densities.

FIG. 35 shows the results of the functional CD137 reporter assay. As shown, ALG.APV-210 was sufficiently able to induce NF-κB signaling when cross-linking CD137 via binding to CHO/hu5T4, H1975, MDA.MB.231 or TF-1 tumor lines, despite the range of cell surface 5T4 expression from 17,000 to over 250,000. Surface 5T4 protein density had an impact on maximum functional activity (Max RLU), with CHO/hu5T4 cells showing the highest RLU values. However, the three tumor cell lines induced robust reporter function. The results indicate that ALG.APV-210 functions as an agonist in the presence of 5T4-positive cells expressing a range of 5T4 densities. Table 28 shows the $EC_{50}$ and Max RLU induced with ALG.APV-210 in the CD137 reporter assay in the presence of the various human 5T4-expressing tumor lines.

TABLE 28

Summary of ALG.APV-210 $EC_{50}$ of and Max RLU

| Tumor line | $EC_{50}$ (nM) | Max RLU |
|---|---|---|
| CHO/5T4 | 0.0092 | 3092200 |
| H1975 | 0.037 | 2743132 |
| MDA.MB-231 | 0.054 | 2243297 |
| TF-1 | 0.063 | 2751522 |

Example 18: In Vitro Activity of a 5T4-CD137 Bispecific Antibody in an IFNγ Release Assay Using Human CD8 T Cells and Human HCT116 Tumor Cells The functional activity of the 5T4-CD137 bispecific antibody ALG.APV-210 was evaluated in a CD8 T cell assay, where CD8+ T cells stimulated with αCD3 antibodies coated on beads were co-cultured in plates with human HCT116 tumor cells expressing endogenous levels of 5T4.

Materials and Methods

Mitomycin C Treatment of HCT116 Cells:

HCT116 tumor cells, a human colon carcinoma cell line (ATCC® CCL247™) expressing endogenous levels of human 5T4 (receptor density=$6.2\times10^4$/cell, Table 21) were pre-treated with Mitomycin C (0.5 mg/mL, Sigma-Aldrich) at a concentration of 50 μg/mL to hamper tumor cell overgrowth. After 45 min of incubation with Mitomycin C in 37° C., cells were washed three times in R10 medium (RPMI, Gibco #61870010 containing 10% heat inactivated FBS, Hyclone #SV30160 lot RB35944 and 10 mM Hepes, Gibco #15630056) and then resuspended at a concentration of $10\times10^6$ cells/mL in new R10 medium. 50 μL ($5\times10^5$ cells/well) of the Mitomycin C treated HCT116 cells were added to TC treated assay plates (Eppendorf #0030 730.119) and incubated in 37° C. overnight.

CD8 T cell assay setup:

The following day, human PBMC were isolated by density gradient centrifugation using Ficoll-Paque (GE Healthcare #17-1440-02) from leucocyte concentrates obtained from healthy donors (Clinical Immunology and Transfusion Medicine, Labmedicin Region Skåne, Lund Sweden). CD8+ cells were enriched by negative selection using the CD8+ T cell isolation kit (Miltenyi 130-096-495). The bispecific antibody, ALG.APV-210, or an isotype control in the Adaptir format, ANC017 (variable heavy and light chain sequences for ANC017 are shown below in Tables 29A and 29B) was diluted in a serial dilution in R10 medium and 50 μL was added to each well of the assay plates and incubated at 37° C. for 30 min, prior to the addition of 50 μL of αCD3 beads ($4\times10^8$/mL of anti-CD3 antibodies clone: OKT-3, Affymetrix eBioscience #16-0037-85, coated on beads, diluted to $2\times10^6$/mL) at a 1:1 CD8+ T cell to beads ratio, followed by the addition of 50 μL of the effector cells (enriched CD8+ cells, $2\times10^6$/mL or $1\times10^5$/well). The assay plates were incubated for 72 h at 37° C., and culture supernatant harvested. IFNγ levels in the supernatants were measured by ELISA (BD OptiEIA #555142) and are presented in FIG. 36 as normalized data (mean and SD values). $EC_{50}$ values were determined by non-linear regression log (agonist) vs. Normalized response (variable slope) using GraphPad Prism 7. TOP value (maximal functional effect) was determined by calculating the mean of the two highest values of IFNγ production in the culture supernatant. The experiment was performed 4 times, including in total 12 donors.

TABLE 29

AACN017 Variable Region Sequences

| | Heavy chain | | Light Chain | |
|---|---|---|---|---|
| | AA sequence | SEQ ID | AA sequence | SEQ ID |
| CDR1 | GFTFSSYA | 30 | QSISSY | 8 |
| CDR2 | ISGSGGST | 32 | AAS | 10 |

TABLE 29-continued

| AACN017 Variable Region Sequences | | | | |
|---|---|---|---|---|
| | Heavy chain | | Light Chain | |
| | AA sequence | SEQ ID | AA sequence | SEQ ID |
| CDR3 | AKGSGSYFDL | 177 | QQYSGYPYT | 178 |
| VH/VL | EVQLLESGGGLVQPGGSLRLSCAASGFT FSSYAMSWVRQAPGKGLEWVSAISGSGG STYYADSVKGRFTISRDNSKNTLYLQMN SLRAEDTAVYYCAKGSGSYFDLWGQGTL VTVSS | 179 | DIQMTQSPSFLSASVGDRVTITCRA SQSISSYLNWYQQKPGKAPKLLIYA ASSLQSGVPSRFSGSGSGTDFTLTI SSLQPEDFATYYCQQYSGYPYTFGQ GTKLEIK | 180 |

TABLE 29B

| Full-length ACN017 Sequence | |
|---|---|
| Full ACN017 Seq (VH-Fc-VL) | SEQ ID |
| EVQLLESGGGLVQPGGSLRLSCAASGFTFSSYAMSWVRQAPGKGLEWVSAISGSGGSTYYADSVKGRF TISRDNSKNTLYLQMNSLRAEDTAVYYCAKGSGSYFDLWGQGTLVTVSSGGGGSGGGGSGGGGSGGGG SDIQMTQSPSFLSASVGDRVTITCRASQSISSYLNWYQQKPGKAPKLLIYAASSLQSGVPSRFSGSGS GTDFTLTISSLQPEDFATYYCQQYSGYPYTFGQGTKLEIKSSEPKSSDKTHTCPPCPAPEAAGAPSVF LFPPKPKDTLMISRTPEVTCVVVDVSHEDPEVKFNWYVDGVEVHNAKTKPREEQYNSTYRVVSVLTVL HQDWLNGKEYKCAVSNKALPAPIEKTISKAKGQPREPQVYTLPPSRDELTKNQVSLTCLVKGFYPSDI AVEWESNGQPENNYKTTPPVLDSDGSFFLYSKLTVDKSRWQQGNVFSCSVMHEALHNHYTQKSLSLSP GSGGGGSGGGGSGGGGSPSEVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCAKGSGSYFDLWGQGTLVTVSS GGGGSGGGGSGGGGSGGGGSDIQMTQSPSFLSASVGDRVTITCRASQSISSYLNWYQQKPGKAPKLLI YAASSLQSGVPSRFSGSGSGTDFTLTISSLQPEDFATYYCQQYSGYPYTFGQGTKLEIKRS | 181 |

Results and Conclusions

Figure 36:
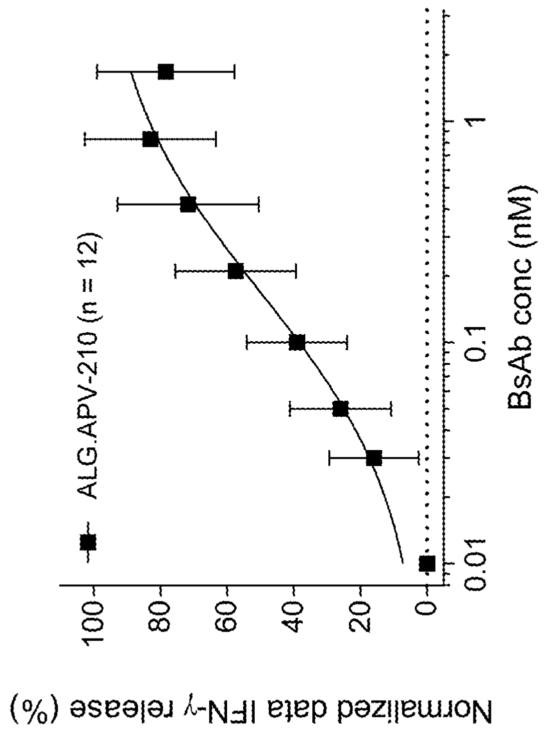
FIG. 36 shows the IFNγ response of human CD8+ T cells cultured with the bispecific antibody ALG.APV-210 in the presence of human HCT116 cells expressing 5T4.
Figure 37:
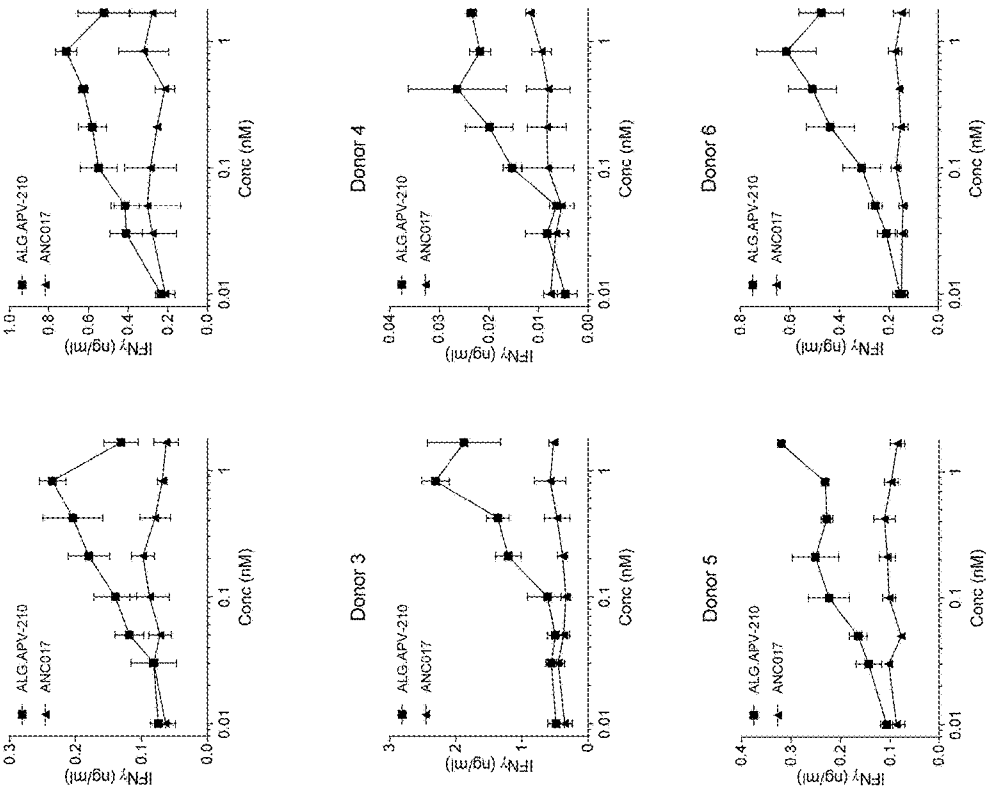
FIG. 37 shows IFNγ response of human CD8+ T cells cultured with the bispecific antibody ALG.APV-210 in the presence of human HCT116 cells expressing 5T4.
Figure 38:
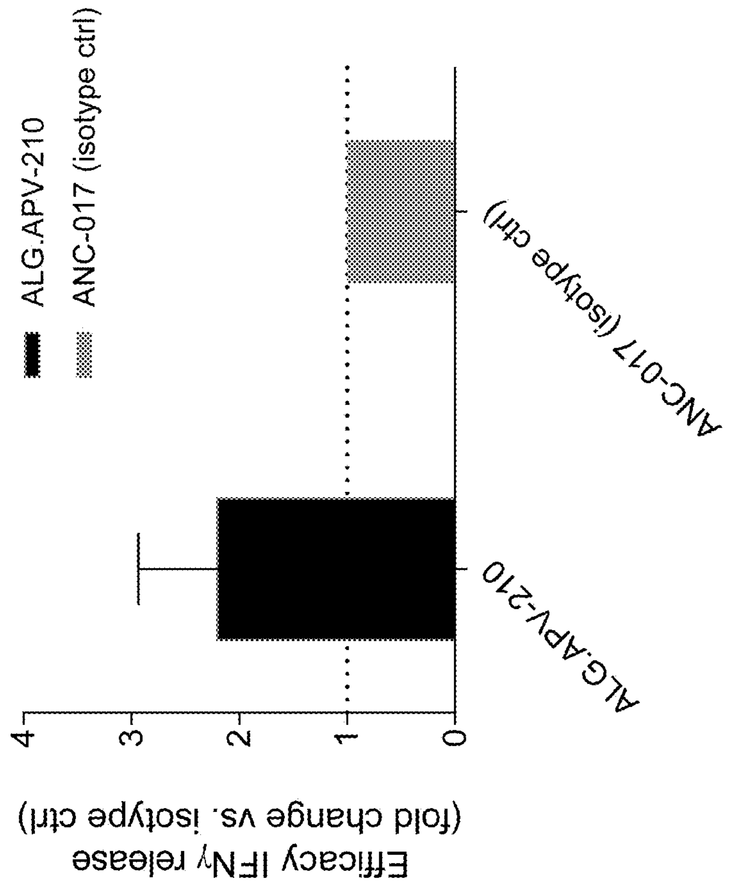
FIG. 38 shows the maximum IFNγ release of human CD8 T cells cultured with the bispecific antibody ALG.APV-210 in the presence of HCT116 cells expressing human 5T4.
Figure 39A:
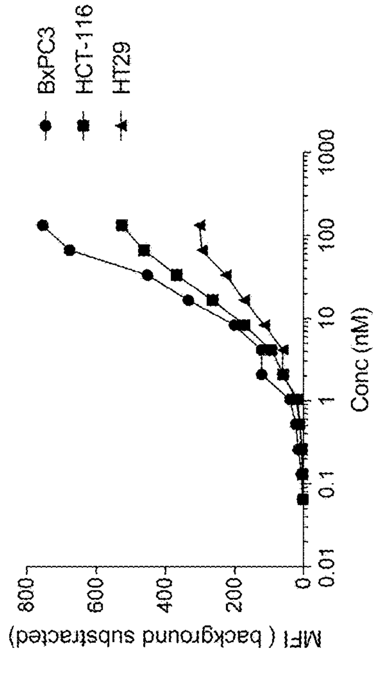
FIG. 39A-FIG. 39D show ALG.APV-210 binding to 5T4 expressing human tumor cells (FIG. 39A and FIG. 39B) or transfected cell lines (FIG. 39C and FIG. 39D).
Figure 39B:
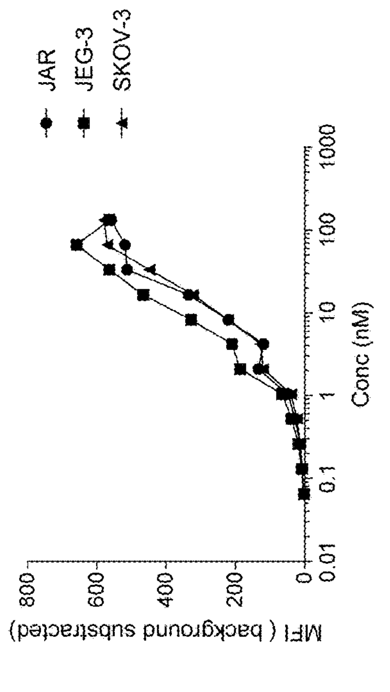
Figure 39C:
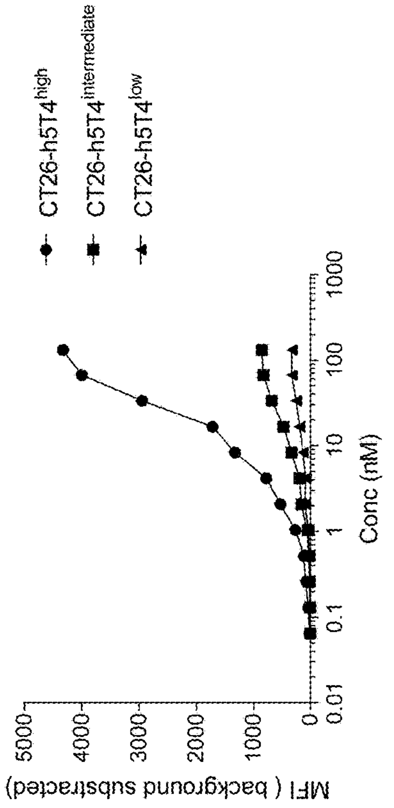
Figure 39D:
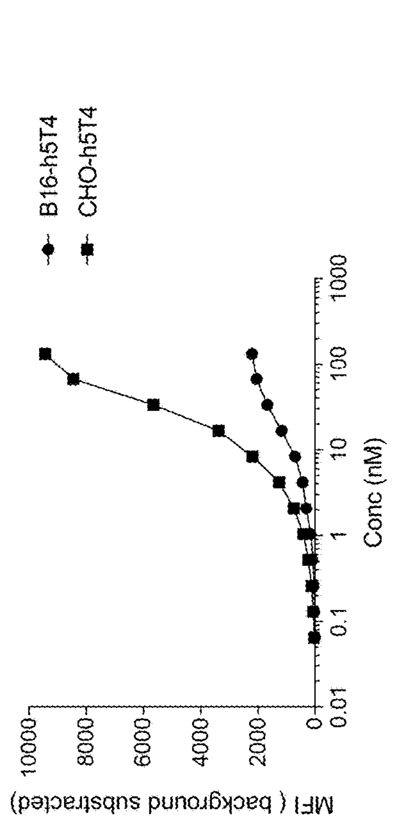
Figure 40A:
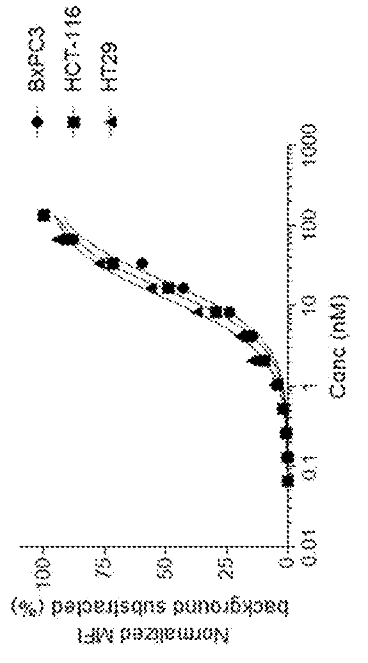
FIG. 40A-FIG. 40D show normalized MFI for experiments demonstrating ALG.APV-210 binding to 5T4 expressing human tumor cells (FIG. 40A and FIG. 40B) or transfected cell lines (FIG. 40C and FIG. 30D).
Figure 40B:
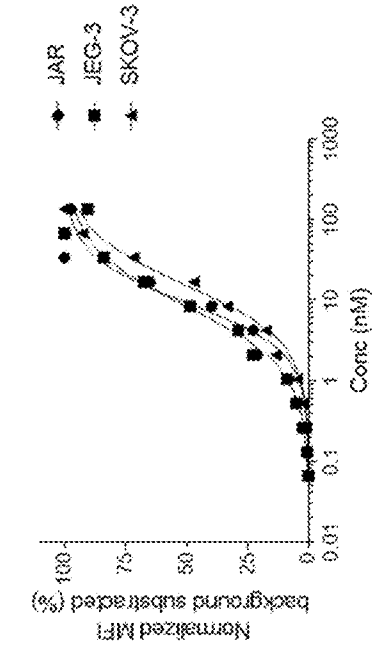
Figure 40C:
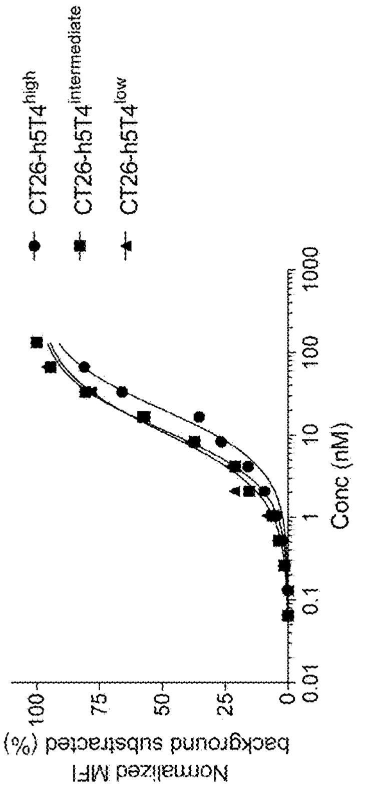
Figure 40D:
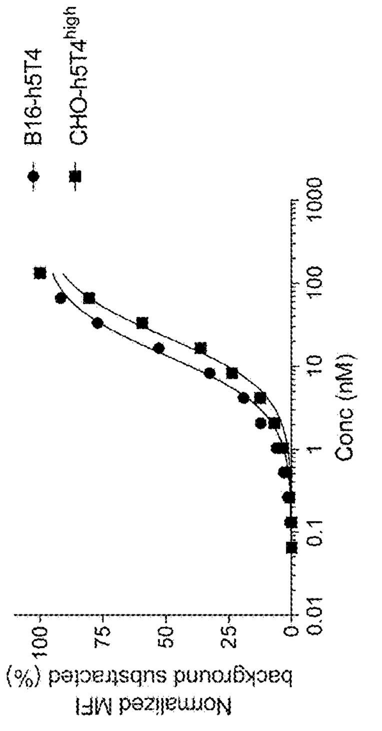

The functional effect of the CD137-5T4 bispecific antibody ALG.APV-210 was determined using human CD8+ T cells (the effector cells) co-cultured in plates with HCT116 cells. As shown in FIG. 36, the bispecific CD137-5T4 antibody ALG.APV-210 induced potent T cell activation, measured by IFNγ release, in a dose-dependent manner in the presence of HCT116 cells expressing endogenous levels of 5T4. For determination of $EC_{50}$, see Table 30, showing mean values and 95% CI of 12 donors from 4 pooled experiments. The endogenous levels of 5T4 expressed by the HCT116 cells is sufficient to induce a high agonistic functional effect of ALG.APV-210 as demonstrated in FIG. 37, where IFNγ levels of 6 individual donors following treatment with ALG.APV-210 is compared with an isotype control (ANC017). The efficacy (maximal IFNγ response) is also presented in FIG. 38 (fold change vs. isotype control, mean and SD of 12 donors).

TABLE 30

| $EC_{50}$ of ALG.APV-210 in a CD8+ T cell assay in the presence of HCT116 cells expressing human 5T4 | |
|---|---|
| Potency of ALG.APV-210 | HCT116 T cell assay |
| $EC_{50}$ (nM) | 0.17 |
| 95% CI | 0.14 to 0.21 |

Example 19: In Vivo Anti-Tumor Efficacy of a Bispecific Antibody in HCT-116 a 5T4 Positive Xenograft Tumor Model in SCID Beige Mice A study was conducted to assess the anti-tumor efficacy in vivo of ALG.APV-210.

Materials and Methods

Female SCID beige mice (6-8 weeks old) from Taconic, Denmark were used in the experiment. All animal procedures were conducted in compliance with Swedish legislation on animal rights and protection, and approved by the Ethical Committee on Animal Experiments, in Lund/Malmö (ethical application number: M151-13). PBMC were isolated from leukocyte concentrates obtained from 4 healthy donors (Clinical Immunology and Transfusion Medicine, Labmedicin Region Slåne, Lund Sweden) by density gradient centrifugation using Ficoll-Paque (GE Healthcare #17-1440-02) according to the manufacturer's instructions. The HCT-116 cell line, a human colon carcinoma cell line positive for the tumor-associated antigen 5T4, was purchased from ATCC (ATCC® CCL-247™, lot#62765668) and cultured according to their recommendations.

On day 0, HCT-116 tumor cells, growing in log phase, were inoculated subcutaneously into the right hind flank of the mice ($3\times10^6$ in 110 μL PBS). The following day (day 1), $7\times10^6$ of human PBMC from 4 donors in 100 μL of PBS were injected intraperitoneally. Intraperitoneal antibody treatments (100 μL in PBS) starting on day 6 with either vehicle (PBS), ALG.APV-210 10 μg/mouse, or ALG.APV-210 100 μg/mouse were given twice/week for a total of 5 injections (n=5 mice/treatment/donor). Tumor growth was observed and measured twice/week with a caliper in width, length and height of which the tumor volume was calculated (w/2×½×h/2×pi×(4/3)). The experimental endpoint was tumor volume ≥2 $cm^3$, wounding, or affected health of the mice. Tumor growth was statistically analyzed using Mann-Whitney non-parametric 2-tailed T-test using GraphPad Prism 7 at different time points (day 9, 13, 16, 20 and 23).

Results

Figure 28:
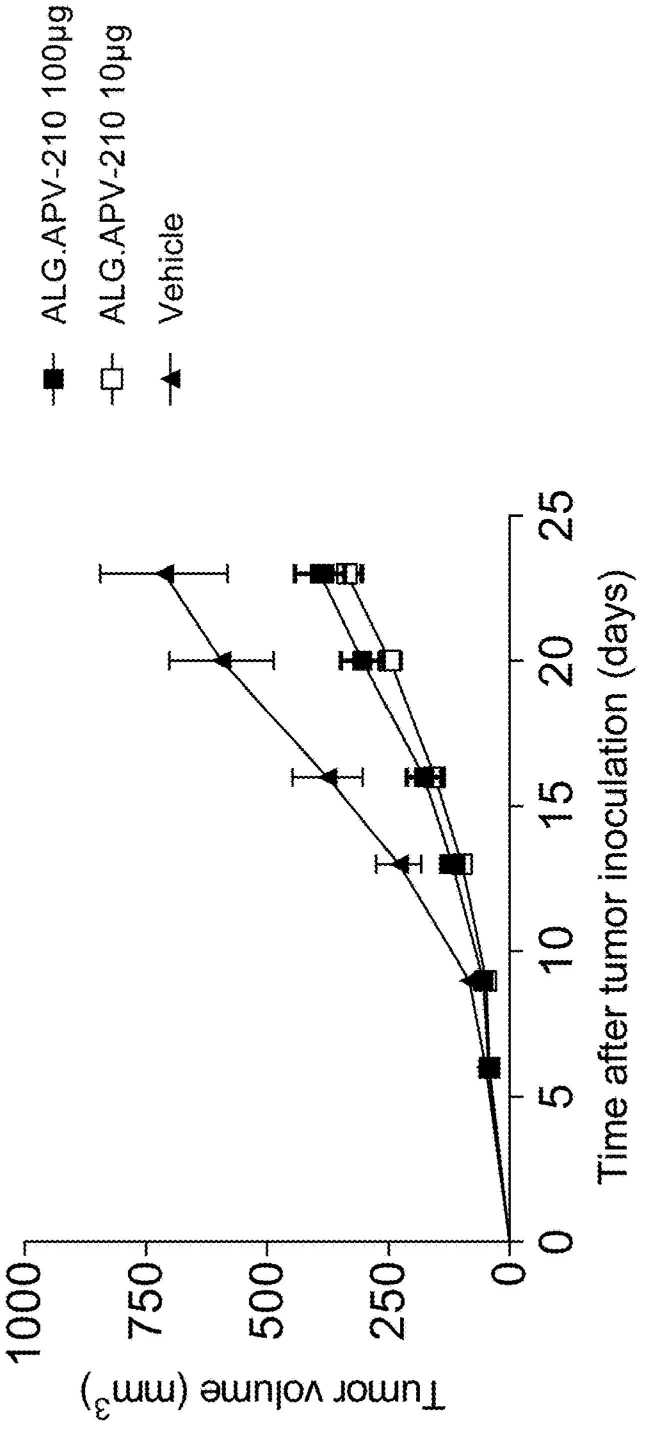
FIG. 28 shows the anti-tumor efficacy of a bispecific antibody ALG.APV-210 in HCT-116, a 5T4 positive human colon carcinoma xenograft tumor model in SCID beige mice.

As shown in FIG. 28, ALG.APV-210 at a dose of either 10 μg/mouse or 100 μg/mouse showed statistically significant anti-tumor efficacy (e.g. tumor volume inhibition) in comparison with the vehicle group from day 13 to 23 (pooled data from 4 donors, for statistical analysis and p-values; see Table 31).

TABLE 31

Statistical analysis of anti-tumor efficacy following treatment with ALG.APV-210 in an HCT-116 xenograft tumor model

| Days following Tumor inoculation | Significant difference (p < 0.05) in tumor volume between treatments, Mann-Whitney, non-parametric 2-tailed T test | |
|---|---|---|
| | ALG.APV-210 10 μg vs. vehicle | ALG.APV-210 100 μg vs. vehicle |
| Day 9 | No | No |
| Day 13 | Yes* p = 0.0109 | Yes* p = 0.0262 |
| Day 16 | Yes*** p = 0.0008 | Yes** p = 0.0010 |
| Day 20 | Yes**** p < 0.0001 | Yes* p = 0.0009 |
| Day 23 | Yes** p = 0.0016 | Yes* p = 0.0225 |

In conclusion, the study showed that ALG.APV-210 had anti-tumoral properties in a 5T4 positive human colon carcinoma xenograft tumor model.

Example 20: Pharmacokinetic Properties of ALG.APV-209 in BALB/c Mice

Figure 29:
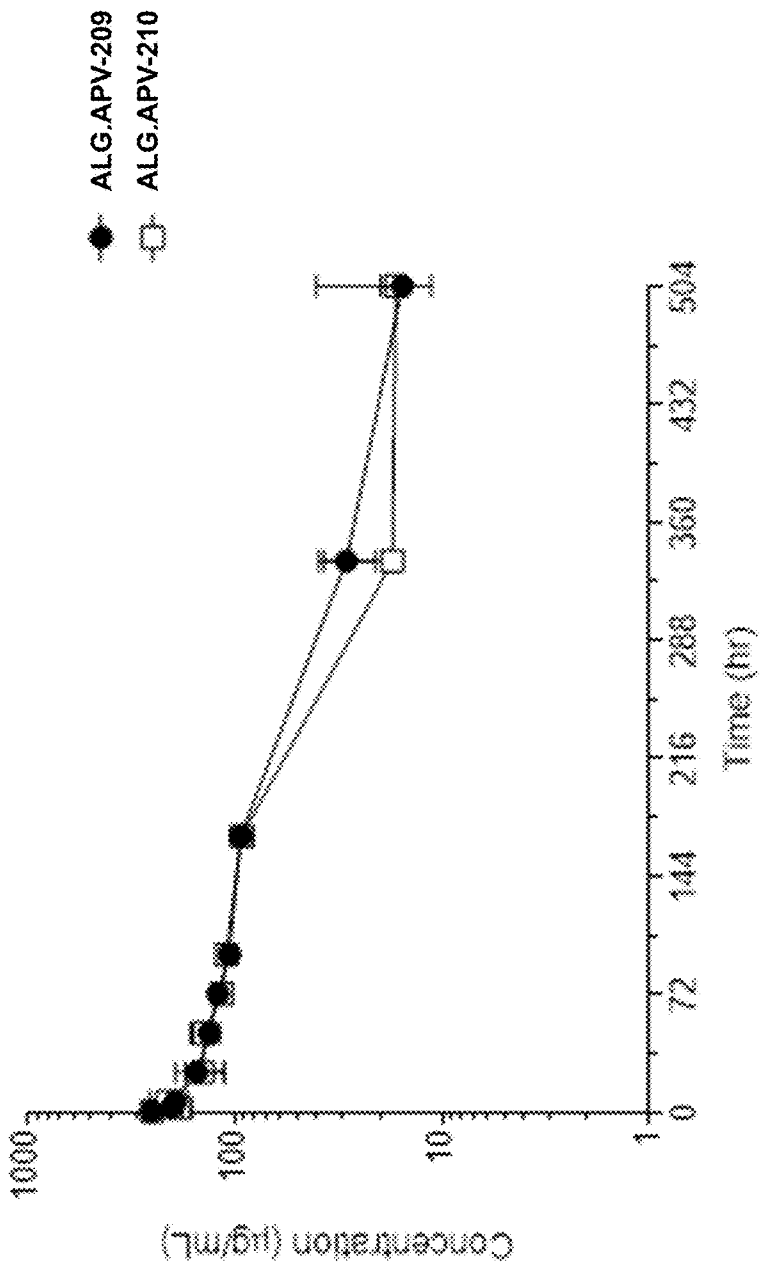
FIG. 29 shows the PK analysis of ALG.APV-210 or ALG.APV-209.

A study was conducted to assess the pharmacokinetic (PK) properties of ALG.APV-209 and ALG.APV-210 in mice. Normal BALB/c female mice were injected intravenously (IV) at time 0 with a single dose of 200 μg of ALG.APV-209 or ALG.APV-210 and blood was collected from 1 to 3 mice per time point. Anesthetized mice were exsanguinated via cardiac puncture and serum was collected at t=15 minutes, and 2, 6, 24, 48, 72, 96, 168, 336 and 504 hours after injection. Concentrations of ALG.APV-209 and ALG.APV-210 in sera were determined with an ELISA method developed to detect only intact protein, using huCD137 ECD-AFH (ALGO27) to capture the anti-CD137 BD, and biotinylated 5T4 ECD-mFc (ALGO29) to detect the anti-5T4 BD. Estimated PK disposition parameters from non-compartmental analysis (NCA) using Phoenix 64 software (v6.4 WinNonlin™ license) are listed in Table 32, and estimates of half-life along with fit statistics are shown in FIG. 29. A precompiled model for IV dosing with sparse sampling and uniform weighting was used during NCA.

In normal female BALB/c mice injected IV with a 200 μg bolus dose of ALG.APV-209 or ALG.APV-210, the apparent terminal elimination half-life determined using NCA was 142 and 215 hours, respectively (excluding samples potentially impacted by ADA). Parameter estimates for half-life determined using compartmental analysis (2-compartments with IV dosing) were similar for ALG.APV-209 and ALG.APV-210. NCA estimated clearance and volume for ALG.APV-209 and ALG.APV-210 to be: 0.263 and 0.204 mL/hr/kg, and 54 and 63 mL/kg respectively. By both analysis methods, ALG.APV-210 had the longest terminal elimination half-life and slightly better clearance values. Sudden drops in serum concentrations indicative of anti-drug antibodies (ADA) were seen in late time points for mice dosed with ALG.APV-210, however the presence of ADA could not be confirmed by ELISA methods due to drug still being present in samples, which also likely resulted in rapid clearance of ADA.

TABLE 32

NCA estimated PK Disposition parameters of ALG.APV-209 and ALG.APV-210

| PK Paramenter | Units | ALG.APV-209 | ALG.APV-210 | ALG.APV-210 excluding ADA + sera |
|---|---|---|---|---|
| Rsq | | 0.82 | 0.900 | 0.966 |
| HL Lambda z | hr | 142.0 | 134.6 | 215.3 |
| Tmax | hr | 0.25 | 0.25 | 0.25 |
| Cmax | μg/mL | 254.04 | 252.34 | 252.34 |
| SE Cmax | μg/mL | N/A | 14.6 | 14.6 |
| Cmax/D | kg*μg/mL/mg | 0.025 | 0.025 | 0.025 |
| $C_0$ | μg/mL | 262.2 | 263.6 | 263.6 |
| AUClast | hr*μg/mL | 34858 | 33054 | 38705 |
| AUCINF_obs | hr*μg/mL | 38043 | 36317 | 49124 |
| AUCINF/D_obs | hr*kg*μg/mL/mg | 3.804 | 3.632 | 4.912 |
| V-obs | mL/kg | 53,84 | 53.46 | 63.22 |
| CL_obs | mL/hr/kg | 0.263 | 0.275 | 0.204 |
| Vss/OBS | mL/kg | 51.1 | 51.5 | 62.7 |
| MRTlast | hr | 147.4 | 136.7 | 171.9 |
| MRTINF-obs | Hr | 194.4 | 187.2 | 308.2 |

Rsq: Goodness of fit statistic for the terminal elimination phase
HL Lambda z: Apparent terminal elimination half life
Tmax: Time of maximum observed concentration
Cmax: Maximum observed concentration, occurring at Tmax
SE Cmax: Standard error of the data at Tmax (time of maximum mean concentration)
Cmax/D: Maximum observed concentration divided by dose
$C_0$: Back extrapolated initial concentration at time 0
_obs: based on the observed concentrations
AUClast: Area under the curve from the time of dosing until the last measured concentration
AUCINF: Area under the curve from the time of dosing extrapolated to infinity
AUCINF/D: AUCINF divided by dose
V: Volume of distribution based on the terminal phase
CL: Serum clearance
Vss: An estimate of the volume of distribution at steady state
MRTlast: Mean residence time until the last measured concentration
MRTINF: Mean residence time extrapolated to infinity Example 21: The Fc Portion of ALG.APV-210 does not Interact with Fcγ Receptors ALG.APV-210 contains mutations introduced to prevent interaction with Fcγ receptors (FcγR) that could lead to FcγR-mediated T-cell activation or ADCC, ADCP, CDC etc. Binding of ALG.APV-210 was therefore tested on CHO cell transfectants stably expressing the following FcγR: FcγRI (CD64), FcγRIIa (CD32a His131), FcγRIIb (CD32b), FcγRIIIa (CD16a Val158 and CD16a Phe158), and FcγRIIIb (CD16b). Untransfected CHO cells were used as negative control. A control human IgG1 molecule was used as a positive control. Different concentrations of ALG.APV-210 or control IgG1 were incubated with the FcγR-expressing cell lines, washed, and labeled with a secondary anti-human IgG reagent. Binding of ALG.APV-210 and the control IgG1 was detected by flow cytometry.

Figure 30B:
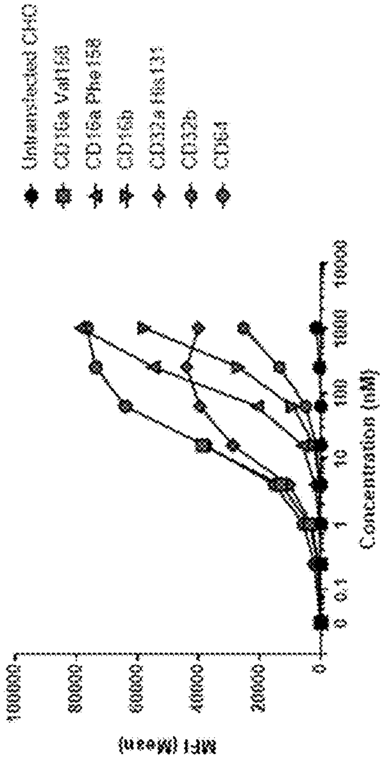
FIG. 30A-FIG. 30B show the binding of the Fc portion of ALG.APV-210 to FcγR. Titrated ALG.APV-210 was incubated with the FcγR-expressing cells and probed with a fluorescently-labelled anti-human IgG secondary antibody (FIG. 30A). Human IgG1 molecule was used as a positive control (FIG. 30B).
Figure 30A:
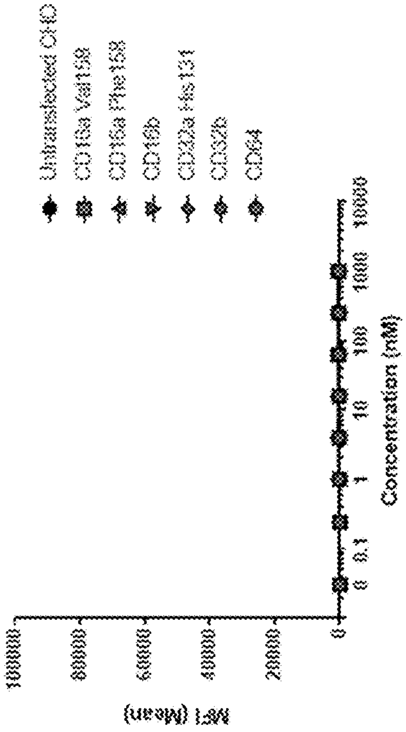

The results are provided in FIGS. 30A and 30B. FIG. 30B shows that the control IgG1 bound to all the tested FcγR expressing cell lines: FcγRI (CD64), FcγRIIa (CD32a His131), FcγRIIb (CD32b), FcγRIIIa (CD16a Val158 and CD16a Phe158), and FcγRIIIb (CD16b), but not to the untransfected CHO cells (negative control). Significant binding of the control IgG1 to some of the FcγR expressing cell lines were observed at concentrations as low as 4 nM. FIG. 30A shows that no detectable binding was observed with the ALG.APV-210 construct to the tested FcγR: FcγRI (CD64), FcγRIIa (CD32a His131), FcγRIIb (CD32b), FcγRIIIa (CD16a Val158 and CD16a Phe158), and FcγRIIIb (CD16b).

Example 22: In Vitro Activity of a 5T4-CD137 Bispecific Antibody in a T-Cell Proliferation Assay Using Human PBMC and CHO-5T4 Cells The functional activity of the 5T4-CD137 bispecific molecules ALG.APV-209 and ALG.APV-210 was evaluated in a T-cell proliferation assay using PBMC. PBMC were isolated from healthy human blood using standard ficoll gradients. Once isolated, the cells were washed in saline buffer to remove platelets. PBMC were cultured with irradiated CHO-K1/human 5T4 cells, at approximately 120,000 PBMC to 30,000 5T4 (+) cells in 96-well plates. CHO-K1/5T4 cells were irradiated (x-ray Cell Rad irradiator, Faxitron Bioptics, LLC), and washed in medium before plating with PBMC. Anti-CD3 antibody OKT3 (eBioscience) was added to all the wells at a concentration of 1 ng/mL. Cells were cultured in a total volume of 200 μL of RPMI 1640 media (GIBCO) supplemented with 10% fetal bovine serum (SIGMA), sodium pyruvate, antibiotics and non-essential amino acids. Plates were incubated at 37° C., 5% $CO_2$ in humidified incubators for 72 hours. Supernatants were removed and cells were labeled in the same assay plates with antibodies to CD4, CD8 and CD5 in PBS buffer with 2% BSA and 2 mM EDTA, for 30 min on ice, 7AAD was added to exclude dead cells. After washing cells were resuspended at 120 μL/well and 70 μL/well volumes were collected from each well in a flow cytometer (a LSR-II™, BD Biosciences). Cell analysis was performed using Flowjo software and analyzed by counting the number of CD4+ or CD8+ live T cell events (CD4+ CD8− CD5+, 7AAD− or CD4− CD8+ CD5+ 7AAD−) events after gating on lymphocytes using FSC versus SSC parameters. Each condition was tested in duplicate and the averages of each duplicate set were graphed using GraphPad Prism 6® graphing and statistics software.

Figure 31A:
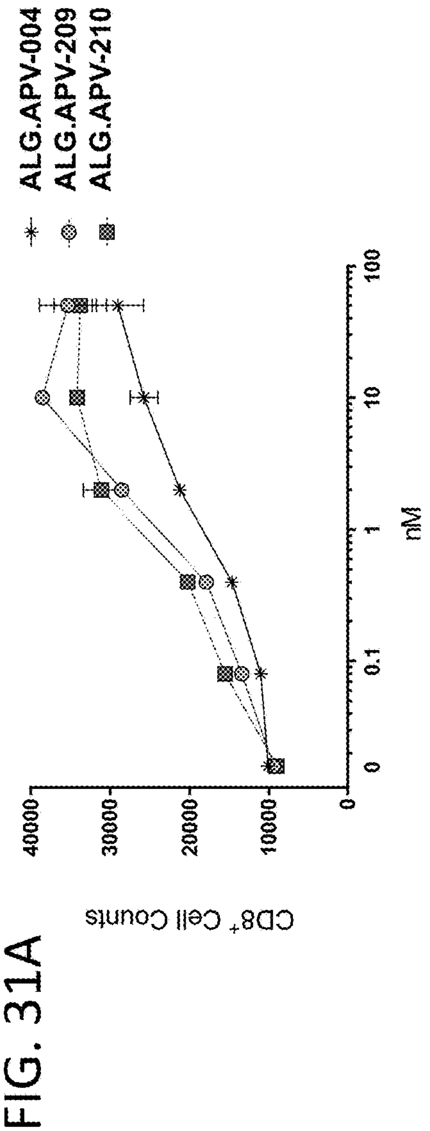
FIG. 31A-FIG. 31B show the CD8+ (FIG. 31A) and CD4+ (FIG. 31B) T-cell proliferation induced by the bispecific molecules ALG.APV-209 and ALG.APV-210 in the presence of CHO-K1 cells expressing human 5T4 and anti-CD3 antibodies.
Figure 31B:
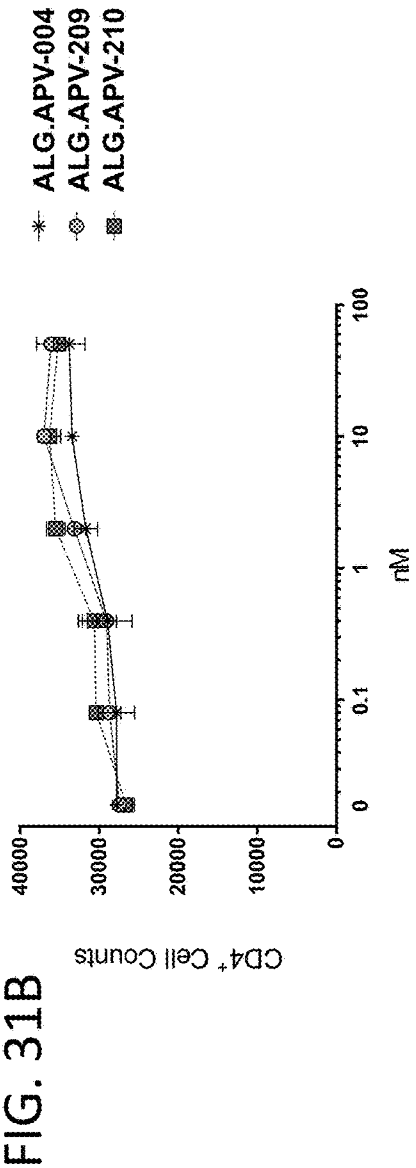

The results of the study are provided in FIGS. 31A and 31B. Antigen-specific proliferation of CD8+ T cells was evaluated after 72 hrs of stimulation of T cells primed with a low concentration of anti-CD3 antibodies. Anti-CD3 stimulation induces upregulation of CD137. Addition of anti-CD3 alone, with no bispecific antibodies, induced a certain amount of CD8+ and CD4+ T-cell proliferation. The addition of ALG.APV-209 or ALG.APV-210 increased the proliferation of CD8+ T cells (FIG. 31A). In contrast, and as expected based on the preferential expression of CD137 on CD8+ T cells, the bispecific antibodies had a limited impact on the anti-CD3 induced proliferation of CD4+ T cells (FIG. 31B). The results were consistent across multiple experiments. A Morrison format control molecule (ALG.APV-004) was included for comparison.

Taken together, the results showed that both ALG.APV-209 and ALG.APV-210 enhanced the proliferation of CD8+ T cells. ALG.APV-209 and ALG.APV-210 induced a higher amount of cell proliferation than the Morrison format construct ALG.APV-004.

Example 23: 5T4 Expression in Normal and Tumor Tissues Assessed by Immunohistochemistry Expression of the tumor antigen 5T4 in normal human tissue and in a range of different tumor types was assessed by immunohistochemistry (IHC).

Development of Staining Method:

Five commercial anti-5T4 antibodies and two in-house generated anti-5T4 antibodies were assessed for 5T4-binding in cryosections versus formalin-fixed, paraffin-embedded (FFPE) sections of the control cells and test human tissues. Isotype control staining was also included. A mouse monoclonal antibody (clone: MAB4975, R&D Systems) was selected as the best performing antibody because it was highly specific and functional in both cryosections and in FFPE sections. Antigen retrieval method and antibody titer were optimized for this antibody.

Tissues and Tissue Microarrays:

Human placental tissue and a murine colon carcinoma cell line CT26 (from ATCC® CRL-2638) transfected to express human 5T4 were used as positive controls. Human cerebrum, liver, and non-transfected CT26 cells were used as negative controls. Human tissues used for positive and negative controls were from Charles River Laboratories' archives. FFPE tissue microarrays (TMAs) were acquired from US Biomax Inc. All stainings were evaluated by a study pathologist at PAI, Charles River Laboratories.

IHC Staining of Normal Human Tissue Microarrays:

In the normal human tissue panel with 24 tissue types from 3 donors (FDA808j-1), 5T4 expression was not found in any major organs.

IHC staining in human tumor tissue types: 5T4 expression was screened in the multiple organ cancer tissue array of 72 tumor cases (FDA808j-2) presented by a single core per tumor. 5T4 expression was detected in tumors of the pancreas, thyroid gland, breast, liver, uterus, cervix, striated muscle, skin (squamous cell carcinoma), nerve (neurofibroma), and bladder.

5T4 expression was assessed in TMAs containing 10-50 tumor cases for each of the selected indications shown in Table 33, represented by duplicate or triplicate cores. In bladder cancer, cancer of the head and neck (H&N), non-small cell lung cancer (NSCLC) and mesothelioma, 50-56% of the tumors investigated were 5T4 positive. A significant number of pancreatic tumors were also 5T4 positive (36%). 50% of the clear cell carcinomas tumors investigated were 5T4 positive.

TABLE 33

5T4 expression in seven selected tumor indications

| | TMA ID | Total No. donors | 5T4 + donors (Total #) | 5T4 + donors (%) |
|---|---|---|---|---|
| Bladder cancer | BL721 | 18 | 10 | 56 |
| Head & neck cancers | HN811 | 19 | 10 | 53 |
| Non-small cell lung cancer | LC10011a | 40 | 20 | 50 |
| Mesothelioma | MS481c | 20 | 10 | 50 |
| Pancreatic cancer | PA721a | 22 | 8 | 36 |
| Kidney cancer | T072b | 10 | 2 | 20 |
| Ovarian cancer | T112c | 10 | 1 | 10 |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not, be taken as an acknowledgment or any form of suggestion that they constitute valid prior art or form part of the common general knowledge in any country in the world.

The invention claimed is:

1. A multispecific polypeptide comprising a first single chain variable fragment (scFv) domain and a second scFv domain linked together by a binding domain linker and an immunoglobulin Fc domain, wherein the immunoglobulin Fc domain comprises a hinge region and an immunoglobulin constant region;

wherein the multispecific polypeptide is capable of forming a homodimer by association with a second identical multispecific polypeptide;

wherein the first scFv domain specifically binds to human 5T4 and comprises:

(i) an immunoglobulin heavy chain variable region comprising a heavy chain complementarity determining region (HCDR)-1 amino acid sequence of SEQ ID NO: 30, an HCDR2 amino acid sequence of SEQ ID NO: 32, and an HCDR3 amino acid sequence of SEQ ID NO: 34; and (ii) an immunoglobulin light chain variable region comprising a light chain complementarity determining region (LCDR)-1 amino acid sequence of SEQ ID NO: 42, an LCDR2 amino acid sequence of SEQ ID NO: 10, and an LCDR3 amino acid sequence of SEQ ID NOs: 36; and wherein the second scFv domain specifically binds to human 4-1BB and comprises:

(i) an immunoglobulin heavy chain variable region comprising an HCDR1 amino acid sequence of SEQ ID NO: 2, an HCDR2 amino acid sequence of SEQ ID NO: 4, and an HCDR3 amino acid sequence of the SEQ ID NO: 6; and (ii) an immunoglobulin light chain variable region comprising an LCDR1 amino acid sequence of SEQ ID NO: 8, an LCDR2 amino acid sequence of SEQ ID NO: 10, and an LCDR3 amino acid sequence of SEQ ID NO: 12.

2. The multispecific polypeptide of claim 1, wherein the multispecific polypeptide comprises, from amino-terminus to carboxyl-terminus: (i) the first scFv domain, (ii) the hinge region, (iii) the immunoglobulin constant region, (iv) the binding domain linker, and (v) the second scFv domain.

3. The multispecific polypeptide of claim 1, wherein the first scFv domain comprises a mutation in the framework region compared to the framework region of SEQ ID NOs: 130 or 170.

4. The multispecific polypeptide of claim 3, wherein the mutation introduces a stabilizing disulfide bond.

5. The multispecific polypeptide of claim 1, wherein the first scFv domain comprises the immunoglobulin heavy chain variable region of SEQ ID NO: 38 and the immunoglobulin light chain variable region of SEQ ID NO: 44.

6. The multispecific polypeptide of claim 1, wherein the first scFv domain comprises the immunoglobulin heavy chain variable region of SEQ ID NO: 46 and the immunoglobulin light chain variable region of SEQ ID NO:48.

7. The multispecific polypeptide of claim 1, wherein the second scFv domain comprises the immunoglobulin heavy chain variable region of SEQ ID NO: 14 and the immunoglobulin light chain variable region of SEQ ID NO: 16.

8. The multispecific polypeptide of claim 1, wherein the first scFv domain comprises the immunoglobulin heavy chain variable region of SEQ ID NO: 46 and the immunoglobulin light chain variable region of SEQ ID NO: 48, and wherein the second scFv domain comprises the immunoglobulin heavy chain variable region of SEQ ID NO: 14 and the immunoglobulin light chain variable region of SEQ ID NO: 16.

9. The multispecific polypeptide of claim 1, wherein the amino acid sequence of the first scFv domain is at least 97% identical to SEQ ID NO: 120, and the amino acid sequence of the second scFv domain is at least 97% identical to SEQ ID NO: 110.

10. The multispecific polypeptide of claim 9, wherein the polypeptide comprises an amino acid sequence at least 95% identical to SEQ ID NO: 172 or comprises an amino acid sequence identical to SEQ ID NO: 172.

11. The multispecific polypeptide of claim 1, wherein the amino acid sequence of the first scFv domain is at least 97% identical to SEQ ID NO: 122 and the amino acid sequence of the second scFv domain is at least 97% identical to SEQ ID NO: 110.

12. The multispecific polypeptide of claim 11, wherein the polypeptide comprises an amino acid sequence at least 95% identical to SEQ ID NO: 174 or comprises an amino acid sequence of SEQ ID NO: 174.

13. The multispecific polypeptide of claim 1, wherein binding of the multispecific polypeptide to an effector cell results in increased effector cell activation, increased effector cell proliferation, or wherein binding of the multispecific polypeptide to an effector cell and a 5T4-expressing cell results in enhanced effector cell-dependent lysis of the 5T4-expressing cell.

14. A method for treating a cancer in a subject in need thereof, comprising administering to the subject a therapeutically effective amount of the multispecific polypeptide of claim 1, wherein said cancer is characterized by expression of 5T4.

15. The method of claim 14, wherein the cancer is breast cancer, pancreatic cancer, ovarian cancer, non-small cell lung cancer, mesothelioma, chronic lymphocytic leukemia (CLL), mantle cell leukemia (MCL), acute lymphoblastic leukemia (ALL), squamous cell carcinoma, melanoma, adrenal cancer, bladder cancer, cervical cancer, renal cancer, gastric cancer, prostate cancer, thyroid cancer, liver cancer, uterine cancer, neurofibroma, sarcoma, carcinoma, or head and neck cancer.

16. The method of claim 14, wherein the multispecific polypeptide comprises, from amino-terminus to carboxyl-terminus: (i) the first scFv domain, (ii) the hinge region, (iii) the immunoglobulin constant region, (iv) the binding domain linker, and (v) the second scFv domain.

17. The method of claim 14, wherein the second scFv domain comprises immunoglobulin heavy chain variable region of SEQ ID NO: 14 and the immunoglobulin light chain variable region of SEQ ID NO: 16, and wherein the first scFv domain comprises (i) the immunoglobulin heavy chain variable region of SEQ ID NO: 38 and the immunoglobulin light chain variable region of SEQ ID NO: 44; or (ii) the immunoglobulin heavy chain variable region of SEQ ID NO: 46 and the immunoglobulin light chain variable region of SEQ ID NO: 48.

18. The method of claim 14, wherein the amino acid sequence of the second scFv domain of the multispecific polypeptide is at least 97% identical to SEQ ID NO: 110, and wherein the amino acid sequence of the first scFv domain of the multispecific polypeptide is at least 97% identical to SEQ ID NO: 120 or SEQ ID NO: 122.

19. The multispecific polypeptide of claim 1, wherein said polypeptide exhibits statistically significant enhanced effector cell activation compared to a second multispecific polypeptide, wherein the second multispecific polypeptide is an IgG-scFv structure comprising an anti-4-1BB antibody comprising a heavy chain variable region comprising SEQ ID NO: 28 and a light chain variable region comprising SEQ ID NO: 16 and an anti-5T4 scFv comprising a heavy chain variable region comprising SEQ ID NO: 46 and a light chain variable region comprising SEQ ID NO: 66.

20. The multispecific polypeptide of claim 1, wherein said polypeptide induces statistically significant increased effector cell proliferation compared to a second multispecific polypeptide, wherein the second multispecific polypeptide is an IgG-scFv structure comprising an anti-4-1BB antibody comprising a heavy chain variable region comprising SEQ ID NO: 28 and a light chain variable region comprising SEQ ID NO:16 and an anti-5T4 scFv comprising a heavy chain variable region comprising SEQ ID NO:46 and a light chain variable region comprising SEQ ID NO:66.

* * * * *